(12) United States Patent
Mitchell et al.

(10) Patent No.: US 9,359,340 B2
(45) Date of Patent: Jun. 7, 2016

(54) HYDROXYLATED AND METHOXYLATED PYRIMIDYL CYCLOPENTANES AS AKT PROTEIN KINASE INHIBITORS

(71) Applicants: Array BioPharma Inc., Boulder, CO (US); Genentech, Inc., South San Francisco, CA (US)

(72) Inventors: Ian S. Mitchell, Boulder, CO (US); James F. Blake, Boulder, CO (US); Rui Xu, Boulder, CO (US); Nicholas C. Kallan, Boulder, CO (US); Dengming Xiao, Boulder, CO (US); Keith Lee Spencer, Boulder, CO (US); Josef R. Bencsik, Boulder, CO (US); Eli M. Wallace, Boulder, CO (US); Stephen T. Schlachter, Boulder, CO (US); Anna L. Leivers, Boulder, CO (US); Jun Liang, South San Francisco, CA (US); Brian Safina, South San Francisco, CA (US); Birong Zhang, South San Francisco, CA (US); Christine Chabot, South San Francisco, CA (US); Steven Do, South San Francisco, CA (US)

(73) Assignees: Array BioPharma Inc., Boulder, CO (US); Genentech, Inc., South San Francisco, CA (US)

( * ) Notice: Subject to any disclaimer, the term of this patent is extended or adjusted under 35 U.S.C. 154(b) by 0 days.

(21) Appl. No.: 14/458,062

(22) Filed: Aug. 12, 2014

(65) Prior Publication Data

US 2014/0349997 A1 Nov. 27, 2014
US 2016/0152606 A9 Jun. 2, 2016

Related U.S. Application Data

(62) Division of application No. 13/272,079, filed on Oct. 12, 2011, now Pat. No. 8,853,199, which is a division of application No. 11/773,949, filed on Jul. 5, 2007, now Pat. No. 8,063,050.

(60) Provisional application No. 60/818,718, filed on Jul. 6, 2006.

(51) Int. Cl.

| C07D 239/70 | (2006.01) |
|---|---|
| C07D 403/04 | (2006.01) |
| C07D 413/12 | (2006.01) |
| C07D 401/12 | (2006.01) |
| C07D 403/12 | (2006.01) |
| C07D 405/12 | (2006.01) |
| C07D 409/12 | (2006.01) |
| C07D 409/14 | (2006.01) |
| C07D 407/12 | (2006.01) |
| A61P 29/00 | (2006.01) |
| A61P 35/00 | (2006.01) |
| A61P 9/00 | (2006.01) |

(Continued)

(52) U.S. Cl.
CPC ............ *C07D 413/12* (2013.01); *C07D 239/70* (2013.01); *C07D 401/12* (2013.01); *C07D 403/12* (2013.01); *C07D 405/12* (2013.01); *C07D 407/12* (2013.01); *C07D 409/12* (2013.01); *C07D 409/14* (2013.01)

(58) Field of Classification Search
CPC ........................... C07D 239/70; A61K 31/517
USPC ....................................... 544/253; 514/252.16
See application file for complete search history.

(56) References Cited

U.S. PATENT DOCUMENTS

| 3,804,899 A | 4/1974 | Ebnother et al. |
| 3,885,035 A | 5/1975 | Simpson |

(Continued)

FOREIGN PATENT DOCUMENTS

| EP | 194161 | 9/1986 |
| JP | 43-3307 | 2/1968 |

(Continued)

OTHER PUBLICATIONS

Blicke et al., "Synthesis of 2-Azetidimones (β-Lactams)", *J. Org. Chem.*, vol. 23, 1102-1107 (1958).

(Continued)

*Primary Examiner* — Susanna Moore
(74) *Attorney, Agent, or Firm* — Viksnins Harris & Padys PLLP

(57) ABSTRACT

The present invention provides compounds, including resolved enantiomers, resolved diastereomers, solvates and pharmaceutically acceptable salts thereof, comprising the Formula I:

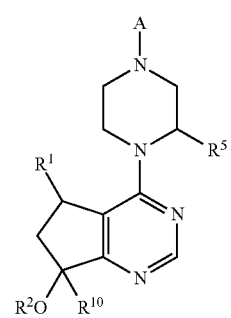

Also provided are methods of using the compounds of this invention as AKT protein kinase inhibitors and for the treatment of hyperproliferative diseases such as cancer.

101 Claims, No Drawings

(51) Int. Cl.

| | |
|---|---|
| A61P 25/28 | (2006.01) |
| A61P 15/00 | (2006.01) |
| A61P 17/00 | (2006.01) |
| A61K 31/517 | (2006.01) |
| A61K 31/496 | (2006.01) |

(56) References Cited

U.S. PATENT DOCUMENTS

| | | | |
|---|---|---|---|
| 3,956,495 | A | 5/1976 | Lacefield |
| 3,966,936 | A | 6/1976 | Cronin et al. |
| 4,060,615 | A | 11/1977 | Matier et al. |
| 4,352,928 | A | 10/1982 | Hiranuma et al. |
| 4,871,739 | A | 10/1989 | Baldwin et al. |
| 4,889,856 | A | 12/1989 | Tolman et al. |
| 4,959,368 | A | 9/1990 | Awaya et al. |
| 4,994,464 | A | 2/1991 | Tolman et al. |
| 5,051,412 | A | 9/1991 | Macor |
| 5,525,625 | A | 6/1996 | Bridges et al. |
| 5,563,152 | A | 10/1996 | Kulagowski et al. |
| 5,610,303 | A | 3/1997 | Kimura et al. |
| 5,750,531 | A | 5/1998 | Lee et al. |
| 5,750,545 | A | 5/1998 | Akahoshi et al. |
| 5,817,671 | A | 10/1998 | Filla et al. |
| 6,310,060 | B1 | 10/2001 | Barrett et al. |
| 6,423,716 | B1 | 7/2002 | Matsuno et al. |
| 6,469,004 | B1 | 10/2002 | Barrett et al. |
| 6,506,798 | B1 | 1/2003 | Barrett et al. |
| 6,627,628 | B1 | 9/2003 | Schindler et al. |
| 6,831,175 | B2 | 12/2004 | Li et al. |
| 7,041,687 | B2 | 5/2006 | Binch et al. |
| 7,067,664 | B1 | 6/2006 | Chen |
| 7,115,741 | B2 | 10/2006 | Levy et al. |
| 7,125,880 | B1 | 10/2006 | Chen |
| 7,223,738 | B2 | 5/2007 | Bilodeau et al. |
| 7,223,767 | B2 | 5/2007 | Clark et al. |
| 7,947,690 | B2 | 5/2011 | Yonetoku et al. |
| 8,003,651 | B2 | 8/2011 | Mitchell et al. |
| 8,063,050 | B2 | 11/2011 | Mitchell et al. |
| 8,329,701 | B2 | 12/2012 | Mitchell et al. |
| 8,680,114 | B2 | 3/2014 | Mitchell et al. |
| 8,846,681 | B2 | 9/2014 | Mitchell et al. |
| 8,853,199 | B2 | 10/2014 | Mitchell et al. |
| 2003/0004193 | A1 | 1/2003 | Barrett et al. |
| 2003/0045521 | A1 | 3/2003 | Tecle |
| 2003/0078428 | A1 | 4/2003 | Barrett et al. |
| 2003/0092748 | A1 | 5/2003 | Barrett et al. |
| 2003/0199511 | A1 | 10/2003 | Li et al. |
| 2003/0216460 | A1 | 11/2003 | Wallace et al. |
| 2003/0232869 | A1 | 12/2003 | Wallace et al. |
| 2004/0053933 | A1 | 3/2004 | Pontillo et al. |
| 2004/0102360 | A1 | 5/2004 | Barnett et al. |
| 2004/0116710 | A1 | 6/2004 | Wallace et al. |
| 2004/0176400 | A1 | 9/2004 | Capelli et al. |
| 2005/0059687 | A1 | 3/2005 | Makings et al. |
| 2005/0130954 | A1 | 6/2005 | Mitchell et al. |
| 2005/0182061 | A1 | 8/2005 | Green et al. |
| 2006/0025074 | A1 | 2/2006 | Liang et al. |
| 2006/0062400 | A1 | 3/2006 | Chia-Chun |
| 2007/0004708 | A1 | 1/2007 | Andreotti et al. |
| 2007/0027156 | A1 | 2/2007 | Nakai et al. |
| 2007/0135466 | A1 | 6/2007 | Ledeboer et al. |
| 2008/0076774 | A1 | 3/2008 | Anand et al. |
| 2008/0188482 | A1 | 8/2008 | Rice et al. |
| 2012/0329808 | A1 | 12/2012 | Mitchell et al. |
| 2013/0065908 | A1 | 3/2013 | Mitchell et al. |
| 2014/0148436 | A1 | 5/2014 | Mitchell et al. |
| 2014/0349996 | A1 | 11/2014 | Mitchell et al. |

FOREIGN PATENT DOCUMENTS

| | | |
|---|---|---|
| JP | 2004-512277 | 4/2004 |
| JP | 2005-500994 A | 1/2005 |
| JP | 2005-521659 | 7/2005 |
| JP | 2005-525303 | 8/2005 |
| WO | WO 95/03286 | 2/1995 |
| WO | WO 98/30546 | 7/1998 |
| WO | WO 98/43960 | 10/1998 |
| WO | WO 99/01421 | 1/1999 |
| WO | WO 99/01426 | 1/1999 |
| WO | WO 00/40235 | 7/2000 |
| WO | WO 00/40237 | 7/2000 |
| WO | WO 00/41505 | 7/2000 |
| WO | WO 00/41994 | 7/2000 |
| WO | WO 00/42002 | 7/2000 |
| WO | WO 00/42003 | 7/2000 |
| WO | WO 00/42022 | 7/2000 |
| WO | WO 00/42029 | 7/2000 |
| WO | WO 00/68201 | 11/2000 |
| WO | WO 01/05390 | 1/2001 |
| WO | WO 01/05391 | 1/2001 |
| WO | WO 01/05392 | 1/2001 |
| WO | WO 01/05393 | 1/2001 |
| WO | WO 01/07397 | 2/2001 |
| WO | WO 01/68619 | 9/2001 |
| WO | WO 02/06213 | 1/2002 |
| WO | WO 02/18319 | 3/2002 |
| WO | WO 02/22604 | 3/2002 |
| WO | WO 02/44166 | 6/2002 |
| WO | WO 02/083083 A2 | 10/2002 |
| WO | WO 02/083139 | 10/2002 |
| WO | WO 03/022214 | 3/2003 |
| WO | WO 03/049678 | 6/2003 |
| WO | WO 03/062225 | 7/2003 |
| WO | WO 03/064397 | 8/2003 |
| WO | WO 03/077855 | 9/2003 |
| WO | WO 03/077914 | 9/2003 |
| WO | WO 03/086279 | 10/2003 |
| WO | WO 03/086394 | 10/2003 |
| WO | WO 03/086403 | 10/2003 |
| WO | WO 03/086404 | 10/2003 |
| WO | WO 03/094918 | 11/2003 |
| WO | WO 2004/041162 | 5/2004 |
| WO | WO 2004/096130 | 11/2004 |
| WO | WO 2005/014558 | 2/2005 |
| WO | WO 2005/051304 A2 | 6/2005 |
| WO | WO 2005/105780 | 11/2005 |
| WO | WO 2005/117909 | 12/2005 |
| WO | WO 2006/046023 | 5/2006 |
| WO | WO 2006/071819 | 7/2006 |
| WO | WO 2006/090261 | 8/2006 |
| WO | WO 2006/094230 | 9/2006 |
| WO | WO 2006/136830 | 12/2006 |
| WO | WO 2007/042298 | 4/2007 |
| WO | WO 2007/077961 | 7/2007 |
| WO | WO 2007/125320 | 11/2007 |
| WO | WO 2008/003697 | 1/2008 |
| WO | WO 2008/003958 | 1/2008 |
| WO | WO 2008/003978 | 1/2008 |
| WO | WO 2008/005511 | 1/2008 |
| WO | WO 2008/005964 | 1/2008 |
| WO | WO 2008/006032 | 1/2008 |
| WO | WO 2008/006039 | 1/2008 |
| WO | WO 2008/006040 | 1/2008 |
| WO | WO 2008/012635 | 1/2008 |

OTHER PUBLICATIONS

Davies et al., "Catalytic Enantioselective Synthesis of β2-Amino Acids", *Angew. Chem. Int.*, vol. 41 (12), 2197-2199 (2002).

Kaiser et al., "Conjugate Addition Reactions of Ethyl Atropate with Certain Alkali Nucleophiles, Alkylations", *The Journal of Organic Chemistry*, vol. 35 (2), 410-414 (1970).

Registry file [online], RN 342630-54-0, ED Jun. 20, 2001, RN 632352-54-6 ED Dec. 30, 2003 (where RN is Registry number, and ED is filed of Registry File.).

Williams et al., "Construction of 4-Hydroxy-2-pyridinones. Total Synthesis of (+)-Sambutoxin", *Organic Letters* vol. 2 (20), 3217-3220 (2000).

Blake et al., "Discovery and Preclinical Pharmacology of a Selective ATP-Competitive Akt Inhibitor (GDC-0068) for the Treatment of Human Tumors", Journal of Medicinal Chemistry, 55, 8110-8127, 2012.

(56) References Cited

OTHER PUBLICATIONS

Bos et al., "Syntheses of O-Methylasparvenone-Derived Serotonin-Receptor Antagonists", *Helvetica Chimica Acta*, vol. 81, 525-538 (1998).
Davies et al., "Catalytic Enantioselective Synthesis of β-2-Amino Acids", *Angew. Chem.* 114 (12), 2301-2303 (2002).
Davies et al., "Enantioselective synthesis of β-amino esters and its application to the synthesis of the enantiomers of the antidepressant Venlafaxine", *Chem. Commun.*, 3110-3112 (2006).
D'Souza et al., "(R)—(+)—3-Amino-2-phenylpropanoic Acid: a Revised Absolute Configureation based on an Enantioselective Synthesis and an X-Ray Crystal Structure of the Salt with (1S)—(+)—Camphor-10-sulfonic Acid", *J. Chem. Soc. Perkins Trans.* 1, 2 pages, (1995).
Funke et al., "A Phase Ib/II Study Testing the Safety and Efficacy of Combined Inhibition of the PI3K/Akt and Androgen Receptor Signaling Pathways in Castration-resistant Prostate Cancer: GDC-0068 or GDC-0980 with Abiraterone Acetate Versus Abiraterone Acetate" American Society of Clinical Oncology (ASCO) Annual Meeting, Chicago, IL, Jun. 1-5, 2012, Poster TPS2616, 1 page.
Funke et al., "A Phase Ib/II Study Testing the Safety and Efficacy of Combined Inhibition of the PI3K/Akt and Androgen Receptor Signaling Pathways in Castration-resistant Prostate Cancer: GDC-0068 or GDC-0980 with Abiraterone Acetate Versus Abiraterone Acetate", J. Clin. Oncology (Meeting Abstracts), 30(suppl.), abstract: TPS2616, 3 pages, 2012.
Li, Qun "Expert Opinion: Recent Progress in the Discovery of Akt Inhibitors as Anticancer Agents", Informa Healthcare, 2007, 17(9), pp. 1077-1130.
Lin, Kui, "GDC-0068, A Novel, Selective, ATP-Competitive Inhibitor of AKT", In: Proceedings of the 102nd Annual Meeting of the American Association for Cancer Research, Apr. 2-6, 2011, Orlando, Florida, Philadelphia (PA): AACR; 2011, Presentation No. DDT02-01, 1 page abstract, and 30 pages of the corresponding presentation given Apr. 3, 2011.
Lin et al., "An ATP-Site On-Off Switch That Restricts Phosphatase Accessibility of Akt", Sci. Signal., 5(223), ra37, pp. 1-10 (2012).
Office Action Corresponding to Related Columbian Patent Application No. 09-010.508, received Mar. 25, 2013.
Ohno, S., et al., "Synthesis and Hypoglycemic Activity of 7,8-Dihydro-6H-thiopyrano[3,2-d]pyrimidine Derivatives and Related Compounds", Chem. Pharm. Bull., 1986, 34(10), 4150-4165.
Patent Cooperation Treaty, "International Search Report and Written Opinion of the International Searching Authority", PCT/US2007/072885, Dec. 3, 2007, 10 pages.
Ross, L., et al., "Potential Anticancer Agents. XVIII. Synthesis of Substituted 4,5-Trimethylenepyrimidines", J. Am. Chem. Soc., 1959, 81, 3108-3113.
Saura, C., et al., "A Phase Ib Study of the Akt Inhibitor GDC-0068 with Docetaxel or mFOLFOX6 in Patients with Advanced Solid Tumors", American Society of Clinical Oncology (ASCO), Annual Meeting, Chicago, IL, Jun. 1-5, 2012, Poster 3021, 1 page.
Saura, C., et al., "A Phase Ib Study of the Akt Inhibitor GDC-0068 with Docetaxel or mFOLFOX6 in Patients with Advanced Solid Tumors", J. Clin. Oncology (Meeting Abstracts), 30(suppl.), abstract: 3021, 3 pages, 2012.
Office Action issued by the Japanese Patent Office for JP Patent Application No. 2009-518636 and translation thereof, Sep. 20, 2012 (mailing date), 8 pages.
Tabernero et al., "First-in-human phase I study evaluating the safety, pharmacokinetics (PK), and intratumor pharmacodynamics (PD) of the novel, oral, ATP-competitive Akt inhibitor GDC-0068", J. Clin. Oncol. (Meeting Abstracts), 29(15_suppl), abstract: 3022, 3 pages, 2011.
Tabernero et al., "First-in-human phase I study evaluating the safety, pharmacokinetics (PK), and intratumor pharmacodynamics (PD) of the novel, oral, ATP-competitive Akt inhibitor GDC-0068", American Society of Clinical Oncology (ASCO), Annual Meeting, Chicago, IL, Jun. 3-7, 2011, Poster 3022, 1 page.
Tabernero et al., "Targeting the PI3K-Akt-mTOR pathway with GDC-0068, a novel selective ATP competitive Akt inhibitor", $9^{th}$ International Symposium on Targeted Anticancer Therapies, Paris, France, Mar. 7-9, 2011; presentation given Mar. 9, 2011, 13 pages.
Truong, T. N., "Office Action for U.S. Appl. No. 10/993,173", United States Patent and Trademark Office, Aug. 6, 2008, 8 pages.
Truong, T. N., "Office Action for U.S. Appl. No. 10/993,173", United States Patent and Trademark Office, May 26, 2009, 8 pages.
Vippagunta, S.R., (Adv. Drug. Delivery Rev., 2001, 48, pp. 3-26).
Yan et al., "A first-in-human trial of GDC-0068: A novel, oral, ATP-competitive Akt inhibitor, demonstrates robust suppression of the Akt pathway in surrogate and tumor tissues", AACR-NCI-EORTC International Conference: Molecular Targets and Cancer Therapeutics, San Francisco, CA, Nov. 12-16, Poster B154, 1 page, 2011.
Zhao, Z., et al., "Discovery of 2,3,5-trisubstituted pyridine derivatives as potent Akt-1 and Akt2 dual inhibitors", Bioorg. Med. Chem. Lett., 2005, 15, 905-909.
Zhu et al., "Discovery and SAR of oxindole—pyridine-based protein kinase B/Akt inhibitors for treating cancers", *Bioorganic & Medicinal Chemistry Letters*, 16, 3424-3429 (2006).
U.S. Appl. No. 14/516,443.

HYDROXYLATED AND METHOXYLATED PYRIMIDYL CYCLOPENTANES AS AKT PROTEIN KINASE INHIBITORS

PRIORITY OF INVENTION

This application is a division of U.S. patent application Ser. No. 13/272,079, filed 12 Oct. 2011, now issued as U.S. Pat. No. 8,853,199, which is a division of U.S. patent application Ser. No. 11/773,949, filed 5 Jul. 2007, now issued as U.S. Pat. No. 8,063,050, which claims priority to U.S. Provisional Application No. 60/818,718, filed 6 Jul. 2006, the entire contents of which are herein incorporated by reference.

BACKGROUND OF THE INVENTION

1. Field of the Invention

This invention relates to novel inhibitors of serine/threonine protein kinases (e.g., AKT and related kinases), pharmaceutical compositions containing the inhibitors, and methods for preparing these inhibitors. The inhibitors are useful, for example, for the treatment of hyperproliferative diseases, such as cancer and inflammation, in mammals.

2. Description of the State of the Art

Protein kinases (PK) are enzymes that catalyze the phosphorylation of hydroxy groups on tyrosine, serine and threonine residues of proteins by transfer of the terminal (gamma) phosphate from ATP. Through signal transduction pathways, these enzymes modulate cell growth, differentiation and proliferation, i.e., virtually all aspects of cell life in one way or another depend on PK activity (Hardie, G. and Hanks, S. (1995) *The Protein Kinase Facts Book. I and II*, Academic Press, San Diego, Calif.). Furthermore, abnormal PK activity has been related to a host of disorders, ranging from relatively non-life threatening diseases such as psoriasis to extremely virulent diseases such as glioblastoma (brain cancer). Protein kinases are an important target class for therapeutic modulation (Cohen, P. (2002) Nature Rev. Drug Discovery 1:309).

Significantly, atypical protein phosphorylation and/or expression is often reported to be one of the causative effects of abnormal cellular proliferation, metastasis and cell survival in cancer. The abnormal regulation and/or expression of various kinases, including Akt, VEGF, ILK, ROCK, p70S6K, Bcl, PKA, PKC, Raf, Src, PDK1, ErbB2, MEK, IKK, Cdk, EGFR, BAD, CHK1, CHK2 and GSK3 amongst numerous others, has been specifically implicated in cancer.

Protein kinases include two classes; protein tyrosine kinases (PTK) and serine-threonine kinases (STK). The Protein Kinase B/Akt enzymes are a group of serine/threonine kinases that are overexpressed in a variety of human tumors. One of the best-characterized targets of the PI3K lipid products is the 57 KD serine/threonine protein kinase Akt, downstream of PI3K in the signal transduction pathway (Hemmings, B. A. (1997) Science 275:628; Hay N. (2005) Cancer Cell 8:179-183). Akt is the human homologue of the protoon-cogene v-akt of the acutely transforming retrovirus AKT8. Due to its high sequence homology to protein kinases A and C, Akt is also called Protein Kinase B (PKB) and Related to A and C (RAC). Three isoforms of Akt are known to exist, namely Akt1, Akt2 and Akt3, which exhibit an overall homology of 80% (Staal, S. P. (1987) Proc. Natl. Acad. Sci. 84:5034; Nakatani, K. (1999) Biochem. Biophys. Res. Commun. 257:906; Li et al (2002) Current Topics in Med. Chem. 2:939-971; WO 2005/113762). The Akt isoforms share a common domain organization that consists of a pleckstrin homology domain at the N-terminus, a kinase catalytic domain, and a short regulatory region at the C-terminus. In addition, both Akt2 and Akt3 exhibit splice variants. Upon recruitment to the cell membrane by PtdInd(3,4,5)$P_3$, Akt is phosphorylated (activated) by PDK1 at T308, T309 and T305 for isoforms Akt1 (PKBα), Akt2 (PKBβ) and Akt3 (PKBγ), respectively, and at S473, S474 and S472 for isoforms Akt1, Akt2 and Akt3, respectively. Such phosphorylation occurs by an as yet unknown kinase (putatively named PDK2), although PDK1 (Balendran, A., (1999) Curr. Biol. 9:393), autophosphorylation (Toker, A. (2000) J. Biol. Chem. 275:8271) and integrin-linked kinase (ILK) (Delcommenne, M. (1998) Proc. Natl. Acad. Sci. USA, 95:11211) have been implicated in this process. Akt activation requires its phosphorylation on residue Ser 473 in the C-terminal hydrophobic motif (Brodbeck et al (1999) J. Biol. Chem. 274:9133-9136; Coffer et al (1991) Eur. J. Biochem. 201:475-481; Alessi et al (1997) Curr. Biol. 7:261-269). Although monophosphorylation of Akt activates the kinase, bis(phosphorylation) is required for maximal kinase activity.

Akt is believed to assert its effect on cancer by suppressing apoptosis and enhancing both angiogenesis and proliferation (Toker et al. (2006) Cancer Res. 66(8):3963-3966). Akt is overexpressed in many forms of human cancer including, but not limited to, colon (Zinda et al (2001) Clin. Cancer Res. 7:2475), ovarian (Cheng et al (1992) Proc. Natl. Acad. Sci. USA 89:9267), brain (Haas Kogan et al (1998) Curr. Biol. 8:1195), lung (Brognard et al (2001) Cancer Res. 61:3986), pancreatic (Bellacosa et al (1995) Int. J. Cancer 64:280-285; Cheng et al (1996) Proc. Natl. Acad. Sci. 93:3636-3641), prostate (Graff et al (2000) J. Biol. Chem. 275:24500) and gastric carcinomas (Staal et al (1987) Proc. Natl. Acad. Sci. USA 84:5034-5037).

The PI3K/Akt/mammalian target of rapamycin (mTOR) pathway has been explored for targeted small molecule inhibitor therapy (Georgakis, G. and Younes, A. (2006) Expert Rev. Anticancer Ther. 6(1):131-140; Granville et al (2006) Clin. Cancer Res. 12(3):679-689). Inhibition of PI3K/Akt signaling induces apoptosis and inhibits the growth of tumor cells that have elevated Akt levels (Kim et al (2005) Current Opinion in Investig. Drugs 6(12):1250-1258; Luo et al (2005) Molecular Cancer Ther. 4(6):977-986).

The development of kinase inhibitors that target abnormally regulated pathways and ultimately result in disease is of enormous ethical and commercial interest to the medical and pharmaceutical community. A compound that inhibits (1) recruitment of Akt to the cell membrane, (2) activation by PDK1 or PDK2, (3) substrate phosphorylation, or (4) one of the downstream targets of Akt could be a valuable anticancer agent, either as a stand-alone therapy or in conjunction with other accepted procedures.

United States Patent Application Publication 2005/0130954 discloses inter alia, a variety of compounds that act as AKT inhibitors. The compounds are said to be useful in the treatment of hyperproliferative diseases such as cancer.

SUMMARY OF THE INVENTION

This invention provides novel compounds that inhibit AKT protein kinases. The compounds of the present invention have utility as therapeutic agents for diseases and conditions that can be treated by the inhibition of AKT protein kinases.

More specifically, the present invention includes compounds having the general Formula I:

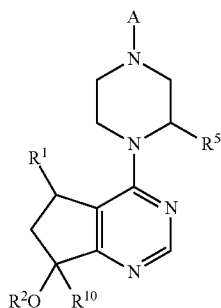

I and tautomers, resolved enantiomers, resolved diastereomers, solvates, metabolites, salts and pharmaceutically acceptable prodrugs thereof, wherein $R^1$, $R^2$, $R^5$, $R^{10}$ and A are as defined herein.

The invention also provides pharmaceutical compositions comprising a compound of Formula I, or an enantiomer, solvate, metabolite, or pharmaceutically acceptable salt or prodrug thereof.

In a further aspect, the present invention provides a method of treating diseases or medical conditions in a mammal mediated by AKT protein kinases, comprising administering to said mammal one or more compounds of Formula I, or an enantiomer, solvate, metabolite, or pharmaceutically acceptable salt or prodrug thereof, in an amount effective to treat or prevent said disorder. AKT protein kinase mediated conditions that can be treated according to the methods of this invention include, but are not limited to, inflammatory, hyperproliferative, cardiovascular, neurodegenerative, gynecological, and dermatological diseases and disorders.

In a further aspect, the present invention provides a method of inhibiting the production of AKT protein kinases in a mammal, which comprises administering to said mammal a compound of Formula I, or an enantiomer, solvate, metabolite, or pharmaceutically acceptable salt or prodrug thereof in an amount effective to inhibit production of an AKT protein kinase.

In a further aspect, the present invention provides methods of inhibiting the activity of AKT protein kinases, comprising contacting said kinase with a compound of Formula I.

The inventive compounds may be used advantageously in combination with other known therapeutic agents. Accordingly, this invention also provides pharmaceutical compositions comprising a compound of Formula I or an enantiomer, solvate, metabolite, or pharmaceutically acceptable salt or prodrug thereof, in combination with a second therapeutic agent.

This invention also provides compounds of Formula I and enantiomers, solvates, metabolites, and pharmaceutically acceptable salts and prodrugs thereof for use as medicaments in the treatment of AKT protein kinase-mediated conditions.

An additional aspect of the invention is the use of a compound of Formula I, or an enantiomer, solvate, metabolite, or pharmaceutically acceptable salt or prodrug thereof, for therapy. In one embodiment, the therapy comprises the treatment of an AKT protein kinase-mediated condition.

This invention further provides kits for the treatment of an AKT protein kinase-mediated disease or disorder, said kit comprising a compound of Formula I, or an enantiomer, solvate, metabolite, or pharmaceutically acceptable salt or prodrug thereof, a container, and optionally a package insert or label indicating a treatment. The kits may further comprise a second compound or formulation comprising a second pharmaceutical agent useful for treating said disease or disorder.

This invention further includes methods of preparing, methods of separating, and methods of purifying of the compounds of this invention.

Additional advantages and novel features of this invention shall be set forth in part in the description that follows, and in part will become apparent to those skilled in the art upon examination of the following specification, or may be learned by the practice of the invention. The advantages of the invention may be realized and attained by means of the instrumentalities, combinations, compositions, and methods particularly pointed out in the appended claims.

DETAILED DESCRIPTION OF THE INVENTION

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature and similar materials differs from or contradicts this application, including but not limited to defined terms, term usage, described techniques, or the like, this application controls.

Definitions

The term "alkyl" as used herein refers to a saturated linear or branched-chain monovalent hydrocarbon radical of one to twelve carbon atoms, wherein the alkyl radical may be optionally substituted independently with one or more substituents described below. Examples of alkyl groups include, but are not limited to, methyl (Me, —CH$_3$), ethyl (Et, —CH$_2$CH$_3$), 1-propyl (n-Pr, n-propyl, —CH$_2$CH$_2$CH$_3$), 2-propyl (i-Pr, i-propyl, —CH(CH$_3$)$_2$), 1-butyl (n-Bu, n-butyl, —CH$_2$CH$_2$CH$_2$CH$_3$), 2-methyl-1-propyl (i-Bu, i-butyl, —CH$_2$CH(CH$_3$)$_2$), 2-butyl (s-Bu, s-butyl, —CH(CH$_3$)CH$_2$CH$_3$), 2-methyl-2-propyl (t-Bu, t-butyl, —C(CH$_3$)$_3$), 1-pentyl (n-pentyl, —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), 1-hexyl (—CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_3$)$_3$, 1-heptyl, 1-octyl, and the like.

The term "alkylene" as used herein refers to a linear or branched saturated divalent hydrocarbon radical of one to twelve carbon atoms, wherein the alkylene radical may be optionally substituted independently with one or more substituents described herein. Examples include, but are not limited to, methylene, ethylene, propylene, 2-methylpropylene, pentylene, and the like.

The term "alkenyl" as used herein refers to a linear or branched-chain monovalent hydrocarbon radical of two to twelve carbon atoms with at least one site of unsaturation, i.e., a carbon-carbon, $sp^2$ double bond, wherein the alkenyl radical may be optionally substituted independently with one or more substituents described herein, and includes radicals having "cis" and "trans" orientations, or alternatively, "E" and "Z" orientations. Examples include, but are not limited to, ethylenyl or vinyl ($-CH=CH_2$), allyl ($-CH_2CH=CH_2$), 1-propenyl, 1-buten-1-yl, 1-buten-2-yl, and the like.

The term "alkynyl" as used herein refers to a linear or branched monovalent hydrocarbon radical of two to twelve carbon atoms with at least one site of unsaturation, i.e., a carbon-carbon, sp triple bond, wherein the alkynyl radical may be optionally substituted independently with one or more substituents described herein. Examples include, but are not limited to, ethynyl ($-C\equiv CH$) and propynyl (propargyl, $-CH_2C\equiv CH$).

The terms "cycloalkyl," "carbocycle," "carbocyclyl" and "carbocyclic ring" as used herein are used interchangeably and refer to saturated or partially unsaturated cyclic hydrocarbon radical having from three to twelve carbon atoms. The term "cycloalkyl" includes monocyclic and polycyclic (e.g., bicyclic and tricyclic) cycloalkyl structures, wherein the polycyclic structures optionally include a saturated or partially unsaturated cycloalkyl ring fused to a saturated, partially unsaturated or aromatic cycloalkyl or heterocyclic ring. Examples of cycloalkyl groups include, but are not limited to, cyclopropyl, cyclobutyl, cyclopentyl, cyclohexyl, cycloheptyl, and the like. Bicyclic carbocycles include those having 7 to 12 ring atoms arranged, for example, as a bicyclo[4,5], [5,5], [5,6] or [6,6] system, or as bridged systems such as bicyclo[2.2.1]heptane, bicyclo[2.2.2]octane, and bicyclo[3.2.2]nonane. The cycloalkyl may be optionally substituted independently with one or more substituents described herein.

The term "($C_3$-$C_6$-cycloalkyl)-($CH_2$)" includes cyclopropyl-$CH_2$, cyclopentyl-$CH_2$, and cyclohexyl-$CH_2$.

"Aryl" as used herein means a monovalent aromatic hydrocarbon radical of 6-20 carbon atoms derived by the removal of one hydrogen atom from a single carbon atom of a parent aromatic ring system. Aryl includes bicyclic radicals comprising an aromatic ring fused to a saturated, partially unsaturated ring, or aromatic carbocyclic or heterocyclic ring. Exemplary aryl groups include, but are not limited to, radicals derived from benzene, naphthalene, anthracene, biphenyl, indene, indane, 1,2-dihydronapthalene, 1,2,3,4-tetrahydronapthalene, and the like. Aryl groups may be optionally substituted independently with one or more substituents described herein.

The terms "heterocycle", "heterocyclyl" and "heterocyclic ring" as used herein are used interchangeably and refer to a saturated or partially unsaturated carbocyclic radical of 3 to 8 ring atoms in which at least one ring atom is a heteroatom independently selected from nitrogen, oxygen and sulfur, the remaining ring atoms being C, where one or more ring atoms may be optionally substituted independently with one or more substituents described below. The radical may be a carbon radical or heteroatom radical. The term "heterocycle" includes heterocycloalkoxy. "Heterocyclyl" also includes radicals where heterocycle radicals are fused with a saturated, partially unsaturated, or aromatic carbocyclic or heterocyclic ring. Examples of heterocyclic rings include, but are not limited to, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco[3.1.0]hexanyl, 3-azabicyclo[4.1.0]heptanyl, azabicyclo[2.2.2]hexanyl, 3H-indolyl quinolizinyl and N-pyridyl ureas. Spiro moieties are also included within the scope of this definition. The heterocycle may be C-attached or N-attached where such is possible. For instance, a group derived from pyrrole may be pyrrol-1-yl (N-attached) or pyrrol-3-yl (C-attached). Further, a group derived from imidazole may be imidazol-1-yl (N-attached) or imidazol-3-yl (C-attached). Examples of heterocyclic groups wherein 2 ring carbon atoms are substituted with oxo ($=O$) moieties are isoindoline-1,3-dionyl and 1,1-dioxo-thiomorpholinyl. The heterocycle groups herein are optionally substituted independently with one or more substituents described herein.

The term "heteroaryl" as used herein refers to a monovalent aromatic radical of a 5-, 6-, or 7-membered ring and includes fused ring systems (at least one of which is aromatic) of 5-10 atoms containing at least one heteroatom independently selected from nitrogen, oxygen, and sulfur. Examples of heteroaryl groups include, but are not limited to, pyridinyl, imidazolyl, imidazopyridinyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Spiro moieties are also included within the scope of this definition. Heteroaryl groups may be optionally substituted independently with one or more substituents described herein.

By way of example and not limitation, carbon bonded heterocycles and heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Further examples of carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles and heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of an isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

The term "halogen" as used herein means fluoro, chloro, bromo or iodo.

The term "a" as used herein means one or more.

As used herein, the terms "compound of this invention," "compounds of the present invention" and "compounds of Formula I" includes compounds of Formula I and tautomers, resolved enantiomers, resolved diastereomers, racemic mixtures, solvates, metabolites, salts (including pharmaceutically acceptable salts) and pharmaceutically acceptable prodrugs thereof.

It is to be understood that in instances where two or more radicals are used in succession to define a substituent attached to a structure, the first named radical is considered to be terminal and the last named radical is considered to be attached to the structure in question. Thus, for example, an arylalkyl radical is attached to the structure in question by the alkyl group.

AKT Inhibitors

The inventive compounds of Formula I are useful for inhibiting AKT protein kinases. Such compounds have utility as therapeutic agents for diseases that can be treated by the inhibition of the AKT protein kinase signaling pathway and tyrosine and serine/threonine kinase receptor pathways.

In particular, certain compounds of Formula I wherein $OR^2$ is OH were found to be at least 50-fold more selective for AKT versus protein kinase A (PKA). For example, at least 100-fold, and as a further example, at least 150-fold more selective for AKT versus PKA. Selectivity over PKA is desirable, since PKA is involved in many cellular processes important for the normal function and physiology of many cell types. Additionally, inhibition of PKA is not believed to contribute to the anti-proliferative and pro-apoptotic effects of AKT inhibition. Thus, inhibition of PKA could lead to adverse events not associated with AKT inhibition without contributing to the disease modifying benefits of AKT inhibition.

The compounds of Formula I may also be useful as inhibitors of tyrosine kinases as well as serine and threonine kinases in addition to AKT.

In general, one aspect of the invention includes compounds of the Formula I:

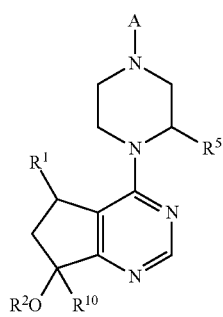

I and tautomers, resolved enantiomers, resolved diastereomers, solvates, metabolites, salts and pharmaceutically acceptable prodrugs thereof, wherein:

$R^1$ is H, Me, Et, vinyl, $CF_3$, $CHF_2$ or $CH_2F$;

$R^2$ is H or Me;

$R^5$ is H, Me, Et, or $CF_3$;

A is

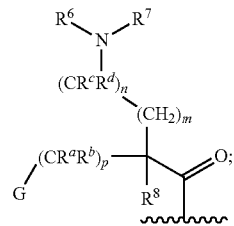

G is phenyl optionally substituted by one to four $R^9$ groups or a 5-6 membered heteroaryl optionally substituted by a halogen;

$R^6$ and $R^7$ are independently H, $OCH_3$, ($C_3$-$C_6$ cycloalkyl)-($CH_2$), ($C_3$-$C_6$ cycloalkyl)-($CH_2CH_2$), V—($CH_2$)$_{0-1}$ wherein V is a 5-6 membered heteroaryl having from one to two ring heteroatoms independently selected from N, O and S, W—($CH_2$)$_{1-2}$ wherein W is phenyl optionally substituted with F, Cl, Br, I, OMe, $CF_3$ or Me, $C_3$-$C_6$-cycloalkyl optionally substituted with $C_1$-$C_3$ alkyl or O($C_1$-$C_3$ alkyl), hydroxy-($C_3$-$C_6$-cycloalkyl), fluoro-($C_3$-$C_6$-cycloalkyl), $CH(CH_3)CH(OH)$phenyl, 4-6 membered heterocycle optionally substituted with F, OH, $C_1$-$C_3$-alkyl, cyclopropylmethyl or C(=O)($C_1$-$C_3$ alkyl), or $C_1$-$C_6$-alkyl optionally substituted with one or more groups independently selected from OH, oxo, O($C_1$-$C_6$-alkyl), CN, F, $NH_2$, NH($C_1$-$C_6$-alkyl), N($C_1$-$C_6$-alkyl)$_2$, cyclopropyl, phenyl, imidazolyl, piperidinyl, pyrrolidinyl, morpholinyl, tetrahydrofuranyl, oxetanyl, or tetrahydropyranyl, or $R^6$ and $R^7$ together with the nitrogen to which they are attached form a 4-7 membered heterocyclic ring, wherein said heterocyclic ring is optionally substituted with one or more groups independently selected from OH, halogen, oxo, $CF_3$, $CH_2CF_3$, $CH_2CH_2OH$, O($C_1$-$C_3$ alkyl), C(=O)$CH_3$, $NH_2$, NHMe, N(Me)$_2$, S(O)$_2CH_3$, cyclopropylmethyl and $C_1$-$C_3$ alkyl;

$R^a$ and $R^b$ are H, or $R^a$ is H, and $R^b$ and $R^6$ together with the atoms to which they are attached form a 5-6 membered heterocyclic ring having one or two ring nitrogen atoms;

$R^c$ and $R^d$ are H or Me, or $R^c$ and $R^d$ together with the atom to which they are attached from a cyclopropyl ring;

$R^8$ is H, Me, F or OH, or $R^8$ and $R^6$ together with the atoms to which they are attached form a 5-6 membered heterocyclic ring having one or two ring nitrogen atoms;

each $R^9$ is independently halogen, $C_1$-$C_6$-alkyl, $C_3$-$C_6$-cycloalkyl, O—($C_1$-$C_6$-alkyl), $CF_3$, $OCF_3$, S($C_1$-$C_6$-alkyl), CN, $OCH_2$-phenyl, $CH_2O$-phenyl, $NH_2$, NH—($C_1$-$C_6$-alkyl), N—($C_1$-$C_6$-alkyl)$_2$, piperidine, pyrrolidine, $CH_2F$, $CHF_2$, $OCH_2F$, $OCHF_2$, OH, $SO_2$($C_1$-$C_6$-alkyl), C(O)$NH_2$, C(O)NH($C_1$-$C_6$-alkyl), and C(O)N($C_1$-$C_6$-alkyl)$_2$;

$R^{10}$ is H or Me; and m, n and p are independently 0 or 1.

In a further embodiment, the compounds of Formula I include compounds wherein G is phenyl optionally substituted by one to four $R^9$ groups; and $R^6$ and $R^7$ are independently H, ($C_3$-$C_6$ cycloalkyl)-($CH_2$), ($C_3$-$C_6$ cycloalkyl)-($CH_2CH_2$), V—($CH_2$)$_{0-1}$ wherein V is a 5-6 membered heteroaryl having from one to two ring heteroatoms independently selected from N, O and S, W—($CH_2$)$_{1-2}$ wherein W is phenyl optionally substituted with F, Cl or Me, $C_3$-$C_6$-cycloalkyl, hydroxy-($C_3$-$C_6$-cycloalkyl), fluoro-($C_3$-$C_6$-cycloalkyl), CH(CH$_3$)CH(OH)phenyl, or $C_1$-$C_6$-alkyl optionally substituted with one or more groups independently selected from OH, O($C_1$-$C_6$-alkyl), CN, F, NH$_2$, NH($C_1$-$C_6$-alkyl), N($C_1$-$C_6$-alkyl)$_2$, piperidinyl, and pyrrolidinyl, or $R^6$ and $R^7$ together with the nitrogen to which they are attached form a 4-6 membered heterocyclic ring, wherein said heterocyclic ring is optionally substituted with one or more groups independently selected from OH, halogen, oxo, CF$_3$, CH$_2$CF$_3$, and ($C_1$-$C_3$)alkyl;

$R^c$ and $R^d$ are H or Me;

$R^8$ is H, Me, or OH; and each $R^9$ is independently halogen, $C_1$-$C_6$-alkyl, $C_3$-$C_6$-cycloalkyl, O—($C_1$-$C_6$-alkyl), CF$_3$, OCF$_3$, S($C_1$-$C_6$-alkyl), CN, CH$_2$O-phenyl, NH$_2$, NH—($C_1$-$C_6$-alkyl), N—($C_1$-$C_6$-alkyl)$_2$, piperidine, pyrrolidine, CH$_2$F, CHF$_2$, OCH$_2$F, OCHF$_2$, OH, SO$_2$($C_1$-$C_6$-alkyl), C(O)NH$_2$, C(O)NH($C_1$-$C_6$-alkyl), and C(O)N($C_1$-$C_6$-alkyl)$_2$.

Referring to the G group of Formula I, examples include phenyl optionally substituted with one or more $R^9$ groups independently selected from F, Cl, Br, CN, methyl, ethyl, isopropyl, OCH$_3$, OCH$_2$CH$_3$, CF$_3$, OCF$_3$, SCH$_3$, OCH$_2$Ph and cyclopropyl. Exemplary embodiments include, but are not limited to, phenyl, 2-chlorophenyl, 3-chlorophenyl, 4-chlorophenyl, 2-fluorophenyl, 3-fluorophenyl, 4-fluorophenyl, 2-bromophenyl, 3-bromophenyl, 4-bromophenyl, 2-methylphenyl, 3-methylphenyl, 4-methylphenyl, 2-ethylphenyl, 3-ethylphenyl, 4-ethylphenyl, 2-isopropylphenyl, 3-isopropylphenyl, 4-isopropylphenyl, 2-trifluoromethylphenyl, 3-trifluoromethylphenyl, 4-trifluoromethylphenyl, 2-cyanophenyl, 3-cyanophenyl, 4-cyanophenyl, 2-methoxyphenyl, 3-methoxyphenyl, 4-methoxyphenyl, 2-ethoxyphenyl, 3-ethoxyphenyl, 4-ethoxyphenyl, 2-thiomethylphenyl, 3-thiomethylphenyl, 4-thiomethylphenyl, 2-trifluoromethoxyphenyl, 3-trifluoromethoxyphenyl, 4-trifluoromethoxyphenyl, 2-cyclopropylphenyl, 3-cyclopropylphenyl, 4-cyclopropylphenyl, 4-chloro-3-fluorophenyl, 3,4-difluorophenyl, 4-bromo-3-fluorophenyl, 3-fluoro-4-methylphenyl, 3-fluoro-4-methoxyphenyl, 3-fluoro-4-trifluoromethylphenyl, 4-cyano-3-fluorophenyl, 3,4-dichlorophenyl, 2,4-dichlorophenyl, 2,4-difluorophenyl, 2-chloro-4-fluorophenyl, 2-fluoro-4-chlorophenyl, 3,5-dichlorophenyl. 3,5-difluorophenyl, 3-chloro-5-fluorophenyl, 3-chloro-4-fluorophenyl, 3-bromo-4-fluorophenyl, 3,5-difluoro-4-chlorophenyl, 2,3-difluoro-4-chlorophenyl, 2,5-difluoro-4-chlorophenyl, 3,5-difluoro-4-bromophenyl, 2,3-difluoro-4-bromophenyl, 2,5-difluoro-4-bromophenyl and 4-(OCH$_2$Ph)-phenyl.

A further example of the G group of Formula I includes when $R^9$ is I. An exemplary embodiment includes 4-iodophenyl.

Referring to the G group of Formula I, the phrase "5-6 membered heteroaryl optionally substituted by a halogen" includes thiophenes and pyridines optionally substituted by halogens. Particular examples include, but are not limited to, the structures:

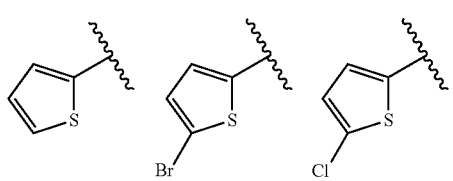

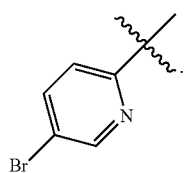

Referring to the $R^6$ and $R^7$ groups of Formula I, the term "($C_3$-$C_6$-cycloalkyl)-(CH$_2$)" includes cyclopropyl-CH$_2$, cyclobutyl-CH$_2$, cyclopentyl-CH$_2$, and cyclohexyl-CH$_2$.

Referring to the $R^6$ and $R^7$ groups of Formula I, the term "V—(CH$_2$)$_{0-1}$" includes, but is not limited to, the following structures:

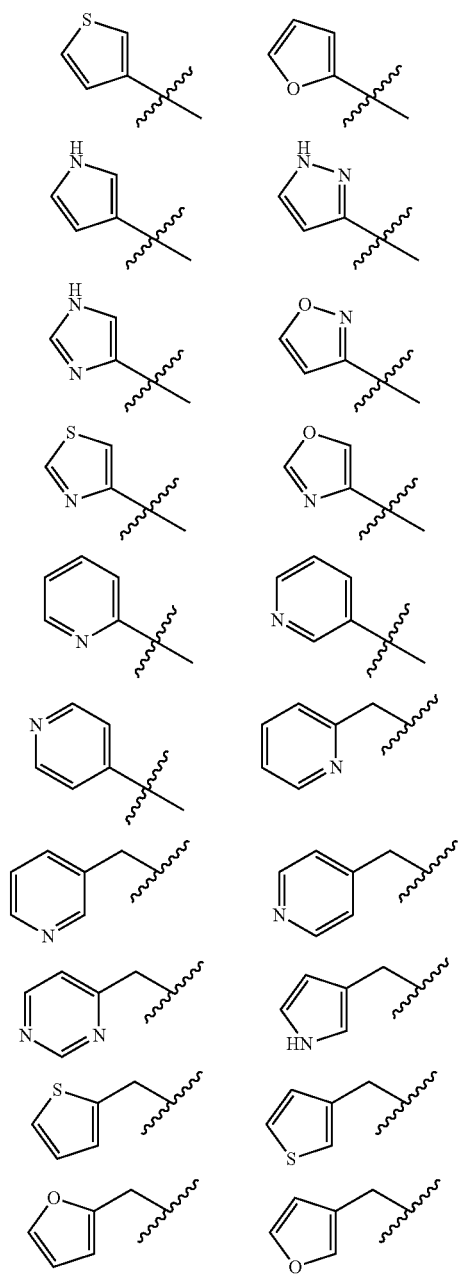

-continued

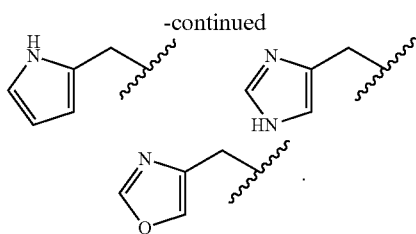

Referring to the $R^6$ and $R^7$ groups of Formula I, the term "hydroxy-($C_3$-$C_6$-cycloalkyl)" includes, but is not limited to, the following structures:

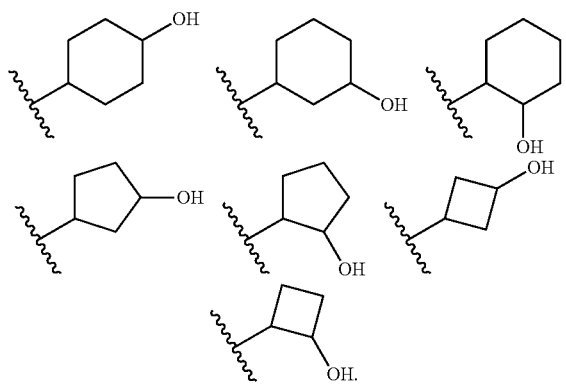

Referring to the $R^6$ and $R^7$ groups of Formula I, the term "fluoro-($C_3$-$C_6$-cycloalkyl)" includes but is not limited to, the following structures:

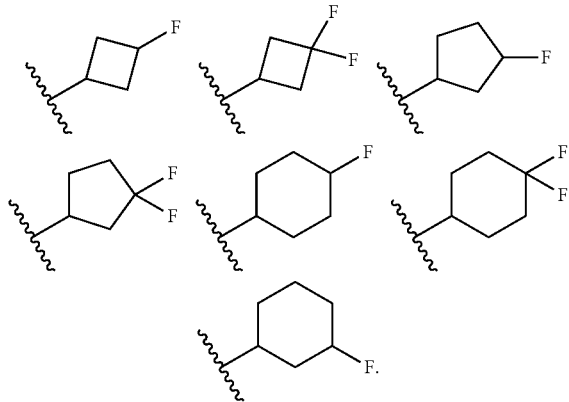

Referring to the $R^6$ and $R^7$ groups of Formula I, the phrase "$C_1$-$C_6$-alkyl optionally substituted with one or more groups independently selected from OH, OMe, and CN" includes, but is not limited to, $CH_2OH$, $CH_2CH_2OH$, $CH_2CH_2CH_2OH$, $CH_2CH(OH)CH_2$, $CH_2CH_2CH(OH)CH_3$, $CH_2C(OH)(CH_3)_2$, $CH_2OMe$, $CH_2CH_2OMe$, $CH_2CH_2CH_2OMe$, $CH_2CH(OMe)CH_2$, $CH_2CH_2CH(OMe)CH_3$, $CH_2C(OMe)(CH_3)_2$, $CH_2CN$, $CH_2CH_2CN$, $CH_2CH_2CH_2CN$, $CH_2CH(CN)CH_2$, $CH_2CH_2CH(CN)CH_3$, $CH_2C(CN)(CH_3)_2$, and the like.

Referring to the $R^6$ and $R^7$ groups of Formula I, in certain embodiments the term "heteroaryl" refers to a 5-6 membered heteroaryl having from one to two ring heteroatoms independently selected from N, O and S.

Referring to the $R^6$ and $R^7$ groups of Formula I, in certain embodiments the phrase "4-6 membered heterocycle optionally substituted with F, OH, $C_1$-$C_3$-alkyl, cyclopropylmethyl or C(=O)($C_1$-$C_3$ alkyl)" refers to a 4-6 membered heterocycle having from one to two ring heteroatoms independently selected from N, O and S, and optionally substituted with a $CH_3$ or C(=O)$CH_3$ substituent. Examples include, but are not limited to, the structures:

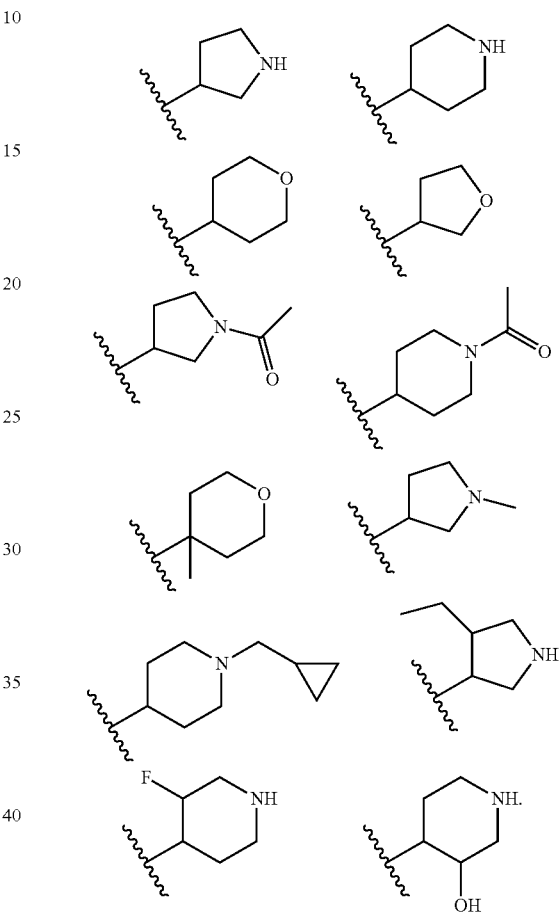

In one embodiment of Formula I, $R^{10}$ is H.
In another embodiment of Formula I, $R^{10}$ is methyl.
In one embodiment of Formula I, $OR^2$ is in the (S) or (R) configuration. In a particular embodiment, $R^2$ is H.
In another embodiment of Formula I, $R^2$ is methyl.
In one embodiment of Formula I, $R^5$ is H. In another embodiment, $R^5$ is methyl, wherein said methyl is optionally in the (S) configuration.
In one embodiment of Formula I, $R^1$ is methyl, wherein said methyl is optionally in the (R) configuration. In another embodiment, $R^1$ is H.
In one embodiment of Formula I, G is phenyl optionally substituted with one or more groups independently selected from F, Cl, Br, Me, Et, isopropyl, CN, $CF_3$, $OCF_3$, SMe, OMe and $CH_2OPh$. Exemplary embodiments of G include phenyl, 2-chlorophenyl, 3-chlorophenyl, 4-chlorophenyl, 4-fluorophenyl, 4-bromophenyl, 4-methylphenyl, 4-ethylphenyl, 4-isopropylphenyl, 4-trifluoromethylphenyl, 4-cyanophenyl, 4-methoxyphenyl, 4-ethoxyphenyl, 4-thiomethylphenyl, 4-trifluoromethoxyphenyl, 4-cyclopropylphenyl, 4-chloro-3-fluorophenyl, 3,4-difluorophenyl, 4-bromo-3-fluorophenyl, 3-fluoro-4-methylphenyl, 3-fluoro-4-methoxyphenyl, 3-fluoro-4-trifluoromethylphenyl, 4-cyano-3-fluorophenyl, 3,4-dichlorophenyl, 2,4-dichlorophenyl, 2,4-difluorophenyl, 2-chloro-4-fluorophenyl, 2-fluoro-4-chlorophenyl, 3,5-dichlorophenyl. 3,5-difluorophenyl, 3-chloro-5-fluorophenyl, 3-chloro-4-fluorophenyl, 3-bromo-4-fluorophenyl, 3,5-difluoro-4-chlorophenyl, 2,3-difluoro-4-chlorophenyl, 2,5-difluoro-4-chlorophenyl, 3,5-difluoro-4-bromophenyl, 2,3-difluoro-4-bromophenyl, 2,5-difluoro-4-bromophenyl or 4-(OCH$_2$Ph)-phenyl.

In particular embodiments, G is 4-chlorophenyl, 2,4-dichlorophenyl, 3-chloro-4-fluorophenyl, 3,4-difluorophenyl, 4-chloro-3-fluorophenyl, 3,4-dichlorophenyl, 3-fluoro-4-bromophenyl, 4-methoxyphenyl, 4-fluorophenyl, 4-bromophenyl, 4-cyanophenyl, 4-trifluoromethylphenyl, 4-thiomethylpyhenyl, or 4-methylphenyl.

In additional embodiments, R$^9$ may be I or OCH$_2$-phenyl.

Additionally, G may be 4-iodophenyl, 4-trifluoromethoxyphenyl, 3,5-difluorophenyl, 4-bromo-3-fluorophenyl, 3-fluoro-4-methoxyphenyl, 3-fluoro-4-trifluoromethylphenyl, 3-trifluoromethoxy-4-chlorophenyl, 3-fluoro-4-trifluoromethoxyphenyl, 3-trifluoromethyl-4-chlorophenyl, 3-trifluoromethoxy-4-fluorophenyl, 3,5-bis(trifluoromethyl)phenyl, 3-chloro-5-fluorophenyl, 3-bromo-4-methoxyphenyl, 2-fluoro-4-chlorophenyl, 2-fluoro-4-bromophenyl, 2-fluoro-4-trifluoromethylphenyl, or 3-trifluoromethyl-4-fluorophenyl.

In one embodiment, G may be a 5-6 membered heteroaryl optionally substituted by a halogen. In certain embodiments, G is a thiophene or pyridine optionally substituted by a halogen. Particular embodiments include:

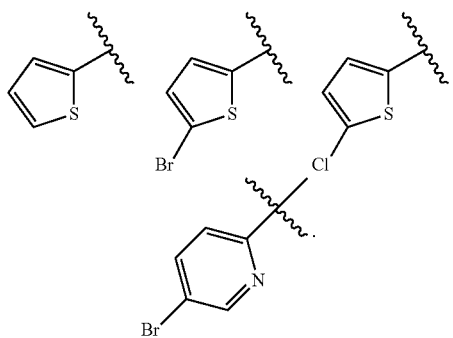

In one embodiment, R$^6$ or R$^7$ may be H.
In one embodiment, R$^6$ or R$^7$ may be OCH$_3$.
In one embodiment, R$^6$ or R$^7$ may be (C$_3$-C$_6$ cycloalkyl)-(CH$_2$).
In one embodiment, R$^6$ or R$^7$ may be (C$_3$-C$_6$ cycloalkyl)-(CH$_2$CH$_2$).
In one embodiment, R$^6$ or R$^7$ may be V—(CH$_2$)$_{0-1}$ wherein V is a 5-6 membered heteroaryl having from one to two ring heteroatoms independently selected from N, O and S.
In one embodiment, R$^6$ or R$^7$ may be W—(CH$_2$)$_{1-2}$ wherein W is phenyl optionally substituted with F, Cl, Br, I, OMe, CF$_3$ or Me.
In one embodiment, R$^6$ or R$^7$ may be C$_3$-C$_6$-cycloalkyl optionally substituted with C$_1$-C$_3$ alkyl or O(C$_1$-C$_3$ alkyl).
In one embodiment, R$^6$ or R$^7$ may be hydroxy-(C$_3$-C$_6$-cycloalkyl).
In one embodiment, R$^6$ or R$^7$ may be fluoro-(C$_3$-C$_6$-cycloalkyl).
In one embodiment, R$^6$ or R$^7$ may be CH(CH$_3$)CH(OH)phenyl.
In one embodiment, R$^6$ or R$^7$ may be 4-6 membered heterocycle optionally substituted with F, OH, C$_1$-C$_3$ alkyl, cyclopropylmethyl or C(=O)CH$_3$. In another embodiment, R$^6$ or R$^7$ may be a 4-6 membered heterocycle optionally substituted with C$_1$-C$_3$ alkyl or C(=O)CH$_3$ In one embodiment, R$^6$ or R$^7$ may be C$_1$-C$_6$-alkyl optionally substituted with one or more groups independently selected from OH, oxo, O(C$_1$-C$_6$-alkyl), CN, F, NH$_2$, NH(C$_1$-C$_6$-alkyl), N(C$_1$-C$_6$-alkyl)$_2$, cyclopropyl, phenyl, imidazolyl, piperidinyl, pyrrolidinyl, morpholinyl, tetrahydrofuranyl, oxetanyl and tetrahydropyranyl. In another embodiment, R$^6$ or R$^7$ may be C$_1$-C$_6$-alkyl optionally substituted with one or more groups independently selected from OH, oxo, O(C$_1$-C$_6$-alkyl), CN, F, NH$_2$, NH(C$_1$-C$_6$-alkyl), N(C$_1$-C$_6$-alkyl)$_2$, cyclopropyl, phenyl, imidazolyl, piperidinyl, pyrrolidinyl, morpholinyl, and tetrahydropyranyl.

In one embodiment, R$^6$ or R$^7$ may be H.

In another embodiment, R$^6$ or R$^7$ may be methyl, ethyl, isopropyl, isobutyl, tert-butyl, 3-pentyl, or CH$_2$-tBu (neopentyl). In an additional embodiment, R$^6$ or R$^7$ may be CH$_2$CH$_2$OH, CH$_2$CH$_2$OMe, CH$_2$CH$_2$CF$_3$, CH$_2$CH(CH$_3$)OH, CH$_2$CH(CF$_3$)OH, CH$_2$CF$_3$, CH$_2$CH$_2$F, CH$_2$C(=O)NH$_2$, CH$_2$C(=O)NH(CH$_3$), CH$_2$C(=O)N(CH$_3$)$_2$, CH$_2$C(=O)NH(iPr), CH$_2$CH$_2$C(=O)NH$_2$, CH(phenyl)CH$_2$OH, CH(tetrahydropyranyl)CH$_2$OH, CH$_2$CH$_2$CH$_2$(imidazolyl), CH$_2$CH$_2$(morpholinyl), CH$_2$(tetrahydropyranyl), or CH$_2$CH$_2$(tetrahydropyranyl) or

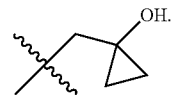 [SMILES: *CC1(O)CC1]

In an additional embodiment, R$^6$ and R$^7$ are independently CH(isopropyl)$_2$, CH$_2$CH$_2$CH$_2$OH, CH(CH$_2$CH$_2$OH)$_2$, CH(CH$_2$CH$_2$OMe)$_2$, CH$_2$CH$_2$CH$_2$OMe, CH$_2$CN, CH$_2$-phenyl.

In another embodiment, R$^6$ or R$^7$ may be OCH$_3$.
In another embodiment, R$^6$ or R$^7$ may be CH$_2$-cyclopropyl, or CH$_2$-cyclopentyl. In an additional embodiment, R$^6$ or R$^7$ may be CH$_2$-cyclobutyl.
In another embodiment, R$^6$ or R$^7$ may be CH$_2$-(pyrid-3-yl). In an additional embodiment, R$^6$ or R$^7$ may be CH$_2$-(pyrid-2-yl) or CH$_2$-(pyrid-4-yl).
In another embodiment, R$^6$ or R$^7$ may be cyclopropyl, cyclopentyl, cyclohexyl, 4-methoxycyclohexyl, 4,4-dimethylcyclohexyl, 3,3-dimethylcyclohexyl, or 4-hydroxycyclohex-1-yl.
In another embodiment, R$^6$ or R$^7$ may be CH(CH$_3$)CH(OH)phenyl.
In another embodiment, R$^6$ or R$^7$ may be pyrrolidinyl, piperidinyl, tetrahydropyranyl, tetrahydrofuranyl, or

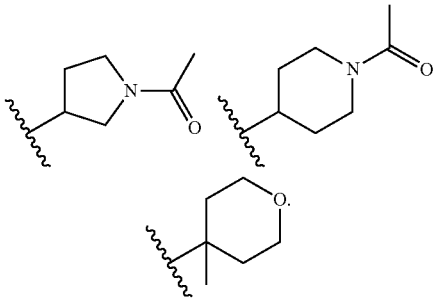

In other embodiments, $R^6$ and $R^7$ together with the nitrogen to which they are attached form a 4-7 membered heterocyclic ring, wherein said heterocyclic ring is optionally substituted with one or more groups independently selected from OH, halogen, oxo, $CF_3$, $CH_2CF_3$, $CH_2CH_2OH$, $OCH_3$, $C(=O)CH_3$, $NH_2$, NHMe, $N(Me)_2$, $S(O)_2CH_3$, and $(C_1-C_3)$alkyl.

In particular embodiments, $NR^6R^7$ is selected from the structures:

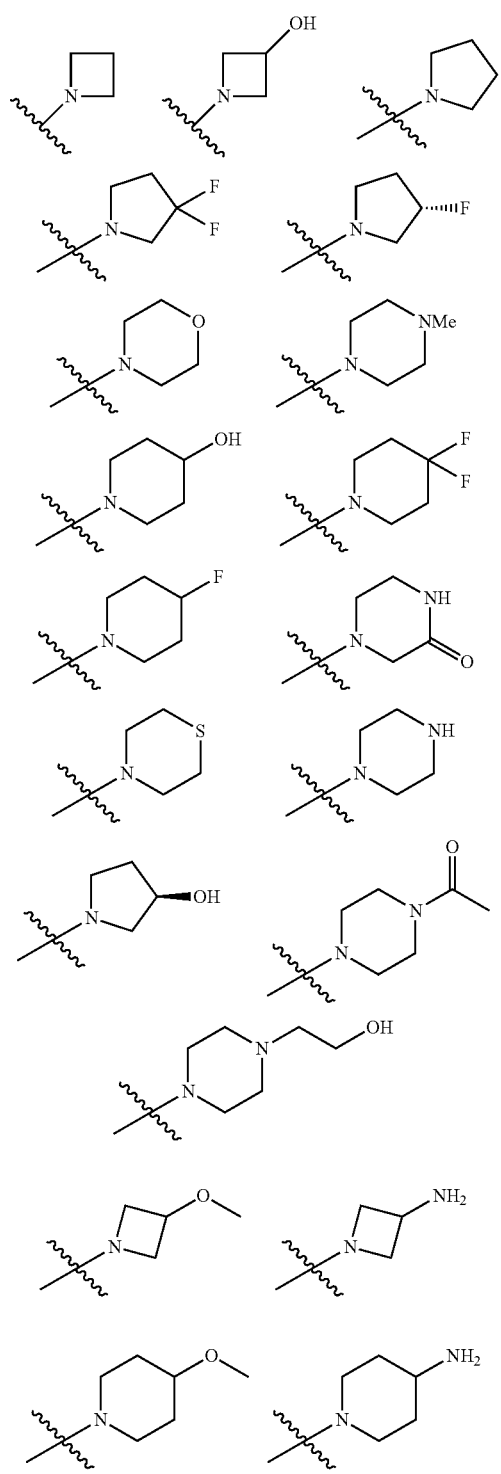

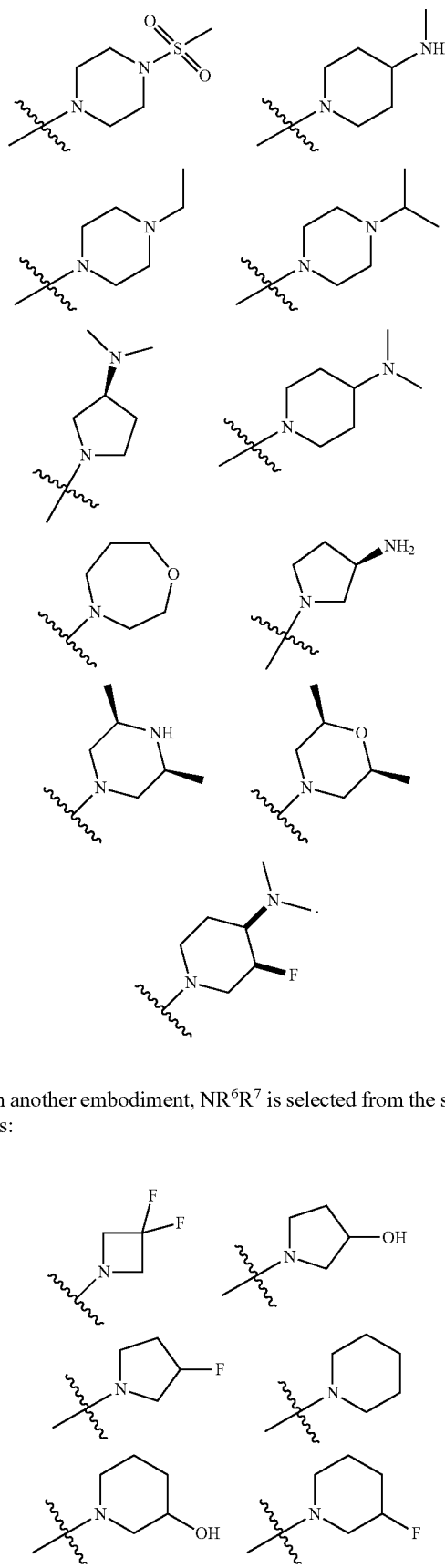

In another embodiment, $NR^6R^7$ is selected from the structures:

-continued

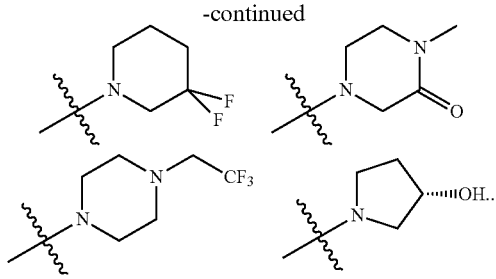

In one embodiment, $R^8$ and $R^6$ together with the atoms to which they are attached form a 5-6 membered heterocyclic ring having one or two ring nitrogen atoms. In certain embodiments, $R^7$ is H.

In another embodiment, $R^8$ and $R^6$ together with the atoms to which they are attached form a 5-6 membered heterocyclic ring having one ring nitrogen atom. In certain embodiments, $R^7$ is H.

In one embodiment, $R^a$ is H, and $R^b$ and $R^6$ together with the atoms to which they are attached form a 5-6 membered heterocyclic ring having one or two ring nitrogen atoms. In certain embodiments, $R^7$ is H.

In another embodiment, $R^a$ is H, and $R^b$ and $R^6$ together with the atoms to which they are attached form a 5-6 membered heterocyclic ring having one ring nitrogen atom. In certain embodiments, $R^7$ is H.

In one embodiment of Formula I, m is 1, n is 0, p is 0, such that A is represented by the Formula 1:

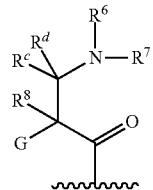

1 wherein G, $R^6$, $R^7$, $R^8$, $R^c$ and $R^d$ are as defined herein.

In certain embodiments of the group A having the Formula 1, $R^8$ is H or OH. In certain embodiments, $R^8$ is H. In particular embodiments, A has the configuration:

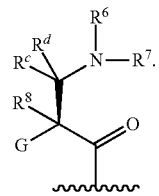

In certain embodiments of the A group having the Formula 1, $R^c$ and $R^d$ are H. In other embodiments, $R^c$ and $R^d$ together with the atom to which they are attached form a cyclopropyl ring.

In certain embodiments of the A group having the Formula 1, $R^6$ and $R^7$ are independently H, $C_3$-$C_6$-cycloalkyl, heteroaryl-($CH_2$), hydroxy-($C_3$-$C_6$-cycloalkyl), $CH(CH_3)CH(OH)phenyl$, or ($C_{1-6}$)-alkyl optionally substituted with one or more groups independently selected from OH, OMe, and CN. In particular embodiments, $R^6$ and $R^7$ are independently H, methyl, ethyl, isopropyl, isobutyl, tert-butyl, 3-pentyl, CH(isopropyl)$_2$, $CH_2CH_2OH$, $CH_2CH_2CH_2OH$, CH($CH_2CH_2OH$)$_2$, $CH_2CH_2OMe$, CH($CH_2CH_2OMe$)$_2$, $CH_2CH_2CH_2OMe$, $CH_2CN$, $CH_2$-cyclopropyl, $CH_2$-cyclobutyl, $CH_2$-tBu, cyclopentyl, cyclohexyl, $CH_2$-phenyl, $CH_2$-(pyrid-2-yl), $CH_2$-(pyrid-3-yl), $CH_2$-(pyrid-4-yl), 4-hydroxycyclohex-1-yl, or CH($CH_3$)CH(OH)phenyl.

In additional embodiments of the A group having the Formula 1, $R^6$ or $R^7$ may be $OCH_3$, $C_3$-$C_6$-cycloalkyl optionally substituted with $OCH_3$, 5-6 membered heterocycle optionally substituted with $CH_3$ or C(=O)$CH_3$, or $C_1$-$C_6$-alkyl optionally substituted with one or more groups independently selected from OH, oxo, O($C_1$-$C_6$-alkyl), CN, F, $NH_2$, NH($C_1$-$C_6$-alkyl), N($C_1$-$C_6$-alkyl)$_2$, cyclopropyl, phenyl, imidazolyl, piperidinyl, pyrrolidinyl, morpholinyl, and tetrahydropyranyl.

In particular embodiments, $R^6$ or $R^7$ may independently be $CH_2CF_3$, $CH_2CH_2F$, $CH_2$-cyclopentyl, 4-methoxycyclohexyl, 4,4-dimethylcyclohexyl, 3,3-dimethylcyclohexyl, pyrrolidinyl, piperidinyl, tetrahydropyranyl, tetrahydrofuranyl,

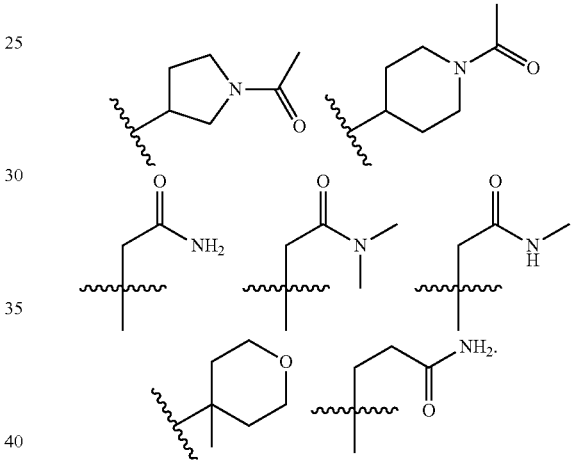

In particular embodiments of the A group having the Formula 1, $NR^6R^7$ is $NH_2$, NHMe, NHEt, NHPr, NHiPr, NHtBu, NH($CH_2$-tBu), NH($CH_2$-cyclopropyl), NH($CH_2$-cyclobutyl), NH(cyclopentyl), NH($CH_2$-pyridyl), NH(cyclohexyl), NH(3-pentyl), NHCH(isopropyl)$_2$, NH($CH_2CH_2OH$), NH($CH_2CH_2CH_2OH$), NH($CH_2CH_2OMe$), NH($CH_2CH_2CH_2OMe$), NH($CH_2CN$), NMe$_2$, NMeEt, NMePr, NMe(iPr), NMe($CH_2$-cyclopropyl), NMe($CH_2$-cyclobutyl), NMe($CH_2CH_2OH$), NMe($CH_2CH_2CH_2OH$), NMe($CH_2CH_2OMe$), NMe($CH_2CH_2CH_2OMe$), NEt$_2$, NEtPr, NEt(iPr), NEt($CH_2$-cyclopropyl), NEt($CH_2$-cyclobutyl), NEt($CH_2CH_2OH$), NEt($CH_2CH_2CH_2OH$),

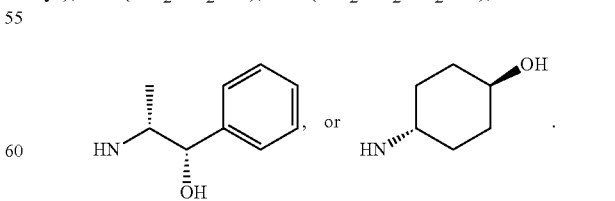

In other embodiments of the A group having the Formula 1, $R^6$ and $R^7$ together with the N to which they are attached form a 4-6 membered heterocyclic ring having a ring nitrogen atom and optionally having a second ring heteroatom selected form N and O, wherein said heterocyclic ring is optionally substituted with one or more groups independently selected from OH, halogen, oxo, $CH_2CF_3$, and $(C_1-C_3)$alkyl. For example, in certain embodiments, $R^6$ and $R^7$ together with the N to which they are attached form a pyrrolidinyl, piperidinyl, azetidinyl, morpholinyl or piperizinyl ring, wherein said pyrrolidinyl, piperidinyl, azetidinyl, morpholinyl and piperazinyl rings are optionally substituted with one or more groups independently selected from OH, F methyl, $CH_2CF_3$, and oxo. In particular embodiments of the A group having the Formula 1, $NR^6R^7$ is selected from the structures:

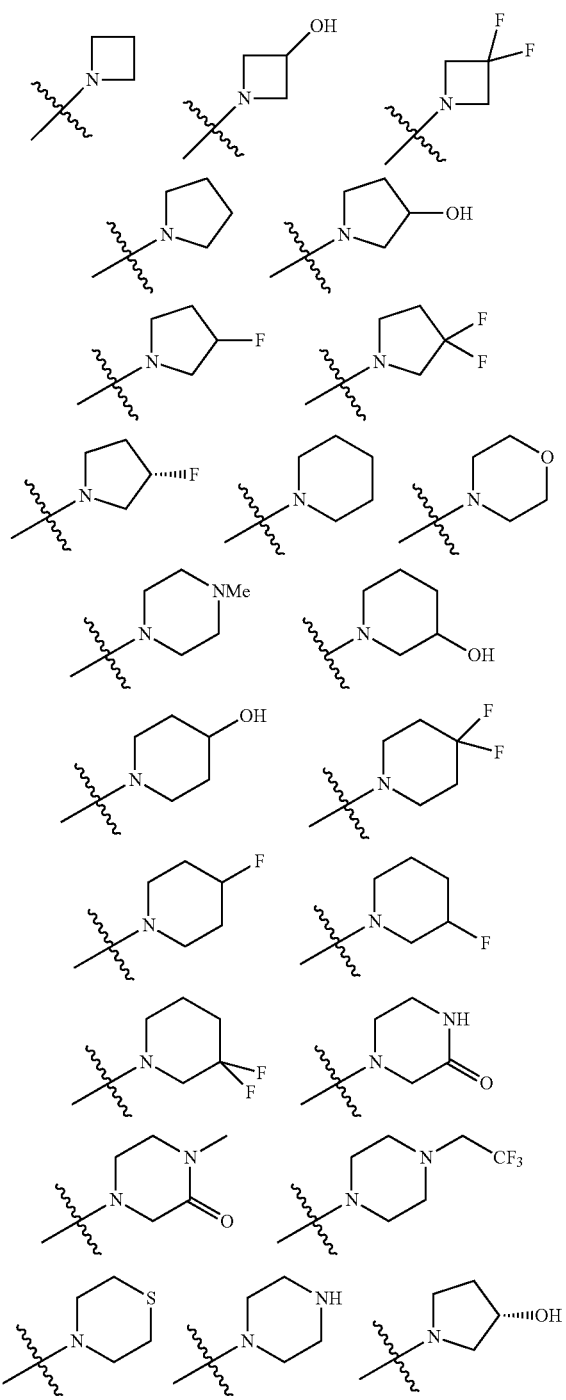

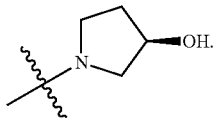

In additional embodiments, $R^6$ and $R^7$ together with the nitrogen to which they are attached form a 4-6 membered heterocyclic ring, wherein said heterocyclic ring is optionally substituted with one or more groups independently selected from OH, halogen, oxo, $CF_3$, $CH_2CF_3$, $CH_2CH_2OH$, $OCH_3$, $C(=O)CH_3$, $NH_2$, NHMe, $N(Me)_2$, $S(O)_2CH_3$, and $(C_1-C_3)$ alkyl. In a particular embodiment, $NR^6R^7$ has the structure:

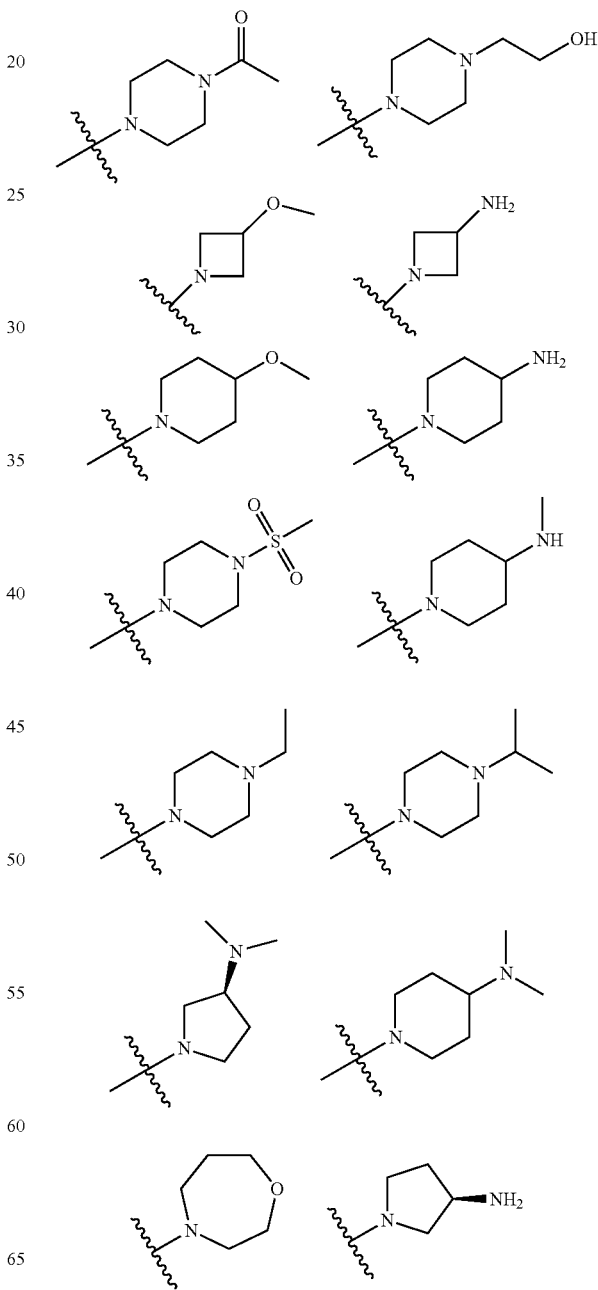

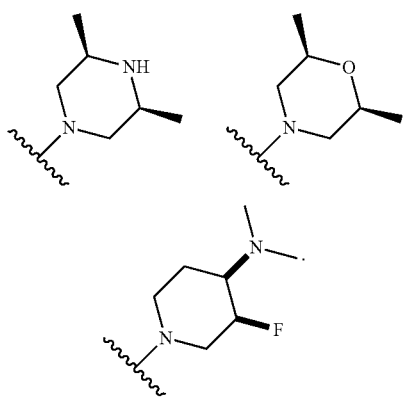

In certain embodiments of the A group having the Formula 1, $R^6$ and $R^8$ together with the atoms to which they are attached form a 5-6 membered heterocyclic ring having one or two ring nitrogen atoms. In other embodiments, $R^6$ and $R^8$ together with the atoms to which they are attached form a pyrrolidinyl or piperidinyl ring.

In particular embodiments, the A group is selected from the formulas:

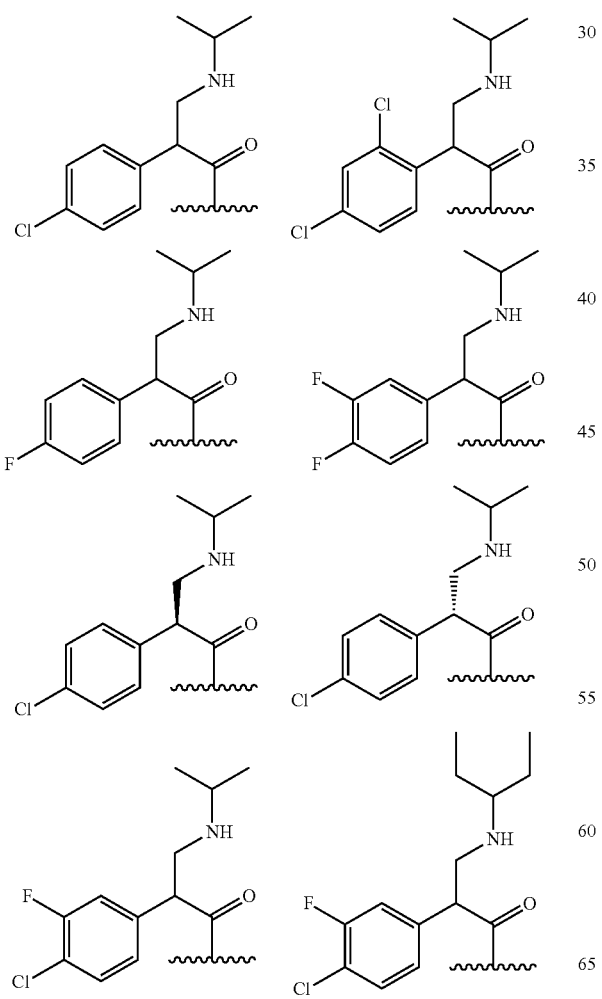

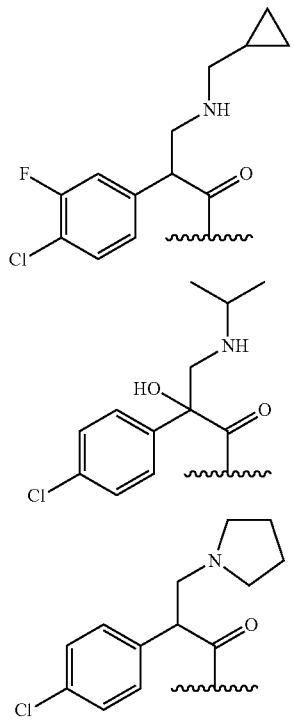

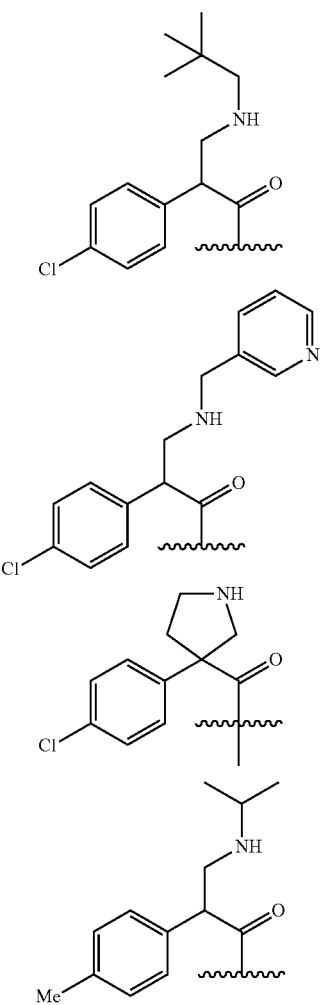

-continued
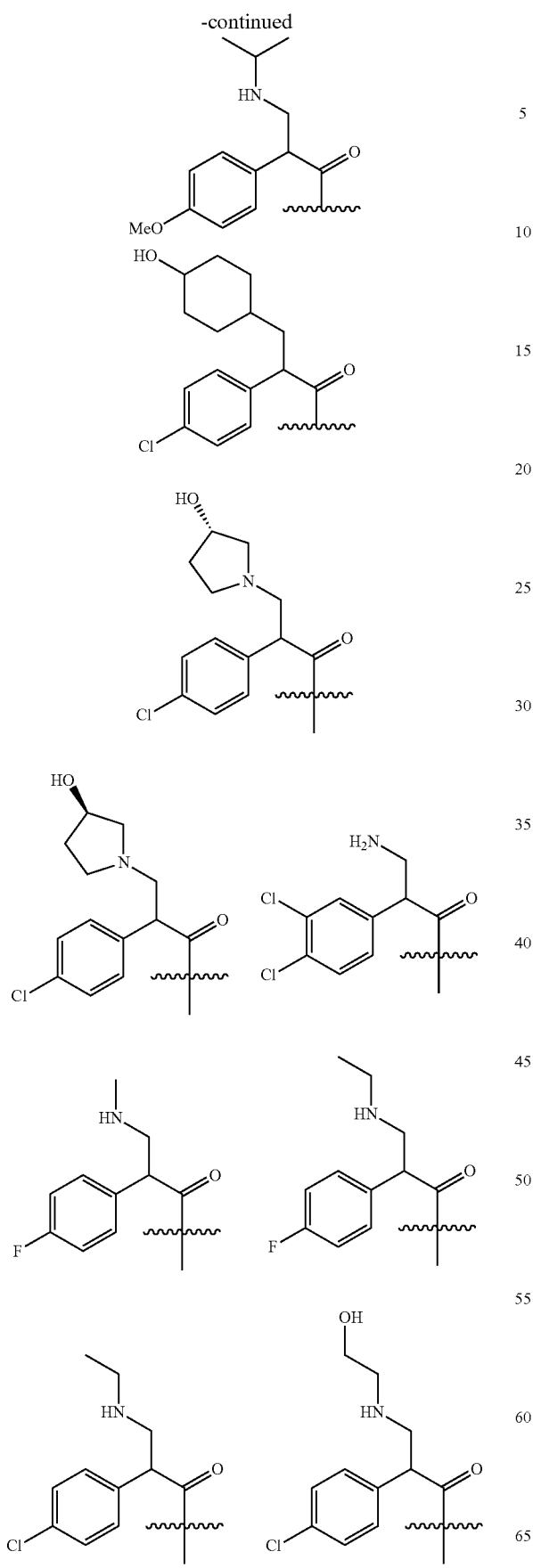
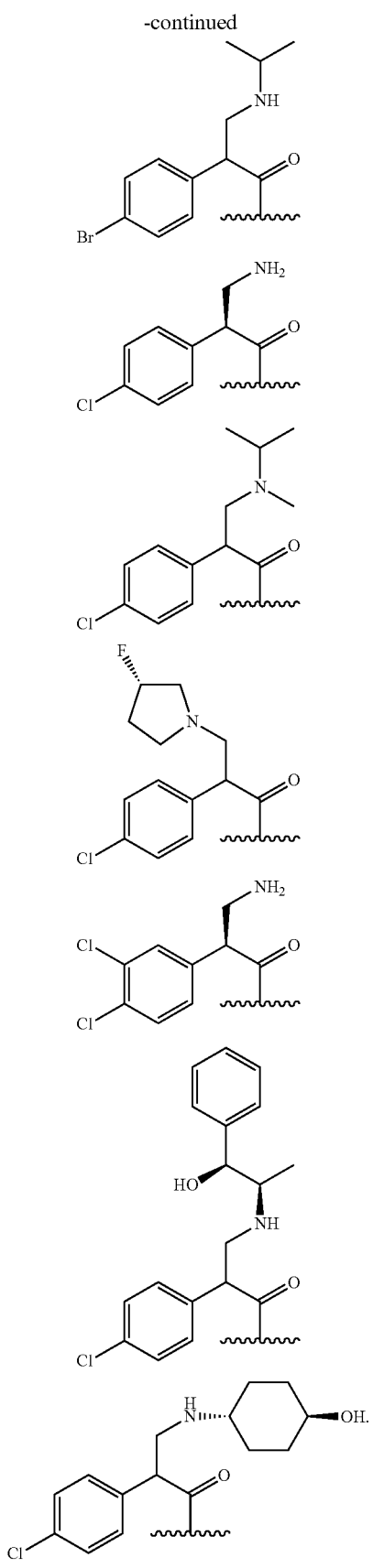

In additional embodiments, the A group is selected from the formulas:
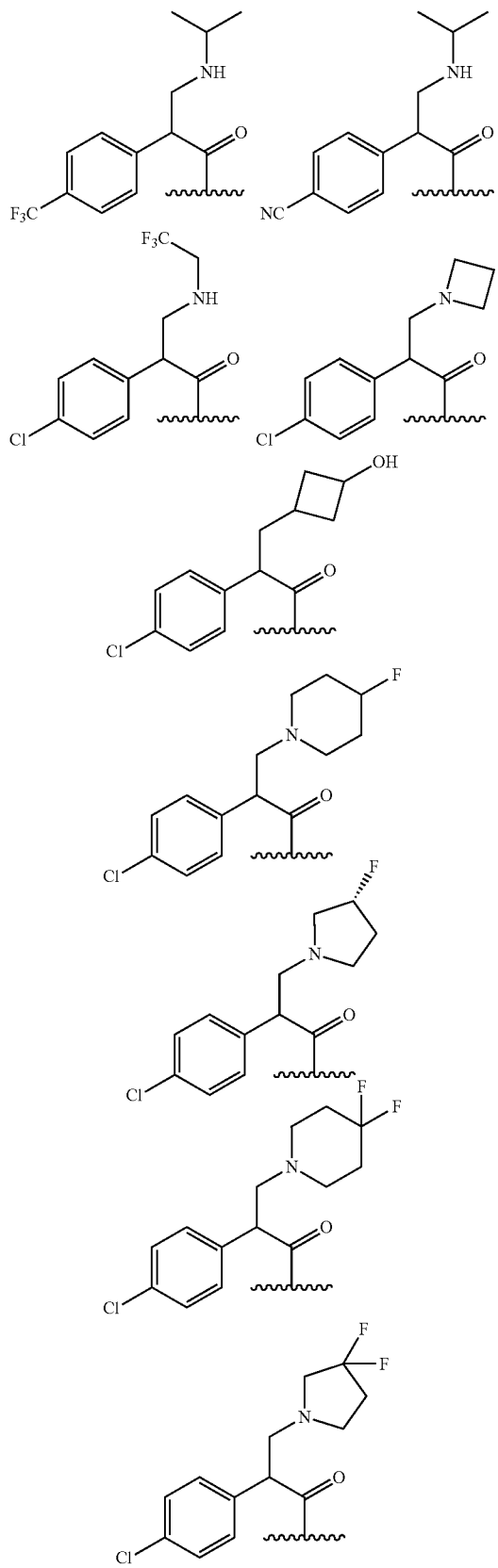
-continued
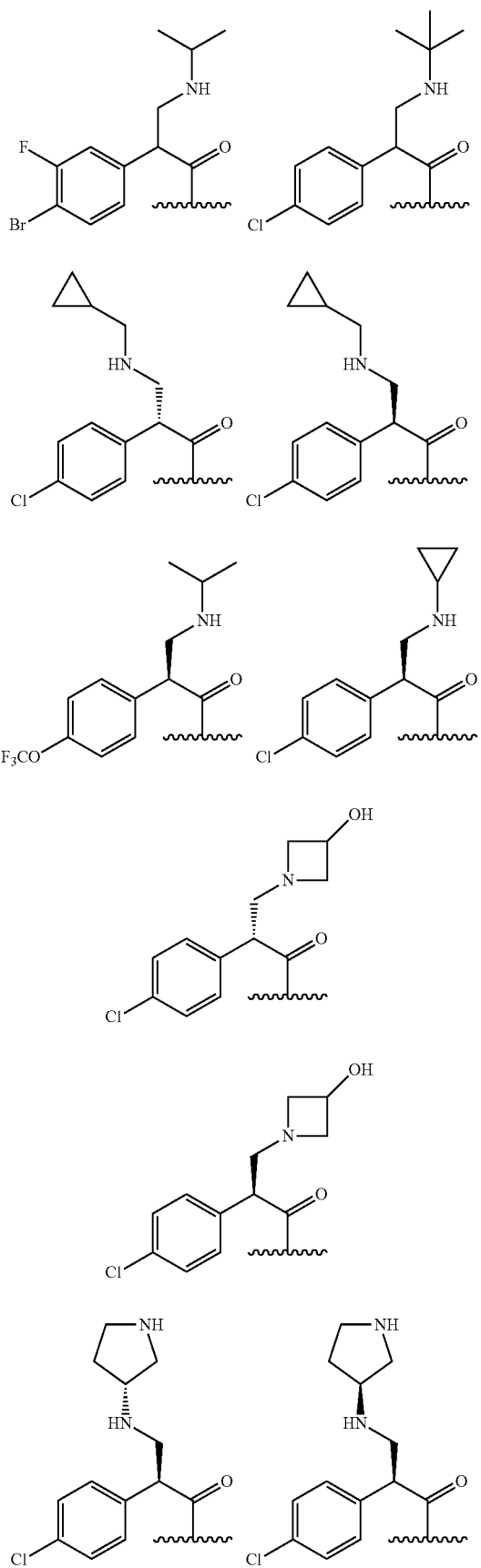

27
-continued
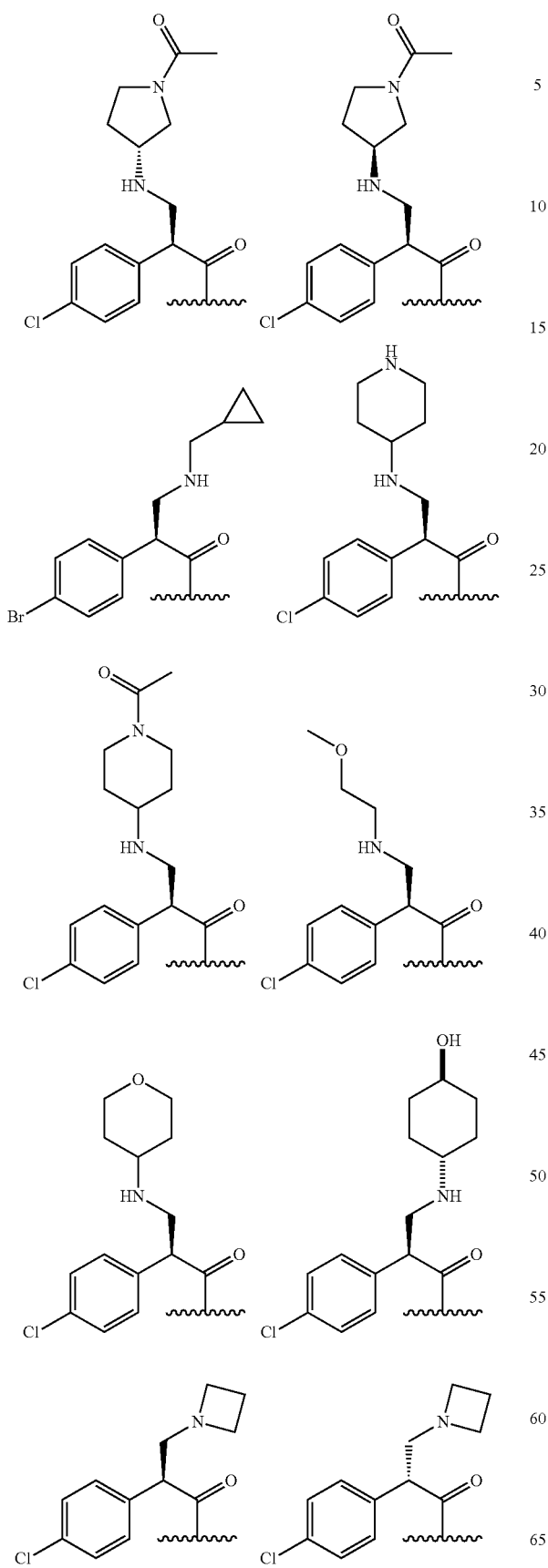
28
-continued
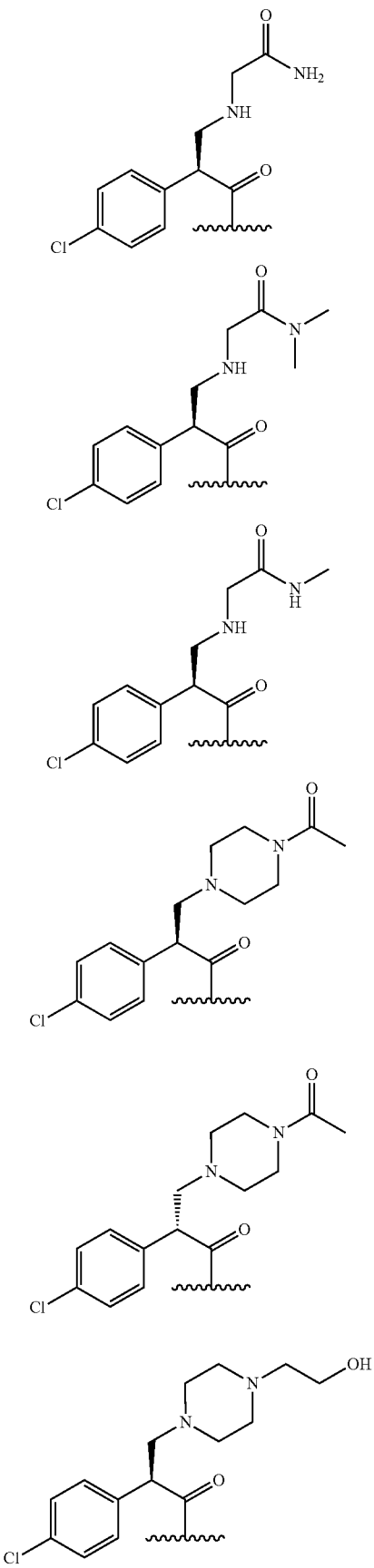

-continued
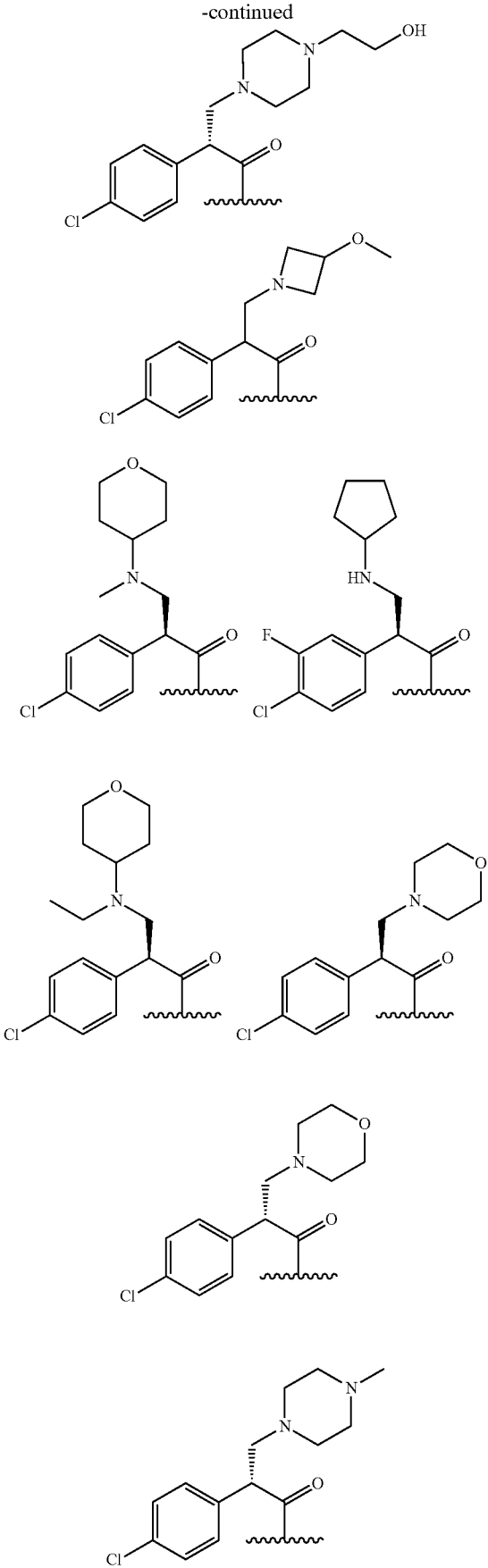
-continued
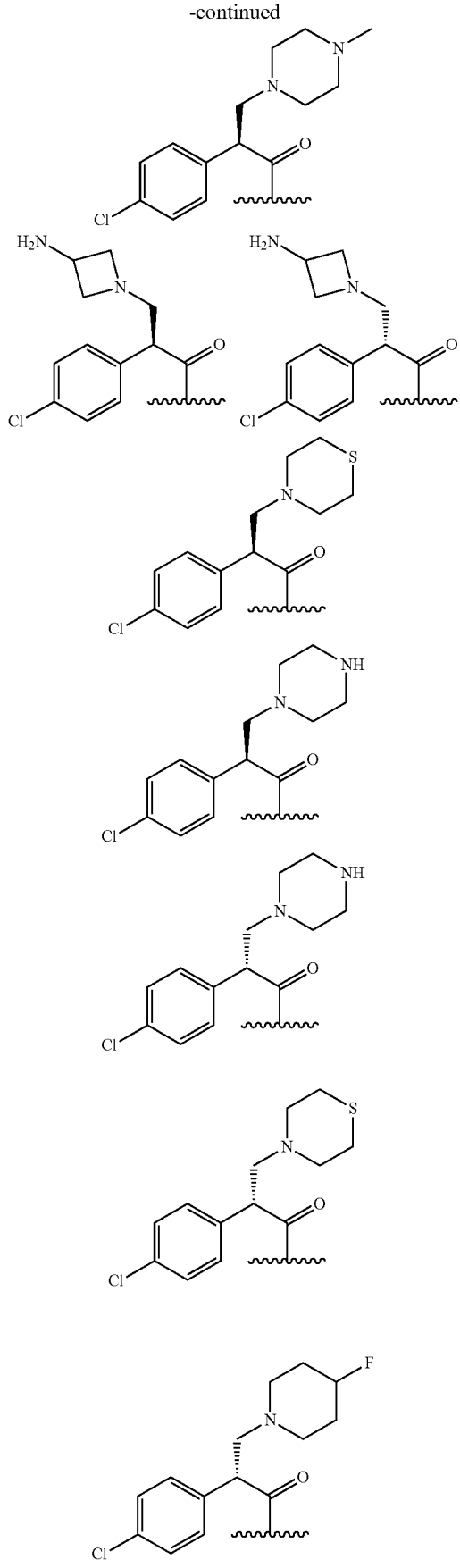

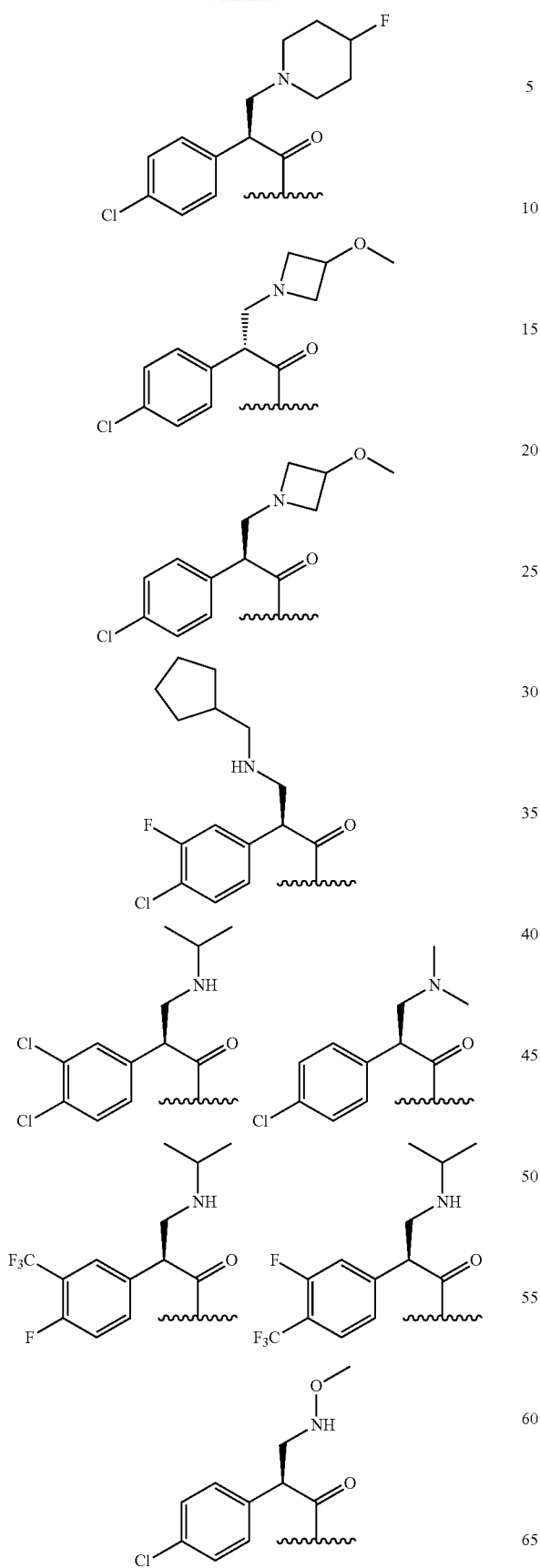
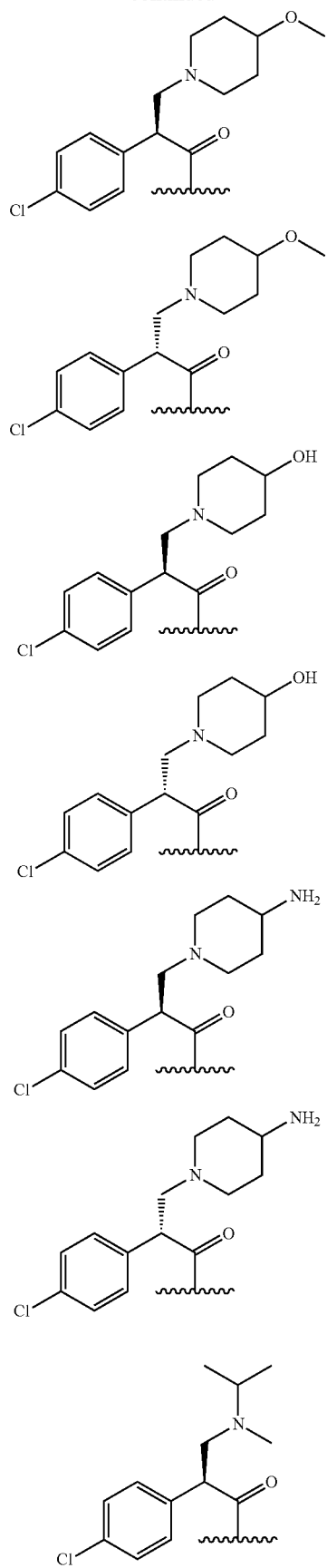

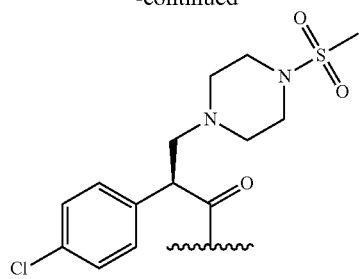
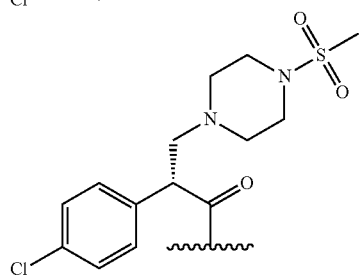
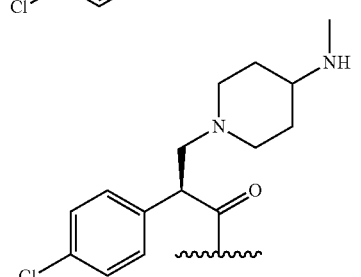
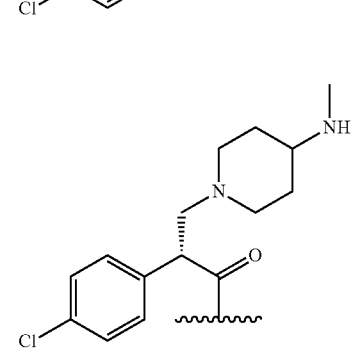
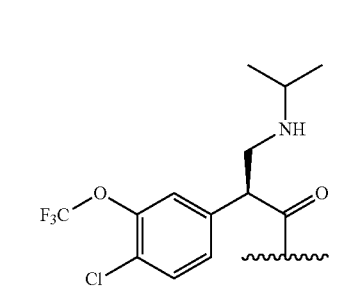
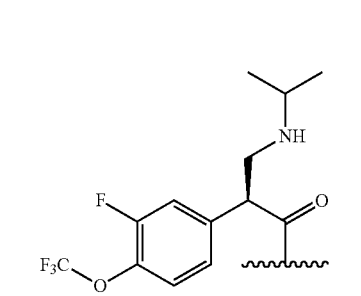
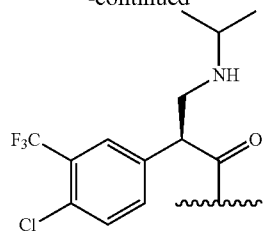
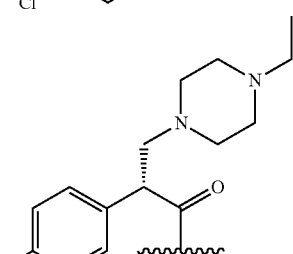
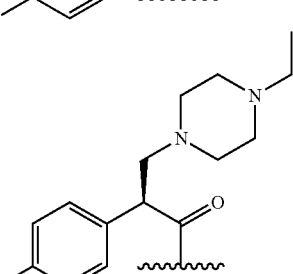
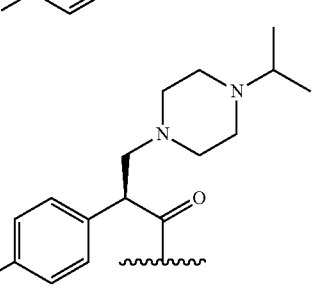
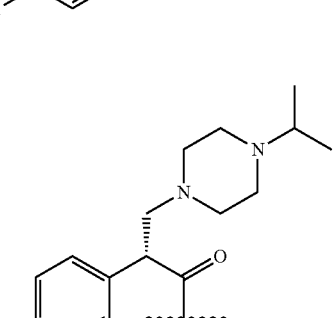
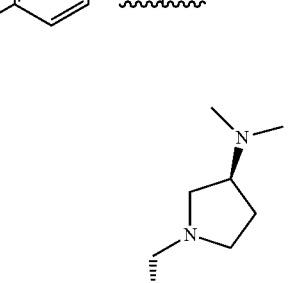

35
-continued
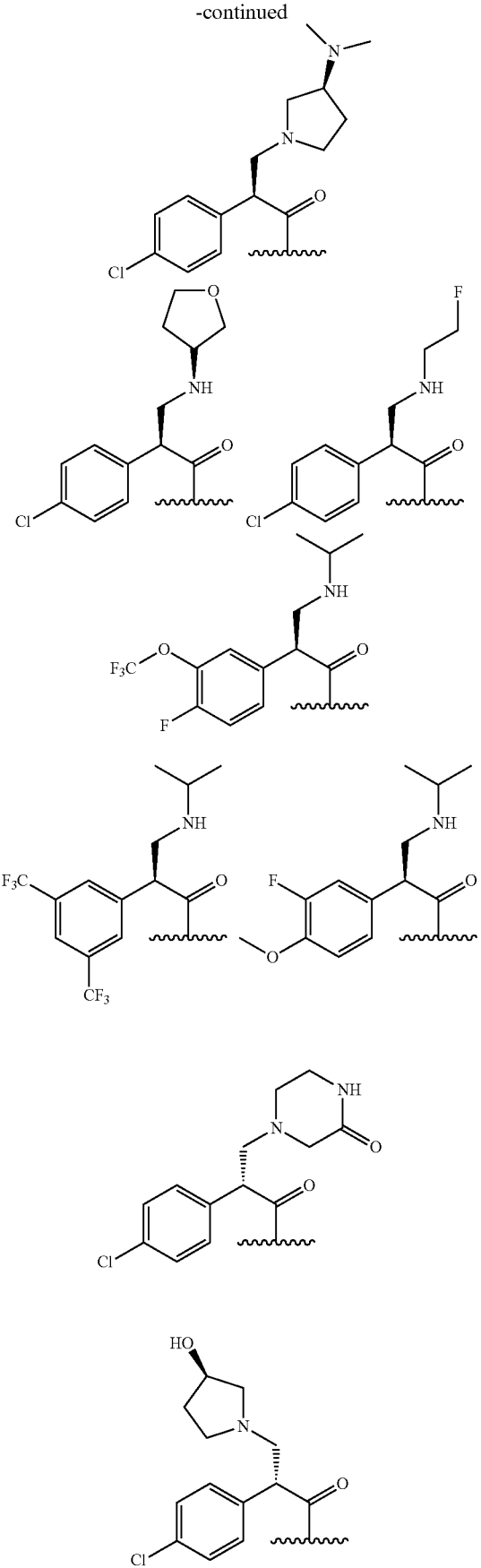
36
-continued
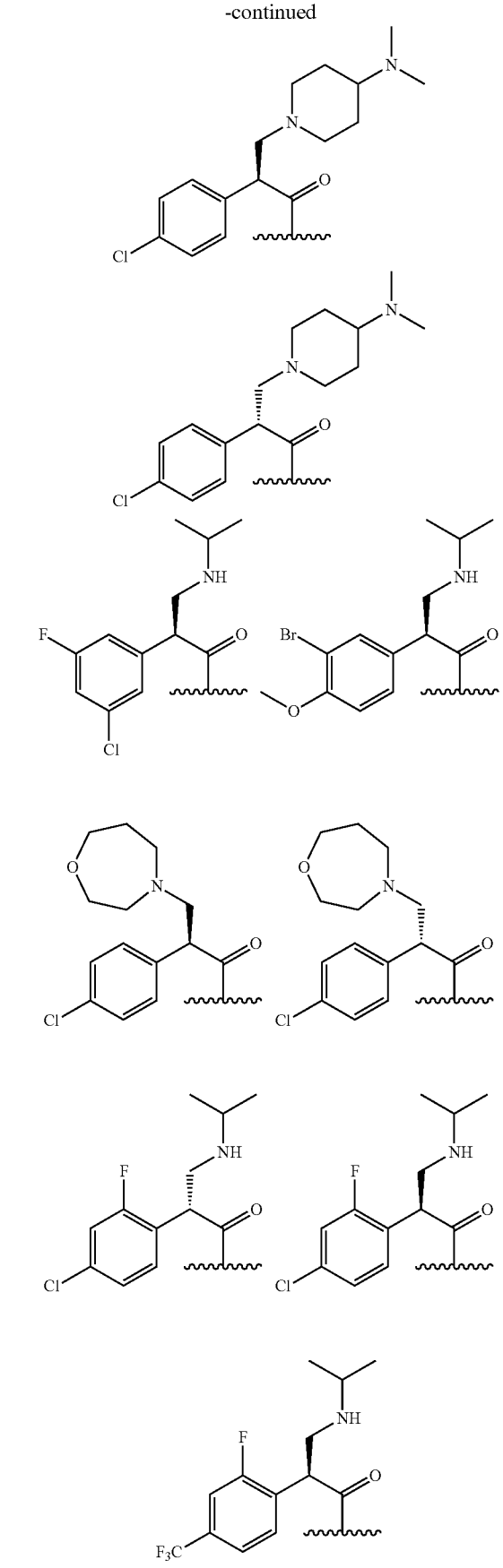

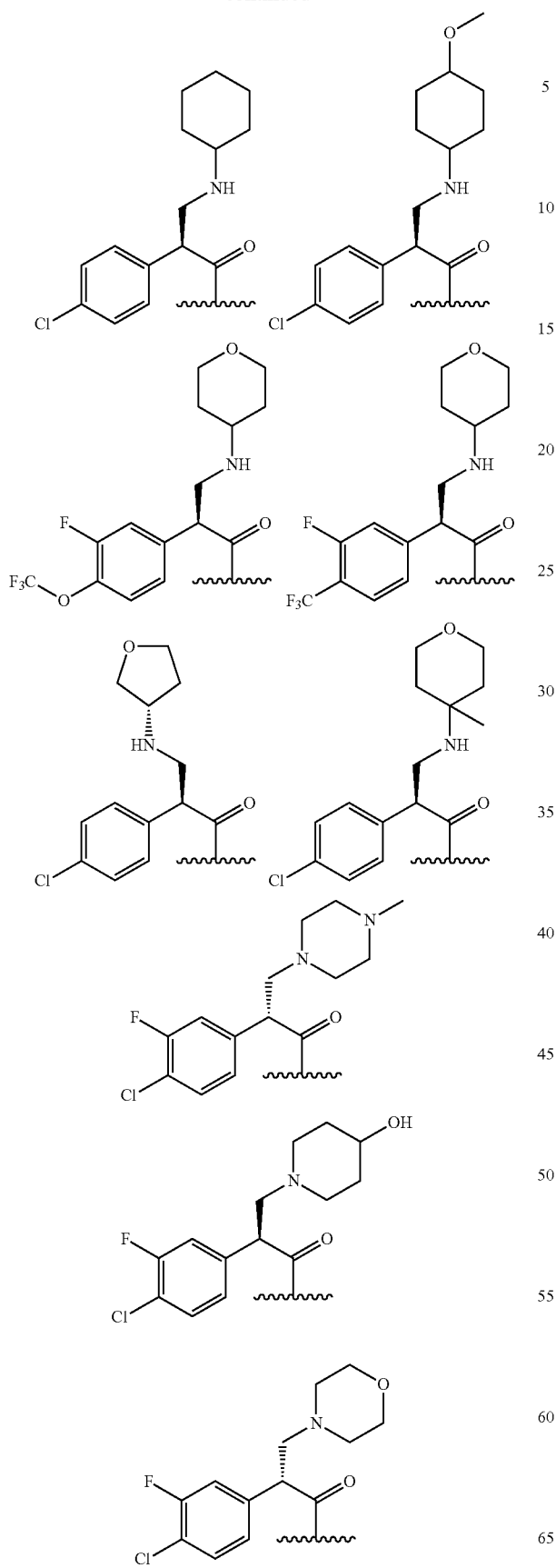
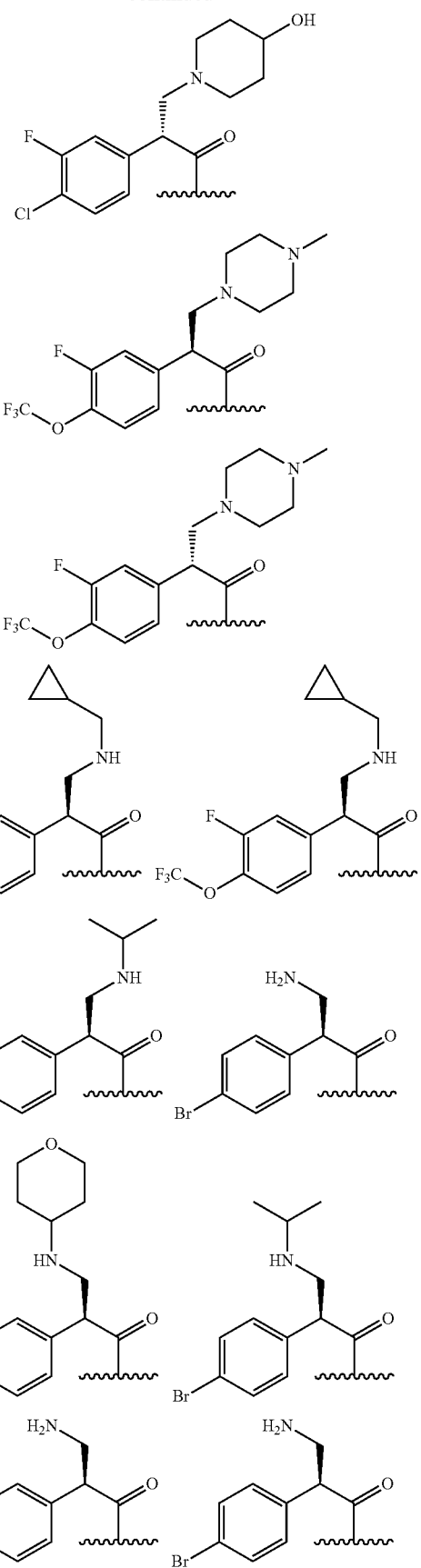

39
-continued
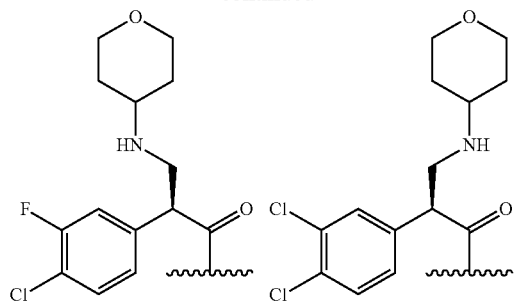
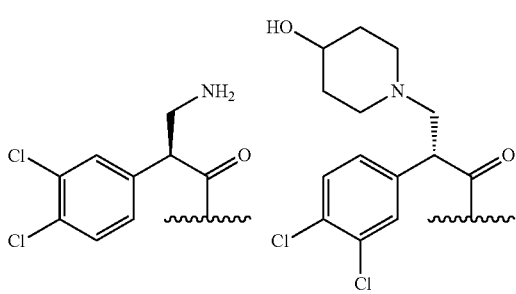
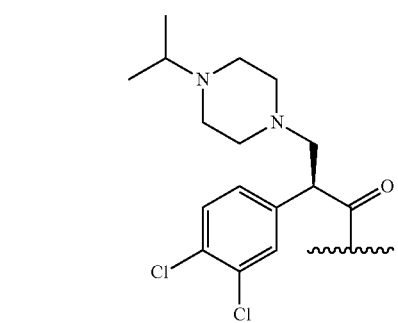
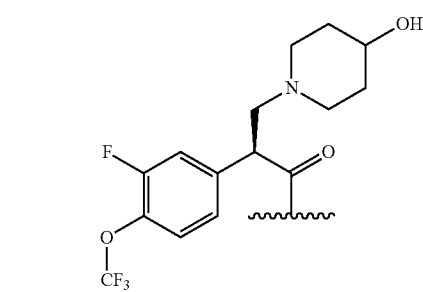
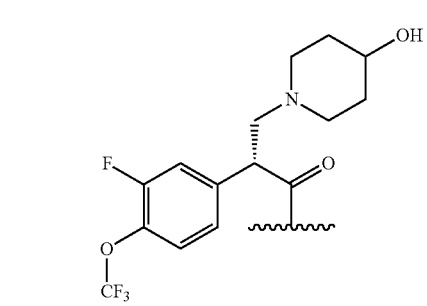
40
-continued
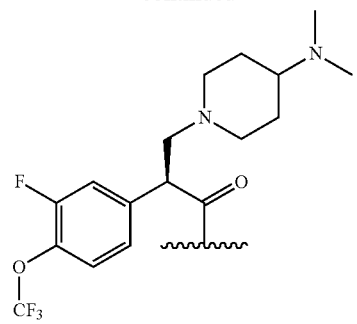
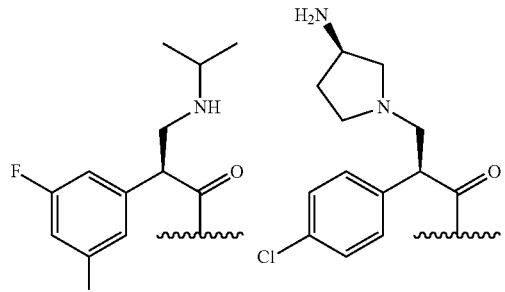
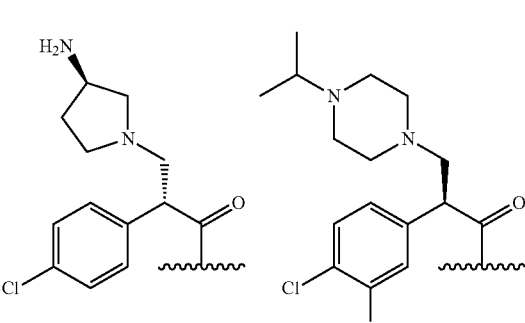
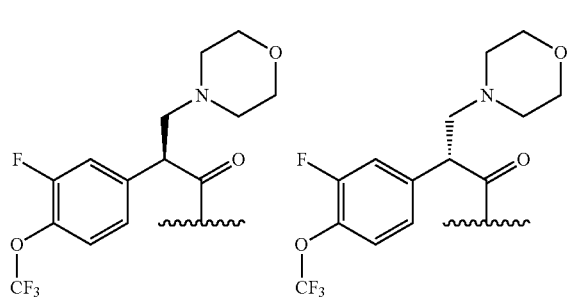
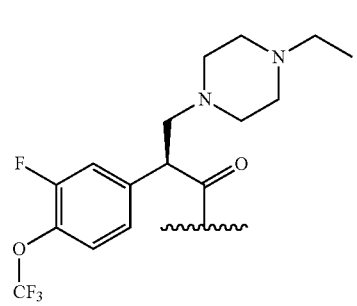

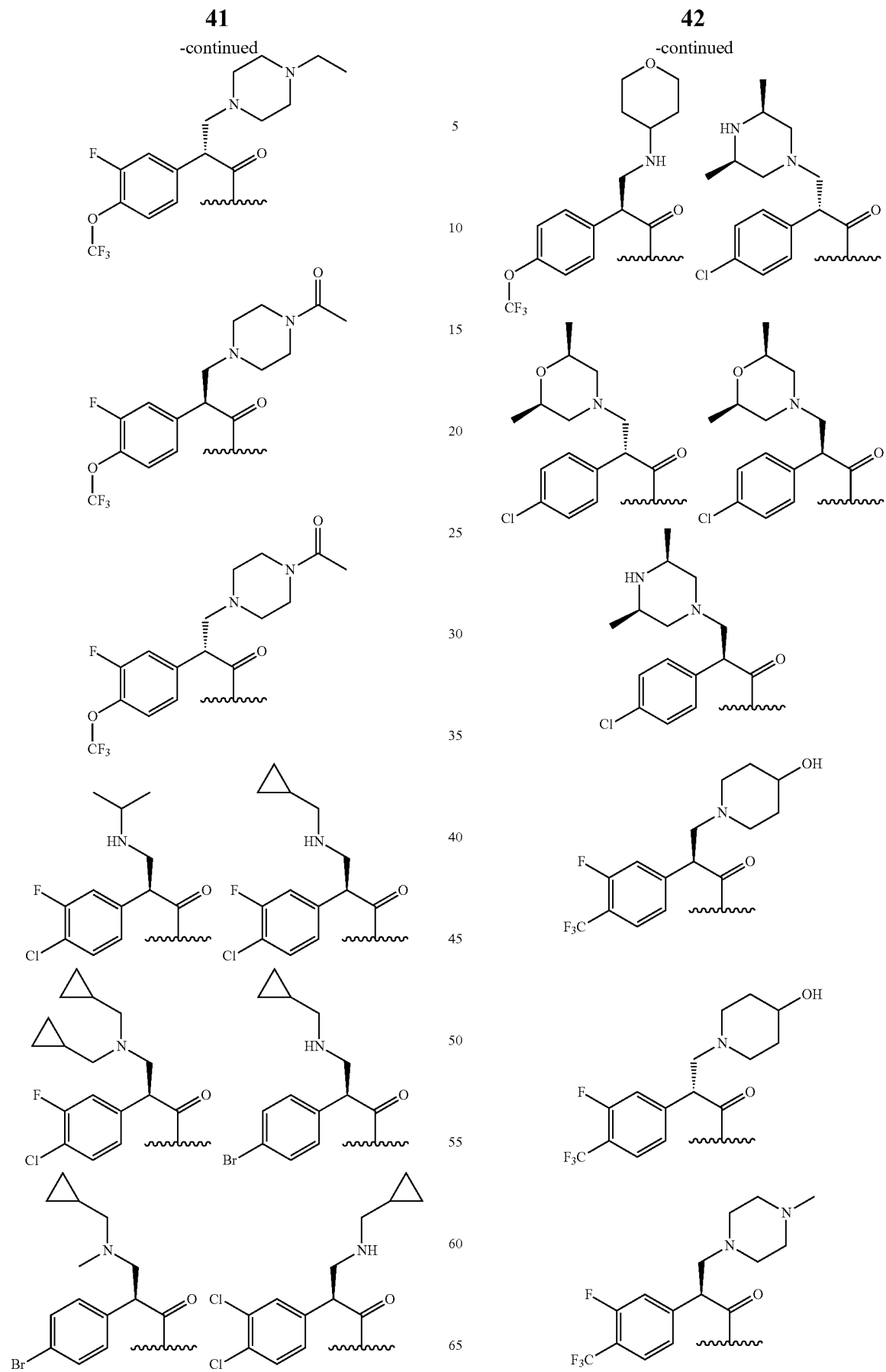

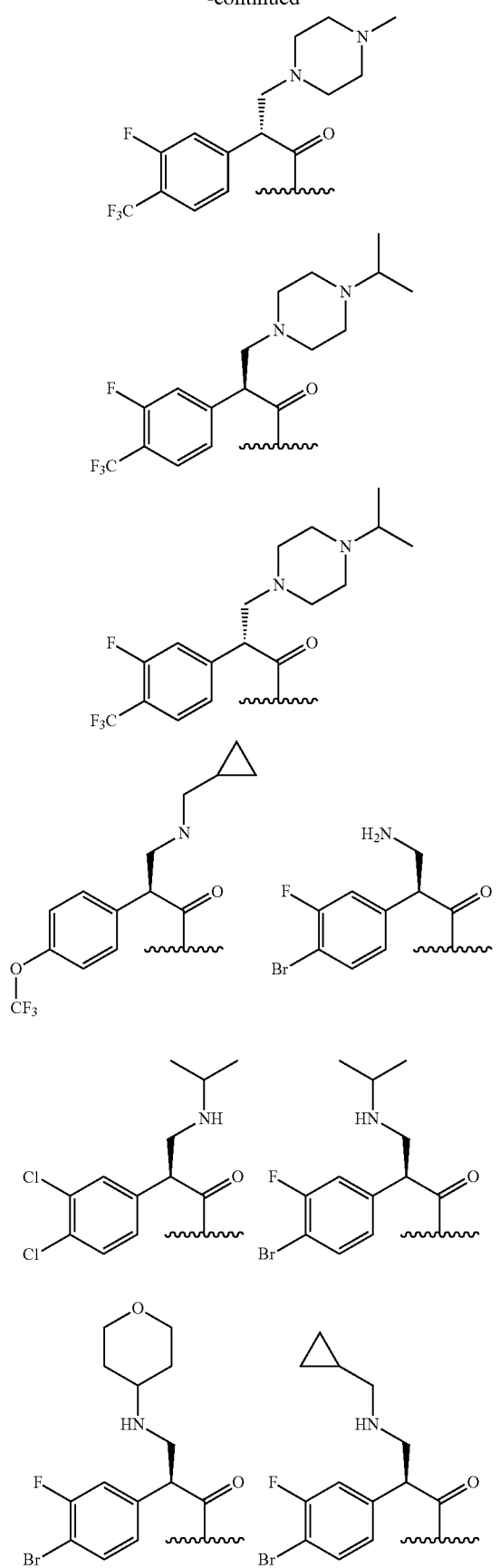
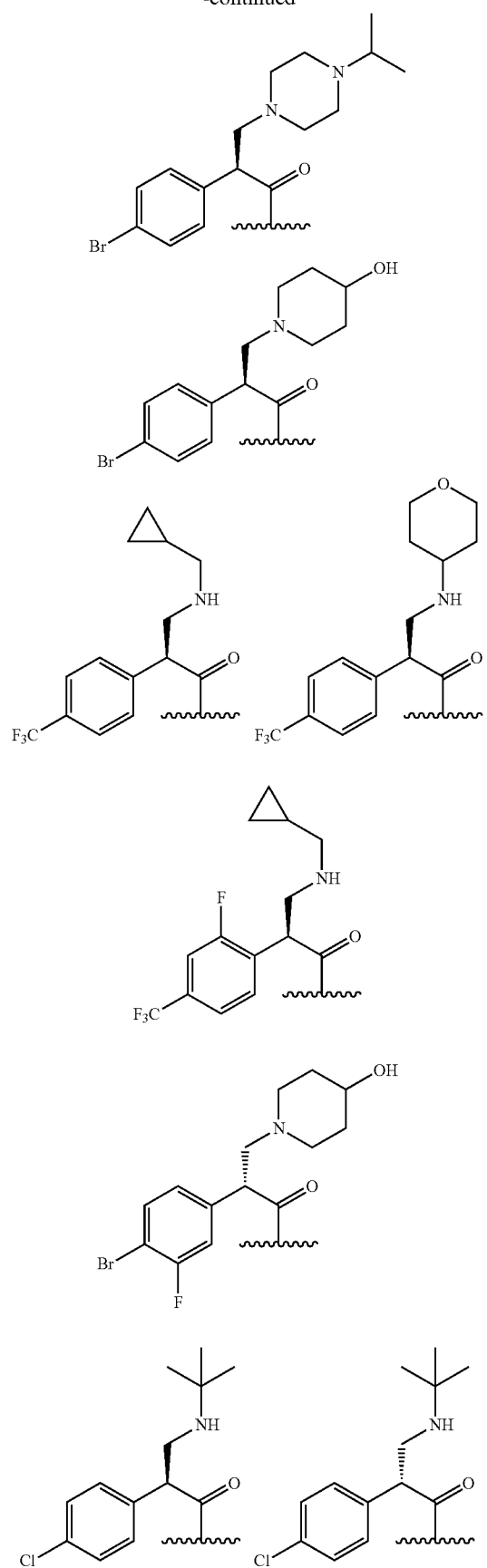

-continued
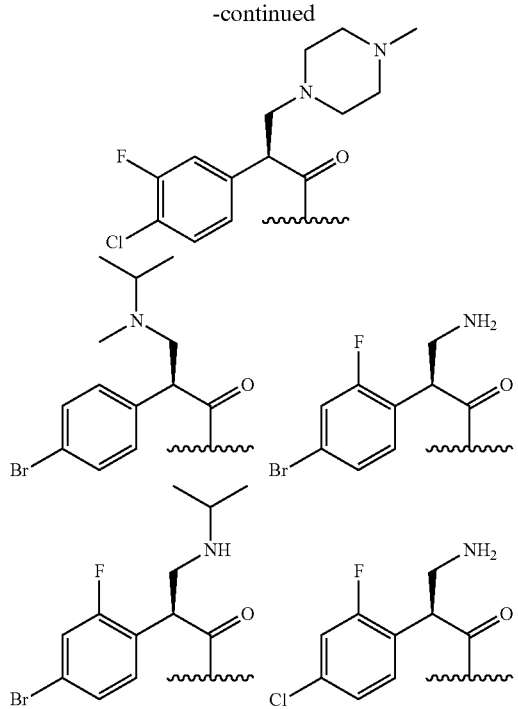
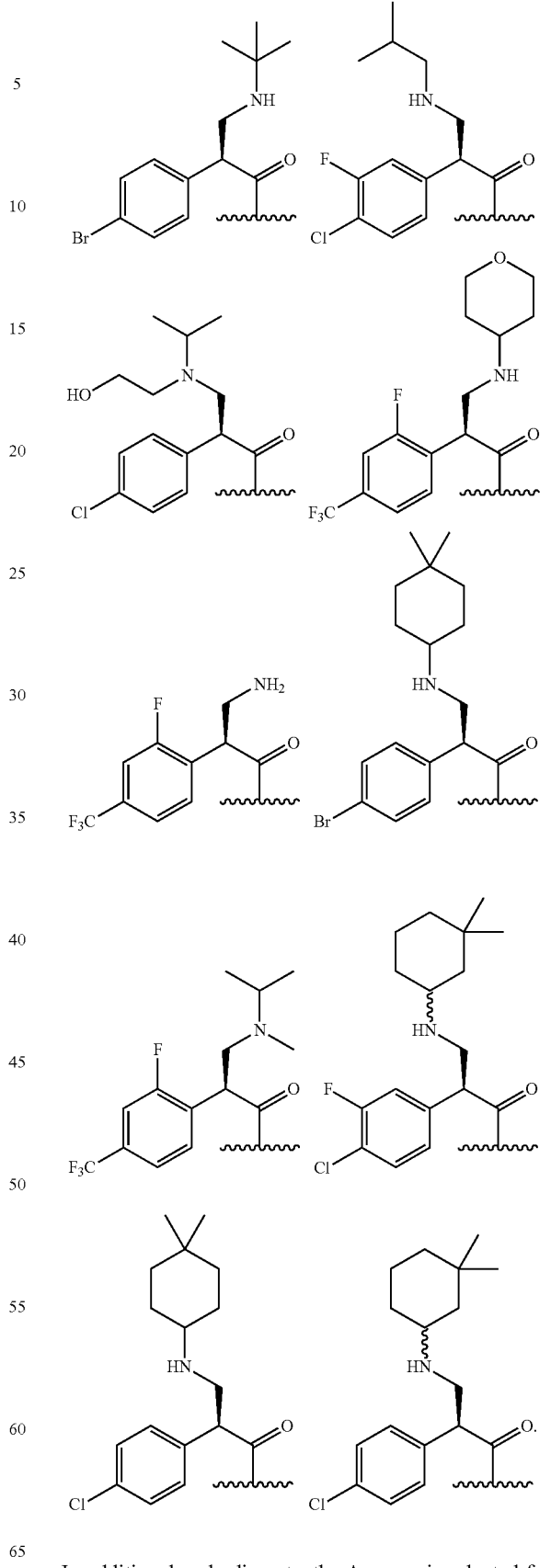
In additional embodiments, the A group is selected from the formulas:

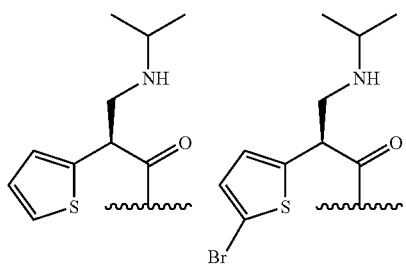
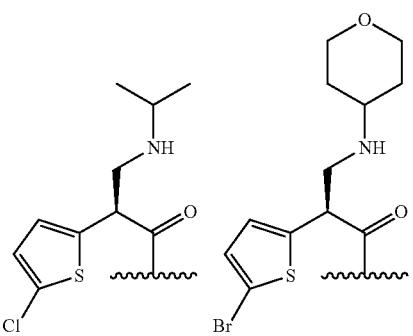
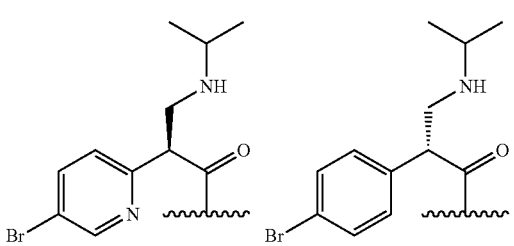
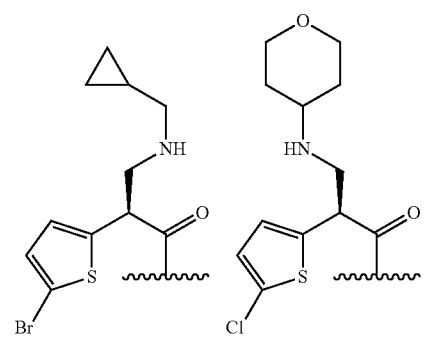
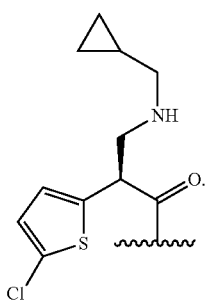

In certain embodiments, compounds of the present invention are represented by Formula 1B:

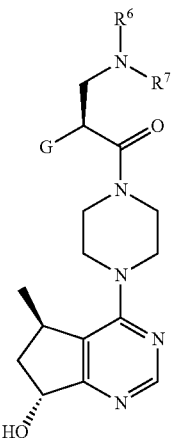

wherein G, $R^6$ and $R^7$ are as defined herein.

In another embodiment of Formula I, m is 1, n is 1, p is 0, such that A is represented by the Formula 2:

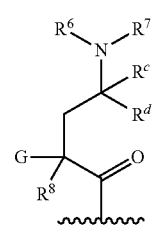

wherein G, $R^6$, $R^7$, $R^8$, $R^c$ and $R^d$ are as defined herein. In certain embodiments, A has the configuration:

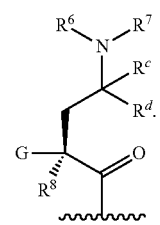

In certain embodiments of the group A having the Formula 2, $R^8$ is H or Me.

In certain embodiments of the group A having the Formula 2, $R^c$ and $R^d$ are methyl. In other embodiments, $R^c$ and $R^d$ are H.

In certain embodiments, $R^c$ and $R^d$ together with the atom to which they are attached form a cyclopropyl ring.

In certain embodiments of the group A having the Formula 2, $R^6$ and $R^7$ are independently H, methyl, ethyl, propyl, isopropyl, $CH_2$-cyclopropyl, or $CH_2$-cyclobutyl, or $R^6$ and $R^7$ together with the nitrogen to which they are attached form a pyrrolidinyl, piperidinyl, or azetidinyl ring, or $R^6$ and $R^8$ together with the atoms to which they are attached form a piperidinyl or pyrrolidinyl ring.

In additional embodiments of the group A having the Formula 2, $R^6$ or $R^7$ may independently be isobutyl, tetrahydropyranyl, CH(phenyl)$CH_2$OH, CH(tetrahydropyranyl)$CH_2$OH, cyclohexyl, $CH_2CH_2$OH, $CH_2CH_2OCH_3$, $CH_2CH$ (CH$_3$)OH, CH$_2$CH(CF$_3$)OH, CH$_2$C(=O)N(CH$_3$)$_2$, CH$_2$C(=O)NH$_2$, CH$_2$CH$_2$CH$_2$(imidazolyl) or

In certain embodiments of the group A having the Formula 2, NR$^6$R$^7$ is NH$_2$, NHMe, NHEt, NHPr, NH(iPr), NH(CH$_2$-cyclopropyl), NH(CH$_2$-cyclobutyl), NMe$_2$, NMeEt, NMePr, NMe(iPr), NEt$_2$, NEtPr, or NEt(iPr).

In certain embodiments of the group A having the Formula 2, NR$^6$R$^7$ is NH(isobutyl), NH(CH$_2$CH$_2$OH), NH(CH$_2$CH$_2$OCH$_3$), NH(CH$_2$C(=O)N(CH$_3$)$_2$), NH(CH$_2$CH(CH$_3$)OH), NH(cyclohexyl), NH(tetrahydropyranyl), NH(CH(phenyl)CH$_2$OH), NH(CH(tetrahydro-pyranyl)CH$_2$OH), NMe(CH$_2$CH$_2$OMe), NH(CH$_2$C(=O)NH$_2$), NH(CH$_2$CH$_2$CH$_2$(imidazolyl)) or

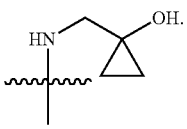 [SMILES: *NCC1(O)CC1]

In other embodiments, NR$^6$R$^7$ is selected from the structures:

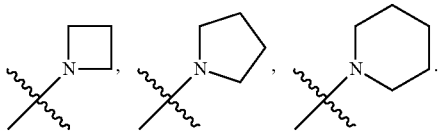 [SMILES: *N1CCC1 ; *N1CCCC1 ; *N1CCCCC1]

In other embodiments, NR$^6$R$^7$ is selected from the structures:

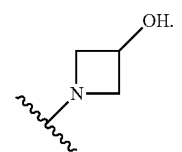 [SMILES: *N1CC(O)C1]

In certain embodiments of the group A having the Formula 2, R$^6$ and R$^7$ are H. In particular embodiments, A is selected from:

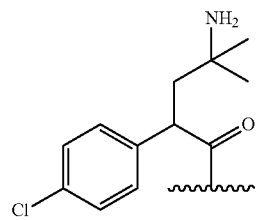

-continued

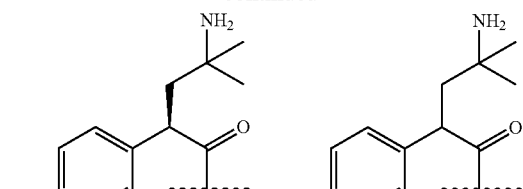
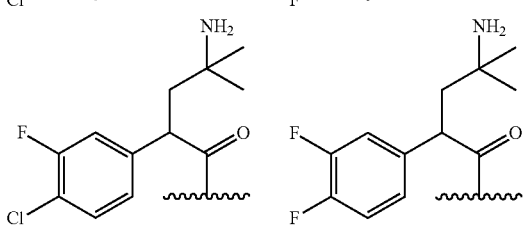
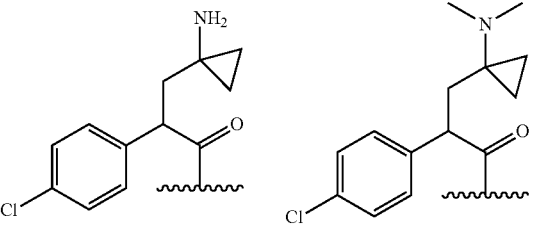
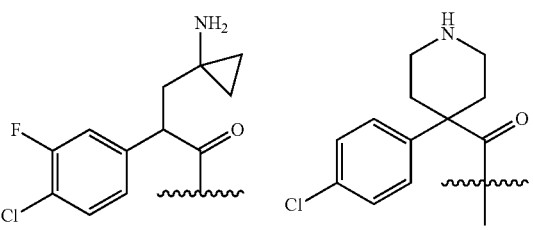
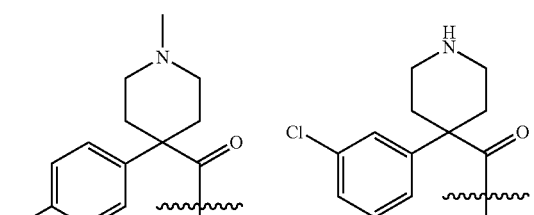
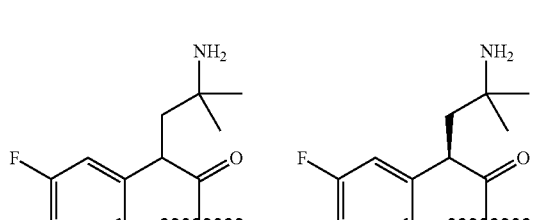
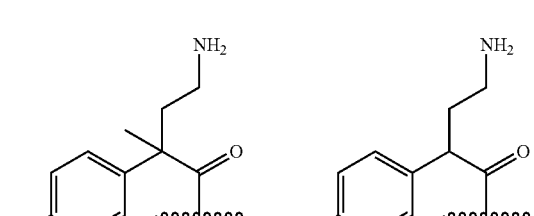

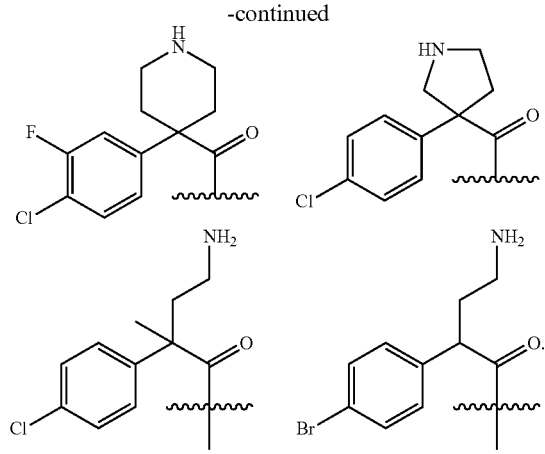
In additional embodiments, A is selected from:
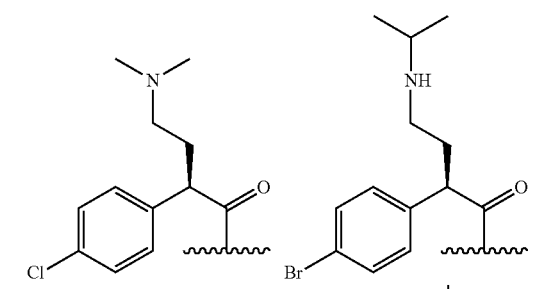
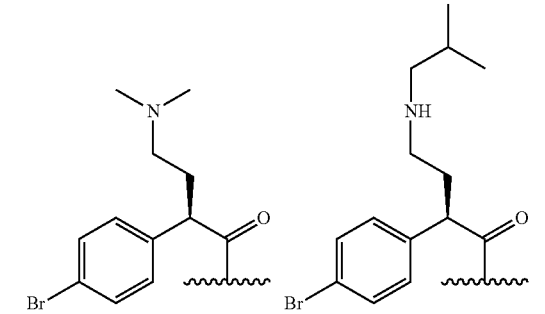
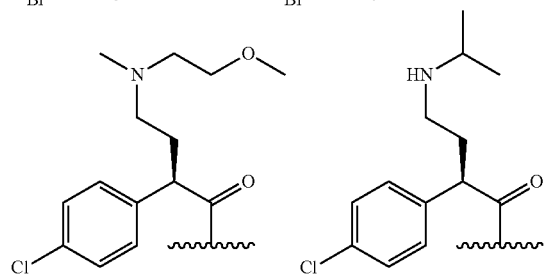
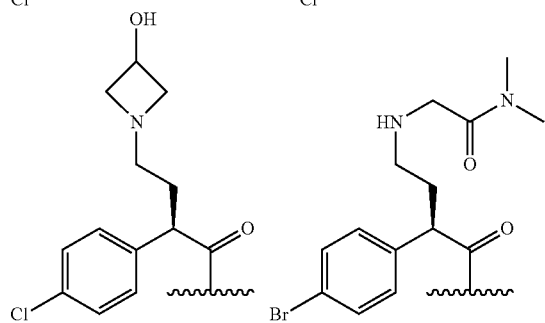
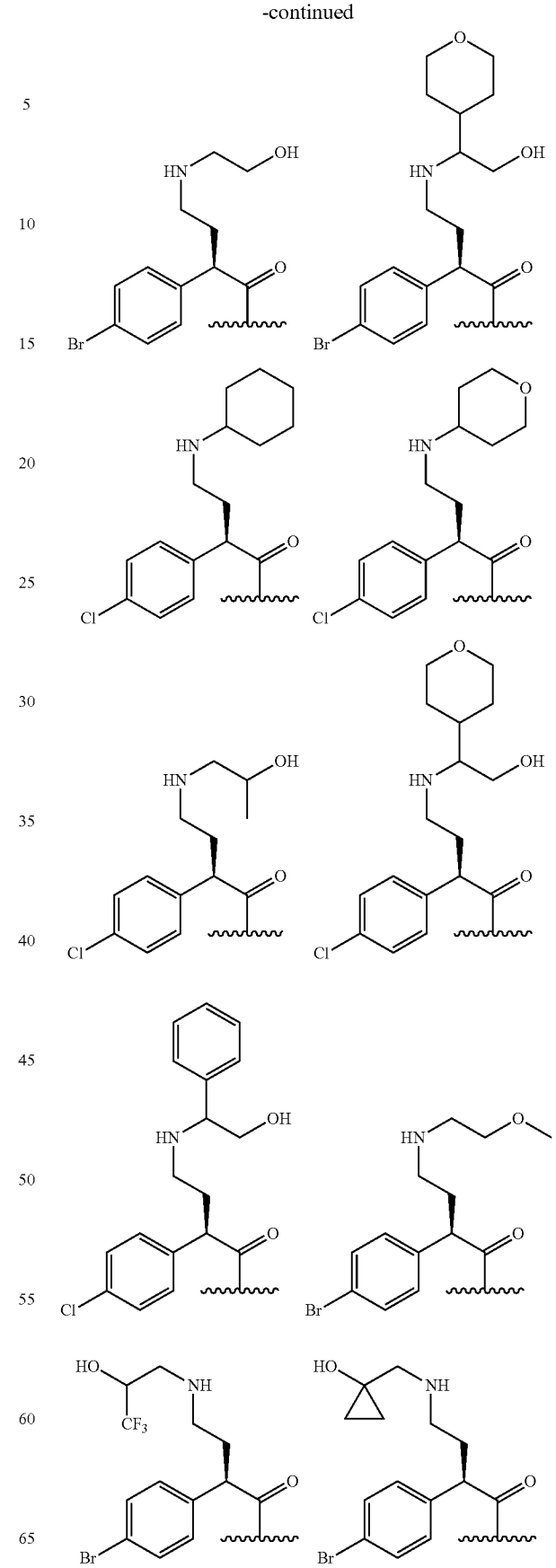

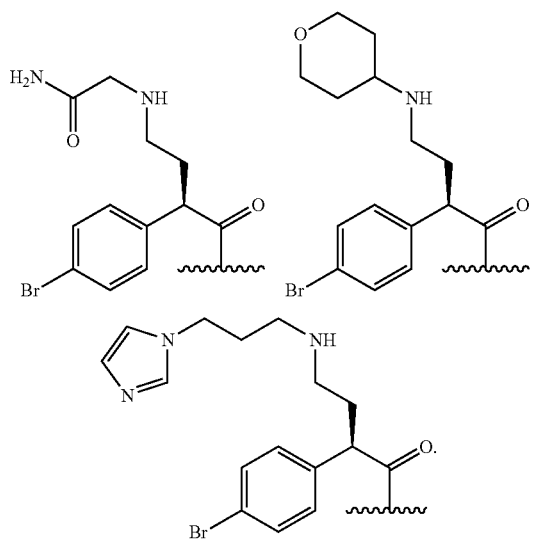

In certain embodiments, compounds of the present invention are represented by Formula 2B:

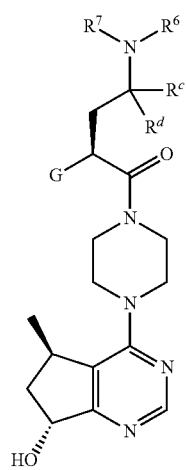

wherein G, $R^c$, $R^d$, $R^6$ and $R^7$ are as defined herein.

In another embodiment of Formula I, m is 1, n is 0 and p is 1, such that A is represented by the Formula 3:

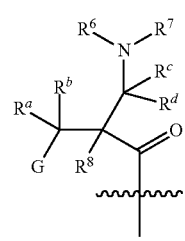

wherein G, $R^6$, $R^7$, $R^8$, $R^a$, $R^b$, $R^c$ and $R^d$ are as defined herein.

In certain embodiments, A has the configuration:

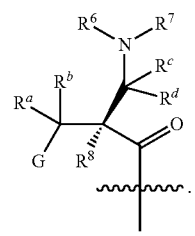

In certain embodiments of the group A having the Formula 3, $R^8$ is H.

In certain embodiments of the group A of Formula 3, $R^c$ and $R^d$ are H. In other embodiments, $R^c$ and $R^d$ together with the atom to which they are attached form a cyclopropyl ring.

In certain embodiments of the group A of Formula 3, $R^6$ and $R^7$ are independently H, methyl, ethyl, propyl, isopropyl, t-butyl, $CH_2$-cyclopropyl, or $CH_2$-cyclobutyl.

In certain embodiments, $NR^6R^7$ of Formula 3 is $NH_2$, NHMe, NHEt, NHPr, NH(iPr), NHtBu, NH($CH_2$-cyclopropyl), or NH($CH_2$-cyclobutyl).

In certain embodiments of the group A having the Formula 3, $R^6$ and $R^7$ are H. In particular embodiments, A is:

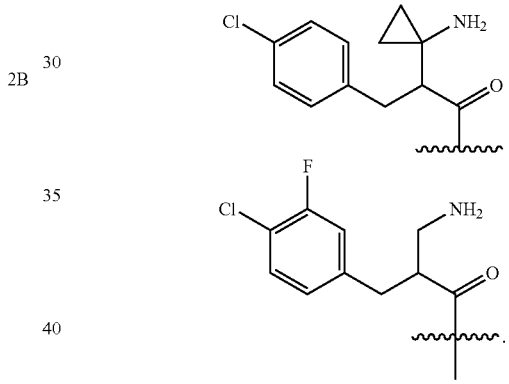

In other embodiments of group A of Formula 3, $R^a$ and $R^8$ are H, and $R^b$ and $R^6$ together with the atoms to which they are attached form a 5 to 6 membered heterocyclic ring wherein one of the ring atoms is nitrogen. In certain embodiments, $R^b$ and $R^6$ together with the atoms to which they are attached form a pyrrolidinyl ring. In certain embodiments, $R^7$ is H. In particular embodiments, A is selected from:

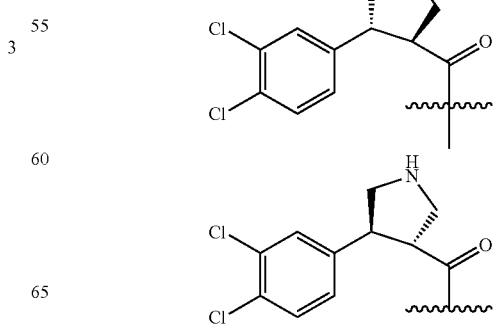

-continued

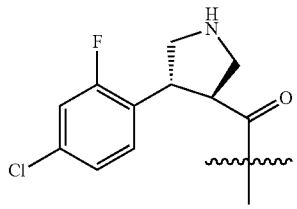

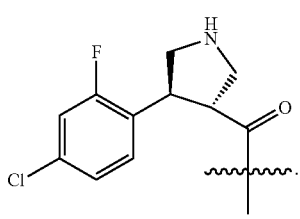

In certain embodiments, compounds of the present invention are represented by Formula 3B:

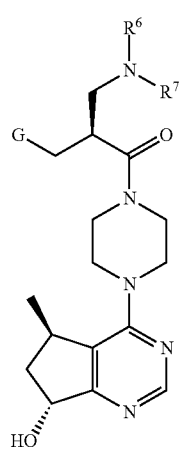

wherein G, $R^6$ and $R^7$ are as defined herein.

In certain embodiments of Formula I, m is 0, n is 0 and p is 1, such that A is represented by the Formula 4:

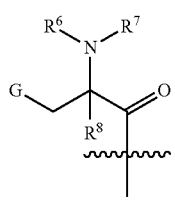

wherein G, $R^6$, $R^7$, and $R^8$ are as defined herein. In certain embodiments, A has the configuration:

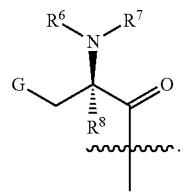

In certain embodiments of the group A having the Formula 4, $R^8$ is H. In certain embodiments, $R^6$ and $R^7$ are independently H or Me. In particular embodiments, A is selected from:

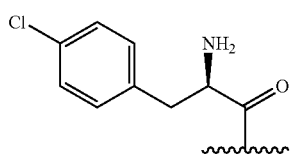

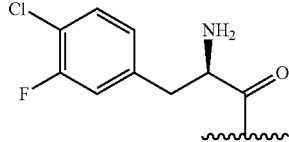

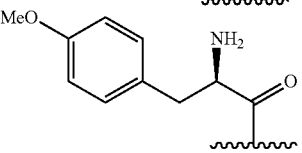

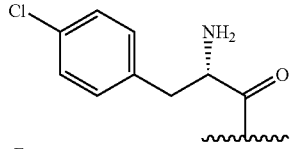

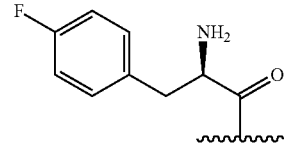

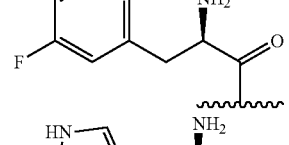

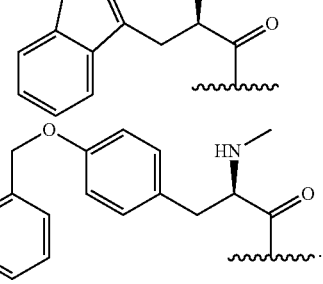

In certain embodiments, $R^6$ or $R^7$ may be methyl, iPr, piperidinyl, tetrahydrofuranyl, $CH_2CH_2CF_3$, $CH_2CH_2$(morpholinyl), $CH_2$(tetrahydropyranyl), $CH_2CH_2$(tetrahydropyranyl), $CH_2C(=O)NH(iPr)$, $CH_2C(=O)N(Me)_2$ or

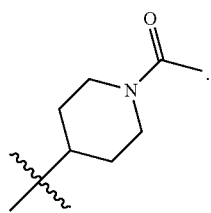 [SMILES: *C1CCN(C(C)=O)CC1]
Additional embodiments of A include:
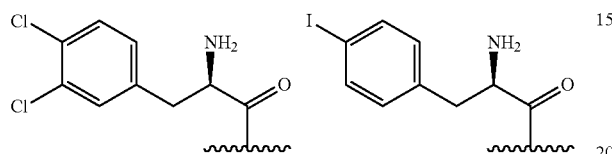
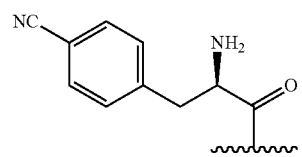
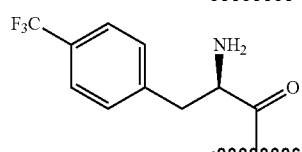
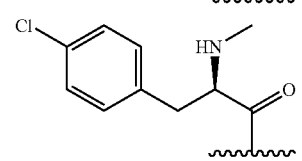
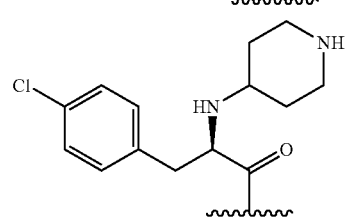
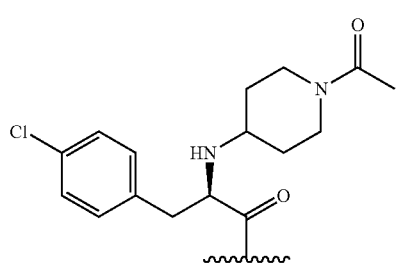
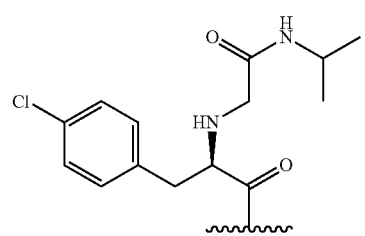
-continued
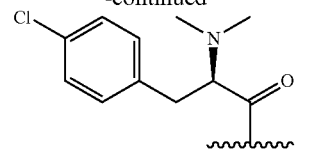
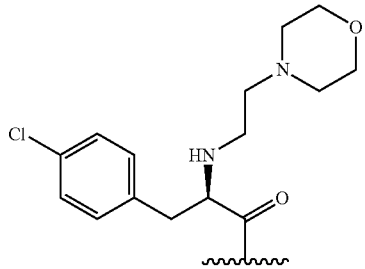
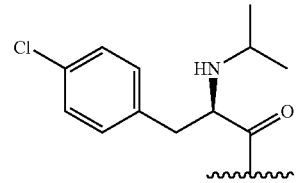
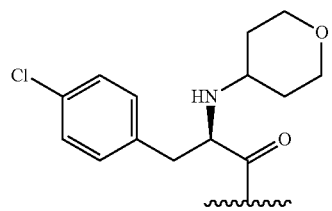
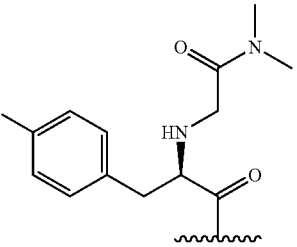
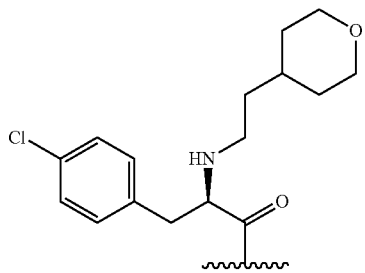
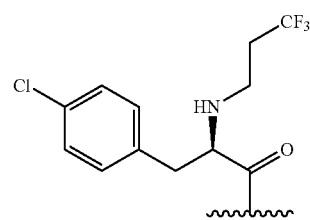

-continued

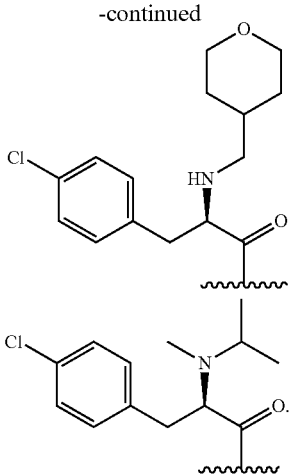

In certain embodiments, compounds of the present invention are represented by Formula 4B:

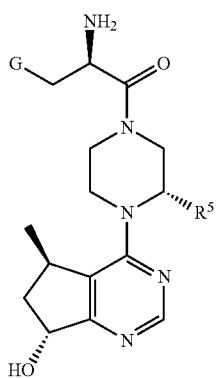

4B wherein G and R⁵ are as defined herein.

In certain embodiments, compounds of the present invention are represented by Formula 4C:

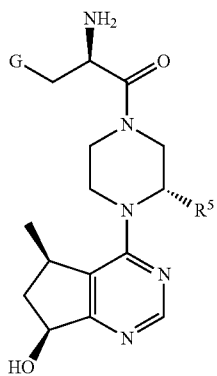

4C wherein G and R⁵ are as defined herein.

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and diastereomers, and mixtures, racemic or otherwise, thereof. Accordingly, this invention also includes all such isomers, including diastereomeric mixtures, pure diastereomers and pure enantiomers of the compounds of this invention. The term "enantiomer" refers to two stereoisomers of a compound which are non-superimposable mirror images of one another. The term "diastereomer" refers to a pair of optical isomers which are not mirror images of one another. Diastereomers have different physical properties, e.g. melting points, boiling points, spectral properties, and reactivities.

The compounds of the present invention may also exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

The compounds of Formula I include solvates, pharmaceutically acceptable prodrugs and salts (including pharmaceutically acceptable salts) of such compounds.

The phrase "pharmaceutically acceptable" indicates that the substance or composition is compatible chemically and/or toxicologically with the other ingredients comprising a formulation, and/or the mammal being treated therewith.

A "solvate" refers to an association or complex of one or more solvent molecules and a compound of the invention. Examples of solvents that form solvates include, but are not limited to, water, isopropanol, ethanol, methanol, DMSO, ethyl acetate, acetic acid, and ethanolamine. The term "hydrate" can also be used to refer to a complex wherein the solvent molecule is water.

A "prodrug" is a compound that may be converted under physiological conditions or by solvolysis to the specified compound or to a salt of such compound. Prodrugs include compounds wherein an amino acid residue, or a polypeptide chain of two or more (e.g., two, three or four) amino acid residues, is covalently joined through an amide or ester bond to a free amino, hydroxy or carboxylic acid group of a compound of the present invention. The amino acid residues include but are not limited to the 20 naturally occurring amino acids commonly designated by three letter symbols and also includes phosphoserine, phosphothreonine, phosphotyrosine, 4-hydroxyproline, hydroxylysine, demosine, isodemosine, gamma-carboxyglutamate, hippuric acid, octahydroindole-2-carboxylic acid, statine, 1,2,3,4-tetrahydroisoquinoline-3-carboxylic acid, penicillamine, ornithine, 3-methylhistidine, norvaline, beta-alanine, gamma-aminobutyric acid, cirtulline, homocysteine, homoserine, methyl-alanine, para-benzoylphenylalanine, phenylglycine, propargylglycine, sarcosine, methionine sulfone and tert-butylglycine.

Additional types of prodrugs are also encompassed. For instance, a free carboxyl group of a compound of Formula I can be derivatized as an amide or alkyl ester. As another example, compounds of this invention comprising free hydroxy groups may be derivatized as prodrugs by converting the hydroxy group into a group such as, but not limited to, a phosphate ester, hemisuccinate, dimethylaminoacetate, or phosphoryloxymethyloxycarbonyl group, as outlined in *Advanced Drug Delivery Reviews,* 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers, wherein the acyl group may be an alkyl ester optionally substituted with groups including, but not limited to, ether, amine and carboxylic acid functionalities, or where the acyl group is an amino acid ester as described above, are also encompassed. Prodrugs of this type are described in *J. Med. Chem.,* 1996, 39, 10. More specific examples include replacement of the hydrogen atom of the alcohol group with a group such as ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$)alkoxy-carbonylaminomethyl, succinoyl, ($C_1$-$C_6$)alkanoyl, α-amino($C_1$-$C_4$)alkanoyl, arylacyl and α-aminoacyl, or α-aminoacyl-α-aminoacyl, where each α-aminoacyl group is independently selected from the naturally occurring L-amino acids, $P(O)(OH)_2$, —$P(O)(O(C_1$-$C_6)alkyl)_2$ or glycosyl (the radical resulting from the removal of a hydroxyl group of the hemiacetal form of a carbohydrate).

Free amines of compounds of Formula I can also be derivatized as amides, sulfonamides or phosphonamides. All of these moieties may incorporate groups including, but not limited to, ether, amine and carboxylic acid functionalities. For example, a prodrug can be formed by the replacement of a hydrogen atom in the amine group with a group such as R-carbonyl, RO-carbonyl, NRR'-carbonyl, wherein R and R' are each independently ($C_1$-$C_{10}$)alkyl, ($C_3$-$C_7$)cycloalkyl, or benzyl, or R-carbonyl is a natural α-aminoacyl or natural α-aminoacyl-natural α-aminoacyl, —C(OH)C(O)OY wherein Y is H, ($C_1$-$C_6$)alkyl or benzyl, —C($OY_0$)$Y_1$ wherein $Y_0$ is ($C_1$-$C_4$) alkyl and $Y_1$ is ($C_1$-$C_6$)alkyl, carboxy($C_1$-$C_6$)alkyl, amino($C_1$-$C_4$)alkyl or mono-N— or di-N,N—($C_1$-$C_6$)alkylaminoalkyl, or —C($Y_2$)$Y_3$ wherein $Y_2$ is H or methyl and $Y_3$ is mono-N— or di-N,N—($C_1$-$C_6$)alkylamino, morpholino, piperidin-1-yl or pyrrolidin-1-yl.

For additional examples of prodrug derivatives, see, for example, a) *Design of Prodrugs,* edited by H. Bundgaard, (Elsevier, 1985) and *Methods in Enzymology,* Vol. 42, p. 309-396, edited by K. Widder, et al. (Academic Press, 1985); b) *A Textbook of Drug Design and Development,* edited by Krogsgaard-Larsen and H. Bundgaard, Chapter 5 "*Design and Application of Prodrugs,*" by H. Bundgaard p. 113-191 (1991); c) H. Bundgaard, *Advanced Drug Delivery Reviews,* 8:1-38 (1992); d) H. Bundgaard, et al., *Journal of Pharmaceutical Sciences,* 77:285 (1988); and e) N. Kakeya, et al., *Chem. Pharm. Bull.,* 32:692 (1984), each of which is specifically incorporated herein by reference.

Alternatively or additionally, compound of the invention may possess a sufficiently acidic group, a sufficiently basic group, or both functional groups, and accordingly react with any of a number of inorganic or organic bases or acids to form a salt. Examples of salts include those salts prepared by reaction of the compounds of the present invention with a mineral or organic acid or an inorganic base, such salts including, but not limited to, sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyn-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycollates, tartrates, methanesulfonates, propanesulfonates, naphthalene-1-sulfonates, naphthalene-2-sulfonates, and mandelates. Since a single compound of the present invention may include more than one acidic or basic moiety, the compounds of the present invention may include mono, di or tri-salts in a single compound.

If the inventive compound is a base, the desired salt may be prepared by any suitable method available in the art, for example, by treatment of the free base with an acidic compound, for example an inorganic acid such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid such as glucuronic acid or galacturonic acid, an alpha hydroxy acid such as citric acid or tartaric acid, an amino acid such as aspartic acid or glutamic acid, an aromatic acid such as benzoic acid or cinnamic acid, a sulfonic acid such as p-toluenesulfonic acid or ethanesulfonic acid, or the like.

If the inventive compound is an acid, the desired salt may be prepared by any suitable method, for example, by treatment of the free acid with an inorganic or organic base. Examples of suitable inorganic salts include those formed with alkali and alkaline earth metals such as lithium, sodium, potassium, barium and calcium. Examples of suitable organic base salts include, for example, ammonium, dibenzylammonium, benzylammonium, 2-hydroxyethylammonium, bis(2-hydroxyethyl)ammonium, phenylethylbenzylamine, dibenzylethylenediamine, and the like salts. Other salts of acidic moieties may include, for example, those salts formed with procaine, quinine and N-methylglucosamine, plus salts formed with basic amino acids such as glycine, ornithine, histidine, phenylglycine, lysine and arginine.

In certain embodiments, the salt is a "pharmaceutically acceptable salt" which, unless otherwise indicated, includes salts that retain the biological effectiveness of the corresponding free acid or base of the specified compound and are not biologically or otherwise undesirable.

The compounds of Formula I also include other salts of such compounds which are not necessarily pharmaceutically acceptable salts, and which may be useful as intermediates for preparing and/or purifying compounds of Formula I and/or for separating enantiomers of compounds of Formula I.

The present invention also embraces isotopically-labeled compounds of the present invention which are identical to those recited herein, but for the fact that one or more atoms are replaced by an atom having an atomic mass or mass number different from the atomic mass or mass number usually found in nature. All isotopes of any particular atom or element as specified are contemplated within the scope of the compounds of the invention, and their uses. Exemplary isotopes that can be incorporated into compounds of the invention include isotopes of hydrogen, carbon, nitrogen, oxygen, phosphorus, sulfur, fluorine, chlorine and iodine, such as $^2$H, $^3$H, $^{11}$C, $^{13}$C, $^{14}$C, $^{13}$N, $^{15}$N, $^{15}$O, $^{17}$O, $^{18}$O, $^{32}$P, $^{33}$P, $^{35}$S, $^{18}$F, $^{36}$Cl, $^{123}$I, and $^{125}$I. Certain isotopically-labeled compounds of the present invention (e.g., those labeled with $^3$H and $^{14}$C) are useful in compound and/or substrate tissue distribution assays. Tritiated (i.e., $^3$H) and carbon-14 (i.e., $^{14}$C) isotopes are useful for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Positron emitting isotopes such as $^{15}O$, $^{13}N$, $^{11}C$ and $^{18}F$ are useful for positron emission tomography (PET) studies to examine substrate receptor occupancy. Isotopically labeled compounds of the present invention can generally be prepared by following procedures analogous to those disclosed in the Schemes and/or in the Examples herein below, by substituting an isotopically labeled reagent for a non-isotopically labeled reagent.

Metabolites of Compounds of Formula I

Also falling within the scope of this invention are the in vivo metabolic products of compounds of Formula I described herein. A "metabolite" is a pharmacologically active product produced through metabolism in the body of a specified compound or salt thereof. Such products may result, for example, from the oxidation, reduction, hydrolysis, amidation, deamidation, esterification, deesterification, enzymatic cleavage, and the like, of the administered compound. Accordingly, the invention includes metabolites of compounds of Formula I, including compounds produced by a process comprising contacting a compound of this invention with a mammal for a period of time sufficient to yield a metabolic product thereof.

Metabolites are identified, for example, by preparing a radiolabelled (e.g., $^{14}C$ or $^{3}H$) isotope of a compound of the invention, administering it parenterally in a detectable dose (e.g., greater than about 0.5 mg/kg) to an animal such as rat, mouse, guinea pig, monkey, or to a human, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolites, so long as they are not otherwise found in vivo, are useful in diagnostic assays for therapeutic dosing of the compounds of the invention.

Synthesis of Compounds of Formula I

Compounds of this invention may be synthesized by synthetic routes that include processes analogous to those well known in the chemical arts, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1-19, Wiley, N.Y. (1967-1999 ed.), or *Beilsteins Handbuch der organischen Chemie*, 4, Aufl. ed. Springer-Verlag, Berlin, including supplements).

Compounds of Formula I may be prepared singly or as compound libraries comprising at least 2, for example 5 to 1,000 compounds, or 10 to 100 compounds. Libraries of compounds of Formula I may be prepared by a combinatorial 'split and mix' approach or by multiple parallel syntheses using either solution phase or solid phase chemistry, by procedures known to those skilled in the art. Thus according to a further aspect of the invention there is provided a compound library comprising at least 2 compounds of Formula I, or salts thereof.

For illustrative purposes, Schemes 1-4 and Schemes A-J shows a general method for preparing the compounds of the present invention as well as key intermediates. For a more detailed description of the individual reaction steps, see the Examples section below. Those skilled in the art will appreciate that other synthetic routes may be used to synthesize the inventive compounds. Although specific starting materials and reagents are depicted in the Schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

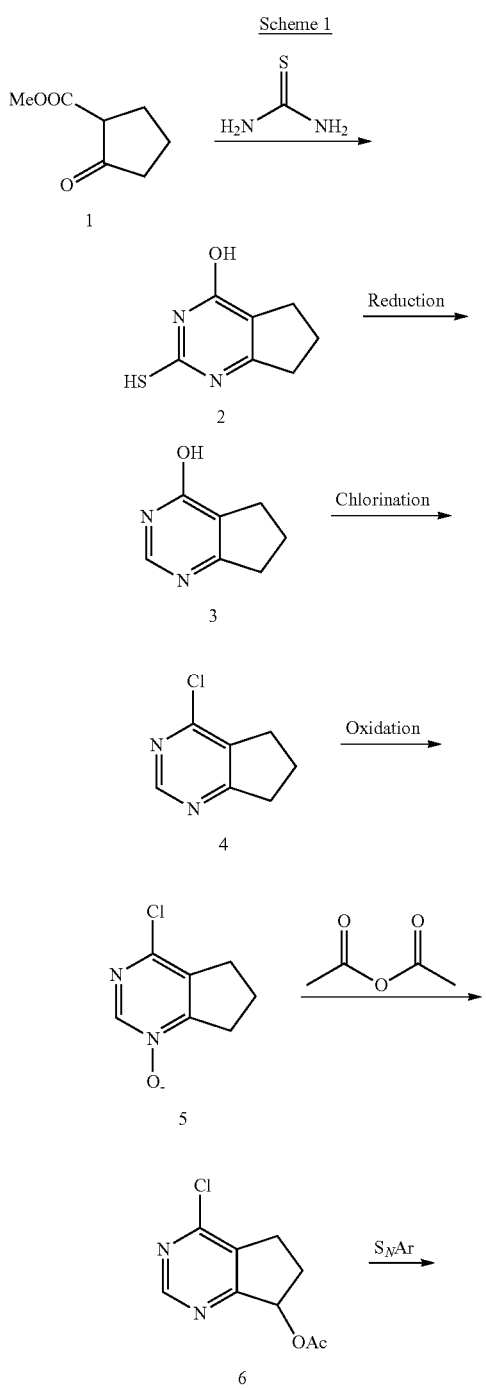

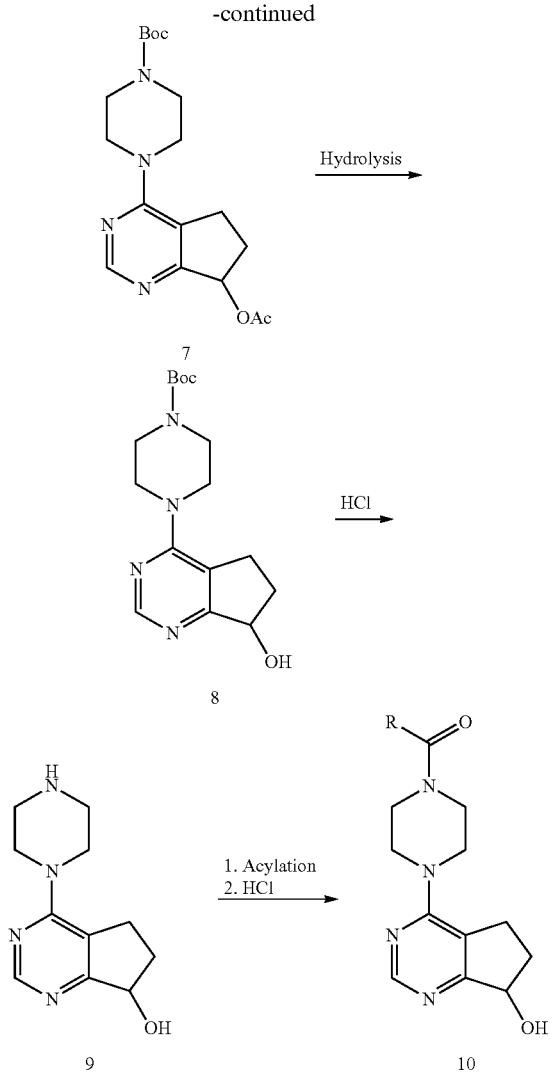

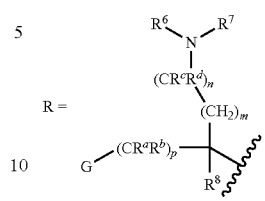

Scheme 1 shows a method of preparing compound 10 of Formula I wherein $R^1$ is H, $R^2$ is OH and $R^5$ is H. Formation of pyrimidine 2 can be accomplished by the reaction of the keto ester 1 with thiourea in the presence of a base such as KOH in an appropriate solvent, such as ethanol. After reduction of the mercapto group of compound 2 under standard reducing conditions (e.g., Raney $N_1$ and $NH_4OH$) to provide compound 3, the hydroxypyrimidine 3 can be chlorinated under standard conditions (e.g., $POCl_3$ in DIEA/DCE) to provide compound 4. Compound 4 is then oxidized under standard conditions (e.g., MCPBA in an appropriate solvent such as $CHCl_3$) to give the pyrimidine-oxide 5. Treatment of the pyrimidine-oxide with acetic anhydride gives the rearrangement product 6. Compound 7 is obtained by reacting compound 6 with an appropriately substituted piperidine under standard $S_NAr$ reaction conditions to provide compound 7. Compound 7 is hydrolyzed to provide compound 8, which is then deprotected to yield the intermediate 9. Acylation of the piperazinyl cyclopenta[d]pyrimidine 9 with an appropriated amino acid in the presence of a coupling reagent such as HBTU, followed by deprotection if necessary, gives compound 10 of Formula I.

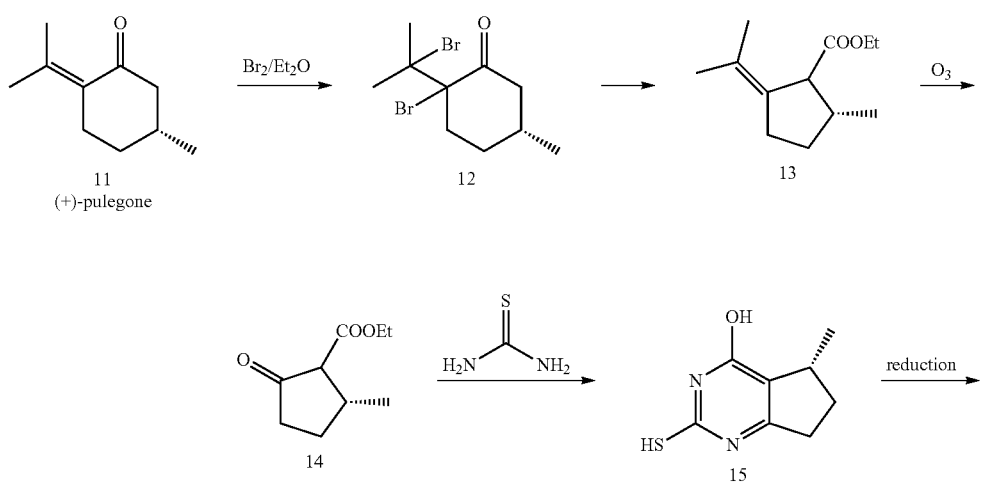

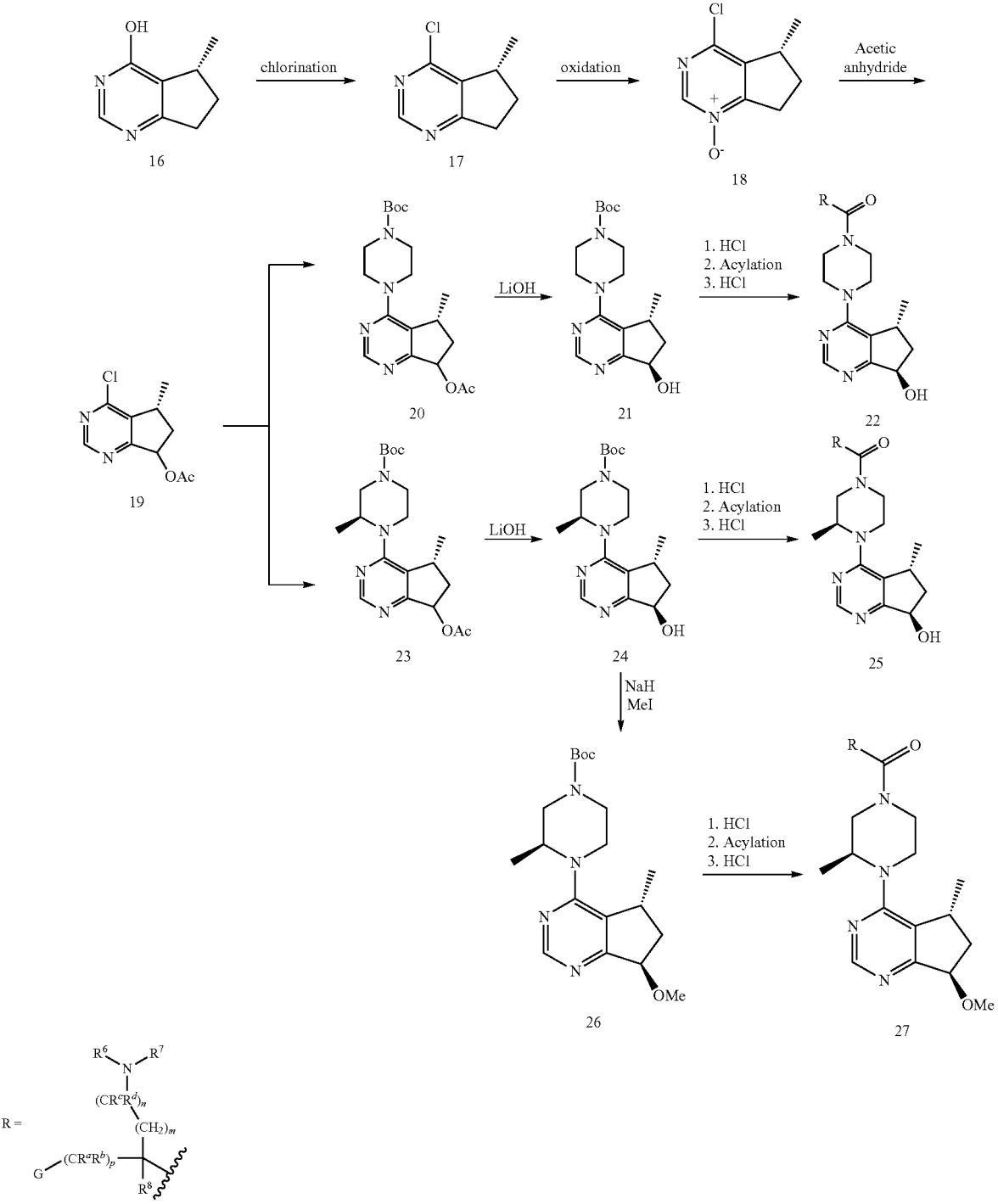

Scheme 2 shows a method of preparing compounds 22, 25 and 27 of Formula I wherein $R^1$, $R^2$ and $R^5$ are methyl. According to Scheme 2, bromination of (+)-pulegone 11 with bromine gives the dibromide 12. The treatment of the dibromide 12 with a base such as sodium ethoxide provides the pulegenate 13. Ozonolysis of the pulegenate 13 gives the ketoester 14. Treatment of the keto ester 14 with thiourea in the presence of a base such as KOH in ethanol, followed by reduction of the mercapto group under standard conditions (e.g. Raney Ni catalyst in ammonia) affords the hydroxypyrimidine 16. Chlorination of the hydroxypyrimidine 16 under standard conditions (e.g., $POCl_3$) provides the 4-chloropyrimidine 17. The oxidation of the 4-chloropyrimidine 17 with an oxidizing agent such as MCPBA or hydrogen peroxide provides the N-oxide 18. Rearrangement of the N-oxide 18 with acetic anhydride yields the intermediate 19. Compound 19 is reacted with the desired piperazine according to the procedure described in Scheme 1 to provide compound 20 where $R^5$ is H and 23 where $R^5$ is Me. Compounds 20 and 23 are subjected to chiral separation using HPLC with chiral stationary and then hydrolyzed upon treatment with a base such as lithium hydroxide to provide compounds 21 and 24, respectively. After deprotection, compounds 21 and 24 are then reacted with the appropriate amino acid to provide compounds 22 and 25, respectively.

Alternatively, the 7-hydroxy group of compound 24 may be alkylated with alkylation reagent such as alkyl halide in the presence of a base such as NaH or KOH to provide compound 26 where $R^2$ is Me. After deprotection, compound 26 is then reacted with the appropriate amino acid to provide compound 27.

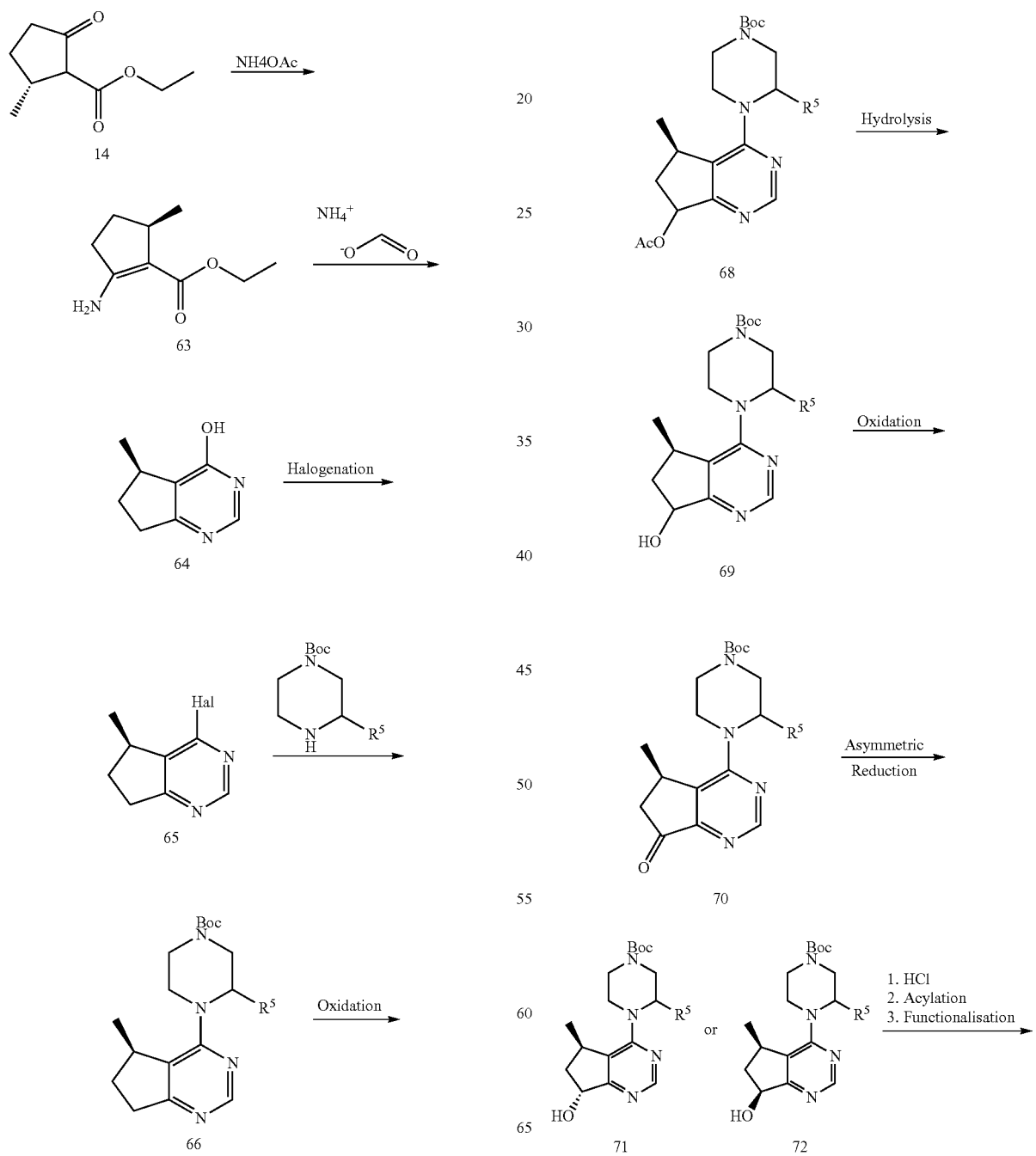

-continued

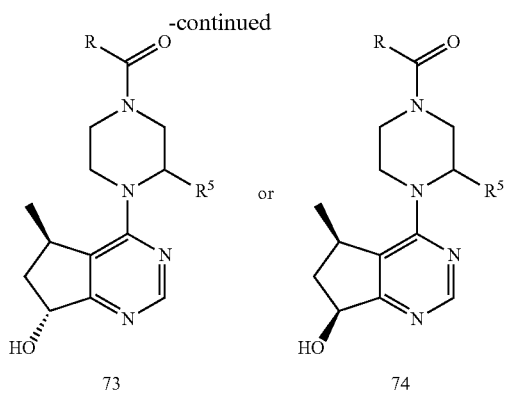

$R^5$ = H, Me, Et, CF3

Scheme 3 shows an alternative method of preparing compounds 73 and 74. According to Scheme 3, amination of 14 using an ammonia synthon gives 63. Pyrimidine formation using, for example, ammonium formate in the presence of formamide at 50° C.-250° C. and/or at high pressure gives the bicyclic unit 64. Activation of 64 using, for example, POCl₃ or SOCl₂ gives the activated pyrimidine 65. Displacement of this leaving group, using a suitable protected/substituted piperidine at 0° C. to 150° C. gives the piperidine 66. Oxidation, using, for example, m-chloroperoxybenzoic acid ("MCPBA" or "m-CPBA") or Oxone® at −20° C. to 50° C. gives the N-oxide 67. Treatment with an acylating agent (eg. acetic anhydride) followed by heating (40° C. to 200° C.) causes rearrangement to give 68. Hydrolysis, using, for example LiOH or NaOH at 0° C. to 50° C. gives the alcohol 69. Oxidation, using for example, Swern conditions, MnO₄ or pyridine-SO₃ complex at appropriate temperatures gives the ketone 70. Asymmetric reduction using, for example, a catalytic chiral catalyst in the presence of hydrogen, the CBS catalyst or a borohydride reducing agent in the presence of a chiral ligand gives rise to either the (R) or the (S) stereochemistry at the alcohol 71 or 72. Alternatively, a non-chiral reducing agent could be used (eg. H₂, Pd/C), allowing the methyl group on the cyclopentane unit to provide facial selectivity and ultimately diastereoselectivity. If the reduction gives a lower diastereoselctivity, the diastereomers could be separated by (for example) chromatography, crystallization or derivitization. Finally deprotection of the Boc-group, using, for example, acid at 0° C. to 50° C., acylation using an appropriately functionalized amino acid and final functionalization of the amine of this amino acid (eg. removal of any protecting group, alkylation, reductive amination or acylation to introduce new substituents) gives rise to the final compounds 73 and 74.

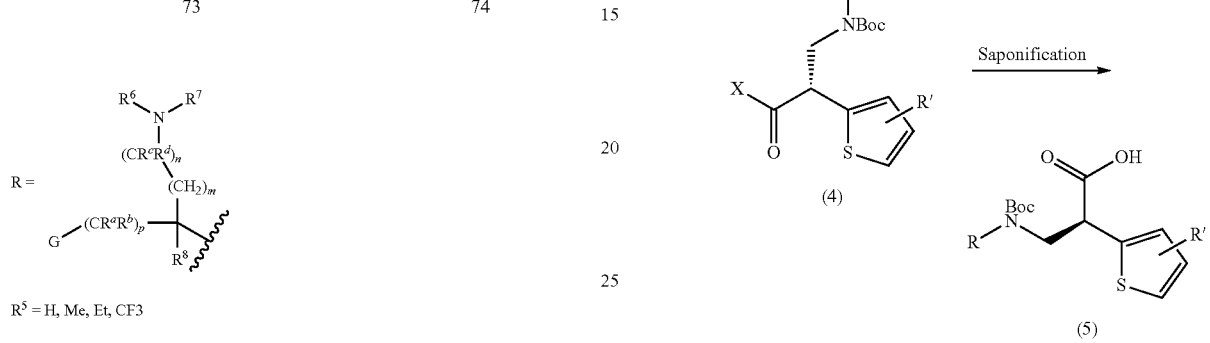

Introduction of a chiral auxiliary (e.g. Evans oxazolidinone, etc.) to compound 1 may be accomplished by standard acylation procedures to give the conjugate 2. For example, treatment of the acid with an activating agent (e.g. COCl₂) or mixed anhydride formation (e.g. 2,2-dimethylpropanoyl chloride) in the presence of an amine base at −20° C. to 100° C. followed by treatment with the appropriate chiral auxiliary (X) gives compound 2. The stereochemistry and choice of the chiral auxiliary may determine the stereochemistry of the newly created chiral center and the diastereoselectivity. Treatment of compound 2 with a Lewis acid (eg. TiCl₄) at low temperature (e.g. −20° C. to −100° C.) and an amine base (e.g. Hunig's base) followed by the use of an appropriately substituted imminium ion precursor 3 at low temperature then gives rise to compound 4. The temperature, Lewis acid and chiral auxiliary may all be expected to influence the diastereoselectivity of the addition adduct. Finally, saponification under mild conditions (e.g. LiOH/H₂O at −10° C. to 30° C.) gives rise to the desired acid 5.

According, another aspect of this invention provides a method of preparing a compound of Formula I, comprising:

reacting a compound having the formula:

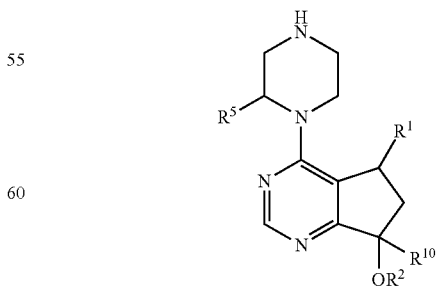

wherein $R^1$, $R^2$, $R^5$ and $R^{10}$ are as defined herein, with an amino acid having the formula:

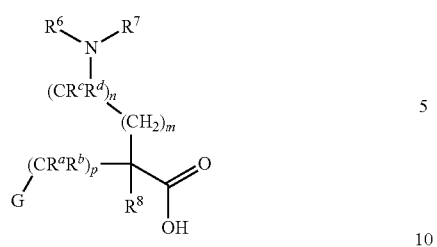

5 wherein $R^6$, $R^7$, $R^a$, $R^b$, $R^c$, $R^d$, G, m, n and p are as defined herein.

The amino acids used in the synthesis of compounds of Formula I as illustrated in Schemes 1-4 and in the Examples are either commercially available or may be prepared according to the methods disclosed herein. For example, in certain embodiments the amino acids used to prepare compounds of Formula I include β-phenylglycine amino acids having the Formula 1A, γ-phenylglycine amino acids having the Formula 2A, β-phenylalanine amino acids having the Formula 3A, and γ-phenylalanine amino acids having the Formula 4A.

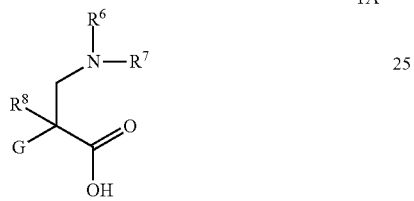

1A

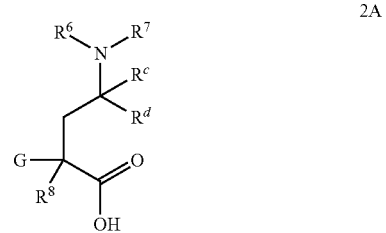

2A

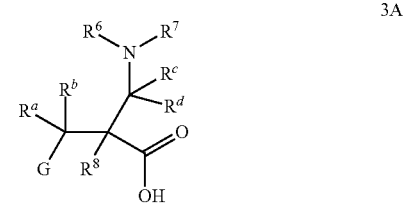

3A

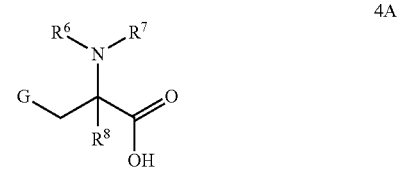

4A

Methods of preparing amino acids of Formulas 1A-4A are shown in Schemes A-J.

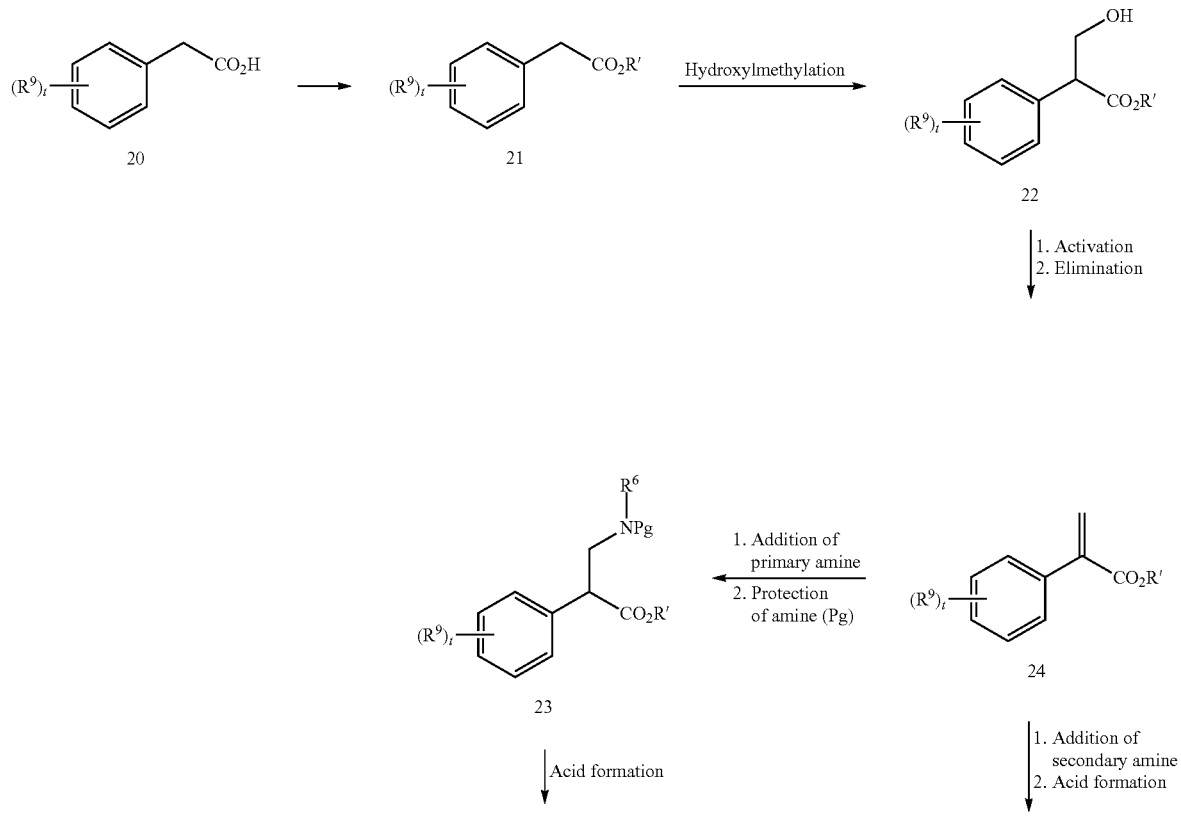

Scheme A

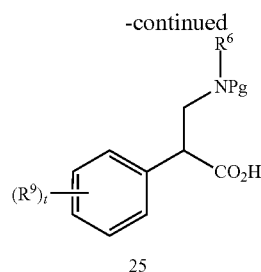

25

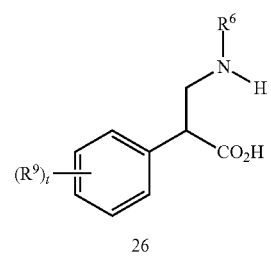

26

Scheme A illustrates a method of preparing optionally substituted β-phenylglycine amino acids 25 and 26 of the Formula 1A wherein $R^8$ is H, and $R^6$, and $R^9$ and are as defined herein, t is 0 to 4, and $R^7$ is H or an amine protecting group. According to Scheme A, the acid 20 is converted to an ester 21 wherein R' is alkyl using standard conditions such as treatment with an appropriate alcohol (e.g. MeOH) in the presence of a catalytic amount of an acid such as concentrated $H_2SO_4$ or a coupling agent such as DCC/DMAP; or alternatively by treatment with an appropriate electrophile (e.g., MeI, EtBr, BnBr) in the presence of a base such as $NEt_3$/DMAP at an appropriate temperature (e.g., −20° C. to 100° C.). The appropriate choice of ester is determined by the conditions required to reform the acid at the end of the synthesis, with many appropriate examples and conditions being listed in 'Protective Groups in Organic Synthesis' by Greene and Wuts, Wiley-Interscience, third edition, Chapter 5. Introduction of the hydroxymethyl group to provide compound 22 may be performed by treatment with an appropriate aldehyde (e.g., formaldehyde) in the presence of base such as NaOEt at an appropriate temperature (e.g., −20° C. to room temperature). Activation of the alcohol group of compound 22 to form a leaving group (e.g., a mesylate, tosylate, halide) may be accomplished by treatment with, for example, methanesulphonyl chloride in the presence of excess base such as $NEt_3$, DIPEA, or DBU at an appropriate temperature (e.g., −20° C. to room temperature). In many cases the olefin 24 can be isolated directly from this procedure, in other cases warming (30° C. to 100° C.) or additional base (e.g. DBU in the case of halide) may be required to complete the elimination to provide compound 24. The activated olefin 24 may be treated with the desired primary amine (e.g., ethylamine) in a suitable solvent, such as THF, at an appropriate temperature (e.g., −20° C. to reflux) to generate the amino ester intermediate. In the case wherein compound 24 has an electron rich aromatic ring or electron poor/bulky primary amine, heating (e.g. 30-240° C. in a sealed tube) or microwave chemistry may be required. Protection of the amine group (for example as Boc-group) may be accomplished using $Boc_2O$ under standard conditions to provide compound 23 wherein Pg is a protecting group. Alternative protecting groups may be used, and many appropriate examples are listed in 'Protective Groups in Organic Synthesis' by Greene and Wuts, Wiley-Interscience, third edition, Chapter 7. Saponification of the ester 23 to form the protected amino acid 25 may be accomplished using conditions appropriate for the ester (e.g., aqueous LiOH for methyl esters, hydrogenation for benzyl esters, acid for t-butyl esters).

Alternatively, the activated olefin 24 may be treated with a secondary amine (e.g., diethylamine) in a suitable solvent such as THF at an appropriate temperature (e.g., −20° C. to reflux) to generate the aminoester intermediate (not shown). In the case wherein compound 24 has an electron rich aromatic ring or electron poor/bulky secondary amine, heating (e.g., 30-240° C. in a sealed tube) or microwave chemistry may be required. Saponification of the ester to form the amino acid 26 may be accomplished using conditions appropriate for the ester (e.g., aqueous LiOH for methyl esters, hydrogenation for benzyl esters, acid for t-butyl esters, etc.).

In an alternative to Scheme A, Pg may be substituted with $R^7$ in compounds 23 and 25.

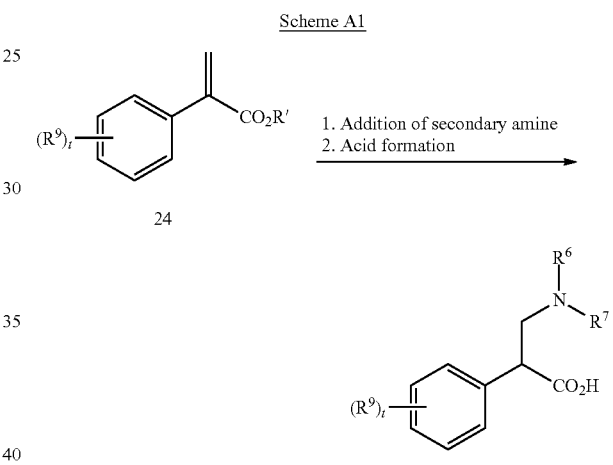

Scheme A1 shows an alternative to Scheme 1, wherein the activated olefin 24 is reacted to form the amino acid 26A.

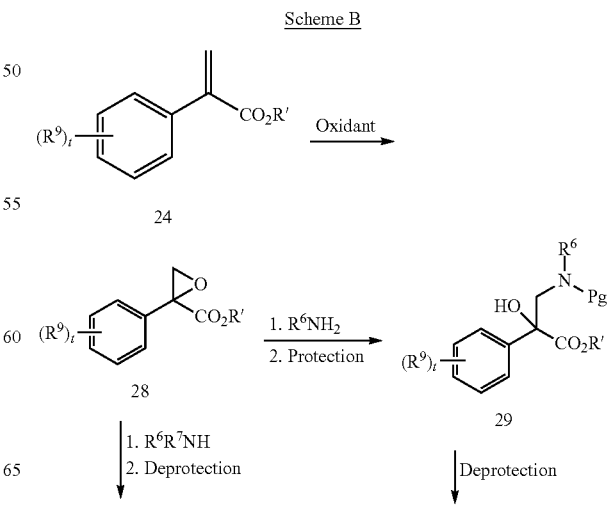

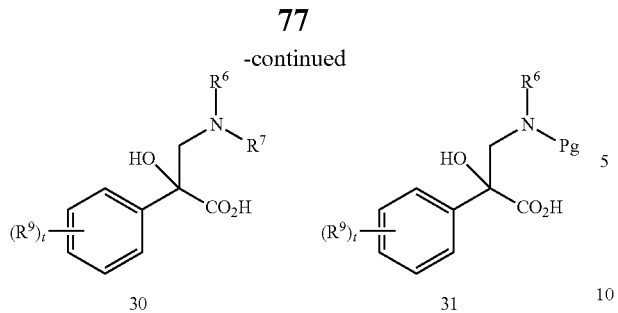

Scheme B shows a method of preparing optionally substituted β-phenylglycine amino acids 30 and 31 of Formula 1A wherein $R^8$ is OH, and $R^6$, and $R^9$ are as defined herein, t is 0 to 4, and $R^7$ is as defined herein or an amine protecting group. Oxidation of the unsaturated ester 24 (prepared according to Scheme A), wherein t is 0-4 and R' is alkyl, using a standard oxidizing agent such as MCPBA at an appropriate temperature (room temperature to reflux) provides the epoxide intermediate 28. Intermediate 28 may be treated with an appropriate amine, typically at high temperature (e.g., 50-300° C.) and high pressure (e.g., in a sealed tube or a bomb) to give the amino alcohol 29 or 30. If a secondary amine is used (such as in the preparation of compound 30), then deprotection of the ester using conditions listed in 'Protective Groups in Organic Synthesis' by Greene and Wuts, Wiley-Interscience, third edition, Chapter 5 may be used (e.g., LiOH for a methyl ester, hydrogenation for a benzyl ester, etc). When a primary amine is used (such as in the preparation of compound 29), protection of the amine (e.g., as a Boc-group using Boc anhydride) followed by deprotection of the ester (using the above conditions) provide the hydroxylated amino acid 31.

Scheme C

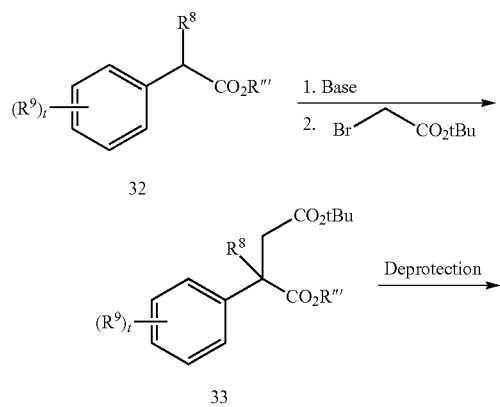

Scheme C shows a method of preparing optionally substituted β-phenylglycine amino acids 36 of the Formula 1A wherein $R^8$ is methyl, $R^6$ is H, $R^7$ is an amine protecting group t is 0 to 4, and $R^9$ is as defined herein. The ester 32, wherein R''' is alkyl, can be treated with a base (e.g. NaOtBu) at an appropriate temperature (e.g., 0° C. to reflux) to form the anion, followed by addition of an electrophile (e.g., tert-butyl 2-bromoacetate) at an appropriate temperature (e.g, –78° C. to room temperature) to give the homologated ester 33. Saponification of the t-butyl ester of compound 33 using an appropriate acid such as TFA or HCl at an appropriate temperature (e.g, 0° C. to reflux) provides compound 34. A Curtius rearrangement of compound 34 using, for example, DPPA in the presence of mild base such as $NEt_3$ at an appropriate temperature (e.g., 0° C. to reflux), followed by treatment of the reactive intermediate with an alcohol (e.g. t-BuOH), optionally in the presence of a Lewis acid (e.g. $SnCl_2$) at higher temperature (e.g., 40-200° C.) provides compound 35 wherein Pg is an amine protecting group. The choice of alcohol used to prepare compound 35 determines the amine protecting group (e.g. t-BuOH provides the Boc-amine). Deprotection of the ester group of compound 35 using standard conditions (e.g., with LiOH when the protecting group is a methyl ester, hydrogenation for a benzyl ester, etc.) gives the acid compound 36.

In one alternative of Scheme C, $R^8$ may be methyl, H or F.

In another alternative of Scheme C, Pg may be substituted with $R^7$ in compounds 35 and 36.

Scheme D

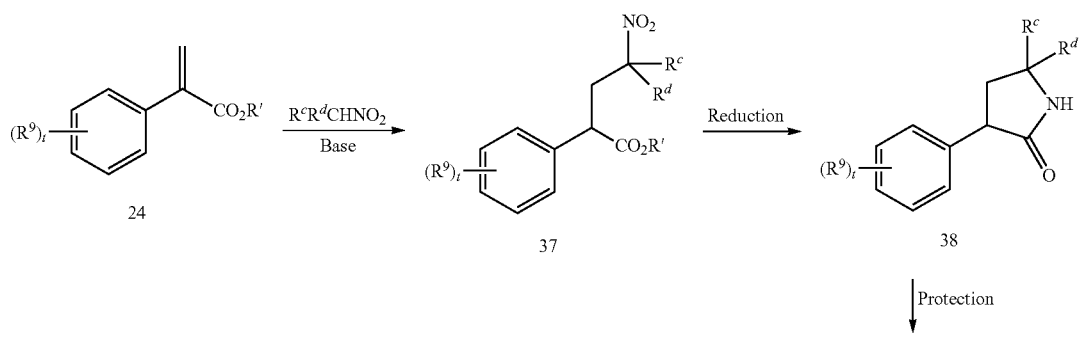

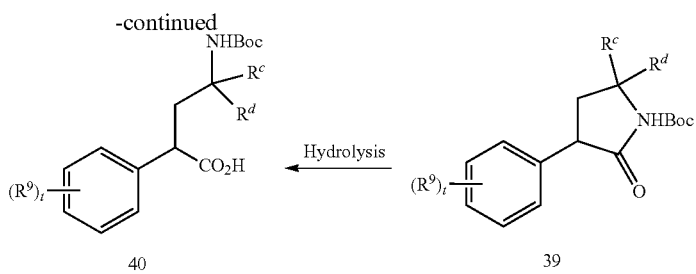

Scheme D shows a method of preparing optionally substituted γ-phenylglycine amino acids 40 of Formula 2A wherein $R^c$, $R^d$, and $R^9$ are as defined herein t is 0 to 4, $R^6$ is H, and $R^7$ is an amine protecting group such as Boc. The starting unsaturated ester 24, prepared according to Scheme A, can be treated with a substituted nitromethane derivative (e.g. nitroethane) in the presence of a base such as DBU at an appropriate temperature (e.g., 0° C. to room temperature) to give the homologated adduct 37. The nitro group of compound 37 can be reduced using standard conditions (e.g., hydrogenation, Zn/acid, etc.) at an appropriate temperature (e.g., room temperature to reflux), and the resulting intermediate can be cyclized to give the lactam intermediate 38. Protection of the amine, for example with a Boc-group to provide compound 39, may be accomplished using $Boc_2O$ under standard conditions. Alternative protecting groups may be used, and many appropriate examples are listed in 'Protective Groups in Organic Synthesis' by Greene and Wuts, Wiley-Interscience, third edition, Chapter 7. Treatment of compound 39 with an aqueous base such as LiOH or KOH at an appropriate temperature (e.g., 0 to 100° C.) effects ring opening of the lactam to give the appropriately substituted protected amino acid compound 40.

In one alternative of Scheme D, Boc may be replaced with $R^7$ in compounds 39 and 40.

Scheme D1

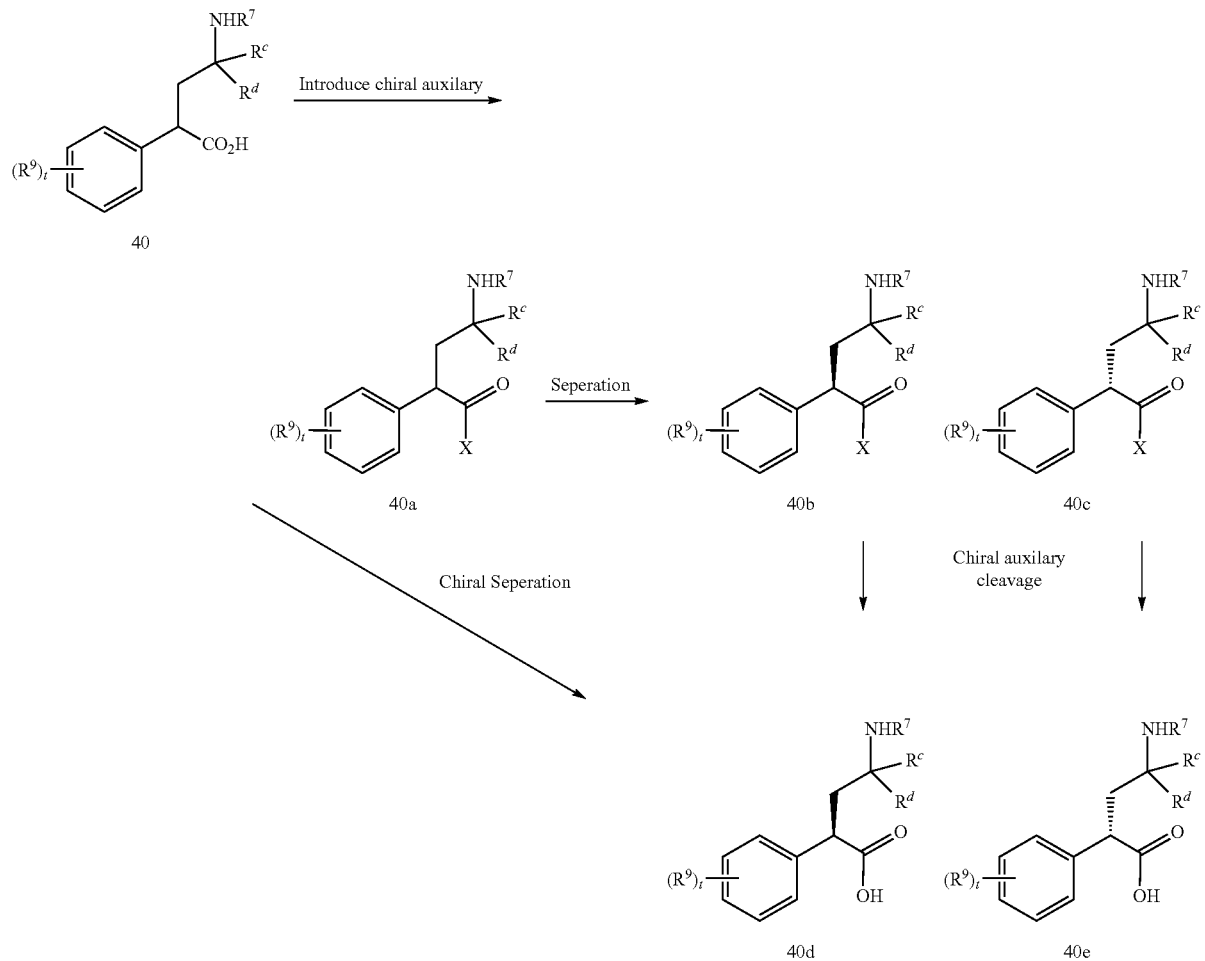

Scheme D1 shows representative methods of forming the single enantionmers of the gamma amino acids 40d and 40e, wherein $R^c$, $R^d$, and $R^9$ are as defined herein, t is 0 to 4, $R^6$ is H, and $R^7$ is an amine protecting group such as Boc. In one possible method, the racemic amino acid is subject to chiral chromatographic separation using a chiral stationary phase. Alternatively, a diastereomeric mixture may be prepared which could be separated by conventional chromatographic techniques. For example, activation of compound 40 (e.g. $COCl_2$, base) and introduction of a chiral auxiliary (e.g. an Evans' oxazolidinone) in the presence of a basic amine (e.g. Hunig's base) at −20° C. to 50° C. gives the diastereomeric mixture of compounds 40b and 40c. This mixture may be separated using standard conditions (e.g. column chromatography, HPLC, SFC, etc.) to give the individual diastereomers. These may be converted to the desired acids by cleavage of the chiral auxiliary (in the case of an Evans' auxiliary, by using (for example) LiOH/HOOH at −15° C. to room temperature) to give the compounds 40d and 40e. The temperature may need to be kept low so as to prevent racemisation of the newly separated chiral center.

Scheme E

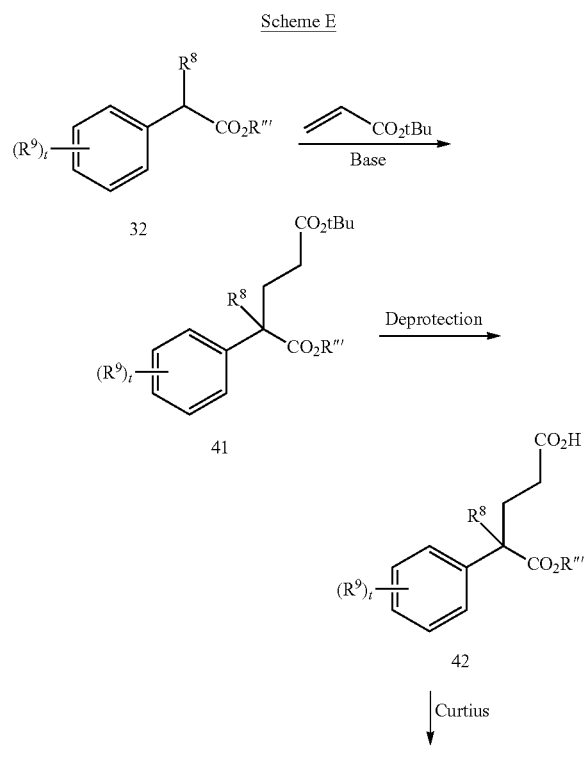

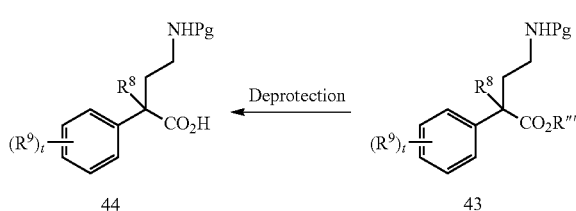

Scheme E shows a method of making optionally substituted γ-phenylglycine amino acids 44 of Formula 2A wherein $R^8$ is methyl, $R^6$ is H, $R^7$ is an amine protecting group, t is 0 to 4, and $R^9$ is as defined herein. The ester 32, wherein R''' is alkyl and t is 0-4, can be treated with a suitable base such as KOtBu at an appropriate temperature (e.g., 0° C. to reflux) to form the anion, followed by addition of an acrylate unit (e.g., t-butylacrylate) at a temperature ranging from −78° C. to room temperature to give the homologated ester 41. Saponification of the t-butyl ester of compound 41 by treatment with a suitable acid such as TFA or HCl at an appropriate temperature (e.g, 0° C. to reflux) provides compound 42. A Curtius rearrangement of compound 42 using, for example, DPPA in the presence of mild base such as $NEt_3$ at an appropriate temperature (e.g., 0° C. to reflux), followed by treatment of the reactive intermediate with an appropriate alcohol (e.g. tBuOH), optionally in the presence of a Lewis acid (e.g. $SnCl_2$) at elevated temperatures (e.g. 40-200° C.) provides compound 43. The choice of alcohol determines the amine protecting group of compound 43 (e.g., tBuOH provides the Boc-amine). Deprotection of the ester of compound 43 under standard conditions (e.g., LiOH for a methyl ester, hydrogenation for a benzyl ester, etc.) gives the acid 44.

In one alternative to Scheme E, Pg may be substituted with $R^7$ in compounds 43 and 44.

Scheme F

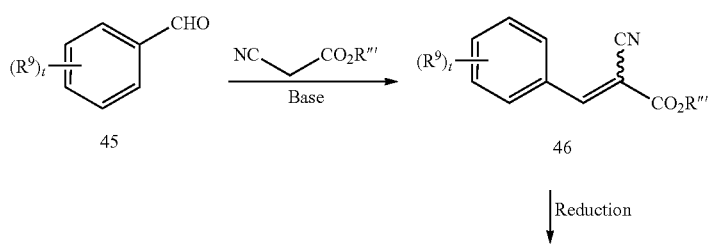

83

-continued

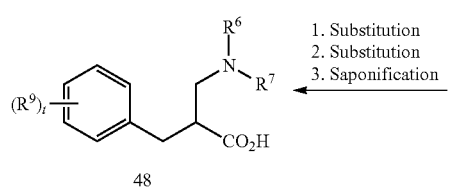 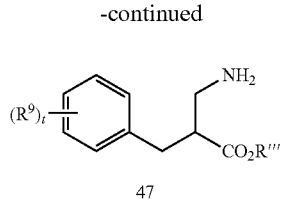 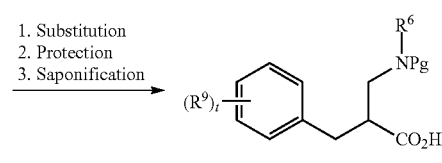

48    47    49

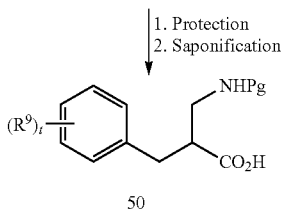

50

Scheme F shows a method of preparing optionally substituted 3-phenylalanine amino acids 48, 49 and 50 of Formula 3A wherein $R^6$ is H, $R^7$ is an amine protecting group, t is 0 to 4, and $R^9$ is as defined herein. An appropriately substituted aldehyde 45 can be treated with a cyanoacetate of the formula $CN-CH_2CO_2R'''$ wherein R''' is alkyl (e.g., ethyl 2-cyanoacetate) in the presence of a suitable base such as piperidine at an appropriate temperature (e.g., room temperature to reflux) to give the unsaturated ester 46. Reduction of the olefin and the nitrile groups of compound 46 to provide compound 47 may be accomplished in a number of ways. For example, the olefin may be reduced with any agent known to effect 1,4-reductions, such as $NaBH_4$. The nitrile may be reduced using agents such as $LiAlH_4$ or $NaBH_4$ in the presence of a Lewis acid such as $BF_3^-OEt_2$ or TFA. A number of alternative reducing agents may be used, such as those listed in 'Reductions in Organic Chemistry' by Hudlicky, ACS monograph, $2^{nd}$ edition, Chapter 18. If desired, the primary amine 47 can be monoalkylated or bisalkylated at this stage using standard conditions (e.g., reductive amination using an appropriate aldehyde, Lewis acid and reducing agent) to provide intermediates (not shown) en route to compounds 48 and 49. To prepare primary and secondary amines, protection may be accomplished using any number of protecting groups (e.g. 'Protective Groups in Organic Synthesis' by Greene and Wuts, Wiley-Interscience, third edition, Chapter 7), for example as a Boc-group using Boc anhydride at 0° C. to room temperature. Cleavage of the ester group to form the amino acid 48, 49 or 50 may be accomplished using an aqueous bases such as LiOH or KOH, or any of the alternative reagents listed in the aforementioned 'Protecting Groups' text (e.g., hydrogenation for a benzyl ester).

In one alternative to Scheme F, Pg may be substituted with $R^7$ in compounds 49 or 50.

Scheme G

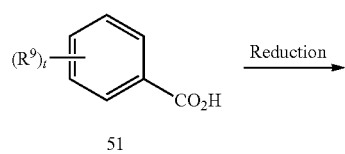

51

84

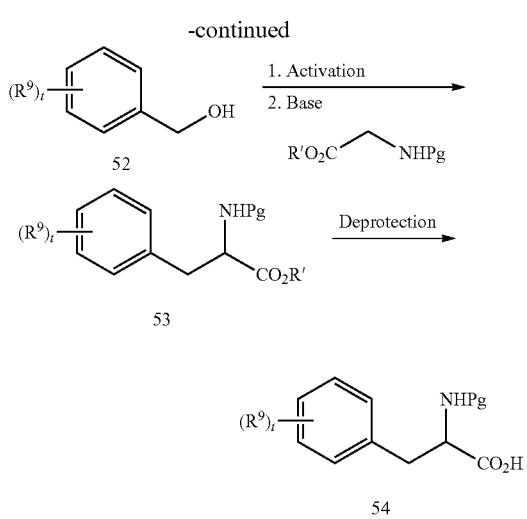

Scheme G shows a method of preparing optionally substituted α-phenylalanine amino acids 54 of Formula 4A, wherein $R^6$ is H, $R^7$ is an amine protecting group, t is 0 to 4, and $R^9$ is as defined herein. An appropriately substituted acid 51 may be reduced to the benzyl alcohol 52 using for example $LiAlH_4$ at a temperature ranging from room temperature to reflux. The alcohol group of compound 52 can be activated as a leaving group (e.g. halide, mesylate, etc.) using, for example, $PBr_3$, $MsCl/NEt_3$, etc. Displacement of this leaving group using a protected glycine derivative such as ethyl 2-(diphenylmethyleneamino)acetate in the presence of strong base such as LDA, nBuLi provides the amino ester intermediate 53 wherein $R^1$ is alkyl and Pg is a protecting group. Appropriate protecting groups are listed in 'Protective Groups in Organic Synthesis' by Greene and Wuts, Wiley-Interscience). The amine protecting group may be changed at this stage, for example to introduce a Boc-group. Subsequent deprotection of the ester 53 (e.g., using 3N HCl, LiOH, hydrogenation for a benzyl ester, etc.) at an appropriate temperature (e.g., 0° C. to reflux) provides the desired N-protected amino acid 54.

In one alternative to Scheme G, Pg may be substituted with $R^7$ in compound 54 after the deprotection of compound 53.

Scheme H

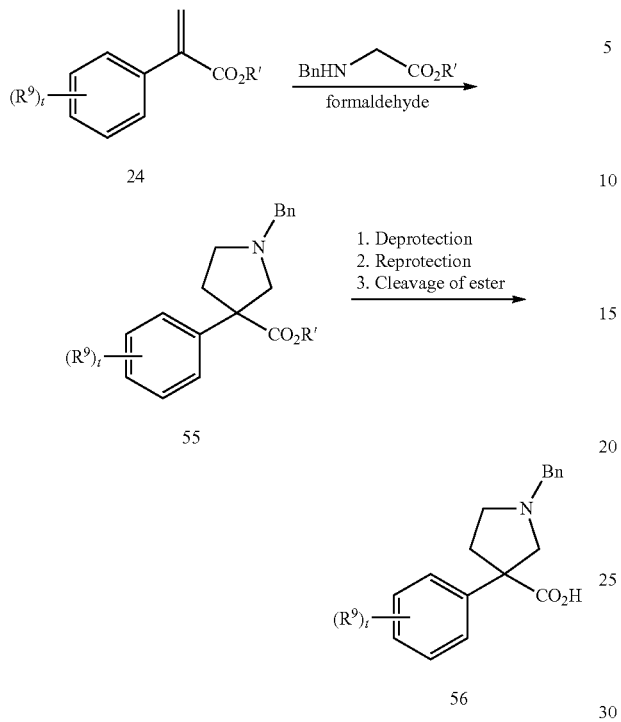

Scheme H shows a method of preparing optionally substituted γ-phenylglycine amino acids 56 of Formula 2A wherein $R^6$ and $R^8$ together with the atoms to which they are attached form a spirocyclic heterocyclic ring, $R^7$ is an amine protecting group, t is 0 to 4, and $R^9$ is as defined herein. According to Scheme H, the unsaturated ester 24 can be treated with a suitably protected glycine derivative (e.g., benzylglycine) and formaldehyde under dry conditions (e.g., with addition of molecular sieves) at an appropriate temperature (e.g., room temperature to reflux) to generate compound 55. Cleavage of the benzyl group using standard conditions (e.g., via hydrogenation, 1-chloroethylformate, etc.) followed by addition of an amine protecting group such as a Boc-group and cleavage of the ester under standard conditions (e.g. LiOH for a methyl ester, acid for a t-butyl ester, etc., at 0° C. to reflux) provides the N-protected amino acid 56.

In one alternative to Scheme H, Pg may be substituted with $R^7$ in compound 56.

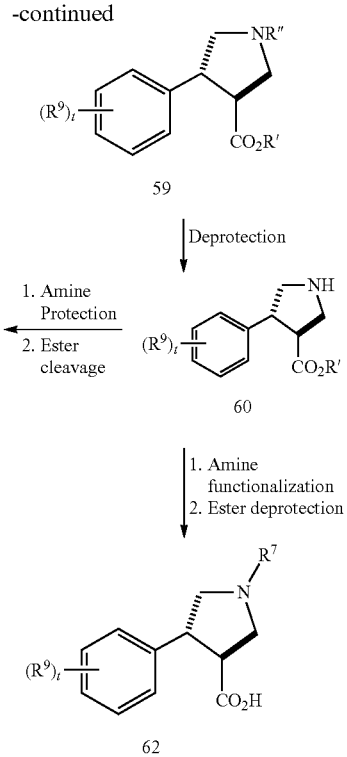

Scheme I shows a method of preparing optionally substituted β-phenylalanine amino acids 61 and 62 of Formula 3A wherein $R^6$ and $R^b$ together with the atoms to which they are attached form a heterocyclic ring, and $R^7$ and $R^9$ are as defined herein and t is 0 to 4. The acid 57 is converted to an ester 58 using standard conditions such as treatment with an appropriate alcohol (e.g., MeOH) in the presence of either catalytic acid (e.g. concentrated $H_2SO_4$ or TMSCl) or a coupling agent (e.g. DCC/DMAP); or alternatively by treatment with an appropriate electrophile (e.g. MeI, EtBr, BnBr) in the presence of a suitable base such as $NEt_3$/DMAP at appropriate temperatures (e.g., −20° C. to 100° C.). The appropriate choice of ester is determined by the conditions required to reform the acid at the end of the synthesis, such as described in 'Protective Groups in Organic Synthesis' by Greene and Wuts, Wiley-Interscience, third edition, Chapter 5. Cyclization of compound 58 to provide compound 59 may be achieved using, for example, N-(methoxymethyl)(phenyl)-N-((trimethylsilyl)methyl)methanamine in the presence of TFA. This particular set of reagents generates the benzylamine, which can be cleaved to provide compound 60 under standard conditions such as such as hydrogenation at −20° C. to 50° C. or any other standard conditions such as those listed in 'Protective Groups in Organic Synthesis' by Greene and Wuts, Wiley-Interscience, third edition, Chapter 7. Protection of the free amine of compound 60 with an alternative protecting group (e.g., Boc) using reagents listed in the aforementioned text, such as Boc-anhydride, followed by cleavage of the ester using standard conditions appropriate for the ester (e.g. aqueous LiOH for methyl esters, hydrogenation for benzyl esters, acid for t-butyl esters) provides the acid compound 61. Alternatively, the free amine can be functionalized further (e.g. using alkylation, reductive amination, or acylation conditions), followed by ester cleavage to generate the tertiary amino acid compound 62.

Scheme J

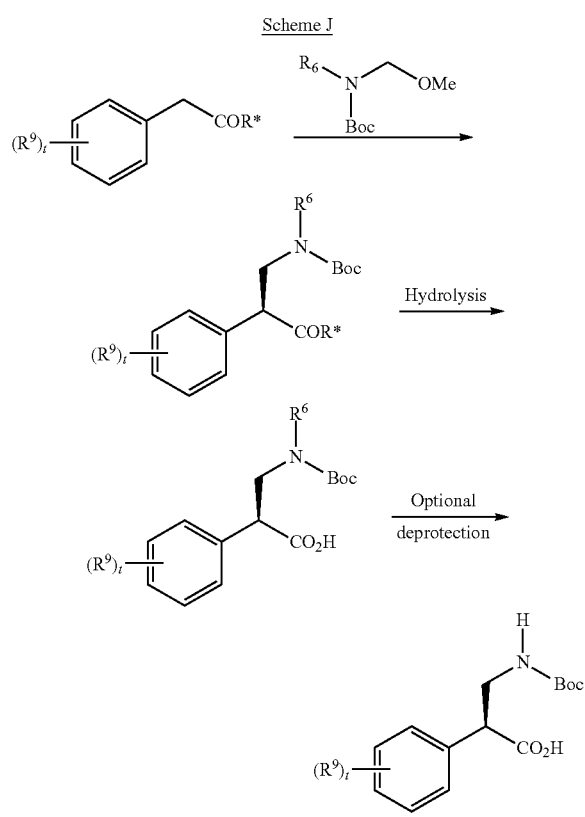

Either enantiomer of the b-amino acids may be prepared using a procedure such as that shown in Scheme J. A 2-phenylacetate coupled with an appropriate chiral auxillary (R*) (for example, an Evans' auxiliary or a Sultam) with the appropriate stereochemistry to generate the desired chemistry at the b-position of the amino acid may be treated with an imine or iminium ion synthon (e.g. prepared in situ by the presence of a Lewis acid (eg. TiCl$_4$) and an appropriately substituted alkoxymethanamine or N-(alkoxymethyl)amide/carbamate at −100° C. to 50° C.). The asymmetric addition may require the presence of Lewis acids (eg. TiCl$_4$), amine bases (eg. Hunig's base) and lower temperatures (e.g. −100° C. to 0° C.) to generate the best levels of stereochemical induction. If the de is lower than required, the separate diastereomers may be separated at this stage by (for example) chromatography or crystallization. Cleavage of the chiral auxillary, using methods known to cleave the chosen auxiliary (e.g. LiOH/H$_2$O$_2$ at −50° C. to 50° C. for the Evans auxiliary) then leads to the desired N-protected b-amino acid with the desired stereochemistry at the b-position. Additionally, if R$^6$ is also a protecting group (e.g. 2,4-dimethoxybenzyl), it may be removed in the presence of the Boc-group (e.g. hydrogenation or DDQ, etc.) to give the Boc-amino acid, which upon removal of the Boc-group would provide the primary amine, which may be further functionalized by alkylation, acylation or reductive amination (either prior to or after coupling with the pyrimidine-piperazine unit).

In preparing compounds of Formula I, protection of remote functionalities (e.g., primary or secondary amines, etc.) of intermediates may be necessary. The need for such protection will vary depending on the nature of the remote functionality and the conditions of the preparation methods. Suitable amino-protecting groups (NH-Pg) include acetyl, trifluoroacetyl, t-butoxycarbonyl (BOC), benzyloxycarbonyl (CBz) and 9-fluorenylmethyleneoxycarbonyl (Fmoc). The need for such protection is readily determined by one skilled in the art. For a general description of protecting groups and their use, see T. W. Greene, Protective Groups in Organic Synthesis, John Wiley & Sons, New York, 1991.

Methods of Separation

In any of the synthetic methods for preparing compounds of Formula I, it may be advantageous to separate reaction products from one another and/or from starting materials. The desired products of each step or series of steps is separated and/or purified to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a reaction mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like.

Selection of appropriate methods of separation depends on the nature of the materials involved. For example, boiling point and molecular weight in distillation and sublimation, presence or absence of polar functional groups in chromatography, stability of materials in acidic and basic media in multiphase extraction, and the like. One skilled in the art will apply techniques most likely to achieve the desired separation.

Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Also, some of the compounds of the present invention may be atropisomers (e.g., substituted biaryls) and are considered as part of this invention. Enantiomers can also be separated by use of a chiral HPLC column.

A single stereoisomer, e.g., an enantiomer, substantially free of its stereoisomer may be obtained by resolution of the racemic mixture using a method such as formation of diastereomers using optically active resolving agents (Eliel, E. and Wilen, S. "Stereochemistry of Organic Compounds," John Wiley & Sons, Inc., New York, 1994; Lochmuller, C. H., J. Chromatogr., (1975) 113(3):283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: "Drug Stereochemistry, Analytical Methods and Pharmacology," Irving W. Wainer, Ed., Marcel Dekker, Inc., New York (1993).

Under method (1), diastereomeric salts can be formed by reaction of enantiomerically pure chiral bases such as brucine, quinine, ephedrine, strychnine, α-methyl-β-phenyl-ethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (E. and Wilen, S. "Stereochemistry of Organic Compounds", John Wiley & Sons, Inc., 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g., (−)menthyl chloroformate in the presence of base, or Mosher ester, α-methoxy-α-(trifluoromethyl)phenyl acetate (Jacob III. *J. Org. Chem*., (1982) 47:4165), of the racemic mixture, and analyzing the $^1$H NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 96/15111). By method (3), a racemic mixture of two enantiomers can be separated by chromatography using a chiral stationary phase ("Chiral Liquid Chromatography" (1989) W. J. Lough, Ed., Chapman and Hall, New York; Okamoto, *J. of Chromatogr*., (1990) 513:375-378). Enriched or purified enantiomers can be distinguished by methods used to distinguish other chiral molecules with asymmetric carbon atoms, such as optical rotation and circular dichroism.

Methods of Treatment with Compounds of Formula I

The compounds of the present invention can be used as prophylactics or therapeutic agents for treating diseases or disorders mediated by modulation or regulation of AKT protein kinases, tyrosine kinases, additional serine/threonine kinases, and/or dual specificity kinases. AKT protein kinase mediated conditions that can be treated according to the methods of this invention include, but are not limited to, inflammatory, hyperproliferative cardiovascular, neurodegenerative, gynecological, and dermatological diseases and disorders.

In one embodiment, said pharmaceutical composition is for the treatment of hyperproliferative disorders, including cancers of the following categories: (1) Cardiac: sarcoma (angiosarcoma, fibrosarcoma, rhabdomyosarcoma, liposarcoma), myxoma, rhabdomyoma, fibroma, lipoma and teratoma; (2) Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma, non-small cell lung, small cell lung; (3) Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); (4) Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); (5) Liver: hepatoma (hepatocellular carcinoma), cholangiocarcinoma, hepatoblastoma, angiosarcoma, hepatocellular adenoma, hemangioma; (6) Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; (7) Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform. oligodendroglioma, schwannoma, retinoblastoma, congenital tumors), spinal cord neurofibroma, meningioma, glioma, sarcoma); (8) Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); (9) Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; (10) Skin: advanced melanoma, malignant melanoma, basal cell carcinoma, squamous cell carcinoma, Karposi's sarcoma, moles dysplastic nevi, lipoma, angioma, dermatofibroma, keloids, psoriasis; (11) Adrenal glands: neuroblastoma; (12) Breast: metastatic breast; breast adenocarcinoma; (13) Colon; (14) Oral cavity; (15) Hairy cell leukemia; (16) Head and neck; (17) and others including refractory metastatic disease; Kaposi's sarcoma; Bannayan-Zonana syndrome; and Cowden disease or Lhermitte-Duclos disease, among other kinds of hyperproliferative disorders.

Compounds and methods of this invention can be also used to treat diseases and conditions such as rheumatoid arthritis, osteoarthritis, Chron's disease, angiofibroma, ocular diseases (e.g., retinal vascularisation, diabetic retinopathy, age-related macular degeneration, macular degeneration, etc.), multiple sclerosis, obesity, Alzheimer's disease, restenosis, autoimmune diseases, allergy, asthma, endometriosis, atherosclerosis, vein graft stenosis, peri-anastomatic prothetic graft stenosis, prostate hyperplasia, chronic obstructive pulmonary disease, psoriasis, inhibition of neurological damage due to tissue repair, scar tissue formation (and can aid in wound healing), multiple sclerosis, inflammatory bowel disease, infections, particularly bacterial, viral, retroviral or parasitic infections (by increasing apoptosis), pulmonary disease, neoplasm, Parkinson's disease, transplant rejection (as an immunosupressant), septic shock, etc.

Accordingly, another aspect of this invention provides a method of treating diseases or medical conditions in a mammal mediated by AKT protein kinases, comprising administering to said mammal one or more compounds of Formula I or a pharmaceutically acceptable salt or prodrug thereof in an amount effective to treat or prevent said disorder.

The phrase "effective amount" means an amount of compound that, when administered to a mammal in need of such treatment, is sufficient to (i) treat or prevent a particular disease, condition, or disorder mediated by the activity of one or more AKT protein kinases, tyrosine kinases, additional serine/threonine kinases, and/or dual specificity kinases, (ii) attenuate, ameliorate, or eliminate one or more symptoms of the particular disease, condition, or disorder, or (iii) prevent or delay the onset of one or more symptoms of the particular disease, condition, or disorder described herein. In the case of cancer, an effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can be measured, for example, by assessing the time to disease progression (TTP) and/or determining the response rate (RR).

The amount of a compound of Formula I that will correspond to such an amount will vary depending upon factors such as the particular compound, disease condition and its severity, the identity (e.g., weight) of the mammal in need of treatment, but can nevertheless be routinely determined by one skilled in the art.

"Treating" is intended to mean at least the mitigation of a disease condition in a mammal, such as a human, that is affected, at least in part, by the activity of one or more AKT protein kinases, tyrosine kinases, additional serine/threonine kinases, and/or dual specificity kinases. The terms "treat" and "treatment" refer to both therapeutic treatment and prophylactic or preventative measures, wherein the object is to prevent or slow down (lessen) an undesired physiological change or disorder. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those found to be predisposed to having the disease condition but have not yet been diagnosed as having it; modulating and/or inhibiting the disease condition. The terms "treating", "treat", or "treatment" embrace both preventative, i.e., prophylactic, and palliative treatment.

As used herein, the term "mammal" refers to a warm-blooded animal that has or is at risk of developing a disease described herein and includes, but is not limited to, guinea pigs, dogs, cats, rats, mice, hamsters, and primates, including humans.

This invention also provides compounds of Formula I for use in the treatment of AKT protein kinase-mediated conditions.

An additional aspect of the invention is the use of a compound of Formula I in the preparation of a medicament for therapy, such as for the treatment or prevention of AKT protein kinase-mediated conditions.

Combination Therapy

The compounds of the present invention can be used in combination with one or more additional drugs such as described below. The dose of the second drug can be appropriately selected based on a clinically employed dose. The proportion of the compound of the present invention and the second drug can be appropriately determined according to the administration subject, the administration route, the target disease, the clinical condition, the combination, and other factors. In cases where the administration subject is a human, for instance, the second drug may be used in an amount of 0.01 to 100 parts by weight per part by weight of the compound of the present invention.

The second compound of the pharmaceutical combination formulation or dosing regimen preferably has complementary activities to the compound of this invention such that they do not adversely affect each other. Such drugs are suitably present in combination in amounts that are effective for the purpose intended. Accordingly, another aspect of the present invention provides a composition comprising a compound of this invention in combination with a second drug, such as described herein.

A compound of this invention and the additional pharmaceutically active drug(s) may be administered together in a unitary pharmaceutical composition or separately and, when administered separately this may occur simultaneously or sequentially in any order. Such sequential administration may be close in time or remote in time. The amounts of the compound of this invention and the second drug(s) and the relative timings of administration will be selected in order to achieve the desired combined therapeutic effect.

The combination therapy may provide "synergy" and prove "synergistic", i.e., the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g., by different injections in separate syringes. In general, during alternation therapy, an effective dosage of each active ingredient is administered sequentially, i.e., serially, whereas in combination therapy, effective dosages of two or more active ingredients are administered together.

A "chemotherapeutic agent" is a chemical compound useful in the treatment of cancer, regardless of mechanism of action. Chemotherapeutic agents include compounds used in "targeted therapy" and conventional chemotherapy.

Examples of chemotherapeutic agents include Erlotinib (TARCEVA®, Genentech/OSI Pharm.), Bortezomib (VELCADE®, Millennium Pharm.), Fulvestrant (FASLODEX®, AstraZeneca), Sutent (SU11248, Pfizer), Letrozole (FEMARA®, Novartis), Imatinib mesylate (GLEEVEC®, Novartis), PTK787/ZK 222584 (Novartis), Oxaliplatin (Eloxatin®, Sanofi), 5-FU (5-fluorouracil), Leucovorin, Rapamycin (Sirolimus, RAPAMUNE®, Wyeth), Lapatinib (TYKERB®, GSK572016, Glaxo Smith Kline), Lonafarnib (SCH 66336), Sorafenib (BAY43-9006, Bayer Labs), Irinotecan (CAMPTOSAR®, Pfizer) and Gefitinib (IRESSA®, AstraZeneca), AG1478, AG1571 (SU 5271; Sugen), alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaI1 and calicheamicin omegaI1 (Angew Chem. Intl. Ed. Engl. (1994) 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2''-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® (paclitaxel; Bristol-Myers Squibb Oncology, Princeton, N.J.), ABRAXANE™ (Cremophor-free), albumin-engineered nanoparticle formulations of paclitaxel (American Pharmaceutical Partners, Schaumberg, Ill.), and TAXOTERE® (doxetaxel; Rhone-Poulenc Rorer, Antony, France); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylornithine (DMFO); retinoids such as retinoic acid; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; a topoisomerase 1 inhibitor such as LURTOTECAN®; ABARELIX® rmRH; (ix) anti-angiogenic agents such as bevacizumab (AVASTIN®, Genentech); and (x) pharmaceutically acceptable salts, acids and derivatives of any of the above.

Also included in the definition of "chemotherapeutic agent" are therapeutic antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG®, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth).

Humanized monoclonal antibodies with therapeutic potential as chemotherapeutic agents in combination with the PI3K inhibitors of the invention include: alemtuzumab, apolizumab, aselizumab, atlizumab, bapineuzumab, bevacizumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pertuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, trastuzumab, tucotuzumab celmoleukin, tucusituzumab, umavizumab, urtoxazumab, and visilizumab.

Routes of Administration

The compounds of the invention may be administered by any route appropriate to the condition to be treated. Suitable routes include oral, parenteral (including subcutaneous, intramuscular, intravenous, intraarterial, intradermal, intrathecal and epidural), transdermal, rectal, nasal, topical (including buccal and sublingual), vaginal, intraperitoneal, intrapulmonary and intranasal. It will be appreciated that the preferred route may vary with for example the condition of the recipient. Where the compound is administered orally, it may be formulated as a pill, capsule, tablet, etc. with a pharmaceutically acceptable carrier or excipient. Where the compound is administered parenterally, it may be formulated with a pharmaceutically acceptable parenteral vehicle and in a unit dosage injectable form, as detailed below.

Pharmaceutical Formulations

In order to use a compound of this invention for the therapeutic treatment (including prophylactic treatment) of mammals including humans, it is normally formulated in accordance with standard pharmaceutical practice as a pharmaceutical composition. According to this aspect of the invention there is provided a pharmaceutical composition that comprises a compound of this invention. In certain embodiments, the pharmaceutical composition comprises a compound of Formula I in association with a pharmaceutically acceptable diluent or carrier.

The pharmaceutical compositions of the invention are formulated, dosed and administered in a fashion, i.e., amounts, concentrations, schedules, course, vehicles and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The therapeutically effective amount of the compound to be administered will be governed by such considerations, and is the minimum amount necessary to prevent, ameliorate, or treat the disorder. The compound of the present invention is typically formulated into pharmaceutical dosage forms to provide an easily controllable dosage of the drug and to enable patient compliance with the prescribed regimen.

The composition for use herein is preferably sterile. In particular, formulations to be used for in vivo administration must be sterile. Such sterilization is readily accomplished, for example, by filtration through sterile filtration membranes. The compound ordinarily can be stored as a solid composition, a lyophilized formulation or as an aqueous solution.

Pharmaceutical formulations of the compounds of the present invention may be prepared for various routes and types of administration. For example, a compound of this invention having the desired degree of purity may optionally be mixed with pharmaceutically acceptable diluents, carriers, excipients or stabilizers (Remington's Pharmaceutical Sciences (1980) 16th edition, Osol, A. Ed.), in the form of a lyophilized formulation, a milled powder, or an aqueous solution. Formulation may be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may range from about 3 to about 8. Formulation in an acetate buffer at pH 5 is a suitable embodiment. The formulations may be prepared using conventional dissolution and mixing procedures. For example, the bulk drug substance (i.e., compound of the present invention or stabilized form of the compound (e.g., complex with a cyclodextrin derivative or other known complexation agent) is dissolved in a suitable solvent in the presence of one or more excipients.

The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). The formulations may also include one or more stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament). The active pharmaceutical ingredients may also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nanoparticles and nanocapsules) or in macroemulsions. Such techniques are disclosed in Remington's Pharmaceutical Sciences 16th edition, Osol, A. Ed. (1980). A "liposome" is a small vesicle composed of various types of lipids, phospholipids and/or surfactant which is useful for delivery of a drug (such as a compound of Formula I and, optionally, an additional therapeutic agent) to a mammal. The components of the liposome are commonly arranged in a bilayer formation, similar to the lipid arrangement of biological membranes.

Sustained-release preparations of compounds of this invention may be prepared. Suitable examples of sustained-release preparations include semipermeable matrices of solid hydrophobic polymers containing a compound of Formula I, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate) and poly-D-(−)-3-hydroxybutyric acid.

The pharmaceutical compositions of compounds of this invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butanediol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The compositions of the invention may also be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder)

Suitable pharmaceutically-acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxyethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), coloring agents, flavoring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavoring and coloring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavoring and preservative agents.

Syrups and elixirs may be formulated with sweetening agents such as glycerol, propylene glycol, sorbitol, aspartame or sucrose, and may also contain a demulcent, preservative, flavoring and/or coloring agent.

Suppository formulations may be prepared by mixing the active ingredient with a suitable non-irritating excipient that is solid at ordinary temperatures but liquid at the rectal temperature and will therefore melt in the rectum to release the drug. Suitable excipients include, for example, cocoa butter and polyethylene glycols. Formulations suitable for vaginal administration may be presented as pessaries, tampons, creams, gels, pastes, foams or spray formulations containing in addition to the active ingredient such carriers as are known in the art to be appropriate.

Topical formulations, such as creams, ointments, gels and aqueous or oily solutions or suspensions, may generally be obtained by formulating an active ingredient with a conventional, topically acceptable, vehicle or diluent using conventional procedures well known in the art.

Compositions for transdermal administration may be in the form of those transdermal skin patches that are well known to those of ordinary skill in the art.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis disorders as described below.

The pharmaceutical composition (or formulation) for application may be packaged in a variety of ways depending upon the method used for administering the drug. For example, an article for distribution can include a container having deposited therein the pharmaceutical formulation in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings. The formulations may also be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

The invention further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

The amount of a compound of this invention that is combined with one or more excipients to produce a single dosage form will necessarily vary depending upon the subject treated, the severity of the disorder or condition, the rate of administration, the disposition of the compound and the discretion of the prescribing physician. In one embodiment, a suitable amount of a compound of this invention is administered to a mammal in need thereof. Administration in one embodiment occurs in an amount between about 0.001 mg/kg of body weight to about 60 mg/kg of body weight per day. In another embodiment, administration occurs in an amount between 0.5 mg/kg of body weight to about 40 mg/kg of body weight per day. In some instances, dosage levels below the lower limit of the aforesaid range may be more than adequate, while in other cases still larger doses may be employed without causing any harmful side effect, provided that such larger doses are first divided into several small doses for administration throughout the day. For further information on routes of administration and dosage regimes, see Chapter 25.3 in Volume 5 of *Comprehensive Medicinal Chemistry* (Corwin Hansch; Chairman of Editorial Board), Pergamon Press 1990, which is specifically incorporated herein by reference.

Articles of Manufacture

In another embodiment of the invention, an article of manufacture, or "kit", containing materials useful for the treatment of the disorders described above is provided. In one embodiment, the kit comprises a container comprising a compound of this invention. Suitable containers include, for example, bottles, vials, syringes, blister pack, etc. The container may be formed from a variety of materials such as glass or plastic. The container may hold a compound of this invention or a formulation thereof which is effective for treating the condition and may have a sterile access port (for example, the container may be an intravenous solution bag or a vial having a stopper pierceable by a hypodermic injection needle).

The kit may further comprise a label or package insert on or associated with the container. The term "package insert" is used to refer to instructions customarily included in commercial packages of therapeutic products, that contain information about the indications, usage, dosage, administration, contraindications and/or warnings concerning the use of such therapeutic products. In one embodiment, the label or package inserts indicates that the composition comprising a compound of this invention can be used to treat a disorder mediated, for example, by AKT kinase. The label or package insert may also indicate that the composition can be used to treat other disorders.

In certain embodiments, the kits are suitable for the delivery of solid oral forms of a compound of this invention, such as tablets or capsules. Such a kit preferably includes a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days in the treatment schedule in which the dosages can be administered.

According to another embodiment, a kit may comprise (a) a first container with a compound of this invention contained therein; and (b) a second container with a second pharmaceutical formulation contained therein, wherein the second pharmaceutical formulation comprises a second compound useful for treating a disorder mediated by AKT kinase. Alternatively, or additionally, the kit may further comprise a third container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kit may further comprise directions for the administration of the compound of this invention and, if present, the second pharmaceutical formulation. For example, if the kit comprises a first composition comprising a compound of this invention and a second pharmaceutical formulation, the kit may further comprise directions for the simultaneous, sequential or separate administration of the first and second pharmaceutical compositions to a patient in need thereof.

In certain other embodiments wherein the kit comprises a composition of this invention and a second therapeutic agent, the kit may comprise a container for containing the separate compositions such as a divided bottle or a divided foil packet, however, the separate compositions may also be contained within a single, undivided container. In certain embodiments, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

Accordingly, a further aspect of this invention provides a kit for treating a disorder or disease mediated by Akt kinase, wherein said kit comprises a) a first pharmaceutical composition comprising a compound of this invention or a pharmaceutically acceptable salt thereof; and b) instructions for use.

In certain embodiments, the kit further comprises (c) a second pharmaceutical composition, wherein the second pharmaceutical composition comprises a second compound suitable for treating a disorder or disease mediated by Akt kinase. In certain embodiment comprising a second pharmaceutical composition, the kit further comprises instructions for the simultaneous, sequential or separate administration of said first and second pharmaceutical compositions to a patient in need thereof. In certain embodiments, said first and second pharmaceutical compositions are contained in separate containers. In other embodiments, said first and second pharmaceutical compositions are contained in the same container.

Although the compounds of Formula I are primarily of value as therapeutic agents for use in mammals, they are also useful whenever it is required to control AKT protein kinases, tyrosine kinases, additional serine/threonine kinases, and/or dual specificity kinases. Thus, they are useful as pharmacological standards for use in the development of new biological tests and in the search for new pharmacological agents.

The activity of the compounds of this invention may be assayed for AKT protein kinases, tyrosine kinases, additional serine/threonine kinases, and/or dual specificity kinases in vitro, in vivo, or in a cell line. In vitro assays include assays that determine inhibition of the kinase activity. Alternate in vitro assays quantitate the ability of the inhibitor to bind to kinases and may be measured either by radiolabelling the inhibitor prior to binding, isolating the inhibitor/kinase complex and determining the amount of radiolabel bound, or by running a competition experiment where new inhibitors are incubated with known radioligands. These and other useful in vitro and cell culture assays are well known to those of skill in the art.

Although the invention has been described and illustrated with a certain degree of particularity, it is understood that the present disclosure has been made only by way of example, and that numerous changes in the combination and arrangement of parts can be resorted to by those skilled in the art without departing from the spirit and scope of the invention, as hereinafter claimed.

BIOLOGICAL EXAMPLES

AKT-1 Kinase Assay

The activity of the compounds described in the present invention may be determined by the following kinase assay, which measures the phosphorylation of a fluorescently-labeled peptide by full-length human recombinant active AKT-1 by fluorescent polarization using a commercially available IMAP kit.

The assay materials are obtained from an IMAP AKT Assay Bulk Kit, product #R8059, from Molecular Devices, Sunnyvale, Calif. The kit materials include an IMAP Reaction Buffer (5×). The diluted 1×IMAP Reaction Buffer contained 10 mM Tris-HCl, pH 7.2, 10 mM $MgCl_2$, 0.1% BSA, 0.05% $NaN_3$. DTT is routinely added to a final concentration of 1 mM immediately prior to use. Also included is IMAP Binding Buffer (5×), and IMAP Binding Reagent. The Binding Solution is prepared as a 1:400 dilution of IMAP Binding Reagent into 1×IMAP Binding Buffer.

The fluorescein-labeled AKT Substrate (Crosstide) has the sequence (F1)-GRPRTSSFAEG. A stock solution of 20 µM is made up in 1×IMAP Reaction Buffer.

The plates used include a Costar 3657 (382-well made of polypropylene and having a white, v-bottom) that is used for compound dilution and for preparing the compound-ATP mixture. The assay plate is a Packard ProxyPlate™-384 F.

The AKT-1 used is made from full-length, human recombinant AKT-1 that is activated with PDK1 and MAP kinase 2.

To perform the assay, stock solutions of compounds at 10 mM in DMSO are prepared. The stock solutions and the control compound are serially diluted 1:2 nine times into DMSO (10 µL of compound+10 µL of DMSO) to give 50× dilution series over the desired dosing range. Next, 2.1-µL, aliquots of the compounds in DMSO are transferred to a Costar 3657 plate containing 50 µL of 10.4 µM ATP in 1×IMAP Reaction Buffer containing 1 mM DTT. After thorough mixing, 2.5-µL aliquots are transferred to a Proxy-Plate™-384 F plate.

The assay is initiated by the addition of 2.5-µL aliquots of a solution containing 200 nM of fluorescently-labeled peptide substrate and 4 nM AKT-1. The plate is centrifuged for 1 minute at 1000 g and incubated for 60 minute at ambient temperature. The reaction is then quenched by the addition of 15 µL of Binding Solution, centrifuged again and incubated for an additional 30 minutes at ambient temperature prior to reading on a Victor 1420 Multilabel HTS Counter configured to measure fluorescence polarization.

The compounds of Examples 1-324 were tested in the above assay and found to have an $IC_{50}$ of less than <10 µM.

PREPARATIVE EXAMPLES

In order to illustrate the invention, the following examples are included. However, it is to be understood that these examples do not limit the invention and are only meant to suggest a method of practicing the invention. Persons skilled in the art will recognize that the chemical reactions described may be readily adapted to prepare a number of other compounds of Formula I, and alternative methods for preparing the compounds of this invention are deemed to be within the scope of this invention. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds of the invention.

In the examples described below, unless otherwise indicated all temperatures are set forth in degrees Celsius. Reagents were purchased from commercial suppliers such as Aldrich Chemical Company, Lancaster, TCI or Maybridge, and were used without further purification unless otherwise indicated. Tetrahydrofuran (THF), dichloromethane (DCM), toluene, and dioxane were purchased from Aldrich in Sure seal bottles and used as received.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

¹H NMR spectra were recorded on a Varian instrument operating at 400 MHz. ¹H-NMR spectra were obtained as CDCl₃, CD₃OD, D₂O or d₆-DMSO solutions (reported in ppm), using tetramethylsilane (0.00 ppm) or residual solvent (CDCl₃: 7.25 ppm; CD₃OD: 3.31 ppm; D₂O: 4.79 ppm; d₆-DMSO: 2.50 ppm) as the reference standard. When peak multiplicities are reported, the following abbreviations are used: s (singlet), d (doublet), t (triplet), m (multiplet), br (broadened), dd (doublet of doublets), dt (doublet of triplets). Coupling constants, when given, are reported in Hertz (Hz).

Example 1

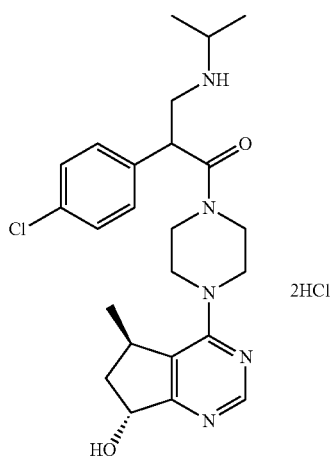 [SMILES: CC(C)NCC(C(=O)N1CCN(c2ncnc3c2[C@H](C)C[C@H]3O)CC1)c1ccc(Cl)cc1]

Preparation of 2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one dihydrochloride

Step 1

To a 1 L round-bottom flask were added (R)-(+)-Pulegone (76.12 g, 0.5 mmol), anhydrous NaHCO₃ (12.5 g) and anhydrous ether (500 mL). The reaction mixture was cooled with ice-bath under nitrogen. The bromine (25.62 mL, 0.5 mmol) was added dropwise over 30 minutes. The mixture was filtered and carefully added to NaOEt (21%, 412 mL, 1.11 mmol) in an ice-cooled bath. The mixture was stirred at room temperature overnight and then 1 L of 5% HCl and 300 mL of ether were added. The aqueous phase was extracted with ether (2×300 mL). The combined organic phase was washed with water, dried and concentrated. The residue was added to a warmed solution of semicarbazide hydrochloride (37.5 g) and NaOAc (37.5 g) in water (300 mL), and then boiling ethanol (300 mL) was added to give a clear solution. The mixture was refluxed for 2.5 hours and then stirred at room temperature overnight. The mixture was treated with 1 L of water and 300 mL of ether. The aqueous phase was extracted with ether (2×300 mL). The combined organic phase was washed with water, dried and concentrated. The residue was purified by vacuum distillation (73-76° C. at 0.8 mm Hg) to give (2R)-ethyl 2-methyl-5-(propan-2-ylidene)cyclopentanecarboxylate (63 g, 64%). ¹H NMR (CDCl₃, 400 MHz) δ 4.13 (m, 2H), 3.38 (d, J=16 Hz, 0.5H), 2.93 (m, 0.5H), 2.50-2.17 (m, 2H), 1.98 (m, 1H), 1.76 (m, 1H), 1.23 (m, 6H), 1.05 (m, 6H).

Step 2

(2R)-Ethyl 2-methyl-5-(propan-2-ylidene)cyclopentanecarboxylate (24 g, 0.122 mol) in ethyl acetate (100 mL) was cooled to −68° C. with dry ice/isopropanol. Ozonized oxygen (5-7 ft³h¹ of O₂) was bubbled through the solution for 3.5 hours. The reaction mixture was flushed with nitrogen at room temperature until the color disappeared. The ethyl acetate was removed under vacuum and the residue was dissolved in 150 mL of acetic acid and cooled by ice water. Then 45 g of zinc powder were added. The solution was stirred for 30 minutes and then filtered. The filtrate was neutralized with 2N NaOH (1.3 L) and NaHCO₃. The aqueous phase was extracted with ether (3×200 mL). The organic phase was combined, washed with water, dried and concentrated to afford (2R)-ethyl 2-methyl-5-oxocyclopentanecarboxylate (20 g, 96%). ¹H NMR (CDCl₃, 400 MHz) δ 4.21 (m, 2H), 2.77 (d, J=11.2 Hz, 1H), 2.60 (m, 1H), 2.50-2.10 (m, 3H), 1.42 (m, 1H), 1.33 (m, 3H), 1.23 (m, 3H).

Step 3

To a solution of a mixture of (2R)-ethyl 2-methyl-5-oxocyclopentanecarboxylate (20 g, 117.5 mmol) and thiourea (9.2 g, 120.9 mmol) in ethanol (100 mL) was added KOH (8.3 g, 147.9 mmol) in water (60 mL). The mixture was refluxed for 10 hours. After cooling, the solvent was removed and the residue was neutralized with concentrated HCl (12 mL) at 0° C. and then extracted with DCM (3×150 mL). The solvent was removed and the residue was purified by silica gel chromatography, eluting with Hexane/ethyl acetate (2:1) to give (R)-2-mercapto-5-methyl-6,7-dihydro-5H-cyclopenta[d]pyrimidin-4-ol (12 g, 56%). MS (APCI+) [M+H] ⁺183.

Step 4

To a suspension of (R)-2-mercapto-5-methyl-6,7-dihydro-5H-cyclopenta[d]pyrimidin-4-ol (12 g, 65.8 mmol) in distilled water (100 mL) was added Raney Nickel (15 g) and NH₄OH (20 mL). The mixture was refluxed for 3 hours then filtered, and the filtrate was concentrated to afford (R)-5-methyl-6,7-dihydro-5H-cyclopenta[d]pyrimidin-4-ol (9.89 g, 99%). MS (APCI+) [M+H] ⁺151.

Step 5

A mixture of (R)-5-methyl-6,7-dihydro-5H-cyclopenta[d]pyrimidin-4-ol (5.8 g, 38.62 mmol) in POCl₃ (20 mL) was refluxed for 5 minutes. Excess POCl₃ was removed under vacuum and the residue was dissolved in DCM (50 mL). The mixture was then added to saturated NaHCO₃ (200 mL). The aqueous phase was extracted with DCM (3×100 mL), and the combined organic phases were dried and concentrated. The residue was purified by silica gel chromatography, eluting with ethyl acetate to give (R)-4-chloro-5-methyl-6,7-dihydro-5H-cyclopenta[d]pyrimidine (3.18 g, 49%). ¹H NMR (CDCl₃, 400 MHz) δ 8.81 (s, 1H), 3.47 (m, 1H), 3.20 (m, 1H), 3.05 (m, 1H), 2.41 (m, 1H), 1.86 (m, 3H), 1.47 (m, 3H).

Step 6

To a solution of (R)-4-chloro-5-methyl-6,7-dihydro-5H-cyclopenta[d]pyrimidine (2.5 g, 14.8 mmol) in CHCl₃ (60 mL) was added MCPBA (8.30 g, 37.0 mmol) in three portions. The mixture was stirred at room temperature for 2 days. The mixture was cooled to 0° C. and to this was added dropwise Na₂S₂O₃ (10 g) in water (60 mL), followed by Na$_2$CO$_3$ (6 g) in water (20 mL). The reaction mixture was stirred for 20 minutes. The aqueous phase was extracted with CHCl$_3$ (2×200 mL), and the combined organic phases were concentrated at low temperature (<25° C.). The residue was purified by silica gel chromatography, eluting with ethyl acetate-DCM/MeOH (20:1) to give (R)-4-chloro-5-methyl-6,7-dihydro-5H-cyclopenta[d]pyrimidine-oxide (1.45 g, 53%). $^1$H NMR (CDCl$_3$, 400 MHz) δ 8.66 (s, 1H), 3.50 (m, 1H), 3.20 (m, 2H), 2.44 (m, 1H), 1.90 (m, 1H), 1.37 (d, J=7.2 Hz, 3H).

Step 7

A solution of (R)-4-chloro-5-methyl-6,7-dihydro-5H-cyclopenta[d]pyrimidine-oxide (1.45 g, 7.85 mmol) in acetic anhydride (20 mL) was heated to 110° C. for 2 hours. After cooling, excess solvent was removed under vacuum. The residue was purified by silica gel chromatography, eluting with Hexane/ethyl acetate (3:1) to give (5R)-4-chloro-5-methyl-6,7-dihydro-5H-cyclopenta[d]pyrimidin-7-yl acetate (1.25 g, 70%). $^1$H NMR (CDCl$_3$, 400 MHz) δ 8.92 (m, 1H), 6.30-6.03 (m, 1H), 3.60-3.30 (m, 1H), 2.84 (m, 1H), 2.40-2.20 (m, 1H), 2.15 (d, J=6 Hz, 2H), 1.75 (m, 2H), 1.47 (d, J=6.8, 2H), 1.38 (d, J=7.2, 1H). MS (APCI+) [M+H] $^+$227.

Step 8

To a solution of (5R)-4-chloro-5-methyl-6,7-dihydro-5H-cyclopenta[d]pyrimidin-7-yl acetate (0.5 g, 2.2 mmol) in NMP (10 mL) was added 1-Boc-piperazine (0.9 g, 4.8 mmol). The reaction mixture was heated to 110° C. for 12 hours. After cooling, the reaction mixture was diluted with ethyl acetate (200 mL) and washed with water (6×100 mL). The organic phase was dried and concentrated. The residue was purified by silica gel chromatography, eluting with ethyl acetate to give tert-butyl 4-((5R)-7-acetoxy-5-methyl-6,7-dihydro-5H-cyclopenta[d]pyrimidin-4-yl)piperazine-1-carboxylate (0.6 g, 72%). $^1$H NMR (CDCl$_3$, 400 MHz) δ 8.60 (d, 1H), 6.05-5.90 (m, 1H), 3.80-3.30 (m, 9H), 2.84 (m, 1H), 2.20 (m, 1H), 1.49 (s, 9H), 1.29-1.20 (m, 3H). MS (APCI+) [M+H] $^+$377. The resulting mixture of the diastereomers was purified by chiral separation HPLC (Chiralcel ODH column, 250×20 mm, Hexane/EtOH 60:40, 21 mL/min). The first peak (RT=3.73 min) gave the tert-butyl 4-((5R,7R)-7-acetoxy-5-methyl-6,7-dihydro-5H-cyclopenta[d]pyrimidin-4-yl)piperazine-1-carboxylate (0.144 g, 24%). The second peak (RT=5.66 min) gave the tert-butyl 4-((5R,7S)-7-acetoxy-5-methyl-6,7-dihydro-5H-cyclopenta[d]pyrimidin-4-yl)piperazine-1-carboxylate (0.172 g, 29%). MS (APCI+) [M+H] $^+$377.

Step 9

To a solution of tert-butyl 4-((5R,7R)-7-acetoxy-5-methyl-6,7-dihydro-5H-cyclopenta[d]pyrimidin-4-yl)piperazine-1-carboxylate (0.144 g, 0.383 mmol) in THF (4 mL) was added LiOH (3M, 2 mL). The mixture was stirred at room temperature for 6 hours and then quenched with 2N HCl (3 mL). The solvent was removed and the residue was purified by silica gel chromatography, eluting with ethyl acetate to give tert-butyl 4-((5R,7R)-7-hydroxy-5-methyl-6,7-dihydro-5H-cyclopenta[d]pyrimidin-4-yl)piperazine-1-carboxylate (89 mg, 70%). %). $^1$H NMR (CDCl$_3$, 400 MHz) δ 8.52 (s, 1H), 5.48 (br, 1H), 5.14 (m, 1H), 3.82-3.40 (m, 9H), 2.20 (m, 2H), 1.49 (s, 9H), 1.19 (d, J=6.8 Hz, 3H). MS (APCI+) [M+H] $^+$335.

Step 10 tert-Butyl 4-((5R,7R)-7-hydroxy-5-methyl-6,7-dihydro-5H-cyclopenta[d]pyrimidin-4-yl)piperazine-1-carboxylate was treated with HCl (4M in dioxane, 2 mL) in DCM (5 mL) for 6 hours to give (5R,7R)-5-methyl-4-(piperazin-1-yl)-6,7-dihydro-5H-cyclopenta[d]pyrimidin-7-ol dihydrochloride. MS (APCI+) [M+H] $^+$235.

Step 11

Methyl 2-(4-chlorophenyl)acrylate (1.00 g, 5.09 mmol) was added as a solution in 2.5 mL of THF to a stirring solution of i-PrNH$_2$ (650 uL, 7.63 mmol) in 10 mL of THF. The reaction was allowed to stir at room temperature overnight to completion by LCMS analysis. The solvent was removed under reduced pressure to give methyl 2-(4-chlorophenyl)-3-(isopropylamino)propanoate (LCMS (APCI+) [M−Boc+H]$^+$ 256.1, Rt: 1.97 min), which was re-dissolved in 15 mL of DCM at room temperature. The Boc2O (1.29 mL, 5.59 mmol) was added to the stirring amine via pipette followed by a catalytic amount (1 mg) of DMAP. The reaction was allowed to stir overnight to completion by LCMS and TLC analysis of the mixture. The solution was concentrated in vacuo to afford methyl 3-(tert-butoxycarbonyl(isopropyl)amino)-2-(4-chlorophenyl)propanoate as an oily residue (LCMS (APCI+) [M−Boc+H]$^+$ 256.1, Rt: 4.13 min) which was re-dissolved in 12.0 mL of THF and 4.0 mL of water. The solution was treated with LiOH—H$_2$O (1.07 g, 25.4 mmol) and allowed to stir for 4 hours to completion by LCMS analysis. The solution was diluted with water and washed with diethyl ether (discarded). The aqueous was treated with 1M HCl solution until pH 2-3 and extracted with ethyl acetate several times. The organics were combined, washed with brine, separated, dried over MgSO$_4$, filtered, and concentrated in vacuo to afford 3-(tert-butoxycarbonykisopropyl)amino)-2-(4-chlorophenyl)propanoic acid as a colorless oil (1.04 g, 60%). LCMS (APCI+) [M−Boc+H]$^+$ 242.0.

Step 12

To a solution of (5R,7R)-5-methyl-4-(piperazin-1-yl)-6,7-dihydro-5H-cyclopenta[d]pyrimidin-7-ol dihydrochloride (41 mg, 0.13 mmol) and 3-(tert-butoxycarbonyl(isopropyl)amino)-2-(4-chlorophenyl)propanoic acid (46 mg, 0.13 mmol) in DCM (10 mL) and triethylamine (1 mL) was added HBTU (51 mg, 0.13 mmol). The reaction mixture was stirred at room temperature for 1 hour. The solvent was removed and the residue was purified by silica gel chromatography, eluting with ethyl acetate-DCM/MeOH (20:1) to give tert-butyl 2-(4-chlorophenyl)-3-(4-((5R,7R)-7-hydroxy-5-methyl-6,7-dihydro-5H-cyclopenta[d]pyrimidin-4-yl)piperazin-1-yl)-3-oxopropyl(isopropyl)carbamate (58 mg, 78%). $^1$H NMR (CDCl$_3$, 400 MHz) δ 8.49 (s, 1H), 7.30-7.22 (m, 4H), 5.11 (m, 1H), 3.80-3.40 (m, 13H), 2.20-2.10 (m, 2H), 1.48 (s, 9H), 1.14 (m, 3H), 1.03 (m, 3H), 0.68 (m, 3H). MS (APCI+) [M+H] $^+$559.

Step 13

Treatment of tert-butyl 2-(4-chlorophenyl)-3-(4-((5R,7R)-7-hydroxy-5-methyl-6,7-dihydro-5H-cyclopenta[d]pyrimidin-4-yl)piperazin-1-yl)-3-oxopropyl(isopropyl)carbamate with HCl (4M in dioxane, 2 mL) in DCM (5 mL) for 6 hours to give 2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one dihydrochloride. $^1$H NMR (D$_2$O, 400 MHz) δ 8.36-8.35 (m, 1H), 7.36-7.35 (d, J=8.0 Hz, 2H), 7.22-7.20 (d, J=8.0 Hz, 2H), 5.23-5.10 (m, 1H), 4.36-4.33 (m, 1H), 3.96-3.00 (m, 12H), 2.17-2.13

(m, 1H), 2.06-2.00 (m, 1H), 1.20-1.17 (m, 6H), 1.08-0.97 (m, 3H). MS (APCI+) [M+H] +459.

Example 2

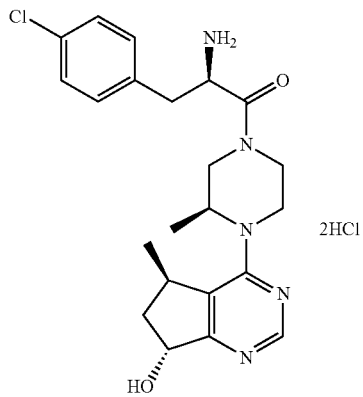 [SMILES: C[C@@H]1C[C@@H](O)c2ncnc(N3CCN(C(=O)[C@H](N)Cc4ccc(Cl)cc4)C[C@@H]3C)c21]

Preparation of (R)-2-amino-3-(4-chlorophenyl)-1-((S)-4-((5R,7R)-7-hydroxy-5-methyl-6,7-dihydro-5H-cyclopenta[d]pyrimidin-4-yl)-3-methylpiperazin-1-yl)propan-1-one dihydrochloride Step 1

To a solution of (R)-4-chloro-5-methyl-6,7-dihydro-5H-cyclopenta[d]pyrimidine (2.5 g, 14.8 mmol) in CHCl$_3$ (60 mL) was added MCPBA (8.30 g, 37.0 mmol) in three portions. The mixture was stirred at room temperature for 2 days. The mixture was cooled to 0° C. and to this was added dropwise Na$_2$S$_2$O$_3$ (10 g) in water (60 mL), followed by Na$_2$CO$_3$ (6 g) in water (20 mL). The reaction mixture was stirred for 20 minutes. The aqueous phase was extracted with CHCl$_3$ (2×200 mL), and the combined organic phases were concentrated at low temperature (<25° C.). The residue was purified by silica gel chromatography, eluting with ethyl acetate-DCM/MeOH (20:1) to give (R)-4-chloro-5-methyl-6,7-dihydro-5H-cyclopenta[d]pyrimidine-oxide (1.45 g, 53%). $^1$H NMR (CDCl$_3$, 400 MHz) δ 8.66 (s, 1H), 3.50 (m, 1H), 3.20 (m, 2H), 2.44 (m, 1H), 1.90 (m, 1H), 1.37 (d, J=7.2 Hz, 3H).

Step 2

A solution of (R)-4-chloro-5-methyl-6,7-dihydro-5H-cyclopenta[d]pyrimidine-oxide (1.45 g, 7.85 mmol) in acetic anhydride (20 mL) was heated to 110° C. for 2 hours. After cooling, excess solvent was removed under vacuum. The residue was purified by silica gel chromatography, eluting with Hexane/ethyl acetate (3:1) to give (5R)-4-chloro-5-methyl-6,7-dihydro-5H-cyclopenta[d]pyrimidin-7-yl acetate (1.25 g, 70%). $^1$H NMR (CDCl$_3$, 400 MHz) δ 8.92 (m, 1H), 6.30-6.03 (m, 1H), 3.60-3.30 (m, 1H), 2.84 (m, 1H), 2.40-2.20 (m, 1H), 2.15 (d, J=6 Hz, 2H), 1.75 (m, 2H), 1.47 (d, J=6.8, 2H), 1.38 (d, J=7.2, 1H). MS (APCI+) [M+H] +227.

Step 3

To a solution of (5R)-4-chloro-5-methyl-6,7-dihydro-5H-cyclopenta[d]pyrimidin-7-yl acetate (0.75 g, 3.3 mmol) in NMP (10 mL) was added (S)-tert-butyl 3-methylpiperazine-1-carboxylate (1.0 g, 5.0 mmol). The mixture was heated to 125° C. for 60 hours. After cooling, the mixture was diluted with ethyl acetate (200 mL) and washed with water (6×100 mL). The organic phase was dried and concentrated. The residue was purified by silica gel chromatography, eluting with ethyl acetate to give (S)-tert-butyl 4-((5R)-7-acetoxy-5-methyl-6,7-dihydro-5H-cyclopenta[d]pyrimidin-4-yl)-3-methylpiperazine-1-carboxylate (0.775 g, 60%). $^1$H NMR (CDCl$_3$, 400 MHz) δ 8.60-8.59 (d, 1H), 6.07-5.89 (m, 1H), 4.73-4.60 (m, 1H), 4.30-3.80 (m, 3H), 3.60-3.35 (m, 1H), 3.22 (m, 1H), 3.02 (br, 1H), 2.78 (m, 1H), 2.35-1.60 (m, 5H), 1.49 (s, 9H), 1.32-1.20 (m, 6H). MS (APCI+) [M+H] +391. The resulting mixture of diastereomers was purified by chiral separation by HPLC (Chiralcel ODH column, 250×20 mm, 15 mL/min, Hexane/EtOH 50:50). The first peak (RT=3.864 min) gave (S)-tert-butyl 4-((5R,7R)-7-acetoxy-5-methyl-6,7-dihydro-5H-cyclopenta[d]pyrimidin-4-yl)-3-methylpiperazine-1-carboxylate (0.281 g, 36%) and the second peak (RT=5.064 min) gave (S)-tert-butyl 4-((5R,7S)-7-acetoxy-5-methyl-6,7-dihydro-5H-cyclopenta[d]pyrimidin-4-yl)-3-methylpiperazine-1-carboxylate (0.389 g, 50%).

Step 4

To a solution of the (S)-tert-butyl 4-((5R,7R)-7-acetoxy-5-methyl-6,7-dihydro-5H-cyclopenta[d]pyrimidin-4-yl)-3-methylpiperazine-1-carboxylate (0.281 g, 0.72 mmol) in THF (5 mL) was added LiOH (3M, 2 mL). The mixture was stirred at room temperature for 6 hours and then quenched with 2N HCl (3 mL). The solvent was removed and the residue was purified by silica gel chromatography, eluting with ethyl acetate to give (S)-tert-butyl 4-((5R,7R)-7-hydroxy-5-methyl-6,7-dihydro-5H-cyclopenta[d]pyrimidin-4-yl)-3-methylpiperazine-1-carboxylate (0.206 g, 82%). $^1$H NMR (CDCl$_3$, 400 MHz) δ 8.52 (s, 1H), 5.12 (m, 1H), 4.76 (br, 1H), 4.30-3.80 (m, 3H), 3.52 (m, 1H), 3.26 (m, 1H), 3.03 (br, 1H), 2.20 (m, 1H), 1.49 (s, 9H), 1.30-1.10 (m, 6H). MS (APCI+) [M+H] +349.

Step 5

To a solution of the (S)-tert-butyl 4-((5R,7R)-7-hydroxy-5-methyl-6,7-dihydro-5H-cyclopenta[d]pyrimidin-4-yl)-3-methylpiperazine-1-carboxylate (0.106 g, 0.304 mmol) in DCM (20 mL) was added HCl (4M in dioxane, 4 mL). The mixture was stirred at room temperature overnight. The solvent was removed to afford (5R,7R)-5-methyl-4-((S)-2-methylpiperazin-1-yl)-6,7-dihydro-5H-cyclopenta[d]pyrimidin-7-ol dihydrochloride (0.098 g, 99%). MS (APCI+) [M+H] +249.

Step 6

To a solution of the (5R,7R)-5-methyl-4-((S)-2-methylpiperazin-1-yl)-6,7-dihydro-5H-cyclopenta[d]pyrimidin-7-ol dihydrochloride (33 mg, 0.10 mmol) and (R)-2-(tert-butoxycarbonyl)-3-(4-chlorophenyl)propanoic acid (31 mg, 0.10 mmol) in DCM (5 mL) and triethylamine (1 mL) was added HBTU (39 mg, 0.1 mmol). The mixture was stirred at room temperature for 1 hour. The solvent was removed and the residue was purified by silica gel chromatography, eluting with DCM/MeOH (20:1) to give tert-butyl (R)-3-(4-chlorophenyl)-1-((S)-4-((5R,7R)-7-hydroxy-5-methyl-6,7-dihydro-5H-cyclopenta[d]pyrimidin-4-yl)-3-methylpiperazin-1-yl)-1-oxopropan-2-ylcarbamate (45 mg, 83%). $^1$H NMR (CDCl$_3$, 400 MHz) δ 8.53 (s, 1H), 7.25-7.10 (m, 4H), 5.60-5.30 (m, 1H), 5.20-4.60 (m, 3H), 4.50-4.00 (m, 2H), 3.90-

3.60 (m, 4H), 3.58-2.90 (m, 3H), 2.17 (m, 1H), 1.46-1.30 (m, 9H), 1.28-0.90 (m, 6H). MS (APCI+) [M+H] +531.

Step 7

Treatment of tert-butyl (R)-3-(4-chlorophenyl)-1-((S)-4-((5R,7R)-7-hydroxy-5-methyl-6,7-dihydro-5H-cyclopenta[d]pyrimidin-4-yl)-3-methylpiperazin-1-yl)-1-oxopropan-2-ylcarbamate with HCl (4M in dioxane, 2 mL) in DCM (5 mL) for 6 hours gave the (R)-2-amino-3-(4-chlorophenyl)-1-((S)-4-((5R,7R)-7-hydroxy-5-methyl-6,7-dihydro-5H-cyclopenta[d]pyrimidin-4-yl)-3-methylpiperazin-1-yl)propan-1-one dihydrochloride. ¹H NMR (D₂O, 400 MHz) δ 8.53-8.40 (m, 1H), 7.40-7.10 (m, 4H), 5.35-5.30 (m, 1H), 4.05-3.95 (m, 1h), 3.70-3.40 (m, 5H), 3.20-2.90 (m, 4H), 2.40-2.20 (m, 2H), 2.04-1.98 (m, 1H), 1.20-0.95 (m, 6H). MS (APCI+) [M+H] +431.

Example 3

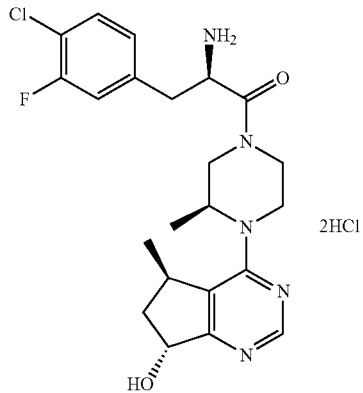 [SMILES: C[C@@H]1C[C@@H](O)c2ncnc(N3CCN(C(=O)[C@H](N)Cc4ccc(Cl)c(F)c4)C[C@@H]3C)c21]

Preparation of (R)-2-amino-3-(4-chloro-3-fluorophenyl)-1-((S)-4-((5R,7R)-7-hydroxy-5-methyl-6,7-dihydro-5H-cyclopenta[d]pyrimidin-4-yl)-3-methylpiperazin-1-yl)propan-1-one dihydrochloride Step 1

To a solution of (R)-4-chloro-5-methyl-6,7-dihydro-5H-cyclopenta[d]pyrimidine (2.5 g, 14.8 mmol) in CHCl₃ (60 mL) was added MCPBA (8.30 g, 37.0 mmol) in three portions. The mixture was stirred at room temperature for 2 days. The mixture was cooled to 0° C. and to this was added dropwise Na₂S₂O₃ (10 g) in water (60 mL), followed by Na₂CO₃ (6 g) in water (20 mL). The reaction mixture was stirred for 20 minutes. The aqueous phase was extracted with CHCl₃ (2×200 mL), and the combined organic phases were concentrated at low temperature (<25° C.). The residue was purified by silica gel chromatography, eluting with ethyl acetate-DCM/MeOH (20:1) to give (R)-4-chloro-5-methyl-6,7-dihydro-5H-cyclopenta[d]pyrimidine-oxide (1.45 g, 53%). ¹H NMR (CDCl₃, 400 MHz) δ 8.66 (s, 1H), 3.50 (m, 1H), 3.20 (m, 2H), 2.44 (m, 1H), 1.90 (m, 1H), 1.37 (d, J=7.2 Hz, 3H).

Step 2

A solution of (R)-4-chloro-5-methyl-6,7-dihydro-5H-cyclopenta[d]pyrimidine-oxide (1.45 g, 7.85 mmol) in acetic anhydride (20 mL) was heated to 110° C. for 2 hours. After cooling, excess solvent was removed under vacuum. The residue was purified by silica gel chromatography, eluting with Hexane/ethyl acetate (3:1) to give (5R)-4-chloro-5-methyl-6,7-dihydro-5H-cyclopenta[d]pyrimidin-7-yl acetate (1.25 g, 70%). ¹H NMR (CDCl₃, 400 MHz) δ 8.92 (m, 1H), 6.30-6.03 (m, 1H), 3.60-3.30 (m, 1H), 2.84 (m, 1H), 2.40-2.20 (m, 1H), 2.15 (d, J=6 Hz, 2H), 1.75 (m, 2H), 1.47 (d, J=6.8, 2H), 1.38 (d, J=7.2, 1H). MS (APCI+) [M+H] +227.

Step 3

To a solution of (5R)-4-chloro-5-methyl-6,7-dihydro-5H-cyclopenta[d]pyrimidin-7-yl acetate (0.75 g, 3.3 mmol) in NMP (10 mL) was added (S)-tert-butyl 3-methylpiperazine-1-carboxylate (1.0 g, 5.0 mmol). The mixture was heated to 125° C. for 60 hours. After cooling, the mixture was diluted with ethyl acetate (200 mL) and washed with water (6×100 mL). The organic phase was dried and concentrated. The residue was purified by silica gel chromatography, eluting with ethyl acetate to give (S)-tert-butyl 4-((5R)-7-acetoxy-5-methyl-6,7-dihydro-5H-cyclopenta[d]pyrimidin-4-yl)-3-methylpiperazine-1-carboxylate (0.775 g, 60%). ¹H NMR (CDCl₃, 400 MHz) δ 8.60-8.59 (d, 1H), 6.07-5.89 (m, 1H), 4.73-4.60 (m, 1H), 4.30-3.80 (m, 3H), 3.60-3.35 (m, 1H), 3.22 (m, 1H), 3.02 (br, 1H), 2.78 (m, 1H), 2.35-1.60 (m, 5H), 1.49 (s, 9H), 1.32-1.20 (m, 6H). MS (APCI+) [M+H] +391. The resulting mixture of diastereomers was purified by chiral separation by HPLC (Chiralcel ODH column, 250×20 mm, 15 mL/min, Hexane/EtOH 50:50). The first peak (RT=3.864 min) gave (S)-tert-butyl 4-((5R,7R)-7-acetoxy-5-methyl-6,7-dihydro-5H-cyclopenta[d]pyrimidin-4-yl)-3-methylpiperazine-1-carboxylate (0.281 g, 36%) and the second peak (RT=5.064 min) gave (S)-tert-butyl 4-((5R,7S)-7-acetoxy-5-methyl-6,7-dihydro-5H-cyclopenta[d]pyrimidin-4-yl)-3-methylpiperazine-1-carboxylate (0.389 g, 50%). Treatment of the (S)-tert-butyl 4-((5R,7R)-7-acetoxy-5-methyl-6,7-dihydro-5H-cyclopenta[d]pyrimidin-4-yl)-3-methylpiperazine-1-carboxylate with HCl in dioxane (4M, 2 ml) gave the (5R,7R)-5-methyl-4-((S)-2-methylpiperazin-1-yl)-6,7-dihydro-5H-cyclopenta[d]pyrimidin-7-ol dihydrochloride in quantitative yield.

Step 4

To a solution of (5R,7R)-5-methyl-4-((S)-2-methylpiperazin-1-yl)-6,7-dihydro-5H-cyclopenta[d]pyrimidin-7-ol dihydrochloride (33 mg, 0.10 mmol) and (R)-2-(tert-butoxycarbonyl)-3-(4-chloro-3-fluorophenyl)propanoic acid (33 mg, 0.10 mmol) in DCM (5 mL) and triethylamine (1 mL) was added HBTU (39 mg, 0.1 mmol). The mixture was stirred at room temperature for 1 hour. The solvent was removed and the residue was purified by silica gel chromatography, eluting with DCM/MeOH (20:1) to give tert-butyl (R)-3-(4-chloro-3-fluorophenyl)-1-((S)-4-((5R,7R)-7-hydroxy-5-methyl-6,7-dihydro-5H-cyclopenta[d]pyrimidin-4-yl)-3-methylpiperazin-1-yl)-1-oxopropan-2-ylcarbamate (44 mg, 78%). ¹H NMR (CDCl₃, 400 MHz) δ 8.53 (s, 1H), 7.31-6.88 (m, 3H), 5.60-5.30 (m, 1H), 5.13 (m, 3H), 4.90-4.70 (m, 2H), 4.60-4.00 (m, 2H), 3.90-2.85 (m, 7H), 2.19 (m, 1H), 1.40 (m, 9H), 1.28-0.98 (m, 6H). MS (APCI+) [M+H] +549.

Step 5

Treatment of tert-butyl (R)-3-(4-chloro-3-fluorophenyl)-1-((S)-4-((5R,7R)-7-hydroxy-5-methyl-6,7-dihydro-5H-cyclopenta[d]pyrimidin-4-yl)-3-methylpiperazin-1-yl)-1-oxopropan-2-ylcarbamate with HCl (4M in dioxane, 2 mL) in DCM (5 mL) for 6 hours gave (R)-2-amino-3-(4-chloro-3-fluorophenyl)-1-((S)-4-((5R,7R)-7-hydroxy-5-methyl-6,7-dihydro-5H-cyclopenta[d]pyrimidin-4-yl)-3-methylpiperazin-1-yl)propan-1-one dihydrochloride. $^1$H NMR (D$_2$O, 400 MHz) δ 8.51-8.40 (m, 1H), 7.29-7.24 (m, 1H), 7.08-7.08 (d, J=10 Hz, 1H), 6.95-6.93 (d, J=8.4 Hz, 1H), 5.36-5.32 (m, 1H), 4.18-3.98 (m, 2H), 3.75-3.50 (m, 5H), 3.20-2.97 (m, 4H), 2.60-2.50 (m, 1H), 2.30-2.20 (m, 1H), 2.05-1.98 (m, 1H), 1.14-1.12 (d, J=6.4 Hz, 3H), 0.98-0.96 (d, J=6.8 Hz, 3H). MS (APCI+) [M+H] $^+$449.

Example 4

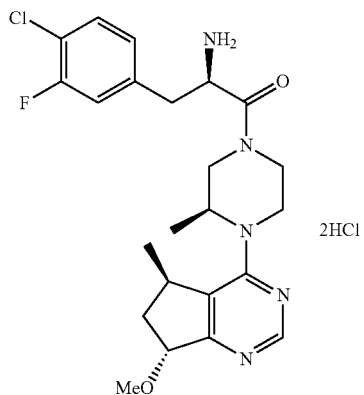 [SMILES: CO[C@@H]1C[C@@H](C)c2c1ncnc2N1CCN(C(=O)[C@H](N)Cc2ccc(Cl)c(F)c2)C[C@@H]1C]

Preparation of (R)-2-amino-3-(4-chloro-3-fluorophenyl)-1-((S)-4-((5R,7R)-7-methoxy-5-methyl-6,7-dihydro-5H-cyclopenta[d]pyrimidin-4-yl)-3-methylpiperazin-1-yl)propan-1-one dihydrochloride Step 1

1,1,3,3-Tetramethylguanidine (2.11 ml, 16.8 mmol) was added to a 0° C. solution of methyl 2-(tert-butoxycarbonyl)-2-(dimethoxyphosphoryl)-acetate (5.00 g, 16.8 mmol) in DCM (70 mL). The reaction mixture was stirred at 0° C. for 30 minutes. Then a solution of 4-chloro-3-fluorobenzaldehyde (2.67 g, 16.8 mmol) in DCM (10 mL) was added by syringe. The reaction mixture was stirred for 10 minutes, then warmed to room temperature and stirred for another 1 hour. H$_2$O was then added, and the mixture was extracted with DCM. The combined extracts were dried (Na$_2$SO$_4$), filtered, and concentrated. The resulting solids were recrystallized from IPA to give (Z)-methyl 2-(tert-butoxycarbonyl)-3-(4-chloro-3-fluorophenyl)acrylate (3.76 g, 67.8% yield) as a white powder (2 crops). LCMS (APCl$^-$) m/z 328 [M–H]$^-$.

Step 2

(Z)-methyl 2-(tert-butoxycarbonyl)-3-(4-chloro-3-fluorophenyl)acrylate (200 mg) and ca. Rh—(R,R)-[Et-DuPhos (COD)]OTf (4 mg) in 1:1 MeOH:EtOAc (3 mL; degassed 1 h with N$_2$ prior to use) was dissolved in 8 Argonaut Endeavor™ reaction tubes. The reaction mixtures were put on the Endeavor™ under 40 psi H$_2$ and stirred for 12 hours at room temperature. All of the reaction mixtures were then combined and concentrated to give (R)-methyl 2-(tert-butoxycarbonyl)-3-(4-chloro-3-fluorophenyl)propanoate (1.52 g, 94.4% yield) as a pale yellow solid, which was used without further purification in next step.

Step 3

LiOH—H$_2$O (0.6246 g, 14.88 mmol) was added to a solution of (R)-methyl 2-(tert-butoxycarbonyl)-3-(4-chloro-3-fluorophenyl)propanoate (1.646 g, 4.961 mmol) in 1:1 THF:H$_2$O (26 mL). The reaction mixture was stirred at room temperature for 2 hours, after which it was diluted with H$_2$O and washed with EtOAc. The aqueous layer was then acidified with solid KHSO$_4$ and extracted with DCM. The combined extracts were dried (Na$_2$SO$_4$), filtered, concentrated, and then re-concentrated from DCM/hexanes to give (R)-2-(tert-butoxycarbonyl)-3-(4-chloro-3-fluorophenyl)-propanoic acid (1.31 g, 83.10% yield) as a white powder. LCMS (APCI) m/z 316 [M–H]$^-$.

Step 4

To a solution of (R)-4-chloro-5-methyl-6,7-dihydro-5H-cyclopenta[d]pyrimidine (2.5 g, 14.8 mmol) in CHCl$_3$ (60 mL) was added MCPBA (8.30 g, 37.0 mmol) in three portions. The mixture was stirred at room temperature for 2 days. The mixture was cooled to 0° C. and to this was added dropwise Na$_2$S$_2$O$_3$ (10 g) in water (60 mL), followed by Na$_2$CO$_3$ (6 g) in water (20 mL). The reaction mixture was stirred for 20 minutes. The aqueous phase was extracted with CHCl$_3$ (2×200 mL), and the combined organic phases were concentrated at low temperature (<25° C.). The residue was purified by silica gel chromatography, eluting with ethyl acetate-DCM/MeOH (20:1) to give (R)-4-chloro-5-methyl-6,7-dihydro-5H-cyclopenta[d]pyrimidine-oxide (1.45 g, 53%). $^1$H NMR (CDCl$_3$, 400 MHz) δ 8.66 (s, 1H), 3.50 (m, 1H), 3.20 (m, 2H), 2.44 (m, 1H), 1.90 (m, 1H), 1.37 (d, J=7.2 Hz, 3H).

Step 5

A solution of (R)-4-chloro-5-methyl-6,7-dihydro-5H-cyclopenta[d]pyrimidine-oxide (1.45 g, 7.85 mmol) in acetic anhydride (20 mL) was heated to 110° C. for 2 hours. After cooling, excess solvent was removed under vacuum. The residue was purified by silica gel chromatography, eluting with Hexane/ethyl acetate (3:1) to give (5R)-4-chloro-5-methyl-6,7-dihydro-5H-cyclopenta[d]pyrimidin-7-yl acetate (1.25 g, 70%). $^1$H NMR (CDCl$_3$, 400 MHz) δ 8.92 (m, 1H), 6.30-6.03 (m, 1H), 3.60-3.30 (m, 1H), 2.84 (m, 1H), 2.40-2.20 (m, 1H), 2.15 (d, J=6 Hz, 2H), 1.75 (m, 2H), 1.47 (d, J=6.8, 2H), 1.38 (d, J=7.2, 1H). MS (APCI+) [M+H] $^+$227.

Step 6

To a solution of (5R)-4-chloro-5-methyl-6,7-dihydro-5H-cyclopenta[d]pyrimidin-7-yl acetate (0.75 g, 3.3 mmol) in NMP (10 mL) was added (S)-tert-butyl 3-methylpiperazine-1-carboxylate (1.0 g, 5.0 mmol). The mixture was heated to 125° C. for 60 hours. After cooling, the mixture was diluted with ethyl acetate (200 mL) and washed with water (6×100 mL). The organic phase was dried and concentrated. The residue was purified by silica gel chromatography, eluting with ethyl acetate to give (S)-tert-butyl 4-((5R)-7-acetoxy-5-methyl-6,7-dihydro-5H-cyclopenta[d]pyrimidin-4-yl)-3-methylpiperazine-1-carboxylate (0.775 g, 60%). $^1$H NMR (CDCl$_3$, 400 MHz) δ 8.60-8.59 (d, 1H), 6.07-5.89 (m, 1H), 4.73-4.60 (m, 1H), 4.30-3.80 (m, 3H), 3.60-3.35 (m, 1H), 3.22 (m, 1H), 3.02 (br, 1H), 2.78 (m, 1H), 2.35-1.60 (m, 5H), 1.49 (s, 9H), 1.32-1.20 (m, 6H). MS (APCI+) [M+H] $^+$391. The resulting mixture of diastereomers was purified by chiral separation by HPLC (Chiralcel ODH column, 250×20 mm, 15 mL/min, Hexane/EtOH 50:50). The first peak (RT=3.864 min) gave (S)-tert-butyl 4-((5R,7R)-7-acetoxy-5-methyl-6,7-dihydro-5H-cyclopenta[d]pyrimidin-4-yl)-3-methylpiperazine-1-carboxylate (0.281 g, 36%) and the second peak (RT=5.064 min) gave (S)-tert-butyl 4-((5R,7S)-7-acetoxy-5-methyl-6,7-dihydro-5H-cyclopenta[d]pyrimidin-4-yl)-3-methylpiperazine-1-carboxylate (0.389 g, 50%).

Step 7

To a solution of (S)-tert-butyl 4-((5R,7R)-7-hydroxy-5-methyl-6,7-dihydro-5H-cyclopenta[d]pyrimidin-4-yl)-3-methylpiperazine-1-carboxylate (0.098 g, 0.28 mmol) in THF (10 mL) were added NaH (60%, 50 mg, 1.25 mmol) and MeI (0.08 mL, 1.28 mmol). The mixture was stirred at room temperature overnight. The solution was removed and the residue was purified by silica gel chromatography, eluting with ethyl acetate to give (S)-tert-butyl 4-((5R,7R)-7-methoxy-5-methyl-6,7-dihydro-5H-cyclopenta[d]pyrimidin-4-yl)-3-methylpiperazine-1-carboxylate (0.056 g, 55%). $^1$H NMR (CDCl$_3$, 400 MHz) δ 8.56 (s, 1H), 4.66 (m, 2H), 4.30-3.80 (m, 3H), 3.55 (s, 3H), 3.54-2.90 (m, 4H), 2.25 (m, 1H), 1.98 (m, 1H), 1.49 (s, 9H), 1.24 (d, J=12.4 Hz, 3H), 1.13 (d, J=7.2 Hz, 3H). MS (APCI+) [M+H] $^+$363.

Step 8

Treatment of (S)-tert-butyl 4-((5R,7R)-7-methoxy-5-methyl-6,7-dihydro-5H-cyclopenta[d]pyrimidin-4-yl)-3-methylpiperazine-1-carboxylate with HCl (4M in dioxane, 4 mL) in DCM (20 mL) for 10 hours gave (5R,7R)-7-methoxy-5-methyl-4-((S)-2-methylpiperazin-1-yl)-6,7-dihydro-5H-cyclopenta[d]pyrimidine dihydrochloride. MS (APCI+) [M+H] $^+$263.

Step 9

To a solution of (5R,7R)-7-methoxy-5-methyl-4-((S)-2-methylpiperazin-1-yl)-6,7-dihydro-5H-cyclopenta[d]pyrimidine dihydrochloride (52 mg, 0.16 mmol) and (R)-2-(tert-butoxycarbonyl)-3-(4-chloro-3-fluorophenyl)propanoic acid (49 mg, 0.16 mmol) in DCM (20 mL) and triethylamine (2 mL) was added HBTU (59 mg, 0.16 mmol). The mixture was stirred at room temperature for 1 hour. The solvent was removed and the residue was purified by silica gel chromatography, eluting with ethyl acetate to give tert-butyl (R)-3-(4-chloro-3-fluorophenyl)-1-((S)-4-((5R,7R)-7-methoxy-5-methyl-6,7-dihydro-5H-cyclopenta[d]pyrimidin-4-yl)-3-methylpiperazin-1-yl)-1-oxopropan-2-ylcarbamate (70 mg, 80%). $^1$H NMR (CDCl$_3$, 400 MHz) δ 8.57 (s, 1H), 7.28 (m, 1H), 7.05-6.90 (m, 2H), 5.40-5.05 (m, 1H), 4.90-4.30 (m, 4H), 4.10-3.60 (m, 3H), 3.55 (s, 3H), 3.53-2.82 (m, 4H), 2.26 (m, 1H), 2.00 (m, 1H). 1.42 (m, 9H), 1.30-1.00 (m, 6H). MS (APCI+) [M+H] $^+$563.

Step 10

Treatment of tert-butyl (R)-3-(4-chloro-3-fluorophenyl)-1-((S)-4-((5R,7R)-7-methoxy-5-methyl-6,7-dihydro-5H-cyclopenta[d]pyrimidin-4-yl)-3-methylpiperazin-1-yl)-1-oxopropan-2-ylcarbamate with HCl (4M in dioxane, 2 mL) in DCM (10 mL) for 10 hours gave (R)-2-amino-3-(4-chloro-3-fluorophenyl)-1-((S)-4-((5R,7R)-7-methoxy-5-methyl-6,7-dihydro-5H-cyclopenta[d]pyrimidin-4-yl)-3-methylpiperazin-1-yl)propan-1-one dihydrochloride. $^1$H NMR (D$_2$O, 400 MHz) δ 8.51-8.40 (m, 1H), 7.29-7.21 (m, 1H), 7.10-7.00 (m, 1H), 6.98-6.90 (m, 1H), 5.15-5.02 (m, 1H), 4.90 (m, 1H), 4.70-4.67 (m, 1H), 4.08-3.98 (m, 2H), 3.75-3.50 (m, 4H), 3.37 (s, 3H), 3.20-2.97 (m, 4H), 2.60-2.50 (m, 1H), 2.30-2.20 (m, 1H), 2.10-2.01 (m, 1H). 1.25-0.95 (m, 6H). MS (APCI+) [M+H] $^+$463.

Example 5

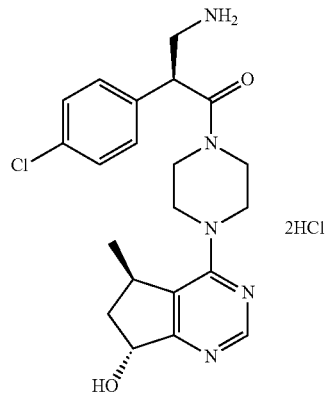 [SMILES: C[C@@H]1C[C@@H](O)c2ncnc(N3CCN(C(=O)[C@H](CN)c4ccc(Cl)cc4)CC3)c21]

Preparation of (S)-3-amino-2-(4-chlorophenyl)-1-(4-((5R,7R)-7-hydroxy-5-methyl-6,7-dihydro-5H-cyclopenta[d]pyrimidin-4-yl)piperazin-1-yl)propan-1-one dihydrochloride

Step 1

To a 1 L round-bottom flask were added (R)-(+)-Pulegone (76.12 g, 0.5 mmol), anhydrous NaHCO$_3$ (12.5 g) and anhydrous ether (500 mL). The reaction mixture was cooled with ice-bath under nitrogen. The bromine (25.62 mL, 0.5 mmol) was added dropwise over 30 minutes. The mixture was filtered and carefully added to NaOEt (21%, 412 mL, 1.11 mmol) in an ice-cooled bath. The mixture was stirred at room temperature overnight and then 1 L of 5% HCl and 300 mL of ether were added. The aqueous phase was extracted with ether (2×300 mL). The combined organic phase was washed with water, dried and concentrated. The residue was added to a warmed solution of semicarbazide hydrochloride (37.5 g) and NaOAc (37.5 g) in water (300 mL), and then boiling ethanol (300 mL) was added to give a clear solution. The mixture was refluxed for 2.5 hours and then stirred at room temperature overnight. The mixture was treated with 1 L of water and 300 mL of ether. The aqueous phase was extracted with ether (2×300 mL). The combined organic phase was washed with water, dried and concentrated. The residue was purified by vacuum distillation (73-76° C. at 0.8 mm Hg) to give (2R)-ethyl 2-methyl-5-(propan-2-ylidene)cyclopentanecarboxylate (63 g, 64%). $^1$H NMR (CDCl$_3$, 400 MHz) δ 4.13 (m, 2H), 3.38 (d, J=16 Hz, 0.5H), 2.93 (m, 0.5H), 2.50-2.17 (m, 2H), 1.98 (m, 1H), 1.76 (m, 1H), 1.23 (m, 6H), 1.05 (m, 6H).

Step 2

(2R)-Ethyl 2-methyl-5-(propan-2-ylidene)cyclopentanecarboxylate (24 g, 0.122 mol) in ethyl acetate (100 mL) was cooled to −68° C. with dry ice/isopropanol. Ozonized oxygen (5-7 ft³h⁻¹ of O₂) was bubbled through the solution for 3.5 hours. The reaction mixture was flushed with nitrogen at room temperature until the color disappeared. The ethyl acetate was removed under vacuum and the residue was dissolved in 150 mL of acetic acid and cooled by ice water, and zinc powder (45 g) was added. The solution was stirred for 30 minutes and then filtered. The filtrate was neutralized with 2N NaOH (1.3 L) and NaHCO₃. The aqueous phase was extracted with ether (3×200 mL). The organic phase was combined, washed with water, dried and concentrated to afford (2R)-ethyl 2-methyl-5-oxocyclopentanecarboxylate (20 g, 96%). $^1$H NMR (CDCl₃, 400 MHz) δ 4.21 (m, 2H), 2.77 (d, J=11.2 Hz, 1H), 2.60 (m, 1H), 2.50-2.10 (m, 3H), 1.42 (m, 1H), 1.33 (m, 3H), 1.23 (m, 3H).

Step 3

To a solution of a mixture of (2R)-ethyl 2-methyl-5-oxocyclopentanecarboxylate (20 g, 117.5 mmol) and thiourea (9.2 g, 120.9 mmol) in ethanol (100 mL) was added KOH (8.3 g, 147.9 mmol) in water (60 mL). The mixture was refluxed for 10 hours. After cooling, the solvent was removed and the residue was neutralized with concentrated HCl (12 mL) at 0° C. and then extracted with DCM (3×150 mL). The solvent was removed and the residue was purified by silica gel chromatography, eluting with Hexane/ethyl acetate (2:1) to give (R)-2-mercapto-5-methyl-6,7-dihydro-5H-cyclopenta[d]pyrimidin-4-ol (12 g, 56%). MS (APCI+) [M+H] $^+$183.

Step 4

To a suspension of (R)-2-mercapto-5-methyl-6,7-dihydro-5H-cyclopenta[d]pyrimidin-4-ol (12 g, 65.8 mmol) in distilled water (100 mL) was added Raney Nickel (15 g) and NH₄OH (20 mL). The mixture was refluxed for 3 hours then filtered, and the filtrate was concentrated to afford (R)-5-methyl-6,7-dihydro-5H-cyclopenta[d]pyrimidin-4-ol (9.89 g, 99%). MS (APCI+) [M+H] $^+$151.

Step 5

A mixture of (R)-5-methyl-6,7-dihydro-5H-cyclopenta[d]pyrimidin-4-ol (5.8 g, 38.62 mmol) in POCl₃ (20 mL) was refluxed for 5 minutes. Excess POCl₃ was removed under vacuum and the residue was dissolved in DCM (50 mL). The mixture was then added to saturated NaHCO₃ (200 mL). The aqueous phase was extracted with DCM (3×100 mL), and the combined organic phases were dried and concentrated. The residue was purified by silica gel chromatography, eluting with ethyl acetate to give (R)-4-chloro-5-methyl-6,7-dihydro-5H-cyclopenta[d]pyrimidine (3.18 g, 49%). $^1$H NMR (CDCl₃, 400 MHz) δ 8.81 (s, 1H), 3.47 (m, 1H), 3.20 (m, 1H), 3.05 (m, 1H), 2.41 (m, 1H), 1.86 (m, 3H), 1.47 (m, 3H).

Step 6

To a solution of (R)-4-chloro-5-methyl-6,7-dihydro-5H-cyclopenta[d]pyrimidine (2.5 g, 14.8 mmol) in CHCl₃ (60 mL) was added MCPBA (8.30 g, 37.0 mmol) in three portions. The mixture was stirred at room temperature for 2 days. The mixture was cooled to 0° C. and to this was added dropwise Na₂S₂O₃ (10 g) in water (60 mL), followed by Na₂CO₃ (6 g) in water (20 mL). The reaction mixture was stirred for 20 minutes. The aqueous phase was extracted with CHCl₃ (2×200 mL), and the combined organic phases were concentrated at low temperature (<25° C.). The residue was purified by silica gel chromatography, eluting with ethyl acetate-DCM/MeOH (20:1) to give (R)-4-chloro-5-methyl-6,7-dihydro-5H-cyclopenta[d]pyrimidine-oxide (1.45 g, 53%). $^1$H NMR (CDCl₃, 400 MHz) δ 8.66 (s, 1H), 3.50 (m, 1H), 3.20 (m, 2H), 2.44 (m, 1H), 1.90 (m, 1H), 1.37 (d, J=7.2 Hz, 3H).

Step 7

A solution of (R)-4-chloro-5-methyl-6,7-dihydro-5H-cyclopenta[d]pyrimidine-oxide (1.45 g, 7.85 mmol) in acetic anhydride (20 mL) was heated to 110° C. for 2 hours. After cooling, excess solvent was removed under vacuum. The residue was purified by silica gel chromatography, eluting with Hexane/ethyl acetate (3:1) to give (5R)-4-chloro-5-methyl-6,7-dihydro-5H-cyclopenta[d]pyrimidin-7-yl acetate (1.25 g, 70%). $^1$H NMR (CDCl₃, 400 MHz) δ 8.92 (m, 1H), 6.30-6.03 (m, 1H), 3.60-3.30 (m, 1H), 2.84 (m, 1H), 2.40-2.20 (m, 1H), 2.15 (d, J=6 Hz, 2H), 1.75 (m, 2H), 1.47 (d, J=6.8, 2H), 1.38 (d, J=7.2, 1H). MS (APCI+) [M+H] $^+$227.

Step 8

To a solution of (5R)-4-chloro-5-methyl-6,7-dihydro-5H-cyclopenta[d]pyrimidin-7-yl acetate (0.5 g, 2.2 mmol) in NMP (10 mL) was added 1-Boc-piperazine (0.9 g, 4.8 mmol). The reaction mixture was heated to 110° C. for 12 hours. After cooling, the reaction mixture was diluted with ethyl acetate (200 mL) and washed with water (6×100 mL). The organic phase was dried and concentrated. The residue was purified by silica gel chromatography, eluting with ethyl acetate to give tert-butyl 4-((5R)-7-acetoxy-5-methyl-6,7-dihydro-5H-cyclopenta[d]pyrimidin-4-yl)piperazine-1-carboxylate (0.6 g, 72%). $^1$H NMR (CDCl₃, 400 MHz) δ 8.60 (d, 1H), 6.05-5.90 (m, 1H), 3.80-3.30 (m, 9H), 2.84 (m, 1H), 2.20- (m, 1H), 1.49 (s, 9H), 1.29-1.20 (m, 3H). MS (APCI+) [M+H] $^+$377. The resulting mixture of the diastereomers was purified by chiral separation HPLC (Chiralcel ODH column, 250×20 mm, Hexane/EtOH 60:40, 21 mL/min). The first peak (RT=3.73 min) gave the tert-butyl 4-((5R,7R)-7-acetoxy-5-methyl-6,7-dihydro-5H-cyclopenta[d]pyrimidin-4-yl)piperazine-1-carboxylate (0.144 g, 24%). The second peak (RT=5.66 min) gave the tert-butyl 4-((5R,7S)-7-acetoxy-5-methyl-6,7-dihydro-5H-cyclopenta[d]pyrimidin-4-yl)piperazine-1-carboxylate (0.172 g, 29%). MS (APCI+) [M+H] $^+$377.

Step 9

To a solution of tert-butyl 4-((5R,7R)-7-acetoxy-5-methyl-6,7-dihydro-5H-cyclopenta[d]pyrimidin-4-yl)piperazine-1-carboxylate (0.144 g, 0.383 mmol) in THF (4 mL) was added LiOH (3M, 2 mL). The mixture was stirred at room temperature for 6 hours and then quenched with 2N HCl (3 mL). The solvent was removed and the residue was purified by silica gel chromatography, eluting with ethyl acetate to give tert-butyl 4-((5R,7R)-7-hydroxy-5-methyl-6,7-dihydro-5H-cyclopenta[d]pyrimidin-4-yl)piperazine-1-carboxylate (89 mg, 70%). %). $^1$H NMR (CDCl₃, 400 MHz) δ 8.52 (s, 1H), 5.48 (br, 1H), 5.14 (m, 1H), 3.82-3.40 (m, 9H), 2.20 (m, 2H), 1.49 (s, 9H), 1.19 (d, J=6.8 Hz, 3H). MS (APCI+) [M+H] $^+$335.

Step 10 tert-Butyl 4-((5R,7R)-7-hydroxy-5-methyl-6,7-dihydro-5H-cyclopenta[d]pyrimidin-4-yl)piperazine-1-carboxylate was treated with HCl (4M in dioxane, 2 mL) in DCM (5 mL)

for 6 hours to give (5R,7R)-5-methyl-4-(piperazin-1-yl)-6,7-dihydro-5H-cyclopenta[d]pyrimidin-7-ol dihydrochloride. MS (APCI+) [M+H] $^+$235.

Step 11

Tert-butyl 2,4-dimethoxybenzylcarbamate (3.96 g, 14.8 mmol) was dissolved in THF (74 mL) and cooled to −78° C. The solution was treated with butyl lithium (7.44 mL, 16.3 mmol) dropwise over a five minute period to afford a pale-yellow solution. The solution was allowed to stir for 15 minutes before the chloro(methoxy)methane (1.35 mL, 17.8 mmol) was added dropwise (neat). The reaction was stirred at −78° C. for 10 minutes, then allowed to warm slowly to ambient temperature overnight. The reaction was concentrated in vacuo to afford a yellow gel which was partitioned between half-saturated $NH_4Cl$ solution and ether. The aqueous layer was extracted once, and the organics were combined. The organic layer was washed with water, then brine, separated, dried over $Na_2SO_4$, filtered, and concentrated in vacuo. $^1H$ NMR supports the desired near-pure (>90%) tert-butyl 2,4-dimethoxybenzyl(methoxymethyl)carbamate (4.81 g, 104% yield) as a pale-yellow oil which was used without purification.

Step 12

(R)-4-benzyl-3-(2-(4-chlorophenyl)acetyl)oxazolidin-2-one (3.00 g, 9.10 mmol) was dissolved in DCM (91 mL) and cooled to −78° C. A 1M toluene solution of $TiCl_4$ (11.4 mL, 11.4 mmol) was added to the solution followed by DIEA (1.66 mL, 9.55 mmol) to afford a dark purple reaction. This was allowed to stir for 15 minutes before the tert-butyl 2,4-dimethoxybenzyl(methoxymethyl)carbamate (3.40 g, 10.9 mmol) was added as a solution in DCM (10 mL) dropwise. The reaction was allowed to stir for 15 minutes at −78° C., then allowed to warm to −18° C. in a brine-ice bath for one hour. This reaction was allowed to warm slowly to 0° C. over a 2.5 hour period. The reaction was then quenched with the addition of saturated $NH_4Cl$ solution (100 mL). The layers were separated, and the organic layers was extracted once with DCM. The combined organic layers were dried over $MgSO_4$, filtered, and concentrated in vacuo to afford a yellow oil. The residue was purified by chromatography (silica gel eluted with 4:1 hexanes:ethyl acetate) to afford the pure material as a colorless oil tert-butyl 2,4-dimethoxybenzyl((S)-3-((R)-4-benzyl-2-oxooxazolidin-3-yl)-2-(4-chlorophenyl)-3-oxopropyl)carbamate (4.07 g, 73.5% yield). This tert-butyl 2,4-dimethoxybenzyl((S)-3-((R)-4-benzyl-2-oxooxazolidin-3-yl)-2-(4-chlorophenyl)-3-oxopropyl)carbamate (680 mg, 1.12 mmol) was dissolved in DCM (10.6 mL) and water (560 uL; 19:1 DCM:water) at ambient temperature. The solution was treated with DDQ (380 mg, 1.67 mmol), and the reaction was allowed to stir for one day to afford reaction completion by TLC and LCMS analysis. The reaction was diluted with DCM and washed twice with half saturated $NaHCO_3$ solution. The organic layer was dried over $MgSO_4$, filtered, and concentrated in vacuo to afford a yellow-orange oil. The residue was purified by chromatography (silica gel eluted with 9:1 hexanes:ethyl acetate) to afford a mixture of the aldehyde by-product and tert-butyl (S)-3-((R)-4-benzyl-2-oxooxazolidin-3-yl)-2-(4-chlorophenyl)-3-oxopropylcarbamate (not separable) as a pale-yellow oil (729 mg combined mass). LC/MS (APCI+) m/z 359.1 [M−BOC+H]$^+$.

Step 13

35% $H_2O_2$ (0.240 mL, 2.91 mmol) was added to a solution of LiOH—$H_2O$ (0.0978 g, 2.33 mmol) in 2:1 THF:$H_2O$ (33 mL). The reaction mixture was stirred at room temperature for 35 minutes, and then cooled to 0° C. A solution containing a mixture of tert-butyl (S)-3-((R)-4-benzyl-2-oxooxazolidin-3-yl)-2-(4-chlorophenyl)-3-oxopropylcarbamate (0.535 g, 1.17 mmol) and 2,4-dimethoxybenzaldehyde (0.194 g, 1.17 mmol) in THF (7 mL) was added dropwise by addition funnel. The ice bath was allowed to slowly warm, and the reaction mixture was stirred overnight. The reaction mixture was then cooled to 0° C., and 1M $Na_2SO_3$ (7 mL) was added. The mixture was stirred for 5 minutes, and then warmed to room temperature and stirred an additional 20 minutes. The reaction mixture was then transferred to a separatory funnel and washed with ether (3×). The aqueous layer was acidified with $KHSO_4$(s), and the mixture was extracted with DCM (2×). The combined extracts were dried ($Na_2SO_4$), filtered, and concentrated to give (S)-3-(tert-butoxycarbonylamino)-2-(4-chlorophenyl)propanoic acid (0.329 g, 94.2% yield) as a white residue. LC/MS (APCI+) m/z 200 [M−BOC+H]$^+$.

Step 14

4M HCl/dioxane (5.49 ml, 22.0 mmol) was added to a solution of (S)-3-(tert-butoxycarbonylamino)-2-(4-chlorophenyl)propanoic acid (0.329 g, 1.10 mmol) in 2:1 dioxane:DCM (10 mL). The reaction mixture was stirred at room temperature overnight (16 hours), after which it was concentrated to ⅓ volume. The resulting cloudy mixture was diluted with ether, and the mixture was concentrated again to ⅓ volume. The mixture was diluted again with ether (20 mL), and the solids were isolated by filtration through a medium frit funnel with nitrogen pressure, rinsed with ether (5×10 mL), dried under nitrogen pressure, and dried in vacuo to give (S)-3-amino-2-(4-chlorophenyl)propanoic acid hydrochloride (0.199 g, 76.8% yield) as a white powder. HPLC >99 area % pure. LC/MS (APCI+) m/z 200.

Step 15

Boc2O (0.368 g, 1.69 mmol) was added to a solution of (S)-3-amino-2-(4-chlorophenyl)propanoic acid hydrochloride (0.199 g, 0.843 mmol) and tetramethylammonium hydroxide pentahydrate (0.382 g, 2.11 mmol) in 10:1 MeCN:$H_2O$ (7.7 mL). The reaction mixture was stirred overnight at room temperature (12 hours), after which the MeCN was removed on a rotary evaporator. The mixture was diluted with water and washed with ether (2×). The aqeuous layer was acidified with $KHSO_4$(s), the mixture was extracted with DCM, and the combined extracts were dried ($Na_2SO_4$), filtered, and concentrated to give (S)-3-(tert-butoxycarbonylamino)-2-(4-chlorophenyl)propanoic acid (0.229 g, 90.6% yield) as a foam. HPLC >99 area % pure. LC/MS (APCI+) m/z 200 [M−BOC+H]$^+$.

Step 16

To a solution of (5R,7R)-5-methyl-4-(piperazin-1-yl)-6,7-dihydro-5H-cyclopenta[d]pyrimidin-7-ol dihydrochloride (88 mg, 0.29 mmol) and (S)-3-(tert-butoxycarbonylamino)-2-(4-chlorophenyl)propanoic acid (86 mg, 0.29 mmol) in DCM (10 mL) and Diisopropylethylamine (0.22 mL, 1.3 mmol) was added HBTU (110 mg, 0.29 mmol). The reaction mixture was stirred at room temperature for 1 hour. The solvent was removed and the residue was dissolved in ethyl acetate (100 mL), washed with water (6×50 ml). The organic phase was dried and concentrated to give tert-butyl (S)-2-(4-chlorophenyl)-3-(4-((5R,7R)-7-hydroxy-5-methyl-6,7-dihydro-5H-cyclopenta[d]pyrimidin-4-yl)piperazin-1-yl)-3-oxo-propylcarbamate (116 mg, 78%). $^1$H NMR (CDCl$_3$, 400 MHz) δ 8.51 (s, 1H), 7.34-7.20 (m, 4H), 5.15-5.09 (m, 2H), 4.15-4.05 (m, 1H), 3.87-3.85 (m, 2H), 3.78-3.38 (m, 7H), 3.22-3.19 (m, 1H), 2.20-2.10 (m, 2H), 1.48 (s, 9H), 1.41 (s, 9H), 1.14-1.12 (d, J=7.2 Hz, 3H). MS (APCI+) [M+H] $^+$516.

Step 17

Treatment of tert-butyl (S)-2-(4-chlorophenyl)-3-(4-((5R,7R)-7-hydroxy-5-methyl-6,7-dihydro-5H-cyclopenta[d]pyrimidin-4-yl)piperazin-1-yl)-3-oxopropylcarbamate with HCl (4M in dioxane, 2 mL) in DCM (5 mL) for 6 hours to give (S)-3-amino-2-(4-chlorophenyl)-1-(4-((5R,7R)-7-hydroxy-5-methyl-6,7-dihydro-5H-cyclopenta[d]pyrimidin-4-yl)piperazin-1-yl)propan-1-one dihydrochloride. $^1$H NMR (D$_2$O, 400 MHz) δ 8.38 (s, 1H), 7.37-7.35 (d, J=8.4 Hz, 2H), 7.23-7.21 (d, J=8.4 Hz, 2H), 5.29-5.25 (m, 1H), 4.64 (s, 9H), 4.31-4.28 (m, 1H), 4.11 (m, 1H), 3.88-3.79 (m, 2H), 3.70-3.20 (m, 10H), 2.23-2.17 (m, 1H), 2.07-1.99 (m, 1H), 1.22-1.20 (m, 2H), 0.98-0.96 (d, J=6.8 Hz, 2H). MS (APCI+) [M+H] $^+$416.

The following compounds have also been prepared according to the above-described methods unless otherwise noted.

Example 6

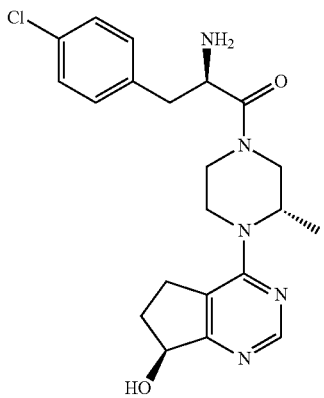 [SMILES: C[C@H]1CN(C(=O)[C@H](N)Cc2ccc(Cl)cc2)CCN1c1ncnc2c1CC[C@@H]2O]

(R)-2-amino-3-(4-chlorophenyl)-1-((S)-4-((S)-7-hydroxy-6,7-dihydro-5H-cyclopenta[d]pyrimidin-4-yl)-3-methylpiperazin-1-yl)propan-1-one $^1$H NMR (D$_2$O, 400 MHz) δ 8.60-8.40 (m, 1H), 7.40-7.10 (m, 4H), 5.25-5.10 (m, 1H), 4.00-2.90 (m, 14H), 2.52-2.40 (m, 1H), 1.95-1.80 (m, 1H), 1.20-1.10 (m, 3H). MS (APCI+) [M+H] $^+$416.

Example 7

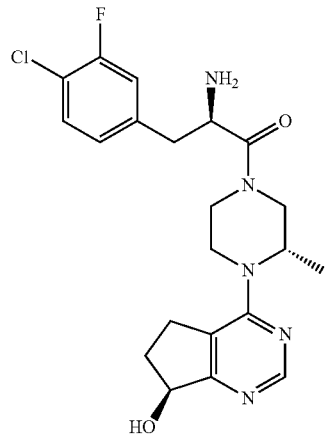 [SMILES: C[C@H]1CN(C(=O)[C@H](N)Cc2ccc(Cl)c(F)c2)CCN1c1ncnc2c1CC[C@@H]2O]

(R)-2-amino-3-(4-chloro-3-fluorophenyl)-1-((S)-4-((S)-7-hydroxy-6,7-dihydro-5H-cyclopenta[d]pyrimidin-4-yl)-3-methylpiperazin-1-yl)propan-1-one $^1$H NMR (D$_2$O, 400 MHz) δ 8.55-8.40 (m, 1H), 7.40-7.10 (m, 3H), 5.25-5.10 (m, 1H), 4.00-2.90 (m, 14H), 2.52-2.40 (m, 1H), 1.95-1.80 (m, 1H), 1.20-1.10 (m, 3H). MS (APCI+) [M+H] $^+$434.

Example 8

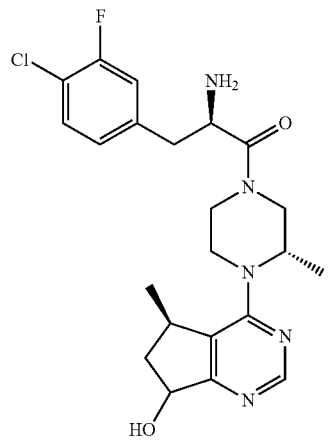 [SMILES: C[C@@H]1CC(O)c2ncnc(N3CCN(C(=O)[C@H](N)Cc4ccc(Cl)c(F)c4)C[C@@H]3C)c21]

(2R)-2-amino-3-(4-chloro-3-fluorophenyl)-1-((3S)-4-((5R)-7-hydroxy-5-methyl-6,7-dihydro-5H-cyclopenta[d]pyrimidin-4-yl)-3-methylpiperazin-1-yl)propan-1-one $^1$H NMR (D$_2$O, 400 MHz) δ 8.52-8.50 (m, 1H), 7.44-7.38 (m, 1H), 7.16-7.00 (m, 2H), 5.15-5.10 (m, 1H), 4.22-4.10 (m, 1H), 3.90-3.00 (m, 9H), 2.49-2.30 (m 2H), 1.60-1.50 (m, 1H), 1.18-0.95 (m, 6H). MS (APCI+) [M+H] +448.

Example 9

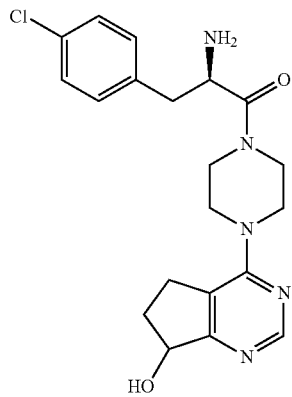 [SMILES: N[C@H](Cc1ccc(Cl)cc1)C(=O)N1CCN(c2ncnc3c2CCC3O)CC1]

(2R)-2-amino-3-(4-chlorophenyl)-1-(4-(7-hydroxy-6,7-dihydro-5H-cyclopenta[d]pyrimidin-4-yl)piperazin-1-yl)propan-1-one $^1$H NMR (D$_2$O, 400 MHz) δ 8.44 (s, 1H), 7.31-7.10 (m, 4H), 5.20-5.16 (m, 1H), 4.00-3.90 (m, 1H), 3.82-2.90 (m, 12H), 2.60-2.50 (m, 1H), 1.90-1.80 (m, 1H), 1.17-1.10 (m, 3H). MS (APCI+) [M+H] +402.

Example 10

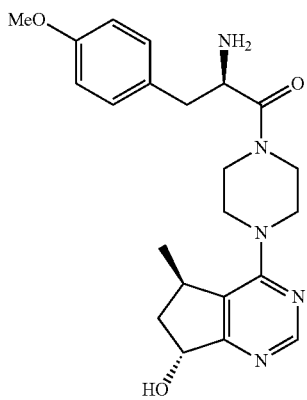 [SMILES: COc1ccc(C[C@@H](N)C(=O)N2CCN(c3ncnc4c3[C@H](C)C[C@H]4O)CC2)cc1]

(R)-2-amino-1-(4-((5R,7R)-7-hydroxy-5-methyl-6,7-dihydro-5H-cyclopenta[d]pyrimidin-4-yl)piperazin-1-yl)-3-(4-methoxyphenyl)propan-1-one $^1$H NMR (D$_2$O, 400 MHz) δ 8.44 (s, 1H), 7.17-7.10 (m, 2H), 6.90-6.80 (m, 2H), 5.31-5.26 (m, 1H), 4.15-4.05 (m, 1H), 3.80-2.90 (m, 11H), 2.68 (s, 3H), 2.26-2.20 (m, 1H), 2.10-2.00 (m, 1H), 1.04-1.00 (m, 3H). MS (APCI+) [M+H] +412.

Example 11

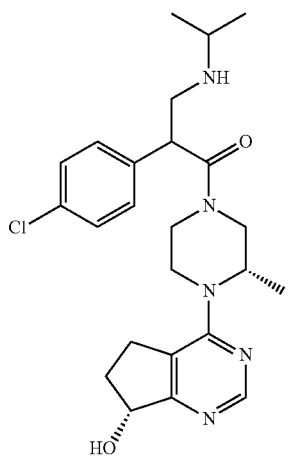 [SMILES: CC(C)NCC(C(=O)N1CCN(c2ncnc3c2CC[C@H]3O)[C@@H](C)C1)c1ccc(Cl)cc1]

2-(4-chlorophenyl)-1-((S)-4-((R)-7-hydroxy-6,7-dihydro-5H-cyclopenta[d]pyrimidin-4-yl)-3-methylpiperazin-1-yl)-3-(isopropylamino)propan-1-one $^1$H NMR (D$_2$O, 400 MHz) δ 8.40-8.25 (m, 1H), 7.45-7.10 (m, 4H), 5.25-5.10 (m, 1H), 4.40-4.19 (m, 1H), 3.80-2.80 (m, 12H), 2.55-2.40 (m, 1H), 1.85-1.70 (m, 1H), 1.22-1.10 (m, 9H). MS (APCI+) [M+H] +458.

Example 12

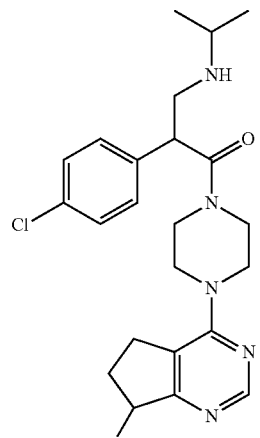

Preparation of 2-(4-chlorophenyl-1)-1-(4-(7-hydroxy-6,7-dihydro-5H-cyclopenta[d]pyrimidin-4-yl)piperazin-1-yl)-3-(isopropylamino)propan-1-one dihydrochloride Step 1

To a solution of the methyl 2-oxocyclopentanecarboxylate (40 g, 281 mmol) and thiourea (21 g, 281 mmol) in ethanol (200 ml) was added KOH (20 g, 356 mmol) in water (120 ml). The mixture was refluxed for 12 hour. The solvent was removed and the residue was quenched with concentrated HCl (25 mL). The precipitate was filtered, washed with water and dried to afford the 2-mercapto-6,7-dihydro-5H-cyclopenta[d]pyrimidin-4-ol (12.5 g, 26%). MS (APCI+) [M+H] $^+$168.

Step 2

To a solution of 2-mercapto-6,7-dihydro-5H-cyclopenta[d]pyrimidin-4-ol (12.2 g, 72.5 mmol) in water (200 ml) was added Raney Ni (8 g, slurry in water) and followed by concentrated ammonia solution (27 mmol). The mixture was refluxed for 6 hour. The catalyst was filtered off. The solvent was removed under vacuum to afford 6,7-dihydro-5H-cyclopenta[d]pyrimidin-4-ol (9.87 g, 99%). $^1$H NMR (CD$_3$OD, 400 MHz) δ 8.07 (s, 1H), 2.89-2.85 (m, 2H), 2.80-2.76 (m, 2H), 2.23 (m, 1H), 2.13-2.05 (m, 2H), 1.64 (m, 1H).

Step 3

To a solution of 6,7-dihydro-5H-cyclopenta[d]pyrimidin-4-ol (9.87 g, 72.5 mmol) in DCE (200 ml) was added DIEA (15 mL, 86.1 mmol). The mixture was stirred at room temperature for 30 minutes and then added POCl$_3$ (15 mL, 163.9 mmol) was added slowly. The mixture was stirred at room temperature for 1 hour and then refluxed for 12 hour. After cooling, the solvent was removed and the residue was dissolved in CHCl$_3$ (200 ml). The mixture was basified by adding ice-cooled concentrated aqueous ammonia (15 mL). The organic phase was separated. The aqueous phase was washed with CHCl$_3$ (3×100 mL). The organic phase was combined, dried and concentrated. The residue was subject to chromatography on silica gel, eluted by Hexanes/ethyl acetate (4:1) to afford 4-chloro-6,7-dihydro-5H-cyclopenta[d]pyrimidine (5.7 g, 51%). $^1$H NMR (CDCl$_3$, 400 MHz) δ 8.76 (s, 1H), 3.12-3.01 (m, 4H), 2.23-2.14 (m, 2H).

Step 4

To a solution of 4-chloro-6,7-dihydro-5H-cyclopenta[d]pyrimidine (5.69 g, 36.8 mmol) in chloroform (200 mL) was added MCPBA (19 g, 84.8 mmol) in chloroform (50 mL) dropwise. The mixture was stirred at room temperature for 16 hour. After cooling with ice-water, the mixture was quenched with Na$_2$S$_2$O$_3$ (27.5 g) in water (110 mL) dropwise and followed by Na$_2$CO$_3$ (14 g) in water (52 mL) dropwise. The organic phase was separated and the aqueous phase was extracted with chloroform (3×200 mL). The organic phase was dried and concentrated at low temperature (<25° C.). The residue was subject to chromatography on silica gel, eluting by ethyl acetate to afford 4-chloro-6,7-dihydro-5H-cyclopenta[d]pyrimidine 1-oxide (2.93 g, 47%). MS (APCI+) [M+H] $^+$171.

Step 5

The solution of 4-chloro-6,7-dihydro-5H-cyclopenta[d]pyrimidine 1-oxide (2.93 g, 17.2 mmol) in acetic anhydride (50 mL) was added dropwise to the acetic anhydride (50 mL) at 50° C. After addition, the mixture was stirred at 110° C. for 2 hour. After cooling, the solvent was removed and the residue was treated with toluene and hexanes (1:1, 200 mL). The mixture was stirred and then the solvent was removed. The residue was subject to chromatography on silica gel, eluted by hexanes/ethyl acetate (4:1-3:1) to afford the 4-chloro-6,7-dihydro-5H-cyclopenta[d]pyrimidin-7-yl acetate (2.3 g, 63%). $^1$H NMR (CDCl$_3$, 400 MHz) δ 8.92 (s, 1H), 6.20-6.16 (m, 1H), 3.20-3.10 (m, 1H), 3.03-2.93 (m, 1H), 2.76-2.67 (m, 1H), 2.20-2.05 (m, 4H).

Step 6

To a solution of 4-chloro-6,7-dihydro-5H-cyclopenta[d]pyrimidin-7-yl acetate (1.15 g, 5.4 mmol) in NMP (4 mL) and TEA (0.5 mL) was added 1-Boc-piperazine (1.05 g, 5.64 mmol). The mixture was microwaved at 100° C. for 30 minutes and then diluted with ethyl acetate (200 mL) and washed with water (6×100 mL). The organic phase was dried and concentrated. The residue was subject to chromatography on silica gel, eluting by hexanes/ethyl acetate (2:1-1:1) to afford the tert-butyl 4-(7-acetoxy-6,7-dihydro-5H-cyclopenta[d]pyrimidin-4-yl)piperazine-1-carboxylate (1.47 g, 75%). $^1$H NMR (CDCl$_3$, 400 MHz) δ 8.56 (s, 1H), 5.99-5.96 (m, 1H), 3.78-3.73 (m, 2H), 3.53-3.50 (m, 2H), 3.15-3.07 (m, 1H), 2.99-2.92 (m, 1H), 2.63-2.54 (m, 1H), 2.04-1.93 (m, 1H), 1.48 (s, 9H). MS (APCI+) [M+H] $^+$363.

Step 7

To a solution of tert-butyl 4-(7-acetoxy-6,7-dihydro-5H-cyclopenta[d]pyrimidin-4-yl)piperazine-1-carboxylate (0.43 g, 1.2 mmol) in THF (15 mL) was added LiOH (3M, 6 mL). The mixture was stirred at room temperature overnight. The mixture was quenched with 2N HCl (9 mL) and then extracted with DCM (3×100 mL). The organic phase was dried and concentrated. The residue was subject to chromatography on silica gel, eluted by DCM/MeOH (20:1) to afford the tert-butyl 4-(7-hydroxy-6,7-dihydro-5H-cyclopenta[d]pyrimidin-4-yl)piperazine-1-carboxylate (0.37 g, 97%). $^1$H NMR (CDCl$_3$, 400 MHz) δ 8.51 (m, 1H), 5.06-5.04 (m, 1H), 3.80-3.69 (m, 4H), 3.56-3.45 (m, 4H), 3.10-3.05 (m, 1H), 2.94-2.86 (m, 1H), 2.51-2.44 (m, 1H), 2.00-1.94 (m, 1H), 1.48 (s, 9H). MS (APCI+) [M+H] $^+$321.

Step 8

To a solution of tert-butyl 4-(7-hydroxy-6,7-dihydro-5H-cyclopenta[d]pyrimidin-4-yl)piperazine-1-carboxylate (0.37 g, 1.2 mmol) in DCM (20 mL) was added HCl in dioxane (4M, 5 mL). The mixture was stirred at room temperature overnight. The solvent was removed to afford the 4-(piperazin-1-yl)-6,7-dihydro-5H-cyclopenta[d]pyrimidin-7-ol dihydrochloride (0.25 g, 98%). MS (APCI+) [M+H] $^+$221.

Step 9

To a solution of 4-(piperazin-1-yl)-6,7-dihydro-5H-cyclopenta[d]pyrimidin-7-ol dihydrochloride (40 mg, 0.14 mmol) in DCM (20 mL) and TEA (2 mL) was added 3-(tert-butoxycarbonyl(isopropyl)amino)-2-(4-chlorophenyl)propanoic acid (47 mg, 0.14 mmol) and HBTU (52 mg, 0.14 mmol). The mixture was stirred at room temperature for 1 hour. The solvent was removed and the residue was subject to chromatography on silica gel, eluted by ethyl acetate to afford the tert-butyl 2-(4-chlorophenyl)-3-(4-(7-hydroxy-6,7-dihydro-5H-cyclopenta[d]pyrimidin-4-yl)piperazin-1-yl)-3-oxopropyl(isopropyl)carbamate (49 mg, 66%). MS (APCI+) [M+H] $^+$544.

Step 11

To a solution of tert-butyl 2-(4-chlorophenyl)-3-(4-(7-hydroxy-6,7-dihydro-5H-cyclopenta[d]pyrimidin-4-yl)piperazin-1-yl)-3-oxopropyl(isopropyl)carbamate (49 mg, 0.09 mmol) in DCM (10 mL) was added HCl in dioxane (4M, 2 mL). The mixture was stirred at room temperature overnight. The solvent was removed to afford the 2-(4-chlorophenyl)-1-(4-(7-hydroxy-6,7-dihydro-5H-cyclopenta[d]pyrimidin-4-yl)piperazin-1-yl)-3-(isopropylamino)propan-1-one dihydrochloride (46 mg, 99%). $^1$H NMR (D$_2$O, 400 MHz) δ 8.38-8.36 (m, 1H), 7.37-7.34 (m, 2H), 7.22-7.19 (m, 2H), 5.18-5.10 (m, 1H), 4.34-4.28 (m, 1H), 4.10-3.00 (m, 12H), 2.50-2.40 (m, 1H), 1.85-1.75 (m, 1H), 1.28-1.26 (m, 6H), 1.20-1.13 (m, 3H). MS (APCI+) [M+H] +444.

Example 13

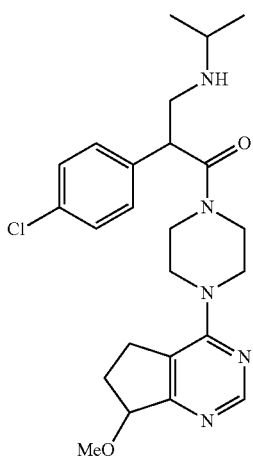 [SMILES: COC1CCc2c1ncnc2N1CCN(C(=O)C(CNC(C)C)c2ccc(Cl)cc2)CC1]

2-(4-chlorophenyl)-3-(isopropylamino)-1-(4-(7-methoxy-6,7-dihydro-5H-cyclopenta[d]pyrimidin-4-yl)piperazin-1-yl)propan-1-one $^1$H NMR (D$_2$O, 400 MHz) δ 8.39 (s, 1H), 7.40-7.36 (m, 2H), 7.22-7.16 (m, 2H), 4.90-4.85 (m, 1H), 4.30-4.28 (m, 1H), 4.12-4.00 (m, 1H), 3.92-3.80 (m, 2H), 3.79-3.70 (m, 1H), 3.58-3.18 (m, 7H), 3.15-2.80 (2H), 2.46-2.35 (m, 1H), 1.95-1.83 (M, 1H), 1.20-1.14 (m, 6H). MS (APCI+) [M+H] +458.

Example 14

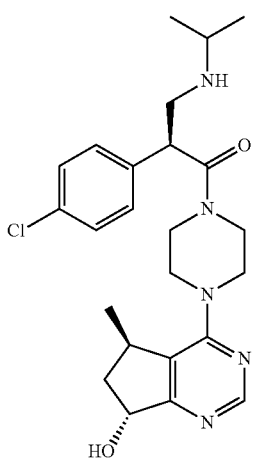 [SMILES: CC(C)NC[C@@H](C(=O)N1CCN(c2ncnc3c2[C@H](C)C[C@H]3O)CC1)c1ccc(Cl)cc1]

(S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one Step 1

Ethyl pulegenate (130 g, 662 mmol) in EtOAc (900 mL) was cooled to −78° C. using a dry ice-isopropanol bath. This mixture was subjected to ozonolysis until the reaction turned purple in color. At this point, ozone generation ceased, and the reaction was removed from the dry-ice bath. Oxygen was bubbled through the reaction mixture until it turned yellow. The reaction mixture was concentrated under vacuum, and the resulting residue was dissolved in glacial acetic acid (400 mL). The solution was cooled to 0° C., and Zn dust (65 g, 993 mmol) was added portionwise over 30 minutes. The reaction was then allowed to stir for 2 hours, at which point the reaction mixture was filtered through a pad of celite to remove the zinc dust. The acetic acid was neutralized to pH 7 with aqueous NaOH and NaHCO$_3$ and extracted with ether (3×800 mL). The combined organics were dried with brine, MgSO$_4$ and concentrated to give (2R)-ethyl 2-methyl-5-oxocyclopentanecarboxylate as a brown liquid (107 g, 95%).

Step 2

Ammonium acetate (240.03 g, 3113.9 mmol) was added to a solution of (R)-ethyl 2-methyl-5-oxocyclopentanecarboxylate (106.0 g, 622.78 mmol) in MeOH (1.2 L). The reaction mixture was stirred at room temperature under nitrogen for 20 hours, after which it was complete as judged by TLC and HPLC. The reaction mixture was concentrated to remove MeOH. The resulting residue was dissolved in DCM, washed twice with H$_2$O, once with brine, dried (Na$_2$SO$_4$), filtered, and concentrated to give (R)-ethyl 2-amino-5-methylcyclopent-1-enecarboxylate (102 g, 97% yield) as an orange oil. LC/MS (APCI+) m/z 170 [M+H]+.

Step 3

A solution containing (R)-ethyl 2-amino-5-methylcyclopent-1-enecarboxylate (161.61 g, 955.024 mmol) and ammonium formate (90.3298 g, 1432.54 mmol) in formamide (303.456 ml, 7640.19 mmol) was heated to an internal temperature of 150° C. and stirred for 17 hours. The reaction mixture was cooled, and transferred to a 2 L single neck flask. Then excess formamidine was removed by high vacuum distillation. Once formamidine stopped coming over, the remaining oil in the still pot was dissolved in DCM and washed with brine (3×200 mL). The combined aqueous washes were extracted with DCM. The combined organic extracts were dried (Na$_2$SO$_4$), filtered, and concentrated. The resulting brown oil was dissolved in minimal DCM, and this solution was added using a separatory funnel to a stirred solution of ether (ca. 5 vol of ether vs. DCM solution), causing some brown precipitate to form. This brown precipitate was removed by filtration through a medium frit funnel which was rinsed with ether and disposed. The filtrate was concentrated, the trituration from ether repeated two more times and then dried on high vacuum line to give (R)-5-methyl-6,7-dihydro-5H-cyclopenta[d]pyrimidin-4-ol (93.225 g, 65.00% yield) as a brown-yellow pasty solid. LC/MS (APCI−) m/z 149.2.

Step 4

Neat POCl$_3$ (463.9 ml, 5067 mmol) was added slowly by addition funnel to a 0° C. solution of (R)-5-methyl-6,7-dihydro-5H-cyclopenta[d]pyrimidin-4-ol (152.2 g, 1013 mmol) in DCE (1.2 L). After the addition was complete, the reaction mixture was warmed to room temperature, then heated to reflux and stirred for 70 minutes. The reaction was complete as determined by HPLC. The reaction mixture was cooled to room temperature, and the excess POCl$_3$ was quenched in 4 portions as follows: Reaction mixture transferred to separatory funnel and dripped into a beaker containing ice and saturated NaHCO₃ solution cooled in an ice bath. Once the addition of each portion of the reaction mixture was completed, the quenched mixture was stirred 30 minutes to ensure complete destruction of POCl₃ prior to transfer to separatory funnel. The mixture was transferred to the separatory funnel and extracted twice with DCM. The combined extracts were dried (Na₂SO₄), filtered, and concentrated. The crude was purified on silica gel as follows: silica gel (1 kg) was slurried in 9:1 hexane:ethyl acetate onto a 3 L fitted funnel, silica settled under vacuum, topped with sand. The crude was loaded with a DCM/hexane mixture, and the compound was eluted using 1 L sidearm flasks under vacuum. High Rf byproducts eluted first, then (R)-4-chloro-5-methyl-6,7-dihydro-5H-cyclopenta[d]pyrimidine (104.4 g, 61.09% yield) as a brown oil. Triethylamine (93.0 ml, 534 mmol) and tert-butyl piperazine-1-carboxylate (34.8 g, 187 mmol) was added to a solution of (R)-4-chloro-5-methyl-6,7-dihydro-5H-cyclopenta[d]pyrimidine (30.0 g, 178 mmol) in n-BuOH (250 mL). The reaction mixture was heated to reflux under nitrogen and stirred overnight (17 hours), after which it was concentrated on a rotavap. The resulting oil was dissolved in DCM, washed with H₂O, dried (Na₂SO₄), filtered, and was concentrated. The resulting brown oil was purified on silica gel eluting first with 2:1 hexanes:ethyl acetate until product eluting cleanly, then gradient 1:1 to 1:5 DCM:ethyl acetate to give (R)-tertbutyl 4-(5-methyl-6,7-dihydro-5H-cyclopenta [d]pyrimidin-4-yl)piperazine-1-carboxylate (42.0 g, 74.1% yield) as a beige powder. LC/MS (APCI+) m/z 319.1 [M+H]⁺.

Step 5

Solid 77% max. MCPBA (23.9 g, 107 mmol) was added portionwise to a 0° C. solution of (R)-tert-butyl 4-(5-methyl-6,7-dihydro-5H-cyclopenta[d]pyrimidin-4-yl)piperazine-1-carboxylate (20.0 g, 62.8 mmol) in CHCl₃ (310 mL). The reaction mixture was stirred 5 for minutes, then warmed to room temperature and stirred for 90 minutes. HPLC looked similar after 7.5 hours. The reaction mixture was cooled to 0° C., then NaHCO₃ (13.2 g, 157 mmol) and another 0.5 equivalents of m-CPBA were added. The reaction mixture was stirred overnight (14 hours). The reaction mixture was cooled to 0° C., and a solution of Na₂S₂O₃ (29.8 g, 188 mmol) in H₂O (50 mL) was added dropwise by addition funnel. This was followed by a solution of Na₂CO₃ (24.6 g, 232 mmol) in H₂O (70 mL) by addition funnel (mixture turns homogeneous). The reaction mixture was stirred for 30 minutes, then the mixture was extracted with CHCl₃ (3×150 mL). The combined extracts were dried (Na₂SO₄), filtered, and concentrated to give the N-oxide. LC/MS (APCI+) m/z 335.1 [M+H]+.

Step 6

Ac₂O (77.0 ml, 816 mmol) was added to the N-oxide (21.0 g, 62.8 mmol) from Step 5. The reaction mixture was heated under nitrogen in a 90° C. sand bath and stirred for 100 minutes. The reaction mixture was cooled to room temperature, and excess acetic anhydride was removed by rotary evaporation. The resulting oil was dissolved in DCM, which was then poured carefully into ice saturated Na₂CO₃. The mixture was extracted with DCM, and the combined extracts were dried (Na₂SO₄), filtered, and concentrated to give (5R)-tert-butyl 4-(7-acetoxy-5-methyl-6,7-dihydro-5H-cyclopenta[d]pyrimidin-4-yl)piperazine-1-carboxylate (23.6 g, 100%) as a brown foam. LC/MS (APCI+) m/z 377.1 [M+H]+.

Step 7

LiOH—H₂O (6.577 g, 156.7 mmol) was added to a 0° C. solution of (5R)-tert-butyl 4-(7-acetoxy-5-methyl-6,7-dihydro-5H-cyclopenta[d]pyrimidin-4-yl)piperazine-1-carboxylate (23.6 g, 62.69 mmol) in 2:1 THF:H₂O (320 mL). The reaction mixture was stirred for 10 minutes, and then warmed to room temperature. LC/MS looked the same at 3 hours and 4.5 hours. The reaction mixture was cooled to 0° C., and then saturated NH₄Cl was added to the mixture. The mixture was stirred for 5 minutes, and most of the THF was removed by rotary evaporation. The mixture was extracted with EtOAc (3×250 mL), and the combined extracts were dried (Na₂SO₄), filtered, and concentrated. The crude was flashed on Biotage 65M: 4:1 DCM:ethyl acetate, then gradient to 1:1 to 1:4 DCM:ethyl acetate. Once the product was eluting, then ethyl acetate was flushed through the column. Then 30:1 DCM: MeOH eluted the rest of the product (8.83 g). The mixed fractions were re-flashed with Biotage 40M using the same conditions to give another 2.99 g which gave a combined yield of (5R)-tert-butyl 4-(7-hydroxy-5-methyl-6,7-dihydro-5H-cyclopenta[d]pyrimidin-4-yl)piperazine-1-carboxylate (11.82 g, 56.38% yield) as a brown foam. LC/MS (APCI+) m/z 335.1 [M+H]+.

Step 8

A solution of DMSO (5.45 ml, 76.8 mmol) in DCM (50 mL) was added dropwise by addition funnel to a −78° C. solution of oxalyl chloride (3.35 ml, 38.4 mmol) in DCM (150 mL). The reaction mixture was stirred for 35 minutes, and then a solution of (5R)-tert-butyl 4-(7-hydroxy-5-methyl-6,7-dihydro-5H-cyclopenta[d]pyrimidin-4-yl)piperazine-1-carboxylate (9.17 g, 27.4 mmol) in DCM (80 mL) was added slowly by addition funnel. The reaction mixture was stirred another 1 hour at −78° C., after which neat triethylamine (18.0 ml, 129 mmol) was added to the mixture. The reaction mixture was then allowed to warm to room temperature, and then it was stirred for 30 minutes. H₂O was added. The mixture was extracted with DCM (3×200 mL), and the combined extracts were dried (Na₂SO₄), filtered, and concentrated in vacuo. The crude was purified on silica gel (Biotage 65M): the column was flushed with ca. 800 mL 4:1 DCM: EtOAc, then gradient to 1:1 DCM:ethyl acetate until product eluting, then 1:4 DCM:EtOAc eluted product to give (R)-tert-butyl 4-(5-methyl-7-oxo-6,7-dihydro-5H-cyclopenta[d]pyrimidin-4-yl)piperazine-1-carboxylate (7.5 g, 82.3% yield) as a brown foam. The foam was concentrated (3×) from DCM/ hexanes, which gave a very light brown foam. HPLC >95% area. LC/MS (APCI+) m/z 333 [M+H]+.

Step 9

Triethylamine (4.33 ml, 31.1 mmol; degassed with nitrogen 30 minutes prior to use) and formic acid (1.36 ml, 36.1 mmol; degassed with nitrogen 30 minutes prior to use) were added to a solution of (R)-tert-butyl 4-(5-methyl-7-oxo-6,7-dihydro-5H-cyclopenta[d]pyrimidin-4-yl)piperazine-1-carboxylate (9.75 g, 29.3 mmol) in DCM (210 mL; degassed with nitrogen 30 minutes prior to use). The mixture was stirred for 5 minutes, then a Ru catalyst (0.0933 g, 0.147 mmol) was added. The reaction was stirred under positive nitrogen pressure overnight (18 hours). The reaction mixture was concentrated to dryness and dried on high vacuum. The impure material was flashed on Biotage 65M loaded 1:1 DCM:ethyl acetate 500 mL flushed, then 1:4 DCM:ethyl acetate until product (2nd spot), then gradient to neat ethyl acetate, then 25:1 DCM:MeOH eluted rest of product. The fractions were combined and concentrated on a rotary evaporator. The residue was concentrated again from DCM/hexanes to give a mixture of tert-butyl 4-((5R,7R)-7-hydroxy-5-methyl-6,7-dihydro-5H-cyclopenta[d]pyrimidin-4-yl) piperazine-1-carboxylate (major) and tert-butyl 4-((5R,7S)-7-hydroxy-5-methyl-6,7-dihydro-5H-cyclopenta[d] pyrimidin-4-yl)piperazine-1-carboxylate (minor) (9.35 g, 95.3% yield) as a beige foam. LC/MS (APCI+) m/z 335 [M+H]+. $^1$H NMR (CDCl$_3$) shows 88% de by integration of carbinol methine.

Step 10

4-Nitrobenzoyl chloride (4.27 g, 23.0 mmol) was added to a 0° C. solution of tert-butyl 4-((5R,7R)-7-hydroxy-5-methyl-6,7-dihydro-5H-cyclopenta[d]pyrimidin-4-yl)piperazine-1-carboxylate (7.0 g, 20.9 mmol) and triethylamine (4.38 ml, 31.4 mmol) in DCM (110 mL). The reaction mixture was stirred at room temperature overnight, after which saturated NaHCO$_3$ was added. The mixture was stirred 10 minutes, and then extracted with DCM. The combined extracts were dried (Na$_2$SO$_4$), filtered, and concentrated. The crude was flashed on Biotage 65M (3:1 hexanes:ethyl acetate loaded crude, then 2:1 hexanes:ethyl acetate eluted tert-butyl 4-((5R,7R)-5-methyl-7-(4-nitrobenzoyloxy)-6,7-dihydro-5H-cyclopenta[d]pyrimidin-4-yl)piperazine-1-carboxylate and a few mixed fractions). Then tert-butyl 4-((5R,7S)-5-methyl-7-(4-nitrobenzoyloxy)-6,7-dihydro-5H-cyclopenta [d]pyrimidin-4-yl)piperazine-1-carboxylate was eluted using 1:2 hexanes:ethyl acetate. The fractions with product were concentrated by rotary evaporation to give tert-butyl 4-((5R, 7R)-5-methyl-7-(4-nitrobenzoyloxy)-6,7-dihydro-5H-cyclopenta[d]pyrimidin-4-yl)piperazine-1-carboxylate (8.55 g, 84.5% yield) as a yellow foam. LC/MS (APCI+) m/z 484 [M+H]+. $^1$H NMR (CDCl$_3$) shows single diastereomer). The fractions with other diastereomer were concentrated by rotary evaporation to give tert-butyl 4-((5R,7S)-5-methyl-7-(4-nitrobenzoyloxy)-6,7-dihydro-5H-cyclopenta[d]pyrimidin-4-yl)piperazine-1-carboxylate (0.356 g, 3.52% yield) as a brown foam. LC/MS (APCI+) m/z 484 [M+H]+.

Step 11

LiOH—H$_2$O (0.499 g, 11.9 mmol) was added to a 0° C. solution of tert-butyl 4-((5R,7R)-5-methyl-7-(4-nitrobenzoyloxy)-6,7-dihydro-5H-cyclopenta[d]pyrimidin-4-yl)piperazine-1-carboxylate (2.30 g, 4.76 mmol) in 2:1 THF:H$_2$O (40 mL). The reaction mixture was warmed to room temperature and stirred for 1 hour. The THF was removed by rotary evaporation, saturated NaHCO$_3$ was added, and the mixture was extracted with ethyl acetate. The combined extracts were washed (1×) with saturated NaHCO$_3$, dried (Na$_2$SO$_4$), filtered, and concentrated to give tert-butyl 4-((5R,7R)-7-hydroxy-5-methyl-6,7-dihydro-5H-cyclopenta[d]pyrimidin-4-yl)piperazine-1-carboxylate (1.59 g, 100.0% yield) as a yellow foam. HPLC after workup just product>98 area % pure. LC/MS (APCI+) m/z 335 [M+H]+. The tert-butyl 4-((5R,7S)-7-hydroxy-5-methyl-6,7-dihydro-5H-cyclopenta [d]pyrimidin-4-yl)piperazine-1-carboxylate was prepared using an analogous method.

Step 12

4M HCl/dioxane (11.2 ml, 44.9 mmol) was added to a solution of tert-butyl 4-((5R,7R)-7-hydroxy-5-methyl-6,7-dihydro-5H-cyclopenta[d]pyrimidin-4-yl)piperazine-1-carboxylate (0.600 g, 1.79 mmol) in dioxane (15 mL). The reaction mixture was stirred at room temperature under nitrogen overnight (20 hours). The mixture was concentrated to dryness and dried on high vacuum line. The crude was suspended in ether, sonicated, and stirred for 5 minutes. The solids were isolated by filtration through a medium frit funnel with nitrogen pressure, rinsed with ether, dried under nitrogen pressure, and dried further on a hi vacuum line to give (5R, 7R)-5-methyl-4-(piperazin-1-yl)-6,7-dihydro-5H-cyclopenta[d]pyrimidin-7-ol dihydrochloride (0.440 g, 79.8% yield) as a yellow powder. LC/MS (APCI+) m/z 235. The (5R,7S)-5-methyl-4-(piperazin-1-yl)-6,7-dihydro-5H-cyclopenta[d]pyrimidin-7-ol dihydrochloride was prepared using an analogous method.

Step 13

Methyl 2-(4-chlorophenyl)acetate (36.7 g, 199 mmol) and paraformaldehyde (6.27 g, 209 mmol) were dissolved/suspended in DMSO (400 mL) and treated with NaOMe (537 mg, 9.94 mmol). The mixture was allowed to stir at room temperature for 2 hours to completion by TLC analysis of the crude. The reaction was poured into ice-cold water (700 mL; white emulsion) and neutralized with the addition of 1M HCl solution. The aqueous layer was extracted with ethyl acetate (3×), and the organics were combined. The organic layer was washed with water (2×), brine (1×), separated, dried over MgSO$_4$, filtered, and concentrated in vacuo to afford the crude product as a yellow oil. The residue was loaded onto a large fritted filtered with silica gel and eluted with 9:1 hexanes: ethyl acetate until the starting material/olefin were collected. The plug was then eluted with 1:1 hexanes:ethyl acetate until the pure desired product was eluted completely. The concentrated pure fractions yielded methyl 2-(4-chlorophenyl)-3-hydroxypropanoate as a colorless oil (39.4 g, 92%).

Step 14

Methyl 2-(4-chlorophenyl)-3-hydroxypropanoate (39.4 g, 184 mmol) was dissolved in DCM (500 mL) and treated with TEA (64.0 mL, 459 mmol). The solution was cooled to 0° C. and slowly treated with MsCl (15.6 mL, 202 mmol), then allowed to stir for 30 minutes to completion by TLC analysis. The solution was partitioned with 1N HCl solution, and the aqueous layer was extracted once with DCM. The combined organic layer was washed once more with 1N HCl solution, separated, washed with diluted NaHCO$_3$ solution, and separated. The organic layer was dried over MgSO$_4$, filtered, and concentrated in vacuo to afford an orange oil. The residue was loaded onto a large fitted filter with a plug of silica gel and eluted with 9:1 hexanes:ethyl acetate affording the pure desired product by TLC analysis. The concentrated pure fractions yielded the methyl 2-(4-chlorophenyl)acrylate as a colorless oil (30.8 g, 85%). This methyl 2-(4-chlorophenyl)acrylate (500 mg, 2.54 mmol) was added as a solution in THF (1.35 mL) to a stirring solution of i-PrNH$_2$ (217 uL, 2.54 mmol) in THF (5.0 mL) at 0° C. The reaction was allowed to stir at room temperature overnight to completion by LCMS analysis. The Boc2O (584 uL, 2.54 mmol) was added to the stirring amine via pipet. The reaction was allowed to stir overnight to completion by LCMS and TLC analysis of the mixture. The solution was concentrated in vacuo to afford methyl 3-(tert-butoxycarbonyl(isopropyl)amino)-2-(4-chlorophenyl)propanoate as a colorless oil (854 mg, 94%). LC/MS (APCI+) m/z 256.1 [M−Boc]+.

Step 15

Methyl 3-(tert-butoxycarbonyl(isopropyl)amino)-2-(4-chlorophenyl)propanoate (133 g, 374 mmol) was dissolved in THF (1.0 L) and treated with KOTMS (56.0 g, 392 mmol) at room temperature. The mixture was allowed to stir overnight to completion by LCMS analysis of the crude. The mixture was concentrated in vacuo to afford a wet foam, which was allowed to dry under vacuum overnight to afford potassium 3-(tert-butoxycarbonyl(isopropyl)amino)-2-(4-chlorophenyl)propanoate as a white solid (148.7 g, 105%). LC/MS (APCI+) m/z 242.1 [M−Boc-K]+.

Step 16

Potassium 3-(tert-butoxycarbonyl(isopropyl)amino)-2-(4-chlorophenyl)propanoate (77.2 g, 203 mmol) was dissolved in THF (515 mL) and treated with pivaloyl chloride (26.3 mL, 213 mmol) at room temperature. The mixture was allowed to stir for 3 hours to form the mixed anhydride. (S)-4-benzyloxazolidin-2-one (46.1 g, 260 mmol) was dissolved in THF (600 mL) and cooled to −78° C. in a separate flask. The solution was treated with n-BuLi (102 mL of a 2.50M solution in hexanes, 254 mmol) and allowed to stir for one hour. The prepared anhydride solution was added to the stirring Li-oxazolidinone via cannula, and the mixture was allowed to warm to room temperature overnight. The mixture was quenched with the addition of saturated ammonium chloride solution, then partitioned between more water and ethyl acetate. The aqueous layer was extracted several times, and the organics were combined. The organic layer was washed with water, then brine, separated, dried over $MgSO_4$, filtered, and concentrated in vacuo. The residue was purified/separated (diastereomers) via chromatography (silica gel eluted with 4:1 hexanes:ethyl acetate) to afford the completely separated diastereomers as viscous oils: tert-butyl (R)-3-((S)-4-benzyl-2-oxooxazolidin-3-yl)-2-(4-chlorophenyl)-3-oxopropyl(isopropyl)carbamate (12.16 g, 24% based on ½ of acid racemate) and tert-butyl (S)-3-((S)-4-benzyl-2-oxooxazolidin-3-yl)-2-(4-chlorophenyl)-3-oxopropyl(isopropyl)carbamate (39.14 g, 77% based on ½ of acid racemate). LC/MS (APCI+) m/z 401.2 [M−Boc]+.

Step 17

LiOH—$H_2O$ (168 mg, 4.00 mmol) was added to a stirring solution of THF (30 mL) and water (15 mL) at room temperature until it was dissolved. The mixture was treated with hydrogen peroxide (658 uL of a 35% wt. solution in water, 8.00 mmol) and allowed to stir at room temperature for 10 minutes. The reaction was cooled to 0° C. in an ice bath, and the tert-butyl (S)-3-((S)-4-benzyl-2-oxooxazolidin-3-yl)-2-(4-chlorophenyl)-3-oxopropyl(isopropyl)carbamate (1.00 g, 2.00 mmol) was added dropwise via addition funnel as a solution in THF (15 mL) over a 10 minutes. The mixture was allowed to stir overnight at room temperature to completion by LCMS analysis of the crude. The reaction was cooled to 0° C., and then treated with 1M $Na_2SO_3$ (9.00 mL) solution via addition funnel over a ten minute period. After the addition was complete, the mixture was allowed to warm to room temperature for 10 minutes. The mixture was concentrated to remove the THF, and then diluted with water. The aqueous layer was washed twice with ethyl acetate (discarded). The aqueous layer was partitioned with ethyl acetate, then treated dropwise while stirring with 1M HCl until pH 2-3 was attained. The aqueous layer was extracted twice with ethyl acetate, and the organics were combined. The organic was washed with brine, separated, dried over $MgSO_4$, filtered, and concentrated in vacuo. The colorless oil product was dried under high vacuum for one hour to afford (S)-3-(tert-butoxycarbonyl(isopropyl)amino)-2-(4-chlorophenyl)propanoic acid as a viscous oil/foam (685 mg, 100%). LC/MS (APCI+) m/z 242.1 [M−Boc]+.

Step 18

A solution of (5R,7R)-5-methyl-4-(piperazin-1-yl)-6,7-dihydro-5H-cyclopenta[d]pyrimidin-7-ol dihydrochloride (2.92 g, 9.51 mmol) and (S)-3-(tert-butoxycarbonyl(isopropyl)amino)-2-(4-chlorophenyl)propanoic acid (3.25 g, 9.51 mmol) in DCM (40 mL) and DIEA (5.0 mL, 28.7 mmol) was stirred at room temperature for 10 minutes. HBTU (3.61 g, 9.51 mmol) was added to the mixture. The mixture was stirred at room temperature for 1 hour. The solvent was removed, and the residue was dissolved in ethyl acetate (500 mL) and washed with water (6×100 mL). The organic phase was dried and concentrated. The residue was subject to column chromatography, eluted by EtOAc-DCM/MeOH (20:1) to give tert-butyl (S)-2-(4-chlorophenyl)-3-(4-((5R,7R)-7-hydroxy-5-methyl-6,7-dihydro-5H-cyclopenta[d]pyrimidin-4-yl)piperazin-1-yl)-3-oxopropyl(isopropyl)carbamate (3.68 g, 69%.) LC/MS (APCI+) m/z 558.2 [M+H]+.

Step 19

The tert-butyl (S)-2-(4-chlorophenyl)-3-(4-((5R,7R)-7-hydroxy-5-methyl-6,7-dihydro-5H-cyclopenta[d]pyrimidin-4-yl)piperazin-1-yl)-3-oxopropyl(isopropyl)carbamate (2.50 g, 4.48 mmol) was dissolved in dioxane (22.4 mL) and treated with 4M HCl in dioxane (22.4 mL, 89.6 mmol) at room temperature. The resulting solution was allowed to stir overnight to completion by LCMS analysis of the crude. The solution was concentrated in vacuo to afford a gel that was dissolved in a minimal amount of methanol (10 mL). The solution was transferred via pipette to stirred ether (300 mL) to afford a white precipitate of desired product. The addition was about half when the white precipitate melted into a yellow gel. The material was concentrated in vacuo to afford a yellow gel which was allowed to stand under reduced pressure overnight to yield (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one dihydrochloride as a light yellow powder (2.14 g, 90%).

$^1$H NMR ($D_2O$, 400 MHz) δ 8.39 (s, 1H), 7.37-7.35 (d, J=8.4 Hz, 2H), 7.23-7.20 (d, J=8.4 Hz, 2H), 5.29-5.25 (m, 1H), 4.33-4.29 (m, 1H), 4.14-4.10 (m, 1H), 3.89-3.19 (m, 11H), 2.23-2.17 (m, 1H), 2.08-1.99 (m, 1H), 1.20-1.18 (m, 6H), 0.98-0.96 (d, J=6.8 Hz, 3H). MS (APCI+) [M+H] $^+$458.

Example 15

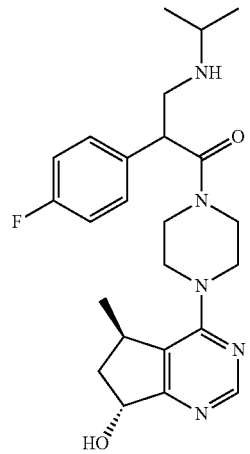 [SMILES: CC(C)NCC(C(=O)N1CCN(c2ncnc3c2[C@H](C)C[C@H]3O)CC1)c1ccc(F)cc1]

2-(4-fluorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one $^1$H NMR ($D_2O$, 400 MHz) δ 8.39 (m, 1H), 7.27-7.25 (m, 2H), 7.11-7.07 (m, 2H), 5.29-5.25 (m, 1H), 4.33-4.30 (m, 1H), 4.20-3.00 (m, 12H), 2.22-2.18 (m, 1H), 2.06-2.00 (m, 1H), 1.20-1.10 (m, 6H), 1.08-0.96 (m, 3H). MS (APCI+) [M+H] $^+$442.

Example 16

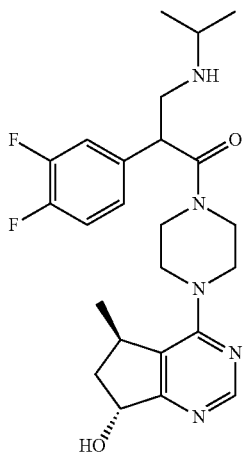 [SMILES: CC(C)NCC(C(=O)N1CCN(c2ncnc3c2[C@H](C)C[C@H]3O)CC1)c1ccc(F)c(F)c1]

2-(3,4-difluorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one $^1$H NMR (D$_2$O, 400 MHz) δ 8.37-8.25 (m, 1H), 7.36-7.16 (m, 9H), 5.37-5.22 (m, 1H), 4.33-4.30 (m, 1H), 4.25-3.00 (m, 13H), 2.22-2.18 (m, 1H), 2.06-1.98 (m, 1H), 1.29-1.22 (m, 3H), 1.20-0.96 (m, 3H). MS (APCI+) [M+H] $^+$550.

Example 17

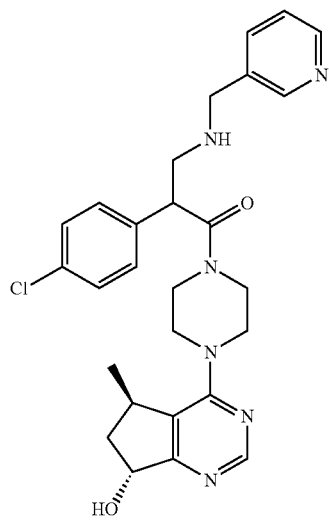 [SMILES: C[C@@H]1C[C@@H](O)c2ncnc(N3CCN(C(=O)C(CNCc4cccnc4)c4ccc(Cl)cc4)CC3)c21]

2-(4-chlorophenyl)-1-(4-((5R,7R)-7-hydroxy-5-methyl-6,7-dihydro-5H-cyclopenta[d]pyrimidin-4-yl)piperazin-1-yl)-3-(pyridin-3-ylmethylamino)propan-1-one $^1$H NMR (D$_2$O, 400 MHz) δ 8.84 (m, 1H), 8.75 (m, 1H), 8.68-8.54 (m, 1H), 8.39 (m, 1H), 8.03-8.01 (m, 1H), 7.36-

7.33 (m, 2H), 7.22-7.19 (m, 2H), 5.28-5.22 (m, 1H), 4.50-4.40 (m, 1H), 4.20-3.05 (m, 12H), 2.21-2.15 (m, 1H), 1.20-1.10 (m, 2H), 1.08-0.95 (m, 3H). MS (APCI+) [M+H] $^+$507.

Example 18

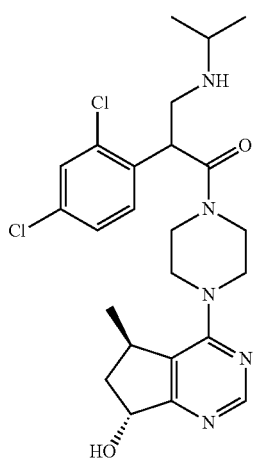

2-(2,4-dichlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one $^1$H NMR (D$_2$O, 400 MHz) δ 8.41-8.38 (m, 1H), 7.58 (s, 1H), 7.40-7.26 (m, 1H), 7.12-7.10 (m, 1H), 5.36-5.27 (m, 1H), 4.18-3.10 (m, 13H), 2.23-2.18 (m, 1H), 2.08-2.00 (m, 1H), 1.30-1.20 (m, 6H), 1.08-0.98 (m, 3H). MS (APCI+) [M+H] $^+$492.

Example 19

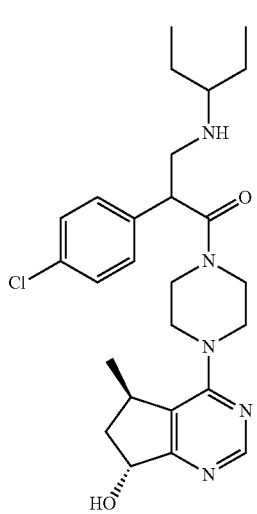 [SMILES: CCC(CC)NCC(C(=O)N1CCN(c2ncnc3c2[C@H](C)C[C@H]3O)CC1)c1ccc(Cl)cc1]

2-(4-chlorophenyl)-1-(4-((5R,7R)-7-hydroxy-5-methyl-6,7-dihydro-5H-cyclopenta[d]pyrimidin-4-yl)piperazin-1-yl)-3-(pentan-3-ylamino)propan-1-one $^1$H NMR (D$_2$O, 400 MHz) δ 8.39-8.37 (d, J=7.2 Hz, 1H), 7.36-7.34 (m, 2H), 7.22-7.20 (d, J=8.4 Hz, 2H), 5.30-5.25 (m, 1H), 4.33-4.29 (m, 1H), 4.18-3.00 (m, 12H), 2.24-2.15 (m, 4H), 2.10-2.00 (m, 1H), 1.30-1.20 (m, 4H), 1.12-0.95 (m, 3H), 0.90-0.86 (m, 6H). MS (APCI+) [M+H] +486.

Example 20

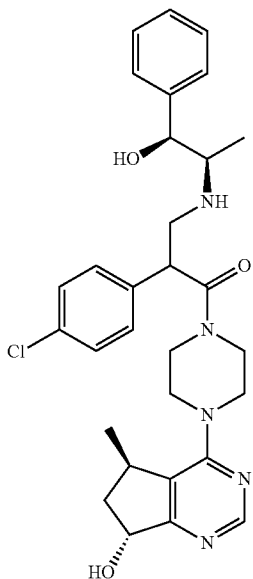 [SMILES: C[C@@H]1C[C@@H](O)c2ncnc(N3CCN(C(=O)C(CN[C@H](C)[C@@H](O)c4ccccc4)c4ccc(Cl)cc4)CC3)c21]

2-(4-chlorophenyl)-3-((1S,2R)-1-hydroxy-1-phenyl-propan-2-ylamino)-1-(4-((5R,7R)-7-hydroxy-5-methyl-6,7-dihydro-5H-cyclopenta[d]pyrimidin-4-yl)piperazin-1-yl)propan-1-one $^1$H NMR (D$_2$O, 400 MHz) δ 8.39 (m, 1H), 7.27-7.16 (m, 2H), 7.06-7.04 (m, 1H), 5.25-5.22 (m, 1H), 4.33-4.30 (m, 1H), 4.25-3.00 (m, 14H), 2.22-2.18 (m, 1H), 2.06-1.98 (m, 1H), 1.20-1.10 (m, 6H), 1.08-0.96 (m, 3H). MS (APCI+) [M+H] +460.

Example 21

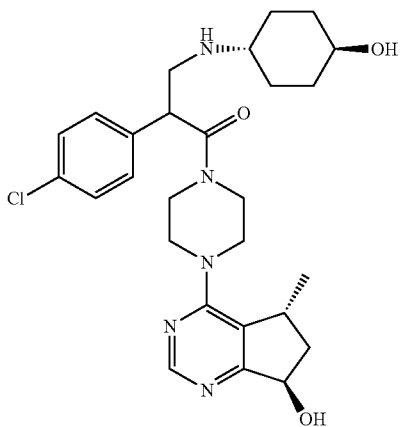 [SMILES: C[C@@H]1C[C@@H](O)c2ncnc(N3CCN(C(=O)C(CN[C@H]4CC[C@H](O)CC4)c4ccc(Cl)cc4)CC3)c21]

2-(4-chlorophenyl)-1-(4-((5R,7R)-7-hydroxy-5-methyl-6,7-dihydro-5H-cyclopenta[d]pyrimidin-4-yl)piperazin-1-yl)-3-((1R,4R)-4-hydroxycyclohexylamino)propan-1-one $^1$H NMR (D$_2$O, 400 MHz) δ 8.30 (m, 1H), 7.38-7.33 (m, 2H), 7.22-7.19 (m, 2H), 5.30-5.20 (m, 1H), 4.40-4.33 (m, 1H), 4.20-3.05 (m, 12H), 2.21-2.15 (m, 1H), 1.80-1.10 (m, 9H), 1.08-0.95 (m, 3H). MS (APCI+) [M+H] +514.

Example 22

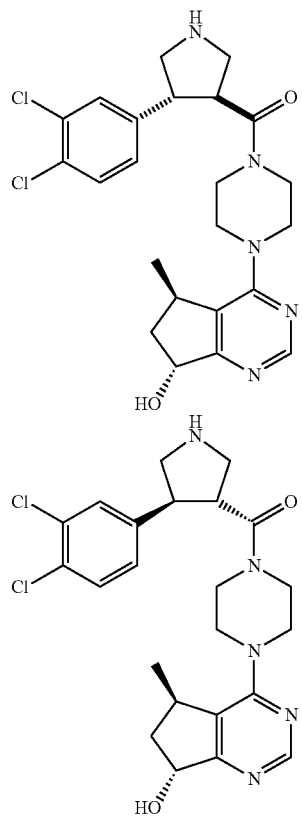

((3S,4R)-4-(3,4-dichlorophenyl)pyrrolidin-3-yl)(4-((5R,7R)-7-hydroxy-5-methyl-6,7-dihydro-5H-cyclopenta[d]pyrimidin-4-yl)piperazin-1-yl)methanone and ((3R,4S)-4-(3,4-dichlorophenyl)pyrrolidin-3-yl)(4-((5R,7R)-7-hydroxy-5-methyl-6,7-dihydro-5H-cyclopenta[d]pyrimidin-4-yl)piperazin-1-yl)methanone Step 1

TFA (0.2 mL, 2.63 mmol) was added to a solution of (E)-methyl 3-(3,4-dichlorophenyl)acrylate (2.6 g, 11.7 mmol) in DCM (40 mL). The mixture was cooled to 0° C. Then benzylmethoxytrimethylsilanyl methylamine (6.0 mL, 23.5 mmol) was added dropwisely while maintaining the temperature between −5° C. and +5° C. After the addition was complete, the mixture was stirred at room temperature overnight. The solvent was removed, and the residue was dissolved in ether and treated with 1N HCl. The mixture was shaken to agitate, and a three layer solution formed. The lower two layers were collected and basified with 2N NaOH to a pH of 14, extracted with CHCl₃ (3×100 mL). The organic phase was dried, filtered and concentrated. The residue was subjected to column chromatography, eluted by hexane/ethyl acetate (4:1) to give (3S,4R)-methyl 1-benzyl-4-(3,4-dichlorophenyl)pyrrolidine-3-carboxylate (4.2 g, 99%.) (LCMS (APCI+) [M+H]⁺ 364.2; Rt: 2.63 min.)

Step 2

1-Chloroethyl chloroformate (1.5 mL, 13.9 mmol) was added to a solution of (3S,4R)-methyl 1-benzyl-4-(3,4-dichlorophenyl)pyrrolidine-3-carboxylate (4.20 g, 11.5 mmol) in DCE (50 mL) at 0° C. The mixture was refluxed for 1 hour. After cooling, the solvent was removed under vacuum at 65° C. for 1 hour. MeOH (50 mL) was added to the residue and refluxed for 1 hour. The MeOH was removed. The solid was redissolved in CHCl₃ and treated with saturated Na₂CO₃. The aqueous layer was separated and extracted with CHCl₃ (2×30 mL). The organic phase was combined and dried. The solvent was removed to afford (3S,4R)-methyl 4-(3,4-dichlorophenyl)pyrrolidine-3-carboxylate (3.1 g, 98%). (LCMS (APCI+) [M+H]⁺ 274.1; Rt: 2.25 min.).

Step 3

Boc anhydride (3.0 g, 13.7 mmol) was added to a solution of (3S,4R)-methyl 4-(3,4-dichlorophenyl)pyrrolidine-3-carboxylate (3.10 g, 11.3 mmol) in THF (100 mL) and TEA (4 mL). The mixture was stirred at room temperature overnight. The solvent was removed, and the residue was subject to column chromatography, eluted by hexane/ethyl acetate (8:1) to give (3S,4R)-1-tert-butyl 3-methyl 4-(3,4-dichlorophenyl)pyrrolidine-1,3-dicarboxylate (LCMS (APCI+) [M−Boc+H]⁺ 274.1; Rt: 4.17 min). The (3S,4R)-1-tert-butyl 3-methyl 4-(3,4-dichlorophenyl)pyrrolidine-1,3-dicarboxylate was redissolved in MeOH (50 mL), and LiOH (3M, 10 mL) was added. The mixture was stirred at room temperature for 6 hours. 2N HCl (15 mL) was added to the mixture. The solvent was removed, and the residue was subject to column chromatography, eluted by DCM/MeOH (40:1-10:1) to give (3S,4R)-1-(tert-butoxycarbonyl)-4-(3,4-dichlorophenyl)pyrrolidine-3-carboxylic acid (1.95 g). (LCMS (APCI+) [M−Boc+H]⁺ 260.1; Rt: 3.67 min.)

Step 4

HBTU (37 mg, 0.098 mmol) was added to a solution of (5R,7R)-5-methyl-4-(piperazin-1-yl)-6,7-dihydro-5H-cyclopenta[d]pyrimidin-7-ol dihydrochloride (30 mg, 0.098 mmol) and 1-(tert-butoxycarbonyl)-4-(3,4-dichlorophenyl)pyrrolidine-3-carboxylic acid (35 mg, 0.098 mmol) in DCM (5 mL) and TEA (1 mL). The mixture was stirred at room temperature for 1 hour. The solvent was removed, and the residue was dissolved in ethyl acetate (50 mL) and washed with brine (5×50 mL). The organic phase was dried and concentrated to afford tert-butyl dichlorophenyl)-4-(4-((5R,7R)-7-hydroxy-5-methyl-6,7-dihydro-5H-cyclopenta[d]pyrimidin-4-yl)piperazine-1-carbonyl)pyrrolidine-1-carboxylate (LCMS (APCI+) [M+H] ⁺576.1; Rt: 2.90 min). The product was treated with 4N HCl in dioxane to afford (4-(3,4-dichlorophenyl)pyrrolidin-3-yl)(4-((5R,7R)-7-hydroxy-5-methyl-6,7-dihydro-5H-cyclopenta[d]pyrimidin-4-yl)piperazin-1-yl)methanone as the HCl salt (30 mg, 64%).

Obtained as a 1:1 mixture of diastereomers. NMR (D₂O, 400 MHz) δ 8.44-8.10 (m, 1H), 7.48-7.40 (m, 2H), 7.24-7.12 (m, 1H), 5.33-5.28 (m, 1H), 4.00-3.85 (m, 1H), 3.80-3.00 (m, 11H), 2.26-2.20 (m, 1H), 2.10-2.00 (m, 1H), 1.08-1.00 (m, 3H). MS (APCI+) [M+H] ⁺476.

Example 23

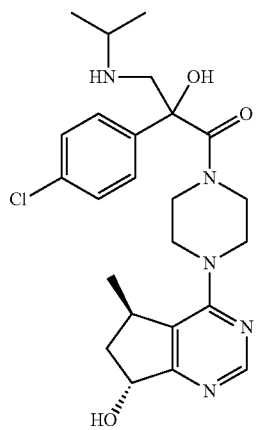 [SMILES: CC(C)NCC(O)(C(=O)N1CCN(c2ncnc3c2[C@H](C)C[C@H]3O)CC1)c1ccc(Cl)cc1]

2-(4-chlorophenyl)-2-hydroxy-1-(4-((5R,7R)-7-hydroxy-5-methyl-6,7-dihydro-5H-cyclopenta[d]pyrimidin-4-yl)piperazin-1-yl)-3-(isopropylamino)propan-1-one Step 1

MCPBA (35 g, 77%, 156 mmol) was added to a solution of methyl 2-(4-chlorophenyl)-acrylate (20 g, 102 mmol) in CHCl₃ (200 mL). The reaction was refluxed for 24 hours. The reaction was cooled to room temperature, diluted with chloroform (200 mL) and washed with 10% Na₂S₂O₃, 10% NaHCO₃ and water. The organic phase was dried and concentrated. The residue was subject to column chromatography, eluted by hexane/ethyl acetate (9:1) to give methyl 2-(4-chlorophenyl)oxirane-2-carboxylate. Methyl 2-(4-chlorophenyl)oxirane-2-carboxylate (2 g, 9.4 mmol) and ethanol (10 mL) and isopropylamine (1 mL, 11.7 mmol) were added to a 50 mL high pressure bomb. The mixture was heated to 90° C. for 12 hours in the bomb. After cooling, the solvent was removed, and the residue was dissolved in DCM (20 mL) and TEA (2 mL). (Boc)2O (4 g, 23.0 mmol) was added to it. The mixture was stirred at room temperature for 48 hours. The solvent was removed, and the residue was dissolved in THF (20 mL). LiOH (3M, 14 mL) was added to the mixture. The mixture was stirred at room temperature for 16 hours and refluxed for 2 hours. After cooling, the mixture was quenched with 2N HCl (21 mL). The solvent was removed and the residue was subject to column chromatography, eluted by hexane/ethyl acetate (1:1) to give 3-(tert-butoxycarbonykisopropyl)amino)-2-(4-chlorophenyl)-2-hydroxypropanoic acid. LCMS (APCI+) [M−Boc+H]⁺ 258.1; Rf: 3.66 min.

Step 2

HBTU (37 mg, 0.098 mmol) was added to a solution of (5R,7R)-5-methyl-4-(piperazin-1-yl)-6,7-dihydro-5H-cyclopenta[d]pyrimidin-7-ol dihydrochloride (30 mg, 0.098 mmol) and 3-(tert-butoxycarbonyl(isopropyl)amino)-2-(4-chlorophenyl)-2-hydroxypropanoic acid (35 mg, 0.098 mmol) in DCM (5 mL) and TEA (1 mL). The mixture was stirred at room temperature for 1 hour. The solvent was removed, and the residue was subject to column chromatography, eluted by DCM/MeOH (40:1). The resulting product was treated with HCl (4M, 2 mL) to afford 2-(4-chlorophenyl)-2-hydroxy-1-(4-((5R,7R)-7-hydroxy-5-methyl-6,7-dihydro-5H-cyclopenta[d]pyrimidin-4-yl)piperazin-1-yl)-3-(isopropylamino)propan-1-one as HCl salt (22 mg, 48%).

$^1$H NMR (D$_2$O, 400 MHz) δ 8.35-8.34 (m, 1H), 7.41-7.36 (m, 4H), 5.26-5.18 (m, 1H), 4.18-3.00 (m, 12H), 2.20-2.14 (m, 1H), 2.08-1.98 (m, 1H), 1.20-1.10 (m, 6H), 1.08-0.98 (m, 3H). MS (APCI+) [M+H] $^+$474.

Example 24

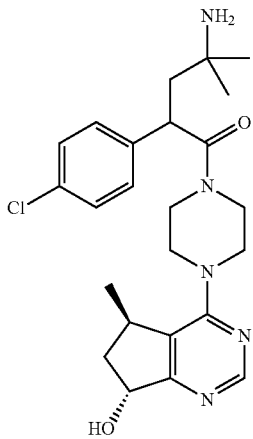 [SMILES: C[C@@H]1C[C@@H](O)c2ncnc(N3CCN(C(=O)C(CC(C)(C)N)c4ccc(Cl)cc4)CC3)c21]

4-amino-2-(4-chlorophenyl)-1-(4-((5R,7R)-7-hydroxy-5-methyl-6,7-dihydro-5H-cyclopenta[d]pyrimidin-4-yl)piperazin-1-yl)-4-methylpentan-1-one Step 1

1,8-Diazabicyclo[5.4.0]undec-7-ene (33.68 mL, 225.2 mmol) was added to a solution of methyl 2-(4-chlorophenyl)acrylate (36.9 g, 187.7 mmol) and 2-nitropropane (20.23 mL, 225.2 mmol) in CH$_3$CN (500 mL) at 0° C. under nitrogen. The mixture was warmed to room temperature and stirred overnight. The solution was concentrated in vacuo and subjected to column chromatography (20% EtOAc/hexanes) to give methyl 2-(4-chlorophenyl)-4-methyl-4-nitropentanoate (52.9 g, 98.66% yield) as a colourless oil. $^1$H NMR (CDCl$_3$, 400 MHz) δ 7.31-7.29 (m, 2H), 7.21-7.19 (m, 2H), 3.66 (s, 3H), 3.60-3.57 (m, 1H), 2.87-2.81 (dd, 1H), 2.39-2.34 (dd, 1H), 1.56 (s, 3H), 1.55 (s, 3H).

Step 2

Zn dust (128 g, 1.960 mol) was treated with a solution of methyl 2-(4-chlorophenyl)-4-methyl-4-nitropentanoate (28 g, 98.0 mmol) dissolved in ethanol (490 mL). Concentrated HCl (26.9 mL, 323 mmol) was added slowly, and then the reaction was heated to 70° C. for 2 hours. The reaction mixture was filtered through a plug of SiO$_2$ and celite. The filter pad was washed with ethyl acetate, and the filtrate was concentrated in vacuo. The residue was dissolved in a minimum amount of ethanol and then treated with water. 3-(4-Chlorophenyl)-5,5-dimethylpyrrolidin-2-one precipitated from the solution and was collected by filtration. The solid was washed with water and air-dried, (11.2 g, 51% yield). $^1$H NMR (CD$_3$OD, 400 MHz) δ 7.35-7.32 (m, 2H), 7.26-7.24 (m, 2H), 3.94-3.90 (m, 1H), 2.50-2.44 (m, 1H), 1.99-1.93 (m, 1H), 1.36 (s, 3H), 1.34 (s, 3H).

Step 3

Lithium bis(trimethylsilyl)amide (36 mL, 36 mmol) was added to a stirred solution of 3-(4-chlorophenyl)-5,5-dimethylpyrrolidin-2-one (6.7 g, 30 mmol) in THF (200 mL) at −78° C. under nitrogen. The solution was stirred at −78° C. for 30 minutes. Then a solution of di-tert-butyl dicarbonate (7.6 mL, 33 mmol) in THF (30 mL) was added in a single portion. The solution was warmed to room temperature and allowed to stir at room temperature overnight. The reaction was poured into 0.5M HCl solution and extracted with ethyl acetate twice. The combined organic layer was washed with water, separated, dried over MgSO$_4$, filtered, and concentrated in vacuo to afford the near-pure product (excess Boc2O) as a colorless oil. Column chromatography (20% EtOAc/hexanes) to give pure tert-butyl 4-(4-chlorophenyl)-2,2-dimethyl-5-oxopyrrolidine-1-carboxylate. LCMS (APCI+) [M−Boc+H]+ 224.1; Rt: 3.68 min. $^1$H NMR (CDCl$_3$, 400 MHz) δ 7.32-7.30 (m, 2H), 7.22-7.20 (m, 2H), 3.80-3.74 (m, 1H), 2.33-2.28 (m, 1H), 2.05-1.97 (m, 1H), 1.58 (s, 3H), 1.55 (s, 9H), 1.53 (s, 3H).

Step 4

Lithium hydroxide hydrate (6.44 mL, 232 mmol) was added to a stirred solution of tert-butyl 4-(4-chlorophenyl)-2,2-dimethyl-5-oxopyrrolidine-1-carboxylate (7.5 g, 23.2 mmol) in THF/MeOH/H$_2$O (30 mL/30 mL/30 mL) at room temperature. The mixture was stirred at room temperature overnight and concentrated in vacuo. The mixture was taken up into water (200 mL), washed with EtOAc (100 mL), acidified with concentrated HCl and extracted into EtOAc (2×200 mL). The mixture was dried over Na$_2$SO$_4$ and concentrated in vacuo. Residual HCl was removed by evaporating from toluene to give 4-(tert-butoxycarbonylamino)-2-(4-chlorophenyl)-4-methylpentanoic acid (5.0 g, 63.2% yield) as a white solid. LCMS (APCI$^+$) [M−Boc+H]$^+$ 242.0; Rt: 2.8 min.

Step 5

HBTU (37 mg, 0.098 mmol) was added to a solution of (5R,7R)-5-methyl-4-(piperazin-1-yl)-6,7-dihydro-5H-cyclopenta[d]pyrimidin-7-ol dihydrochloride (30 mg, 0.098 mmol) and 4-(tert-butoxycarbonylamino)-2-(4-chlorophenyl)-4-methylpentanoic acid (33 mg, 0.098 mmol) in DCM (5 mL) and TEA (1 mL). The mixture was stirred at room temperature for 1 hour. The solvent was removed, and the residue was dissolved in ethyl acetate (50 mL) and washed with brine (5×50 mL). The organic phase was dried and concentrated to afford the product. The product was treated with HCl to afford 4-amino-2-(4-chlorophenyl)-1-(4-((5R,7R)-7-hydroxy-5-methyl-6,7-dihydro-5H-cyclopenta[d]pyrimidin-4-yl)piperazin-1-yl)-4-methylpentan-1-one as HCl salt (22 mg, 49%).

$^1$H NMR (D$_2$O, 400 MHz) δ 8.40-8.37 (m, 1H), 7.32-7.29 (m, 2H), 7.25-7.19 (m, 2H), 5.29-5.25 (m, 1H), 4.12-4.09 (m, 1H), 4.06-3.18 (m, 9H), 2.58-2.48 (m, 1H), 2.24-1.98 (m,

1H), 2.08-2.00 (m, 1H), 1.90-1.80 (m, 1H), 1.26-1.09 (m, 6H), 1.08-0.98 (m, 3H). MS (APCI+) [M+H] +458.

Example 25

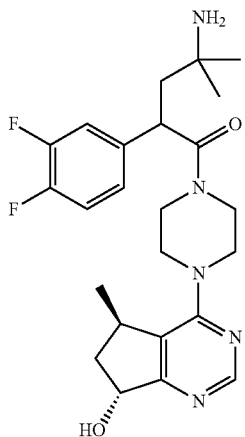 [SMILES: C[C@@H]1C[C@@H](O)c2ncnc(N3CCN(C(=O)C(CC(C)(C)N)c4ccc(F)c(F)c4)CC3)c21]

4-amino-2-(3,4-difluorophenyl)-1-(4-((5R,7R)-7-hydroxy-5-methyl-6,7-dihydro-5H-cyclopenta[d]pyrimidin-4-yl)piperazin-1-yl)-4-methylpentan-1-one $^1$H NMR (D$_2$O, 400 MHz) δ 8.40 (m, 1H), 7.32-7.29 (m, 2H), 7.06-7.00 (m, 1H), 5.29-5.25 (m, 1H), 4.19-3.22 (m, 10H), 2.58-2.48 (m, 1H), 2.24-1.98 (m, 1H), 2.08-2.00 (m, 1H), 1.90-1.80 (m, 1H), 1.26-1.09 (m, 6H), 1.08-0.98 (m, 3H). MS (APCI+) [M+H] +460.

Example 26

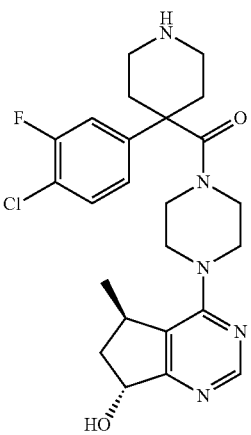 [SMILES: C[C@@H]1C[C@@H](O)c2ncnc(N3CCN(C(=O)C4(c5ccc(Cl)c(F)c5)CCNCC4)CC3)c21]

(4-(4-chloro-3-fluorophenyl)piperidin-4-yl)(4-((5R,7R)-7-hydroxy-5-methyl-6,7-dihydro-5H-cyclopenta[d]pyrimidin-4-yl)piperazin-1-yl)methanone Step 1

KCN (1.25 g, 19.2 mmol) was added to a solution of 4-(bromomethyl)-1-chloro-2-fluorobenzene (3.90 g, 17.5 mmol) in DMSO (60 mL). Several milliliters of H$_2$O were added to help dissolve the KCN. After 1 hour, the reaction mixture was diluted with H$_2$O and extracted with EtOAc. The extracts were dried (Na$_2$SO$_4$), filtered, and concentrated. The crude product was flashed on silica (Biotage 40M, 9:1 to 4:1 hex:EtOAc) to give 2-(4-chloro-3-fluorophenyl)acetonitrile (1.81 g, 61.2% yield) as a yellow crystalline solid.

Step 2

60% NaH (1.07 g, 26.7 mmol) was added in 2 portions to a 0° C. solution of 2-(4-chloro-3-fluorophenyl)acetonitrile (1.81 g, 10.7 mmol) and 15-crown-5 (0.235 g, 1.07 mmol) in DMF (45 mL). The reaction mixture was warmed to room temperature and stirred for 35 minutes. The reaction mixture was then cooled to 0° C. NaI (1.60 g, 10.7 mmol) was added, and then a solution of freshly prepared tert-butyl bis(2-chloroethyl)carbamate (2.58 g, 10.7 mmol) in DMF (10 mL) was added by syringe. The reaction mixture was warmed to room temperature and stirred overnight (19 hours). The reaction mixture was poured into ice saturated NH$_4$Cl, and the mixture was extracted with EtOAc. The combined extracts were dried (Na$_2$SO$_4$), filtered, and concentrated. The crude was flashed on silica (Biotage 40L, 9:1 hex:EtOAc until product eluted, then 6:1 hex:EtOAc to elute product) to give tert-butyl 4-(4-chloro-3-fluorophenyl)-4-cyanopiperidine-1-carboxylate (1.96 g, 54.2% yield) as a yellow oil. LC/MS (APCI+) m/z 239 [M−Boc+H]+.

Step 3

Tert-butyl 4-(4-chloro-3-fluorophenyl)-4-cyanopiperidine-1-carboxylate (1.96 g, 5.785 mmol) was dissolved in concentrated HCl (48.21 mL, 578.5 mmol), heated to reflux, and then stirred over the weekend (approximately 60 hours). The reaction mixture was cooled to room temperature, transferred to a separatory funnel, and washed with ether. The aqueous layer was concentrated on a rotary evaporator and dried on a high vacuum line. The resulting solids were dissolved in 10% NaOH (9.255 g, 23.14 mmol), dioxane (40 mL) was added, followed by a Boc2O addition (1.326 g, 6.074 mmol). The reaction mixture was stirred at room temperature overnight (16 hours). The reaction mixture was then diluted with H$_2$O and washed with ether. The aqueous layer was acidified with solid KHSO$_4$, and then extracted with DCM. The combined extracts were dried (Na$_2$SO$_4$), filtered, concentrated and dried on a high vacuum line to give 1-(tert-butoxycarbonyl)-4-(4-chloro-3-fluorophenyl)piperidine-4-carboxylic acid (0.910 g, 43.96% yield) as a foam. LC/MS (APCI−) m/z 713 [2M−H]−.

Step 4

(5R,7R)-5-methyl-4-(piperazin-1-yl)-6,7-dihydro-5H-cyclopenta[d]pyrimidin-7-ol dihydrochloride (35.0 mg, 0.114 mmol) and 1-(tert-butoxycarbonyl)-4-(4-chloro-3-fluorophenyl)piperidine-4-carboxylic acid (40.8 mg, 0.114 mmol) were dissolved in DCM (1.1 mL) and treated with DIEA (0.0595 ml, 0.342 mmol) at ambient temperature. The mixture was allowed to homogenize before the HBTU (47.5 mg, 0.125 mmol) was added in one lot. The reaction was allowed to stir for four hours to completion by LCMS analysis of the crude. The reaction was diluted with DCM, washed with diluted NaHCO$_3$ solution, washed with water, washed with brine, and separated. The organic layer was dried over Na$_2$SO$_4$, filtered, and concentrated in vacuo. The residue was purified by chromatography (silica gel eluted with 5% methanol in ethyl acetate) to afford the pure tert-butyl 4-(4-chloro-3-fluorophenyl)-4-(1-((5R,7R)-7-hydroxy-5-methyl-6,7-dihydro-5H-cyclopenta[d]pyrimidin-4-yl)piperazine-4- carbonyl)piperidine-1-carboxylate (15.0 mg, 22.9% yield) as a pale yellow oil. MS (APCI+) [M+H] +574; Rf: 2.92.

Step 5

The tert-butyl 4-(4-chloro-3-fluorophenyl)-4-(1-((5R,7R)-7-hydroxy-5-methyl-6,7-dihydro-5H-cyclopenta[d]pyrimidin-4-yl)piperazine-4-carbonyl)piperidine-1-carboxylate (15.0 mg, 0.0261 mmol) was dissolved in dioxane (131 uL) and treated with 4M HCl (0.131 ml, 0.523 mmol) in dioxane. The mixture was allowed to stir overnight to afford the pure product as a gel precipitate. The solvent was removed under reduced pressure, and the foam was triturated with ether (sonicated) to afford a white suspension. The ether was removed under reduced pressure to afford the pure (4-(4-chloro-3-fluorophenyl)piperidin-4-yl)(4-((5R,7R)-7-hydroxy-5-methyl-6,7-dihydro-5H-cyclopenta[d]pyrimidin-4-yl)piperazin-1-yl)methanone dihydrochloride (12.0 mg, 84.0% yield) as a white powder. Rf: 1.96.

$^1$H NMR (D$_2$O, 400 MHz) δ 8.36 (m, 1H), 7.25-7.00 (m, 3H), 5.28-5.20 (m, 1H), 4.00-3.00 (m, 14H), 2.50-2.38 (m, 2H), 2.26-2.00 (m, 2H), 1.04-1.00 (m, 3H). MS (APCI+) [M+H] +474.

Example 27

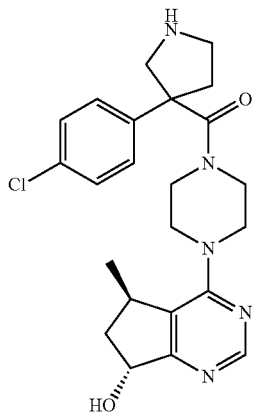 [SMILES: C[C@@H]1C[C@@H](O)c2ncnc(N3CCN(C(=O)C4(c5ccc(Cl)cc5)CCNC4)CC3)c21]

(3-(4-chlorophenyl)pyrrolidin-3-yl)(4-((5R,7R)-7-hydroxy-5-methyl-6,7-dihydro-5H-cyclopenta[d]pyrimidin-4-yl)piperazin-1-yl)methanone Step 1

TFA (0.34 ml, 4.41 mmol) was added to a solution of N-(methoxymethyl)(phenyl)-N-((trimethylsilyl)methyl)methanamine (3.9 g, 19.8 mmol) in DCM (40 mL). The mixture was cooled to 0° C. The benzylmethoxytrimethylsilanyl methylamine (10.5 mL, 41 mmol) was added dropwise at 0° C. The mixture was stirred at room temperature for 2 hours. The solvent was removed, and the residue was dissolved in ether and treated with 1N HCl. The mixture was shaken, and the aqueous layer was separated and basified with 2N NaOH to a pH of 14. The aqueous layer was extracted with CHCl$_3$ (3×100 mL). The organic phase was dried and concentrated. The residue was subjected to column chromatography, eluted by hexanes/ethyl acetate (10:1) to give methyl 1-benzyl-3-(4-chlorophenyl)pyrrolidine-3-carboxylate (LCMS (APCI+) [M−Boc+H]+ 330.2; Rt: 2.46 min).

Step 2

1-Chloroethylformate (1.0 mL, 9.27 mmol) was added to a solution of methyl 1-benzyl-3-(4-chlorophenyl)pyrrolidine-3-carboxylate (3.05 g, 9.25 mmol) in toluene (40 mL) at 0° C. The mixture was refluxed for 10 hours. After cooling, the solvent was removed under vacuum. The residue was treated with MeOH (20 mL) and refluxed for 1 hour. The solvent was removed, and the residue was dissolved in ethyl acetate (200 mL). The residue was washed with 1N NaOH (50 mL) and then washed with water. The organic phase was dried and concentrated. The residue was subjected to column chromatography, eluted by EtOAc-DCM/MeOH (10:1). The resulting methyl 3-(4-chlorophenyl)pyrrolidine-3-carboxylate (LCMS (APCI+) [M−Boc+H]+ 240.1; Rt: 2.06 min) was dissolved in DCM (20 mL) and TEA (1 mL). Then is was treated with Boc anhydride (1 g, 4.58 mmol). After stirring for 2 hours, the solvent was removed, and the 1-tert-butyl 3-methyl 3-(4-chlorophenyl)pyrrolidine-1,3-dicarboxylate (LCMS (APCI+) [M−Boc+H]+ 240.1; Rt: 3.78 min) was dissolved in THF (50 mL). LiOH (3M, 6 mL) was added to the mixture. The mixture was stirred at room temperature overnight. The mixture was quenched with 2N HCl (9 mL). The solvent was removed and the residue was subjected to column chromatography, eluted by Hex/EtOAc(4:1)-DCM/MeOH (20:1) to give 1-(tert-butoxycarbonyl)-3-(4-chlorophenyl)pyrrolidine-3-carboxylic acid. LCMS (APCI+) [M−Boc+H]+ 224.1; Rt: 2.90 min.

Step 3

HBTU (37 mg, 0.098 mmol) was added to a solution of (5R,7R)-5-methyl-4-(piperazin-1-yl)-6,7-dihydro-5H-cyclopenta[d]pyrimidin-7-ol dihydrochloride (30 mg, 0.098 mmol) and 1-(tert-butoxycarbonyl)-3-(4-chlorophenyl)pyrrolidine-3-carboxylic acid (32 mg, 0.098 mmol) in DCM (5 mL) and TEA (1 mL). The mixture was stirred at room temperature for 10 hours. The solvent was removed, and the residue was subjected to column chromatography, eluted by ethyl acetate-DCM/MeOH (20:1). The product was treated with HCl (4M, 2 mL) in DCM (5 mL) to afford (3-(4-chlorophenyl)pyrrolidin-3-yl)(4-((5R,7R)-7-hydroxy-5-methyl-6,7-dihydro-5H-cyclopenta[d]pyrimidin-4-yl)piperazin-1-yl)methanone as the HCl salt (35 mg, 81%).

$^1$H NMR (D$_2$O, 400 MHz) δ 8.39-8.37 (d, J=2.8 Hz, 1H), 7.40-7.38 (d, J=8.4 Hz, 2H), 7.27-7.25 (d, J=8.4 Hz, 2H), 5.28-5.24 (m, 1H), 4.18-4.10 (m, 1H), 4.08-2.98 (m, 12H), 2.83-2.78 (m, 1H), 2.59-2.50 (m, 1H), 2.24-2.15 (m, 1H), 2.10-2.00 (m, 1H), 1.20-0.95 (m, 7H). MS (APCI+) [M+H] +442.

Example 28

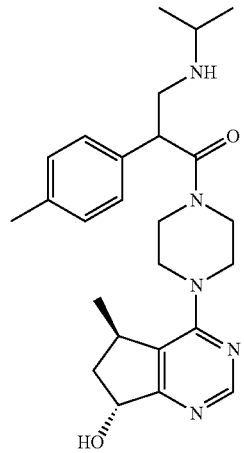 [SMILES: Cc1ccc(C(CNC(C)C)C(=O)N2CCN(c3ncnc4c3[C@H](C)C[C@H]4O)CC2)cc1]

1-(4-((5R,7R)-7-hydroxy-5-methyl-6,7-dihydro-5H-cyclopenta[d]pyrimidin-4-yl)piperazin-1-yl)-3-(isopropylamino)-2-p-tolylpropan-1-one ¹H NMR (D$_2$O, 400 MHz) δ 8.40-8.39 (m, 1H), 7.20-7.10 (m, 4H), 5.30-5.25 (m, 1H), 4.30-4.26 (m, 1H), 4.19-3.00 (m, 12H), 2.24-2.15 (m, 4H), 2.10-2.00 (m, 1H), 1.30-1.10 (m, 6H), 1.08-0.95 (m, 3H). MS (APCI+) [M+H]$^+$438.

Example 29

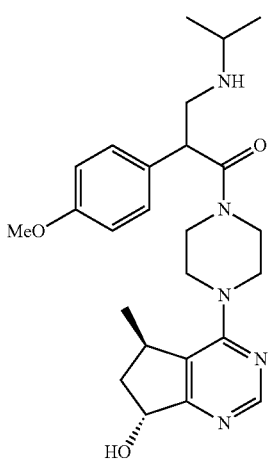 [SMILES: COc1ccc(C(CNC(C)C)C(=O)N2CCN(c3ncnc4c3[C@H](C)C[C@H]4O)CC2)cc1]

1-(4-((5R,7R)-7-hydroxy-5-methyl-6,7-dihydro-5H-cyclopenta[d]pyrimidin-4-yl)piperazin-1-yl)-3-(isopropylamino)-2-(4-methoxyphenyl)propan-1-one ¹H NMR (D$_2$O, 400 MHz) δ 8.38 (m, 1H), 7.18-7.16 (m, 2H), 6.95-6.92 (d, J=8.8 Hz, 2H), 5.29-5.25 (m, 1H), 4.29-4.25 (m, 1H), 4.20-3.00 (m, 15H), 2.23-2.17 (m, 1H), 2.07-1.98 (m, 1H), 1.30-0.95 (m, 9H). MS (APCI+) [M+H]$^+$454.

Example 30

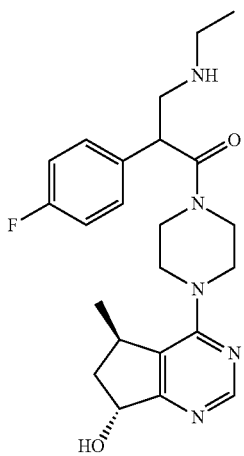 [SMILES: CCNCC(C(=O)N1CCN(c2ncnc3c2[C@H](C)C[C@H]3O)CC1)c1ccc(F)cc1]

3-(ethylamino)-2-(4-fluorophenyl)-1-(4-((5R,7R)-7-hydroxy-5-methyl-6,7-dihydro-5H-cyclopenta[d]pyrimidin-4-yl)piperazin-1-yl)propan-1-one ¹H NMR (D$_2$O, 400 MHz) δ 8.39 (m, 1H), 7.28-7.25 (m, 2H), 7.10-7.07 (m, 2H), 5.28-5.25 (m, 1H), 4.39-4.37 (m, 1H), 4.20-2.95 (m, 13H), 2.22-2.18 (m, 1H), 2.06-1.98 (m, 1H), 1.22-1.14 (m, 3H), 1.04-0.96 (m, 3H). MS (APCI+) [M+H]$^+$428.

Example 31

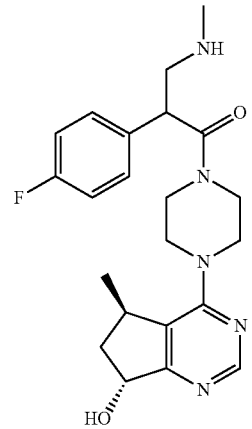 [SMILES: CNCC(C(=O)N1CCN(c2ncnc3c2[C@H](C)C[C@H]3O)CC1)c1ccc(F)cc1]

2-(4-fluorophenyl)-1-(4-((5R,7R)-7-hydroxy-5-methyl-6,7-dihydro-5H-cyclopenta[d]pyrimidin-4-yl)piperazin-1-yl)-3-(methylamino)propan-1-one ¹H NMR (D$_2$O, 400 MHz) δ 8.40 (m, 1H), 7.28-7.24 (m, 2H), 7.12-7.08 (m, 2H), 5.29-5.25 (m, 1H), 4.39-4.37 (m, 1H), 4.20-3.00 (m, 11H), 2.62 (s, 3H), 2.22-2.18 (m, 1H), 2.06-1.98 (m, 1H), 1.17-1.14 (m, 1H), 1.04-0.96 (m, 3H). MS (APCI+) [M+H]$^+$414.

Example 32

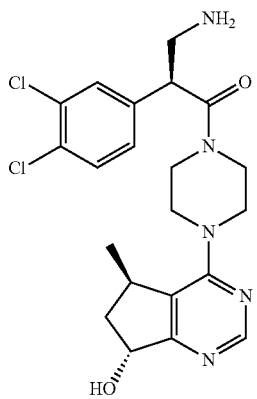 [SMILES: C[C@@H]1C[C@@H](O)c2ncnc(N3CCN(C(=O)[C@H](CN)c4ccc(Cl)c(Cl)c4)CC3)c21]

(S)-3-amino-2-(3,4-dichlorophenyl)-1-(4-((5R,7R)-7-hydroxy-5-methyl-6,7-dihydro-5H-cyclopenta[d]pyrimidin-4-yl)piperazin-1-yl)propan-1-one ¹H NMR (D$_2$O, 400 MHz) δ 8.40-8.39 (d, J=5.2 Hz, 1H), 7.50-7.43 (m, 2H), 7.19-7.16 (d, J=8.0 Hz, 2H), 5.30-5.25 (m, 1H), 4.32-4.29 (m, 1H), 4.15-3.00 (m, 11H), 2.26-2.20 (m, 1H), 2.10-2.00 (m, 1H), 1.30-0.98 (m, 3H), MS (APCI+) [M+H] +450.

Example 33

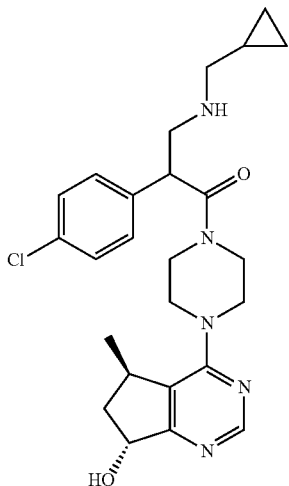 [SMILES: C[C@@H]1C[C@@H](O)c2ncnc(N3CCN(C(=O)C(CNCC4CC4)c4ccc(Cl)cc4)CC3)c21]

2-(4-chlorophenyl)-3-(cyclopropylmethylamino)-1-(4-((5R,7R)-7-hydroxy-5-methyl-6,7-dihydro-5H-cyclopenta[d]pyrimidin-4-yl)piperazin-1-yl)propan-1-one $^1$H NMR (D$_2$O, 400 MHz) δ 8.16-8.14 (d, J=7.6 Hz, 1H), 7.18-7.16 (m, 2H), 7.02-7.00 (d, J=8.0 Hz, 2H), 5.02-4.95 (m, 1H), 4.14-4.10 (m, 1H), 3.98-3.00 (m, 11H), 2.89-2.84 (m, 1H), 2.65-2.62 (m, 1H), 1.98-1.90 (m, 1H), 1.85-1.77 (m, 1H), 1.05-0.70 (m, 6H), 0.35-0.33 (m, 2H), 0.02-0.00 (m, 2H). MS (APCI+) [M+H] +470.

Example 34

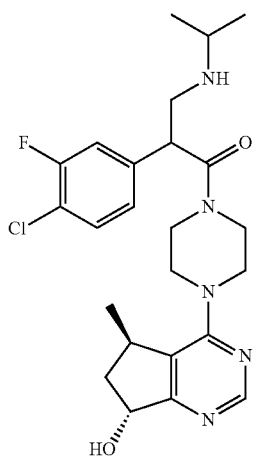 [SMILES: CC(C)NCC(C(=O)N1CCN(c2ncnc3c2[C@H](C)C[C@H]3O)CC1)c1ccc(Cl)c(F)c1]

2-(4-chloro-3-fluorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one $^1$H NMR (D$_2$O, 400 MHz) δ 8.40 (m, 1H), 7.47-7.43 (m, 1H), 7.16-7.14 (d, J=9.6 Hz, 1H), 7.06-7.04 (d, J=8.4 Hz, 1H), 5.30-5.25 (m, 1H), 4.38-4.35 (m, 1H), 4.20-3.65 (m, 4H), 3.60-3.20 (m, 7H), 3.10-3.04 (m, 1H), 2.22-2.18 (m, 1H), 2.10-1.98 (m, 1H), 1.20-1.10 (m, 6H), 1.08-0.96 (m, 3H). MS (APCI+) [M+H] +476.

Example 35

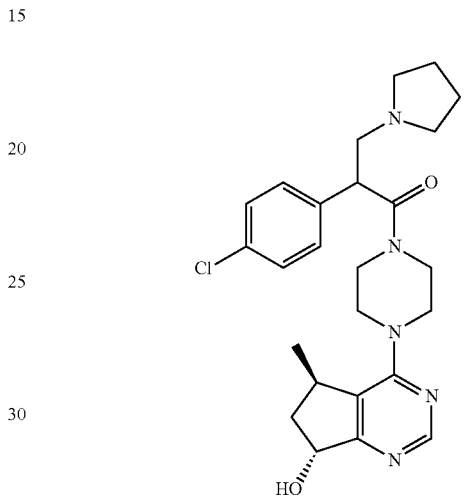

2-(4-chlorophenyl)-1-(4-((5R,7R)-7-hydroxy-5-methyl-6,7-dihydro-5H-cyclopenta[d]pyrimidin-4-yl)piperazin-1-yl)-3-(pyrrolidin-1-yl)propan-1-one Step 1

Methyl 2-(4-chlorophenyl)acrylate (500 mg, 2.54 mmol) was diluted in THF (6.0 mL) and treated with pyrrolidine (233 uL, 2.80 mmol) at 0° C. After 1 hour, the crude LCMS indicated that the reaction was complete (LCMS (APCI+) [M+H]$^+$ 268.1; Rf: 2.13 min). The solution was treated with water (2.0 mL) and LiOH—H$_2$O (320 mg, 7.63 mmol), respectively, and the reaction was allowed to stir overnight to completion by LCMS analysis. The mixture was partitioned between water and ethyl acetate. The aqueous layer was washed again with ethyl acetate, and the organics were discarded. The aqueous layer was treated with excess 3N HCl solution (3.82 mL) and washed with ethyl acetate. The separated aqueous layer was concentrated in vacuo to afford the pure product (as a HCl-3LiCl salt) as a white solid (1.15 g). MS (APCI+) [M+H]$^+$ 254.1; Rf: 1.30 min.

Step 2

HBTU (37 mg, 0.098 mmol) was added to a solution of (5R,7R)-5-methyl-4-(piperazin-1-yl)-6,7-dihydro-5H-cyclopenta[d]pyrimidin-7-ol dihydrochloride (30 mg, 0.098 mmol) and 2-(4-chlorophenyl)-3-(pyrrolidin-1-yl)propanoic acid hydrochloride-3LiCl complex (83 mg) in DCM (4 mL) and TEA (1 mL). The mixture was stirred at room temperature for 2 hours. The solvent was removed, and the residue was subject to column chromatography, eluted by EtOAc- DCM/MeOH (10:1). The product was treated with HCl to afford 2-(4-chlorophenyl)-1-(4-((5R,7R)-7-hydroxy-5-methyl-6,7-dihydro-5H-cyclopenta[d]pyrimidin-4-yl)piperazin-1-yl)-3-(pyrrolidin-1-yl)propan-1-one as the HCl salt (12 mg, 26%).

$^1$H NMR (CDCl$_3$, 400 MHz) δ 8.46 (s, 1H), 7.83-7.81 (d, J=8.4 Hz, 1H), 7.63-7.61 (d, J=8.0 Hz, 1H), 7.31-7.23 (m, 2H), 5.11-4.98 (m, 2H), 3.95-3.90 (m, 1H), 3.80-3.00 (m, 10H), 2.20-1.90 (m, 7H), 1.32-1.20 (m, 3H), 1.12-1.08 (m, 4H). MS (APCI+) [M+H] $^+$470.

Example 36

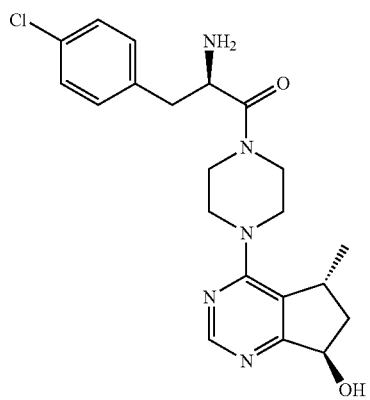 [SMILES: C[C@@H]1C[C@@H](O)c2ncnc(N3CCN(C(=O)[C@H](N)Cc4ccc(Cl)cc4)CC3)c21]

(R)-2-amino-3-(4-chlorophenyl)-1-(4-((5R,7R)-7-hydroxy-5-methyl-6,7-dihydro-5H-cyclopenta[d]pyrimidin-4-yl)piperazin-1-yl)propan-1-one

MS (APCI+) [M+H] $^+$416.

Example 37

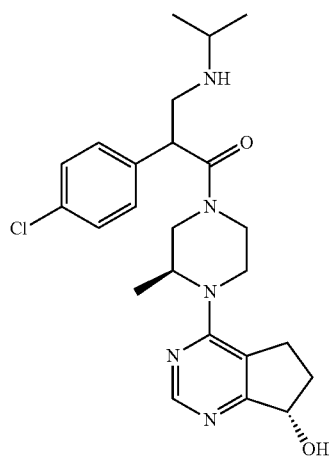 [SMILES: CC(C)NCC(C(=O)N1CCN(c2ncnc3c2CC[C@@H]3O)[C@@H](C)C1)c1ccc(Cl)cc1]

2-(4-chlorophenyl)-1-((S)-4-((S)-7-hydroxy-6,7-dihydro-5H-cyclopenta[d]pyrimidin-4-yl)-3-methylpiperazin-1-yl)-3-(isopropylamino)propan-1-one $^1$H NMR (D$_2$O, 400 MHz) δ 8.10-8.00 (m, 1H), 7.10-6.85 (m, 2H), 6.80-6.70 (m, 2H), 4.82-4.70 (m, 1H), 4.00-2.50 (m, 12H), 2.10-1.90 (m, 1H), 1.50-1.40 (m, 1H), 0.90-0.70 (m, 9H). MS (APCI+) [M+H] $^+$458.

Example 38

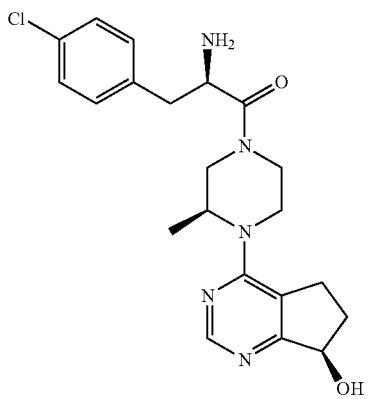 [SMILES: C[C@H]1CN(C(=O)[C@H](N)Cc2ccc(Cl)cc2)CCN1c1ncnc2c1CC[C@H]2O]

(R)-2-amino-3-(4-chlorophenyl)-1-((S)-4-((R)-7-hydroxy-6,7-dihydro-5H-cyclopenta[d]pyrimidin-4-yl)-3-methylpiperazin-1-yl)propan-1-one $^1$H NMR (D$_2$O, 400 MHz) δ 8.50-8.40 (m, 1H), 7.40-7.10 (m, 4H), 5.25-5.10 (m, 1H), 4.00-2.90 (m, 14H), 2.52-2.40 (m, 1H), 1.95-1.80 (m, 1H), 1.20-1.10 (m, 3H). MS (APCI+) [M+H] $^+$416.

Example 39

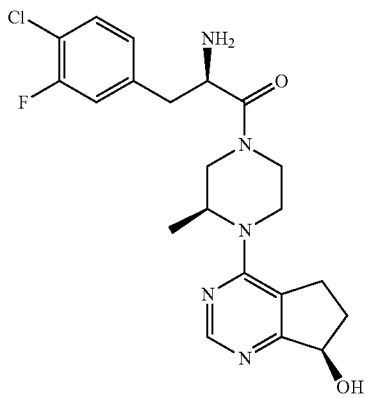 [SMILES: C[C@H]1CN(C(=O)[C@H](N)Cc2ccc(Cl)c(F)c2)CCN1c1ncnc2c1CC[C@H]2O]

(R)-2-amino-3-(4-chloro-3-fluorophenyl)-1-((S)-4-((R)-7-hydroxy-6,7-dihydro-5H-cyclopenta[d]pyrimidin-4-yl)-3-methylpiperazin-1-yl)propan-1-one $^1$H NMR (D$_2$O, 400 MHz) δ 8.55-8.40 (m, 1H), 7.40-6.90 (m, 3H), 5.25-5.10 (m, 1H), 4.00-2.90 (m, 14H), 2.52-2.40 (m, 1H), 1.95-1.80 (m, 1H), 1.20-1.10 (m, 3H). MS (APCI+) [M+H] $^+$434.

Example 40

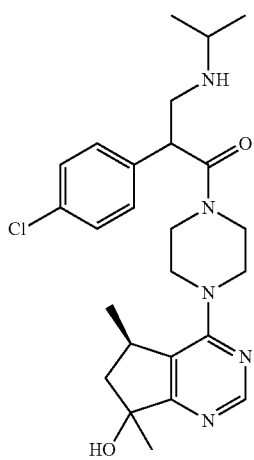 [SMILES: CC(C)NCC(C(=O)N1CCN(c2ncnc3c2[C@H](C)CC3(C)O)CC1)c1ccc(Cl)cc1]

2-(4-chlorophenyl)-1-(4-((5R)-7-hydroxy-5,7-dimethyl-6,7-dihydro-5H-cyclopenta[d]pyrimidin-4-yl)piperazin-1-yl)-3-(isopropylamino)propan-1-one Step 1

A solution of (R)-tert-butyl 4-(5-methyl-7-oxo-6,7-dihydro-5H-cyclopenta[d]pyrimidin-4-yl)piperazine-1-carboxylate (40 mg, 0.120 mmol) in THF (4 mL) was added to a 1.5M solution of methyllithium in diethyl ether (0.088 mL, 0.132 mmol) at −78° C. The resulting mixture was stirred at −78° C. for 1 hour and quenched by saturated aqueous NH$_4$Cl. The aqueous layer was extracted with EtOAc (2×). The organic layer was dried (MgSO$_4$) and concentrated. The residue was purified by a silica cartridge (5.0 g) eluted by EtOAc to give tert-butyl 4-((5R)-7-hydroxy-5,7-dimethyl-6,7-dihydro-5H-cyclopenta[d]pyrimidin-4-yl)piperazine-1-carboxylate as an off-white solid (29 mg, 69%). LCMS (APCI+) [M−Boc+H] $^+$349.1; Rt: 2.49 min.

Step 2

A solution of tert-butyl 4-((5R)-7-hydroxy-5,7-dimethyl-6,7-dihydro-5H-cyclopenta[d]pyrimidin-4-yl)piperazine-1-carboxylate (28 mg, 0.080 mmol) in DCM (6 mL) was added to a 4.0M HCl solution in dioxane (1.4 mL, 5.63 mmol). The mixture was stirred at room temperature for 4 hours. A 4.0M HCl solution in dioxane (1.4 mL, 5.63 mmol) from a different bottle was added. The resulting mixture was stirred for 18 hours. The solvents were removed in vacuo to give (5R)-5,7-dimethyl-4-(piperazin-1-yl)-6,7-dihydro-5H-cyclopenta[d]pyrimidin-7-ol dihydrochloride. DIPEA (41.5 mg, 0.321 mmol) was added to a suspension of this (5R)-5,7-dimethyl-4-(piperazin-1-yl)-6,7-dihydro-5H-cyclopenta[d]pyrimidin-7-ol dihydrochloride (25.8 mg, 0.0803 mmol), 3-(tert-butoxycarbonykisopropyl)amino)-2-(4-chlorophenyl) propanoic acid (32.9 mg, 0.0964 mmol), and O-(1H-benzotriazol-1-yl)-N,N,N',N'-tetramethyluronium hexafluorophosphate (36.6 mg, 0.0964 mmol) in CH$_2$Cl$_2$ (6 mL) at room temperature. The resulting mixture was stirred for 1 hour. The solvent was removed in vacuo. The residue was purified by a silica cartridge (5.0 g) eluted by EtOAc to give tert-butyl 2-(4-chlorophenyl)-3-(4-((5R)-7-hydroxy-5,7-dimethyl-6,7-dihydro-5H-cyclopenta[d]pyrimidin-4-yl)piperazin-1-yl)-3-oxopropyl(isopropyl)carbamate (46 mg, 100%) as a gel. LCMS (APCI+) [M−Boc+H] $^+$472.2; Rt: 3.51 min.

Step 3

A solution of tert-butyl 2-(4-chlorophenyl)-3-(4-((5R)-7-hydroxy-5,7-dimethyl-6,7-dihydro-5H-cyclopenta[d]pyrimidin-4-yl)piperazin-1-yl)-3-oxopropyl(isopropyl)carbamate (46 mg, 0.080 mmol) in DCM (6 mL) was added to a 4.0M HCl solution in dioxane (1.4 mL, 5.63 mmol). The mixture was stirred at room temperature for 16 hours. The solvents were removed in vacuo to give 2-(4-chlorophenyl)-1-(4-((5R)-7-hydroxy-5,7-dimethyl-6,7-dihydro-5H-cyclopenta[d]pyrimidin-4-yl)piperazin-1-yl)-3-(isopropylamino)propan-1-one dihydrochloride (49 mg, 100%) as a mixture of diastereomers. Rt: 2.05 and 2.18 min.

LCMS (APCI+) [M+H] $^+$472.

Example 41

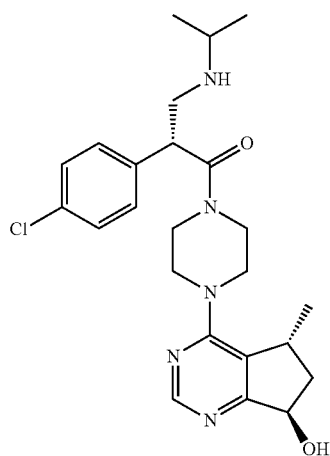 [SMILES: CC(C)NC[C@H](C(=O)N1CCN(c2ncnc3c2[C@H](C)C[C@H]3O)CC1)c1ccc(Cl)cc1]

(R)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one $^1$H NMR (D$_2$O, 400 MHz) δ 8.39 (s, 1H), 7.38-7.36 (d, J=8.0 Hz, 2H), 7.23-7.20 (d, J=8.4 Hz, 2H), 5.29-5.25 (m, 1H), 4.33-4.29 (m, 1H), 4.09-3.90 (m, 2H), 3.82-3.10 (m, 10H), 2.23-2.17 (m, 1H), 2.07-1.98 (m, 1H), 1.20-1.18 (m, 6H), 1.03-1.01 (d, J=6.8 Hz, 3H). MS (APCI+) [M+H] $^+$458.

Example 42

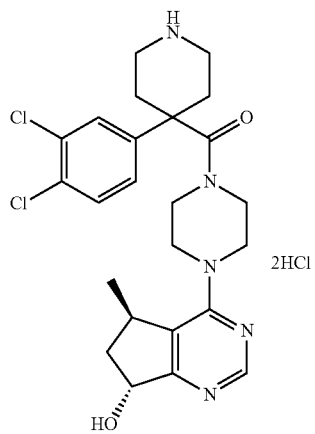 [SMILES: C[C@@H]1C[C@@H](O)c2ncnc(N3CCN(C(=O)C4(c5ccc(Cl)c(Cl)c5)CCNCC4)CC3)c21]

(4-(3,4-dichlorophenyl)piperidin-4-yl)(4-((5R,7R)-7-hydroxy-5-methyl-6,7-dihydro-5H-cyclopenta[d]pyrimidin-4-yl)piperazin-1-yl)methanone dihydrochloride $^1$H NMR (D$_2$O, 400 MHz) δ 8.36 (m, 1H), 7.25-7.00 (m, 3H), 5.28-5.20 (m, 1H), 4.00-3.00 (m, 14H), 2.50-2.38 (m, 2H), 2.26-2.00 (m, 2H), 1.04-1.00 (m, 3H). MS (APCI+) [M+H] $^+$490.

Example 43

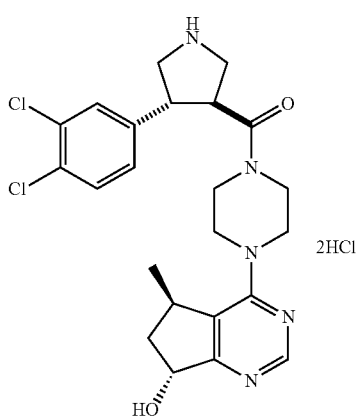

4-(3,4-dichlorophenyl)pyrrolidin-3-yl)(4-((5R,7R)-7-hydroxy-5-methyl-6,7-dihydro-5H-cyclopenta[d]pyrimidin-4-yl) piperazin-1-yl)methanone dihydrochloride $^1$H NMR (D$_2$O, 400 MHz) δ 8.44-8.10 (m, 1H), 7.48-7.40 (m, 2H), 7.24-7.12 (m, 1H), 5.33-5.28 (m, 1H), 4.00-3.85 (m, 1H), 3.80-3.00 (m, 11H), 2.26-2.20 (m, 1H), 2.10-2.00 (m, 1H), 1.08-1.00 (m, 3H). MS (APCI+) [M+H] $^+$476.

Example 44

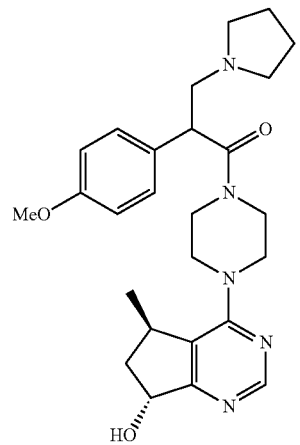 [SMILES: COc1ccc(C(CN2CCCC2)C(=O)N2CCN(c3ncnc4c3[C@H](C)C[C@H]4O)CC2)cc1]

1-(4-((5R,7R)-7-hydroxy-5-methyl-6,7-dihydro-5H-cyclopenta[d]pyrimidin-4-yl)piperazin-1-yl)-2-(4-methoxyphenyl)-3-(pyrrolidin-1-yl)propan-1-one $^1$H NMR (CDCl$_3$, 400 MHz) δ 8.46 (s, 1H), 7.83-7.81 (d, J=8.4 Hz, 1H), 7.63-7.61 (d, J=8.0 Hz, 1H), 7.31-7.23 (m, 2H), 5.11-4.98 (m, 2H), 3.95-3.90 (m, 1H), 3.80-3.00 (m, 10H), 2.20-1.90 (m, 7H), 1.32-1.20 (m, 3H), 1.12-1.08 (m, 4H). MS (APCI+) [M+H] $^+$466.

Example 45

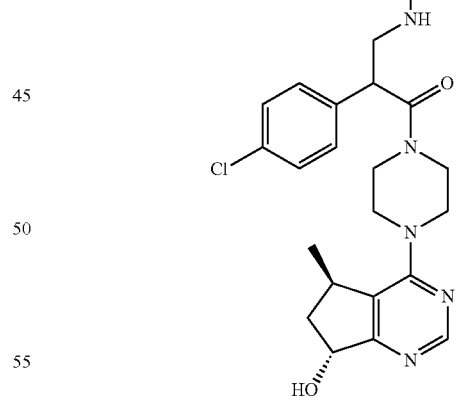

2-(4-chlorophenyl)-1-(4-((5R,7R)-7-hydroxy-5-methyl-6,7-dihydro-5H-cyclopenta[d]pyrimidin-4-yl)piperazin-1-yl)-3-(2,2,2-trifluoroethylamino)propan-1-one Step 1

A solution of 2-(4-chlorophenyl)acetic acid (20.0 g, 117 mmol) in dry methanol (235 mL) was treated with 5 drops of concentrated H₂SO₄ (cat.) at room temperature. The mixture was stirred overnight to completion, and then concentrated in vacuo to about 40 milliliters. The concentrate was partitioned between ether and half saturated NaHCO₃ solution. The aqueous portion was back-extracted once with ether, and the organics were combined. The organic portion was washed with water, then brine, dried over MgSO₄, and concentrated in vacuo. The material was placed under high vacuum for one hour to afford the pure methyl 2-(4-chlorophenyl)acetate as a pale yellow oil (19.8 g, 92%). $^1$H NMR (CDCl₃, 400 MHz) δ 7.30 (d, J=8.4 Hz, 2H), 7.21 (d, J=8.4 Hz, 2H), 3.70 (s, 3H), 3.60 (2, 2H).

Step 2 n-BuLi (1.60M in hexanes, 35.6 mL, 56.9 mmol) was added to a 0° C. solution of diisopropylamine (8.35 mL, 59.6 mmol) in THF (200 mL). The mixture was allowed to stir at 0° C. for 30 minutes, and was then cooled to −78° C. A solution of methyl 2-(4-chlorophenyl)acetate (10.0 g, 54.2 mmol) in THF (10 mL) was added to the −78° C. LDA solution by syringe, which was then stirred for 45 minutes. Neat tert-butyl bromoacetate (9.60 mL, 65.0 mmol) was added by syringe, and the reaction was stirred for 15 minutes at −78° C. The bath was removed, and the reaction was allowed to warm to room temperature. After stirring an additional 5 hours, the reaction mixture was quenched with saturated NH₄Cl solution, and the solvent(s) were removed in vacuo. The oily mixture was extracted with ethyl acetate, and the organics were combined. The organic portion was dried over MgSO₄, filtered, and concentrated in vacuo. The crude oil was purified on silica gel (95:5 hexanes:EtOAc) to afford the 4-tert-butyl 1-methyl 2-(4-chlorophenyl)succinate as a pale yellow oil (14.3 g, 88%). $^1$H NMR (CDCl₃, 400 MHz) δ 7.29 (d, J=7.2 Hz, 2H), 7.22 (d, J=7.2 Hz, 2H), 4.00 (dd, J=9.6, 5.6 Hz, 1H), 3.67 (s, 3H), 3.07 (dd, J=16.4, 9.6 Hz, 1H), 2.58 (dd, J=16.8, 6.0 Hz, 1H), 1.40 (m, 3H).

Step 3

A solution of 4-tert-butyl 1-methyl 2-(4-chlorophenyl)succinate (14.3 g, 47.7 mmol) in DCM (75 mL) was treated with neat TFA (75 mL) at room temperature. The mixture was stirred for five hours to completion, after which the reaction mixture was concentrated and dried in vacuo overnight to afford a white solid. The solid was suspended in toluene (160 mL), cooled to 0° C., and treated successively with diphenylphosphoryl azide (11.2 mL, 52.1 mmol) and triethylamine (13.2 mL, 94.7 mmol). The reaction mixture (homogeneous) was allowed to warm to room temperature and stirred for four hours to completion. The solution was quenched with 1% citric acid solution and extracted with EtOAc (3×). The combined organic portion was washed with brine, dried over Na₂SO₄, filtered, and concentrated in vacuo to give a light brown oil. The crude azide was dissolved in tert-butanol (160 mL), treated with neat SnCl₄ (1.0M solution, 2.37 mL, 2.37 mmol), and carefully heated to 90° C. with evolution of nitrogen. The mixture was stirred at 90° C. for 2.5 hours and cooled to room temperature. The solution was quenched with saturated NaHCO₃ solution and then concentrated. The oily mixture was extracted with EtOAc (3×), and the combined organic portion was washed with brine, dried over MgSO₄, filtered, and concentrated in vacuo. The residue was purified by on silica gel (4:1 hexanes:EtOAc) to afford the methyl 3-(tert-butoxycarbonylamino)-2-(4-chlorophenyl)propanoate as a pale yellow oil (11.7 g, 79%). $^1$H NMR (CDCl₃, 400 MHz) δ 7.31 (d, J=8.0 Hz, 2H), 7.20 (d, J=8.0 Hz, 2H), 4.86 (br s, 1H), 3.88 (m, 1H), 3.69 (s, 3H), 3.58 (m, 1H), 3.49 (m, 1H), 1.42 (s, 9H).

Step 4

A solution of methyl 3-(tert-butoxycarbonylamino)-2-(4-chlorophenyl)propanoate (451 mg, 1.44 mmol) in dioxane (6.0 mL) was treated with 4M HCl in dioxane (about 6.0 mL, 23.0 mmol) at room temperature. The mixture was stirred for 18 hours to completion, after which the reaction mixture was diluted with ether to afford a precipitate. The slurry was filtered under nitrogen to afford a white solid, which was washed with ether. The solid was dried under vacuum to afford the methyl 3-amino-2-(4-chlorophenyl)propanoate hydrochloride as a white solid (321 mg, 89%). LCMS (APCI+) m/z 214.0 [M+H]⁺.

Step 5

A solution of methyl 3-amino-2-(4-chlorophenyl)propanoate hydrochloride (215 mg, 0.86 mmol) in 1:1 THF:DMF (3.0 mL) was treated with DIEA (389 uL, 2.23 mmol) at room temperature. Trifluoroethyl triflate (299 mg, 1.29 mmol) was added to the mixture, and the reaction was stirred for 20 hours to completion. The mixture was partitioned between ethyl acetate and diluted NaHCO₃ solution. The aqueous portion was extracted twice, and the combined organic portions were washed with water (3×). The organic portion was washed with brine, separated, dried over MgSO₄, filtered, and concentrated in vacuo. The residue was purified by chromatography (silica gel eluted with 4:1 hexanes:ethyl acetate, Rf=0.18) to afford the pure methyl 2-(4-chlorophenyl)-3-(2,2,2-trifluoroethylamino)propanoate (235 mg, 93%) as a colorless oil. LCMS (APCI+) m/z 296.0 [M+H]⁺.

Step 6

A solution of methyl 2-(4-chlorophenyl)-3-(2,2,2-trifluoroethylamino)propanoate (235 mg, 0.795 mmol) in THF (3.0 mL) was treated with KOTMS (153 mg, 1.19 mmol) at room temperature. The reaction was allowed to stir 18 hours to completion, and the mixture was diluted with ether. The resulting precipitate was isolated by filtration and placed under high vacuum for two hours to afford the potassium 2-(4-chlorophenyl)-3-(2,2,2-trifluoroethylamino)propanoate (299 mg, 118%, excess salts) as a white solid. LCMS (APCI+) m/z 282.0 [M+H]⁺.

Step 7

A solution of (5R,7R)-5-methyl-4-(piperazin-1-yl)-6,7-dihydro-5H-cyclopenta[d]pyrimidin-7-ol dihydrochloride (30 mg, 98 umol) and potassium 2-(4-chlorophenyl)-3-(2,2,2-trifluoroethylamino)propanoate (31.2 mg, 98 umol) in DMF (1.0 mL) was treated with DIEA (36 uL, 205 umol) and HBTU (41 mg, 107 umol), respectively, at room temperature. The mixture was allowed to stir for 18 hours to completion, and the solution was partitioned between ethyl acetate and water. The aqueous portion was extracted twice, and the organics were combined. The organic portion was washed with water (3×), then brine, separated, dried over MgSO$_4$, filtered, and concentrated in vacuo. The residue was purified by chromatography (silica gel eluted with 9:1 ethyl acetate: MeOH) to afford the pure free-base as a colorless oil. This material was dissolved in ether (1.0 mL), then treated with excess 2.0M HCl in ether. The suspension was concentrated in vacuo to afford the pure 2-(4-chlorophenyl)-1-(4-((5R, 7R)-7-hydroxy-5-methyl-6,7-dihydro-5H-cyclopenta[d]pyrimidin-4-yl)piperazin-1-yl)-3-(2,2,2-trifluoroethylamino) propan-1-one dihydrochloride (31 mg, 99%) as a white solid. LCMS (APCI+) m/z 498.2 [M+H]+.

Example 46

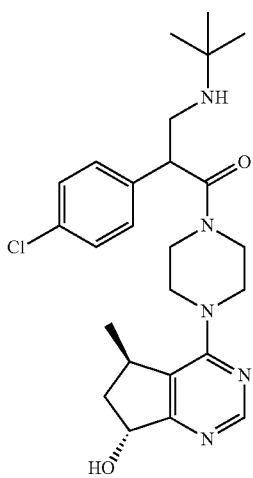 [SMILES: C[C@@H]1C[C@@H](O)c2ncnc(N3CCN(C(=O)C(CNC(C)(C)C)c4ccc(Cl)cc4)CC3)c21]

3-(tert-butylamino)-2-(4-chlorophenyl)-1-(4-((5R, 7R)-7-hydroxy-5-methyl-6,7-dihydro-5H-cyclopenta [d]pyrimidin-4-yl)piperazin-1-yl)propan-1-one Step 1

A stirring solution of methyl 2-(4-chlorophenyl)acetate (36.7 g, 199 mmol) (From Example 1, Step 1) and paraformaldehyde (6.27 g, 209 mmol) in DMSO (400 mL) was treated with sodium methoxide (537 mg, 9.94 mmol) at room temperature. The mixture was allowed to stir for two hours to completion and then poured into ice-cold water (700 mL) forming a white emulsion. The quench was neutralized with the addition of 1M HCl solution, and the aqueous was extracted with ethyl acetate (3×). The combined organic portions were washed with water (2×), then brine, dried over MgSO$_4$, and concentrated in vacuo. The residue was filtered through a plug of silica gel eluted stepwise with 9:1 to 1:1 hexanes:ethyl acetate to afford the pure methyl 2-(4-chlorophenyl)-3-hydroxypropanoate (39.4 g, 92%) as a colorless oil. $^1$H NMR (CDCl$_3$, 400 MHz) δ 7.32 (d, J=8.4 Hz, 2H), 7.21 (d, J=8.4 Hz, 2H), 4.10 (m, 1H), 3.82 (m, 2H), 3.72 (s, 3H), 2.25 (m, 1H).

Step 2

A solution of methyl 2-(4-chlorophenyl)-3-hydroxypropanoate (39.4 g, 184 mmol) in DCM (500 mL) was treated with triethylamine (64.0 mL, 459 mmol) and cooled to 0° C. The solution was treated with methane sulfonyl chloride (15.6 mL, 202 mmol) slowly, then allowed to stir for 30 minutes to completion. The solution was partitioned with 1N HCl solution, and the aqueous portion was back-extracted once with DCM. The combined organic portions were washed again with 1N HCl solution, separated, then washed with a half saturated NaHCO$_3$ solution. The organic portion was dried over MgSO$_4$ and concentrated in vacuo to afford an orange oil. The residue was filtered through a plug of silica gel eluted with 9:1 hexanes:ethyl acetate to afford the pure methyl 2-(4-chlorophenyl)-3-hydroxypropanoate (30.8 g, 85%) as a colorless oil. $^1$H NMR (CDCl$_3$, 400 MHz) δ 7.36 (d, J=8.4 Hz, 2H), 7.32 (d, J=8.4 Hz, 2H), 6.38 (s, 1H), 5.90 (s, 1H), 3.82 (s, 3H).

Step 3

A solution of methyl 2-(4-chlorophenyl)acrylate (2.00 g, 10.2 mmol) in 1:1 THF:ethanol (20 mL) was treated with tert-butyl amine (389 uL, 2.23 mmol) at 60° C. The reaction stirred for 20 hours to completion, and the solvent/excess amine were removed in vacuo. The residue was purified by chromatography on silica gel (eluted with 1:1 hexanes:ethyl acetate) to afford the pure methyl 3-(tert-butylamino)-2-(4-chlorophenyl)propanoate (2.54 g, 93%) as a colorless oil. LCMS (APCI+) m/z 270.0 [M+H]$^+$.

Step 4

A solution of methyl 3-(tert-butylamino)-2-(4-chlorophenyl)propanoate (1.00 g, 3.71 mmol) in THF (15 mL) was treated with KOTMS (555 mg, 3.89 mmol) at room temperature. The reaction was allowed to stir 18 hours to completion, and the mixture was concentrated in vacuo. The residue was placed under high vacuum for three hours to afford the near-pure potassium 3-(tert-butylamino)-2-(4-chlorophenyl)propanoate (1.06 g, 97%) as a white solid. This material was used without purification. LCMS (APCI+) m/z 256.0 [M+H]$^+$.

Step 5

A solution of (5R,7R)-5-methyl-4-(piperazin-1-yl)-6,7-dihydro-5H-cyclopenta[d]pyrimidin-7-ol dihydrochloride (31.7 mg, 0.103 mmol) and potassium 3-(tert-butylamino)-2-(4-chlorophenyl)propanoate (30.3 mg, 0.103 mmol) in DMF (1.0 mL) was treated with DIEA (38 uL, 0.217 mmol) and HBTU (43 mg, 114 mmol), respectively, at room temperature. The mixture was allowed to stir for 18 hours to completion, and the solution was partitioned between ethyl acetate and water. The aqueous was extracted twice, and the organics were combined. The organic portion was washed with water (3×), then brine, separated, dried over MgSO$_4$, filtered, and concentrated in vacuo. The residue was purified by reverse phase chromatography (eluted with water:acetonitrile gradients modified with 1% ammonium acetate) to afford the pure 3-(tert-butylamino)-2-(4-chlorophenyl)-1-(4-((5R,7R)-7-hydroxy-5-methyl-6,7-dihydro-5H-cyclopenta[d]pyrimidin- 4-yl)piperazin-1-yl)propan-1-one (20 mg, 41%) as a white solid. LCMS (APCI+) m/z 472.2 [M+H]+.

Example 47

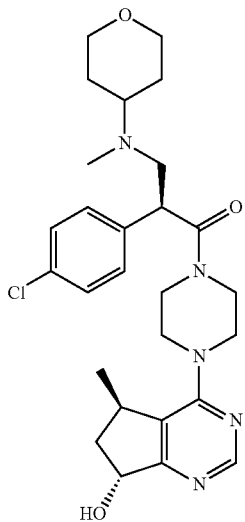 [SMILES: C[C@@H]1C[C@@H](O)c2ncnc(N3CCN(C(=O)[C@H](CN(C)C4CCOCC4)c4ccc(Cl)cc4)CC3)c21]

(S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(methyl(tetrahydro-2H-pyran-4-yl)amino)propan-1-one 37% w/w formaldehyde/$H_2O$ (0.1489 ml, 2.000 mmol) was added to a solution of (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(tetrahydro-2H-pyran-4-ylamino)propan-1-one dihydrochloride (0.115 g, 0.2000 mmol) and DIEA (0.105 mL, 0.600 mmol) in DCE (1.5 mL) and THF (0.5 mL), followed by addition of Na(OAc)$_3$BH (0.08477 g, 0.4000 mmol). The reaction mixture was stirred for 2 hours, and 1 equivalent of Na(OAc)$_3$BH was added. The reaction mixture was stirred for 14 hours. Another 5 equivalents of formaldehyde solution and 1.5 equivalents of Na(OAc)$_3$BH were added, and the reaction mixture was stirred another 3 hours. Saturated NaHCO$_3$ was added, the mixture was extracted with DCM, and the combined extracts were dried (Na$_2$SO$_4$), filtered, and concentrated. The crude was purified on silica using Biotage 12M (1:1 DCM:EtOAc loaded and 125 mL flushed, then 25:1 to 10:1 DCM:MeOH gradient), and fractions with product were concentrated. The resulting residue was dissolved in minimal DCM/ether, and excess 2M HCl/ether was added, causing precipitation. The mixture was stirred for 5 minutes, then concentrated to dryness and dried in vacuo. The solids were suspended in ether and isolated by filtration through 20 μm nylon filter paper with nitrogen pressure, rinsed with ether, and dried in vacuo to give (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(methyl(tetrahydro-2H-pyran-4-yl)amino)propan-1-one dihydrochloride (0.080 g, 68.15% yield) as a white powder. LCMS (APCI+) m/z 514 [M+H]+.

Example 48

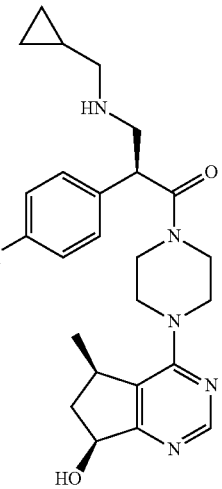

(S)-2-(4-chlorophenyl)-3-(cyclopropylmethylamino)-1-(4-((5R,7S)-7-hydroxy-5-methyl-6,7-dihydro-5H-cyclopenta[d]pyrimidin-4-yl)piperazin-1-yl)propan-1-one

Step 1

Tert-butyl cyclopropylmethylcarbamate (11.2 g, 65.4 mmol) was dissolved into THF (60 mL) and set to stir at −78° C. BuLi (2.5M, 28.8 mL) was then added portionwise over 10 minutes. The reaction was allowed to stir while warming to −20° C. for 10 minutes, and continued stirring at that temperature for another 10 minutes. The reaction was then recooled to −78° C. at which point chloro(methoxy)methane (5.79 g, 72.0 mmol) was added via syringe. The reaction was then allowed to stir overnight with warming. The reaction was then quenched with 1N HCl and the organic layer separated. The aquoues layer was then extracted with DCM (2×), and the combined organic portions were dried with MgSO$_4$, filtered and concentrated. The crude material was purified by passing through a silica plug eluting 10:1 Hex/EtOAc to give tert-butyl cyclopropylmethyl(methoxymethyl)carbamate (12.8 g, 91%) as a clear liquid.

Step 2

(R)-4-Benzyl-3-(2-(4-chlorophenyl)acetyl)oxazolidin-2-one (2.0 g, 6.06 mmol) was added to a flask in DCM (75 ml) followed by TiCl$_4$ (1.38 g, 7.28 mmol) and DIEA (0.823 g, 6.37 mmol). The reaction was allowed to stir for about 15 to about 20 minutes at −78° C. at which point tert-butyl cyclopropylmethyl(methoxymethyl)carbamate (1.57 g, 7.28 mmol) was added. The reaction allowed to stir for 5 minutes, and the −78° C. bath was replaced with a 0° C. bath. The reaction was then allowed to stir for 3 hours at room temperature. After the reaction was determined to be complete by HPLC, the reaction was cooled to 0° C. and quenched by the slow addition of aqueous NaHCO$_3$ while stirring for 10 minutes. The organic layer was separated, and the aqueous layer was re-extracted (3× EtOAc). The combined organics were dried with MgSO$_4$, filtered and concentrated. The crude residue was purified by column chromatography, eluting 6:1 to 2:1 hexane/EtOAc to give tert-butyl (S)-3-((R)-4-benzyl-2-oxooxazolidin-3-yl)-2-(4-chlorophenyl)-3-oxopropyl(cyclopropylmethyl)carbamate (2.70 g, 87%) as light brown oil. (LCMS (APCI+) [M−Boc+H]$^+$ 412.9; Rt: 4.42 min)

Step 3

LiOH (1.41 g, 33.5 mmol) was added to a flask containing THF (360 mL) and H$_2$O (120 mL), which was stirred until dissolved. At this point, the reaction was cooled to 0° C. with ice, and hydrogen peroxide (35 wt. %, 6.52 g) was added. This solution was stirred for 10 minutes, at which point tert-butyl (S)-3-((R)-4-benzyl-2-oxooxazolidin-3-yl)-2-(4-chlorophenyl)-3-oxopropyl(cyclopropylmethyl)carbamate (8.6 g, 16.8 mmol) was added as a solution in THF (20 mL). The reaction was stirred overnight with warming. The reaction was quenched by the addition of 10% aqueous Na$_2$SO$_3$ (1 mL) and saturated aqueous NaHCO$_3$ (1 mL) and stirred for 10 minutes. The reaction was concentrated to remove THF and the aqueous layer extracted with ether (3×). The aqueous layer was diluted with EtOAc and acidified with 1N HCl. The organic layer was removed, and the aqueous layer was extracted with EtOAc (2×). The combined organics were dried with MgSO$_4$ and concentrated to give the crude product, (S)-3-(tert-butoxycarbonyl(cyclopropylmethyl)amino)-2-(4-chlorophenyl)propanoic acid as a clear oil (LCMS (APCI+) [M−Boc+H]$^+$ 254.1; Rt: 3.03 min).

Step 4

Crude (S)-3-(tert-butoxycarbonyl(cyclopropylmethyl)amino)-2-(4-chlorophenyl)propanoic acid (4.6 g, 13 mmol) was dissolved into DCM (130 mL) and excess 4N HCl was added. The reaction was allowed to stir overnight, after which it was concentrated. The resulting white solid was taken up into EtOAC and filtered. The resulting solid was washed with EtOAc (4×) to give pure (S)-2-(4-chlorophenyl)-3-(cyclopropylmethylamino)propanoic acid hydrochloride (3.60 g, 95%). This (S)-2-(4-chlorophenyl)-3-(cyclopropylmethylamino)propanoic acid (0.57 g, 2.24 mmol) was dissolved into 10:1 CH$_3$CN:H$_2$O (50 mL) and tetramethylammonium hydroxide pentahydrate (1.00 g) was added followed by Boc2O (0.73 g, 3.36 mmol). The reaction mixture was allowed to stir at room temperature overnight, and the reaction was quenched by the addition of 1N HCl. The reaction was concentrated, and the residue was diluted with EtOAc. The organics were separated, and the aqueous portion was extracted with EtOAc. The combined organics were dried with MgSO$_4$, filtered and concentrated. The crude residue was purified by silica plug eluting Hex to 1:1 Hex/EtOAc to give (S)-3-(tert-butoxycarbonyl(cyclopropylmethyl)amino)-2-(4-chlorophenyl)propanoic acid (0.58 g, 73%) as a clear oil. (LCMS (APCI+) [M−Boc+H]$^+$ 254.0)

Step 5

(5R,7S)-5-methyl-4-(piperazin-1-yl)-6,7-dihydro-5H-cyclopenta[d]pyrimidin-7-ol dihydrochloride (0.0444 g, 0.1445 mmol) and (S)-3-(tert-butoxycarbonyl(cyclopropylmethyl)amino)-2-(4-chlorophenyl)propanoic acid (0.05114 g, 0.1445 mmol) were combined in methylene chloride (1.25 mL). They were then treated with diisopropylethylamine (0.07552 ml, 0.4336 mmol), followed by HBTU (0.05495 g, 0.1445 mmol). The reaction was stirred at ambient temperature for 16 hours. The reaction was quenched with 10% Na$_2$CO$_3$, diluted with methylene chloride and separated. The aqueous portion was washed with methylene chloride (2×), and the combined organic layers were dried over Na$_2$SO$_4$ and concentrated in vacuo. The material was chromatographed on SiO$_2$ (Biotage 12M) and eluted with 4% MeOH/MC. The material was concentrated in vacuo to give tert-butyl (S)-2-(4-chlorophenyl)-3-(4-((5R,7S)-7-hydroxy-5-methyl-6,7-dihydro-5H-cyclopenta[d]pyrimidin-4-yl)piperazin-1-yl)-3-oxopropyl(cyclopropylmethyl)carbamate as a white solid (67.4 mg, 82%). LCMS (APCI+) [M+H]$^+$570.0.

Step 6

Tert-butyl (S)-2-(4-chlorophenyl)-3-(4-((5R,7S)-7-hydroxy-5-methyl-6,7-dihydro-5H-cyclopenta[d]pyrimidin-4-yl)piperazin-1-yl)-3-oxopropyl(cyclopropylmethyl)carbamate (0.0674 g, 0.1182 mmol) was dissolved in dioxane (0.5 mL) and treated with HCl in dioxane (0.7389 ml, 2.956 mmol) (4M). The reaction was stirred at ambient temperature for 48 hours. The reaction mixture was concentrated in vacuo. The residue was redissolved in MeOH and re-concentrated three times. This residue was resuspended in MeOH (0.2+0.1 mL) and added dropwise to a stirred flask of Et$_2$O (10 mL). After stirring for 30 minutes, the solids were filtered, washed with Et$_2$O, and dried under a blanket of nitrogen to give (S)-2-(4-chlorophenyl)-3-(cyclopropylmethylamino)-1-(4-((5R,7S)-7-hydroxy-5-methyl-6,7-dihydro-5H-cyclopenta[d]pyrimidin-4-yl)piperazin-1-yl)propan-1-one as a white solid (60.2 mg, 94%.) LCMS (APCI+) [M+H]$^+$ 470.2.

Example 49

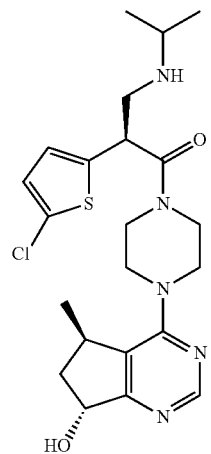 [SMILES: CC(C)NC[C@@H](C(=O)N1CCN(c2ncnc3c2[C@H](C)C[C@H]3O)CC1)c1ccc(Cl)s1]

(S)-2-(5-chlorothiophen-2-yl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one Step 1

Triethylamine (7.32 mL, 52.5 mmol) was added to a solution of 5-chlorothiophene-2-acetic acid (8.83 g, 50.0 mmol) in ether (200 mL) at −78° C., followed by 2,2-dimethylpropanoyl chloride (6.46 mL, 52.5 mmol). The resulting mixture was stirred at 0° C. for 2 hours, and then re-cooled to −78° C. Meanwhile, a solution of (R)-4-benzyl-2-oxazolidinone (9.30 g, 52.5 mmol) in THF (100 mL) in a separated flask was cooled to −78° C. 2.5M of n-butyllithium in hexane (22.0 mL) was added dropwise. The resulting solution was stirred at −78° C. for 1 hour, and then added via cannula into the solution of the mixed anhydride. The reaction mixture was stirred at −78° C. for 15 minutes, at 0° C. for 30 minutes, then at room temperature overnight. Saturated NHCl (300 mL) was added to quench the reaction. The mixture was extracted with EtOAc (3×200 mL). The combined organics were dried (Na$_2$SO$_4$), filtered and concentrated. The crude product was purified by silica gel chromatography, eluting with EtOAc/hexane (0-25%) to give (R)-4-benzyl-3-(2-(5-chlorothiophen-2-yl)acetyl)oxazolidin-2-one (9.43 g, 56%). $^1$H NMR (CDCl$_3$, 400 MHz) δ 7.33-7.25 (m, 3H), 7.16-7.13 (m, 2H), 6.79-6.76 (m, 2H), 4.70-4.65 (m, 1H), 4.38 (q, J=17.2 Hz, 2H), 4.25-4.18 (m, 2H), 3.27 (dd, J=13.6 Hz, J=3.6 Hz, 1H), 2.77 (dd, J=13.6 Hz, J=3.6 Hz, 1H).

Step 2

1.0M of titanium tetrachloride in DCM (30.9 mL, 30.9 mmol) was added dropwise to a solution of (R)-4-benzyl-3-(2-(5-chlorothiophen-2-yl)acetyl)oxazolidin-2-one (9.43 g, 28.1 mmol) in DCM (170 mL) at −78° C., followed by N,N-diisopropylethylamine (9.78 mL, 56.2 mmol). The resulting dark blue mixture was stirred at −78° C. for 1 hour. tert-Butyl isopropyl(methoxymethyl)carbamate (11.4 g, 56.2 mmol) was then added. The mixture was stirred at −78° C. for 1 hour, and then allowed to warm up to room temperature. The mixture was stirred at room temperature for 2 hours, quenched with saturated NH$_4$Cl (300 mL), and extracted with DCM (3×200 mL). The combined organics were dried (Na$_2$SO$_4$), filtered and concentrated. The crude product was purified by silica gel chromatography eluting with EtOAc/hexane (0-20%) to give tert-butyl (S)-3-((R)-4-benzyl-2-oxooxazolidin-3-yl)-2-(5-chlorothiophen-2-yl)-3-oxopropyl(isopropyl)carbamate (10.2 g, 72%). MS (APCI+) [M+H]$^+$ 507.2. $^1$H NMR (CDCl$_3$, 400 MHz) δ 7.36-7.22 (m, 5H), 6.79 (d, J=4.0 Hz, 1H), 6.75 (d, J=4.0 Hz, 1H). 4.67-4.62 (m, 1H), 4.15-4.09 (m, 4H), 3.45-3.38 (m, 2H), 2.80-2.72 (m, 1H), 1.49 (s, 9H), 1.12 (d, J=6.0 Hz, 3H), 1.05 (d, J=6.0 Hz, 3H).

Step 3

A mixture solution of lithium hydroxide (374 mg, 15.6 mmol) in H$_2$O (60 mL) and 30% hydrogen peroxide (1.60 mL, 15.6 mmol) was added dropwise to a solution of tert-butyl (S)-3-((R)-4-benzyl-2-oxooxazolidin-3-yl)-2-(5-chlorothiophen-2-yl)-3-oxopropyl(isopropyl)carbamate (7.54 g, 14.9 mmol) in THF (150 mL) at −5° C. The mixture was stirred at −5° C. After 10 minutes, the reaction was quenched with 10% Na$_2$SO$_3$ (16 mL) at −5° C. and stirred at room temperature for 30 minutes. The THF was removed in vacuo. The aqueous layer was acidified with 1M NaH$_2$PO$_4$ and extracted with DCM (3×100 mL). The combined organics were dried (Na$_2$SO$_4$), filtered and concentrated to give (S)-3-(tert-butoxycarbonyl(isopropyl)amino)-2-(5-chlorothiophen-2-yl)propanoic acid which was used in the next step without purification. MS (APCI+) [M+H] $^+$348.2.

Step 4

A solution of (5R,7R)-5-methyl-4-((S)-piperazin-1-yl)-6,7-dihydro-5H-cyclopenta[d]pyrimidin-7-ol ditrifluoroacetic acid (351 mg, 1.50 mmol) and N,N-diisopropylethylamine (2.61 mL, 15.0 mmol) in DCM (5 mL) was added to a solution of (S)-3-(tert-butoxycarbonyl(isopropyl)amino)-2-(5-chlorothiophen-2-yl)propanoic acid (0.522 g, 1.50 mmol) in DCM (5 mL) and DMF (1 mL), followed by O-(benzotriazol-1-yl)-N,N,N',N'-tetramethyluronium hexafluorophosphate (0.597 g, 1.57 mmol). The mixture was stirred at room temperature for 1 hour. The reaction was quenched with saturated NH$_4$Cl (20 mL) and extracted with DCM (2×20 mL). The combined organics were dried (Na$_2$SO$_4$), filtered and concentrated. The crude product was purified by silica gel chromatography eluting first with EtOAc/hexane (0-100%), then with MeOH/DCM (0-6%) to give tert-butyl (S)-2-(5-chlorothiophen-2-yl)-3-(4-((5R,7R)-6,7-dihydro-7-hydroxy-5-methyl-5H-cyclopenta[d]pyrimidin-4-yl)piperazin-1-yl)-3-oxopropylisopropylcarbamate (535 mg, 63%). MS (APCI+) [M+H] $^+$564.0. $^1$H NMR (CDCl$_3$, 400 MHz) δ8.53 (s, 1H), 6.75 (d, J=4.0 Hz, 1H), 6.68 (d, J=4.0 Hz, 1H), 5.11 (t, J=6.8 Hz, 1H), 4.94 (brs, 1H), 3.83-3.35 (m, 13H), 2.24-2.12 (m, 2H), 1.49 (s, 9H), 1.18 (d, J=7.2 Hz, 3H), 1.01 (d, J=6.0 Hz, 3H), 0.82 (d, J=6.0 Hz, 3H).

Step 5

4.0M hydrogen chloride in 1,4-dioxane (2.508 mL) was added to a solution of tert-butyl (S)-2-(5-chlorothiophen-2-yl)-3-(4-((5R,7R)-6,7-dihydro-7-hydroxy-5-methyl-5H-cyclopenta[d]pyrimidin-4-yl)piperazin-1-yl)-3-oxopropylisopropylcarbamate (283 mg, 0.502 mmol) in 1,4-dioxane (2.5 mL) and methylene chloride (2.5 mL) at 0° C. The mixture was allowed to warm up to room temperature and stirred for 1 hour. The mixture was concentrated in vacuo. The residue was then dissolved in a minimum volume of DCM (1 mL) and added dropwise to ether (10 mL) at 0° C. with stirring. A white solid precipitated. The solvents were evaporated with a rotovap in a 25° C. bath. The off-white solid was dried under high vacuum overnight to give (S)-2-(5-chlorothiophen-2-yl)-1-(4-((5R,7R)-6,7-dihydro-7-hydroxy-5-methyl-5H-cyclopenta[d]pyrimidin-4-yl)piperazin-1-yl)-3-(isopropylamino)propan-1-one dihydrochloride (537 mg, 99.9%). MS (APCI+) [M+H] $^+$464.1. $^1$H NMR (D20, 400 MHz) δ 8.53 (s, 1H), 6.97 (d, J=4.0 Hz, 1H), 6.96 (d, J=4.0 Hz, 1H), 5.40 (t, J=8.0 Hz, 1H), 4.78-4.71 (m, 1H), 4.31-4.27 (m, 1H), 4.09-3.97 (m, 2H), 3.84-3.42 (m, 10H), 2.36-2.30 (m, 1H), 2.21-2.13 (M, 1H), 1.33 (d, J=6.4 Hz, 3H), 1.32 (d, J=6.4 Hz, 3H), 1.14 (d, J=6.4 Hz, 3H).

Examples 50-324 shown in Table 1 can also be made according to the above-described methods.

TABLE 1

| Example | Structure | Name | LCMS or ¹H NMR |
|---|---|---|---|
| 50 | 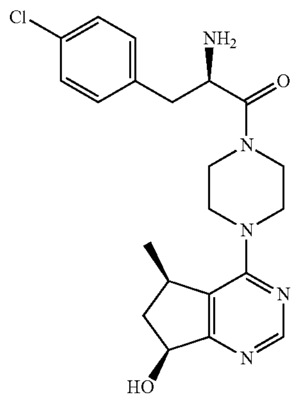 [SMILES: C[C@@H]1C[C@H](O)c2ncnc(N3CCN(C(=O)[C@H](N)Cc4ccc(Cl)cc4)CC3)c21] | (R)-2-amino-3-(4-chlorophenyl)-1-(4-((5R,7S)-7-hydroxy-5-methyl-6,7-dihydro-5H-cyclopenta[d]pyrimidin-4-yl)piperazin-1-yl)propan-1-one | 416.2 |
| 51 | 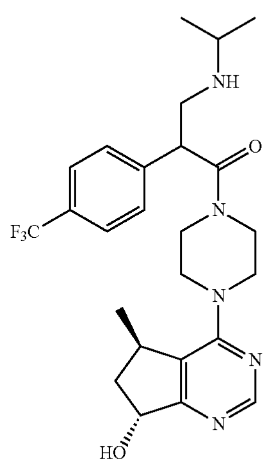 [SMILES: CC(C)NCC(C(=O)N1CCN(c2ncnc3c2[C@H](C)C[C@H]3O)CC1)c1ccc(C(F)(F)F)cc1] | 1-(4-((5R,7R)-7-hydroxy-5-methyl-6,7-dihydro-5H-cyclopenta[d]pyrimidin-4-yl)piperazin-1-yl)-3-(isopropylamino)-2-(4-(trifluoromethyl)phenyl)propan-1-one | 492.2 |
| 52 | 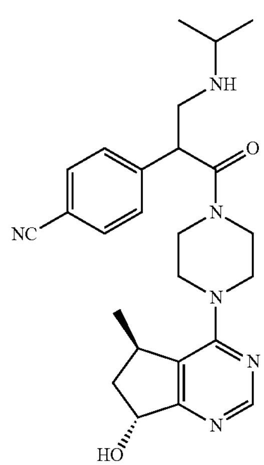 [SMILES: CC(C)NCC(C(=O)N1CCN(c2ncnc3c2[C@H](C)C[C@H]3O)CC1)c1ccc(C#N)cc1] | 4-(1-(4-((5R,7R)-7-hydroxy-5-methyl-6,7-dihydro-5H-cyclopenta[d]pyrimidin-4-yl)piperazin-1-yl)-3-(isopropylamino)-1-oxopropan-2-yl)benzonitrile | 449.2 |

TABLE 1-continued

| Example | Structure | Name | LCMS or ¹H NMR |
|---|---|---|---|
| 53 | 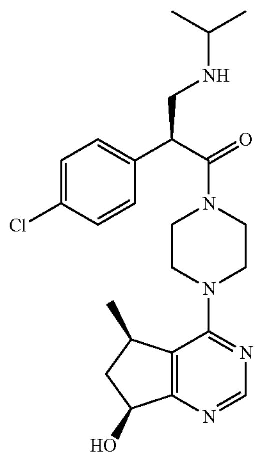 [SMILES: CC(C)NC[C@@H](C(=O)N1CCN(c2ncnc3c2[C@H](C)C[C@@H]3O)CC1)c1ccc(Cl)cc1] | (S)-2-(4-chlorophenyl)-1-(4-((5R,7S)-7-hydroxy-5-methyl-6,7-dihydro-5H-cyclopenta[d]pyrimidin-4-yl)piperazin-1-yl)-3-(isopropylamino)propan-1-one | 458.3 |
| 54 | 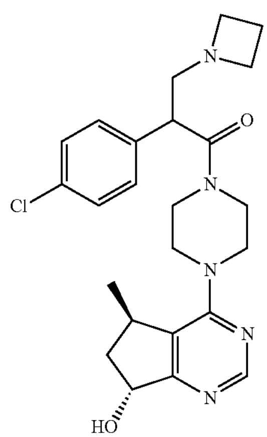 [SMILES: C[C@@H]1C[C@@H](O)c2ncnc(N3CCN(C(=O)C(CN4CCC4)c4ccc(Cl)cc4)CC3)c21] | 3-(azetidin-1-yl)-2-(4-chlorophenyl)-1-(4-((5R,7R)-7-hydroxy-5-methyl-6,7-dihydro-5H-cyclopenta[d]pyrimidin-4-yl)piperazin-1-yl)propan-1-one | 456.2 |
| 55 | 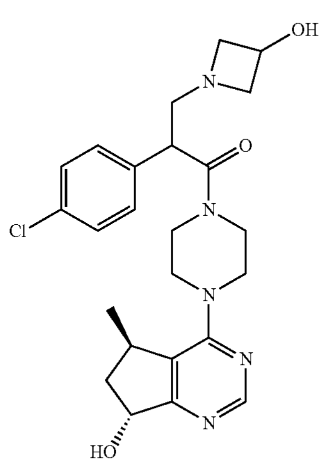 [SMILES: C[C@@H]1C[C@@H](O)c2ncnc(N3CCN(C(=O)C(CN4CC(O)C4)c4ccc(Cl)cc4)CC3)c21] | 2-(4-chlorophenyl)-1-(4-((5R,7R)-7-hydroxy-5-methyl-6,7-dihydro-5H-cyclopenta[d]pyrimidin-4-yl)piperazin-1-yl)-3-(3-hydroxyazetidin-1-yl)propan-1-one | 472.2 |

TABLE 1-continued

| Example | Structure | Name | LCMS or ¹H NMR |
|---|---|---|---|
| 56 | 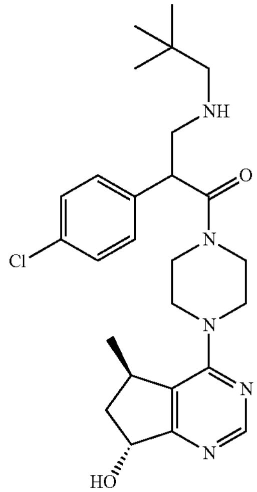 [SMILES: C[C@@H]1C[C@@H](O)c2ncnc(N3CCN(C(=O)C(CNCC(C)(C)C)c4ccc(Cl)cc4)CC3)c21] | 2-(4-chlorophenyl)-1-(4-((5R,7R)-7-hydroxy-5-methyl-6,7-dihydro-5H-cyclopenta[d]pyrimidin-4-yl)piperazin-1-yl)-3-(neopentylamino)propan-1-one | 486.3 |
| 57 | 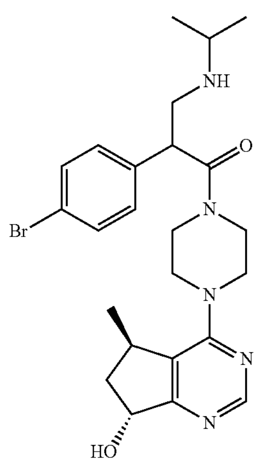 | 2-(4-bromophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one | 504.2 |
| 58 | 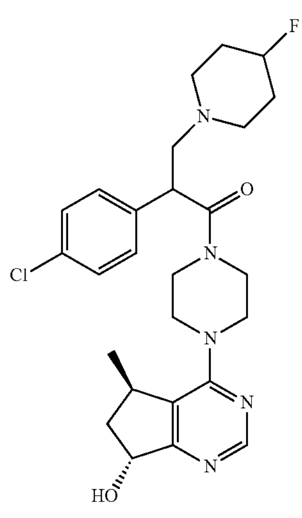 [SMILES: C[C@@H]1C[C@@H](O)c2ncnc(N3CCN(C(=O)C(CN4CCC(F)CC4)c4ccc(Cl)cc4)CC3)c21] | 2-(4-chlorophenyl)-3-(4-fluoropiperidin-1-yl)-1-(4-((5R,7R)-7-hydroxy-5-methyl-6,7-dihydro-5H-cyclopenta[d]pyrimidin-4-yl)piperazin-1-yl)propan-1-one | 502.2 |

TABLE 1-continued

| Example | Structure | Name | LCMS or ¹H NMR |
|---|---|---|---|
| 59 | 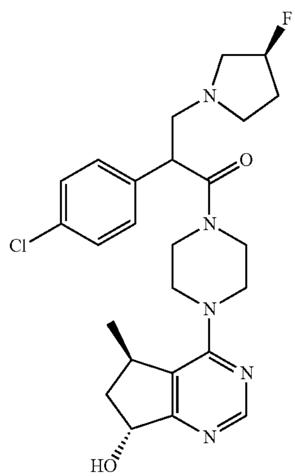 [SMILES: C[C@@H]1C[C@@H](O)c2ncnc(N3CCN(C(=O)C(CN4CC[C@H](F)C4)c4ccc(Cl)cc4)CC3)c21] | 2-(4-chlorophenyl)-3-((S)-3-fluoropyrrolidin-1-yl)-1-(4-((5R,7R)-7-hydroxy-5-methyl-6,7-dihydro-5H-cyclopenta[d]pyrimidin-4-yl)piperazin-1-yl)propan-1-one | 488.2 |
| 60 | 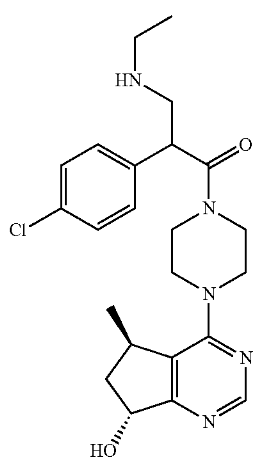 [SMILES: CCNCC(C(=O)N1CCN(c2ncnc3c2[C@H](C)C[C@H]3O)CC1)c1ccc(Cl)cc1] | 2-(4-chlorophenyl)-3-(ethylamino)-1-(4-((5R,7R)-7-hydroxy-5-methyl-6,7-dihydro-5H-cyclopenta[d]pyrimidin-4-yl)piperazin-1-yl)propan-1-one | 444.3 |
| 61 | 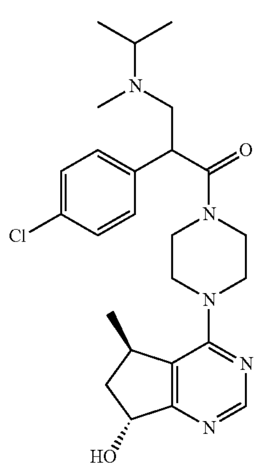 [SMILES: CC(C)N(C)CC(C(=O)N1CCN(c2ncnc3c2[C@H](C)C[C@H]3O)CC1)c1ccc(Cl)cc1] | 2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropyl(methyl)amino)propan-1-one | 472.2 |

TABLE 1-continued

| Example | Structure | Name | LCMS or ¹H NMR |
|---|---|---|---|
| 62 | 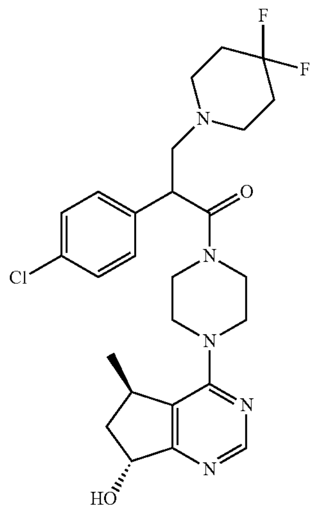 [SMILES: C[C@@H]1C[C@@H](O)c2ncnc(N3CCN(C(=O)C(CN4CCC(F)(F)CC4)c4ccc(Cl)cc4)CC3)c21] | 2-(4-chlorophenyl)-3-(4,4-difluoropiperidin-1-yl)-1-(4-((5R,7R)-7-hydroxy-5-methyl-6,7-dihydro-5H-cyclopenta[d]pyrimidin-4-yl)piperazin-1-yl)propan-1-one | 520.2 |
| 63 | 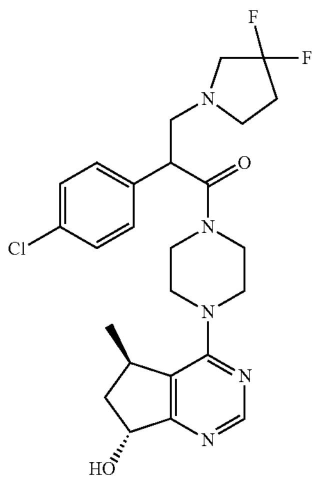 [SMILES: C[C@@H]1C[C@@H](O)c2ncnc(N3CCN(C(=O)C(CN4CCC(F)(F)C4)c4ccc(Cl)cc4)CC3)c21] | 2-(4-chlorophenyl)-3-(3,3-difluoropyrrolidin-1-yl)-1-(4-((5R,7R)-7-hydroxy-5-methyl-6,7-dihydro-5H-cyclopenta[d]pyrimidin-4-yl)piperazin-1-yl)propan-1-one | 506.2 |
| 64 | 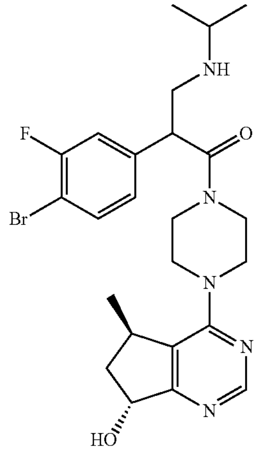 | 2-(4-bromo-3-fluorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one | 520.2 |

TABLE 1-continued

| Example | Structure | Name | LCMS or ¹H NMR |
|---|---|---|---|
| 65 | 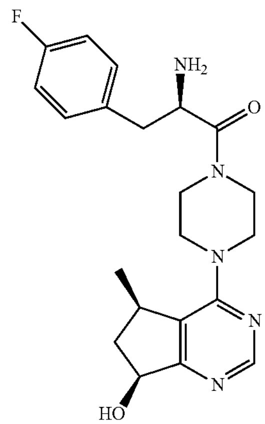 [SMILES: C[C@@H]1C[C@H](O)c2ncnc(N3CCN(C(=O)[C@H](N)Cc4ccc(F)cc4)CC3)c21] | (R)-2-amino-3-(4-fluorophenyl)-1-(4-((5R,7S)-7-hydroxy-5-methyl-6,7-dihydro-5H-cyclopenta[d]pyrimidin-4-yl)piperazin-1-yl)propan-1-one | 400.2 |
| 66 | 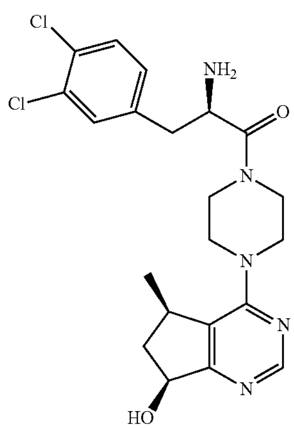 [SMILES: C[C@@H]1C[C@H](O)c2ncnc(N3CCN(C(=O)[C@H](N)Cc4ccc(Cl)c(Cl)c4)CC3)c21] | (R)-2-amino-3-(3,4-dichlorophenyl)-1-(4-((5R,7S)-7-hydroxy-5-methyl-6,7-dihydro-5H-cyclopenta[d]pyrimidin-4-yl)piperazin-1-yl)propan-1-one | 450.2 |
| 67 | 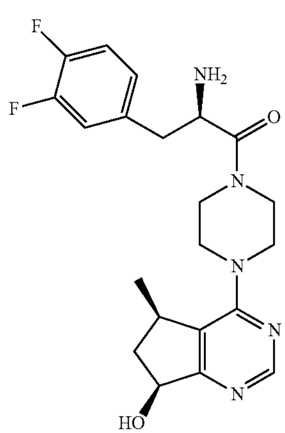 [SMILES: C[C@@H]1C[C@H](O)c2ncnc(N3CCN(C(=O)[C@H](N)Cc4ccc(F)c(F)c4)CC3)c21] | (R)-2-amino-3-(3,4-difluorophenyl)-1-(4-((5R,7S)-7-hydroxy-5-methyl-6,7-dihydro-5H-cyclopenta[d]pyrimidin-4-yl)piperazin-1-yl)propan-1-one | 418.2 |

TABLE 1-continued

| Example | Structure | Name | LCMS or ¹H NMR |
|---|---|---|---|
| 68 | 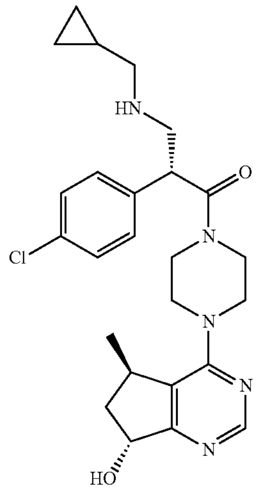 [SMILES: C[C@@H]1C[C@@H](O)c2ncnc(N3CCN(C(=O)[C@@H](CNCC4CC4)c4ccc(Cl)cc4)CC3)c21] | (R)-2-(4-chlorophenyl)-3-(cyclopropylmethylamino)-1-(4-((5R,7R)-7-hydroxy-5-methyl-6,7-dihydro-5H-cyclopenta[d]pyrimidin-4-yl)piperazin-1-yl)propan-1-one | m/z 470 [M + H]+ |
| 69 | 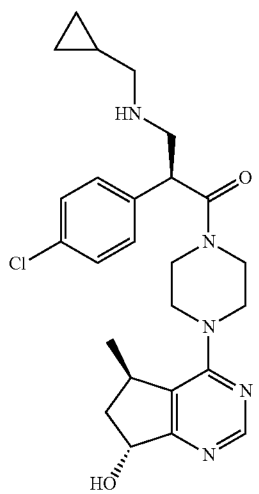 [SMILES: C[C@@H]1C[C@@H](O)c2ncnc(N3CCN(C(=O)[C@H](CNCC4CC4)c4ccc(Cl)cc4)CC3)c21] | (S)-2-(4-chlorophenyl)-3-(cyclopropylmethylamino)-1-(4-((5R,7R)-7-hydroxy-5-methyl-6,7-dihydro-5H-cyclopenta[d]pyrimidin-4-yl)piperazin-1-yl)propan-1-one | m/z 470 [M + H]+ |
| 70 | 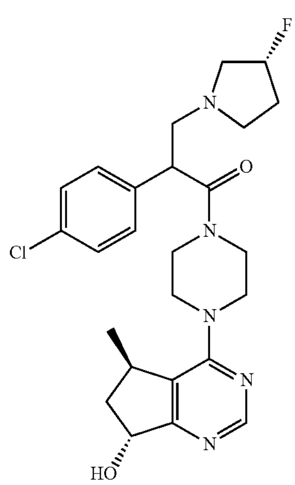 [SMILES: C[C@@H]1C[C@@H](O)c2ncnc(N3CCN(C(=O)C(CN4CC[C@@H](F)C4)c4ccc(Cl)cc4)CC3)c21] | 2-(4-chlorophenyl)-3-((R)-3-fluoropyrrolidin-1-yl)-1-(4-((5R,7R)-7-hydroxy-5-methyl-6,7-dihydro-5H-cyclopenta[d]pyrimidin-4-yl)piperazin-1-yl)propan-1-one | 488.2 |

TABLE 1-continued

| Example | Structure | Name | LCMS or ¹H NMR |
|---|---|---|---|
| 71 | 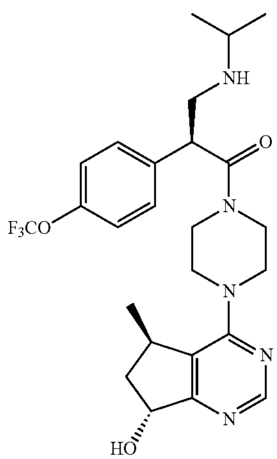 [SMILES: CC(C)NC[C@@H](C(=O)N1CCN(c2ncnc3c2[C@H](C)C[C@H]3O)CC1)c1ccc(OC(F)(F)F)cc1] | (S)-1-(4-((5R,7R)-7-hydroxy-5-methyl-6,7-dihydro-5H-cyclopenta[d]pyrimidin-4-yl)piperazin-1-yl)-3-(isopropylamino)-2-(4-(trifluoromethoxy)phenyl)propan-1-one | 508.3 |
| 72 | 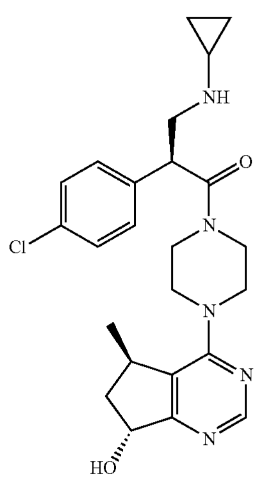 [SMILES: C[C@@H]1C[C@@H](O)c2ncnc(N3CCN(C(=O)[C@H](CNC4CC4)c4ccc(Cl)cc4)CC3)c21] | (S)-2-(4-chlorophenyl)-3-(cyclopropylamino)-1-(4-((5R,7R)-7-hydroxy-5-methyl-6,7-dihydro-5H-cyclopenta[d]pyrimidin-4-yl)piperazin-1-yl)propan-1-one | 456.2 |
| 73 | 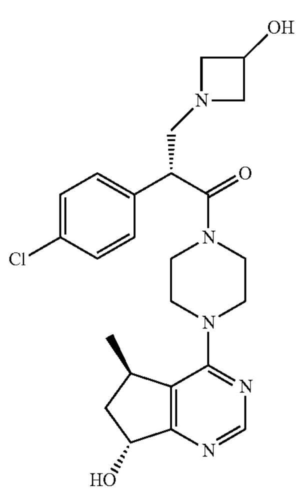 [SMILES: C[C@@H]1C[C@@H](O)c2ncnc(N3CCN(C(=O)[C@@H](CN4CC(O)C4)c4ccc(Cl)cc4)CC3)c21] | (R)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(3-hydroxyazetidin-1-yl)propan-1-one | 472.1 |

TABLE 1-continued

| Example | Structure | Name | LCMS or ¹H NMR |
|---|---|---|---|
| 74 | 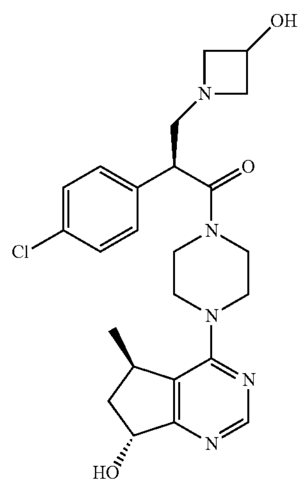 [SMILES: C[C@@H]1C[C@@H](O)c2ncnc(N3CCN(C(=O)[C@H](CN4CC(O)C4)c4ccc(Cl)cc4)CC3)c21] | (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(3-hydroxyazetidin-1-yl)propan-1-one | 472.1 |
| 75 | 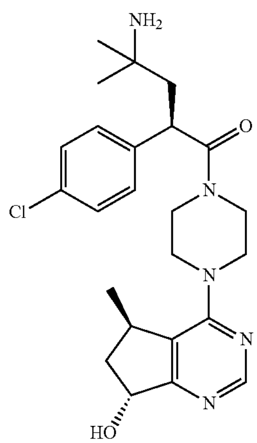 [SMILES: C[C@@H]1C[C@@H](O)c2ncnc(N3CCN(C(=O)[C@H](CC(C)(C)N)c4ccc(Cl)cc4)CC3)c21] | (R)-4-amino-2-(4-chlorophenyl)-1-(4-((5R,7R)-7-hydroxy-5-methyl-6,7-dihydro-5H-cyclopenta[d]pyrimidin-4-yl)piperazin-1-yl)-4-methylpentan-1-one | ¹H NMR (CD$_3$OD), 400 MHz, 8.51 (s, 1H), 7.40-7.33 (m, 4H), 5.17 (dd, J = 14.9, 7.04 Hz, 1H), 4.26 (dd, J = 9.4, 3.1 Hz, 1H), 4.06 (m, 1H), 3.85-3.60 (brm, 7H), 3.42 (m, 1H), 2.76 (dd, J = 14.9, 10.1 Hz, 1H), 2.2 (m, 2H), 1.81 (dd, J = 14.1, 3.1 Hz, 1H), 1.35 (s, 3H), 1.32 (s, 3H), 1.15 (d, J = 7.04 Hz, 3H). |
| 76 | 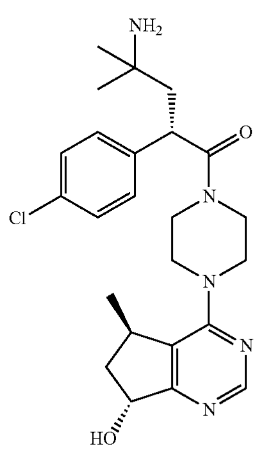 [SMILES: C[C@@H]1C[C@@H](O)c2ncnc(N3CCN(C(=O)[C@@H](CC(C)(C)N)c4ccc(Cl)cc4)CC3)c21] | (S)-4-amino-2-(4-chlorophenyl)-1-(4-((5R,7R)-7-hydroxy-5-methyl-6,7-dihydro-5H-cyclopenta[d]pyrimidin-4-yl)piperazin-1-yl)-4-methylpentan-1-one | ¹H NMR (CD$_3$OD), 400 MHz, 8.51 (s, 1H), 7.40-7.32 (m, 4H), 5.17 (dd, J = 14.9, 7.04 Hz, 1H), 4.25 (dd, J = 9.4, 3.1 Hz, 1H), 4.03-3.52 (bm, 8H), 3.30 (m, 1H), 2.75 (dd, J = 14.9, 9.4 Hz, 1H), 2.18 (m, 2H), 1.82 (dd, J = 14.1, 3.1 Hz, 1H), 1.35 (s, 3H), 1.32 (s, 3H), 1.18 (d, J = 6.3 Hz, 3H) |

TABLE 1-continued

| Example | Structure | Name | LCMS or ¹H NMR |
|---|---|---|---|
| 77 | 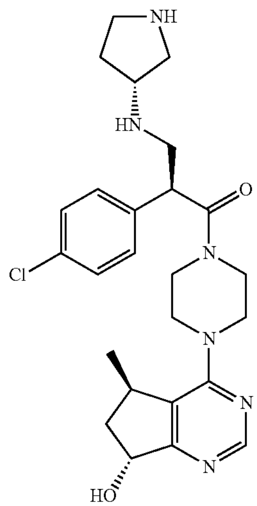 [SMILES: C[C@@H]1C[C@@H](O)c2ncnc(N3CCN(C(=O)[C@H](CN[C@@H]4CCNC4)c4ccc(Cl)cc4)CC3)c21] | (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-((R)-pyrrolidin-3-ylamino)propan-1-one | 485.2 |
| 78 | 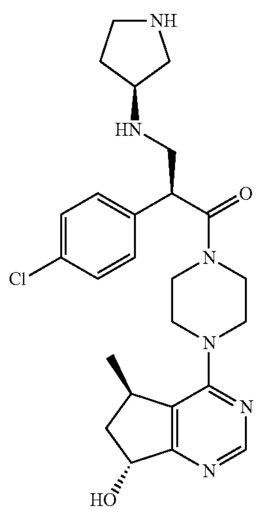 [SMILES: C[C@@H]1C[C@@H](O)c2ncnc(N3CCN(C(=O)[C@H](CN[C@H]4CCNC4)c4ccc(Cl)cc4)CC3)c21] | (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-((S)-pyrrolidin-3-yalmino)propan-1-one | 485.2 |
| 79 | 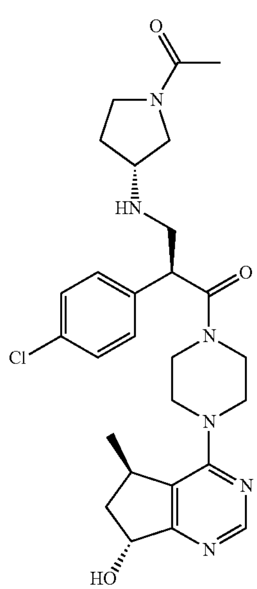 [SMILES: CC(=O)N1CC[C@@H](NC[C@@H](C(=O)N2CCN(c3ncnc4c3[C@H](C)C[C@H]4O)CC2)c2ccc(Cl)cc2)C1] | (S)-3-((R)-1-acetylpyrrolidin-3-ylamino)-2-(4-chlorophenyl)-1-(4-((5R,7R)-7-hydroxy-5-methyl-6,7-dihydro-5H-cyclopenta[d]pyrimidin-4-yl)piperazin-1-yl)propan-1-one | 527.2 |

TABLE 1-continued

| Example | Structure | Name | LCMS or ¹H NMR |
|---|---|---|---|
| 80 | 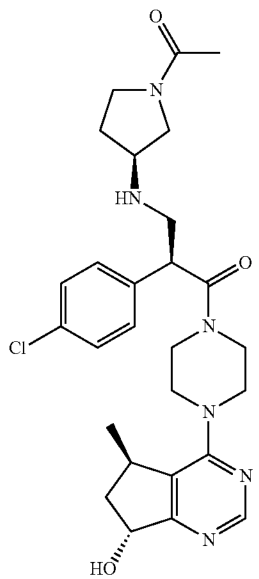 [SMILES: CC(=O)N1CC[C@H](NC[C@@H](C(=O)N2CCN(c3ncnc4c3[C@H](C)C[C@H]4O)CC2)c2ccc(Cl)cc2)C1] | (S)-3-((S)-1-acetylpyrrolidin-3-ylamino)-2-(4-chlorophenyl)-1-(4-((5R,7R)-7-hydroxy-5-methyl-6,7-dihydro-5H-cyclopenta[d]pyrimidin-4-yl)piperazin-1-yl)propan-1-one | 527.2 |
| 81 | 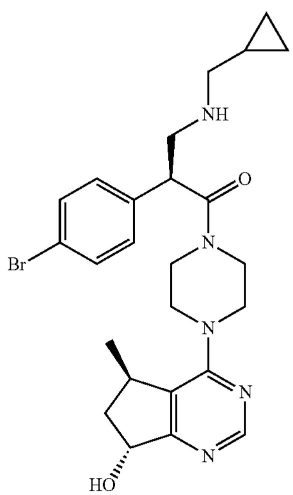 | (S)-2-(4-bromophenyl)-3-(cyclopropylmethylamino)-1-(4-((5R,7R)-7-hydroxy-5-methyl-6,7-dihydro-5H-cyclopenta[d]pyrimidin-4-yl)piperazin-1-yl)propan-1-one | 514.0 |
| 82 | 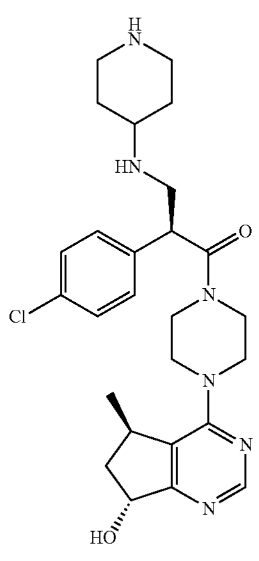 [SMILES: C[C@@H]1C[C@@H](O)c2ncnc(N3CCN(C(=O)[C@H](CNC4CCNCC4)c4ccc(Cl)cc4)CC3)c21] | (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(piperidin-4-ylamino)propan-1-one | m/z 499 [M + H]+ |

TABLE 1-continued

| Example | Structure | Name | LCMS or ¹H NMR |
|---|---|---|---|
| 83 | 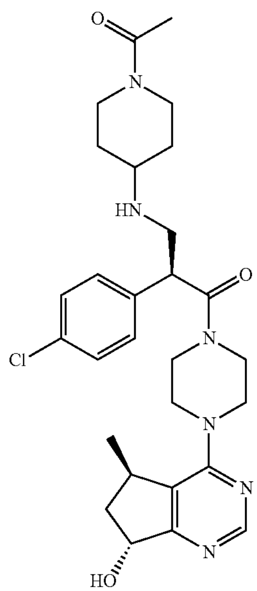 [SMILES: CC(=O)N1CCC(NC[C@@H](C(=O)N2CCN(c3ncnc4c3[C@H](C)C[C@H]4O)CC2)c2ccc(Cl)cc2)CC1] | (S)-3-(1-acetylpiperidin-4-ylamino)-2-(4-chlorophenyl)-1-(4-((5R,7R)-7-hydroxy-5-methyl-6,7-dihydro-5H-cyclopenta[d]pyrimidin-4-yl)piperazin-1-yl)propan-1-one | m/z 541 [M + H]+ |
| 84 | 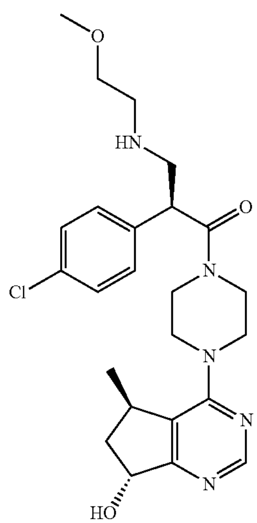 [SMILES: COCCNC[C@@H](C(=O)N1CCN(c2ncnc3c2[C@H](C)C[C@H]3O)CC1)c1ccc(Cl)cc1] | (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(2-methoxyethylamino)propan1-1-one | m/z 474 [M + H]+ |
| 85 | 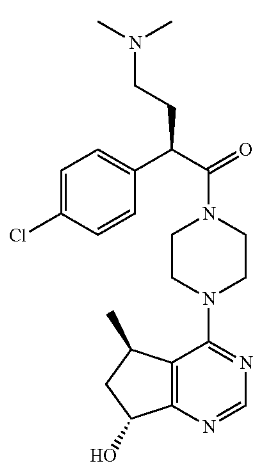 [SMILES: C[C@@H]1C[C@@H](O)c2ncnc(N3CCN(C(=O)[C@H](CCN(C)C)c4ccc(Cl)cc4)CC3)c21] | (R)-2-(4-chlorophenyl)-4-(dimethylamino)-1-(4-((5R,7R)-7-hydroxy-5-methyl-6,7-dihydro-5H-cyclopenta[d]pyrimidin-4-yl)piperazin-1-yl)butan-1-one | 458.1 |

TABLE 1-continued

| Example | Structure | Name | LCMS or ¹H NMR |
|---|---|---|---|
| 86 | 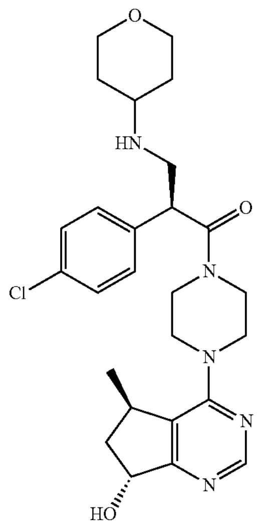 [SMILES: C[C@@H]1C[C@@H](O)c2ncnc(N3CCN(C(=O)[C@H](CNC4CCOCC4)c4ccc(Cl)cc4)CC3)c21] | (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(tetrahydro-2H-pyran-4-ylamino)propan-1-one | m/z 500 [M + H]+ |
| 87 | 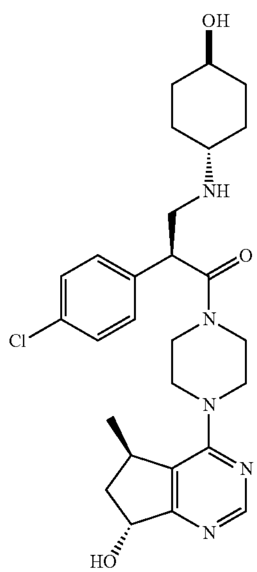 [SMILES: C[C@@H]1C[C@@H](O)c2ncnc(N3CCN(C(=O)[C@H](CN[C@H]4CC[C@H](O)CC4)c4ccc(Cl)cc4)CC3)c21] | (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-((1r,4S)-4-hydroxycyclohexylamino)propan-1-one | 514.3 |
| 88 | 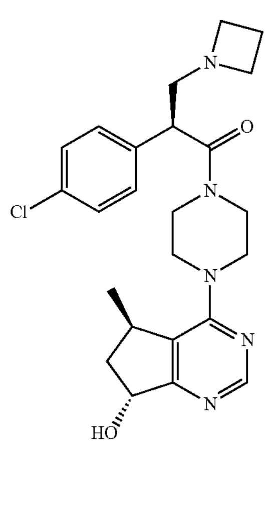 [SMILES: C[C@@H]1C[C@@H](O)c2ncnc(N3CCN(C(=O)[C@H](CN4CCC4)c4ccc(Cl)cc4)CC3)c21] | (S)-3-(azetidin-1-yl)-2-(4-chlorophenyl)-1-(4-((5R,7R)-7-hydroxy-5-methyl-6,7-dihydro-5H-cyclopenta[d]pyrimidin-4-yl)piperazin-1-yl)propan-1-one | 456.3 |

TABLE 1-continued

| Example | Structure | Name | LCMS or ¹H NMR |
|---|---|---|---|
| 89 | 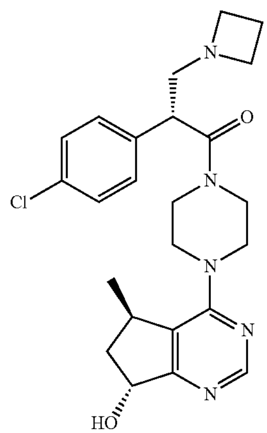 [SMILES: C[C@@H]1C[C@@H](O)c2ncnc(N3CCN(C(=O)[C@@H](CN4CCC4)c4ccc(Cl)cc4)CC3)c21] | (R)-3-(azetidin-1-yl)-2-(4-chlorophenyl)-1-(4-((5R,7R)-7-hydroxy-5-methyl-6,7-dihydro-5H-cyclopenta[d]pyrimidin-4-yl)piperazin-1-yl)propan-1-one | 456.3 |
| 90 | 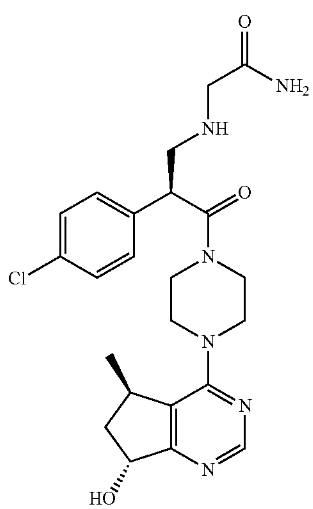 [SMILES: C[C@@H]1C[C@@H](O)c2ncnc(N3CCN(C(=O)[C@H](CNCC(N)=O)c4ccc(Cl)cc4)CC3)c21] | 2-((S)-2-(4-chlorophenyl)-3-(4-((5R,7R)-7-hydroxy-5-methyl-6,7-dihydro-5H-cyclopenta[d]pyrimidin-4-yl)piperazin-1-yl)-3-oxopropylamino)acetamide | 473.2 |
| 91 | 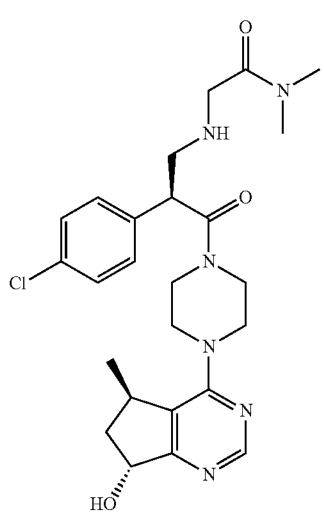 [SMILES: C[C@@H]1C[C@@H](O)c2ncnc(N3CCN(C(=O)[C@H](CNCC(=O)N(C)C)c4ccc(Cl)cc4)CC3)c21] | 2-((S)-2-(4-chlorophenyl)-3-(4-((5R,7R)-7-hydroxy-5-methyl-6,7-dihydro-5H-cyclopenta[d]pyrimidin-4-yl)piperazin-1-yl)-3-oxopropylamino)-N,N-dimethylacetamide | 501.3 |

TABLE 1-continued

| Example | Structure | Name | LCMS or ¹H NMR |
|---|---|---|---|
| 92 | 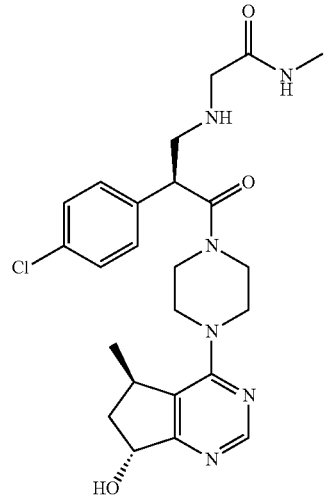 [SMILES: CNC(=O)CNC[C@@H](C(=O)N1CCN(c2ncnc3c2[C@H](C)C[C@H]3O)CC1)c1ccc(Cl)cc1] | 2-((S)-2-(4-chlorophenyl)-3-(4-((5R,7R)-7-hydroxy-5-methyl-6,7-dihydro-5H-cyclopenta[d]pyrimidin-4-yl)piperazin-1-yl)-3-oxopropylamino)-N-methylacetamide | 487.2 |
| 93 | 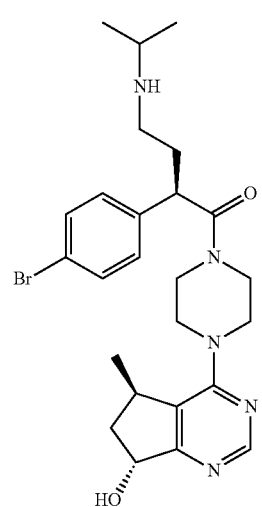 [SMILES: CC(C)NCC[C@@H](C(=O)N1CCN(c2ncnc3c2[C@H](C)C[C@H]3O)CC1)c1ccc(Br)cc1] | (R)-2-(4-bromophenyl)-1-(4-((5R,7R)-7-hydroxy-5-methyl-6,7-dihydro-5H-cyclopenta[d]pyrimidin-4-yl)piperazin-1-yl)-4-(isopropylamino)butan-1-one | 516.2/518.1 |
| 94 | 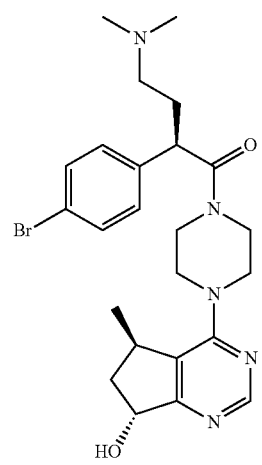 | (R)-2-(4-bromophenyl)-4-(dimethylamino)-1-(4-((5R,7R)-7-hydroxy-5-methyl-6,7-dihydro-5H-cyclopenta[d]pyrimidin-4-yl)piperazin-1-yl)butan-1-one | 502.1/504.1 |

TABLE 1-continued

| Example | Structure | Name | LCMS or ¹H NMR |
|---|---|---|---|
| 95 | 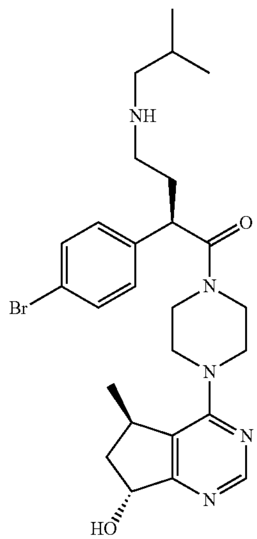 [SMILES: CC(C)CNCC[C@@H](C(=O)N1CCN(c2ncnc3c2[C@H](C)C[C@H]3O)CC1)c1ccc(Br)cc1] | (R)-2-(4-bromophenyl)-1-(4-((5R,7R)-7-hydroxy-5-methyl-6,7-dihydro-5H-cyclopenta[d]pyrimidin-4-yl)piperazin-1-yl)-4-(isobutylamino)butan-1-one | 530.2 |
| 96 | 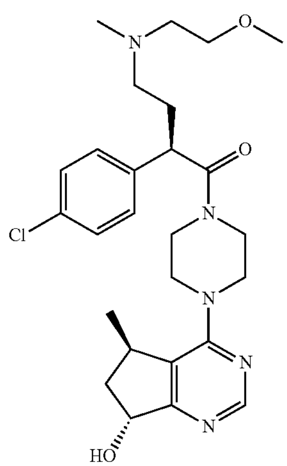 [SMILES: COCCN(C)CC[C@@H](C(=O)N1CCN(c2ncnc3c2[C@H](C)C[C@H]3O)CC1)c1ccc(Cl)cc1] | (R)-2-(4-chlorophenyl)-1-(4-((5R,7R)-7-hydroxy-5-methyl-6,7-dihydro-5H-cyclopenta[d]pyrimidin-4-yl)piperazin-1-yl)-4-((2-methoxyethyl)(methyl)amino)butan-1-one | 502.1 |
| 97 | 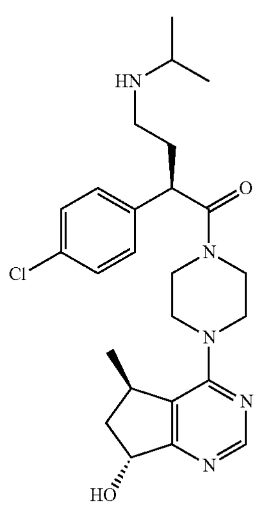 [SMILES: CC(C)NCC[C@@H](C(=O)N1CCN(c2ncnc3c2[C@H](C)C[C@H]3O)CC1)c1ccc(Cl)cc1] | (R)-2-(4-chlorophenyl)-1-(4-((5R,7R)-7-hydroxy-5-methyl-6,7-dihydro-5H-cyclopenta[d]pyrimidin-4-yl)piperazin-1-yl)-4-(isopropylamino)butan-1-one | 472.2 |

TABLE 1-continued

| Example | Structure | Name | LCMS or ¹H NMR |
|---|---|---|---|
| 98 | 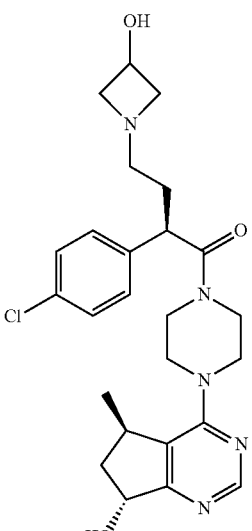 | (R)-2-(4-chlorophenyl)-1-(4-((5R,7R)-7-hydroxy-5-methyl-6,7-dihydro-5H-cyclopenta[d]pyrimidin-4-yl)piperazin-1-yl)-4-(3-hydroxyazetidin-1-yl)butan-1-one | 486.2 |
| 99 | 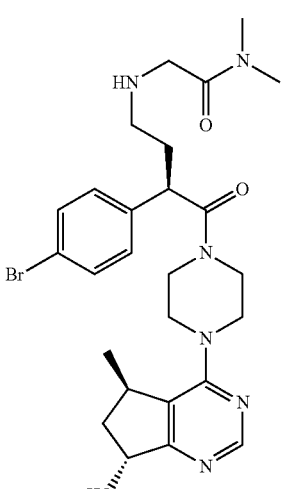 | 2-((R)-3-(4-bromophenyl)-4-(4-((5R,7R)-7-hydroxy-5-methyl-6,7-dihydro-5H-cyclopenta[d]pyrimidin-4-yl)piperazin-1-yl)-4-oxobutylamino)-N,N-dimethylacetamide | 559.1 |
| 100 | 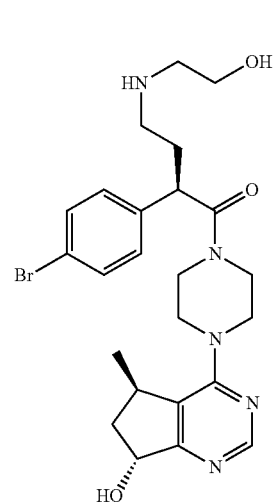 | (R)-2-(4-bromophenyl)-1-(4-((5R,7R)-7-hydroxy-5-methyl-6,7-dihydro-5H-cyclopenta[d]pyrimidin-4-yl)piperazin-1-yl)-4-(2-hydroxyethylamino)butan-1-one | 518.2/520.1 |

TABLE 1-continued

| Example | Structure | Name | LCMS or ¹H NMR |
|---|---|---|---|
| 101 | 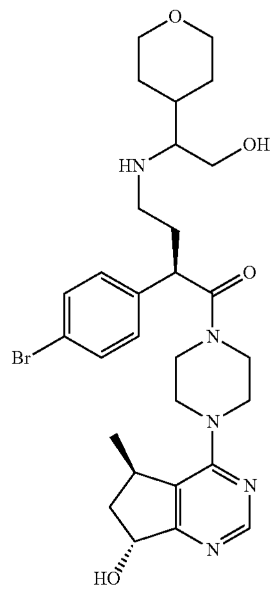 | (2R)-2-(4-bromophenyl)-4-(2-hydroxy-1-(tetrahydro-2H-pyran-4-yl)ethylamino)-1-(4-((5R,7R)-7-hydroxy-5-methyl-6,7-dihydro-5H-cyclopenta[d]pyrimidin-4-yl)piperazin-1-yl)butan-1-one | 604.2 |
| 102 | 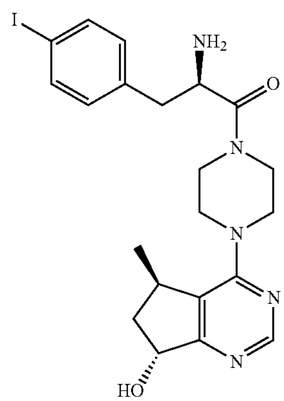 [SMILES: C[C@@H]1C[C@@H](O)c2ncnc(N3CCN(C(=O)[C@H](N)Cc4ccc(I)cc4)CC3)c21] | (R)-2-amino-1-(4-((5R,7R)-7-hydroxy-5-methyl-6,7-dihydro-5H-cyclopenta[d]pyrimidin-4-yl)piperazin-1-yl)-3-(4-iodophenyl)propan-1-one | 508.1 |
| 103 | 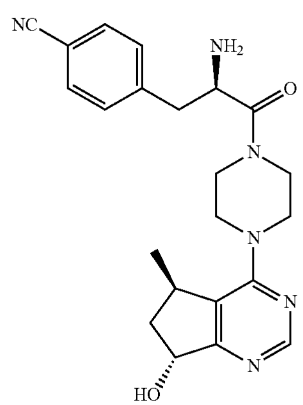 [SMILES: C[C@@H]1C[C@@H](O)c2ncnc(N3CCN(C(=O)[C@H](N)Cc4ccc(C#N)cc4)CC3)c21] | 4-((R)-2-amino-3-(4-((5R,7R)-7-hydroxy-5-methyl-6,7-dihydro-5H-cyclopenta[d]pyrimidin-4-yl)piperazin-1-yl)-3-oxopropyl)benzonitrile | 407.2 |

TABLE 1-continued

| Example | Structure | Name | LCMS or ¹H NMR |
|---|---|---|---|
| 104 | 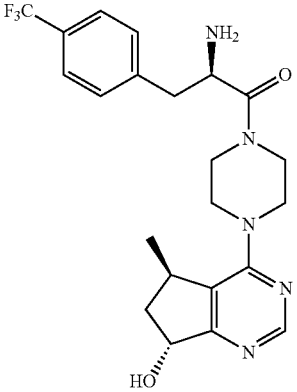 [SMILES: C[C@@H]1C[C@@H](O)c2ncnc(N3CCN(C(=O)[C@H](N)Cc4ccc(C(F)(F)F)cc4)CC3)c21] | (R)-2-amino-1-(4-((5R,7R)-7-hydroxy-5-methyl-6,7-dihydro-5H-cyclopenta[d]pyrimidin-4-yl)piperazin-1-yl)-3-(4-(trifluoromethyl)phenyl)propan-1-one | 450.2 |
| 105 | 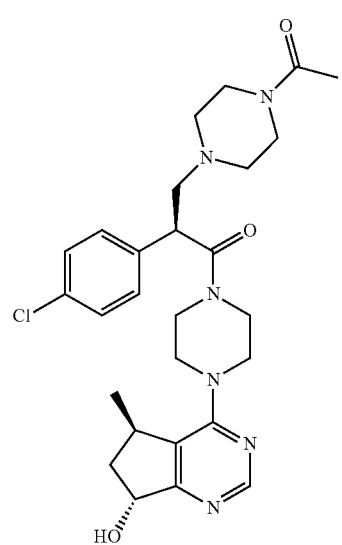 [SMILES: CC(=O)N1CCN(C[C@@H](C(=O)N2CCN(c3ncnc4c3[C@H](C)C[C@H]4O)CC2)c2ccc(Cl)cc2)CC1] | (S)-3-(4-acetylpiperazin-1-yl)-2-(4-chlorophenyl)-1-(4-((5R,7R)-7-hydroxy-5-methyl-6,7-dihydro-5H-cyclopenta[d]pyrimidin-4-yl)piperazin-1-yl)propan-1-one | 527.2 |
| 106 | 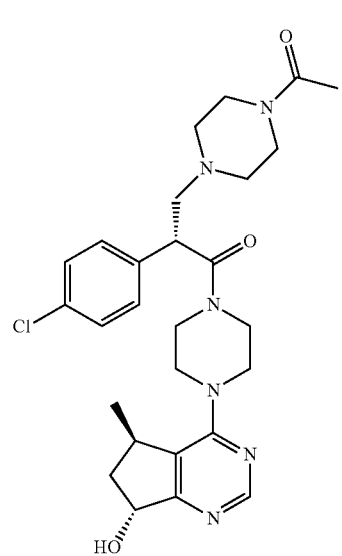 [SMILES: CC(=O)N1CCN(C[C@H](C(=O)N2CCN(c3ncnc4c3[C@H](C)C[C@H]4O)CC2)c2ccc(Cl)cc2)CC1] | (R)-3-(4-acetylpiperazin-1-yl)-2-(4-chlorophenyl)-1-(4-((5R,7R)-7-hydroxy-5-methyl-6,7-dihydro-5H-cyclopenta[d]pyrimidin-4-yl)piperazin-1-yl)propan-1-one | 527.2 |

TABLE 1-continued

| Example | Structure | Name | LCMS or ¹H NMR |
|---|---|---|---|
| 107 | 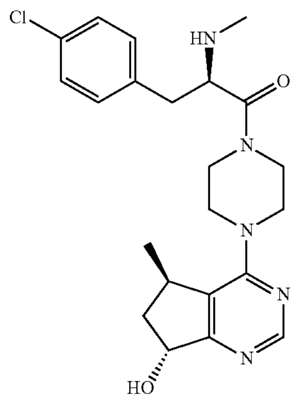 [SMILES: CN[C@H](Cc1ccc(Cl)cc1)C(=O)N1CCN(c2ncnc3c2[C@H](C)C[C@H]3O)CC1] | (R)-3-(4-chlorophenyl)-1-(4-((5R,7R)-7-hydroxy-5-methyl-6,7-dihydro-5H-cyclopenta[d]pyrimidin-4-yl)piperazin-1-yl)-2-(methylamino)propan-1-one | 430.2 |
| 108 | 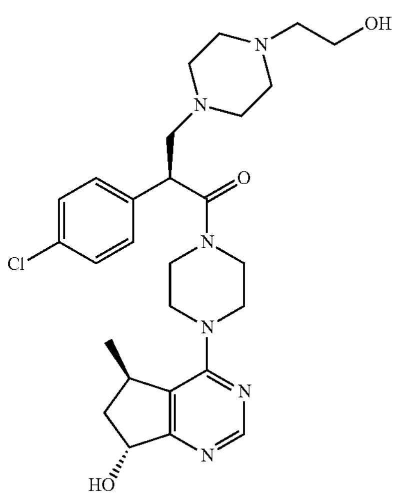 [SMILES: C[C@@H]1C[C@@H](O)c2ncnc(N3CCN(C(=O)[C@H](CN4CCN(CCO)CC4)c4ccc(Cl)cc4)CC3)c21] | (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(4-(2-hydroxyethyl)piperazin-1-yl)propan-1-one | 529.4 |
| 109 | 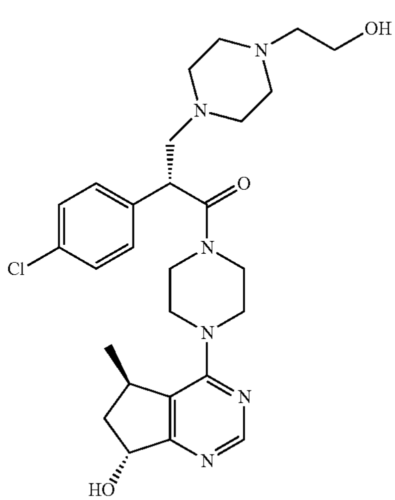 [SMILES: C[C@@H]1C[C@@H](O)c2ncnc(N3CCN(C(=O)[C@@H](CN4CCN(CCO)CC4)c4ccc(Cl)cc4)CC3)c21] | (R)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(4-(2-hydroxyethyl)piperazin-1-yl)propan-1-one | 529.4 |

TABLE 1-continued

| Example | Structure | Name | LCMS or ¹H NMR |
|---|---|---|---|
| 110 | 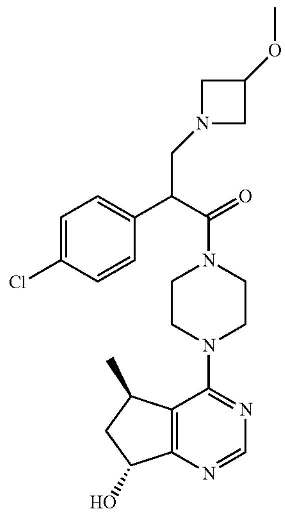 [SMILES: COC1CN(CC(C(=O)N2CCN(c3ncnc4c3[C@H](C)C[C@H]4O)CC2)c2ccc(Cl)cc2)C1] | 2-(4-chlorophenyl)-1-(4-((5R,7R)-7-hydroxy-5-methyl-6,7-dihydro-5H-cyclopenta[d]pyrimidin-4-yl)piperazin-1-yl)-3-(3-methoxyazetidin-1-yl)propan-1-one | 486.2 |
| 111 | 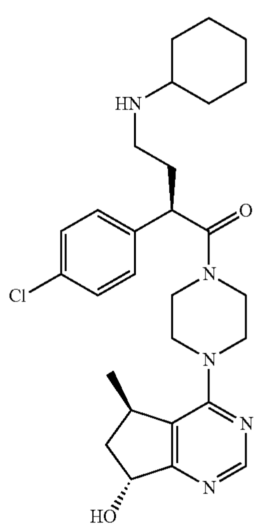 [SMILES: C[C@@H]1C[C@@H](O)c2ncnc(N3CCN(C(=O)[C@H](CCNC4CCCCC4)c4ccc(Cl)cc4)CC3)c21] | (R)-2-(4-chlorophenyl)-4-(cyclohexylamino)-1-(4-((5R,7R)-7-hydroxy-5-methyl-6,7-dihydro-5H-cyclopenta[d]pyrimidin-4-yl)piperazin-1-yl)butan-1-one | 512.3 |
| 112 | 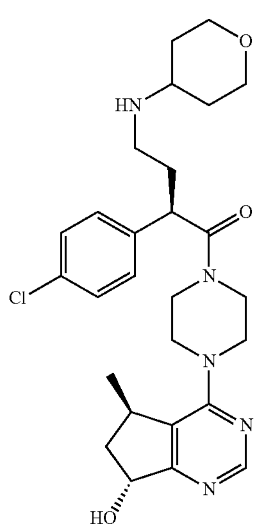 [SMILES: C[C@@H]1C[C@@H](O)c2ncnc(N3CCN(C(=O)[C@H](CCNC4CCOCC4)c4ccc(Cl)cc4)CC3)c21] | (R)-2-(4-chlorophenyl)-1-(4-((5R,7R)-7-hydroxy-5-methyl-6,7-dihydro-5H-cyclopenta[d]pyrimidin-4-yl)piperazin-1-yl)-4-(tetrahydro-2H-pyran-4-ylamino)butan-1-one | 514.2 |

TABLE 1-continued

| Example | Structure | Name | LCMS or ¹H NMR |
|---|---|---|---|
| 113 | 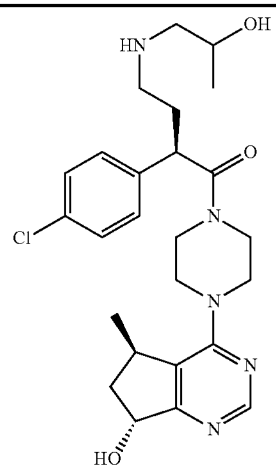 | (2R)-2-(4-chlorophenyl)-1-(4-((5R,7R)-7-hydroxy-5-methyl-6,7-dihydro-5H-cyclopenta[d]pyrimidin-4-yl)piperazin-1-yl)-4-(2-hydroxypropylamino)butan-1-one | 488.2 |
| 114 | 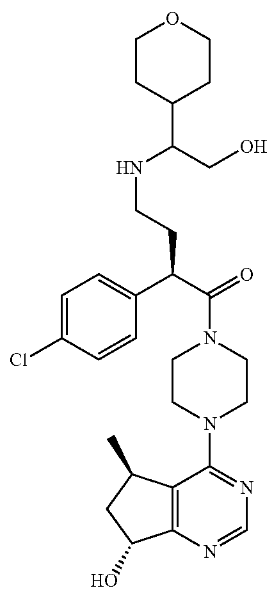 [SMILES: C[C@@H]1C[C@@H](O)c2ncnc(N3CCN(C(=O)[C@H](CCNC(CO)C4CCOCC4)c4ccc(Cl)cc4)CC3)c21] | (2R)-2-(4-chlorophenyl)-4-(2-hydroxy-1-(tetrahydro-2H-pyran-4-yl)ethylamino)-1-(4-((5R,7R)-7-hydroxy-5-methyl-6,7-dihydro-5H-cyclopenta[d]pyrimidin-4-yl)piperazin-1-yl)butan-1-one | 558.2 |
| 115 | 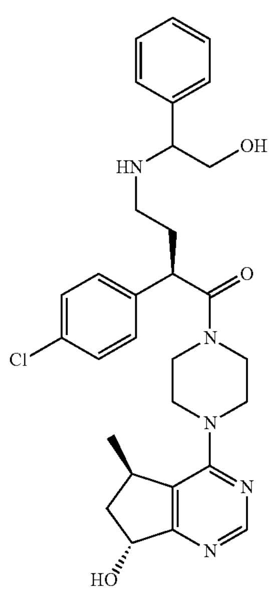 [SMILES: C[C@@H]1C[C@@H](O)c2ncnc(N3CCN(C(=O)[C@H](CCNC(CO)c4ccccc4)c4ccc(Cl)cc4)CC3)c21] | (2R)-2-(4-chlorophenyl)-4-(2-hydroxy-1-phenylethylamino)-1-(4-((5R,7R)-7-hydroxy-5-methyl-6,7-dihydro-5H-cyclopenta[d]pyrimidin-4-yl)piperazin-1-yl)butan-1-one | 550.2 |

TABLE 1-continued

| Example | Structure | Name | LCMS or ¹H NMR |
|---|---|---|---|
| 116 | 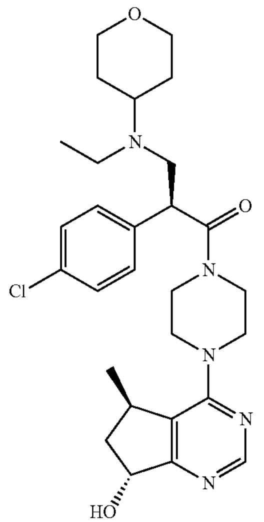 [SMILES: CCN(C[C@@H](C(=O)N1CCN(c2ncnc3c2[C@H](C)C[C@H]3O)CC1)c1ccc(Cl)cc1)C1CCOCC1] | (S)-2-(4-chlorophenyl)-3-(ethyl(tetrahydro-2H-pyran-4-yl)amino)-1-(4-((5R,7R)-7-hydroxy-5-methyl-6,7-dihydro-5H-cyclopenta[d]pyrimidin-4-yl)piperazin-1-yl)propan-1-one | m/z 528 [M + H]+ |
| 117 | 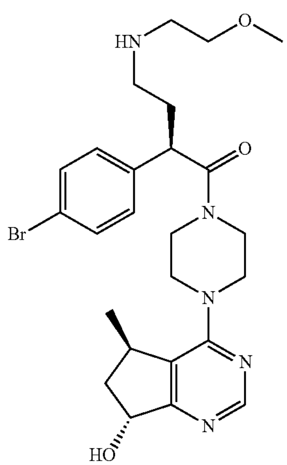 | (R)-2-(4-bromophenyl)-1-(4-((5R,7R)-7-hydroxy-5-methyl-6,7-dihydro-5H-cyclopenta[d]pyrimidin-4-yl)piperazin-1-yl)-4-(2-methoxyethylamino)butan-1-one | 534.1 |
| 118 | 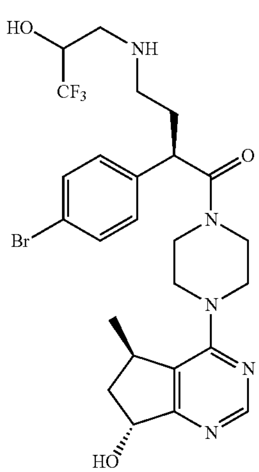 [SMILES: C[C@@H]1C[C@@H](O)c2ncnc(N3CCN(C(=O)[C@H](CCNCC(O)C(F)(F)F)c4ccc(Br)cc4)CC3)c21] | (2R)-2-(4-bromophenyl)-1-(4-((5R,7R)-7-hydroxy-5-methyl-6,7-dihydro-5H-cyclopenta[d]pyrimidin-4-yl)piperazin-1-yl)-4-(3,3,3-trifluoro-2-hydroxypropylamino)butan-1-one | 586.2 |

TABLE 1-continued

| Example | Structure | Name | LCMS or ¹H NMR |
|---|---|---|---|
| 119 | 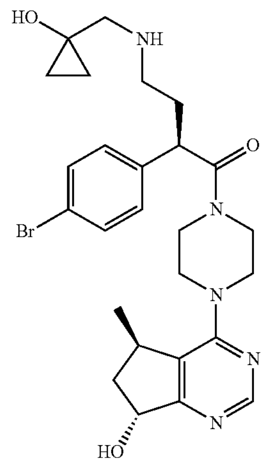 [SMILES: C[C@@H]1C[C@@H](O)c2ncnc(N3CCN(C(=O)[C@H](CCNCC4(O)CC4)c4ccc(Br)cc4)CC3)c21] | (R)-2-(4-bromophenyl)-1-(4-((5R,7R)-7-hydroxy-5-methyl-6,7-dihydro-5H-cyclopenta[d]pyrimidin-4-yl)piperazin-1-yl)-4-((1-hydroxycyclopropyl)methylamino)butan-1-one | 544.2/546.2 |
| 120 | 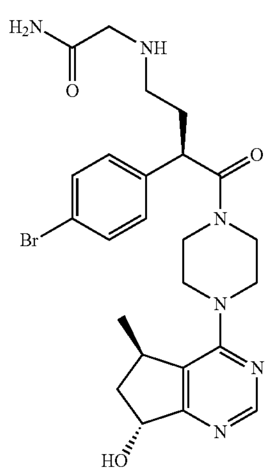 [SMILES: C[C@@H]1C[C@@H](O)c2ncnc(N3CCN(C(=O)[C@H](CCNCC(N)=O)c4ccc(Br)cc4)CC3)c21] | 2-((R)-3-(4-bromophenyl)-4-(4-((5R,7R)-7-hydroxy-5-methyl-6,7-dihydro-5H-cyclopenta[d]pyrimidin-4-yl)piperazin-1-yl)-4-oxobutylamino)acetamide | 531.1/533.1 |
| 121 | 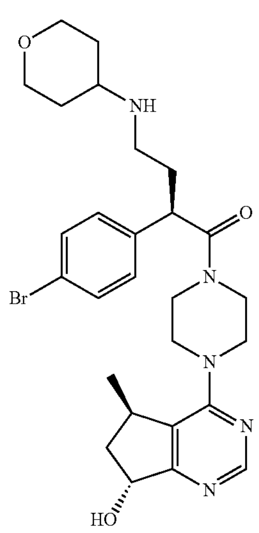 [SMILES: C[C@@H]1C[C@@H](O)c2ncnc(N3CCN(C(=O)[C@H](CCNC4CCOCC4)c4ccc(Br)cc4)CC3)c21] | (R)-2-(4-bromophenyl)-1-(4-((5R,7R)-7-hydroxy-5-methyl-6,7-dihydro-5H-cyclopenta[d]pyrimidin-4-yl)piperazin-1-yl)-4-(tetrahydro-2H-pyran-4-ylamino)butan-1-one | 558.2 |

| Example | Structure | Name | LCMS or ¹H NMR |
| --- | --- | --- | --- |
| 122 | 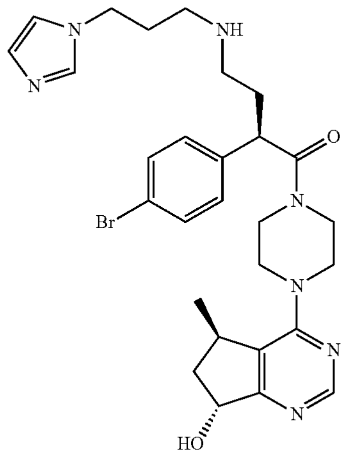 [SMILES: C[C@@H]1C[C@@H](O)c2ncnc(N3CCN(C(=O)[C@H](CCNCCCn4ccnc4)c4ccc(Br)cc4)CC3)c21] | (R)-4-(3-(1H-imidazol-1-yl)propylamino)-2-(4-bromophenyl)-1-(4-((5R,7R)-7-hydroxy-5-methyl-6,7-dihydro-5H-cyclopenta[d]pyrimidin-4-yl)piperazin-1-yl)butan-1-one | 584.2 |
| 123 | 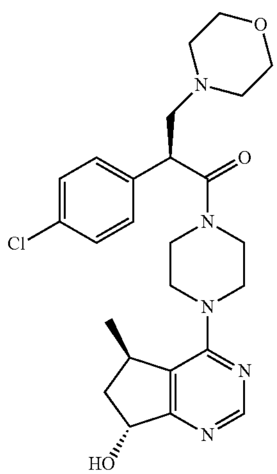 [SMILES: C[C@@H]1C[C@@H](O)c2ncnc(N3CCN(C(=O)[C@H](CN4CCOCC4)c4ccc(Cl)cc4)CC3)c21] | (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-morpholinopropan-1-one | 486.3 |
| 124 | 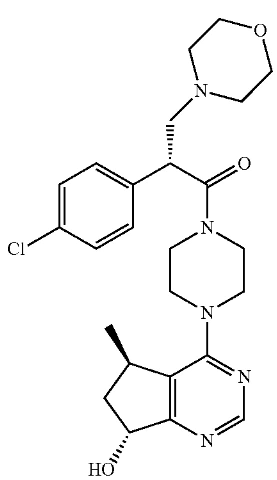 [SMILES: C[C@@H]1C[C@@H](O)c2ncnc(N3CCN(C(=O)[C@@H](CN4CCOCC4)c4ccc(Cl)cc4)CC3)c21] | (R)-2-(4-chlorophenyl)-1-(4-((5R,7R)-7-hydroxy-5-methyl-6,7-dihydro-5H-cyclopenta[d]pyrimidin-4-yl)piperazin-1-yl)-3-morpholinopropan-1-one | 486.3 |

TABLE 1-continued

| Example | Structure | Name | LCMS or ¹H NMR |
|---|---|---|---|
| 125 | 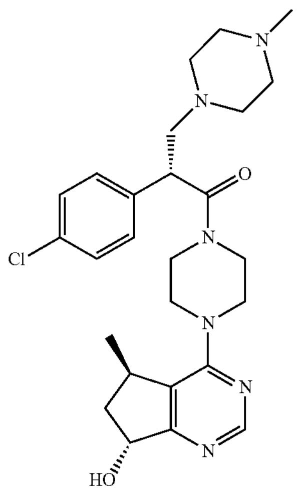 [SMILES: C[C@@H]1C[C@@H](O)c2ncnc(N3CCN(C(=O)[C@@H](CN4CCN(C)CC4)c4ccc(Cl)cc4)CC3)c21] | (R)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(4-methylpiperazin-1-yl)propan-1-one | 499.4 |
| 126 | 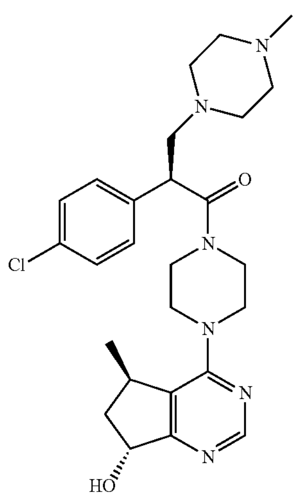 [SMILES: C[C@@H]1C[C@@H](O)c2ncnc(N3CCN(C(=O)[C@H](CN4CCN(C)CC4)c4ccc(Cl)cc4)CC3)c21] | (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(4-methylpiperazin-1-yl)propan-1-one | 499.4 |
| 127 | 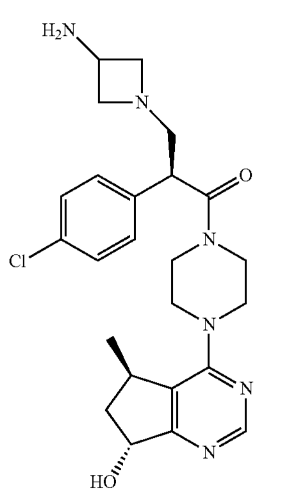 [SMILES: C[C@@H]1C[C@@H](O)c2ncnc(N3CCN(C(=O)[C@H](CN4CC(N)C4)c4ccc(Cl)cc4)CC3)c21] | (S)-3-(3-aminoazetidin-1-yl)-2-(4-chlorophenyl)-1-(4-((5R,7R)-7-hydroxy-5-methyl-6,7-dihydro-5H-cyclopenta[d]pyrimidin-4-yl)piperazin-1-yl)propan-1-one | 471.2 |

TABLE 1-continued

| Example | Structure | Name | LCMS or ¹H NMR |
|---|---|---|---|
| 128 | 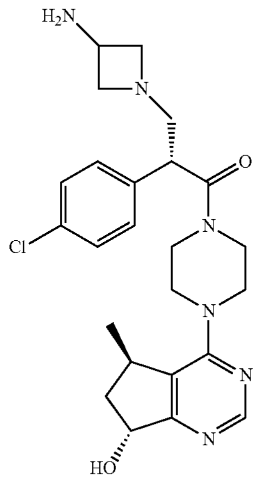 [SMILES: C[C@@H]1C[C@@H](O)c2ncnc(N3CCN(C(=O)[C@@H](CN4CC(N)C4)c4ccc(Cl)cc4)CC3)c21] | (R)-3-(3-aminoazetidin-1-yl)-2-(4-chlorophenyl)-1-(4-((5R,7R)-7-hydroxy-5-methyl-6,7-dihydro-5H-cyclopenta[d]pyrimidin-4-yl)piperazin-1-yl)propan-1-one | 471.2 |
| 129 | 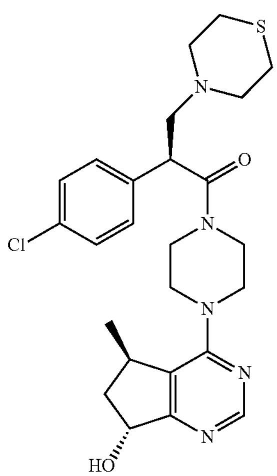 [SMILES: C[C@@H]1C[C@@H](O)c2ncnc(N3CCN(C(=O)[C@H](CN4CCSCC4)c4ccc(Cl)cc4)CC3)c21] | (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-thiomorpholinopropan-1-one | 502.2 |
| 130 | 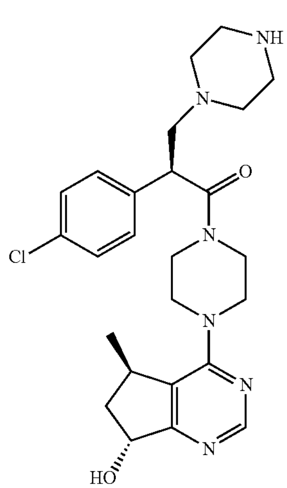 [SMILES: C[C@@H]1C[C@@H](O)c2ncnc(N3CCN(C(=O)[C@H](CN4CCNCC4)c4ccc(Cl)cc4)CC3)c21] | (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(piperazin-1-yl)propan-1-one | 485.3 |

TABLE 1-continued

| Example | Name | LCMS or ¹H NMR |
|---------|------|----------------|
| 131 | (R)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(piperazin-1-yl)propan-1-one | 485.3 |
| 132 | (R)-2-(4-chlorophenyl)-1-(4-((5R,7R)-7-hydroxy-5-methyl-6,7-dihydro-5H-cyclopenta[d]pyrimidin-4-yl)piperazin-1-yl)-3-thiomorpholinopropan-1-one | 502.2 |
| 133 | (R)-2-(4-chlorophenyl)-3-(4-fluoropiperidin-1-yl)-1-(4-((5R,7R)-7-hydroxy-5-methyl-6,7-dihydro-5H-cyclopenta[d]pyrimidin-4-yl)piperazin-1-yl)propan-1-one | 502.2 |

TABLE 1-continued

| Example | Structure | Name | LCMS or ¹H NMR |
|---|---|---|---|
| 134 | 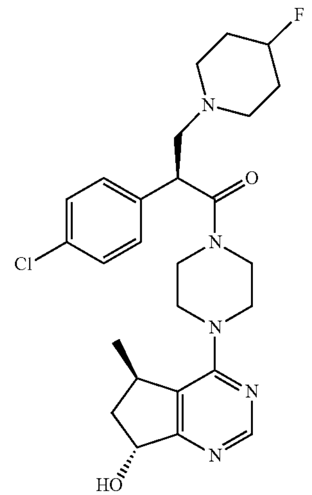 [SMILES: C[C@@H]1C[C@@H](O)c2ncnc(N3CCN(C(=O)[C@H](CN4CCC(F)CC4)c4ccc(Cl)cc4)CC3)c21] | (S)-2-(4-chlorophenyl)-3-(4-fluoropiperidin-1-yl)-1-(4-((5R,7R)-7-hydroxy-5-methyl-6,7-dihydro-5H-cyclopenta[d]pyrimidin-4-yl)piperazin-1-yl)propan-1-one | 502.2 |
| 135 | 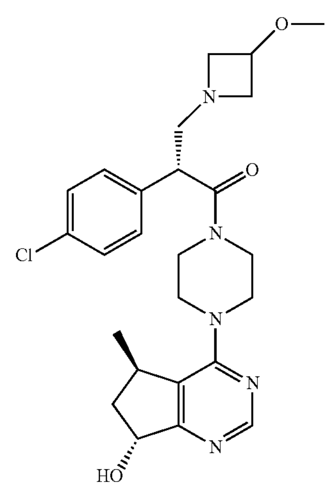 [SMILES: COC1CN(C[C@H](C(=O)N2CCN(c3ncnc4c3[C@H](C)C[C@H]4O)CC2)c2ccc(Cl)cc2)C1] | (R)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(3-methoxyazetidin-1-yl)propan-1-one | 486.2 |
| 136 | 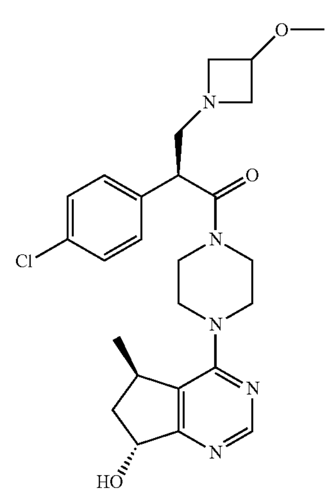 [SMILES: COC1CN(C[C@@H](C(=O)N2CCN(c3ncnc4c3[C@H](C)C[C@H]4O)CC2)c2ccc(Cl)cc2)C1] | (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(3-methoxyazetidin-1-yl)propan-1-one | 486.2 |

| Example | Structure | Name | LCMS or ¹H NMR |
|---|---|---|---|
| 137 | 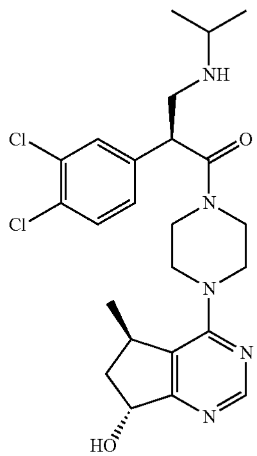 [SMILES: CC(C)NC[C@@H](C(=O)N1CCN(c2ncnc3c2[C@H](C)C[C@H]3O)CC1)c1ccc(Cl)c(Cl)c1] | (S)-2-(3,4-dichlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one | 492.2 |
| 138 | 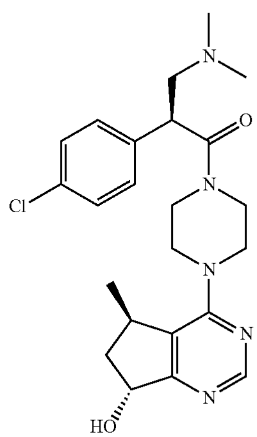 [SMILES: C[C@@H]1C[C@@H](O)c2ncnc(N3CCN(C(=O)[C@H](CN(C)C)c4ccc(Cl)cc4)CC3)c21] | (S)-2-(4-chlorophenyl)-3-(dimethylamino)-1-(4-((5R,7R)-7-hydroxy-5-methyl-6,7-dihydro-5H-cyclopenta[d]pyrimidin-4-yl)piperazin-1-yl)propan-1-one | 444.1 |
| 139 | 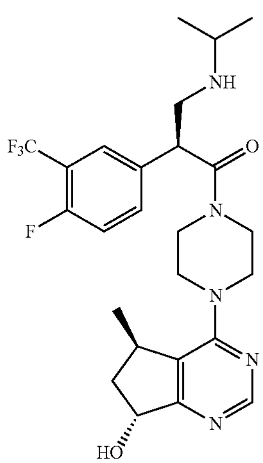 [SMILES: CC(C)NC[C@@H](C(=O)N1CCN(c2ncnc3c2[C@H](C)C[C@H]3O)CC1)c1ccc(F)c(C(F)(F)F)c1] | (S)-2-(4-fluoro-3-(trifluoromethy)phenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one | 510.2 |

TABLE 1-continued

| Example | Structure | Name | LCMS or $^1$H NMR |
|---|---|---|---|
| 140 | 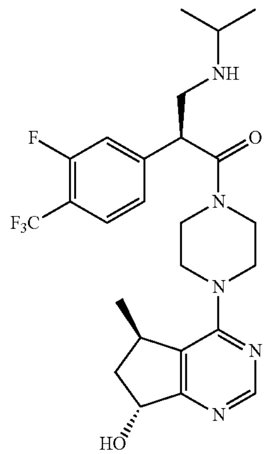 [SMILES: CC(C)NC[C@@H](C(=O)N1CCN(c2ncnc3c2[C@H](C)C[C@H]3O)CC1)c1ccc(C(F)(F)F)c(F)c1] | (S)-2-(3-fluoro-4-(trifluoromethyl)phenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one | 510.4 |
| 141 | 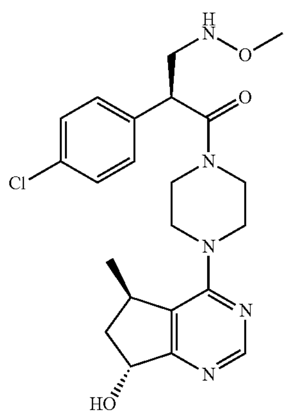 [SMILES: CONC[C@@H](C(=O)N1CCN(c2ncnc3c2[C@H](C)C[C@H]3O)CC1)c1ccc(Cl)cc1] | (S)-2-(4-chlorophenyl)-1-(4-((5R,7R)-7-hydroxy-5-methyl-6,7-dihydro-5H-cyclopenta[d]pyrimidin-4-yl)piperaizn-1-yl)-3-(methoxyamino)propan-1-one | 446.2 |
| 142 | 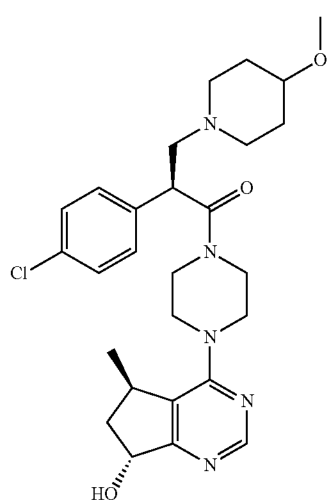 [SMILES: COC1CCN(C[C@@H](C(=O)N2CCN(c3ncnc4c3[C@H](C)C[C@H]4O)CC2)c2ccc(Cl)cc2)CC1] | (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(4-methoxypiperidin-1-yl)propan-1-one | 514.3 |

TABLE 1-continued

| Example | Structure | Name | LCMS or ¹H NMR |
|---|---|---|---|
| 143 | 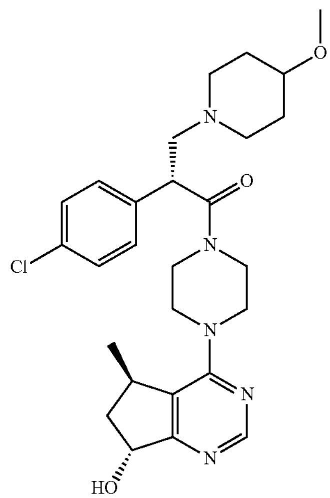 [SMILES: COC1CCN(C[C@H](C(=O)N2CCN(c3ncnc4c3[C@H](C)C[C@H]4O)CC2)c2ccc(Cl)cc2)CC1] | (R)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(4-methoxypiperidin-1-yl)propan-1-one | 514.3 |
| 144 | 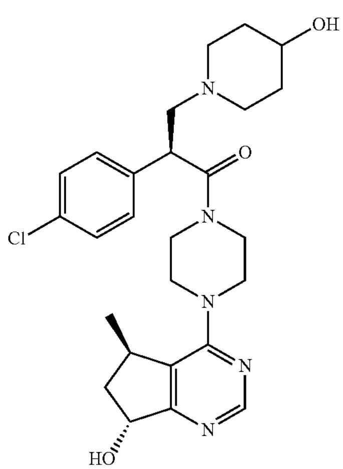 [SMILES: C[C@@H]1C[C@@H](O)c2ncnc(N3CCN(C(=O)[C@H](CN4CCC(O)CC4)c4ccc(Cl)cc4)CC3)c21] | (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(4-hydroxypiperidin-1-yl)propan-1-one | 500.3 |
| 145 | 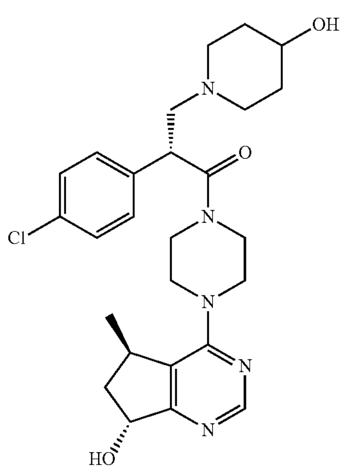 [SMILES: C[C@@H]1C[C@@H](O)c2ncnc(N3CCN(C(=O)[C@@H](CN4CCC(O)CC4)c4ccc(Cl)cc4)CC3)c21] | (R)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(4-hydroxypiperidin-1-yl)propan-1-one | 500.3 |

TABLE 1-continued

| Example | Structure | Name | LCMS or ¹H NMR |
|---|---|---|---|
| 146 | 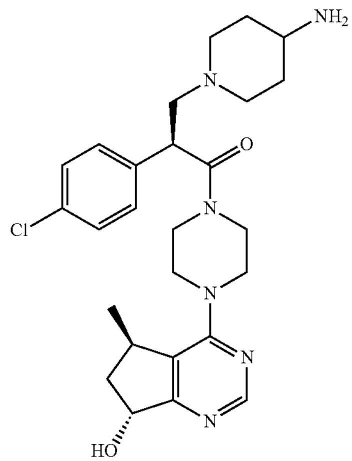 [SMILES: C[C@@H]1C[C@@H](O)c2ncnc(N3CCN(C(=O)[C@H](CN4CCC(N)CC4)c4ccc(Cl)cc4)CC3)c21] | (S)-3-(4-aminopiperidin-1-yl)-2-(4-chlorophenyl)-1-(4-((5R,7R)-7-hydroxy-5-methyl-6,7-dihydro-5H-cyclopenta[d]pyrimidin-4-yl)piperazin-1-yl)propan-1-one | 499.3 |
| 147 | 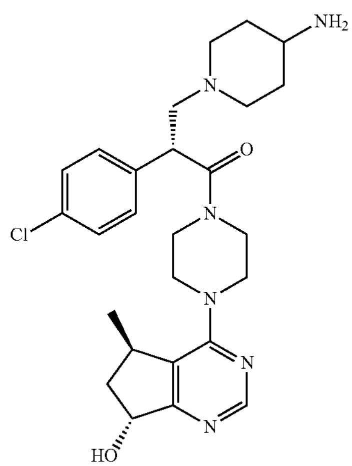 [SMILES: C[C@@H]1C[C@@H](O)c2ncnc(N3CCN(C(=O)[C@@H](CN4CCC(N)CC4)c4ccc(Cl)cc4)CC3)c21] | (R)-3-(4-aminopiperidin-1-yl)-2-(4-chlorophenyl)-1-(4-((5R,7R)-7-hydroxy-5-methyl-6,7-dihydro-5H-cyclopenta[d]pyrimidin-4-yl)piperazin-1-yl)propan-1-one | 499.3 |
| 148 | 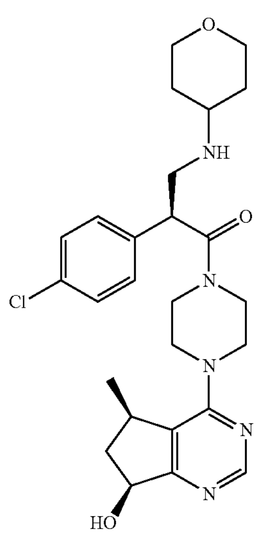 [SMILES: C[C@@H]1C[C@H](O)c2ncnc(N3CCN(C(=O)[C@H](CNC4CCOCC4)c4ccc(Cl)cc4)CC3)c21] | (S)-2-(4-chlorophenyl)-1-(4-((5R,7S)-7-hydroxy-5-methyl-6,7-dihydro-5H-cyclopenta[d]pyrimidin-4-yl)piperazin-1-yl)-3-(tetrahydro-2H-pyran-4-ylamino)propan-1-one | 500.2 |

TABLE 1-continued

| Example | Structure | Name | LCMS or ¹H NMR |
|---|---|---|---|
| 149 | 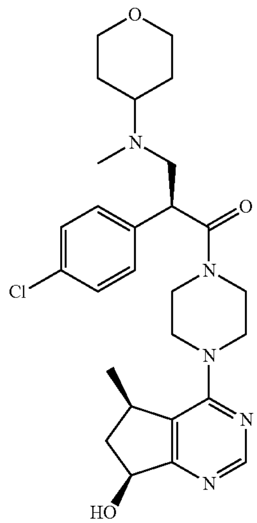 [SMILES: C[C@@H]1C[C@H](O)c2ncnc(N3CCN(C(=O)[C@H](CN(C)C4CCOCC4)c4ccc(Cl)cc4)CC3)c21] | (S)-2-(4-chlorophenyl)-1-(4-((5R,7S)-7-hydroxy-5-methyl-6,7-dihydro-5H-cyclopenta[d]pyrimidin-4-yl)piperazin-1-yl)-3-(methyl(tetrahydro-2H-pyran-4-yl)amino)propan-1-one | m/z 514 [M + H]+ |
| 150 | 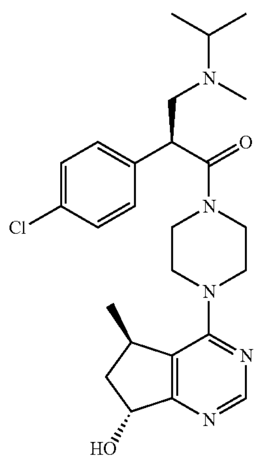 [SMILES: CC(C)N(C)C[C@@H](C(=O)N1CCN(c2ncnc3c2[C@H](C)C[C@H]3O)CC1)c1ccc(Cl)cc1] | (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropyl(methyl)amino)propan-1-one | 472.3 |
| 151 | 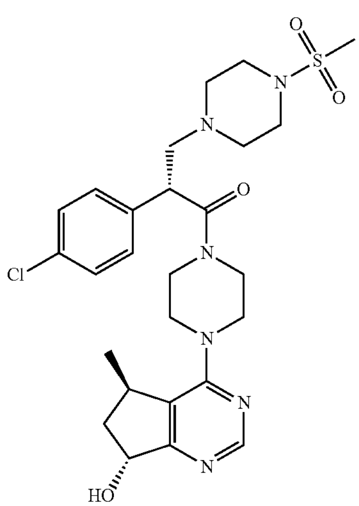 [SMILES: C[C@@H]1C[C@@H](O)c2ncnc(N3CCN(C(=O)[C@@H](CN4CCN(S(C)(=O)=O)CC4)c4ccc(Cl)cc4)CC3)c21] | (R)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(4-(methylsulfonyl)piperazin-1-yl)propan-1-one | 563.2 |

TABLE 1-continued

| Example | Structure | Name | LCMS or ¹H NMR |
|---|---|---|---|
| 152 | 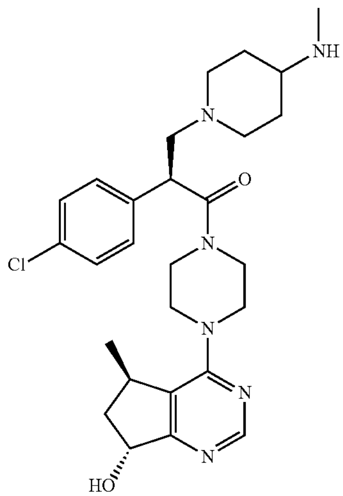 [SMILES: CNC1CCN(C[C@@H](C(=O)N2CCN(c3ncnc4c3[C@H](C)C[C@H]4O)CC2)c2ccc(Cl)cc2)CC1] | (S)-2-(4-chlorophenyl)-1-(4-((5R,7R)-7-hydroyx-5-methyl-6,7-dihydro-5H-cyclopenta[d]pyrimidin-4-yl)piperazin-1-yl)-3-(4-(methylamino)piperidin-1-yl)propan-1-one | 513.3 |
| 153 | 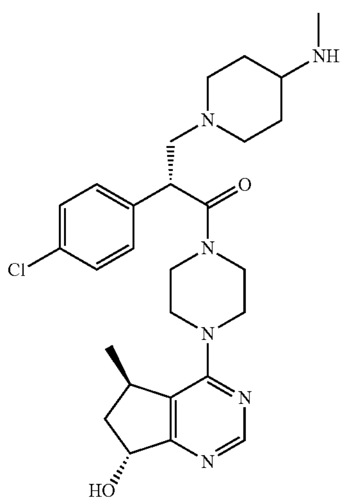 [SMILES: CNC1CCN(C[C@H](C(=O)N2CCN(c3ncnc4c3[C@H](C)C[C@H]4O)CC2)c2ccc(Cl)cc2)CC1] | (R)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(4-(methylamino)piperidin-1-yl)propan-1-one | 513.3 |
| 154 | 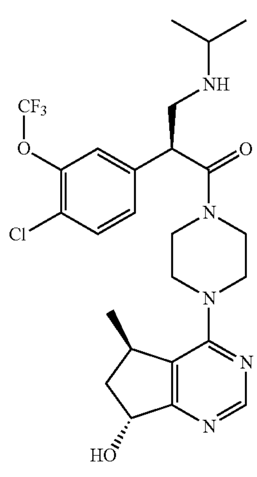 [SMILES: CC(C)NC[C@@H](C(=O)N1CCN(c2ncnc3c2[C@H](C)C[C@H]3O)CC1)c1ccc(Cl)c(OC(F)(F)F)c1] | (S)-2-(4-chloro-3-(trifluoromethoxy)phenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one | 542.2 |

TABLE 1-continued

| Example | Structure | Name | LCMS or ¹H NMR |
|---|---|---|---|
| 155 | 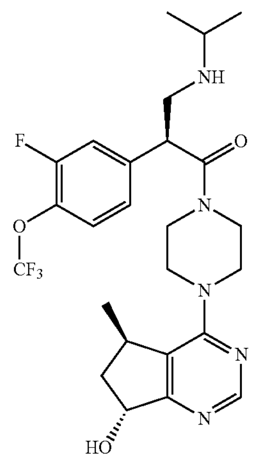 [SMILES: CC(C)NC[C@@H](C(=O)N1CCN(c2ncnc3c2[C@H](C)C[C@H]3O)CC1)c1ccc(OC(F)(F)F)c(F)c1] | (S)-2-(3-fluoro-4-(trifloromethoxy)phenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one | 526.3 |
| 156 | 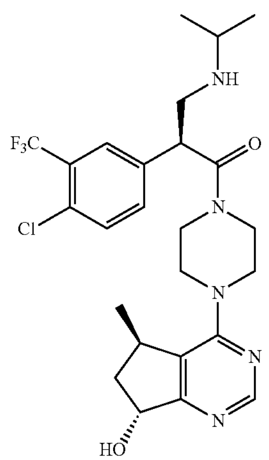 [SMILES: CC(C)NC[C@@H](C(=O)N1CCN(c2ncnc3c2[C@H](C)C[C@H]3O)CC1)c1ccc(Cl)c(C(F)(F)F)c1] | (S)-2-(4-chloro-3-(trifluoromethyl)phenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one | 526.2 |
| 157 | 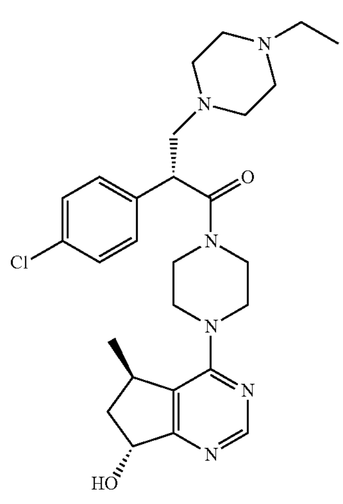 [SMILES: CCN1CCN(C[C@H](C(=O)N2CCN(c3ncnc4c3[C@H](C)C[C@H]4O)CC2)c2ccc(Cl)cc2)CC1] | (R)-2-(4-chlorophenyl)-3-(4-ethylpiperazin-1-yl)-1-(4-((5R,7R)-7-hydroxy-5-methyl-6,7-dihydro-5H-cyclopenta[d]pyrimidin-4-yl)piperazin-1-yl)propan-1-one | 513.3 |

TABLE 1-continued

| Example | Structure | Name | LCMS or ¹H NMR |
|---|---|---|---|
| 158 | 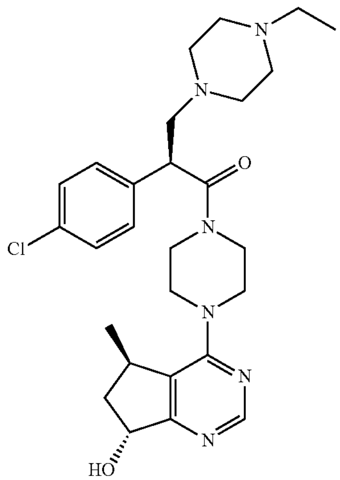 [SMILES: CCN1CCN(C[C@@H](C(=O)N2CCN(c3ncnc4c3[C@H](C)C[C@H]4O)CC2)c2ccc(Cl)cc2)CC1] | (S)-2-(4-chlorophenyl)-3-(4-ethylpiperazin-1-yl)-1-(4-((5R,7R)-7-hydroxy-5-methyl-6,7-dihydro-5H-cyclopenta[d]pyrimidin-4-yl)piperazin-1-yl)propan-1-one | 513.3 |
| 159 | 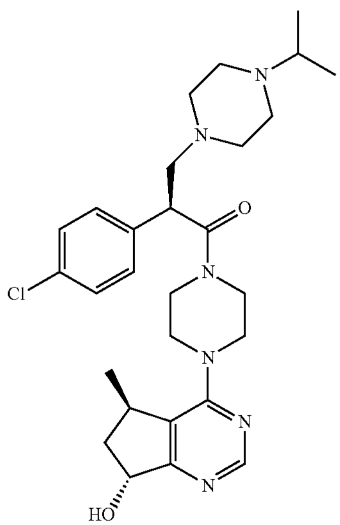 [SMILES: CC(C)N1CCN(C[C@@H](C(=O)N2CCN(c3ncnc4c3[C@H](C)C[C@H]4O)CC2)c2ccc(Cl)cc2)CC1] | (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(4-isopropylpiperazin-1-yl)propan-1-one | 527.6 |
| 160 | 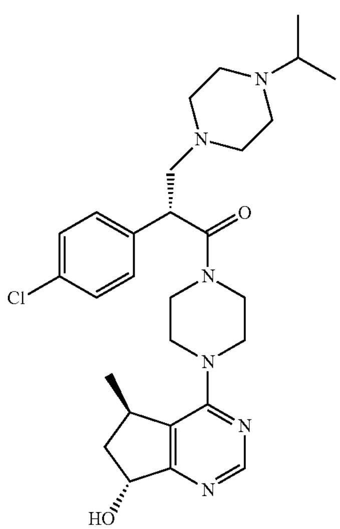 [SMILES: CC(C)N1CCN(C[C@H](C(=O)N2CCN(c3ncnc4c3[C@H](C)C[C@H]4O)CC2)c2ccc(Cl)cc2)CC1] | (R)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(4-isopropylpiperazin-1-yl)propan-1-one | 527.6 |

| Example | Structure | Name | LCMS or ¹H NMR |
|---|---|---|---|
| 161 | 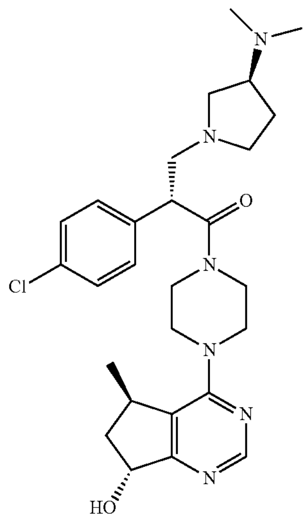 [SMILES: C[C@@H]1C[C@@H](O)c2ncnc(N3CCN(C(=O)[C@@H](CN4CC[C@H](N(C)C)C4)c4ccc(Cl)cc4)CC3)c21] | (R)-2-(4-chlorophenyl)-3-((S)-3-(dimethylamino)pyrrolidin-1-yl)-1-(4-((5R,7R)-7-hydroxy-5-methyl-6,7-dihydro-5H-cyclopenta[d]pyrimidin-4-yl)piperazin-1-yl)propan-1-one | 513.6 |
| 162 | 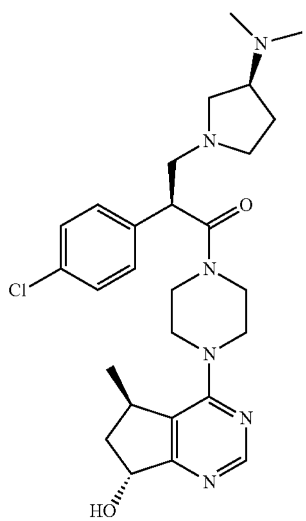 [SMILES: C[C@@H]1C[C@@H](O)c2ncnc(N3CCN(C(=O)[C@H](CN4CC[C@H](N(C)C)C4)c4ccc(Cl)cc4)CC3)c21] | (S)-2-(4-chlorophenyl)-3-((S)-3-(dimethylamino)pyrrolidin-1-yl)-1-(4-((5R,7R)-7-hydroxy-5-methyl-6,7-dihydro-5H-cyclopenta[d]pyrimidin-4-yl)piperazin-1-yl)propan-1-one | 513.6 |
| 163 | 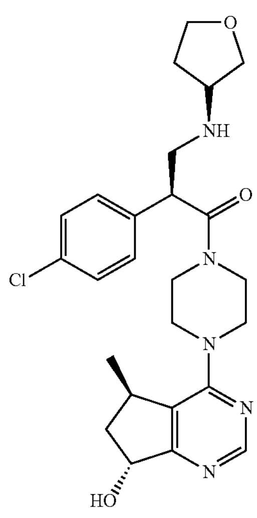 | (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-((R)-tetrahydrofuran-3-ylamino)propan-1-one | 486.2 |

| Example | Name | LCMS or ¹H NMR |
|---|---|---|
| 164 | (S)-2-(4-chlorophenyl)-1-(4-((5R,7S)-7-hydroxy-5-methyl-6,7-dihydro-5H-cyclopenta[d]pyrimidin-4-yl)piperazin-1-yl)-3-((R)-tetrahydrofuran-3-ylamino)propan-1-one | 486.2 |
| 165 | (S)-2-(4-chlorophenyl)-3-(2-fluoroethylamino)-1-(4-((5R,7R)-7-hydroxy-5-methyl-6,7-dihydro-5H-cyclopenta[d]pyrimidin-4-yl)piperazin-1-yl)propan-1-one | 462.2 |
| 166 | (S)-2-(4-fluoro-3-(trifluoromethoxy)phenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one | 526.4 |

TABLE 1-continued

| Example | Structure | Name | LCMS or ¹H NMR |
|---|---|---|---|
| 167 | 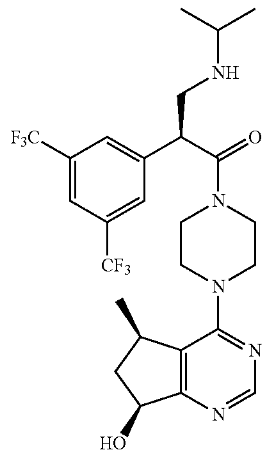 [SMILES: CC(C)NC[C@@H](C(=O)N1CCN(c2ncnc3c2[C@H](C)C[C@@H]3O)CC1)c1cc(C(F)(F)F)cc(C(F)(F)F)c1] | (S)-2-(3,5-bis(trifluoromethyl)phenyl)-1-(4-((5R,7S)-7-hydroxy-5-methyl-6,7-dihydro-5H-cyclopenta[d]pyrimidin-4-yl)piperazin-1-yl)-3-(isopropylamino)propan-1-one | 560.3 |
| 168 | 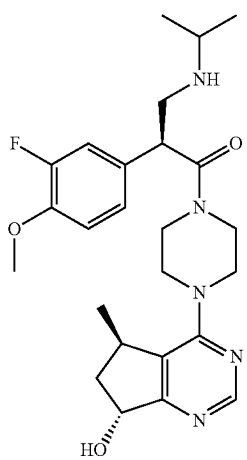 [SMILES: COc1ccc([C@@H](CNC(C)C)C(=O)N2CCN(c3ncnc4c3[C@H](C)C[C@H]4O)CC2)cc1F] | (S)-2-(3-fluoro-4-methoxyphenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one | 472.5 |
| 169 | 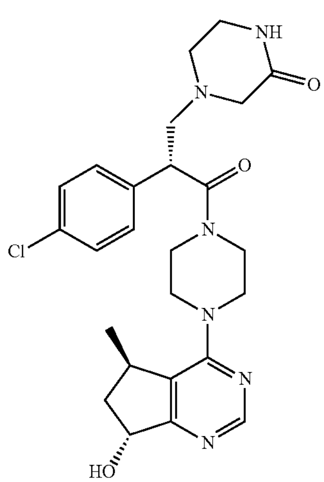 [SMILES: C[C@@H]1C[C@@H](O)c2ncnc(N3CCN(C(=O)[C@@H](CN4CCNC(=O)C4)c4ccc(Cl)cc4)CC3)c21] | 4-((R)-2-(4-chlorophenyl)-3-(4-((5R,7R)-7-hydroxy-5-methyl-6,7-dihydro-5H-cyclopenta[d]pyrimidin-4-yl)piperazin-1-yl)-3-oxopropyl)piperazin-2-one | 499.3 |

| Example | Structure | Name | LCMS or ¹H NMR |
|---|---|---|---|
| 170 | 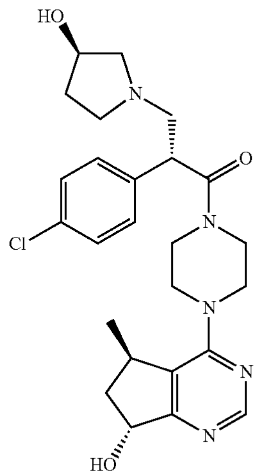 [SMILES: C[C@@H]1C[C@@H](O)c2ncnc(N3CCN(C(=O)[C@@H](CN4CC[C@@H](O)C4)c4ccc(Cl)cc4)CC3)c21] | (R)-2-(4-chlorophenyl)-1-(4-((5R,7R)-7-hydroxy-5-methyl-6,7-dihydro-5H-cyclopenta[d]pyrimidin-4-yl)piperazin-1-yl)-3-((R)-3-hydroxypyrrolidin-1-yl)propan-1-one | 486.3 |
| 171 | 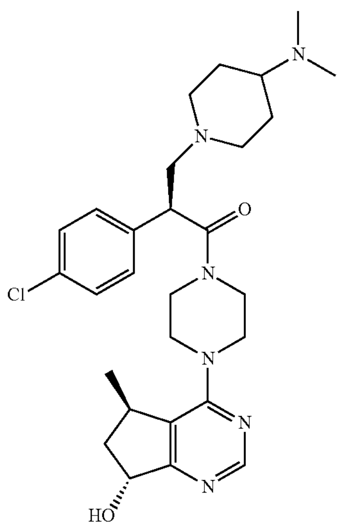 [SMILES: C[C@@H]1C[C@@H](O)c2ncnc(N3CCN(C(=O)[C@H](CN4CCC(N(C)C)CC4)c4ccc(Cl)cc4)CC3)c21] | (S)-2-(4-chlorophenyl)-3-(4-(dimethylamino)piperidin-1-yl)-1-(4-((5R,7R)-7-hydroxy-5-methyl-6,7-dihydro-5H-cyclopenta[d]pyrimidin-4-yl)piperazin-1-yl)propan-1-one | 527.3 |
| 172 | 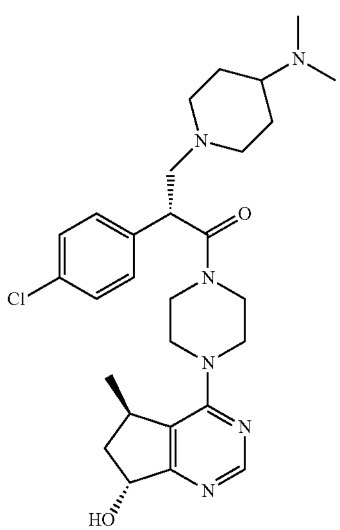 | (R)-2-(4-chlorophenyl)-3-(4-(dimethylamino)piperidin-1-yl)-1-(4-((5R,7R)-7-hydroxy-5-methyl-6,7-dihydro-5H-cyclopenta[d]pyrimidin-4-yl)piperazin-1-yl)propan-1-one | 527.3 |

TABLE 1-continued

| Example | Structure | Name | LCMS or ¹H NMR |
|---|---|---|---|
| 173 | 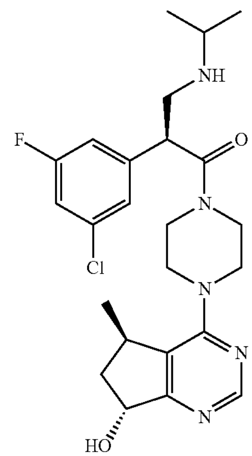 [SMILES: CC(C)NC[C@@H](C(=O)N1CCN(c2ncnc3c2[C@H](C)C[C@H]3O)CC1)c1cc(F)cc(Cl)c1] | (S)-2-(3-chloro-5-fluorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one | 476.2 |
| 174 | 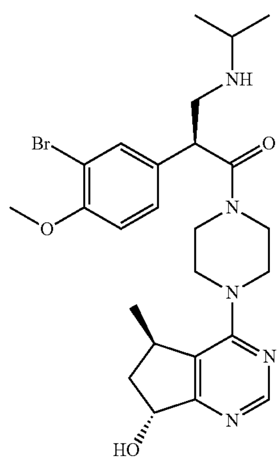 [SMILES: COc1ccc([C@@H](CNC(C)C)C(=O)N2CCN(c3ncnc4c3[C@H](C)C[C@H]4O)CC2)cc1Br] | (S)-2-(3-bromo-4-methoxyphenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one | 532.2 |
| 175 | 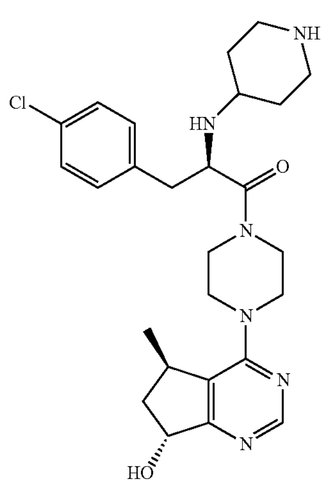 [SMILES: C[C@@H]1C[C@@H](O)c2ncnc(N3CCN(C(=O)[C@@H](Cc4ccc(Cl)cc4)NC4CCNCC4)CC3)c21] | (R)-3-(4-chlorophenyl)-1-(4-((5R,7R)-7-hydroxy-5-methyl-6,7-dihydro-5H-cyclopenta[d]pyrimidin-4-yl)piperazin-1-yl)-2-(piperidin-4-ylamino)propan-1-one | 499.3 |

TABLE 1-continued

| Example | Name | LCMS or ¹H NMR |
|---------|------|----------------|
| 176 | (R)-2-(1-acetylpiperidin-4-ylamino)-3-(4-chlorophenyl)-1-(4-((5R,7R)-7-hydroxy-5-methyl-6,7-dihydro-5H-cyclopenta[d]pyrimidin-4-yl)piperazin-1-yl)propan-1-one | 541.3 |
| 177 | 2-((R)-3-(4-chlorophenyl)-1-(4-((5R,7R)-7-hydroxy-5-methyl-6,7-dihydro-5H-cyclopenta[d]pyrimidin-4-yl)piperazin-1-yl)-1-oxopropan-2-ylamino)-N-isopropylacetamide | 515.3 |
| 178 | (R)-3-(4-chlorophenyl)-2-(dimethylamino)-1-(4-((5R,7R)-7-hydroxy-5-methyl-6,7-dihydro-5H-cyclopenta[d]pyrimidin-4-yl)piperazin-1-yl)propan-1-one | 444.2 |

TABLE 1-continued

| Example | Structure | Name | LCMS or ¹H NMR |
|---|---|---|---|
| 179 | 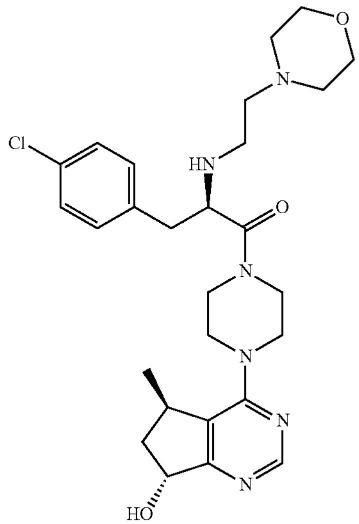 | (R)-3-(4-chlorophenyl)-1-(4-((5R,7R)-7-hydroxy-5-methyl-6,7-dihydro-5H-cyclopenta[d]pyrimidin-4-yl)piperazin-1-yl)-2-(2-moprholinoethylamino)propan-1-one | 529.3 |
| 180 | 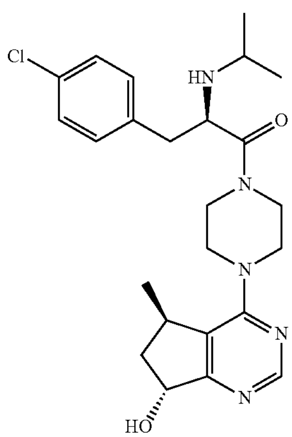 [SMILES: CC(C)N[C@H](Cc1ccc(Cl)cc1)C(=O)N1CCN(c2ncnc3c2[C@H](C)C[C@H]3O)CC1] | (R)-3-(4-chlorophenyl)-1-(4-((5R,7R)-7-hydroxy-5-methyl-6,7-dihydro-5H-cyclopenta[d]pyrimidin-4-yl)piperazin-1-yl)-2-(isopropylamino)propan-1-one | 458.2 |
| 181 | 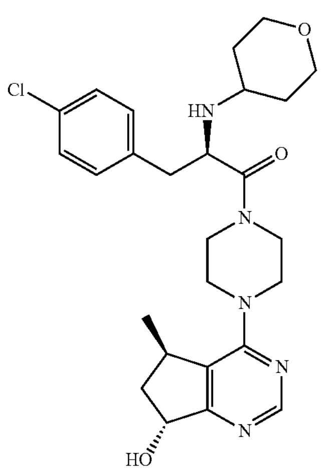 [SMILES: C[C@@H]1C[C@@H](O)c2ncnc(N3CCN(C(=O)[C@@H](Cc4ccc(Cl)cc4)NC4CCOCC4)CC3)c21] | (R)-3-(4-chlorophenyl)-1-(4-((5R,7R)-7-hydroxy-5-methyl-6,7-dihydro-5H-cyclopenta[d]pyrimidin-4-yl)piperazin-1-yl)-2-(tetrahydro-2H-pyran-4-ylamino)propan-1-one | 500.3 |

TABLE 1-continued

| Example | Structure | Name | LCMS or ¹H NMR |
|---|---|---|---|
| 182 | 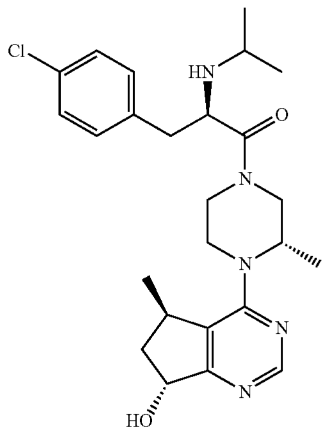 [SMILES: CC(C)N[C@H](Cc1ccc(Cl)cc1)C(=O)N1CCN(c2ncnc3c2[C@H](C)C[C@H]3O)[C@@H](C)C1] | (R)-3-(4-chlorophenyl)-1-((S)-4-((5R,7R)-7-hydroxy-5-methyl-6,7-dihydro-5H-cyclopenta[d]pyrimidin-4-yl)-3-methylpiperaizn-1-yl)-2-(isopropylamino)propan-1-one | 472.3 |
| 183 | 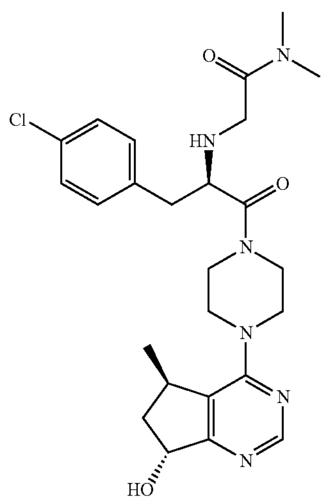 [SMILES: C[C@@H]1C[C@@H](O)c2ncnc(N3CCN(C(=O)[C@@H](Cc4ccc(Cl)cc4)NCC(=O)N(C)C)CC3)c21] | 2-((R)-3-(4-chlorophenyl)-1-(4-((5R,7R)-7-hydroxy-5-methyl-6,7-dihydro-5H-cyclopenta[d]pyrimidin-4-yl)piperazin-1-yl)-1-oxopropan-2-ylamino)-N,N-dimethylacetamide | 501.2 |
| 184 | 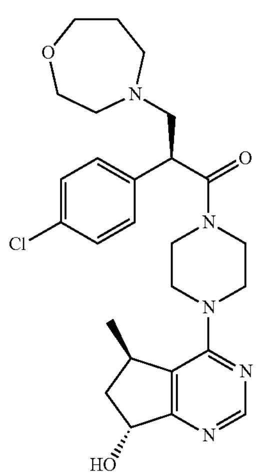 [SMILES: C[C@@H]1C[C@@H](O)c2ncnc(N3CCN(C(=O)[C@H](CN4CCCOCC4)c4ccc(Cl)cc4)CC3)c21] | (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(1,4-oxazepan-4-yl)propan-1-one | 500.3 |

TABLE 1-continued

| Example | Structure | Name | LCMS or ¹H NMR |
|---|---|---|---|
| 185 | 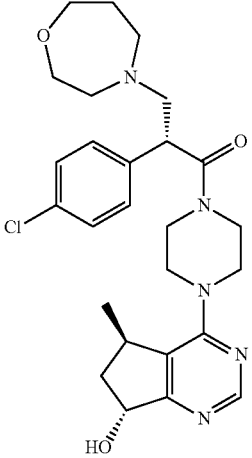 [SMILES: C[C@@H]1C[C@@H](O)c2ncnc(N3CCN(C(=O)[C@@H](CN4CCCOCC4)c4ccc(Cl)cc4)CC3)c21] | (R)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(1,4-oxazepan-4-yl)propan-1-one | 500.3 |
| 186 | 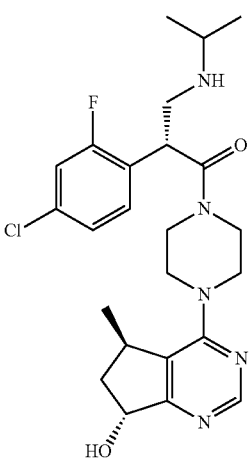 [SMILES: CC(C)NC[C@H](C(=O)N1CCN(c2ncnc3c2[C@H](C)C[C@H]3O)CC1)c1ccc(Cl)cc1F] | (R)-2-(4-chloro-2-fluorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one | 476.2 |
| 187 | 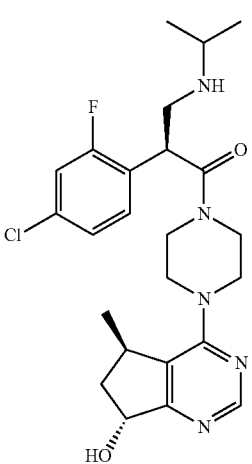 [SMILES: CC(C)NC[C@@H](C(=O)N1CCN(c2ncnc3c2[C@H](C)C[C@H]3O)CC1)c1ccc(Cl)cc1F] | (S)-2-(4-chloro-2-fluorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one | 476.2 |

TABLE 1-continued

| Example | Structure | Name | LCMS or ¹H NMR |
|---|---|---|---|
| 188 | 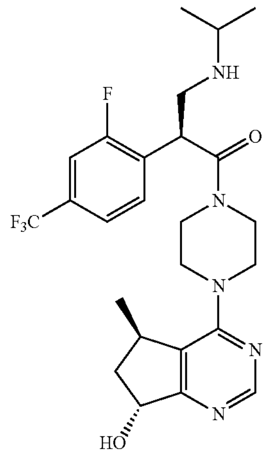 [SMILES: CC(C)NC[C@@H](C(=O)N1CCN(c2ncnc3c2[C@H](C)C[C@H]3O)CC1)c1ccc(C(F)(F)F)cc1F] | (S)-2-(2-fluoro-4-(trifluoromethyl)phenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one | 510.2 |
| 189 | 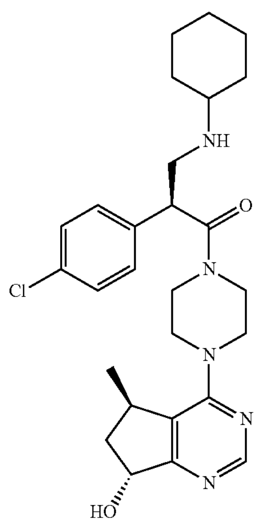 [SMILES: C[C@@H]1C[C@@H](O)c2ncnc(N3CCN(C(=O)[C@H](CNC4CCCCC4)c4ccc(Cl)cc4)CC3)c21] | (S)-2-(4-chlorophenyl)-3-(cyclohexylamino)-1-(4-((5R,7R)-7-hydroxy-5-methyl-6,7-dihydro-5H-cyclopenta[d]pyrimidin-4-yl)piperazin-1-yl)propan-1-one | 498.3 |
| 190 | 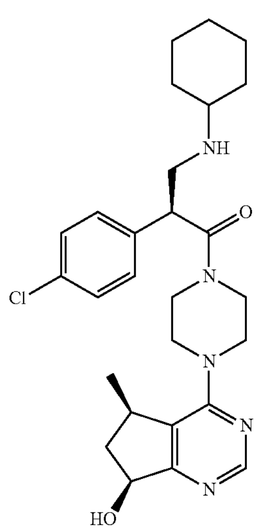 [SMILES: C[C@@H]1C[C@H](O)c2ncnc(N3CCN(C(=O)[C@H](CNC4CCCCC4)c4ccc(Cl)cc4)CC3)c21] | (S)-2-(4-chlorophenyl)-3-(cyclohexylamino)-1-(4-((5R,7S)-7-hydroxy-5-methyl-6,7-dihydro-5H-cyclopenta[d]pyrimidin-4-yl)piperazin-1-yl)propan-1-one | 498.3 |

TABLE 1-continued

| Example | Structure | Name | LCMS or ¹H NMR |
|---|---|---|---|
| 191 | 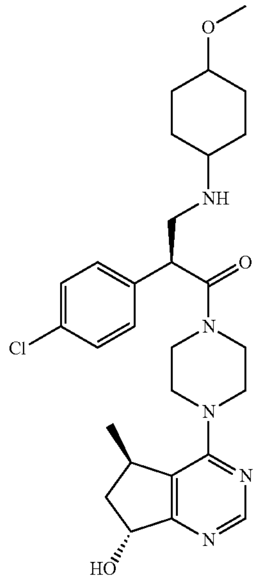 [SMILES: COC1CCC(NC[C@@H](C(=O)N2CCN(c3ncnc4c3[C@H](C)C[C@H]4O)CC2)c2ccc(Cl)cc2)CC1] | (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(4-methoxycyclohexylamino)propan-1-one | 528.4 |
| 192 | 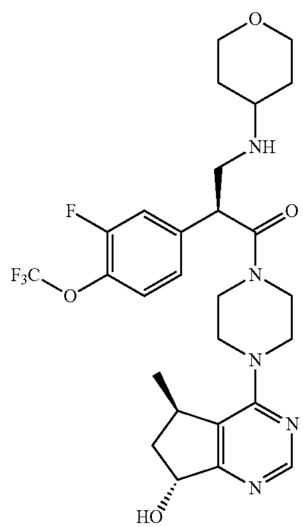 [SMILES: C[C@@H]1C[C@@H](O)c2ncnc(N3CCN(C(=O)[C@H](CNC4CCOCC4)c4ccc(OC(F)(F)F)c(F)c4)CC3)c21] | (S)-2-(3-fluoro-4-(trifluoromethoxy)phenyl)-1-(4-((5R,7R)-7-hydroxy-5-methyl-6,7-dihydro-5H-cyclopenta[d]pyrimidin-4-yl)piperazin-1-yl)-3-(tetrahydro-2H-pyran-4-ylamino)propan-1-one | 568.3 |
| 193 | 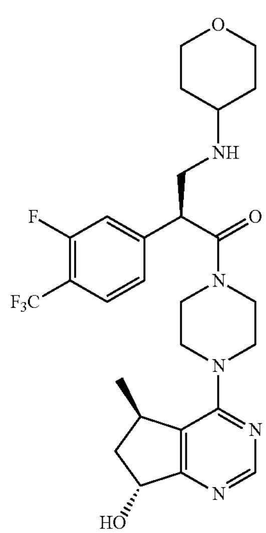 [SMILES: C[C@@H]1C[C@@H](O)c2ncnc(N3CCN(C(=O)[C@H](CNC4CCOCC4)c4ccc(C(F)(F)F)c(F)c4)CC3)c21] | (S)-2-(3-fluoro-4-(trifluoromethyl)phenyl)-1-(4-((5R,7R)-7-hydroxy-5-methyl-6,7-dihydro-5H-cyclopenta[d]pyrimidin-4-yl)piperazin-1-yl)-3-(tetrahydro-2H-pyran-4-ylamino)propan-1-one | 552.2 |

TABLE 1-continued

| Example | Structure | Name | LCMS or ¹H NMR |
|---|---|---|---|
| 194 | 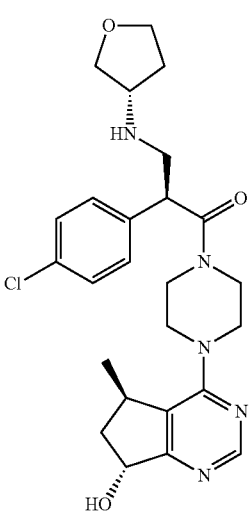 [SMILES: C[C@@H]1C[C@@H](O)c2ncnc(N3CCN(C(=O)[C@H](CN[C@H]4CCOC4)c4ccc(Cl)cc4)CC3)c21] | (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-((S)-tetrahydrofuran-3-ylamino)propan-1-one | 486.3 |
| 195 | 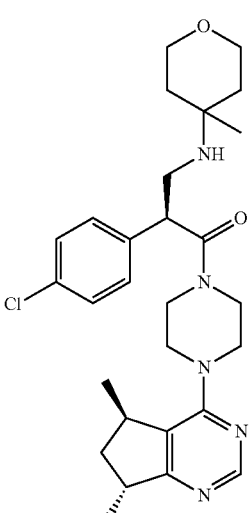 | (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(4-methyltetrahydro-2H-pyran-2-ylamino)propan-1-one | 513.2 |
| 196 | 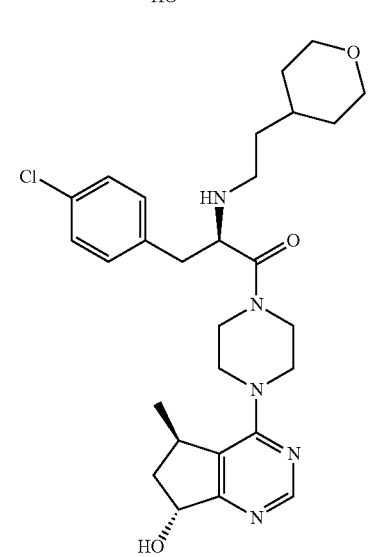 | (R)-3-(4-chlorophenyl)-1-(4-((5R,7R)-7-hydroxy-5-methyl-6,7-dihydro-5H-cyclopenta[d]pyrimidin-4-yl)piperazin-1-yl)-2-(2-(tetrahydro-2H-pyran-4-yl)ethylamino)propan-1-one | 528.3 |

TABLE 1-continued

| Example | Structure | Name | LCMS or ¹H NMR |
|---|---|---|---|
| 197 | 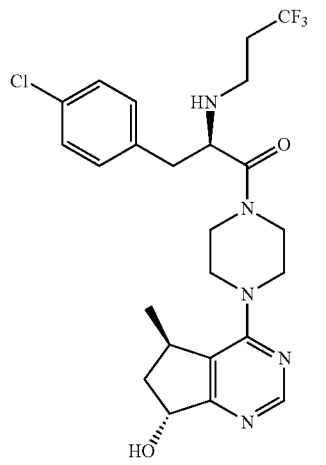 [SMILES: C[C@@H]1C[C@@H](O)c2ncnc(N3CCN(C(=O)[C@@H](Cc4ccc(Cl)cc4)NCCC(F)(F)F)CC3)c21] | (R)-3-(4-chlorophenyl)-1-(4-((5R,7R)-7-hydroxy-5-methyl-6,7-dihydro-5H-cyclopenta[d]pyrimidin-4-yl)piperazin-1-yl)-2-(3,3,3-trifluoropropylamino)propan-1-one | 512.2 |
| 198 | 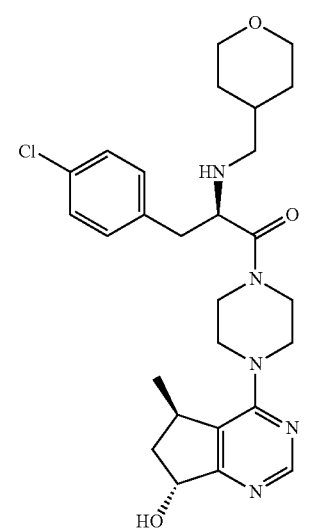 [SMILES: C[C@@H]1C[C@@H](O)c2ncnc(N3CCN(C(=O)[C@@H](Cc4ccc(Cl)cc4)NCC4CCOCC4)CC3)c21] | (R)-3-(4-chlorophenyl)-1-(4-((5R,7R)-7-hydroxy-5-methyl-6,7-dihydro-5H-cyclopenta[d]pyrimidin-4-yl)piperazin-1-yl)-2-((tetrahydro-2H-pyran-4-yl)methylamino)propan-1-one | 514.2 |
| 199 | 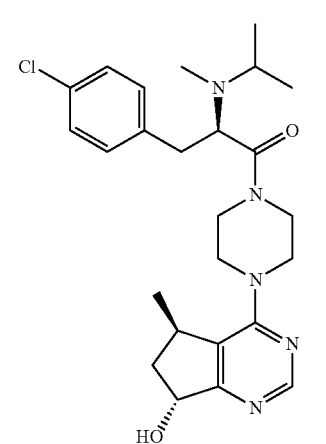 [SMILES: CC(C)N(C)[C@H](Cc1ccc(Cl)cc1)C(=O)N1CCN(c2ncnc3c2[C@H](C)C[C@H]3O)CC1] | (R)-3-(4-chlorophenyl)-1-(4-((5R,7R)-7-hydroxy-5-methyl-6,7-dihydro-5H-cyclopenta[d]pyrimidin-4-yl)piperazin-1-yl)-2-(isopropyl(methyl)amino)propan-1-one | 472.3 |

TABLE 1-continued

| Example | Structure | Name | LCMS or ¹H NMR |
|---|---|---|---|
| 200 | 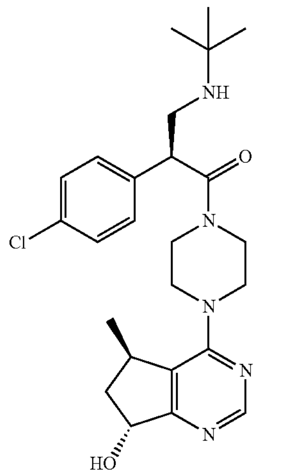 [SMILES: C[C@@H]1C[C@@H](O)c2ncnc(N3CCN(C(=O)[C@H](CNC(C)(C)C)c4ccc(Cl)cc4)CC3)c21] | (S)-3-(tert-butylamino)-2-(4-chlorophenyl)-1-(4-((5R,7R)-7-hydroxy-5-methyl-6,7-dihydro-5H-cyclopenta[d]pyrimidin-4-yl)piperazin-1-yl)propan-1-one | 472.1 |
| 201 | 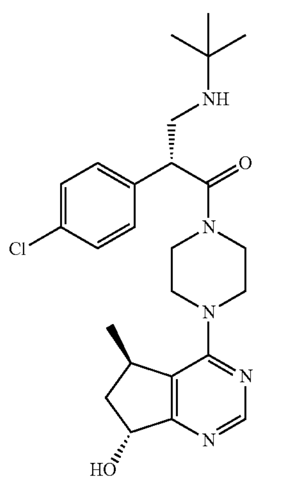 | (R)-3-(tert-butyalmino)-2-(4-chlorophenyl)-1-(4-((5R,7R)-7-hydroxy-5-methyl-6,7-dihydro-5H-cyclopenta[d]pyrimidin-4-yl)piperazin-1-yl)propan-1-one | 472.1 |
| 202 | 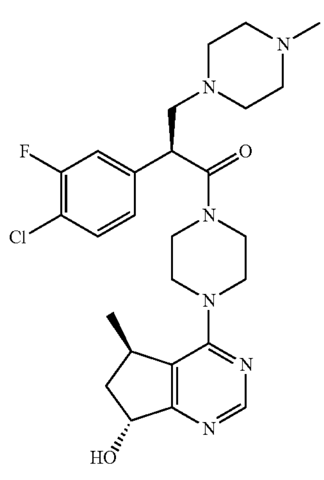 [SMILES: C[C@@H]1C[C@@H](O)c2ncnc(N3CCN(C(=O)[C@H](CN4CCN(C)CC4)c4ccc(Cl)c(F)c4)CC3)c21] | (S)-2-(4-chloro-3-fluorophenyl)-1-(4-((5R,7R)-7-hydroxy-5-methyl-6,7-dihydro-5H-cyclopenta[d]pyrimidin-4-yl)piperazin-1-yl)-3-(4-methylpiperazin-1-yl)propan-1-one | 517.2 |

TABLE 1-continued

| Example | Structure | Name | LCMS or ¹H NMR |
|---|---|---|---|
| 203 | 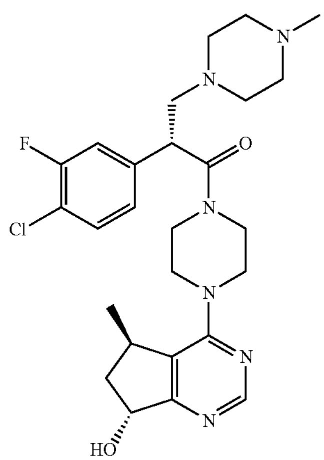 [SMILES: C[C@@H]1C[C@@H](O)c2ncnc(N3CCN(C(=O)[C@@H](CN4CCN(C)CC4)c4ccc(Cl)c(F)c4)CC3)c21] | (R)-2-(4-chloro-3-fluorophenyl)-1-(4-((5R,7R)-7-hydroxy-5-methyl-6,7-dihydro-5H-cyclopenta[d]pyrimidin-4-yl)piperazin-1-yl)-3-(4-methylpiperazin-1-yl)propan-1-one | 517.2 |
| 204 | 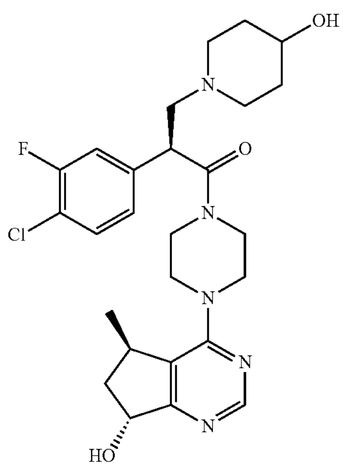 [SMILES: C[C@@H]1C[C@@H](O)c2ncnc(N3CCN(C(=O)[C@H](CN4CCC(O)CC4)c4ccc(Cl)c(F)c4)CC3)c21] | (S)-2-(4-chloro-3-fluorophenyl)-1-(4-((5R,7R)-7-hydroxy-5-methyl-6,7-dihydro-5H-cyclopenta[d]pyrimidin-4-yl)piperazin-1-yl)-3-(4-hydroxypiperidin-1-yl)propan-1-one | 518.2 |
| 205 | 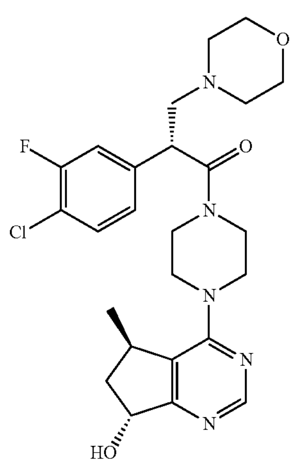 [SMILES: C[C@@H]1C[C@@H](O)c2ncnc(N3CCN(C(=O)[C@@H](CN4CCOCC4)c4ccc(Cl)c(F)c4)CC3)c21] | (R)-2-(4-chloro-3-fluorophenyl)-1-(4-((5R,7R)-7-hydroxy-5-methyl-6,7-dihydro-5H-cyclopenta[d]pyrimidin-4-yl)piperazin-1-yl)-3-morpholinopropan-1-one | 504.2 |

TABLE 1-continued

| Example | Structure | Name | LCMS or ¹H NMR |
|---|---|---|---|
| 206 | 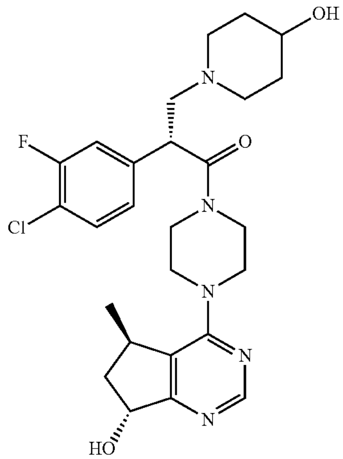 [SMILES: C[C@@H]1C[C@@H](O)c2ncnc(N3CCN(C(=O)[C@@H](CN4CCC(O)CC4)c4ccc(Cl)c(F)c4)CC3)c21] | (R)-2-(4-chloro-3-fluorophenyl)-1-(4-((5R,7R)-7-hydroxy-5-methyl-6,7-dihydro-5H-cyclopenta[d]pyrimidin-4-yl)piperazin-1-yl)-3-(4-hydroxypiperidin-1-yl)propan-1-one | 518.2 |
| 207 | 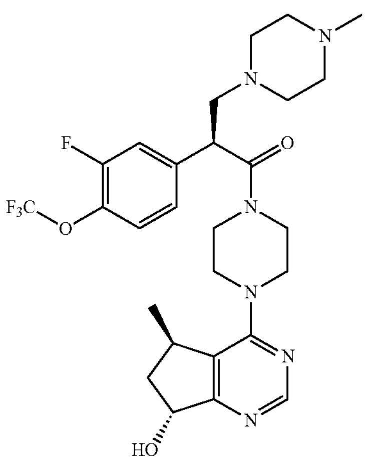 [SMILES: C[C@@H]1C[C@@H](O)c2ncnc(N3CCN(C(=O)[C@H](CN4CCN(C)CC4)c4ccc(OC(F)(F)F)c(F)c4)CC3)c21] | (S)-2-(3-fluoro-4-(trifluoromethoxy)phenyl)-1-(4-((5R,7R)-7-hydroxy-5-methyl-6,7-dihydro-5H-cyclopenta[d]pyrimidin-4-yl)piperazin-1-yl)-3-(4-methylpiperazin-1-yl)propan-1-one | 567.2 |
| 208 | 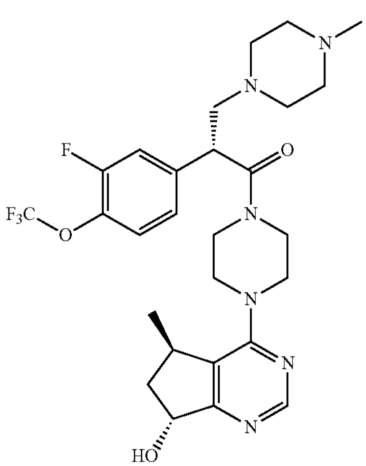 [SMILES: C[C@@H]1C[C@@H](O)c2ncnc(N3CCN(C(=O)[C@@H](CN4CCN(C)CC4)c4ccc(OC(F)(F)F)c(F)c4)CC3)c21] | (R)-2-(3-fluoro-4-(trifluoromethoxy)phenyl)-1-(4-((5R,7R)-7-hydroxy-5-methyl-6,7-dihydro-5H-cyclopenta[d]pyrimidin-4-yl)piperazin-1-yl)-3-(4-methylpiperazin-1-yl)propan-1-one | 567.2 |

TABLE 1-continued

| Example | Name | LCMS or ¹H NMR |
|---|---|---|
| 209 | (S)-3-(cyclopropylmethylamino)-2-(3-fluoro-4-(trifluoromethyl)phenyl)-1-(4-((5R,7R)-7-hydroxy-5-methyl-6,7-dihydro-5H-cyclopenta[d]pyrimidin-4-yl)piperazin-1-yl)propan-1-one | 522.2 |
| 210 | (S)-3-(cyclopropylmethylamino)-2-(3-fluoro-4-(trifluoromethoxy)phenyl)-1-(4-((5R,7R)-7-hydroxy-5-methyl-6,7-dihydro-5H-cyclopenta[d]pyrimidin-4-yl)piperazin-1-yl)propan-1-one | 538.2 |
| 211 | (S)-1-(4-((5R,7R)-7-hydroxy-5-methyl-6,7-dihydro-5H-cyclopenta[d]pyrimidin-4-yl)piperazin-1-yl)-3-(isopropylamino)-2-(4-(trifluoromethyl)phenyl)propan-1-one | 492.3 |

TABLE 1-continued

| Example | Structure | Name | LCMS or ¹H NMR |
|---|---|---|---|
| 212 | 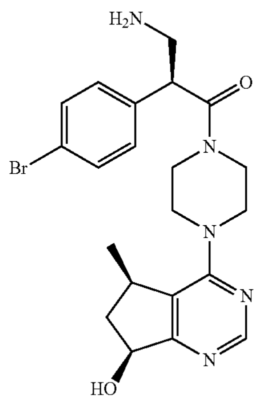 [SMILES: C[C@@H]1C[C@H](O)c2ncnc(N3CCN(C(=O)[C@H](CN)c4ccc(Br)cc4)CC3)c21] | (S)-3-amino-2-(4-bromophenyl)-1-(4-((5R,7S)-7-hydroxy-5-methyl-6,7-dihydro-5H-cyclopenta[d]pyrimidin-4-yl)piperazin-1-yl)propan-1-one | m/z 460/462 (Br isotope) [M + H]+ |
| 213 | 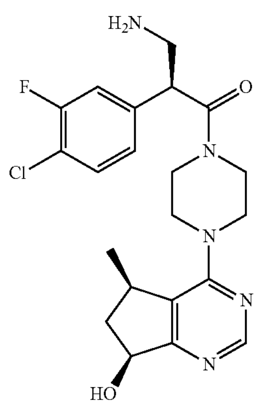 [SMILES: C[C@@H]1C[C@H](O)c2ncnc(N3CCN(C(=O)[C@H](CN)c4ccc(Cl)c(F)c4)CC3)c21] | (S)-3-amino-2-(4-chloro-3-fluorophenyl)-1-(4-((5R,7S)-7-hydroxy-5-methyl-6,7-dihydro-5H-cyclopenta[d]pyrimidin-4-yl)piperazin-1-yl)propan-1-one | m/z 434 [M + H]+ |
| 214 | 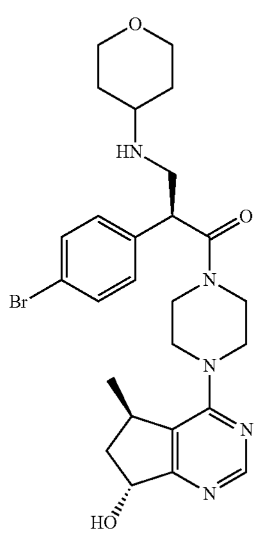 | (S)-2-(4-bromophenyl)-1-(4-((5R,7R)-7-hydroxy-5-methyl-6,7-dihydro-5H-cyclopenta[d]pyrimidin-4-yl)piperazin-1-yl)-3-(tetrahydro-2H-pyran-4-ylamino)propan-1-one | 546.2 |

TABLE 1-continued

| Example | Structure | Name | LCMS or ¹H NMR |
|---|---|---|---|
| 215 | 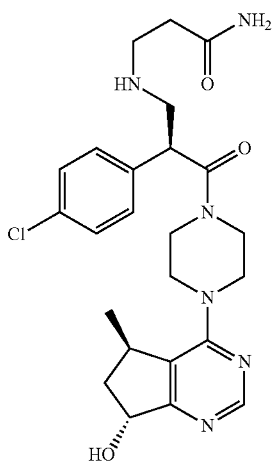 [SMILES: C[C@@H]1C[C@@H](O)c2ncnc(N3CCN(C(=O)[C@H](CNCCC(N)=O)c4ccc(Cl)cc4)CC3)c21] | 3-((S)-2-(4-chlorophenyl)-3-(4-((5R,7R)-7-hydroxy-5-methyl-6,7-dihydro-5H-cyclopenta[d]pyrimidin-4-yl)piperazin-1-yl)-3-oxopropylamino)propanamide | 487.2 |
| 216 | 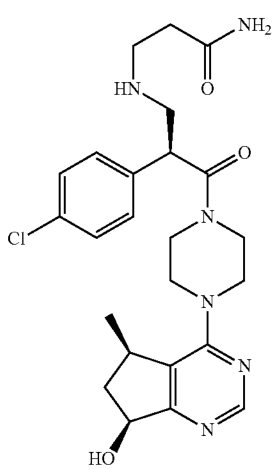 [SMILES: C[C@@H]1C[C@H](O)c2ncnc(N3CCN(C(=O)[C@H](CNCCC(N)=O)c4ccc(Cl)cc4)CC3)c21] | 3-((S)-2-(4-chlorophenyl)-3-(4-((5R,7S)-7-hydroxy-5-methyl-6,7-dihydro-5H-cyclopenta[d]pyrimidin-4-yl)piperazin-1-yl)-3-oxopropylamino)propanamide | 487.2 |
| 217 | 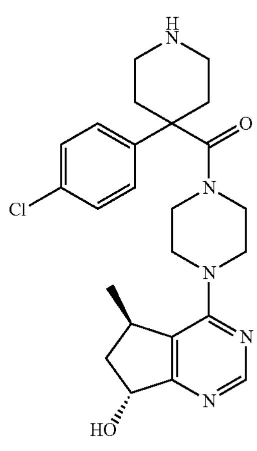 [SMILES: C[C@@H]1C[C@@H](O)c2ncnc(N3CCN(C(=O)C4(c5ccc(Cl)cc5)CCNCC4)CC3)c21] | (4-(4-chlorophenyl)piperidin-4-yl)(4-((5R,7R)-7-hydroxy-5-methyl-6,7-dihydro-5H-cyclopenta[d]pyrimidin-4-yl)piperazin-1-yl)methanone | 456.2 |

TABLE 1-continued

| Example | Structure | Name | LCMS or ¹H NMR |
|---|---|---|---|
| 218 | 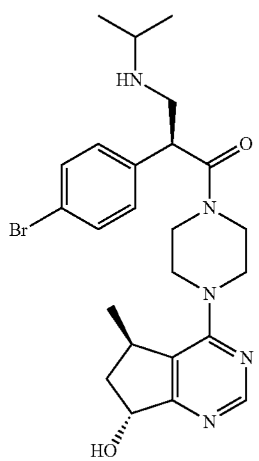 | (S)-2-(4-bromophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one | 504.2 |
| 219 | 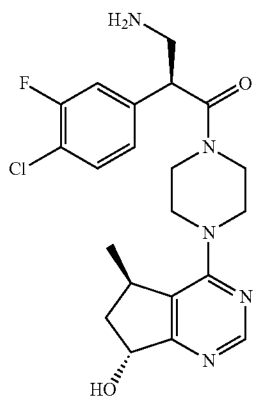 [SMILES: C[C@@H]1C[C@@H](O)c2ncnc(N3CCN(C(=O)[C@H](CN)c4ccc(Cl)c(F)c4)CC3)c21] | (S)-3-amino-2-(4-chloro-3-fluorophenyl)-1-(4-((5R,7R)-7-hydroxy-5-methyl-6,7-dihydro-5H-cyclopenta[d]pyrimidin-4-yl)piperazin-1-yl)propan-1-one | 434.3 |
| 220 | 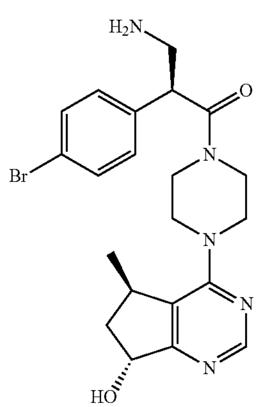 [SMILES: C[C@@H]1C[C@@H](O)c2ncnc(N3CCN(C(=O)[C@H](CN)c4ccc(Br)cc4)CC3)c21] | (S)-3-amino-2-(4-bromophenyl)-1-(4-((5R,7R)-7-hydroxy-5-methyl-6,7-dihydro-5H-cyclopenta[d]pyrimidin-4-yl)piperazin-1-yl)propan-1-one | 462.2 |

TABLE 1-continued

| Example | Structure | Name | LCMS or ¹H NMR |
|---|---|---|---|
| 221 | 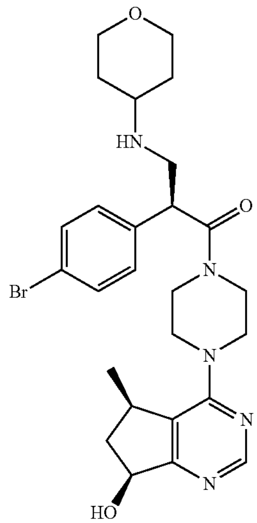 | (S)-2-(4-bromophenyl)-1-(4-((5R,7S)-7-hydroxy-5-methyl-6,7-dihydro-5H-cyclopenta[d]pyrimidin-4-yl)piperazin-1-yl)-3-(tetrahydro-2H-pyran-4-ylamino)propan-1-one | m/z 544/546 (Br isotope) [M + H]+ |
| 222 | 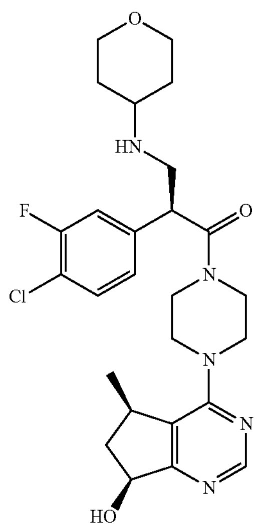 [SMILES: C[C@@H]1C[C@H](O)c2ncnc(N3CCN(C(=O)[C@H](CNC4CCOCC4)c4ccc(Cl)c(F)c4)CC3)c21] | (S)-2-(4-chloro-3-fluorophenyl)-1-(4-((5R,7S)-7-hydroxy-5-methyl-6,7-dihydro-5H-cyclopenta[d]pyrimidin-4-yl)piperazin-1-yl)-3-(tetrahydro-2H-pyran-4-ylamino)propan-1-one | m/z 518 [M + H]+ |
| 223 | 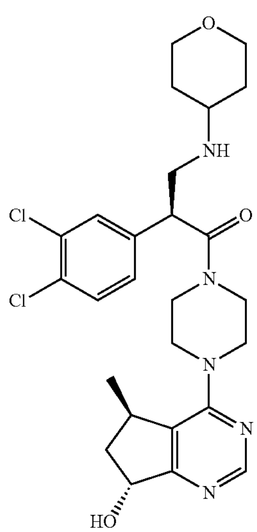 [SMILES: C[C@@H]1C[C@@H](O)c2ncnc(N3CCN(C(=O)[C@H](CNC4CCOCC4)c4ccc(Cl)c(Cl)c4)CC3)c21] | (S)-2-(3,4-dichlorophenyl)-1-(4-((5R,7R)-7-hydroxy-5-methyl-6,7-dihydro-5H-cyclopenta[d]pyrimidin-4-yl)piperazin-1-yl)-3-(tetrahydro-2H-pyran-4-ylamino)propan-1-one | 534.2 |

TABLE 1-continued

| Example | Structure | Name | LCMS or ¹H NMR |
|---|---|---|---|
| 224 | 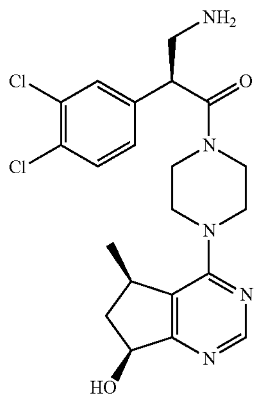 [SMILES: C[C@@H]1C[C@H](O)c2ncnc(N3CCN(C(=O)[C@H](CN)c4ccc(Cl)c(Cl)c4)CC3)c21] | (S)-3-amino-2-(3,4-dichlorophenyl)-1-(4-((5R,7S)-7-hydroxy-5-methyl-6,7-dihydro-5H-cyclopenta[d]pyrimidin-4-yl)piperazin-1-yl)propan-1-one | 450.3 |
| 225 | 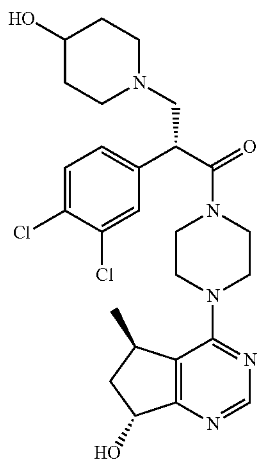 [SMILES: C[C@@H]1C[C@@H](O)c2ncnc(N3CCN(C(=O)[C@@H](CN4CCC(O)CC4)c4ccc(Cl)c(Cl)c4)CC3)c21] | (R)-2-(3,4-dichlorophenyl)-1-(4-((5R,7R)-7-hydroxy-5-methyl-6,7-dihydro-5H-cyclopenta[d]pyrimidin-4-yl)piperazin-1-yl)-3-(4-hydroxypiperidin-1-yl)propan-1-one | 534.2 |
| 226 | 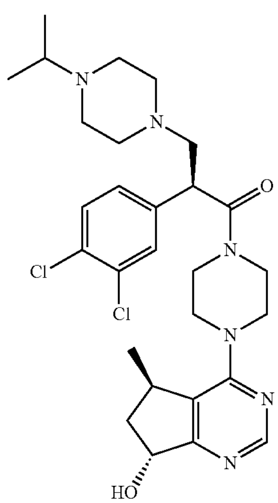 [SMILES: CC(C)N1CCN(C[C@@H](C(=O)N2CCN(c3ncnc4c3[C@H](C)C[C@H]4O)CC2)c2ccc(Cl)c(Cl)c2)CC1] | (S)-2-(3,4-dichlorophenyl)-1-(4-((5R,7R)-7-hydroxy-5-methyl-6,7-dihydro-5H-cyclopenta[d]pyrimidin-4-yl)piperazin-1-yl)-3-(4-isopropylpiperazin-1-yl)propan-1-one | 561.3 |

TABLE 1-continued

| Example | Structure | Name | LCMS or ¹H NMR |
|---|---|---|---|
| 227 | 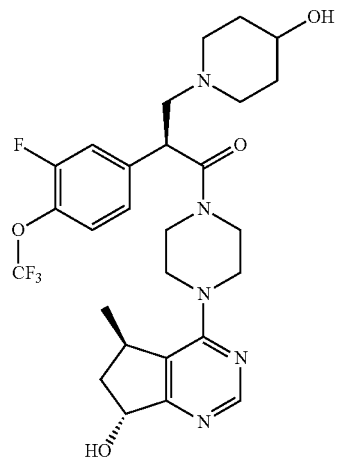 [SMILES: C[C@@H]1C[C@@H](O)c2ncnc(N3CCN(C(=O)[C@H](CN4CCC(O)CC4)c4ccc(OC(F)(F)F)c(F)c4)CC3)c21] | (S)-2-(3-fluoro-4-(trifluoromethoxy)phenyl)-1-(4-((5R,7R)-7-hydroxy-5-methyl-6,7-dihydro-5H-cyclopenta[d]pyrimidin-4-yl)piperazin-1-yl)-3-(4-hydroxypiperidin-1-yl)propan-1-one | 568.2 |
| 228 | 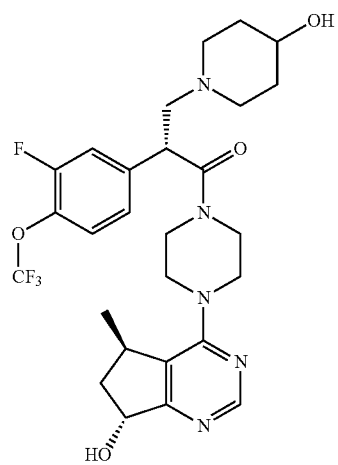 [SMILES: C[C@@H]1C[C@@H](O)c2ncnc(N3CCN(C(=O)[C@@H](CN4CCC(O)CC4)c4ccc(OC(F)(F)F)c(F)c4)CC3)c21] | (R)-2-(3-fluoro-4-(trifluoromethoxy)phenyl)-1-(4-((5R,7R)-7-hydroxy-5-methyl-6,7-dihydro-5H-cyclopenta[d]pyrimidin-4-yl)piperazin-1-yl)-3-(4-hydroxypiperidin-1-yl)propan-1-one | 568.2 |
| 229 | 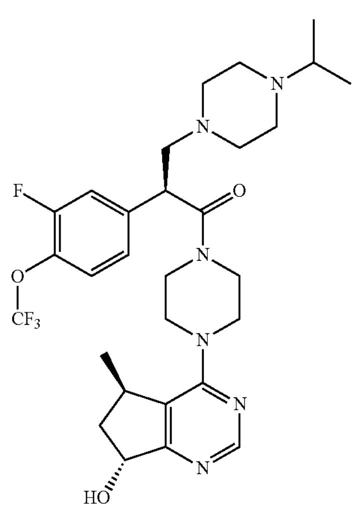 [SMILES: CC(C)N1CCN(C[C@@H](C(=O)N2CCN(c3ncnc4c3[C@H](C)C[C@H]4O)CC2)c2ccc(OC(F)(F)F)c(F)c2)CC1] | (S)-2-(3-fluoro-4-(trifluoromethoxy)phenyl)-1-(4-((5R,7R)-7-hydroxy-5-methyl-6,7-dihydro-5H-cyclopenta[d]pyrimidin-4-yl)piperazin-1-yl)-3-(4-isopropylpiperazin-1-yl)propan-1-one | 595.3 |

TABLE 1-continued

| Example | Structure | Name | LCMS or ¹H NMR |
|---------|-----------|------|----------------|
| 230 | 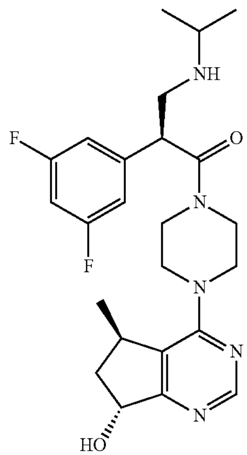 [SMILES: CC(C)NC[C@@H](C(=O)N1CCN(c2ncnc3c2[C@H](C)C[C@H]3O)CC1)c1cc(F)cc(F)c1] | (S)-2-(3,5-difluorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one | 460.3 |
| 231 | 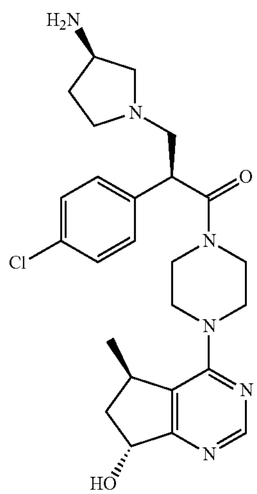 [SMILES: C[C@@H]1C[C@@H](O)c2ncnc(N3CCN(C(=O)[C@H](CN4CC[C@@H](N)C4)c4ccc(Cl)cc4)CC3)c21] | (S)-3-((R)-3-aminopyrrolidin-1-yl)-2-(4-chlorophenyl)-1-(4-((5R,7R)-7-hydroxy-5-methyl-6,7-dihydro-5H-cyclopenta[d]pyrimidin-4-yl)piperazin-1-yl)propan-1-one | 485.3 |
| 232 | 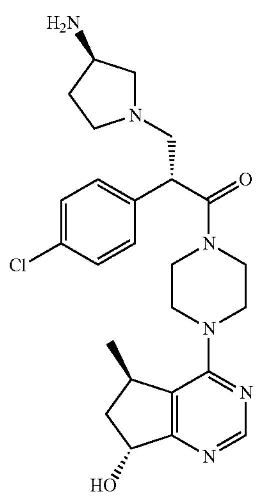 [SMILES: C[C@@H]1C[C@@H](O)c2ncnc(N3CCN(C(=O)[C@@H](CN4CC[C@@H](N)C4)c4ccc(Cl)cc4)CC3)c21] | (R)-3-((R)-3-aminopyrrolidin-1-yl)-2-(4-chlorophenyl)-1-(4-((5R,7R)-7-hydroxy-5-methyl-6,7-dihydro-5H-cyclopenta[d]pyrimidin-4-yl)piperazin-1-yl)propan-1-one | 485.3 |

TABLE 1-continued

| Example | Structure | Name | LCMS or ¹H NMR |
|---|---|---|---|
| 233 | 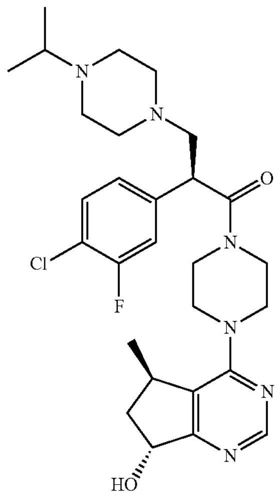 [SMILES: CC(C)N1CCN(C[C@@H](C(=O)N2CCN(c3ncnc4c3[C@H](C)C[C@H]4O)CC2)c2ccc(Cl)c(F)c2)CC1] | (S)-2-(4-chloro-3-fluorophenyl)-1-(4-((5R,7R)-7-hydroxy-5-methyl-6,7-dihydro-5H-cyclopenta[d]pyrimidin-4-yl)piperazin-1-yl)-3-(4-isopropylpiperazin-1-yl)propan-1-one | 545.3 |
| 234 | 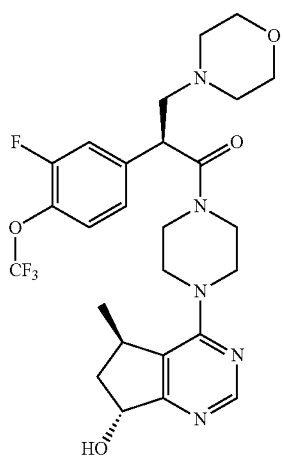 [SMILES: C[C@@H]1C[C@@H](O)c2ncnc(N3CCN(C(=O)[C@H](CN4CCOCC4)c4ccc(OC(F)(F)F)c(F)c4)CC3)c21] | (S)-2-(3-fluoro-4-(trifluoromethoxy)phenyl)-1-(4-((5R,7R)-7-hydroxy-5-methyl-6,7-dihydro-5H-cyclopenta[d]pyrimidin-4-yl)piperazin-1-yl)-3-morpholinopropan-1-one | 554.3 |
| 235 | 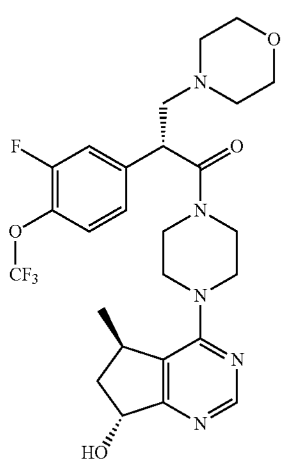 [SMILES: C[C@@H]1C[C@@H](O)c2ncnc(N3CCN(C(=O)[C@@H](CN4CCOCC4)c4ccc(OC(F)(F)F)c(F)c4)CC3)c21] | (R)-2-(3-fluoro-4-(trifluoromethoxy)phenyl)-1-(4-((5R,7R)-7-hydroxy-5-methyl-6,7-dihydro-5H-cyclopenta[d]pyrimidin-4-yl)piperazin-1-yl)-3-morpholinpropan-1-one | 554.3 |

TABLE 1-continued

| Example | Structure | Name | LCMS or ¹H NMR |
|---|---|---|---|
| 236 | 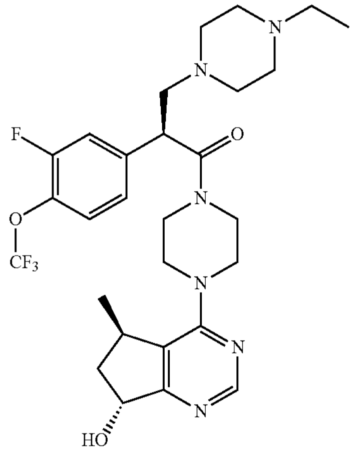 [SMILES: CCN1CCN(C[C@@H](C(=O)N2CCN(c3ncnc4c3[C@H](C)C[C@H]4O)CC2)c2ccc(OC(F)(F)F)c(F)c2)CC1] | (S)-3-(4-ethylpiperazin-1-yl)-2-(3-fluoro-4-(trifluoromethoxy)phenyl)-1-(4-((5R,7R)-7-hydroxy-5-methyl-6,7-dihydro-5H-cyclopenta[d]pyrimidin-4-yl)piperazin-1-yl)propan-1-one | 581.3 |
| 237 | 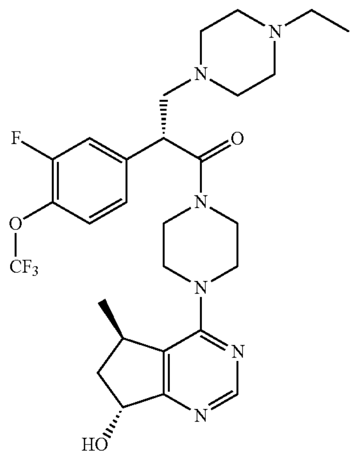 [SMILES: CCN1CCN(C[C@H](C(=O)N2CCN(c3ncnc4c3[C@H](C)C[C@H]4O)CC2)c2ccc(OC(F)(F)F)c(F)c2)CC1] | (R)-3-(4-ethylpiperazin-1-yl)-2-(3-fluoro-4-(trifluoromethoxy)phenyl)-1-(4-((5R,7R)-7-hydroxy-5-methyl-6,7-dihydro-5H-cyclopenta[d]pyrimidin-4-yl)piperazin-1-yl)propan-1-one | 581.3 |
| 238 | 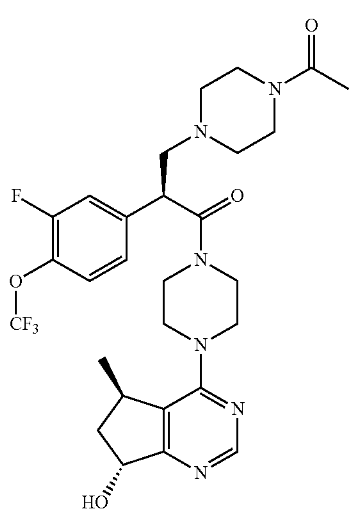 [SMILES: CC(=O)N1CCN(C[C@@H](C(=O)N2CCN(c3ncnc4c3[C@H](C)C[C@H]4O)CC2)c2ccc(OC(F)(F)F)c(F)c2)CC1] | (S)-3-(4-acetylpiperazin-1-yl)-2-(3-fluoro-4-(trifluoromethoxy)phenyl)-1-(4-((5R,7R)-7-hydroxy-5-methyl-6,7-dihydro-5H-cyclopenta[d]pyrimidin-4-yl)piperazin-1-yl)propan-1-one | 595.3 |

TABLE 1-continued

| Example | Structure | Name | LCMS or ¹H NMR |
|---|---|---|---|
| 239 | 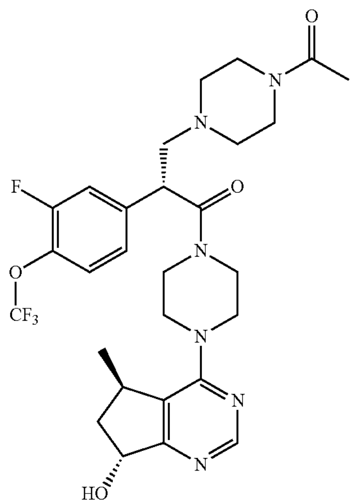 [SMILES: CC(=O)N1CCN(C[C@H](C(=O)N2CCN(c3ncnc4c3[C@H](C)C[C@H]4O)CC2)c2ccc(OC(F)(F)F)c(F)c2)CC1] | (R)-3-(4-acetylpiperazin-1-yl)-2-(3-fluoro-4-(trifluoromethoxy)phenyl)-1-(4-((5R,7R)-7-hydroxy-5-methyl-6,7-dihydro-5H-cyclopenta[d]pyrimidin-4-yl)piperazin-1-yl)propan-1-one | 595.3 |
| 240 | 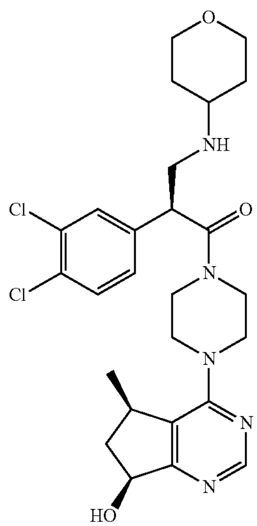 [SMILES: C[C@@H]1C[C@H](O)c2ncnc(N3CCN(C(=O)[C@H](CNC4CCOCC4)c4ccc(Cl)c(Cl)c4)CC3)c21] | (S)-2-(3,4-dichlorophenyl)-1-(4-((5R,7S)-7-hydroxy-5-methyl-6,7-dihydro-5H-cyclopenta[d]pyrimidin-4-yl)piperazin-1-yl)-3-(tetrahydro-2H-pyran-4-ylamino)propan-1-one | 534.2 |
| 241 | 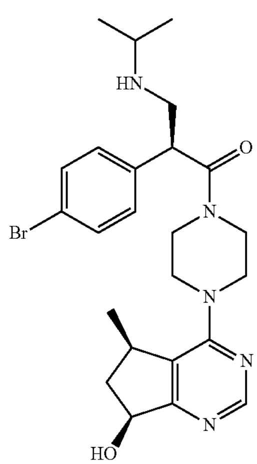 | (S)-2-(4-bromophenyl)-1-(4-((5R,7S)-7-hydroxy-5-methyl-6,7-dihydro-5H-cyclopenta[d]pyrimidin-4-yl)piperazin-1-yl)-3-(isopropylamino)propan-1-one | m/z 502/504 (Br isotope) [M + H]+ |

TABLE 1-continued

| Example | Structure | Name | LCMS or ¹H NMR |
|---|---|---|---|
| 242 | 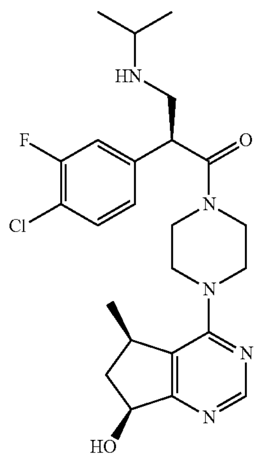 | (S)-2-(4-chloro-3-fluorophenyl)-1-(4-((5R,7S)-7-hydroxy-5-methyl-6,7-dihydro-5H-cyclopenta[d]pyrimidin-4-yl)piperazin-1-yl)-3-(isopropylamino)propan-1-one | m/z 476 [M + H]+ |
| 243 | 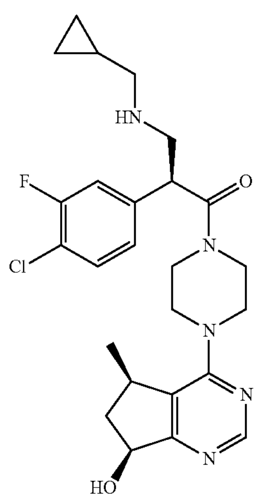 [SMILES: C[C@@H]1C[C@H](O)c2ncnc(N3CCN(C(=O)[C@H](CNCC4CC4)c4ccc(Cl)c(F)c4)CC3)c21] | (S)-2-(4-chloro-3-fluorophenyl)-3-(cyclopropylmethylamino)-1-(4-((5R,7S)-7-hydroxy-5-methyl-6,7-dihydro-5H-cyclopenta[d]pyrimidin-4-yl)piperazin-1-yl)propan-1-on | m/z 488 [M + H]+ |
| 244 | 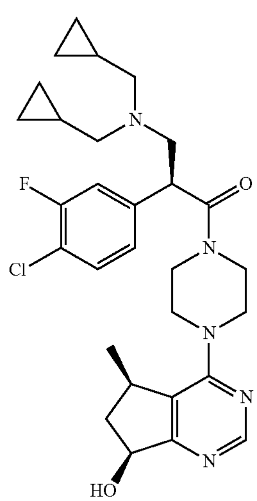 [SMILES: C[C@@H]1C[C@H](O)c2ncnc(N3CCN(C(=O)[C@H](CN(CC4CC4)CC4CC4)c4ccc(Cl)c(F)c4)CC3)c21] | (S)-3-(bis(cyclopropylmethyl)amino)-2-(4-chloro-3-fluorophenyl)-1-(4-((5R,7S)-7-hydroxy-5-methyl-6,7-dihydro-5H-cyclopenta[d]pyrimidin-4-yl)piperazin-1-yl)propan-1-one | m/z 542 [M + H]+ |

| Example | Structure | Name | LCMS or ¹H NMR |
|---|---|---|---|
| 245 | 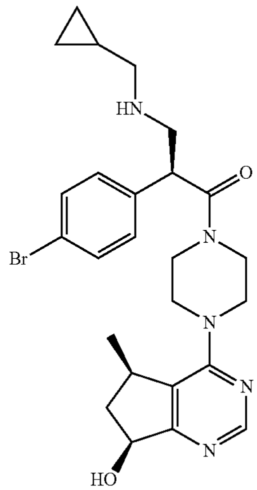 | (S)-2-(4-bromophenyl)-3-(cyclopropylmethylamino)-1-(4-((5R,7S)-7-hydroxy-5-methyl-6,7-dihydro-5H-cyclopenta[d]pyrimidin-4-yl)piperazin-1-yl)propan-1-one | m/z 514/516 (Br isotope) [M + H]+ |
| 246 | 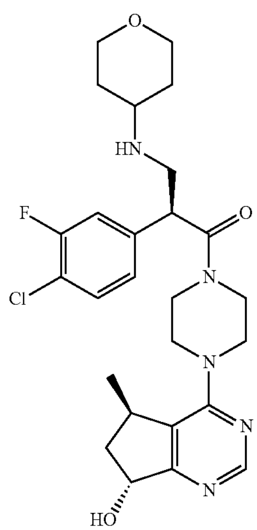 [SMILES: C[C@@H]1C[C@@H](O)c2ncnc(N3CCN(C(=O)[C@H](CNC4CCOCC4)c4ccc(Cl)c(F)c4)CC3)c21] | (S)-2-(4-chloro-3-fluorophenyl)-1-(4-((5R,7R)-7-hydroxy-5-methyl-6,7-dihydro-5H-cyclopenta[d]pyrimidin-4-yl)piperazin-1-yl)-3-(tetrahydro-2H-pyran-4-ylamino)propan-1-one | LCMS (APCI+) m/z 518, 520 [M + H]+ |
| 247 | 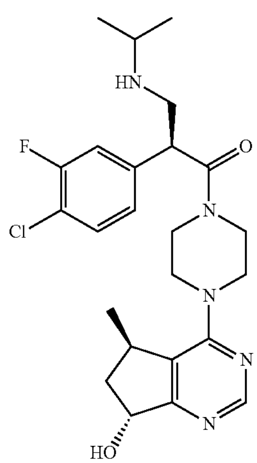 [SMILES: CC(C)NC[C@@H](C(=O)N1CCN(c2ncnc3c2[C@H](C)C[C@H]3O)CC1)c1ccc(Cl)c(F)c1] | (S)-2-(4-chloro-3-fluorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one | LCMS (APCI+) m/z 476, 478 [M + H]+ |

TABLE 1-continued

| Example | Structure | Name | LCMS or ¹H NMR |
|---|---|---|---|
| 248 | 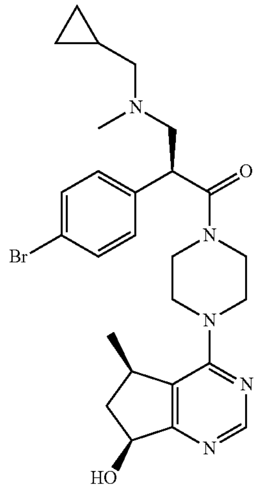 [SMILES: C[C@@H]1C[C@H](O)c2ncnc(N3CCN(C(=O)[C@H](CN(C)CC4CC4)c4ccc(Br)cc4)CC3)c21] | (S)-2-(4-bromophenyl)-3-((cyclopropylmethyl)(methyl)amino)-1-(4-((5R,7S)-7-hydroxy-5-methyl-6,7-dihydro-5H-cyclopenta[d]pyrimidin-4-yl)piperazin-1-yl)propan-1-one | m/z 528/530 (Br isotope) [M + H]+ |
| 249 | 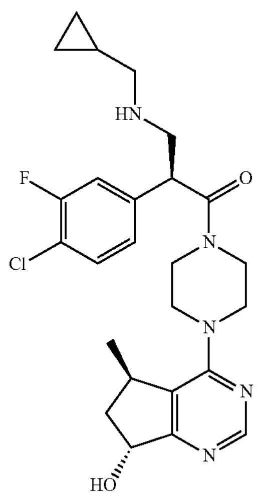 [SMILES: C[C@@H]1C[C@@H](O)c2ncnc(N3CCN(C(=O)[C@H](CNCC4CC4)c4ccc(Cl)c(F)c4)CC3)c21] | (S)-2-(4-chloro-3-fluorophenyl)-3-(cyclopropylmethylamino)-1-(4-((5R,7R)-7-hydroxy-5-methyl-6,7-dihydro-5H-cyclopenta[d]pyrimidin-4-yl)piperazin-1-yl)propan-1-one | LCMS (APCI+) m/z 488, 490 [M + H]+ |
| 250 | 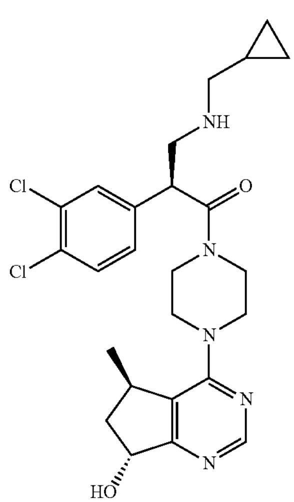 [SMILES: C[C@@H]1C[C@@H](O)c2ncnc(N3CCN(C(=O)[C@H](CNCC4CC4)c4ccc(Cl)c(Cl)c4)CC3)c21] | (S)-3-(cyclopropylmethylamino)-2-(3,4-dichlorophenyl)-1-(4-((5R,7R)-7-hydroxy-5-methyl-6,7-dihydro-5H-cyclopenta[d]pyrimidin-4-yl)piperazin-1-yl)propan-1-one | 504.3 |

TABLE 1-continued

| Example | Structure | Name | LCMS or ¹H NMR |
|---------|-----------|------|----------------|
| 251 | 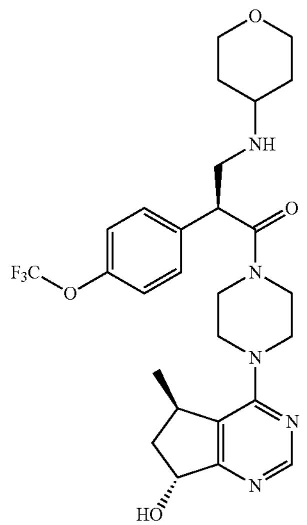 [SMILES: C[C@@H]1C[C@@H](O)c2ncnc(N3CCN(C(=O)[C@H](CNC4CCOCC4)c4ccc(OC(F)(F)F)cc4)CC3)c21] | (S)-1-(4-((5R,7R)-7-hydroxy-5-methyl-6,7-dihydro-5H-cyclopenta[d]pyrimidin-4-yl)piperazin-1-yl)-3-(tetrahydro-2H-pyran-4-ylamino)-2-(4-(trifluoromethoxy)phenyl)propan-1-one | 550.3 |
| 252 | 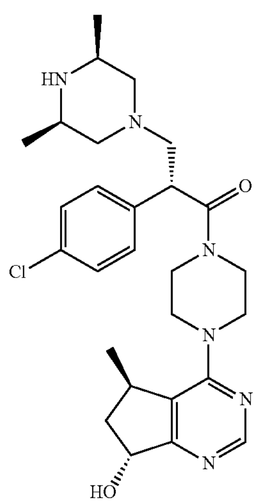 [SMILES: C[C@@H]1CN(C[C@H](C(=O)N2CCN(c3ncnc4c3[C@H](C)C[C@H]4O)CC2)c2ccc(Cl)cc2)C[C@H](C)N1] | (R)-2-(4-chlorophenyl)-3-((3S,5R)-3,5-dimethylpiperazin-1-yl)-1-(4-((5R,7R)-7-hydroxy-5-methyl-6,7-dihydro-5H-cyclopenta[d]pyrimidin-4-yl)piperazin-1-yl)propan-1-one | 513.3 |
| 253 | 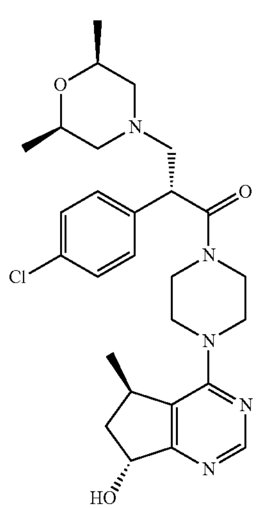 [SMILES: C[C@@H]1CN(C[C@H](C(=O)N2CCN(c3ncnc4c3[C@H](C)C[C@H]4O)CC2)c2ccc(Cl)cc2)C[C@H](C)O1] | (R)-2-(4-chlorophenyl)-3-((2S,6R)-2,6-dimethylmorpholino)-1-(4-((5R,7R)-7-hydroxy-5-methyl-6,7-dihydro-5H-cyclopenta[d]pyrimidin-4-yl)piperazin-1-yl)propan-1-one | 514.3 |

TABLE 1-continued

| Example | Structure | Name | LCMS or ¹H NMR |
|---|---|---|---|
| 254 | 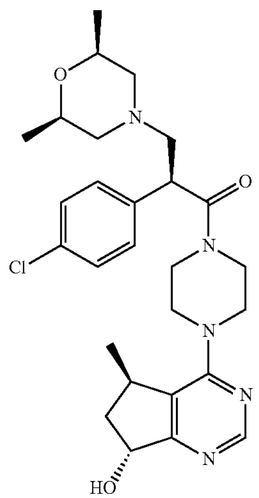 [SMILES: C[C@@H]1CN(C[C@@H](C(=O)N2CCN(c3ncnc4c3[C@H](C)C[C@H]4O)CC2)c2ccc(Cl)cc2)C[C@H](C)O1] | (S)-2-(4-chlorophenyl)-3-((2S,6R)-2,6-dimethylmorpholino)-1-(4-((5R,7R)-7-hydroxy-5-methyl-6,7-dihydro-5H-cyclopenta[d]pyrimidin-4-yl)piperazin-1-yl)propan-1-one | 514.3 |
| 255 | 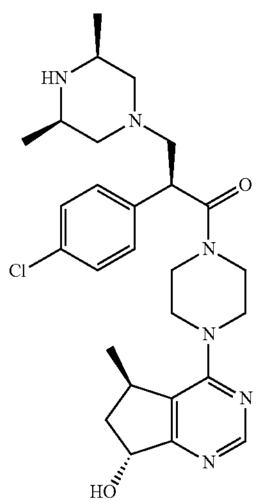 [SMILES: C[C@@H]1CN(C[C@@H](C(=O)N2CCN(c3ncnc4c3[C@H](C)C[C@H]4O)CC2)c2ccc(Cl)cc2)C[C@H](C)N1] | (S)-2-(4-chlorophenyl)-3-((3S,5R)-3,5-dimethylpiperazin-1-yl)-1-(4-((5R,7R)-7-hydroxy-5-methyl-6,7-dihydro-5H-cyclopenta[d]pyrimidin-4-yl)piperazin-1-yl)propan-1-one | 513.3 |
| 256 | 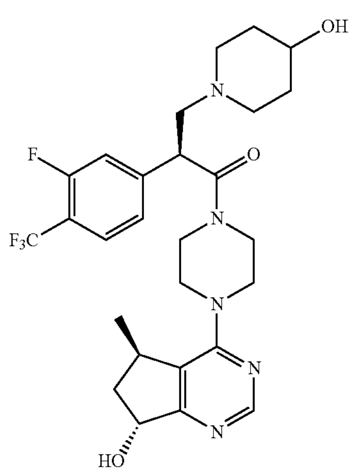 [SMILES: C[C@@H]1C[C@@H](O)c2ncnc(N3CCN(C(=O)[C@H](CN4CCC(O)CC4)c4ccc(C(F)(F)F)c(F)c4)CC3)c21] | (S)-2-(3-fluoro-4-(trifluoromethyl)phenyl)-1-(4-((5R,7R)-7-hydroxy-5-methyl-6,7-dihydro-5H-cyclopenta[d]pyrimidin-4-yl)piperazin-1-yl)-3-(4-hydroxypiperidin-1-yl)propan-1-one | 552.3 |

TABLE 1-continued

| Example | Structure | Name | LCMS or ¹H NMR |
|---|---|---|---|
| 257 | 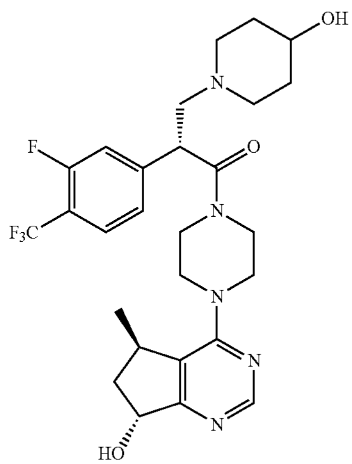 [SMILES: C[C@@H]1C[C@@H](O)c2ncnc(N3CCN(C(=O)[C@@H](CN4CCC(O)CC4)c4ccc(C(F)(F)F)c(F)c4)CC3)c21] | (R)-2-(3-fluoro-4-(trifluoromethyl)phenyl)-1-(4-((5R,7R)-7-hydroxy-5-methyl-6,7-dihydro-5H-cyclopenta[d]pyrimidin-4-yl)piperazin-1-yl)-3-(4-hydroxypiperidin-1-yl)propan-1-one | 552.3 |
| 258 | 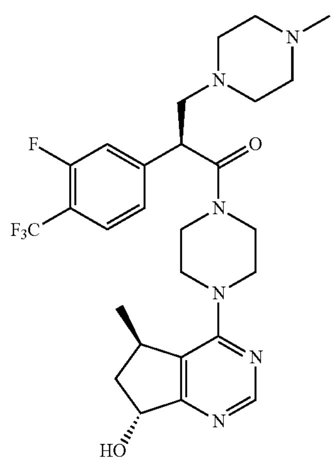 [SMILES: C[C@@H]1C[C@@H](O)c2ncnc(N3CCN(C(=O)[C@H](CN4CCN(C)CC4)c4ccc(C(F)(F)F)c(F)c4)CC3)c21] | (S)-2-(3-fluoro-4-(trifluoromethyl)phenyl)-1-(4-((5R,7R)-7-hydroxy-5-methyl-6,7-dihydro-5H-cyclopenta[d]pyrimidin-4-yl)piperazin-1-yl)-3-(4-methylpiperazin-1-yl)propan-1-one | 551.3 |
| 259 | 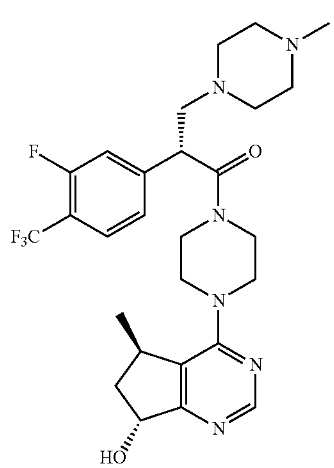 [SMILES: C[C@@H]1C[C@@H](O)c2ncnc(N3CCN(C(=O)[C@@H](CN4CCN(C)CC4)c4ccc(C(F)(F)F)c(F)c4)CC3)c21] | (R)-2-(3-fluoro-4-(trifluoromethyl)phenyl)-1-(4-((5R,7R)-7-hydroxy-5-methyl-6,7-dihydro-5H-cyclopenta[d]pyrimidin-4-yl)piperazin-1-yl)-3-(4-methylpiperazin-1-yl)propan-1-one | 551.3 |

TABLE 1-continued

| Example | Structure | Name | LCMS or ¹H NMR |
|---|---|---|---|
| 260 | 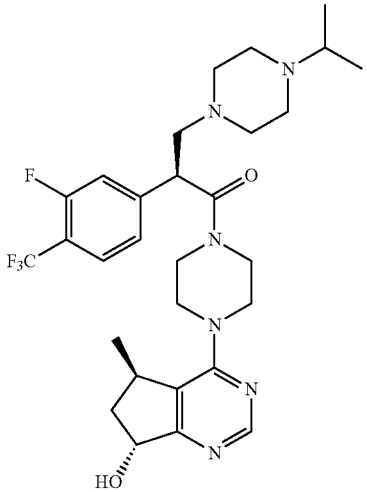 [SMILES: CC(C)N1CCN(C[C@@H](C(=O)N2CCN(c3ncnc4c3[C@H](C)C[C@H]4O)CC2)c2ccc(C(F)(F)F)c(F)c2)CC1] | (S)-2-(3-fluoro-4-(trifluoromethyl)phenyl)-1-(4-((5R,7R)-7-hydroxy-5-methyl-6,7-dihydro-5H-cyclopenta[d]pyrimidin-4-yl)piperazin-1-yl)-3-(4-isopropylpiperazin-1-yl)propan-1-one | 579.3 |
| 261 | 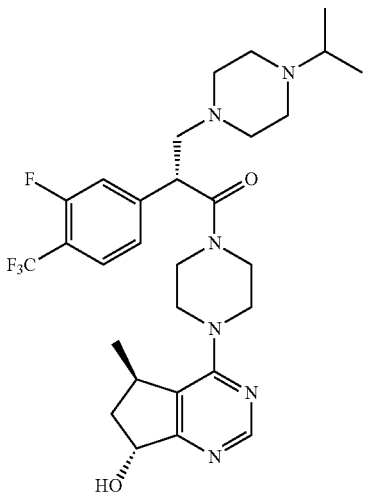 [SMILES: CC(C)N1CCN(C[C@H](C(=O)N2CCN(c3ncnc4c3[C@H](C)C[C@H]4O)CC2)c2ccc(C(F)(F)F)c(F)c2)CC1] | (R)-2-(3-fluoro-4-(trifluoromethyl)phenyl)-1-(4-((5R,7R)-7-hydroxy-5-methyl-6,7-dihydro-5H-cyclopenta[d]pyrimidin-4-yl)piperazin-1-yl)-3-(4-isopropylpiperazin-1-yl)propan-1-one | 579.3 |
| 262 | 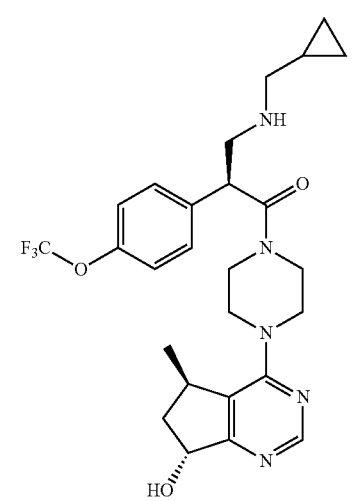 [SMILES: C[C@@H]1C[C@@H](O)c2ncnc(N3CCN(C(=O)[C@H](CNCC4CC4)c4ccc(OC(F)(F)F)cc4)CC3)c21] | (S)-3-(cyclopropylmethylamino)-1-(4-((5R,7R)-7-hydroxy-5-methyl-6,7-dihydro-5H-cyclopenta[d]pyrimidin-4-yl)piperazin-1-yl)-2-(4-(trifluoromethoxy)phenyl)propan-1-one | 520.3 |

TABLE 1-continued

| Example | Structure | Name | LCMS or ¹H NMR |
|---|---|---|---|
| 263 | 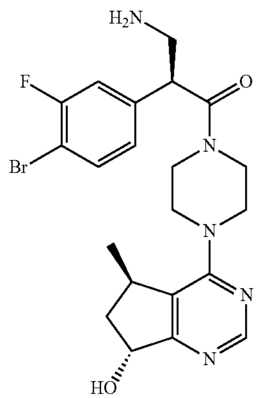 | (S)-3-amino-2-(4-bromo-3-fluorophenyl)-1-(4-((5R,7R)-7-hydroxy-5-methyl-6,7-dihydro-5H-cyclopenta[d]pyrimidin-4-yl)piperazin-1-yl)propan-1-one | 480.2 |
| 264 | 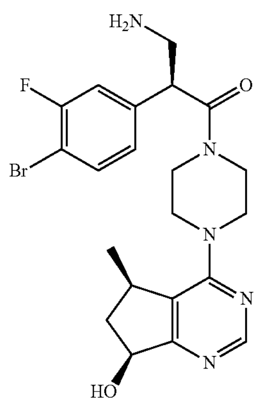 | (S)-3-amino-2-(4-bromo-3-fluorophenyl)-1-(4-((5R,7S)-7-hydroxy-5-methyl-6,7-dihydro-5H-cyclopenta[d]pyrimidin-4-yl)piperazin-1-yl)propan-1-one | 480.1 |
| 265 | 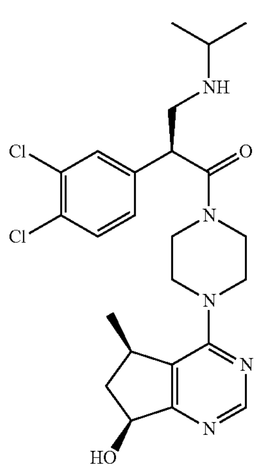 [SMILES: CC(C)NC[C@@H](C(=O)N1CCN(c2ncnc3c2[C@H](C)C[C@@H]3O)CC1)c1ccc(Cl)c(Cl)c1] | (S)-2-(3,4-dichlorophenyl)-1-(4-((5R,7S)-7-hydroxy-5-methyl-6,7-dihydro-5H-cyclopenta[d]pyrimidin-4-yl)piperazin-1-yl)-3-(isopropylamino)propan-1-one | 492.3 |

TABLE 1-continued

| Example | Structure | Name | LCMS or ¹H NMR |
|---|---|---|---|
| 266 | 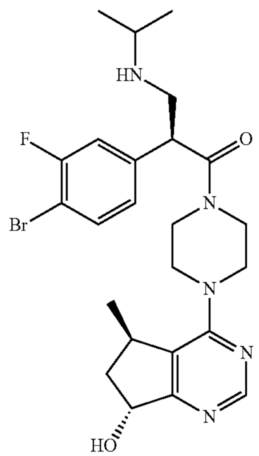 | (S)-2-(4-bromo-3-fluorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one | m/z 520, 522 [M + H]+ |
| 267 | 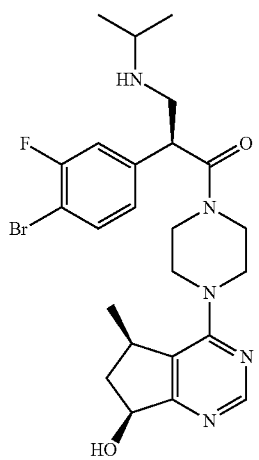 | (S)-2-(4-bromo-3-fluorophenyl)-1-(4-((5R,7S)-7-hydroxy-5-methyl-6,7-dihydro-5H-cyclopenta[d]pyrimidin-4-yl)piperazin-1-yl)-3-(isopropylamino)propan-1-one | m/z 520, 522 [M + H]+ |
| 268 | 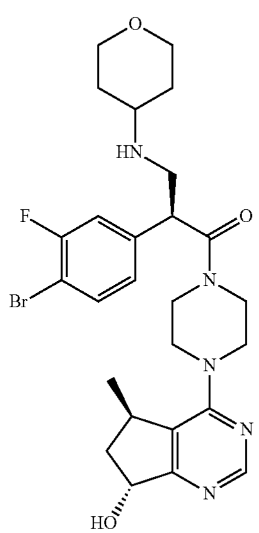 | (S)-2-(4-bromo-3-fluorophenyl)-1-(4-((5R,7R)-7-hydroxy-5-methyl-6,7-dihydro-5H-cyclopenta[d]pyrimidin-4-yl)piperazin-1-yl)-3-(tetrahydro-2H-pyran-4-ylamino)propan-1-one | m/z 562, 564 [M + H]+ |

TABLE 1-continued

| Example | Structure | Name | LCMS or ¹H NMR |
|---|---|---|---|
| 269 | 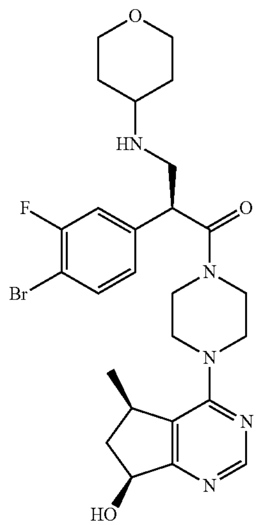 | (S)-2-(4-bromo-3-fluorophenyl)-1-(4-((5R,7S)-7-hydroxy-5-methyl-6,7-dihydro-5H-cyclopenta[d]pyrimidin-4-yl)piperazin-1-yl)-3-(tetrahydro-2H-pyran-4-ylamino)propan-1-one | m/z 562, 564 [M + H]+ |
| 270 | 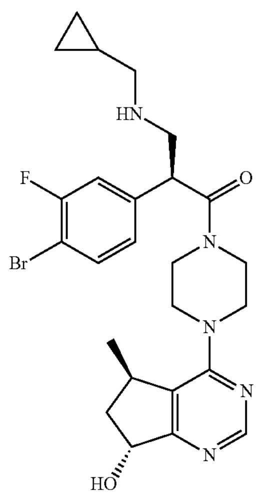 | (S)-2-(4-bromo-3-fluorophenyl)-3-(cyclopropylmethylamino)-1-(4-((5R,7R)-7-hydroxy-5-methyl-6,7-dihydro-5H-cyclopenta[d]pyrimidin-4-yl)piperazin-1-yl)propan-1-one | m/z 532, 534 [M + H]+ |
| 271 | 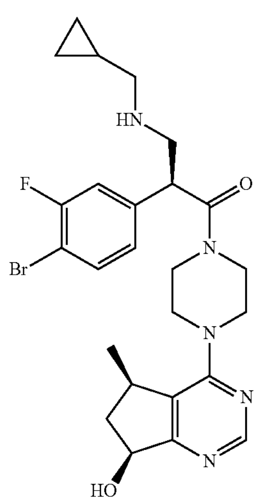 | (S)-2-(4-bromo-3-fluorophenyl)-3-(cyclopropylmethylamino)-1-(4-((5R,7S)-7-hydroxy-5-methyl-6,7-dihydro-5H-cyclopenta[d]pyrimidin-4-yl)piperazin-1-yl)propan-1-one | m/z 532, 534 [M + H]+ |

TABLE 1-continued

| Example | Structure | Name | LCMS or ¹H NMR |
|---|---|---|---|
| 272 | 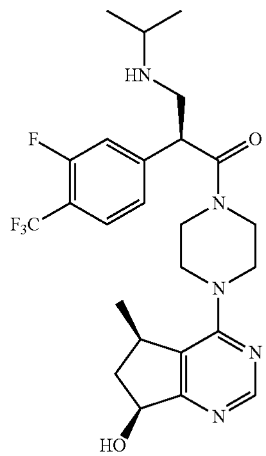 [SMILES: CC(C)NC[C@@H](C(=O)N1CCN(c2ncnc3c2[C@H](C)C[C@@H]3O)CC1)c1ccc(C(F)(F)F)c(F)c1] | (S)-2-(3-fluoro-4-(trifluoromethyl)phenyl)-1-(4-((5R,7S)-7-hydroxy-5-methyl-6,7-dihydro-5H-cyclopenta[d]pyrimidin-4-yl)piperazin-1-yl)-3-(isopropylamino)propan-1-one | 510.3 |
| 273 | 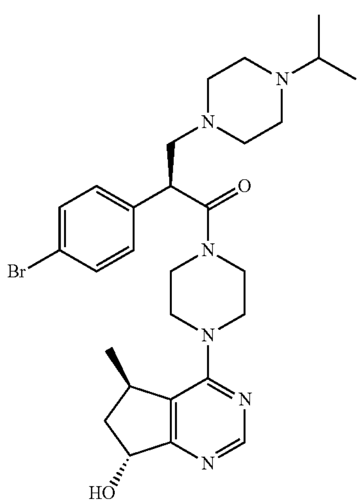 [SMILES: CC(C)N1CCN(C[C@@H](C(=O)N2CCN(c3ncnc4c3[C@H](C)C[C@H]4O)CC2)c2ccc(Br)cc2)CC1] | (S)-2-(4-bromophenyl)-1-(4-((5R,7R)-7-hydroxy-5-methyl-6,7-dihydro-5H-cyclopenta[d]pyrimidin-4-yl)piperazin-1-yl)-3-(4-isopropylpiperazin-1-yl)propan-1-one | 571.3 |
| 274 | 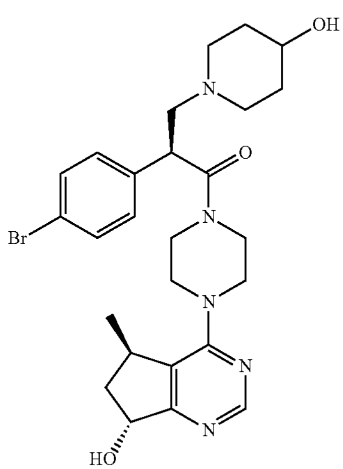 | (S)-2-(4-bromophenyl)-1-(4-((5R,7R)-7-hydroxy-5-methyl-6,7-dihydro-5H-cyclopenta[d]pyrimidin-4-yl)piperazin-1-yl)-3-(4-hydroxypiperidin-1-yl)propan-1-one | 546.2 |

| Example | Structure | Name | LCMS or ¹H NMR |
|---|---|---|---|
| 275 | 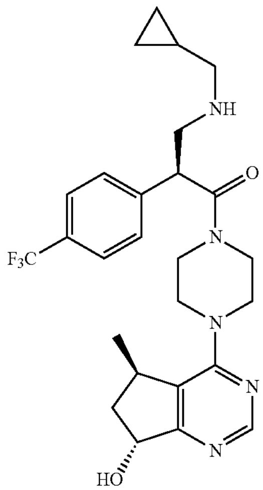 [SMILES: C[C@@H]1C[C@@H](O)c2ncnc(N3CCN(C(=O)[C@H](CNCC4CC4)c4ccc(C(F)(F)F)cc4)CC3)c21] | (S)-3-(cyclopropylmethylamino)-1-(4-((5R,7R)-7-hydroxy-5-methyl-6,7-dihydro-5H-cyclopenta[d]pyrimidin-4-yl)piperazin-1-yl)-2-(4-(trifluoromethyl)phenyl)propan-1-one | 504.3 |
| 276 | 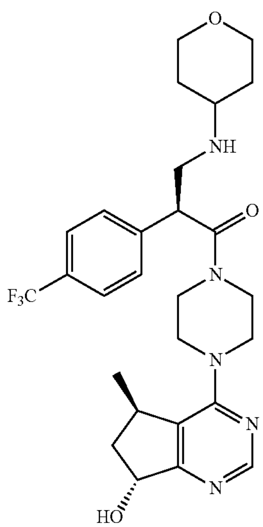 [SMILES: C[C@@H]1C[C@@H](O)c2ncnc(N3CCN(C(=O)[C@H](CNC4CCOCC4)c4ccc(C(F)(F)F)cc4)CC3)c21] | (S)-1-(4-((5R,7R)-7-hydroxy-5-methyl-6,7-dihydro-5H-cyclopenta[d]pyrimidin-4-yl)piperazin-1-yl)-3-(tetrahydro-2H-pyran-4-ylamino)-2-(4-(trifluoromethyl)phenyl)propan-1-one | 534.3 |
| 277 | 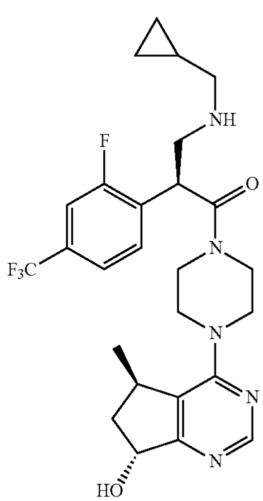 [SMILES: C[C@@H]1C[C@@H](O)c2ncnc(N3CCN(C(=O)[C@H](CNCC4CC4)c4ccc(C(F)(F)F)cc4F)CC3)c21] | (S)-3-(cyclopropylmethylamino)-2-(2-fluoro-4-(trifluoromethyl)phenyl)-1-(4-((5R,7R)-7-hydroxy-5-methyl-6,7-dihydro-5H-cyclopenta[d]pyrimidin-4-yl)piperazin-1-yl)propan-1-one | 522.3 |

TABLE 1-continued

| Example | Structure | Name | LCMS or ¹H NMR |
|---|---|---|---|
| 278 | 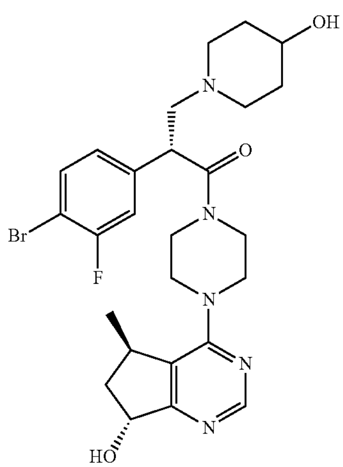 | (R)-2-(4-bromo-3-fluorophenyl)-1-(4-((5R,7R)-7-hydroxy-5-methyl-6,7-dihydro-5H-cyclopenta[d]pyrimidin-4-yl)piperazin-1-yl)-3-(4-hydroxypiperidin-1-yl)propan-1-one | 562.2 |
| 279 | 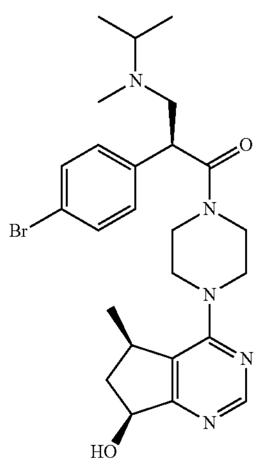 [SMILES: CC(C)N(C)C[C@@H](C(=O)N1CCN(c2ncnc3c2[C@H](C)C[C@@H]3O)CC1)c1ccc(Br)cc1] | (S)-2-(4-bromophenyl)-1-(4-((5R,7S)-7-hydroxy-5-methyl-6,7-dihydro-5H-cyclopenta[d]pyrimidin-4-yl)piperazin-1-yl)-3-(isopropyl(methyl)amino)propan-1-one | 518.2 |
| 280 | 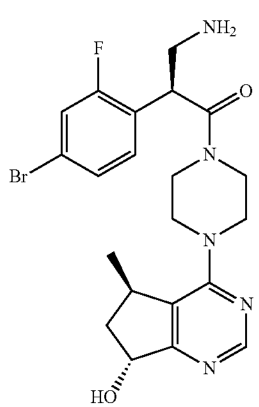 | (S)-3-amino-2-(4-bromo-2-fluorophenyl)-1-(4-((5R,7R)-7-hydroxy-5-methyl-6,7-dihydro-5H-cyclopenta[d]pyrimidin-4-yl)piperazin-1-yl)propan-1-one | 478.2 |

TABLE 1-continued

| Example | Structure | Name | LCMS or ¹H NMR |
|---|---|---|---|
| 281 | 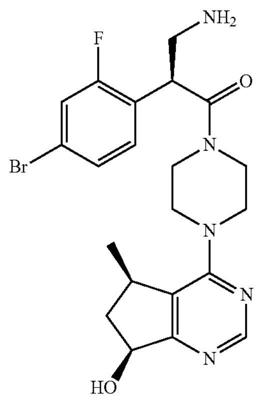 [SMILES: C[C@@H]1C[C@H](O)c2ncnc(N3CCN(C(=O)[C@H](CN)c4ccc(Br)cc4F)CC3)c21] | (S)-3-amino-2-(4-bromo-2-fluorophenyl)-1-(4-((5R,7S)-7-hydroxy-5-methyl-6,7-dihydro-5H-cyclopenta[d]pyrimidin-4-yl)piperazin-1-yl)propan-1-one | 478.2 |
| 282 | 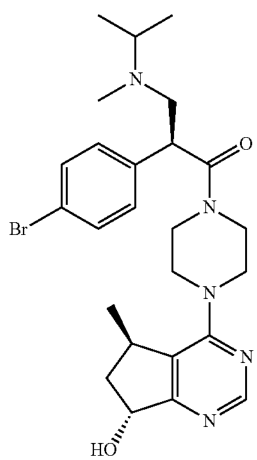 | (S)-2-(4-bromophenyl)-1-(4-((5R,7R)-7-hydroxy-5-methyl-6,7-dihydro-5H-cyclopenta[d]pyrimidin-4-yl)piperazin-1-l)-3-(isopropyl(methyl)amino)propan-1-one | 443.2 |
| 283 | 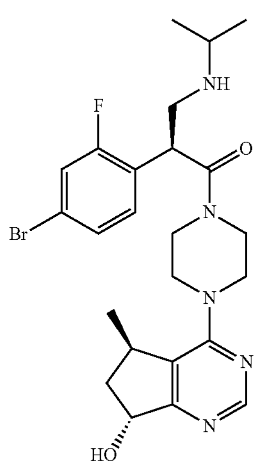 | (S)-2-(4-bromo-2-fluorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one | 520.2 |

| Example | Structure | Name | LCMS or ¹H NMR |
|---|---|---|---|
| 284 | 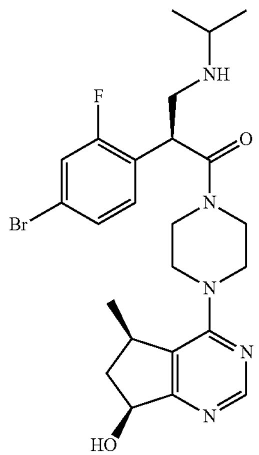 | (S)-2-(4-bromo-2-fluorophenyl)-1-(4-((5R,7S)-7-hydroxy-5-methyl-6,7-dihydro-5H-cyclopenta[d]pyrimidin-4-yl)piperazin-1-yl)-3-(isopropylamino)propan-1-one | 520.2 |
| 285 | 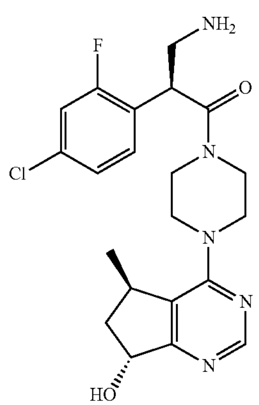 [SMILES: C[C@@H]1C[C@@H](O)c2ncnc(N3CCN(C(=O)[C@H](CN)c4ccc(Cl)cc4F)CC3)c21] | (S)-3-amino-2-(4-chloro-2-fluorophenyl)-1-(4-((5R,7R)-7-hydroxy-5-methyl-6,7-dihydro-5H-cyclopenta[d]pyrimidin-4-yl)piperazin-1-yl)propan-1-one | 434.2 |
| 286 | 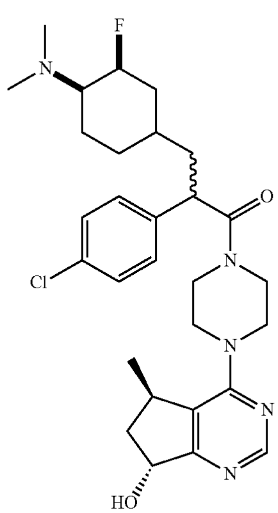 [SMILES: C[C@@H]1C[C@@H](O)c2ncnc(N3CCN(C(=O)C(CC4CC[C@@H](N(C)C)[C@@H](F)C4)c4ccc(Cl)cc4)CC3)c21] | 2-(4-chlorophenyl)-3-((3S,4R)-4-(dimethylamino)-3-fluoropiperidin-1-yl)-1-(4-((5R,7R)-7-hydroxy-5-methyl-6,7-dihydro-5H-cyclopenta[d]pyrimidin-4-yl)piperazin-1-yl)propan-1-one | 545.3 |

TABLE 1-continued

| Example | Name | LCMS or ¹H NMR |
|---|---|---|
| 287 | (S)-2-(4-bromo-2-fluorophenyl)-3-(cyclopropylmethylamino)-1-(4-((5R,7S)-7-hydroxy-5-methyl-6,7-dihydro-5H-cyclopenta[d]pyrimidin-4-yl)piperazin-1-yl)propan-1-one | 532.2 |
| 288 | (S)-3-(tert-butylamino)-1-(4-((5R,7R)-7-hydroxy-5-methyl-6,7-dihydro-5H-cyclopenta[d]pyrimidin-4-yl)piperazin-1-yl)-2-(4-(trifluoromethyl)phenyl)propan-1-one | 506.3 |
| 289 | (S)-2-(3-fluoro-4-(trifluoromethoxy)phenyl)-1-(4-((5R,7S)-7-hydroxy-5-methyl-6,7-dihydro-5H-cyclopenta[d]pyrimidin-4-yl)piperazin-1-yl)-3-(tetrahydro-2H-pyran-4-ylamino)propan-1-one | 567.6 |

TABLE 1-continued

| Example | Structure | Name | LCMS or ¹H NMR |
|---|---|---|---|
| 290 | 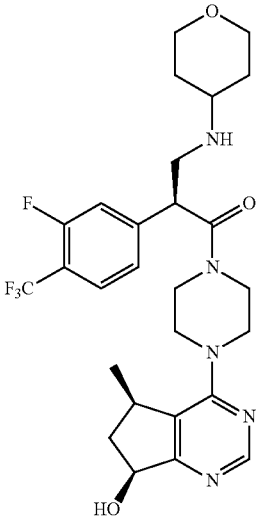 [SMILES: C[C@@H]1C[C@H](O)c2ncnc(N3CCN(C(=O)[C@H](CNC4CCOCC4)c4ccc(C(F)(F)F)c(F)c4)CC3)c21] | (S)-2-(3-fluoro-4-(trifluoromethyl)phenyl)-1-(4-((5R,7S)-7-hydroxy-5-methyl-6,7-dihydro-5H-cyclopenta[d]pyrimidin-4-yl)piperazin-1-yl)-3-(tetrahydro-2H-pyran-4-ylamino)propan-1-one | 552.3 |
| 291 | 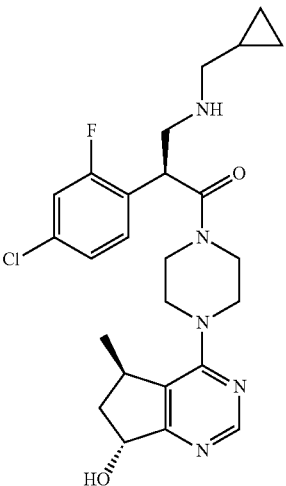 [SMILES: C[C@@H]1C[C@@H](O)c2ncnc(N3CCN(C(=O)[C@H](CNCC4CC4)c4ccc(Cl)cc4F)CC3)c21] | (S)-2-(4-chloro-2-fluorophenyl)-3-(cyclopropylmethylamino)-1-(4-((5R,7R)-7-hydroxy-5-methyl-6,7-dihydro-5H-cyclopenta[d]pyrimidin-4-yl)piperazin-1-yl)propan-1-one | 488.3 |
| 292 | 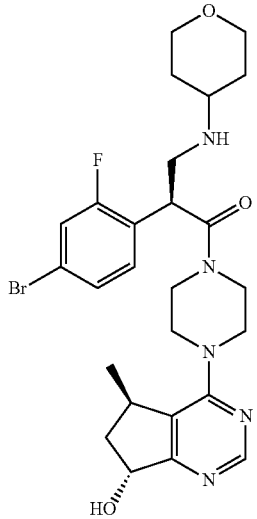 | (S)-2-(4-bromo-2-fluorophenyl)-1-(4-((5R,7R)-7-hydroxy-5-methyl-6,7-dihydro-5H-cyclopenta[d]pyrimidin-4-yl)piperazin-1-yl)-3-(tetrahydro-2H-pyran-4-ylamino)propan-1-one | 562.2 |

TABLE 1-continued

| Example | Structure | Name | LCMS or ¹H NMR |
|---|---|---|---|
| 293 | 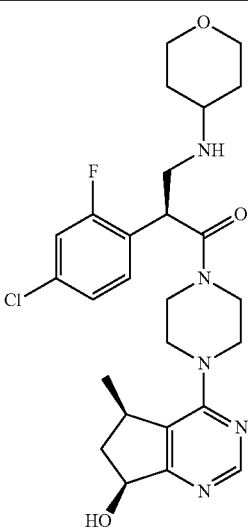 | (S)-2-(4-chloro-2-fluorophenyl)-1-(4-((5R,7S)-7-hydroxy-5-methyl-6,7-dihydro-5H-cyclopenta[d]pyrimidin-4-yl)piperazin-1-yl)-3-(tetrahydro-2H-pyran-4-ylamino)propan-1-one | 518.2 |
| 294 | 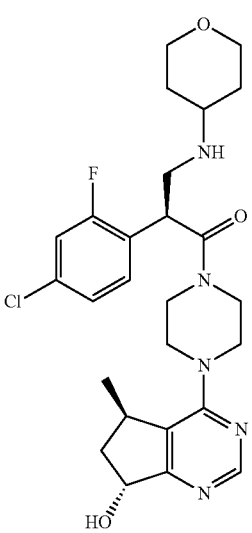 [SMILES: C[C@@H]1C[C@@H](O)c2ncnc(N3CCN(C(=O)[C@H](CNC4CCOCC4)c4ccc(Cl)cc4F)CC3)c21] | (S)-2-(4-chloro-2-fluorophenyl)-1-(4-((5R,7R)-7-hydroxy-5-methyl-6,7-dihydro-5H-cyclopenta[d]pyrimidin-4-yl)piperazin-1-yl)-3-(tetrahydro-2H-pyran-4-ylamino)propan-1-one | 518.3 |
| 295 | 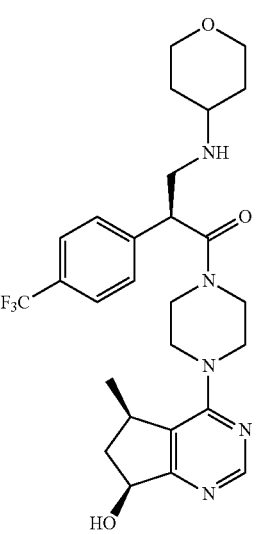 [SMILES: C[C@@H]1C[C@H](O)c2ncnc(N3CCN(C(=O)[C@H](CNC4CCOCC4)c4ccc(C(F)(F)F)cc4)CC3)c21] | (S)-1-(4-((5R,7S)-7-hydroxy-5-methyl-6,7-dihydro-5H-cyclopenta[d]pyrimidin-4-yl)piperazin-1-yl)-3-(tetrahydro-2H-pyran-4-ylamino)-2-(4-(trifluoromethyl)phenyl)propan-1-one | 534.2 |

TABLE 1-continued

| Example | Name | LCMS or ¹H NMR |
|---|---|---|
| 296 | (S)-3-(cyclopropylmethylamino)-1-(4-((5R,7S)-7-hydroxy-5-methyl-6,7-dihydro-5H-cyclopenta[d]pyrimidin-4-yl)piperazin-1-yl)-2-(4-(trifluoromethyl)phenyl)propan-1-one | 504.2 |
| 297 | (S)-2-(4-bromophenyl)-3-(tert-butylamino)-1-(4-((5R,7R)-7-hydroxy-5-methyl-6,7-dihydro-5H-cyclopenta[d]pyrimidin-4-yl)piperazin-1-yl)propan-1-one | 516.2 |
| 298 | (S)-2-(4-chloro-3-fluorophenyl)-1-(4-((5R,7R)-7-hydroxy-5-methyl-6,7-dihydro-5H-cyclopenta[d]pyrimidin-4-yl)piperazin-1-yl)-3-(isobutylamino)propan-1-one | m/z 490, 492 [M + H]+ |

TABLE 1-continued

| Example | Structure | Name | LCMS or ¹H NMR |
| --- | --- | --- | --- |
| 299 | 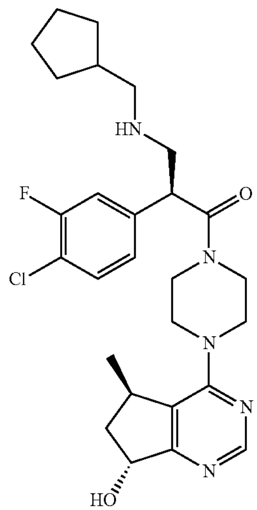 [SMILES: C[C@@H]1C[C@@H](O)c2ncnc(N3CCN(C(=O)[C@H](CNCC4CCCC4)c4ccc(Cl)c(F)c4)CC3)c21] | (S)-2-(4-chloro-3-fluorophenyl)-3-(cyclopentylmethylamino)-1-(4-((5R,7R)-7-hydroxy-5-methyl-6,7-dihydro-5H-cyclopenta[d]pyrimidin-4-yl)piperazin-1-yl)propan-1-one | m/z 516, 518 [M + H]+ |
| 300 | 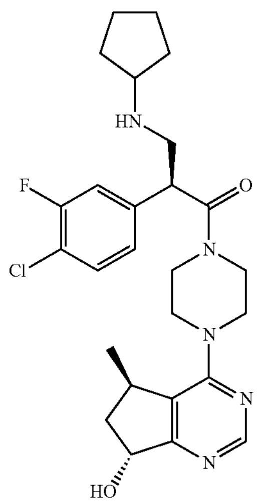 [SMILES: C[C@@H]1C[C@@H](O)c2ncnc(N3CCN(C(=O)[C@H](CNC4CCCC4)c4ccc(Cl)c(F)c4)CC3)c21] | (S)-2-(4-chloro-3-fluorophenyl)-3-(cyclopentylamino)-1-(4-((5R,7R)-7-hydroxy-5-methyl-6,7-dihydro-5H-cyclopenta[d]pyrimidin-4-yl)piperazin-1-yl)propan-1-one | m/z 502, 504 [M + H]+ |
| 301 | 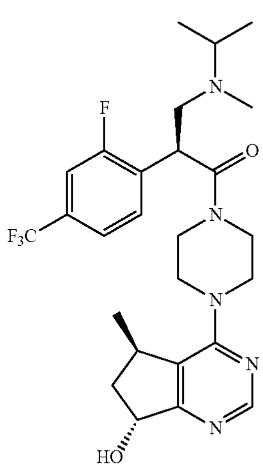 [SMILES: CC(C)N(C)C[C@@H](C(=O)N1CCN(c2ncnc3c2[C@H](C)C[C@H]3O)CC1)c1ccc(C(F)(F)F)cc1F] | (S)-2-(2-fluoro-4-(trifluoromethyl)phenyl)-1-(4-((5R,7R)-7-hydroxy-5-methyl-6,7-dihydro-5H-cyclopenta[d]pyrimidin-4-yl)piperazin-1-yl)-3-(isopropyl(methyl)amino)propan-1-one | 524.2 |

TABLE 1-continued

| Example | Structure | Name | LCMS or ¹H NMR |
|---|---|---|---|
| 302 | 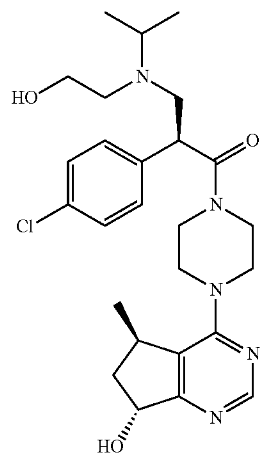 [SMILES: CC(C)N(CCO)C[C@@H](C(=O)N1CCN(c2ncnc3c2[C@H](C)C[C@H]3O)CC1)c1ccc(Cl)cc1] | (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-((2-hydroxyethyl)(isopropyl)amino)propan-1-one | 502.3 |
| 303 | 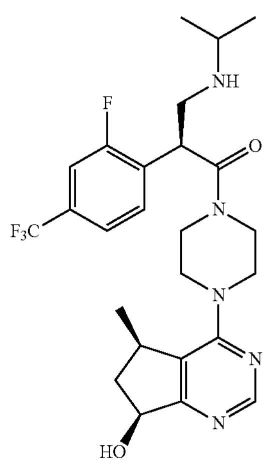 [SMILES: CC(C)NC[C@@H](C(=O)N1CCN(c2ncnc3c2[C@H](C)C[C@@H]3O)CC1)c1ccc(C(F)(F)F)cc1F] | (S)-2-(2-fluoro-4-(trifluoromethyl)phenyl)-1-(4-((5R,7S)-7-hydroxy-5-methyl-6,7-dihydro-5H-cyclopenta[d]pyrimidin-4-yl)piperazin-1-yl)-3-(isopropylamino)propan-1-one | 510.2 |
| 304 | 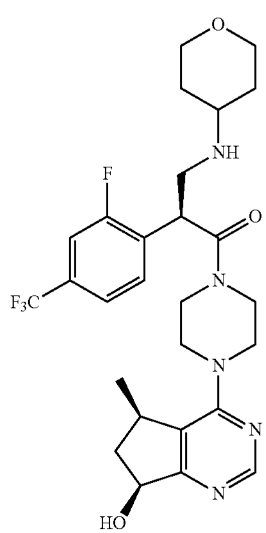 [SMILES: C[C@@H]1C[C@H](O)c2ncnc(N3CCN(C(=O)[C@H](CNC4CCOCC4)c4ccc(C(F)(F)F)cc4F)CC3)c21] | (S)-2-(2-fluoro-4-(trifluoromethyl)phenyl)-1-(4-((5R,7S)-7-hydroxy-5-methyl-6,7-dihydro-5H-cyclopenta[d]pyrimidin-4-yl)piperazin-1-yl)-3-(tetrahydro-2H-pyran-4-ylamino)propan-1-one | 552.3 |

TABLE 1-continued

| Example | Structure | Name | LCMS or ¹H NMR |
|---|---|---|---|
| 305 | 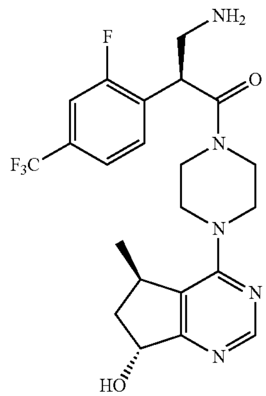 [SMILES: C[C@@H]1C[C@@H](O)c2ncnc(N3CCN(C(=O)[C@H](CN)c4ccc(C(F)(F)F)cc4F)CC3)c21] | (S)-3-amino-2-(2-fluoro-4-(trifluoromethyl)phenyl)-1-(4-((5R,7R)-7-hydroxy-5-methyl-6,7-dihydro-5H-cyclopenta[d]pyrimidin-4-yl)piperazin-1-yl)propan-1-one | 467.2 |
| 306 | 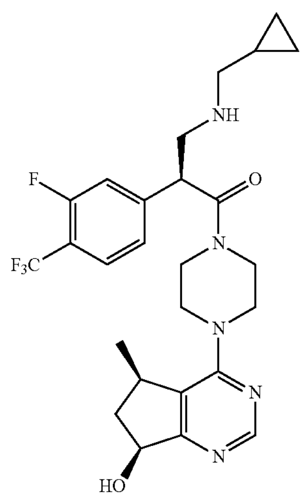 [SMILES: C[C@@H]1C[C@H](O)c2ncnc(N3CCN(C(=O)[C@H](CNCC4CC4)c4ccc(C(F)(F)F)c(F)c4)CC3)c21] | (S)-3-(cyclopropylmethylamino)-2-(3-fluoro-4-(trifluoromethyl)phenyl)-1-(4-((5R,7S)-7-hydroxy-5-methyl-6,7-dihydro-5H-cyclopenta[d]pyrimidin-4-yl)piperazin-1-yl)propan-1-one | 552.2 |
| 307 | 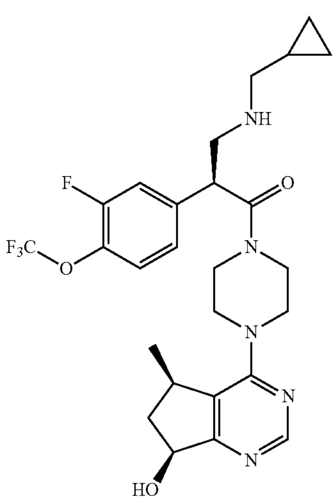 [SMILES: C[C@@H]1C[C@H](O)c2ncnc(N3CCN(C(=O)[C@H](CNCC4CC4)c4ccc(OC(F)(F)F)c(F)c4)CC3)c21] | (S)-3-(cyclopropylmethylamino)-2-(3-fluoro-4-(trifluoromethoxy)phenyl)-1-(4-((5R,7S)-7-hydroxy-5-methyl-6,7-dihydro-5H-cyclopenta[d]pyrimidin-4-yl)piperazin-1-yl)propan-1-one | 538.2 |

TABLE 1-continued

| Example | Structure | Name | LCMS or ¹H NMR |
|---------|-----------|------|----------------|
| 308 | 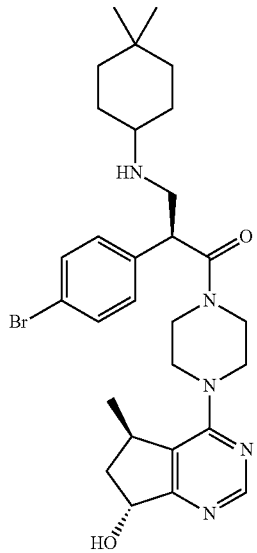 [SMILES: C[C@@H]1C[C@@H](O)c2ncnc(N3CCN(C(=O)[C@H](CNC4CCC(C)(C)CC4)c4ccc(Cl)cc4)CC3)c21] | (S)-2-(4-bromophenyl)-3-(4,4-dimethylcyclohexylamino)-1-(4-((5R,7R)-7-hydroxy-5-methyl-6,7-dihydro-5H-cyclopenta[d]pyrimidin-4-yl)piperaizn-1-yl)propan-1-one | 572.3 |
| 309 | 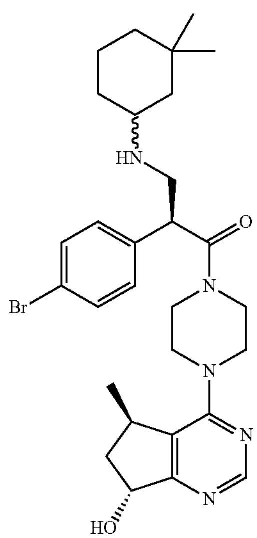 | (S)-2-(4-bromophenyl)-3-(3,3-dimethylcyclohexylamino)-1-(4-((5R,7R)-7-hydroxy-5-methyl-6,7-dihydro-5H-cyclopenta[d]pyrimidin-4-yl)piperazin-1-yl)propan-1-one | 570.3 |

| Example | Structure | Name | LCMS or ¹H NMR |
|---|---|---|---|
| 310 | 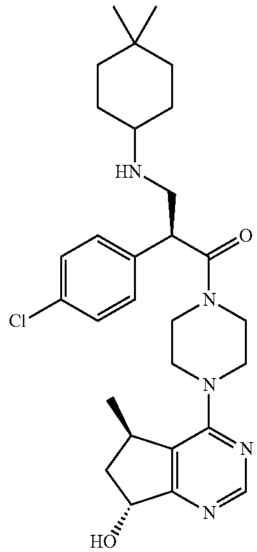 | (S)-2-(4-chlorophenyl)-3-(4,4-dimethylcyclohexylamino)-1-(4-((5R,7R)-7-hydroxy-5-methyl-6,7-dihydro-5H-cyclopenta[d]pyrimidin-4-yl)piperazin-1-yl)propan-1-one | 526.4 |
| 311 | 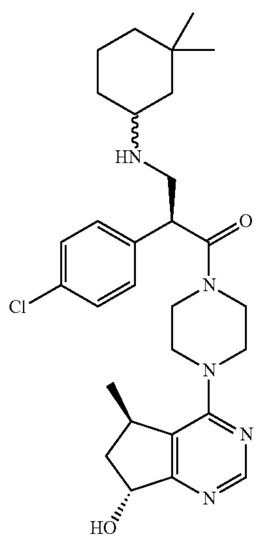 [SMILES: C[C@@H]1C[C@@H](O)c2ncnc(N3CCN(C(=O)[C@H](CNC4CCCC(C)(C)C4)c4ccc(Cl)cc4)CC3)c21] | (S)-2-(4-chlorophenyl)-3-(3,3-dimethylcyclohexylamino)-1-(4-((5R,7R)-7-hydroxy-5-methyl-6,7-dihydro-5H-cyclopenta[d]pyrimidin-4-yl)piperazin-1-yl)propan-1-one | 526.3 |
| 312 | 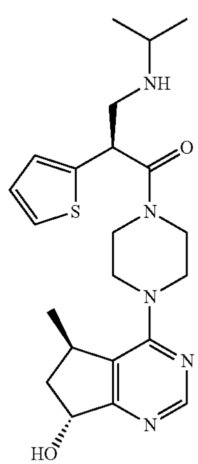 [SMILES: CC(C)NC[C@@H](C(=O)N1CCN(c2ncnc3c2[C@H](C)C[C@H]3O)CC1)c1cccs1] | (S)-1-(4-((5R,7R)-7-hydroxy-5-methyl-6,7-dihydro-5H-cyclopenta[d]pyrimidin-4-yl)piperazin-1-yl)-3-(isopropylamino)-2-(thiophen-2-yl)propan-1-one | 430.3 |

TABLE 1-continued

| Example | Structure | Name | LCMS or ¹H NMR |
|---------|-----------|------|----------------|
| 313 | 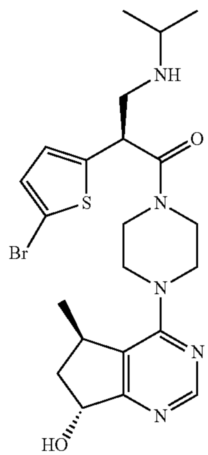 | (S)-2-(5-bromothiophen-2-yl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one | 508.2 |
| 314 | 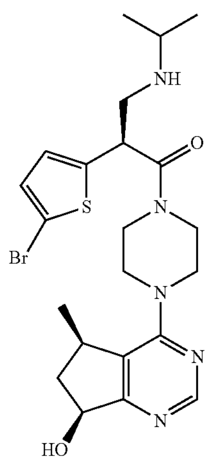 [SMILES: CC(C)NC[C@@H](C(=O)N1CCN(c2ncnc3c2[C@H](C)C[C@@H]3O)CC1)c1ccc(Br)s1] | (S)-2-(5-bromothiophen-2-yl)-1-(4-((5R,7S)-7-hydroxy-5-methyl-6,7-dihydro-5H-cyclopenta[d]pyrimidin-4-yl)piperazin-1-yl)-3-(isopropylamino)propan-1-one | 508.2 |
| 315 | 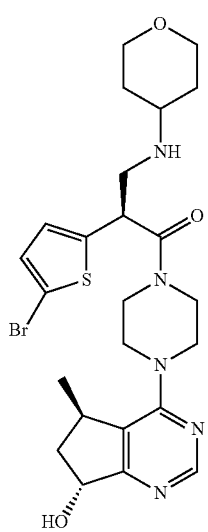 | (S)-2-(5-bromothiophen-2-yl)-1-(4-((5R,7R)-7-hydroxy-5-methyl-6,7-dihydro-5H-cyclopenta[d]pyrimidin-4-yl)piperazin-1-yl)-3-(tetrahydro-2H-pyran-4-ylamino)propan-1-one | 550.2 |

TABLE 1-continued

| Example | Structure | Name | LCMS or ¹H NMR |
|---|---|---|---|
| 316 | 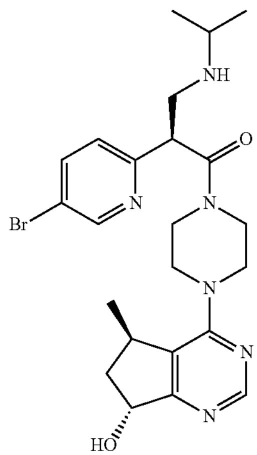 | (R)-2-(5-bromopyridin-2-yl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one | 503.2 |
| 317 | 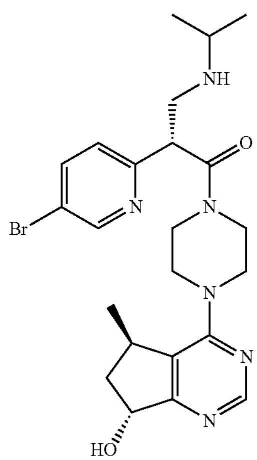 [SMILES: CC(C)NC[C@H](C(=O)N1CCN(c2ncnc3c2[C@H](C)C[C@H]3O)CC1)c1ccc(Br)cn1] | (S)-2-(5-bromopyridin-2-yl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one | 503.2 |
| 318 | 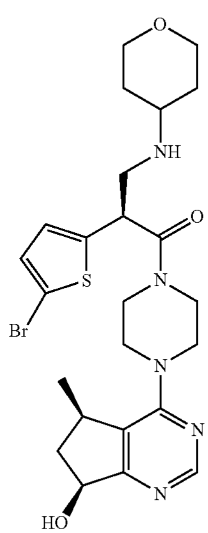 [SMILES: C[C@@H]1C[C@H](O)c2ncnc(N3CCN(C(=O)[C@H](CNC4CCOCC4)c4ccc(Br)s4)CC3)c21] | (S)-2-(5-bromothiophen-2-yl)-1-(4-((5R,7S)-7-hydroxy-5-methyl-6,7-dihydro-5H-cyclopenta[d]pyrimidin-4-yl)piperazin-1-yl)-3-(tetrahydro-2H-pyran-4-ylamino)propan-1-one | 550.2 |

TABLE 1-continued

| Example | Name | LCMS or ¹H NMR |
|---|---|---|
| 319 | (S)-2-(5-bromothiophen-2-yl)-3-(cyclopropylmethylamino)-1-(4-((5R,7R)-7-hydroxy-5-methyl-6,7-dihydro-5H-cyclopenta[d]pyrimidin-4-yl)piperazin-1-yl)propan-1-one | 520.2 |
| 320 | (S)-2-(5-chlorothiophen-2-yl)-1-(4-((5R,7S)-7-hydroxy-5-methyl-6,7-dihydro-5H-cyclopenta[d]pyrimidin-4-yl)piperazin-1-yl)-3-(tetrahydro-2H-pyran-4-ylamino)propan-1-one | 506.2 |
| 321 | (S)-2-(5-chlorothiophen-2-yl)-1-(4-((5R,7S)-7-hydroxy-5-methyl-6,7-dihydro-5H-cyclopenta[d]pyrimidin-4-yl)piperazin-1-yl)-3-(isopropylamino)propan-1-one | 464.2 |

TABLE 1-continued

| Example | Structure | Name | LCMS or ¹H NMR |
|---|---|---|---|
| 322 | 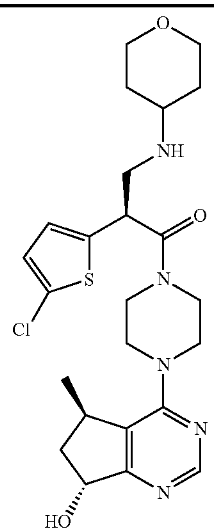 | (S)-2-(5-chlorothiophen-2-yl)-1-(4-((5R,7R)-7-hydroxy-5-methyl-6,7-dihydro-5H-cyclopenta[d]pyrimidin-4-yl)piperazin-1-yl)-3-(tetrahydro-2H-pyran-4-ylamino)propan-1-one | 506.2 |
| 323 | 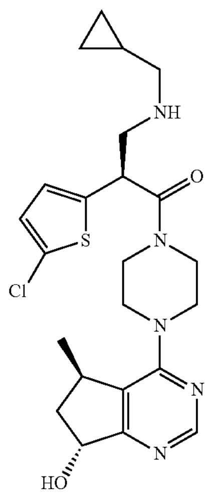 [SMILES: C[C@@H]1C[C@@H](O)c2ncnc(N3CCN(C(=O)[C@H](CNCC4CC4)c4ccc(Cl)s4)CC3)c21] | (S)-2-(5-chlorothiophen-2-yl)-3-(cyclopropylmethylamino)-1-(4-((5R,7R)-7-hydroxy-5-methyl-6,7-dihydro-5H-cyclopenta[d]pyrimidin-4-yl)piperazin-1-yl)propan-1-one | 476.2 |
| 324 | 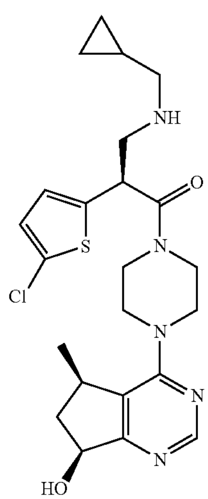 [SMILES: C[C@@H]1C[C@H](O)c2ncnc(N3CCN(C(=O)[C@H](CNCC4CC4)c4ccc(Cl)s4)CC3)c21] | (S)-2-(5-chlorothiophen-2-yl)-3-(cyclopropylmethylamino)-1-(4-((5R,7S)-7-hydroxy-5-methyl-6,7-dihydro-5H-cyclopenta[d]pyrimidin-4-yl)piperazin-1-yl)propan-1-one | 476.2 |

The foregoing description is considered as illustrative only of the principles of the invention. Further, since numerous modifications and changes will be readily apparent to those skilled in the art, it is not desired to limit the invention to the exact construction and process shown as described above. Accordingly, all suitable modifications and equivalents may be considered to fall within the scope of the invention as defined by the claims that follow.

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups.

What is claimed is:

1. A method of preparing a compound of Formula I:

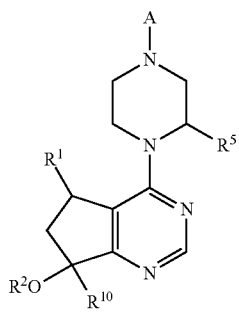

or a tautomer, resolved enantiomer, resolved diastereomer, or salt thereof, wherein:

$R^1$ is H, Me, Et, vinyl, $CF_3$, $CHF_2$ or $CH_2F$;
$R^2$ is H or Me;
$R^5$ is H, Me, Et, or $CF_3$;
A is

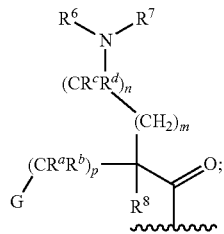

G is phenyl optionally substituted by one to four $R^9$ groups or a 5-6 membered heteroaryl optionally substituted by a halogen;

$R^6$ and $R^7$ are independently H, $OCH_3$, ($C_3$-$C_6$ cycloalkyl)-($CH_2$), ($C_3$-$C_6$ cycloalkyl)-($CH_2CH_2$), V—$(CH)_{0-1}$ wherein V is a 5-6 membered heteroaryl, W—$(CH_2)_{1-2}$ wherein W is phenyl optionally substituted with F, Cl, Br, I, OMe, $CF_3$ or Me, $C_3$-$C_6$-cycloalkyl optionally substituted with $C_1$-$C_3$ alkyl or $O(C_1$-$C_3$ alkyl), hydroxy-($C_3$-$C_6$-cycloalkyl), fluoro-($C_3$-$C_6$-cycloalkyl), $CH(CH_3)CH(OH)$phenyl, 4-6 membered heterocycle optionally substituted with F, OH, $C_1$-$C_3$ alkyl, cyclopropylmethyl or C(=O)($C_1$-$C_3$ alkyl), or $C_1$-$C_6$-alkyl optionally substituted with one or more groups independently selected from OH, oxo, O($C_1$-$C_6$-alkyl), CN, F, $NH_2$, NH($C_1$-$C_6$-alkyl), N($C_1$-$C_6$-alkyl)$_2$, cyclopropyl, phenyl, imidazolyl, piperidinyl, pyrrolidinyl, morpholinyl, tetrahydrofuranyl, oxetanyl or tetrahydropyranyl, or $R^6$ and $R^7$ together with the nitrogen to which they are attached form a 4-7 membered heterocyclic ring optionally substituted with one or more groups independently selected from OH, halogen, oxo, $CF_3$, $CH_2CF_3$, $CH_2CH_2OH$, O($C_1$-$C_3$ alkyl), C(=O)$CH_3$, $NH_2$, NHMe, $N(Me)_2$, $S(O)_2CH_3$, cyclopropylmethyl and $C_1$-$C_3$ alkyl;

$R^a$ and $R^b$ are H,
or $R^a$ is H, and $R^b$ and $R^6$ together with the atoms to which they are attached form a 5-6 membered heterocyclic ring having one or two ring nitrogen atoms;

$R^c$ and $R^d$ are H or Me,
or $R^c$ and $R^d$ together with the atom to which they are attached form a cyclopropyl ring;

$R^8$ is H, Me, F or OH,
or $R^8$ and $R^6$ together with the atoms to which they are attached form a 5-6 membered heterocyclic ring having one or two ring nitrogen atoms;

each $R^9$ is independently halogen, $C_1$-$C_6$-alkyl, $C_3$-$C_6$-cycloalkyl, O—($C_1$-$C_6$-alkyl), $CF_3$, $OCF_3$, S($C_1$-$C_6$-alkyl), CN, $OCH_2$-phenyl, $CH_2O$-phenyl, $NH_2$, NH—($C_1$-$C_6$-alkyl), N—($C_1$-$C_6$-alkyl)$_2$, piperidine, pyrrolidine, $CH_2F$, $CHF_2$, $OCH_2F$, $OCHF_2$, OH, $SO_2$($C_1$-$C_6$-alkyl), C(O)$NH_2$, C(O)NH($C_1$-$C_6$-alkyl), and C(O)N($C_1$-$C_6$-alkyl)$_2$;

$R^{10}$ is H or Me; and
m, n and p are independently 0 or 1
said method comprising:
reacting a corresponding compound having the formula:

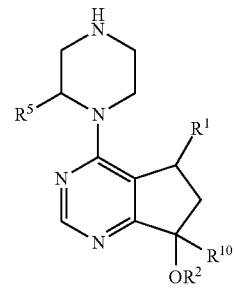

with a corresponding compound having the formula

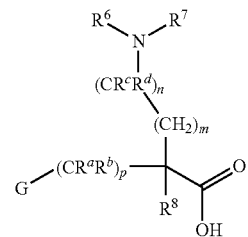

to provide the compound of formula I, the tautomer, the resolved enantiomer, the resolved diastereomer, or the salt thereof.

2. The method of claim 1, wherein $R^{10}$ is H.
3. The method of claim 1, wherein $R^{10}$ is methyl.
4. The method of claim 1, wherein $OR^2$ is in the (R) configuration.
5. The method of claim 1, wherein $R^2$ is H.
6. The method of claim 1, wherein $R^2$ is methyl.
7. The method of claim 1, wherein $R^5$ is H.
8. The method of claim 1, wherein $R^5$ is methyl.
9. The method of claim 1, wherein $R^5$ is in the (S) configuration.
10. The method of claim 1, wherein $R^5$ is methyl.

11. The method of claim 1, wherein $R^1$ is in the (R) configuration.

12. The method of claim 1, wherein $R^1$ is H.

13. The method of claim 1, wherein each $R^9$ group is independently selected from F, Cl, Br, I, Me, ethyl, isopropyl, CN, $CF_3$, $OCF_3$, SMe, OMe and $OCH_2Ph$.

14. The method of claim 1, wherein G is 4-chlorophenyl, 2,4-dichlorophenyl, 3-chloro-4-fluorophenyl, 3,4-difluorophenyl, 4-chloro-3-fluorophenyl, 3-fluoro-4-bromophenyl, 3,4-dichlorophenyl, 4-methoxyphenyl, 4-fluorophenyl, 4-bromophenyl, 4-cyanophenyl, 4-trifluoromethylphenyl, 4-thiomethylpyhenyl, or 4-methylphenyl.

15. The method of claim 1, wherein G is 4-iodophenyl, 4-trifluoromethoxyphenyl, 3,5-difluorophenyl, 4-bromo-3-fluorophenyl, 3-fluoro-4-methoxyphenyl, 3-fluoro-4-trifluoromethylphenyl, 3-trifluoromethoxy-4-chlorophenyl, 3-fluoro-4-trifluoromethoxyphenyl, 3-trifluoromethyl-4-chlorophenyl, 3-trifluoromethoxy-4-fluorophenyl, 3,5-bis(trifluoromethyl)phenyl, 3-chloro-5-fluorophenyl, 3-bromo-4-methoxyphenyl, 2-fluoro-4-chlorophenyl, 2-fluoro-4-bromophenyl, 2-fluoro-4-trifluoromethylphenyl, or 3-trifluoromethyl-4-fluorophenyl.

16. The method of claim 1, wherein G is a 5-6 membered heteroaryl optionally substituted by a halogen.

17. The method of claim 1, wherein G is a thiophene or pyridine optionally substituted by a halogen.

18. The method of claim 1, wherein G is selected from the structures:

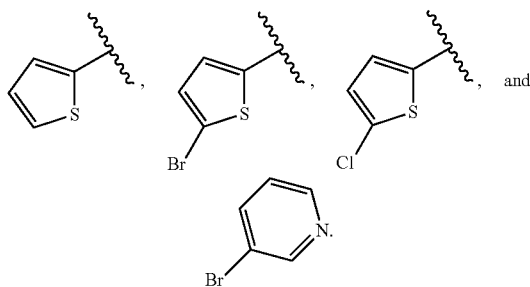

19. The method of claim 1, wherein $R^6$ and $R^7$ are independently selected from H, $OCH_3$, ($C_3$-$C_6$ cycloalkyl)-($CH_2$), ($C_3$-$C_6$ cycloalkyl)-($CH_2CH_2$), V—$(CH_2)_{0-1}$ wherein V is a 5-6 membered heteroaryl having from one to two ring heteroatoms independently selected from N, O and S, W—$(CH_2)_{1-2}$ wherein W is phenyl optionally substituted with F, Cl or Me, $C_3$-$C_6$-cycloalkyl optionally substituted with $OCH_3$, hydroxy-($C_3$-$C_6$-cycloalkyl), fluoro-($C_3$-$C_6$-cycloalkyl), $CH(CH_3)CH(OH)$phenyl, 5-6 membered heterocycle optionally substituted with $CH_3$ or $C(=O)CH_3$, or $C_1$-$C_6$-alkyl optionally substituted with one or more groups independently selected from OH, oxo, $O(C_1$-$C_6$-alkyl), CN, F, $NH_2$, $NH(C_1$-$C_6$-alkyl), $N(C_1$-$C_6$-alkyl)$_2$, phenyl, imidazolyl, piperidinyl, pyrrolidinyl, morpholinyl, and tetrahydropyranyl.

20. The method of claim 1, wherein $R^6$ and $R^7$ are independently selected from H, methyl, ethyl, isopropyl, isobutyl, tert-butyl, 3-pentyl, $OCH_3$, $CH_2CH_2OH$, $CH_2CH_2OMe$, $CH_2CH_2CF_3$, $CH_2CH(CH_3)OH$, $CH_2CH(CF_3)OH$, $CH_2CF_3$, $CH_2CH_2F$, $CH_2C(=O)NH_2$, $CH_2C(=O)NH(CH_3)$, $CH_2C(=O)N(CH_3)_2$, $CH_2C(=O)NH(iPr)$, $CH_2CH_2C(=O)NH_2$, $CH_2$-cyclopropyl, $CH_2$-cyclopentyl, $CH_2$-tBu (neopentyl), cyclopropyl, cyclopentyl, cyclohexyl, 4-methoxycyclohexyl, 4,4-dimethylcyclohexyl, 3,3-dimethylcyclohexyl, $CH_2$-(pyrid-3-yl), 4-hydroxycyclohex-1-yl, $CH(CH_3)CH(OH)$phenyl, $CH(phenyl)CH_2OH$, $CH(tetrahydropyranyl)CH_2OH$, $CH_2CH_2CH_2$(imidazolyl), $CH_2CH_2$(morpholinyl), $CH_2$(tetrahydropyranyl), $CH_2CH_2$(tetrahydropyranyl), pyrrolidinyl, piperidinyl, tetrahydropyranyl, tetrahydrofuranyl,

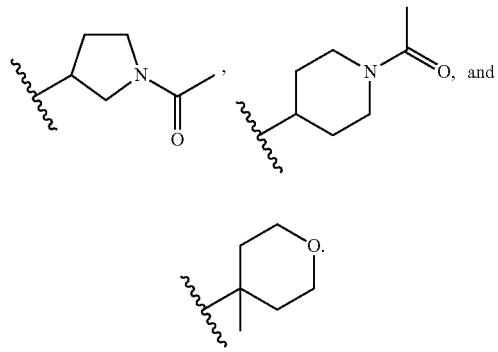

21. The method of claim 1, wherein $R^6$ and $R^7$ together with the nitrogen to which they are attached form a 4-7 membered heterocyclic ring, wherein said heterocyclic ring is optionally substituted with one or more groups independently selected from OH, halogen, oxo, $CF_3$, $CH_2CF_3$, $CH_2CH_2OH$, $OCH_3$, $C(=O)CH_3$, $NH_2$, NHMe, $N(Me)_2$, $S(O)_2CH_3$, and ($C_1$-$C_3$)alkyl.

22. The method of claim 21, wherein $NR^6R^7$ is selected from the structures:

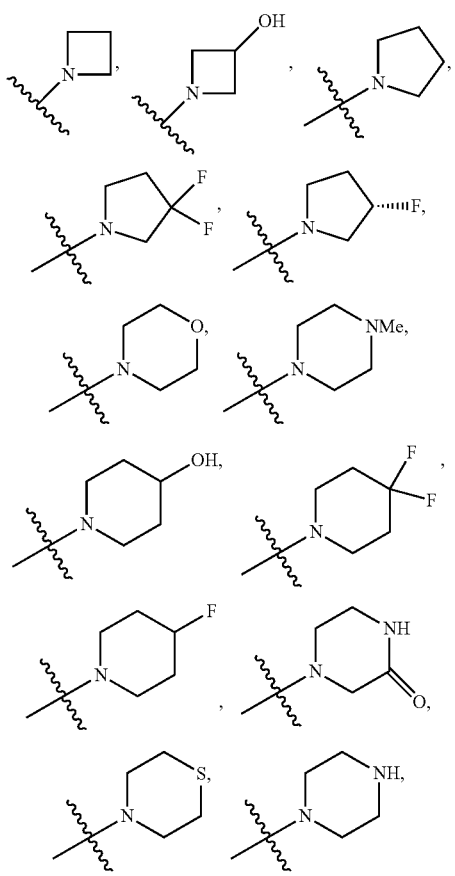

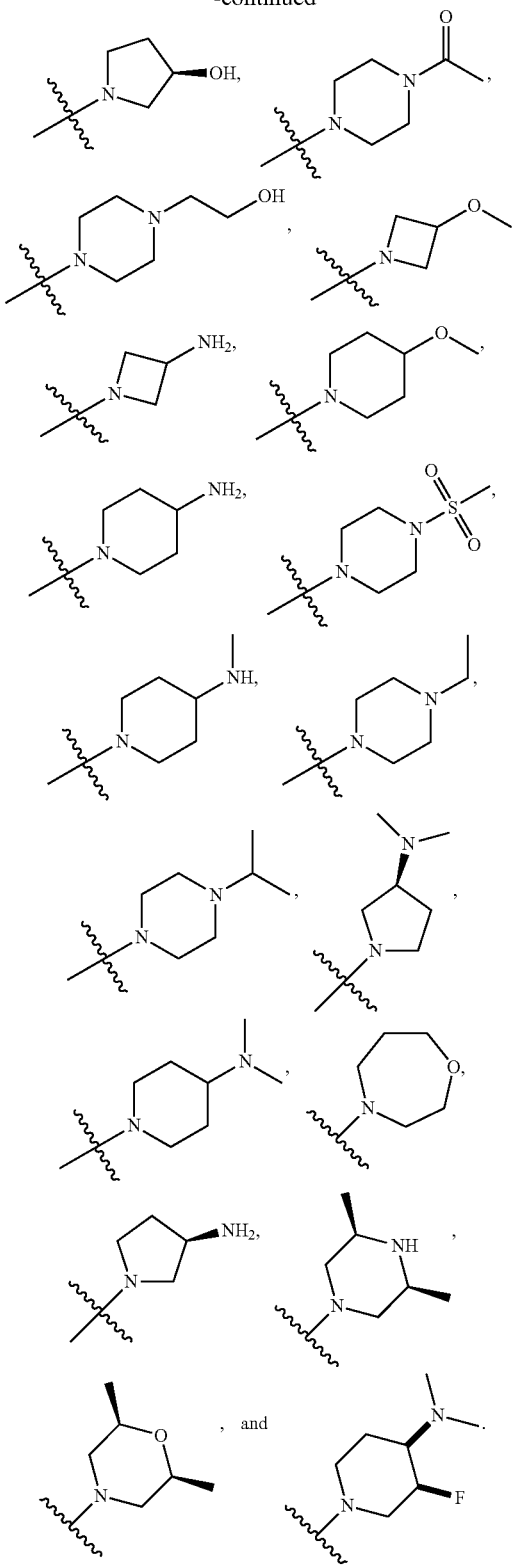

23. The method of claim 1, wherein $R^8$ and $R^6$ together with the atoms to which they are attached form a 5-6 membered heterocyclic ring having one or two ring nitrogen atoms.

24. The method of claim 23, wherein $R^7$ is H.

25. The method of claim 1, wherein $R^a$ is H, and $R^b$ and $R^6$ together with the atoms to which they are attached form a 5-6 membered heterocyclic ring having one or two ring nitrogen atoms.

26. The method of claim 25, wherein $R^7$ is H.

27. The method of claim 1, wherein m is 1, n is 0, p is 0, and A is represented by the formula:

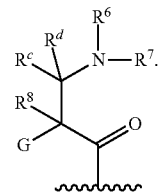

28. The method of claim 27, wherein A has the configuration:

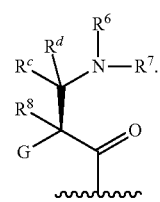

29. The method of claim 27, wherein $R^8$ is H or OH.

30. The method of claim 29, wherein $R^8$ is H.

31. The method of claim 28, wherein $R^6$ and $R^7$ are independently H, methyl, ethyl, isopropyl, isobutyl, tert-butyl, 3-pentyl, $CH_2CH_2OH$, $CH_2CH_2CH_2OH$, $CH(CH_2CH_2OH)_2$, $CH_2CH_2OMe$, $CH(CH_2CH_2OMe)_2$, $CH_2CH_2CH_2OMe$, $CH_2CN$, $CH_2$-cyclopropyl, $CH_2$-cyclobutyl, $CH_2$-tBu, cyclopentyl, cyclohexyl, $CH_2$-phenyl, $CH_2$-(pyrid-2-yl), $CH_2$-(pyrid-3-yl), $CH_2$-(pyrid-4-yl), 4-hydroxycyclohex-1-yl, or $CH(CH_3)CH(OH)$phenyl, or $R^6$ and $R^7$ together with the nitrogen to which they are attached form a pyrrolidinyl, piperidinyl, azetidinyl, morpholinyl, or piperizinyl ring optionally substituted with one or more groups independently selected from F, OH and Me.

32. The method of claim 28, wherein $R^6$ or $R^7$ may independently be $CH_2CF_3$, $CH_2CH_2F$, $CH_2$-cyclopentyl, 4-methoxycyclohexyl, 4,4-dimethylcyclohexyl, 3,3-dimethylcyclohexyl, pyrrolidinyl, piperidinyl, tetrahydropyranyl, tetrahydrofuranyl,

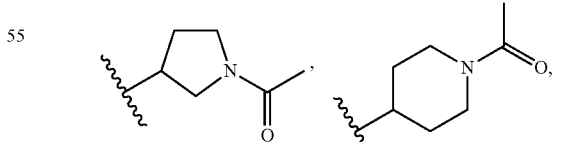

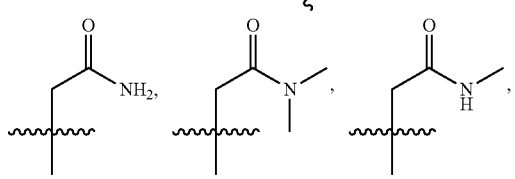

-continued

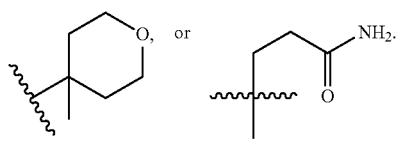

33. The method of claim 28, wherein NR⁶R⁷ is $NH_2$, NHMe, NHEt, NHPr, NHiPr, NHtBu, $NH(CH_2\text{-}tBu)$, $NH(CH_2\text{-cyclopropyl})$, $NH(CH_2\text{-cyclobutyl})$, NH(cyclopentyl), $NH(CH_2\text{-pyridyl})$, NH(cyclohexyl), NH(3-pentyl), $NHCH(isopropyl)_2$, $NH(CH_2CH_2OH)$, $NH(CH_2CH_2CH_2OH)$, $NH(CH_2CH_2OMe)$, $NH(CH_2CH_2CH_2OMe)$, $NH(CH_2CN)$, $NMe_2$, NMeEt, NMePr, NMe(iPr), $NMe(CH_2\text{-cyclopropyl})$, $NMe(CH_2\text{-cyclobutyl})$, $NMe(CH_2CH_2OH)$, $NMe(CH_2CH_2CH_2OH)$, $NMe(CH_2CH_2OMe)$, $NMe(CH_2CH_2CH_2OMe)$, $NEt_2$, NEtPr, NEt(iPr), $NEt(CH_2\text{-cyclopropyl})$, $NEt(CH_2\text{-cyclobutyl})$, $NEt(CH_2CH_2OH)$, $NEt(CH_2CH_2CH_2OH)$,

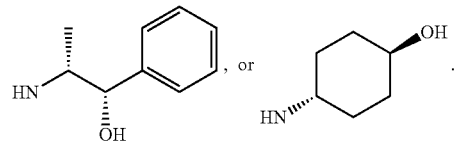

34. The method of claim 1, wherein NR⁶R⁷ is selected from the structures:

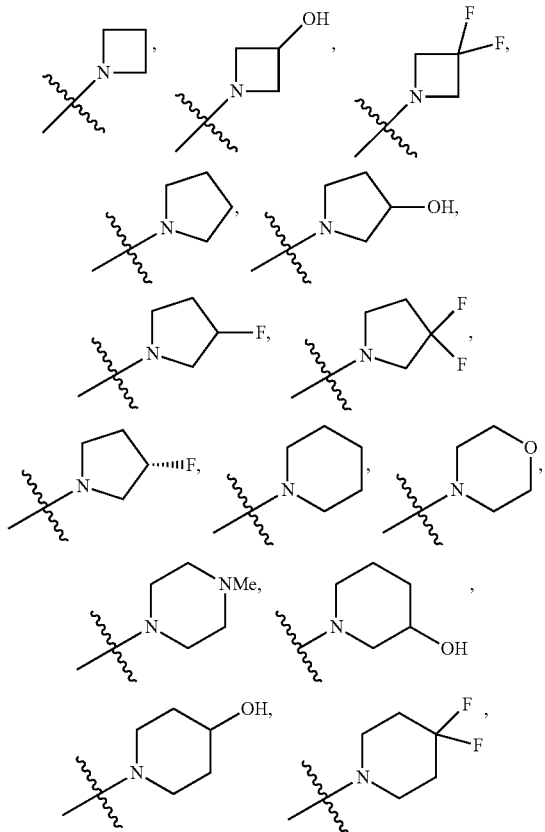

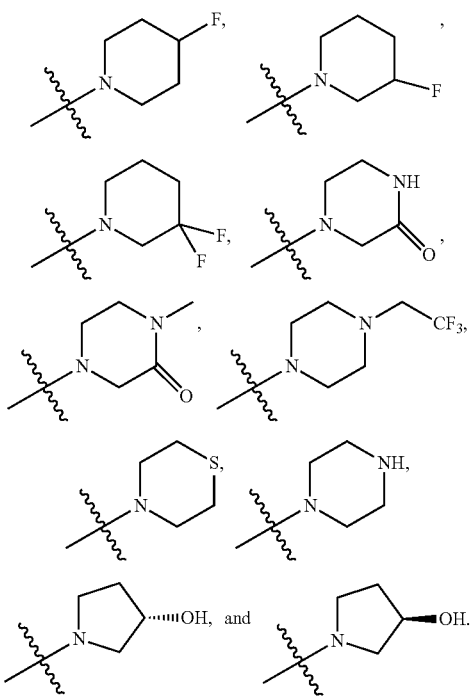

35. The method of claim 30, wherein R⁶ and R⁷ together with the nitrogen to which they are attached form a 4-6 membered heterocyclic ring, wherein said heterocyclic ring is optionally substituted with one or more groups independently selected from OH, halogen, oxo, $CF_3$, $CH_2CF_3$, $CH_2CH_2OH$, $OCH_3$, $C(=O)CH_3$, $NH_2$, NHMe, $N(Me)_2$, $S(O)_2CH_3$, and $(C_1\text{-}C_3)$alkyl.

36. The method of claim 1, wherein NR⁶R⁷ has the structure:

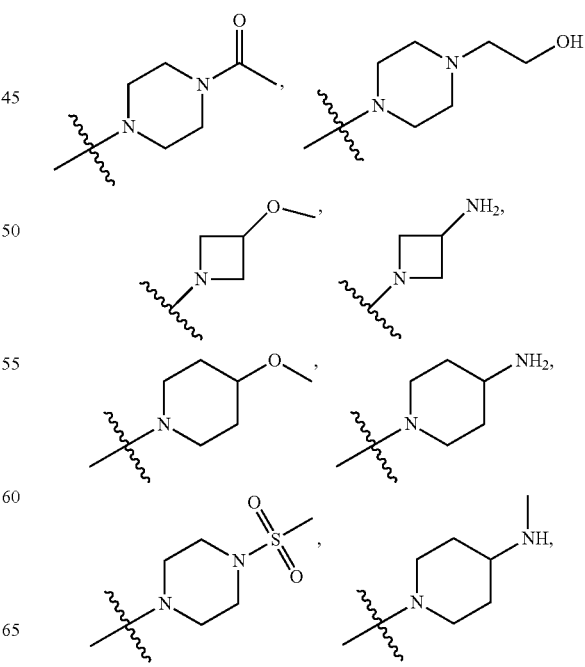

357
-continued
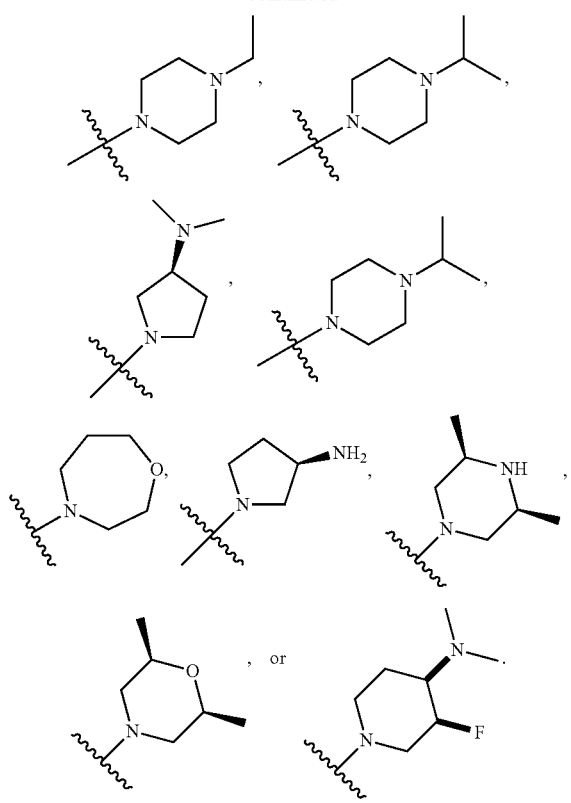
37. The method of claim 27, wherein A is selected from:
358
-continued
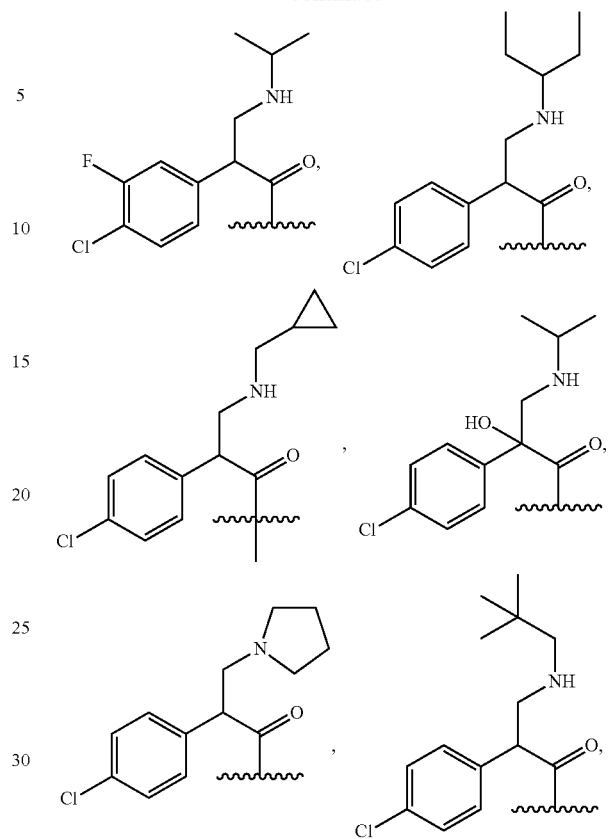
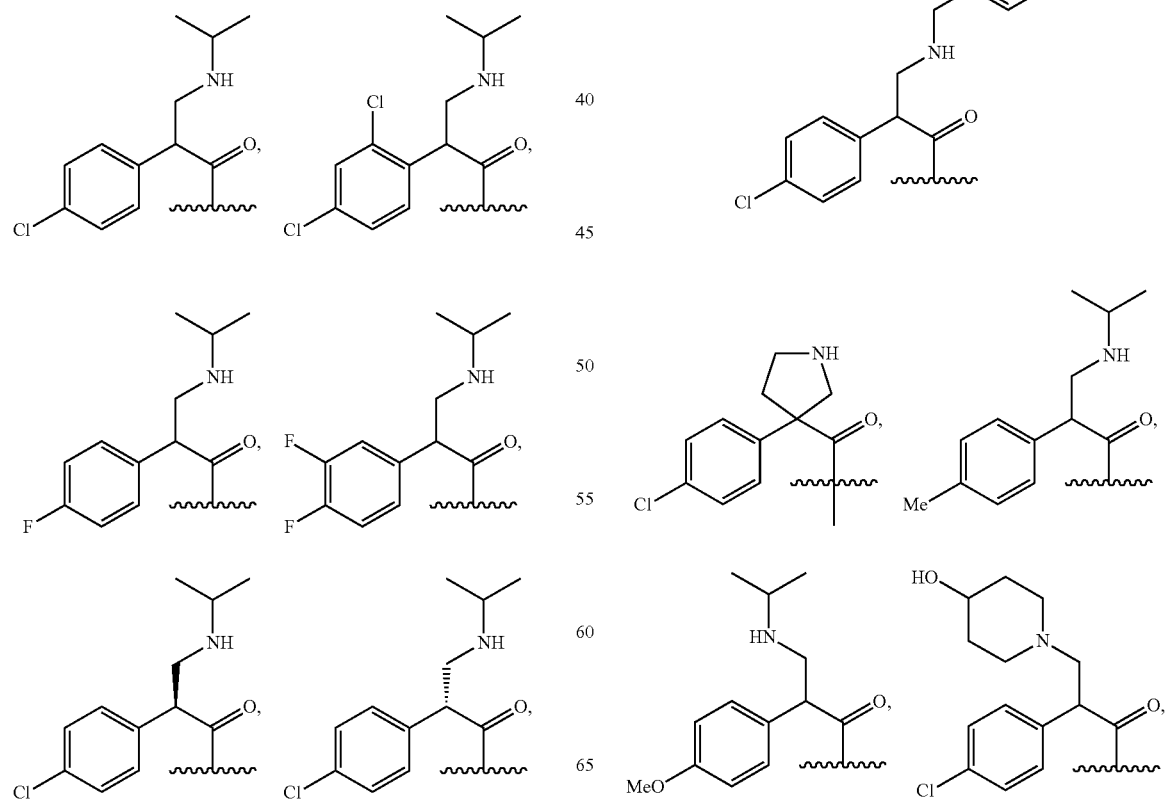

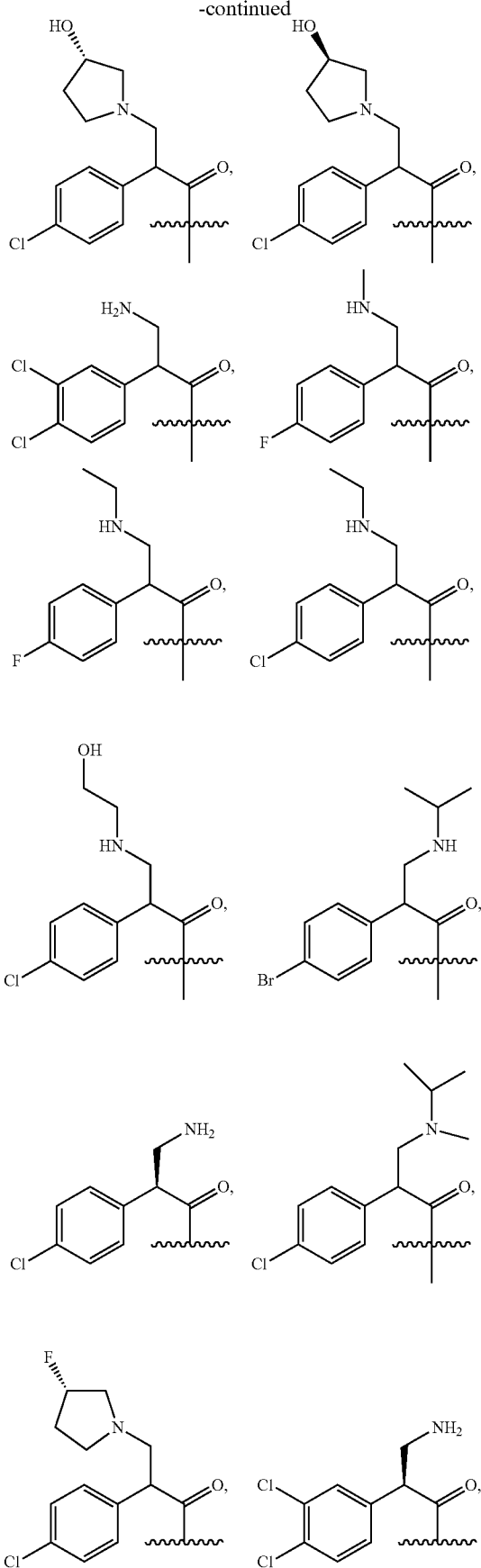
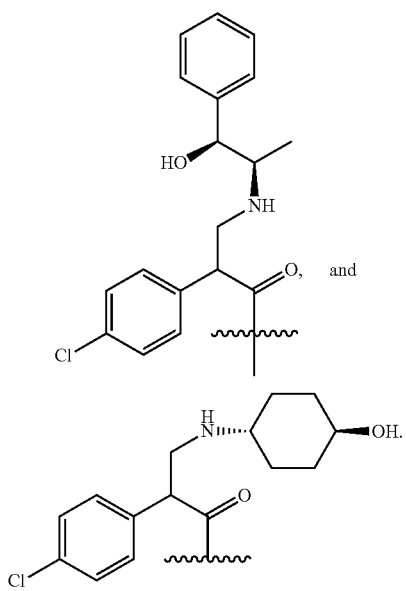
38. The method of claim 1, wherein A is selected from:
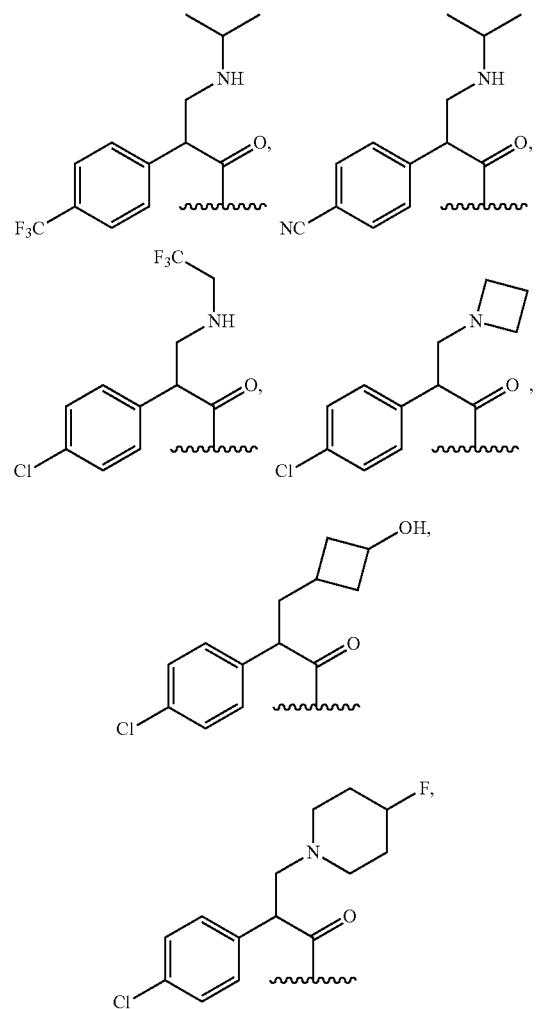

361
-continued
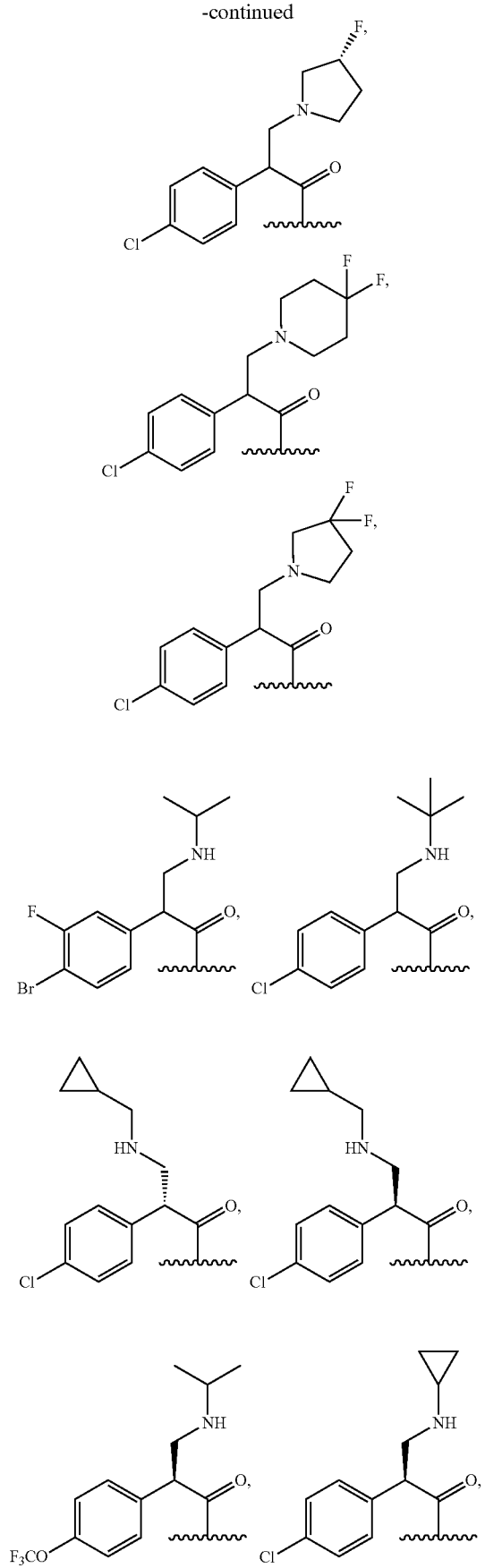
362
-continued
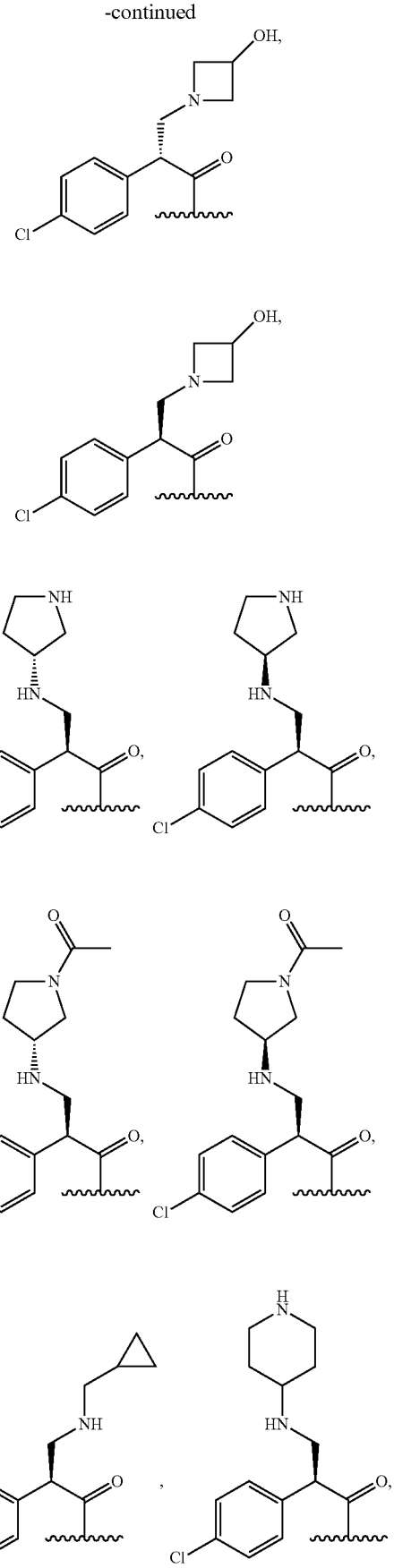

363
-continued
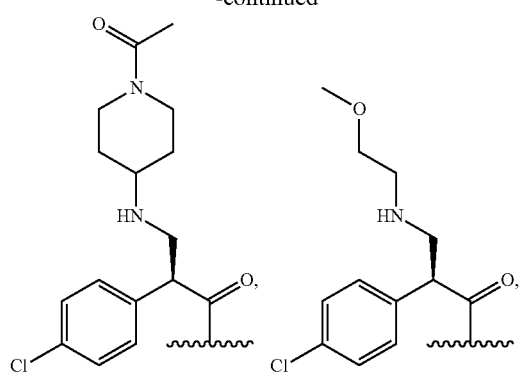
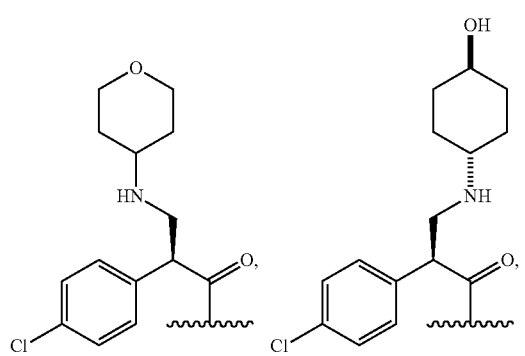
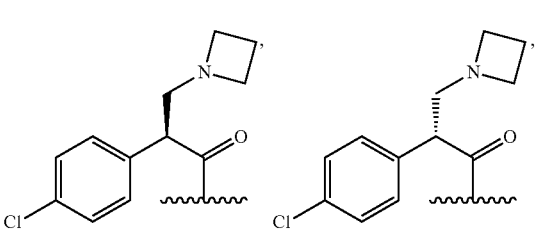
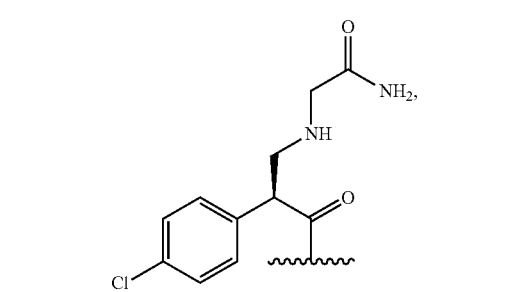
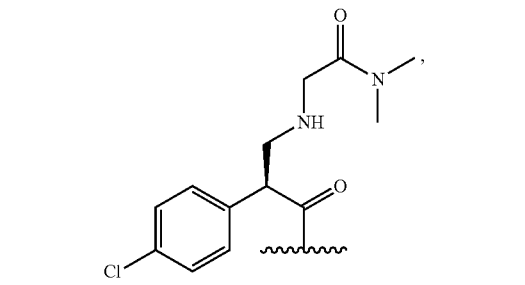
364
-continued
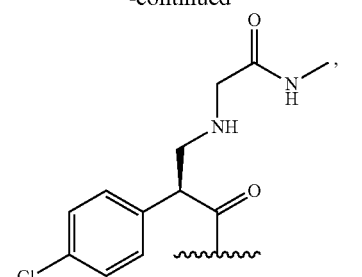
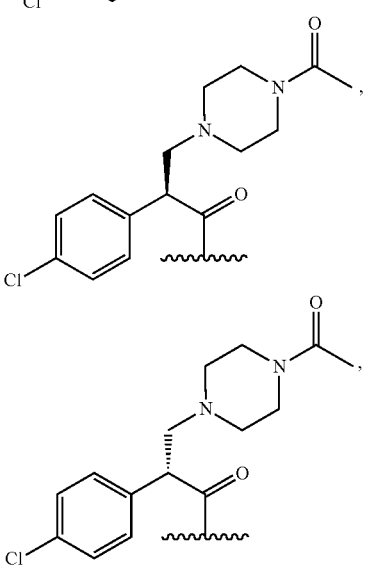
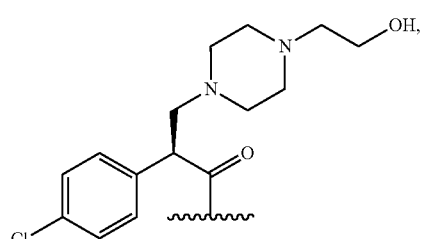
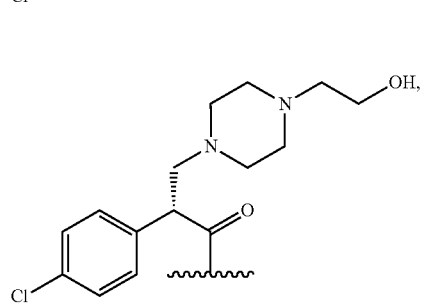
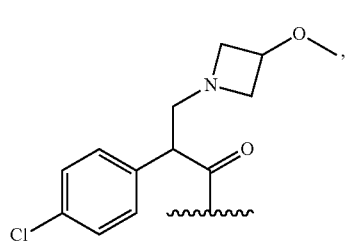

365
-continued
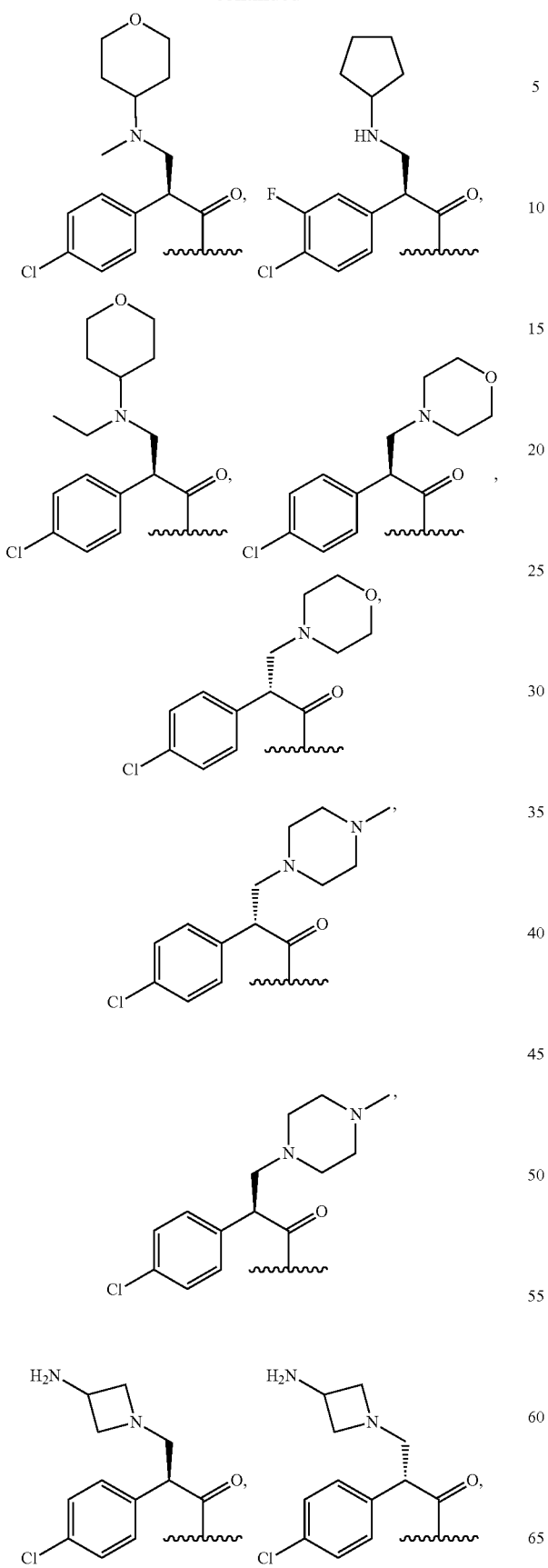
366
-continued
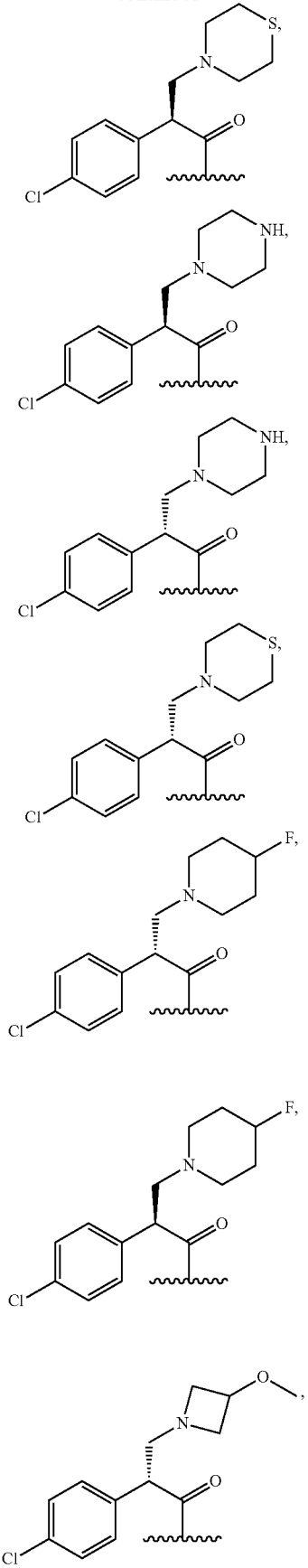

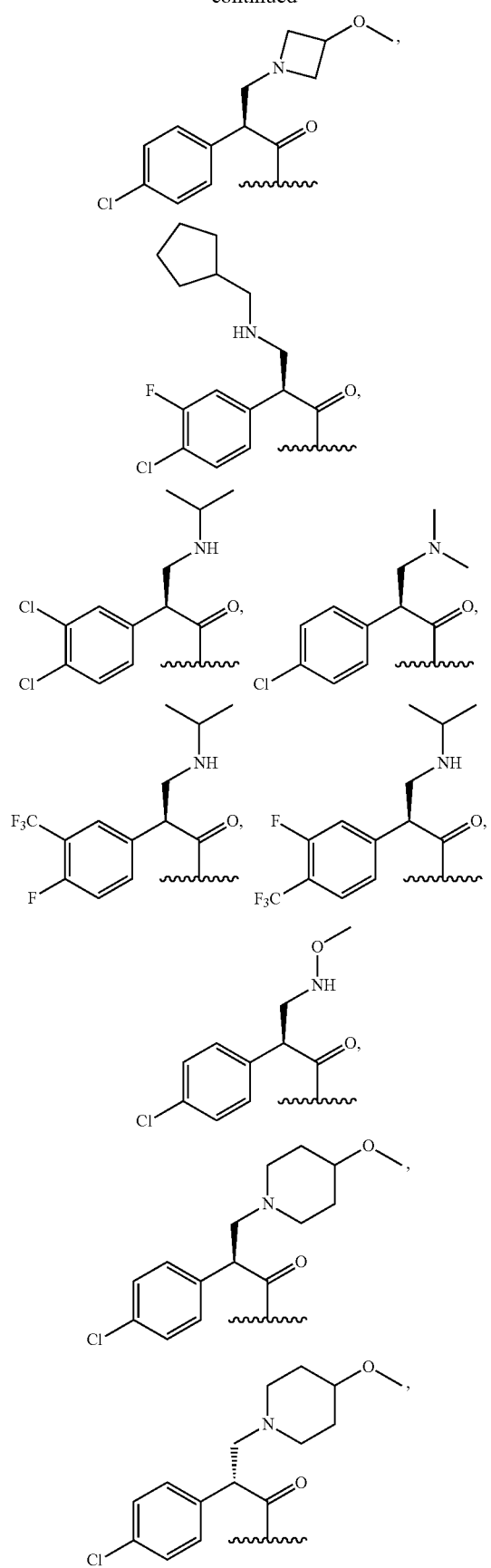
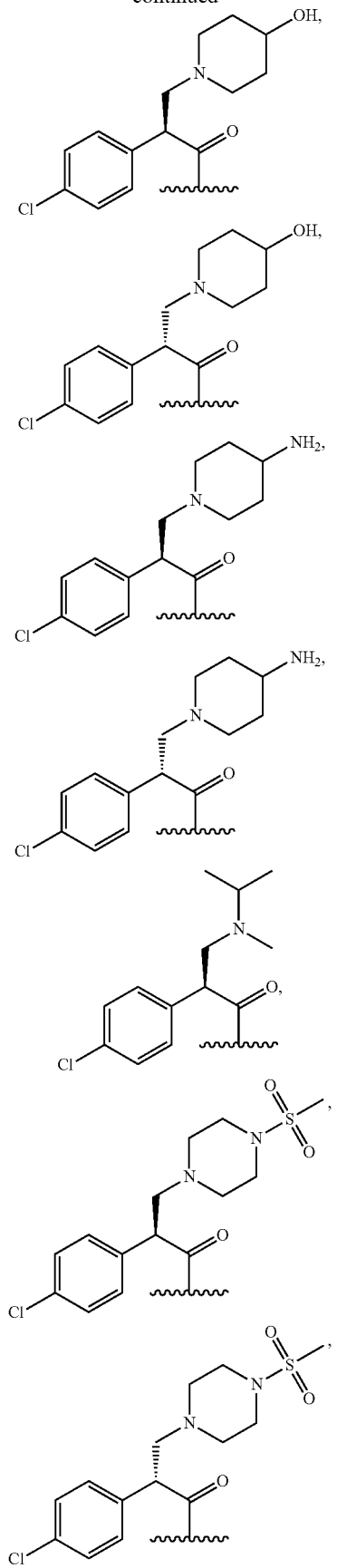

369
-continued
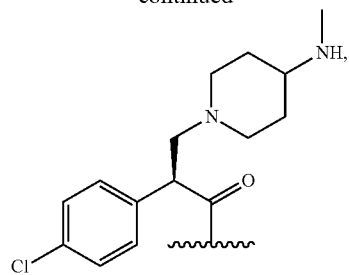
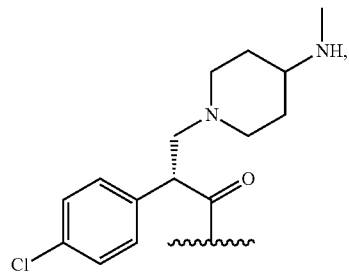
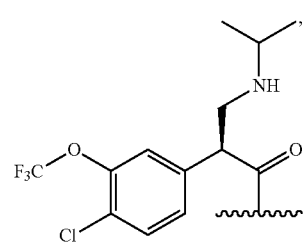
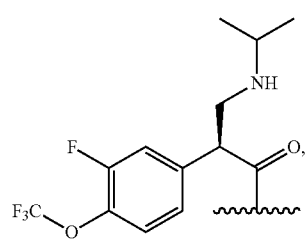
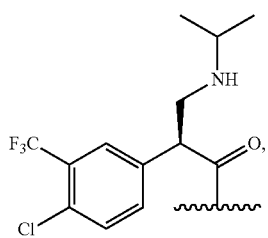
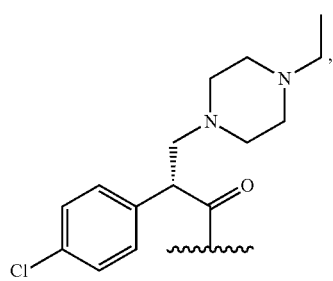
370
-continued
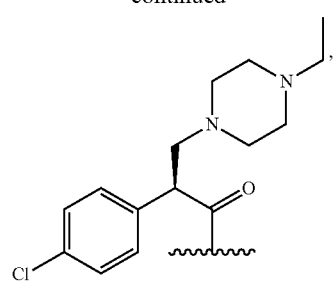
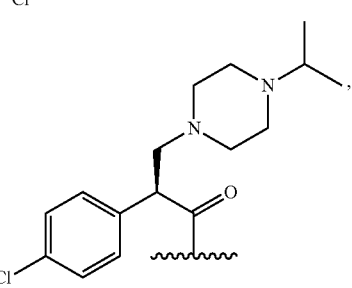
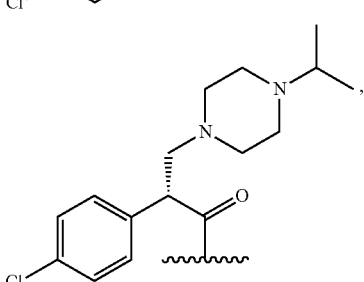
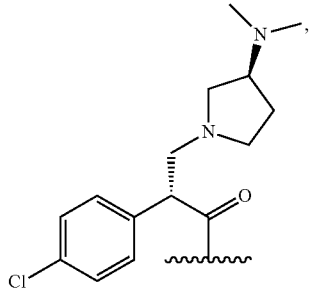
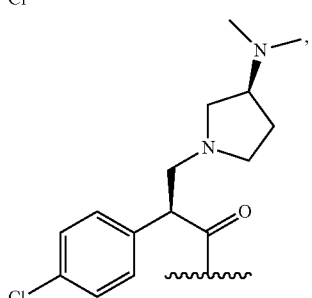
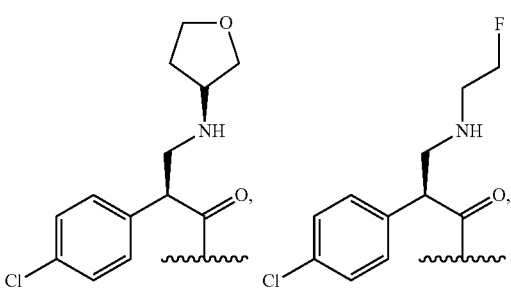

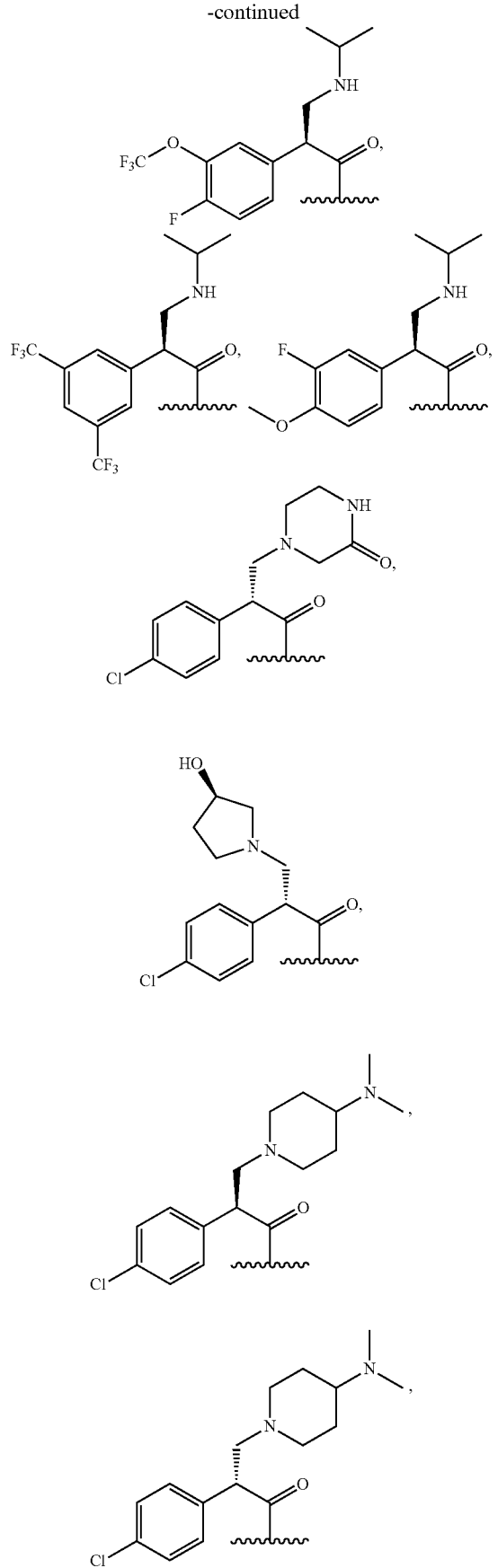
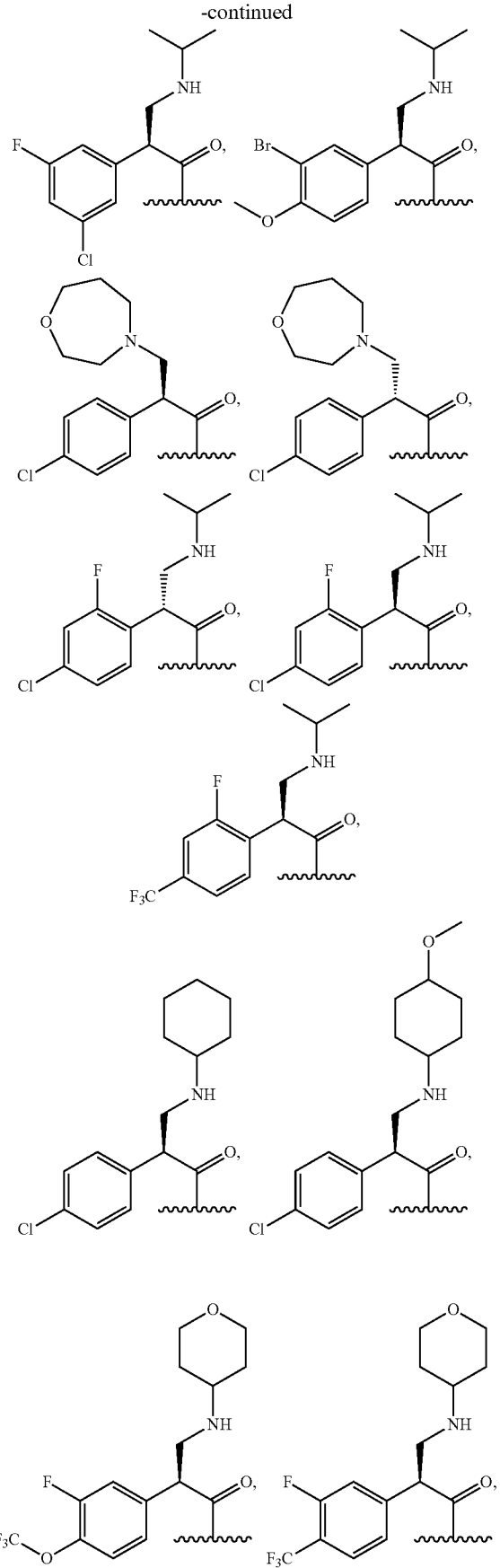

373
-continued
374
-continued
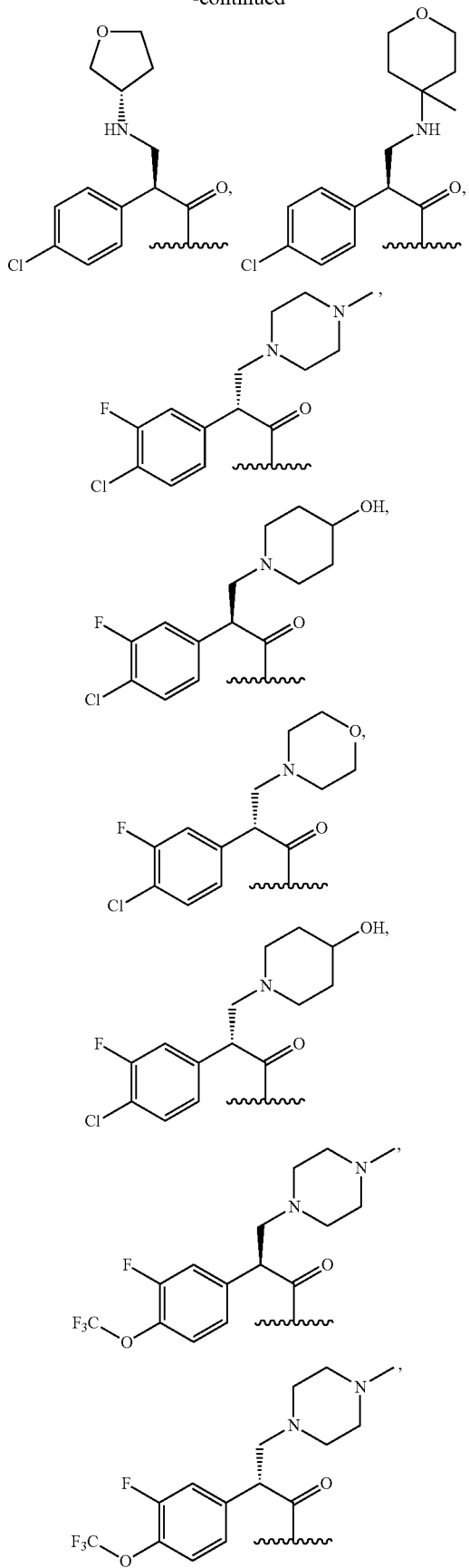
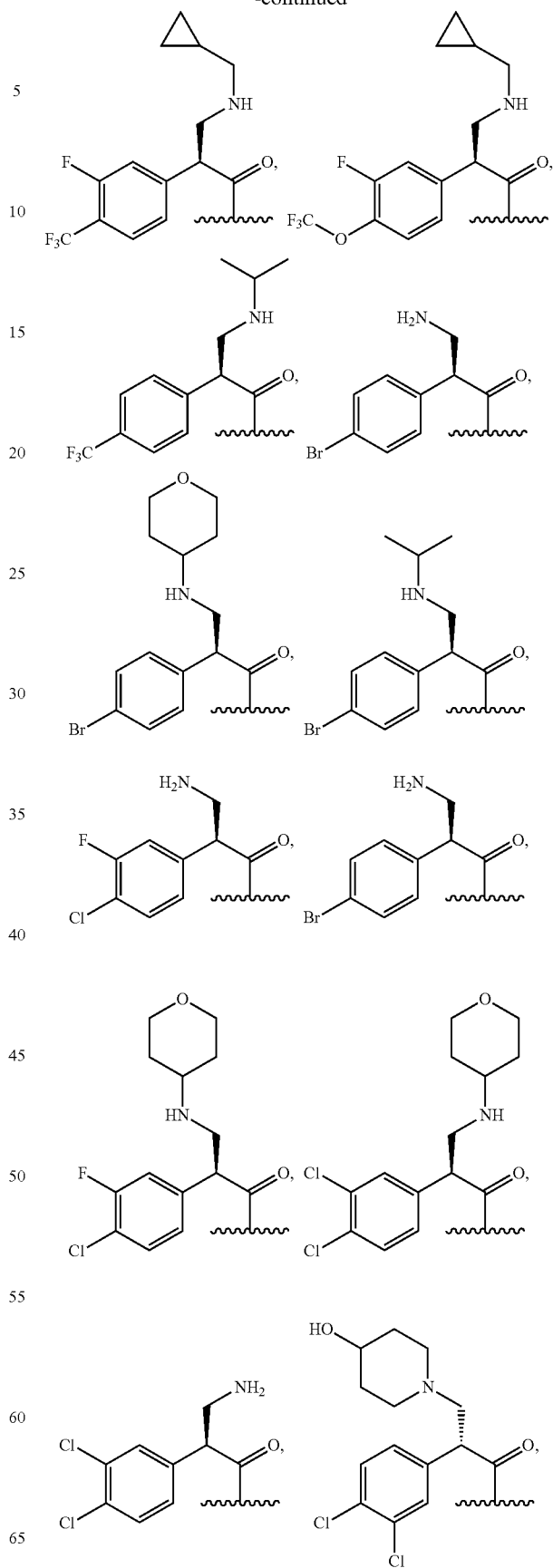

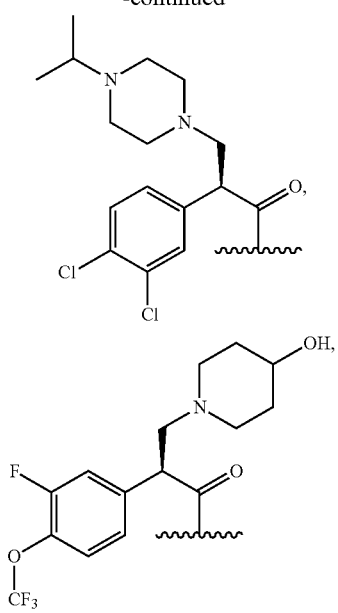
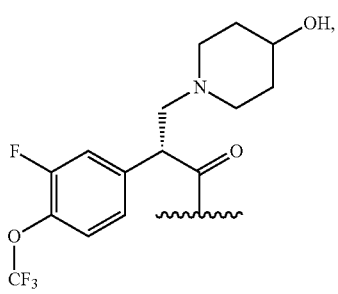
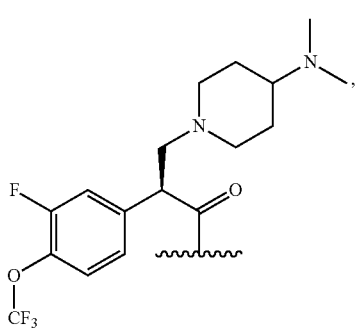
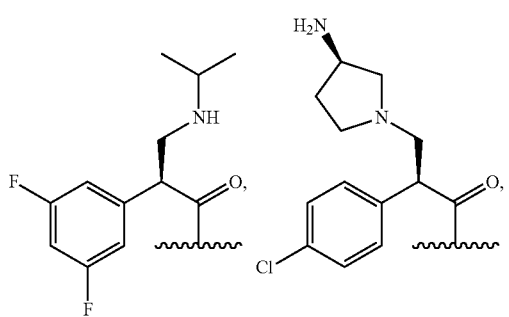
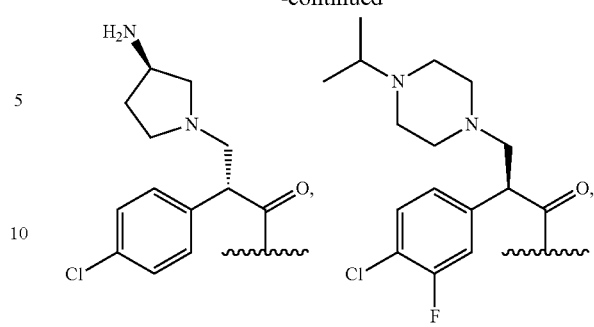
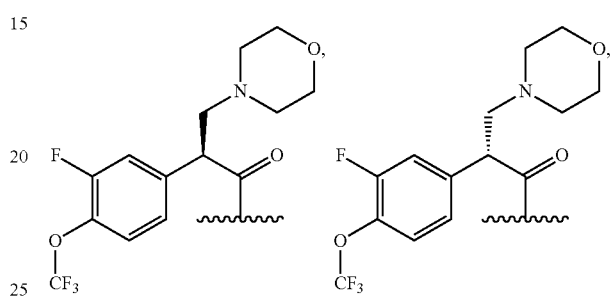
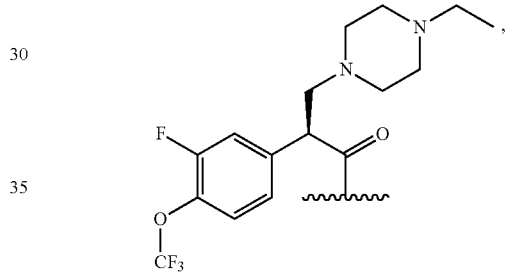
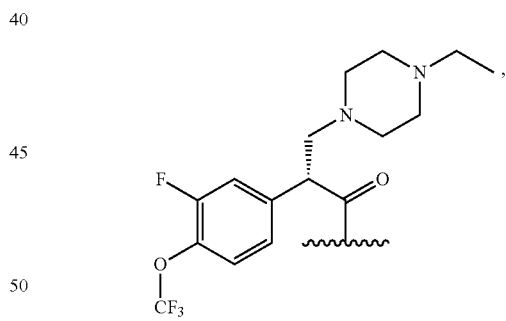
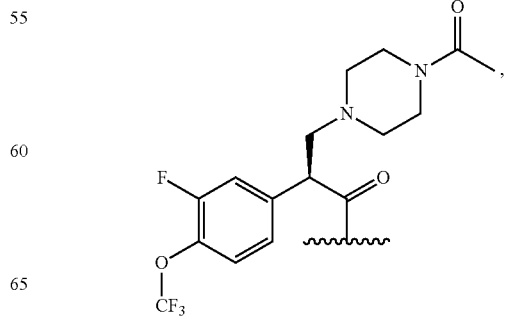

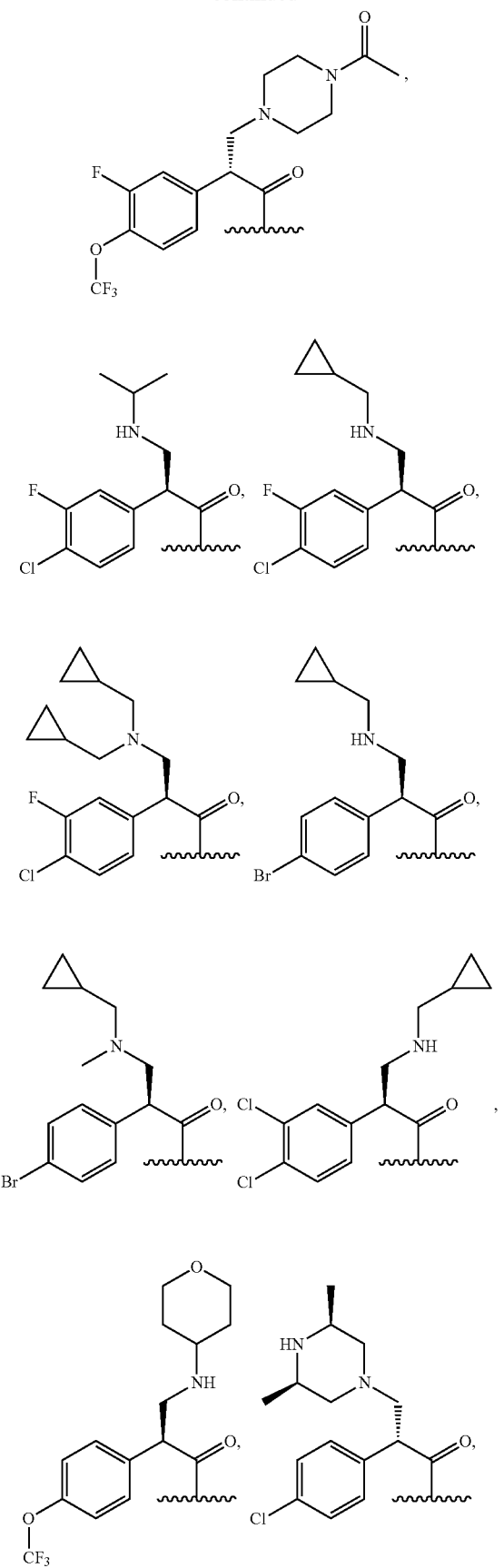
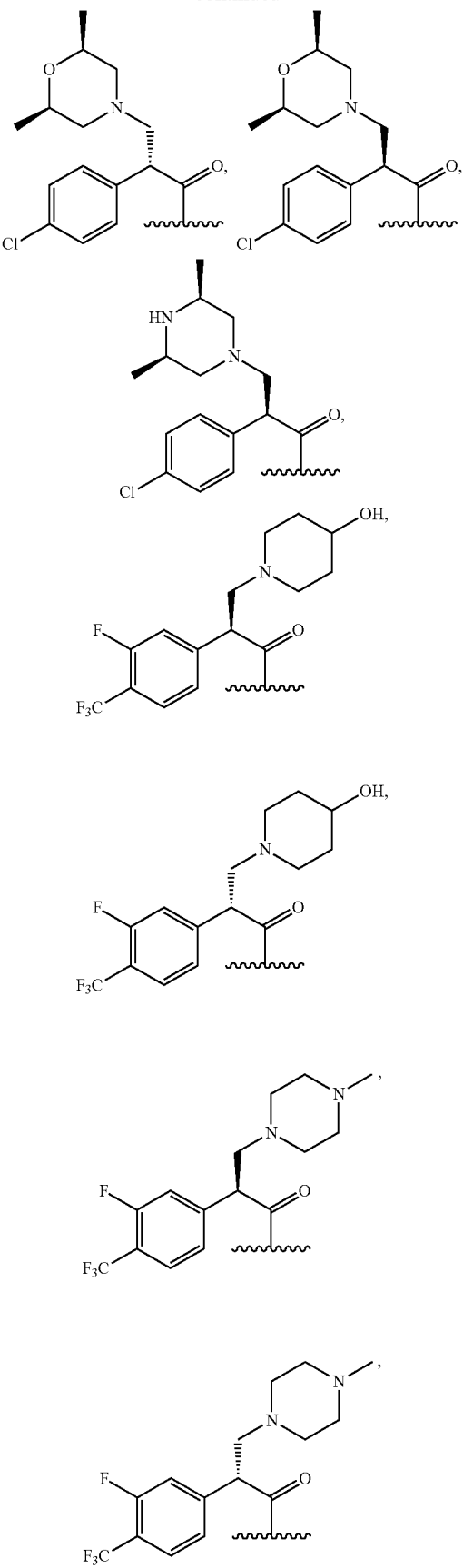

379
-continued
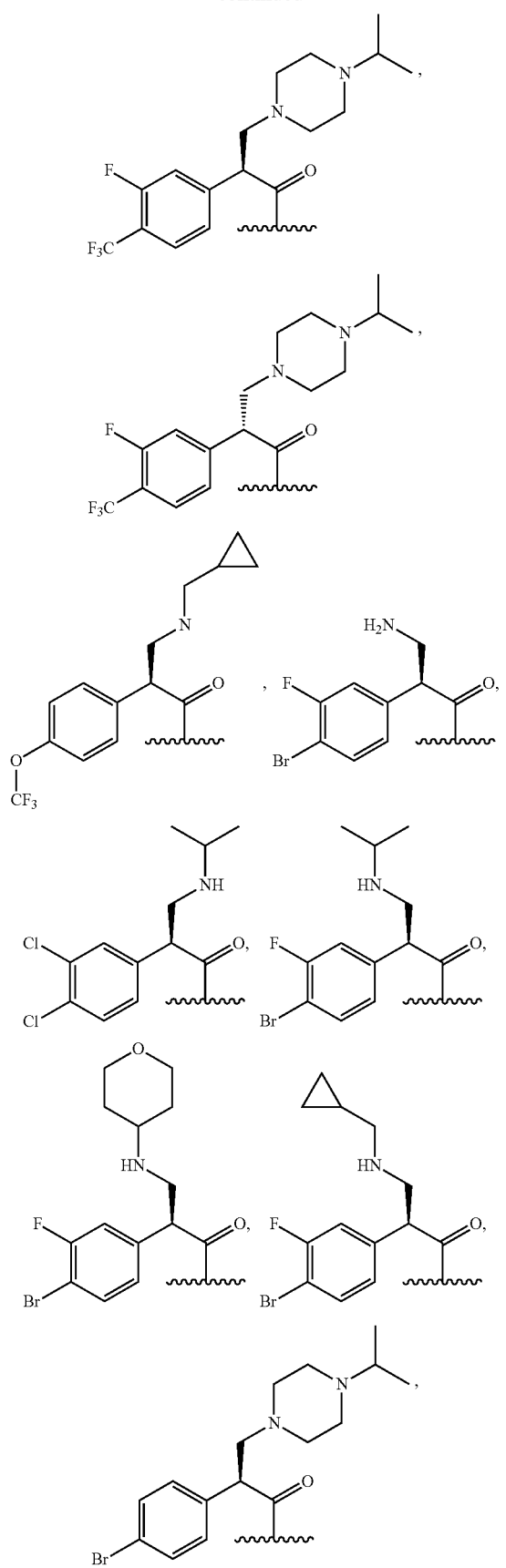
380
-continued
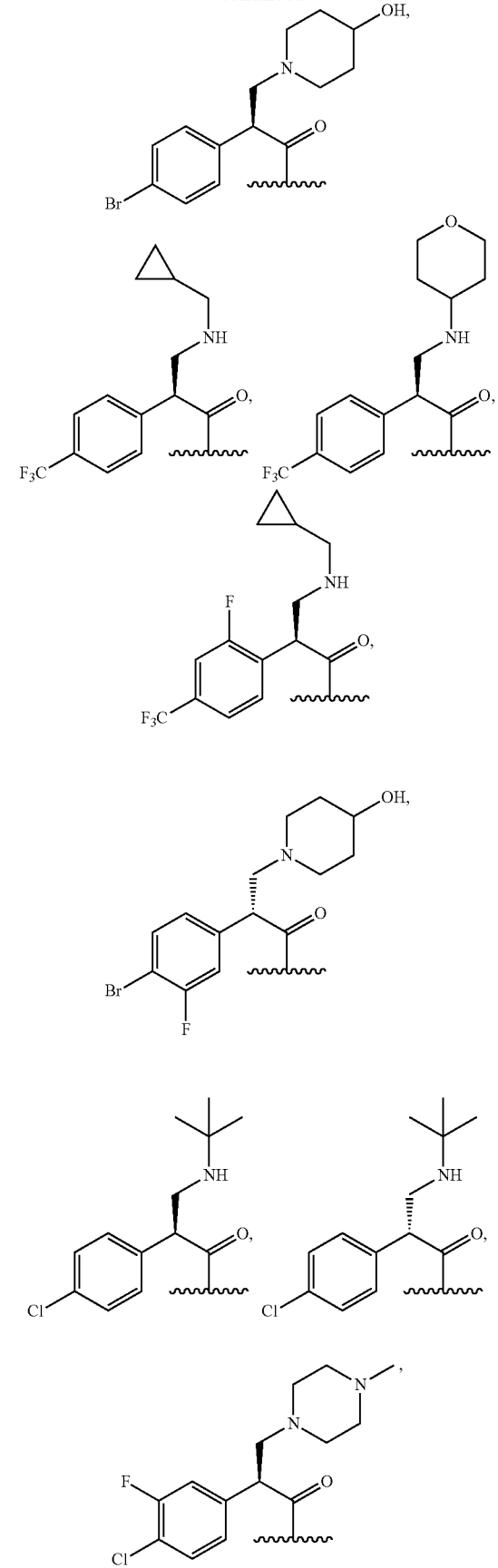

-continued
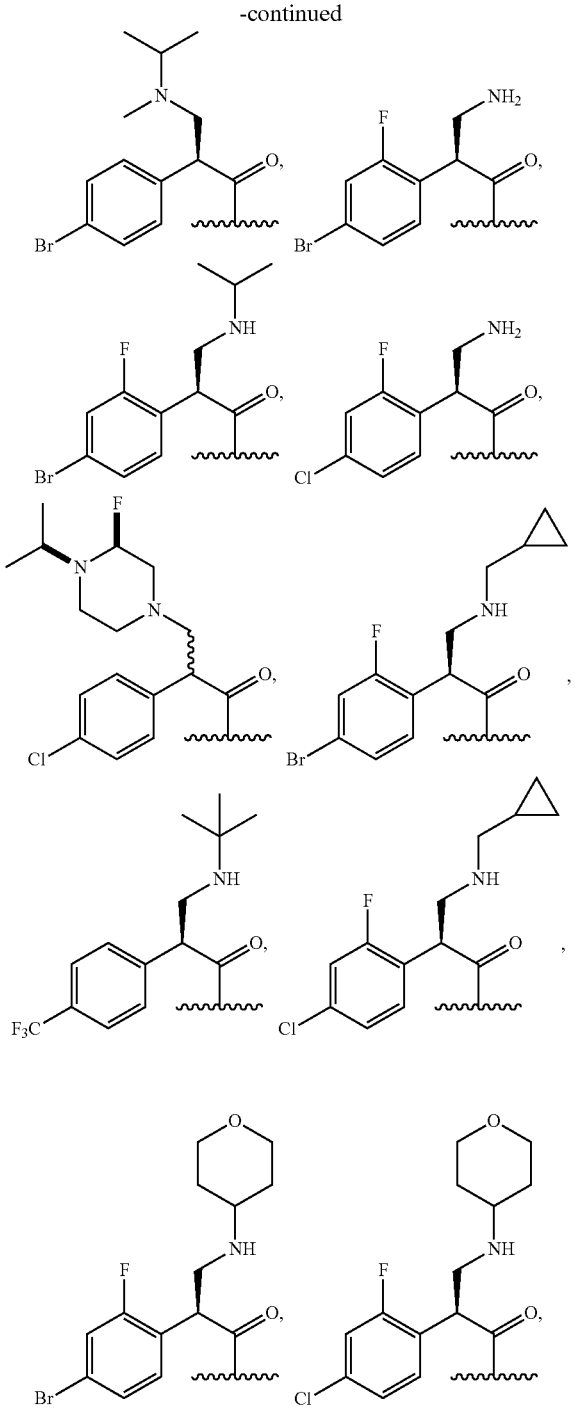
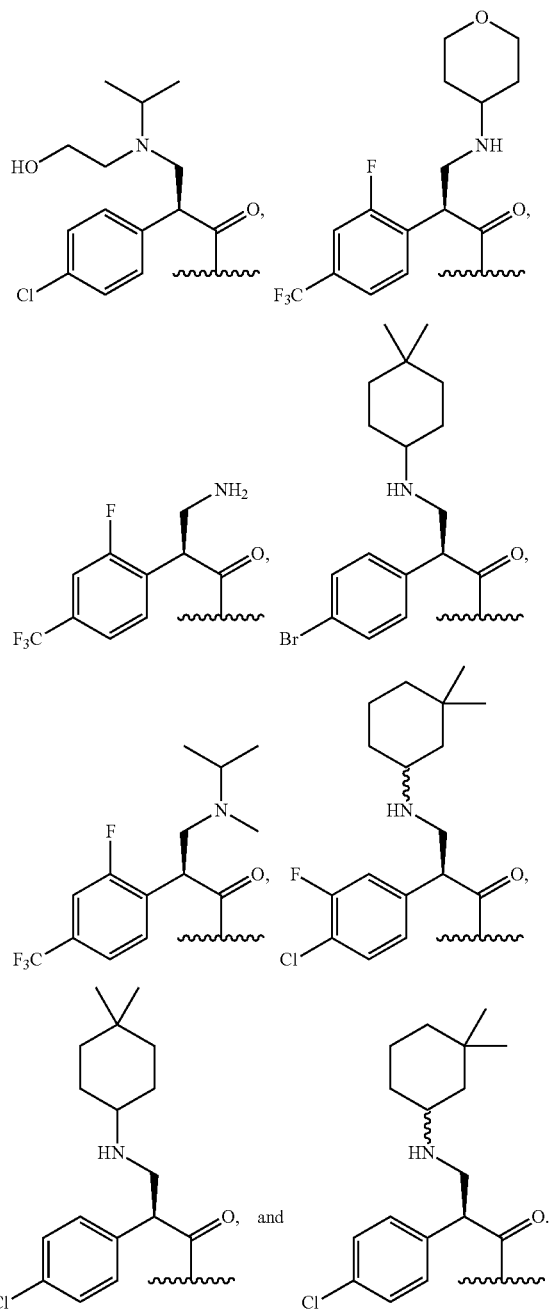
39. The method of claim 27, wherein A is selected from:
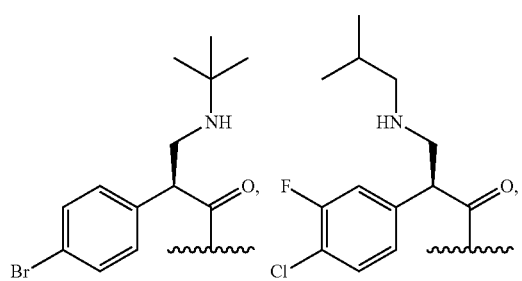
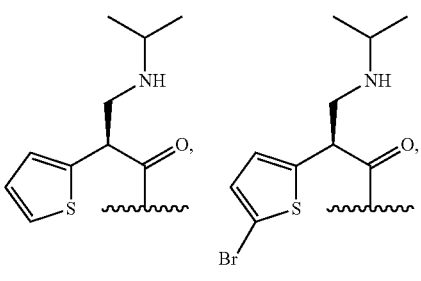

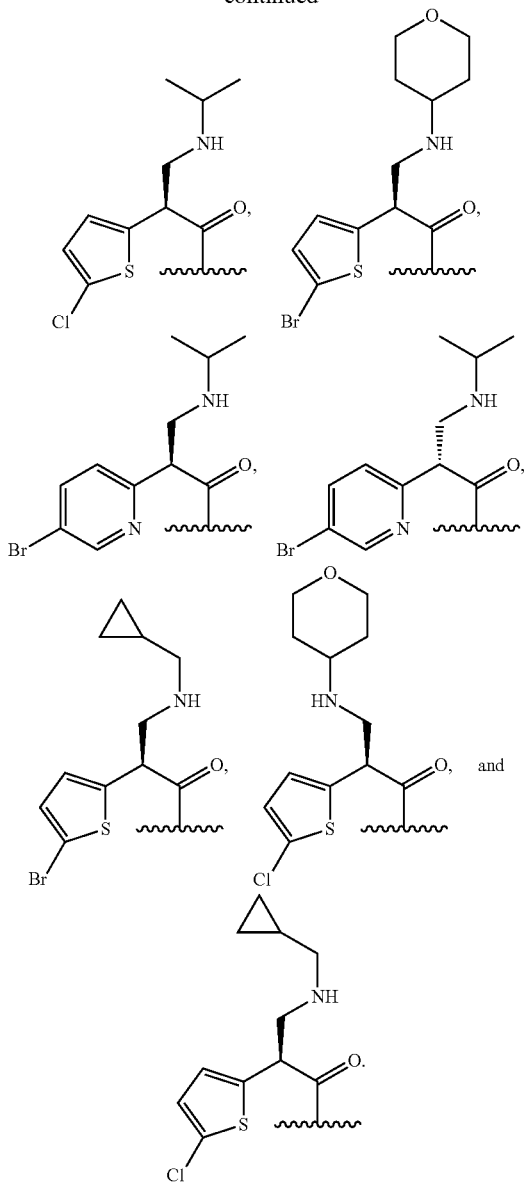

40. The method of claim 1, wherein m is 1, n is 1, p is 0, and A is represented by the formula:

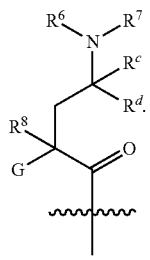

41. The method of claim 40, wherein A has the configuration:

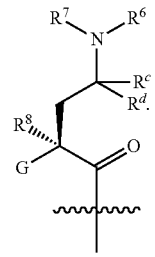

42. The method of claim 40, wherein $R^8$ is H.

43. The method of claim 42, wherein $R^c$ and $R^d$ are methyl.

44. The method of claim 42, wherein $R^c$ and $R^d$ are H.

45. The method of claim 42, wherein $R^c$ and $R^d$ together with the atom to which they are attached form a cyclopropyl ring.

46. The method of claim 40, wherein $R^6$ and $R^7$ are independently H, methyl, propyl, isopropyl, $CH_2$-cyclopropyl, or $CH_2$-cyclobutyl, or $R^6$ and $R^7$ together with the nitrogen to which they are attached form a piperidinyl, pyrrolidinyl or azetidinyl ring, or $R^6$ and $R^8$ together with the atoms to which they are attached form a piperidinyl or pyrrolidinyl ring.

47. The method of claim 1, wherein $R^6$ or $R^7$ may independently be isobutyl, tetrahydropyranyl, CH(phenyl)$CH_2$OH, CH(tetrahydropyranyl)$CH_2$OH, cyclohexyl, $CH_2CH_2$OH, $CH_2CH_2OCH_3$, $CH_2CH(CH_3)$OH, $CH_2CH(CF_3)$OH, $CH_2C(=O)N(CH_3)_2$, $CH_2C(=O)NH_2$, or $CH_2CH_2CH_2$(imidazolyl).

48. The method of claim 40, wherein $NR^6R^7$ is $NH_2$, NHMe, NHEt, NHPr, NH(iPr), NH($CH_2$-cyclopropyl), NH($CH_2$-cyclobutyl), $NMe_2$, NMeEt, NMePr, NMe(iPr), $NEt_2$, NEtPr, or NEt(iPr).

49. The method of claim 1, wherein $NR^6R^7$ is NH(isobutyl), NH($CH_2CH_2$OH), NH($CH_2CH_2OCH_3$), NH($CH_2C(=O)N(CH_3)_2$), NH($CH_2CH(CH_3)$OH), NH(cyclohexyl), NH(tetrahydropyranyl), NH(CH(phenyl)$CH_2$OH), NH(CH(tetrahydropyranyl)$CH_2$OH), NMe($CH_2CH_2$OMe), NH($CH_2C(=O)NH_2$), or NH($CH_2CH_2CH_2$(imidazolyl)).

50. The method of claim 1, wherein $NR^6R^7$ is selected from the structures:

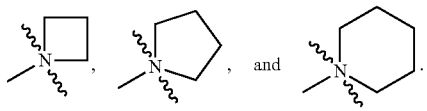

51. The method of claim 40, wherein $NR^6R^7$ is selected from the structures:

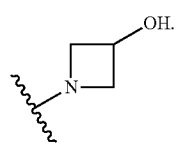 [SMILES: *N1CC(O)C1]

52. The method of claim 40, wherein $R^6$ and $R^7$ are H.

53. The method of claim 40, wherein A is selected from:
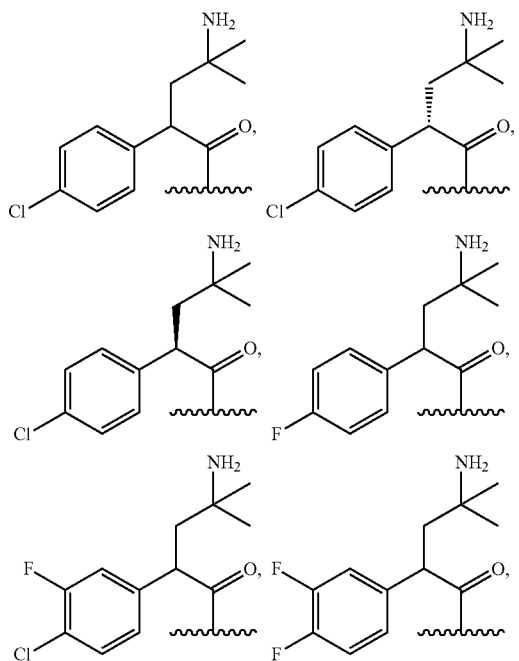
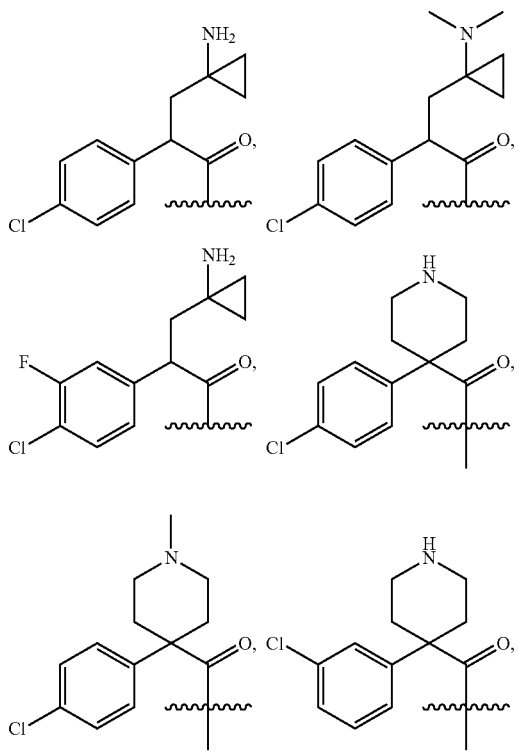
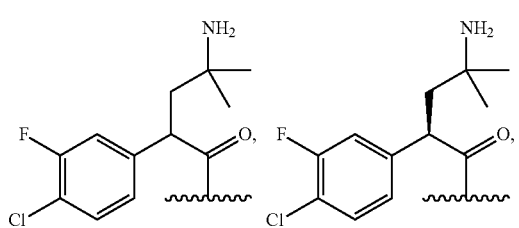
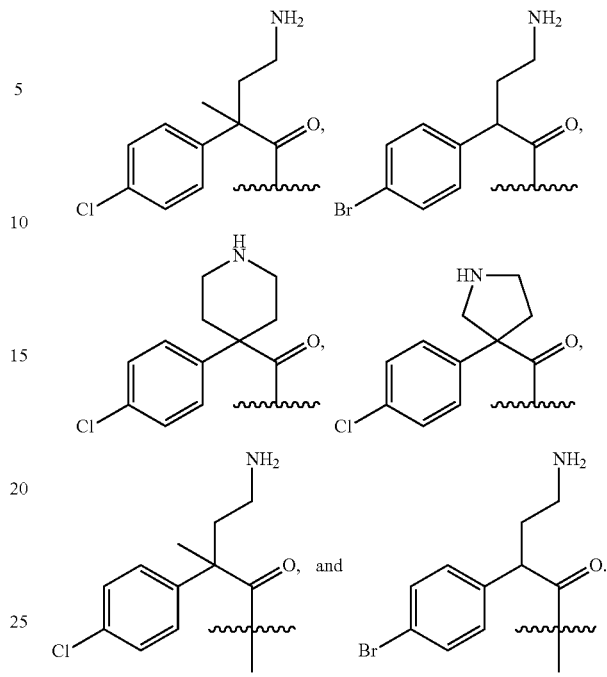
54. The method of claim 1, wherein A is selected from:
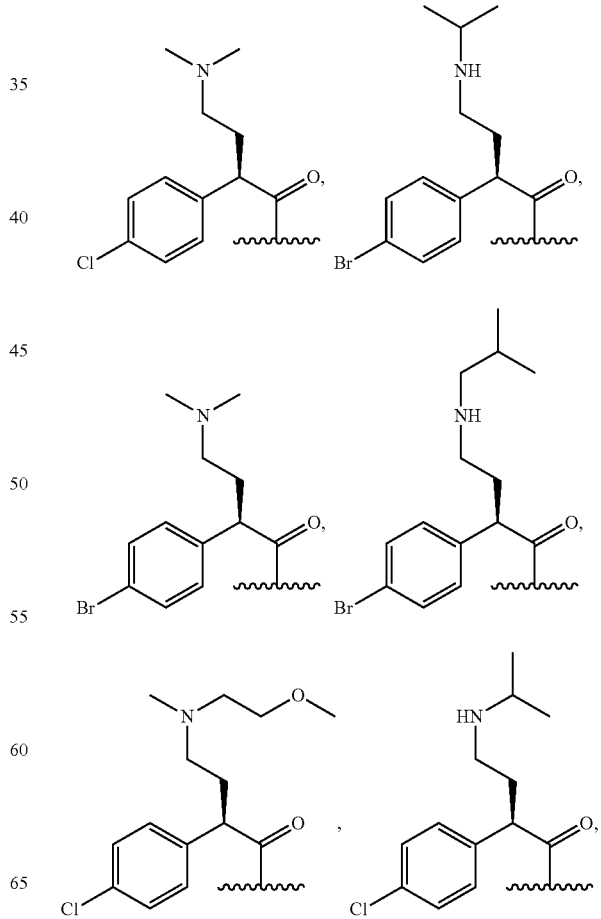

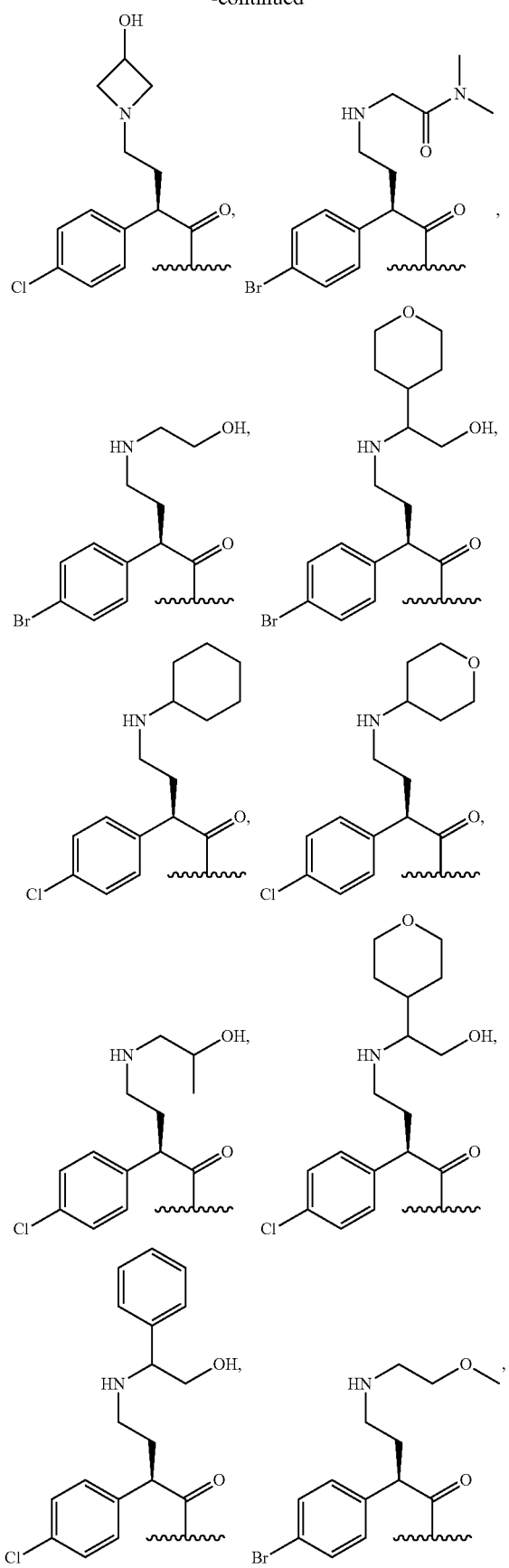

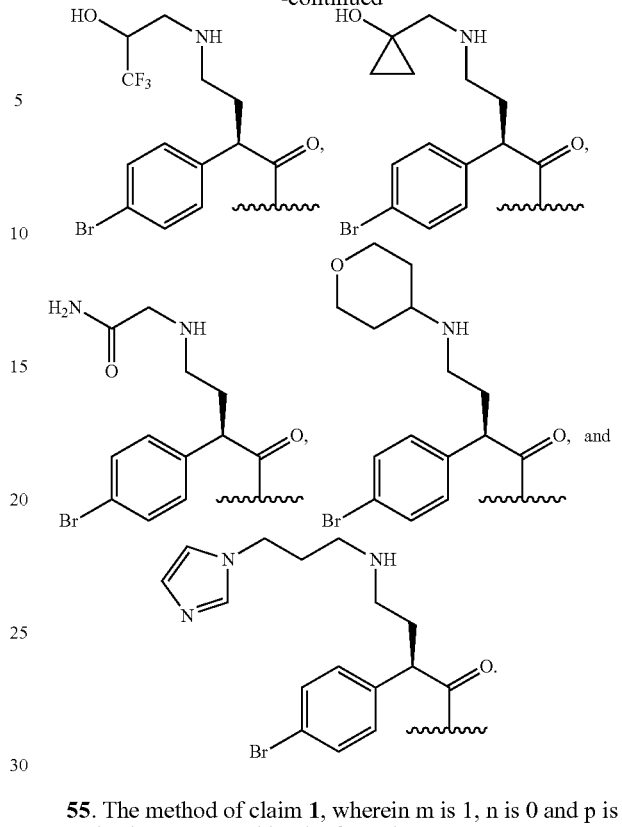

55. The method of claim 1, wherein m is 1, n is 0 and p is 1, and A is represented by the formula:

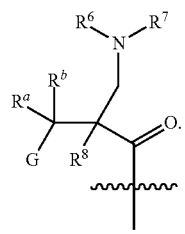

56. The method of claim 55, wherein A has the configuration:

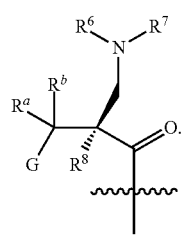

57. The method of claim 55, wherein $R^8$ is H.

58. The method of claim 1, wherein $R^c$ and $R^d$ together with the atom to which they are attached form a cyclopropyl ring.

59. The method of claim 55, wherein $R^6$ and $R^7$ are independently H, methyl, ethyl, propyl, isopropyl, t-butyl, $CH_2$-cyclopropyl or $CH_2$-cyclobutyl.

60. The method of claim 55, wherein $NR^6R^7$ is $NH_2$, NHMe, NHEt, NHPr, NH(iPr), NHtBu, NH($CH_2$-cyclopropyl), or NH($CH_2$-cyclobutyl).

61. The method of claim 60, wherein NR$^6$R$^7$ is NH$_2$.

62. The method of claim 1, wherein A is selected from the structures:

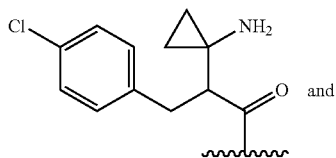

and

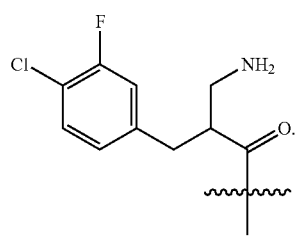

63. The method of claim 55, wherein R$^a$ and R$^8$ are H, and R$^b$ and R$^6$ together with the atoms to which they are attached form a 5 membered heterocyclic ring.

64. The method of claim 63, wherein R$^b$ and R$^6$ together with the atoms to which they are attached form a pyrrolidinyl ring.

65. The method of claim 64, wherein A is selected from:

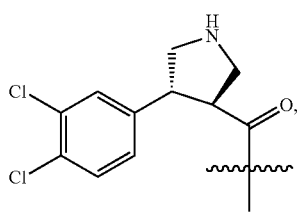

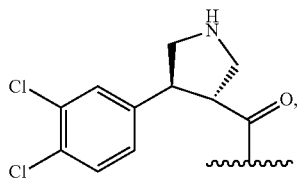

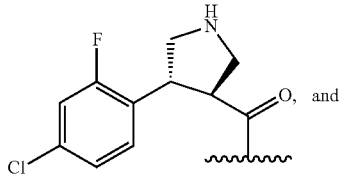

and

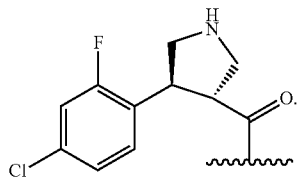

66. The method of claim 1, wherein m is 0, n is 0, p is 1, R$^a$ and R$^h$ are H, and A is represented by the formula:

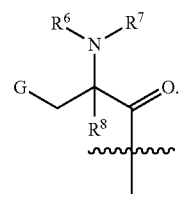

67. The method of claim 66, wherein A has the configuration:

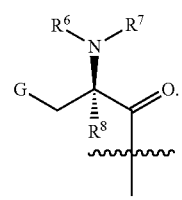

68. The method of claim 66, wherein R$^8$ is H.

69. The method of claim 68, wherein R$^6$ and R$^7$ are independently H or Me.

70. The method of claim 68, wherein R$^6$ or R$^7$ may be methyl, iPr, piperidinyl, tetrahydrofuranyl, CH$_2$CH$_2$CF$_3$, CH$_2$CH$_2$(morpholinyl), CH$_2$(tetrahydropyranyl), CH$_2$CH$_2$(tetrahydropyranyl), CH$_2$C(=O)NH(iPr), CH$_2$C(=O)N(Me)$_2$ or

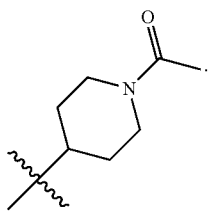 [SMILES: *C1CCN(C(C)=O)CC1]

71. The method of claim 66 wherein A is selected from:

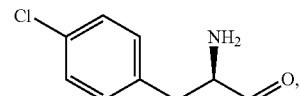

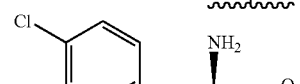

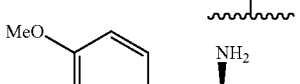

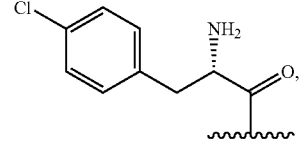

-continued
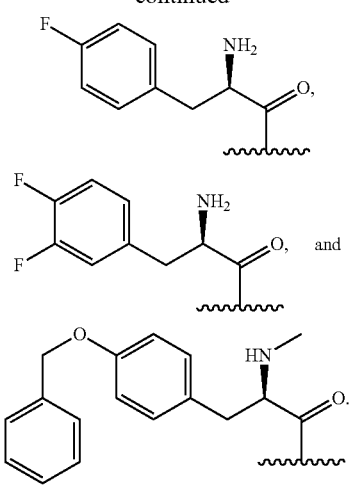
72. The method of claim 66, wherein A is selected from:
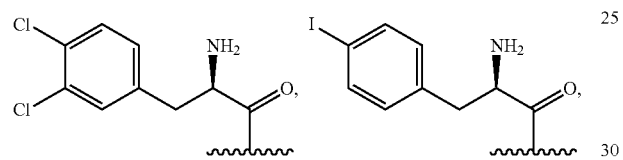
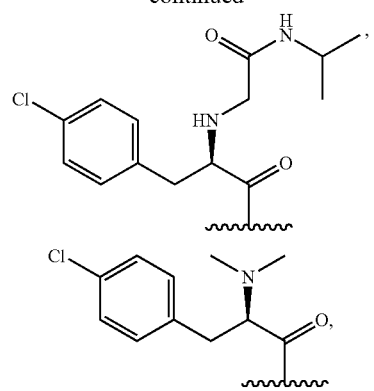
-continued
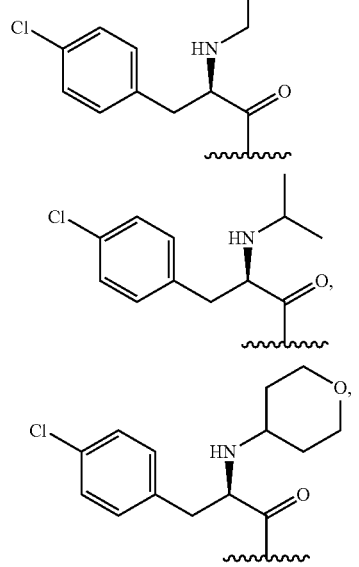
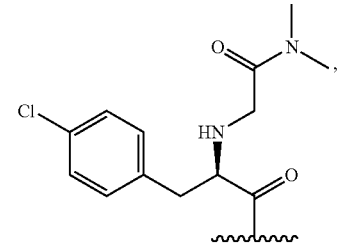
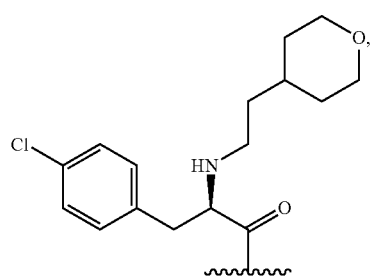

-continued

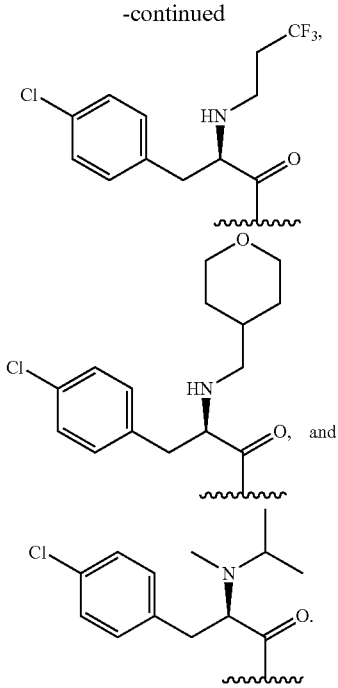

73. The method of claim 1 wherein the compound is a compound of Formula I:

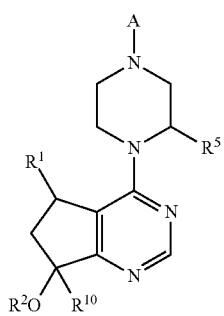

or a tautomer, resolved enantiomer, resolved diastereomer, or salt thereof, wherein:
$R^1$ is H, Me, Et, $CF_3$, $CHF_2$ or $CH_2F$;
$R^2$ is H or Me;
$R^5$ is H, Me, Et, or $CF_3$;
A is

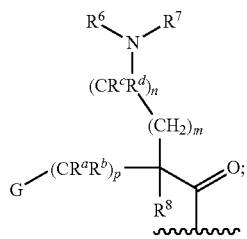

G is phenyl optionally substituted by one to four $R^9$ groups;
$R^6$ and $R^7$ are independently H, ($C_3$-$C_6$ cycloalkyl)-($CH_2$), ($C_3$-$C_6$ cycloalkyl)-($CH_2CH_2$), V—($CH_2$)$_{0-1}$ wherein V is a 5-6 membered heteroaryl, W—($CH_2$)$_{1-2}$ wherein W is phenyl optionally substituted with F, Cl or Me, $C_3$-$C_6$-cycloalkyl, hydroxy-($C_3$-$C_6$-cycloalkyl), fluoro-($C_3$-$C_6$-cycloalkyl), $CH(CH_3)CH(OH)$phenyl, or $C_1$-$C_6$-alkyl optionally substituted with one or more groups independently selected from OH, O($C_1$-$C_6$-alkyl), CN, F, $NH_2$, NH($C_1$-$C_6$-alkyl), N($C_1$-$C_6$-alkyl)$_2$, piperidinyl, and pyrrolidinyl,
or $R^6$ and $R^7$ together with the nitrogen to which they are attached form a 4-6 membered heterocyclic ring optionally substituted with one or more groups independently selected from OH, halogen, oxo, $CF_3$, $CH_2CF_3$, and ($C_1$-$C_3$)alkyl;
$R^a$ and $R^b$ are H,
or $R^a$ is H, and $R^b$ and $R^6$ together with the atoms to which they are attached form a 5-6 membered heterocyclic ring having one or two ring nitrogen atoms;
$R^c$ and $R^d$ are H or Me;
$R^8$ is H, Me, or OH,
or $R^8$ and $R^6$ together with the atoms to which they are attached form a 5-6 membered heterocyclic ring having one or two ring nitrogen atoms;
each $R^9$ is independently halogen, $C_1$-$C_6$-alkyl, $C_3$-$C_6$-cycloalkyl, O—($C_1$-$C_6$-alkyl), $CF_3$, $OCF_3$, S($C_1$-$C_6$-alkyl), CN, $CH_2O$-phenyl, $NH_2$, NH—($C_1$-$C_6$-alkyl), N—($C_1$-$C_6$-alkyl)$_2$, piperidine, pyrrolidine, $CH_2F$, $CHF_2$, $OCH_2F$, $OCHF_2$, OH, $SO_2$($C_1$-$C_6$-alkyl), C(O)$NH_2$, C(O)NH($C_1$-$C_6$-alkyl), and C(O)N($C_1$-$C_6$-alkyl)$_2$;
$R^{10}$ is H or Me; and
m, n and p are independently 0 or 1.
74. The method of claim 1 wherein the compound is selected from:
2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one;
(R)-2-amino-3-(4-chlorophenyl)-1-((S)-4-((5R,7R)-7-hydroxy-5-methyl-6,7-dihydro-5H-cyclopenta[d]pyrimidin-4-yl)-3-methylpiperazin-1-yl)propan-1-one;
(R)-2-amino-3-(4-chloro-3-fluorophenyl)-1-((S)-4-((5R,7R)-7-hydroxy-5-methyl-6,7-dihydro-5H-cyclopenta[d]pyrimidin-4-yl)-3-methylpiperazin-1-yl)propan-1-one;
(R)-2-amino-3-(4-chloro-3-fluorophenyl)-1-((S)-4-((5R,7R)-7-methoxy-5-methyl-6,7-dihydro-5H-cyclopenta[d]pyrimidin-4-yl)-3-methylpiperazin-1-yl)propan-1-one;
(S)-3-amino-2-(4-chlorophenyl)-1-(4-((5R,7R)-7-hydroxy-5-methyl-6,7-dihydro-5H-cyclopenta[d]pyrimidin-4-yl)piperazin-1-yl)propan-1-one;
(R)-2-amino-3-(4-chlorophenyl)-1-((S)-4-((S)-7-hydroxy-6,7-dihydro-5H-cyclopenta[d]pyrimidin-4-yl)-3-methylpiperazin-1-yl)propan-1-one;
(R)-2-amino-3-(4-chloro-3-fluorophenyl)-1-((S)-4-((S)-7-hydroxy-6,7-dihydro-5H-cyclopenta[d]pyrimidin-4-yl)-3-methylpiperazin-1-yl)propan-1-one;
(2R)-2-amino-3-(4-chloro-3-fluorophenyl)-1-((3S)-4-((5R)-7-hydroxy-5-methyl-6,7-dihydro-5H-cyclopenta[d]pyrimidin-4-yl)-3-methylpiperazin-1-yl)propan-1-one;
(2R)-2-amino-3-(4-chlorophenyl)-1-(4-(7-hydroxy-6,7-dihydro-5H-cyclopenta[d]pyrimidin-4-yl)piperazin-1-yl)propan-1-one;
(R)-2-amino-1-(4-((5R,7R)-7-hydroxy-5-methyl-6,7-dihydro-5H-cyclopenta[d]pyrimidin-4-yl)piperazin-1-yl)-3-(4-methoxyphenyl)propan-1-one;

2-(4-chlorophenyl)-1-((S)-4-((R)-7-hydroxy-6,7-dihydro-5H-cyclopenta[d]pyrimidin-4-yl)-3-methylpiperazin-1-yl)-3-(isopropylamino)propan-1-one;

2-(4-chlorophenyl)-1-(4-(7-hydroxy-6,7-dihydro-5H-cyclopenta[d]pyrimidin-4-yl)piperazin-1-yl)-3-(isopropylamino)propan-1-one;

2-(4-chlorophenyl)-3-(isopropylamino)-1-(4-(7-methoxy-6,7-dihydro-5H-cyclopenta[d]pyrimidin-4-yl)piperazin-1-yl)propan-1-one;

(S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one;

2-(4-fluorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one;

2-(3,4-difluorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one;

2-(4-chlorophenyl)-1-(4-((5R,7R)-7-hydroxy-5-methyl-6,7-dihydro-5H-cyclopenta[d]pyrimidin-4-yl)piperazin-1-yl)-3-(pyridin-3-ylmethylamino)propan-1-one;

2-(2,4-dichlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one;

2-(4-chlorophenyl)-1-(4-((5R,7R)-7-hydroxy-5-methyl-6,7-dihydro-5H-cyclopenta[d]pyrimidin-4-yl)piperazin-1-yl)-3-(pentan-3-ylamino)propan-1-one;

2-(4-chlorophenyl)-3-((1S,2R)-1-hydroxy-1-phenylpropan-2-ylamino)-1-(4-((5R,7R)-7-hydroxy-5-methyl-6,7-dihydro-5H-cyclopenta[d]pyrimidin-4-yl)piperazin-1-yl)propan-1-one;

2-(4-chlorophenyl)-1-(4-((5R,7R)-7-hydroxy-5-methyl-6,7-dihydro-5H-cyclopenta[d]pyrimidin-4-yl)piperazin-1-yl)-34(1R,4R)-4-hydroxycyclohexylamino)propan-1-one;

((3S,4R)-4-(3,4-dichlorophenyl)pyrrolidin-3-yl)(4-((5R,7R)-7-hydroxy-5-methyl-6,7-dihydro-5H-cyclopenta[d]pyrimidin-4-yl)piperazin-1-yl)methanone;

((3R,4S)-4-(3,4-dichlorophenyl)pyrrolidin-3-yl)(4-((5R,7R)-7-hydroxy-5-methyl-6,7-dihydro-5H-cyclopenta[d]pyrimidin-4-yl)piperazin-1-yl)methanone;

2-(4-chlorophenyl)-2-hydroxy-1-(4-((5R,7R)-7-hydroxy-5-methyl-6,7-dihydro-5H-cyclopenta[d]pyrimidin-4-yl)piperazin-1-yl)-3-(isopropylamino)propan-1-one;

4-amino-2-(4-chlorophenyl)-1-(4-((5R,7R)-7-hydroxy-5-methyl-6,7-dihydro-5H-cyclopenta[d]pyrimidin-4-yl)piperazin-1-yl)-4-methylpentan-1-one;

4-amino-2-(3,4-difluorophenyl)-1-(4-((5R,7R)-7-hydroxy-5-methyl-6,7-dihydro-5H-cyclopenta[d]pyrimidin-4-yl)piperazin-1-yl)-4-methylpentan-1-one;

(4-(4-chloro-3-fluorophenyl)piperidin-4-yl)(4-((5R,7R)-7-hydroxy-5-methyl-6,7-dihydro-5H-cyclopenta[d]pyrimidin-4-yl)piperazin-1-yl)methanone;

(3-(4-chlorophenyl)pyrrolidin-3-yl)(4-((5R,7R)-7-hydroxy-5-methyl-6,7-dihydro-5H-cyclopenta[d]pyrimidin-4-yl)piperazin-1-yl)methanone;

1-(4-((5R,7R)-7-hydroxy-5-methyl-6,7-dihydro-5H-cyclopenta[d]pyrimidin-4-yl)piperazin-1-yl)-3-(isopropylamino)-2-p-tolylpropan-1-one;

1-(4-((5R,7R)-7-hydroxy-5-methyl-6,7-dihydro-5H-cyclopenta[d]pyrimidin-4-yl)piperazin-1-yl)-3-(isopropylamino)-2-(4-methoxyphenyl)propan-1-one;

3-(ethylamino)-2-(4-fluorophenyl)-1-(4-((5R,7R)-7-hydroxy-5-methyl-6,7-dihydro-5H-cyclopenta[d]pyrimidin-4-yl)piperazin-1-yl)propan-1-one;

2-(4-fluorophenyl)-1-(4-((5R,7R)-7-hydroxy-5-methyl-6,7-dihydro-5H-cyclopenta[d]pyrimidin-4-yl)piperazin-1-yl)-3-(methylamino)propan-1-one;

(S)-3-amino-2-(3,4-dichlorophenyl)-1-(4-((5R,7R)-7-hydroxy-5-methyl-6,7-dihydro-5H-cyclopenta[d]pyrimidin-4-yl)piperazin-1-yl)propan-1-one;

2-(4-chlorophenyl)-3-(cyclopropylmethylamino)-1-(4-((5R,7R)-7-hydroxy-5-methyl-6,7-dihydro-5H-cyclopenta[d]pyrimidin-4-yl)piperazin-1-yl)propan-1-one;

2-(4-chloro-3-fluorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one;

2-(4-chlorophenyl)-1-(4-((5R,7R)-7-hydroxy-5-methyl-6,7-dihydro-5H-cyclopenta[d]pyrimidin-4-yl)piperazin-1-yl)-3-(pyrrolidin-1-yl)propan-1-one;

(R)-2-amino-3-(4-chlorophenyl)-1-(4-((5R,7R)-7-hydroxy-5-methyl-6,7-dihydro-5H-cyclopenta[d]pyrimidin-4-yl)piperazin-1-yl)propan-1-one;

2-(4-chlorophenyl)-1-((S)-4-((S)-7-hydroxy-6,7-dihydro-5H-cyclopenta[d]pyrimidin-4-yl)-3-methylpiperazin-1-yl)-3-(isopropylamino)propan-1-one;

(R)-2-amino-3-(4-chlorophenyl)-1-((S)-4-((R)-7-hydroxy-6,7-dihydro-5H-cyclopenta[d]pyrimidin-4-yl)-3-methylpiperazin-1-yl)propan-1-one;

(R)-2-amino-3-(4-chloro-3-fluorophenyl)-1-((S)-4-((R)-7-hydroxy-6,7-dihydro-5H-cyclopenta[d]pyrimidin-4-yl)-3-methylpiperazin-1-yl)propan-1-one;

2-(4-chlorophenyl)-1-(4-((5R)-7-hydroxy-5,7-dimethyl-6,7-dihydro-5H-cyclopenta[d]pyrimidin-4-yl)piperazin-1-yl)-3-(isopropylamino)propan-1-one;

(R)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one;

(4-(3,4-dichlorophenyl)piperidin-4-yl)(4-((5R,7R)-7-hydroxy-5-methyl-6,7-dihydro-5H-cyclopenta[d]pyrimidin-4-yl)piperazin-1-yl)methanone;

4-(3,4-dichlorophenyl)pyrrolidin-3-yl)(4-((5R,7R)-7-hydroxy-5-methyl-6,7-dihydro-5H-cyclopenta[d]pyrimidin-4-yl)piperazin-1-yl)methanone;

1-(4-((5R,7R)-7-hydroxy-5-methyl-6,7-dihydro-5H-cyclopenta[d]pyrimidin-4-yl)piperazin-1-yl)-2-(4-methoxyphenyl)-3-(pyrrolidin-1-yl)propan-1-one;

2-(4-chlorophenyl)-1-(4-((5R,7R)-7-hydroxy-5-methyl-6,7-dihydro-5H-cyclopenta[d]pyrimidin-4-yl)piperazin-1-yl)-3-(2,2,2-trifluoroethylamino)propan-1-one;

3-(tert-butylamino)-2-(4-chlorophenyl)-1-(4-((5R,7R)-7-hydroxy-5-methyl-6,7-dihydro-5H-cyclopenta[d]pyrimidin-4-yl)piperazin-1-yl)propan-1-one;

(S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(methyl(tetrahydro-2H-pyran-4-yl)amino)propan-1-one;

(S)-2-(4-chlorophenyl)-3-(cyclopropylmethylamino)-1-(4-((5R,7S)-7-hydroxy-5-methyl-6,7-dihydro-5H-cyclopenta[d]pyrimidin-4-yl)piperazin-1-yl)propan-1-one;

(S)-2-(5-chlorothiophen-2-yl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one;

(R)-2-amino-3-(4-chlorophenyl)-1-(4-((5R,7S)-7-hydroxy-5-methyl-6,7-dihydro-5H-cyclopenta[d]pyrimidin-4-yl)piperazin-1-yl)propan-1-one;

1-(4-((5R,7R)-7-hydroxy-5-methyl-6,7-dihydro-5H-cyclopenta[d]pyrimidin-4-yl)piperazin-1-yl)-3-(isopropylamino)-2-(4-(trifluoromethyl)phenyl)propan-1-one;

4-(4-(((5R,7R)-7-hydroxy-5-methyl-6,7-dihydro-5H-cyclopenta[d]pyrimidin-4-yl)piperazin-1-yl)-3-(isopropylamino)-1-oxopropan-2-yl)benzonitrile;

(S)-2-(4-chlorophenyl)-1-(4-(((5R,7S)-7-hydroxy-5-methyl-6,7-dihydro-5H-cyclopenta[d]pyrimidin-4-yl)piperazin-1-yl)-3-(isopropylamino)propan-1-one;

3-(azetidin-1-yl)-2-(4-chlorophenyl)-1-(4-(((5R,7R)-7-hydroxy-5-methyl-6,7-dihydro-5H-cyclopenta[d]pyrimidin-4-yl)piperazin-1-yl)propan-1-one;

2-(4-chlorophenyl)-1-(4-(((5R,7R)-7-hydroxy-5-methyl-6,7-dihydro-5H-cyclopenta[d]pyrimidin-4-yl)piperazin-1-yl)-3-(3-hydroxyazetidin-1-yl)propan-1-one;

2-(4-chlorophenyl)-1-(4-(((5R,7R)-7-hydroxy-5-methyl-6,7-dihydro-5H-cyclopenta[d]pyrimidin-4-yl)piperazin-1-yl)-3-(neopentylamino)propan-1-one;

2-(4-bromophenyl)-1-(4-(((5R,7R)-7-hydroxy-5-methyl-6,7-dihydro-5H-cyclopenta[d]pyrimidin-4-yl)piperazin-1-yl)-3-(isopropylamino)propan-1-one;

2-(4-chlorophenyl)-3-(4-fluoropiperidin-1-yl)-1-(4-(((5R,7R)-7-hydroxy-5-methyl-6,7-dihydro-5H-cyclopenta[d]pyrimidin-4-yl)piperazin-1-yl)propan-1-one;

2-(4-chlorophenyl)-3-((S)-3-fluoropyrrolidin-1-yl)-1-(4-(((5R,7R)-7-hydroxy-5-methyl-6,7-dihydro-5H-cyclopenta[d]pyrimidin-4-yl)piperazin-1-yl)propan-1-one;

2-(4-chlorophenyl)-3-(ethylamino)-1-(4-(((5R,7R)-7-hydroxy-5-methyl-6,7-dihydro-5H-cyclopenta[d]pyrimidin-4-yl)piperazin-1-yl)propan-1-one;

2-(4-chlorophenyl)-1-(4-(((5R,7R)-7-hydroxy-5-methyl-6,7-dihydro-5H-cyclopenta[d]pyrimidin-4-yl)piperazin-1-yl)-3-(isopropyl(methyl)amino)propan-1-one;

2-(4-chlorophenyl)-3-(4,4-difluoropiperidin-1-yl)-1-(4-(((5R,7R)-7-hydroxy-5-methyl-6,7-dihydro-5H-cyclopenta[d]pyrimidin-4-yl)piperazin-1-yl)propan-1-one;

2-(4-chlorophenyl)-3-(3,3-difluoropyrrolidin-1-yl)-1-(4-(((5R,7R)-7-hydroxy-5-methyl-6,7-dihydro-5H-cyclopenta[d]pyrimidin-4-yl)piperazin-1-yl)propan-1-one;

2-(4-bromo-3-fluorophenyl)-1-(4-(((5R,7R)-7-hydroxy-5-methyl-6,7-dihydro-5H-cyclopenta[d]pyrimidin-4-yl)piperazin-1-yl)-3-(isopropylamino)propan-1-one;

(R)-2-amino-3-(4-fluorophenyl)-1-(4-(((5R,7S)-7-hydroxy-5-methyl-6,7-dihydro-5H-cyclopenta[d]pyrimidin-4-yl)piperazin-1-yl)propan-1-one;

(R)-2-amino-3-(3,4-dichlorophenyl)-1-(4-(((5R,7S)-7-hydroxy-5-methyl-6,7-dihydro-5H-cyclopenta[d]pyrimidin-4-yl)piperazin-1-yl)propan-1-one;

(R)-2-amino-3-(3,4-difluorophenyl)-1-(4-(((5R,7S)-7-hydroxy-5-methyl-6,7-dihydro-5H-cyclopenta[d]pyrimidin-4-yl)piperazin-1-yl)propan-1-one;

(R)-2-(4-chlorophenyl)-3-(cyclopropylmethylamino)-1-(4-(((5R,7R)-7-hydroxy-5-methyl-6,7-dihydro-5H-cyclopenta[d]pyrimidin-4-yl)piperazin-1-yl)propan-1-one;

(S)-2-(4-chlorophenyl)-3-(cyclopropylmethylamino)-1-(4-(((5R,7R)-7-hydroxy-5-methyl-6,7-dihydro-5H-cyclopenta[d]pyrimidin-4-yl)piperazin-1-yl)propan-1-one;

2-(4-chlorophenyl)-3-((R)-3-fluoropyrrolidin-1-yl)-1-(4-(((5R,7R)-7-hydroxy-5-methyl-6,7-dihydro-5H-cyclopenta[d]pyrimidin-4-yl)piperazin-1-yl)propan-1-one;

(S)-1-(4-(((5R,7R)-7-hydroxy-5-methyl-6,7-dihydro-5H-cyclopenta[d]pyrimidin-4-yl)piperazin-1-yl)-3-(isopropylamino)-2-(4-(trifluoromethoxy)phenyl)propan-1-one;

(S)-2-(4-chlorophenyl)-3-(cyclopropylamino)-1-(4-(((5R,7R)-7-hydroxy-5-methyl-6,7-dihydro-5H-cyclopenta[d]pyrimidin-4-yl)piperazin-1-yl)propan-1-one;

(R)-2-(4-chlorophenyl)-1-(4-(((5R,7R)-7-hydroxy-5-methyl-6,7-dihydro-5H-cyclopenta[d]pyrimidin-4-yl)piperazin-1-yl)-3-(3-hydroxyazetidin-1-yl)propan-1-one;

(S)-2-(4-chlorophenyl)-1-(4-(((5R,7R)-7-hydroxy-5-methyl-6,7-dihydro-5H-cyclopenta[d]pyrimidin-4-yl)piperazin-1-yl)-3-(3-hydroxyazetidin-1-yl)propan-1-one;

(R)-4-amino-2-(4-chlorophenyl)-1-(4-(((5R,7R)-7-hydroxy-5-methyl-6,7-dihydro-5H-cyclopenta[d]pyrimidin-4-yl)piperazin-1-yl)-4-methylpentan-1-one;

(S)-4-amino-2-(4-chlorophenyl)-1-(4-(((5R,7R)-7-hydroxy-5-methyl-6,7-dihydro-5H-cyclopenta[d]pyrimidin-4-yl)piperazin-1-yl)-4-methylpentan-1-one;

(S)-2-(4-chlorophenyl)-1-(4-(((5R,7R)-7-hydroxy-5-methyl-6,7-dihydro-5H-cyclopenta[d]pyrimidin-4-yl)piperazin-1-yl)-3-((R)-pyrrolidin-3-ylamino)propan-1-one;

(S)-2-(4-chlorophenyl)-1-(4-(((5R,7R)-7-hydroxy-5-methyl-6,7-dihydro-5H-cyclopenta[d]pyrimidin-4-yl)piperazin-1-yl)-3-((S)-pyrrolidin-3-ylamino)propan-1-one;

(S)-3-((R)-1-acetylpyrrolidin-3-ylamino)-2-(4-chlorophenyl)-1-(4-(((5R,7R)-7-hydroxy-5-methyl-6,7-dihydro-5H-cyclopenta[d]pyrimidin-4-yl)piperazin-1-yl)propan-1-one;

(S)-3-((S)-1-acetylpyrrolidin-3-ylamino)-2-(4-chlorophenyl)-1-(4-(((5R,7R)-7-hydroxy-5-methyl-6,7-dihydro-5H-cyclopenta[d]pyrimidin-4-yl)piperazin-1-yl)propan-1-one;

(S)-2-(4-bromophenyl)-3-(cyclopropylmethylamino)-1-(4-(((5R,7R)-7-hydroxy-5-methyl-6,7-dihydro-5H-cyclopenta[d]pyrimidin-4-yl)piperazin-1-yl)propan-1-one;

(S)-2-(4-chlorophenyl)-1-(4-(((5R,7R)-7-hydroxy-5-methyl-6,7-dihydro-5H-cyclopenta[d]pyrimidin-4-yl)piperazin-1-yl)-3-(piperidin-4-ylamino)propan-1-one;

(S)-3-(1-acetylpiperidin-4-ylamino)-2-(4-chlorophenyl)-1-(4-(((5R,7R)-7-hydroxy-5-methyl-6,7-dihydro-5H-cyclopenta[d]pyrimidin-4-yl)piperazin-1-yl)propan-1-one;

(S)-2-(4-chlorophenyl)-1-(4-(((5R,7R)-7-hydroxy-5-methyl-6,7-dihydro-5H-cyclopenta[d]pyrimidin-4-yl)piperazin-1-yl)-3-(2-methoxyethylamino)propan-1-one;

(R)-2-(4-chlorophenyl)-4-(dimethylamino)-1-(4-(((5R,7R)-7-hydroxy-5-methyl-6,7-dihydro-5H-cyclopenta[d]pyrimidin-4-yl)piperazin-1-yl)butan-1-one;

(S)-2-(4-chlorophenyl)-1-(4-(((5R,7R)-7-hydroxy-5-methyl-6,7-dihydro-5H-cyclopenta[d]pyrimidin-4-yl)piperazin-1-yl)-3-(tetrahydro-2H-pyran-4-ylamino)propan-1-one;

(S)-2-(4-chlorophenyl)-1-(4-(((5R,7R)-7-hydroxy-5-methyl-6,7-dihydro-5H-cyclopenta[d]pyrimidin-4-yl)piperazin-1-yl)-3-((1r,4S)-4-hydroxycyclohexylamino)propan-1-one;

(S)-3-(azetidin-1-yl)-2-(4-chlorophenyl)-1-(4-(((5R,7R)-7-hydroxy-5-methyl-6,7-dihydro-5H-cyclopenta[d]pyrimidin-4-yl)piperazin-1-yl)propan-1-one;

(R)-3-(azetidin-1-yl)-2-(4-chlorophenyl)-1-(4-(((5R,7R)-7-hydroxy-5-methyl-6,7-dihydro-5H-cyclopenta[d]pyrimidin-4-yl)piperazin-1-yl)propan-1-one;

2-((S)-2-(4-chlorophenyl)-3-(4-(((5R,7R)-7-hydroxy-5-methyl-6,7-dihydro-5H-cyclopenta[d]pyrimidin-4-yl)piperazin-1-yl)-3-oxopropylamino)acetamide;

2-((S)-2-(4-chlorophenyl)-3-(4-(((5R,7R)-7-hydroxy-5-methyl-6,7-dihydro-5H-cyclopenta[d]pyrimidin-4-yl)piperazin-1-yl)-3-oxopropylamino)-N,N-dimethylacetamide;

2-((S)-2-(4-chlorophenyl)-3-(4-((5R,7R)-7-hydroxy-5-methyl-6,7-dihydro-5H-cyclopenta[d]pyrimidin-4-yl)piperazin-1-yl)-3-oxopropylamino)-N-methylacetamide;

(R)-2-(4-bromophenyl)-1-(4-((5R,7R)-7-hydroxy-5-methyl-6,7-dihydro-5H-cyclopenta[d]pyrimidin-4-yl)piperazin-1-yl)-4-(isopropylamino)butan-1-one;

(R)-2-(4-bromophenyl)-4-(dimethylamino)-1-(4-((5R,7R)-7-hydroxy-5-methyl-6,7-dihydro-5H-cyclopenta[d]pyrimidin-4-yl)piperazin-1-yl)butan-1-one;

(R)-2-(4-bromophenyl)-1-(4-((5R,7R)-7-hydroxy-5-methyl-6,7-dihydro-5H-cyclopenta[d]pyrimidin-4-yl)piperazin-1-yl)-4-(isobutylamino)butan-1-one;

(R)-2-(4-chlorophenyl)-1-(4-((5R,7R)-7-hydroxy-5-methyl-6,7-dihydro-5H-cyclopenta[d]pyrimidin-4-yl)piperazin-1-yl)-4((2-methoxyethyl)(methyl)amino)butan-1-one;

(R)-2-(4-chlorophenyl)-1-(4-((5R,7R)-7-hydroxy-5-methyl-6,7-dihydro-5H-cyclopenta[d]pyrimidin-4-yl)piperazin-1-yl)-4-(isopropylamino)butan-1-one;

(R)-2-(4-chlorophenyl)-1-(4-((5R,7R)-7-hydroxy-5-methyl-6,7-dihydro-5H-cyclopenta[d]pyrimidin-4-yl)piperazin-1-yl)-4-(3-hydroxyazetidin-1-yl)butan-1-one;

2-((R)-3-(4-bromophenyl)-4-(4-((5R,7R)-7-hydroxy-5-methyl-6,7-dihydro-5H-cyclopenta[d]pyrimidin-4-yl)piperazin-1-yl)-4-oxobutylamino)-N,N-dimethylacetamide;

(R)-2-(4-bromophenyl)-1-(4-((5R,7R)-7-hydroxy-5-methyl-6,7-dihydro-5H-cyclopenta[d]pyrimidin-4-yl)piperazin-1-yl)-4-(2-hydroxyethylamino)butan-1-one;

(2R)-2-(4-bromophenyl)-4-(2-hydroxy-1-(tetrahydro-2H-pyran-4-yl)ethylamino)-1-(4-((5R,7R)-7-hydroxy-5-methyl-6,7-dihydro-5H-cyclopenta[d]pyrimidin-4-yl)piperazin-1-yl)butan-1-one;

(R)-2-amino-1-(4-((5R,7R)-7-hydroxy-5-methyl-6,7-dihydro-5H-cyclopenta[d]pyrimidin-4-yl)piperazin-1-yl)-3-(4-iodophenyl)propan-1-one;

4-((R)-2-amino-3-(4-((5R,7R)-7-hydroxy-5-methyl-6,7-dihydro-5H-cyclopenta[d]pyrimidin-4-yl)piperazin-1-yl)-3-oxopropyl)benzonitrile;

(R)-2-amino-1-(4-((5R,7R)-7-hydroxy-5-methyl-6,7-dihydro-5H-cyclopenta[d]pyrimidin-4-yl)piperazin-1-yl)-3-(4-(trifluoromethyl)phenyl)propan-1-one;

(S)-3-(4-acetylpiperazin-1-yl)-2-(4-chlorophenyl)-1-(4-((5R,7R)-7-hydroxy-5,6,7-dihydro-5H-cyclopenta[d]pyrimidin-4-yl)piperazin-1-yl)propan-1-one;

(R)-3-(4-acetylpiperazin-1-yl)-2-(4-chlorophenyl)-1-(4-((5R,7R)-7-hydroxy-5-methyl-6,7-dihydro-5H-cyclopenta[d]pyrimidin-4-yl)piperazin-1-yl)propan-1-one;

(R)-3-(4-chlorophenyl)-1-(4-((5R,7R)-7-hydroxy-5-methyl-6,7-dihydro-5H-cyclopenta[d]pyrimidin-4-yl)piperazin-1-yl)-2-(methylamino)propan-1-one;

(S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(4-(2-hydroxyethyl)piperazin-1-yl)propan-1-one;

(R)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(4-(2-hydroxyethyl)piperazin-1-yl)propan-1-one;

2-(4-chlorophenyl)-1-(4-((5R,7R)-7-hydroxy-5-methyl-6,7-dihydro-5H-cyclopenta[d]pyrimidin-4-yl)piperazin-1-yl)-3-(3-methoxyazetidin-1-yl)propan-1-one;

(R)-2-(4-chlorophenyl)-4-(cyclohexylamino)-1-(4-((5R,7R)-7-hydroxy-5-methyl-6,7-dihydro-5H-cyclopenta[d]pyrimidin-4-yl)piperazin-1-yl)butan-1-one;

(R)-2-(4-chlorophenyl)-1-(4-((5R,7R)-7-hydroxy-5-methyl-6,7-dihydro-5H-cyclopenta[d]pyrimidin-4-yl)piperazin-1-yl)-4-(tetrahydro-2H-pyran-4-ylamino)butan-1-one;

(2R)-2-(4-chlorophenyl)-1-(4-((5R,7R)-7-hydroxy-5-methyl-6,7-dihydro-5H-cyclopenta[d]pyrimidin-4-yl)piperazin-1-yl)-4-(2-hydroxypropylamino)butan-1-one;

(2R)-2-(4-chlorophenyl)-4-(2-hydroxy-1-(tetrahydro-2H-pyran-4-yl)ethylamino)-1-(4-((5R,7R)-7-hydroxy-5-methyl-6,7-dihydro-5H-cyclopenta[d]pyrimidin-4-yl)piperazin-1-yl)butan-1-one;

(2R)-2-(4-chlorophenyl)-4-(2-hydroxy-1-phenylethylamino)-1-(4-((5R,7R)-7-hydroxy-5-methyl-6,7-dihydro-5H-cyclopenta[d]pyrimidin-4-yl)piperazin-1-yl)butan-1-one;

(S)-2-(4-chlorophenyl)-3-(ethyl(tetrahydro-2H-pyran-4-yl)amino)-1-(4-((5R,7R)-7-hydroxy-5-methyl-6,7-dihydro-5H-cyclopenta[d]pyrimidin-4-yl)piperazin-1-yl)propan-1-one;

(R)-2-(4-bromophenyl)-1-(4-((5R,7R)-7-hydroxy-5-methyl-6,7-dihydro-5H-cyclopenta[d]pyrimidin-4-yl)piperazin-1-yl)-4-(2-methoxyethylamino)butan-1-one;

(2R)-2-(4-bromophenyl)-1-(4-((5R,7R)-7-hydroxy-5-methyl-6,7-dihydro-5H-cyclopenta[d]pyrimidin-4-yl)piperazin-1-yl)-4-(3,3,3-trifluoro-2-hydroxypropylamino)butan-1-one;

(R)-2-(4-bromophenyl)-1-(4-((5R,7R)-7-hydroxy-5-methyl-6,7-dihydro-5H-cyclopenta[d]pyrimidin-4-yl)piperazin-1-yl)-44(1-hydroxycyclopropyl)methylamino)butan-1-one;

2-((R)-3-(4-bromophenyl)-4-(4-((5R,7R)-7-hydroxy-5-methyl-6,7-dihydro-5H-cyclopenta[d]pyrimidin-4-yl)piperazin-1-yl)-4-oxobutylamino)acetamide;

(R)-2-(4-bromophenyl)-1-(4-((5R,7R)-7-hydroxy-5-methyl-6,7-dihydro-5H-cyclopenta[d]pyrimidin-4-yl)piperazin-1-yl)-4-(tetrahydro-2H-pyran-4-ylamino)butan-1-one;

(R)-4-(3-(1H-imidazol-1-yl)propylamino)-2-(4-bromophenyl)-1-(4-((5R,7R)-7-hydroxy-5-methyl-6,7-dihydro-5H-cyclopenta[d]pyrimidin-4-yl)piperazin-1-yl)butan-1-one;

(S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-morpholinopropan-1-one;

(R)-2-(4-chlorophenyl)-1-(4-((5R,7R)-7-hydroxy-5-methyl-6,7-dihydro-5H-cyclopenta[d]pyrimidin-4-yl)piperazin-1-yl)-3-morpholinopropan-1-one;

(R)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(4-methylpiperazin-1-yl)propan-1-one;

(S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(4-methylpiperazin-1-yl)propan-1-one;

(S)-3-(3-aminoazetidin-1-yl)-2-(4-chlorophenyl)-1-(4-((5R,7R)-7-hydroxy-5-methyl-6,7-dihydro-5H-cyclopenta[d]pyrimidin-4-yl)piperazin-1-yl)propan-1-one;

(R)-3-(3-aminoazetidin-1-yl)-2-(4-chlorophenyl)-1-(4-((5R,7R)-7-hydroxy-5-methyl-6,7-dihydro-5H-cyclopenta[d]pyrimidin-4-yl)piperazin-1-yl)propan-1-one;

(S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-thiomorpholinopropan-1-one;

(S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(piperazin-1-yl)propan-1-one;

(R)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(piperazin-1-yl)propan-1-one;
(R)-2-(4-chlorophenyl)-1-(4-((5R,7R)-7-hydroxy-5-methyl-6,7-dihydro-5H-cyclopenta[d]pyrimidin-4-yl)piperazin-1-yl)-3-thiomorpholinopropan-1-one;
(R)-2-(4-chlorophenyl)-3-(4-fluoropiperidin-1-yl)-1-(4-((5R,7R)-7-hydroxy-5-methyl-6,7-dihydro-5H-cyclopenta[d]pyrimidin-4-yl)piperazin-1-yl)propan-1-one;
(S)-2-(4-chlorophenyl)-3-(4-fluoropiperidin-1-yl)-1-(4-((5R,7R)-7-hydroxy-5-methyl-6,7-dihydro-5H-cyclopenta[d]pyrimidin-4-yl)piperazin-1-yl)propan-1-one;
(R)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(3-methoxyazetidin-1-yl)propan-1-one;
(S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(3-methoxyazetidin-1-yl)propan-1-one;
(S)-2-(3,4-dichlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one;
(S)-2-(4-chlorophenyl)-3-(dimethylamino)-1-(4-((5R,7R)-7-hydroxy-5-methyl-6,7-dihydro-5H-cyclopenta[d]pyrimidin-4-yl)piperazin-1-yl)propan-1-one;
(S)-2-(4-fluoro-3-(trifluoromethyl)phenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one;
(S)-2-(3-fluoro-4-(trifluoromethyl)phenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one;
(S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(methoxyamino)propan-1-one;
(S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(4-methoxypiperidin-1-yl)propan-1-one;
(R)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(4-methoxypiperidin-1-yl)propan-1-one;
(S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(4-hydroxypiperidin-1-yl)propan-1-one;
(R)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(4-hydroxypiperidin-1-yl)propan-1-one;
(S)-3-(4-aminopiperidin-1-yl)-2-(4-chlorophenyl)-1-(4-((5R,7R)-7-hydroxy-5-methyl-6,7-dihydro-5H-cyclopenta[d]pyrimidin-4-yl)piperazin-1-yl)propan-1-one;
(R)-3-(4-aminopiperidin-1-yl)-2-(4-chlorophenyl)-1-(4-((5R,7R)-7-hydroxy-5-methyl-6,7-dihydro-5H-cyclopenta[d]pyrimidin-4-yl)piperazin-1-yl)propan-1-one;
(S)-2-(4-chlorophenyl)-1-(4-((5R,7S)-7-hydroxy-5-methyl-6,7-dihydro-5H-cyclopenta[d]pyrimidin-4-yl)piperazin-1-yl)-3-(tetrahydro-2H-pyran-4-ylamino)propan-1-one;
(S)-2-(4-chlorophenyl)-1-(4-((5R,7S)-7-hydroxy-5-methyl-6,7-dihydro-5H-cyclopenta[d]pyrimidin-4-yl)piperazin-1-yl)-3-(methyl(tetrahydro-2H-pyran-4-yl)amino)propan-1-one;
(S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropyl(methyl)amino)propan-1-one;
(R)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(4-(methylsulfonyl)piperazin-1-yl)propan-1-one;
(S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(4-(methylamino)piperidin-1-yl)propan-1-one;
(R)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(4-(methylamino)piperidin-1-yl)propan-1-one;
(S)-2-(4-chloro-3-(trifluoromethoxy)phenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one;
(S)-2-(3-fluoro-4-(trifluoromethoxy)phenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one;
(S)-2-(4-chloro-3-(trifluoromethyl)phenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one;
(R)-2-(4-chlorophenyl)-3-(4-ethylpiperazin-1-yl)-1-(4-((5R,7R)-7-hydroxy-5-methyl-6,7-dihydro-5H-cyclopenta[d]pyrimidin-4-yl)piperazin-1-yl)propan-1-one;
(S)-2-(4-chlorophenyl)-3-(4-ethylpiperazin-1-yl)-1-(4-((5R,7R)-7-hydroxy-5-methyl-6,7-dihydro-5H-cyclopenta[d]pyrimidin-4-yl)piperazin-1-yl)propan-1-one;
(S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(4-isopropylpiperazin-1-yl)propan-1-one;
(R)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(4-isopropylpiperazin-1-yl)propan-1-one;
(R)-2-(4-chlorophenyl)-3-((S)-3-(dimethylamino)pyrrolidin-1-yl)-1-(4-((5R,7R)-7-hydroxy-5-methyl-6,7-dihydro-5H-cyclopenta[d]pyrimidin-4-yl)piperazin-1-yl)propan-1-one;
(S)-2-(4-chlorophenyl)-3-((S)-3-(dimethylamino)pyrrolidin-1-yl)-1-(4-((5R,7R)-7-hydroxy-5-methyl-6,7-dihydro-5H-cyclopenta[d]pyrimidin-4-yl)piperazin-1-yl)propan-1-one;
(S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-((R)-tetrahydrofuran-3-ylamino)propan-1-one;
(S)-2-(4-chlorophenyl)-1-(4-((5R,7S)-7-hydroxy-5-methyl-6,7-dihydro-5H-cyclopenta[d]pyrimidin-4-yl)piperazin-1-yl)-3-((R)-tetrahydrofuran-3-ylamino)propan-1-one;
(S)-2-(4-chlorophenyl)-3-(2-fluoroethylamino)-1-(4-((5R,7R)-7-hydroxy-5-methyl-6,7-dihydro-5H-cyclopenta[d]pyrimidin-4-yl)piperazin-1-yl)propan-1-one;
(S)-2-(4-fluoro-3-(trifluoromethoxy)phenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one;
(S)-2-(3,5-bis(trifluoromethyl)phenyl)-1-(4-((5R,7S)-7-hydroxy-5-methyl-6,7-dihydro-5H-cyclopenta[d]pyrimidin-4-yl)piperazin-1-yl)-3-(isopropylamino)propan-1-one;

(S)-2-(3-fluoro-4-methoxyphenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one;

4-((R)-2-(4-chlorophenyl)-3-(4-((5R,7R)-7-hydroxy-5-methyl-6,7-dihydro-5H-cyclopenta[d]pyrimidin-4-yl)piperazin-1-yl)-3-oxopropyl)piperazin-2-one;

(R)-2-(4-chlorophenyl)-1-(4-((5R,7R)-7-hydroxy-5-methyl-6,7-dihydro-5H-cyclopenta[d]pyrimidin-4-yl)piperazin-1-yl)-3-((R)-3-hydroxypyrrolidin-1-yl)propan-1-one;

(S)-2-(4-chlorophenyl)-3-(4-(dimethylamino)piperidin-1-yl)-1-(4-((5R,7R)-7-hydroxy-5-methyl-6,7-dihydro-5H-cyclopenta[d]pyrimidin-4-yl)piperazin-1-yl)propan-1-one;

(R)-2-(4-chlorophenyl)-3-(4-(dimethylamino)piperidin-1-yl)-1-(4-((5R,7R)-7-hydroxy-5-methyl-6,7-dihydro-5H-cyclopenta[d]pyrimidin-4-yl)piperazin-1-yl)propan-1-one;

(S)-2-(3-chloro-5-fluorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one;

(S)-2-(3-bromo-4-methoxyphenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one;

(R)-3-(4-chlorophenyl)-1-(4-((5R,7R)-7-hydroxy-5-methyl-6,7-dihydro-5H-cyclopenta[d]pyrimidin-4-yl)piperazin-1-yl)-2-(piperidin-4-ylamino)propan-1-one;

(R)-2-(1-acetylpiperidin-4-ylamino)-3-(4-chlorophenyl)-1-(4-((5R,7R)-7-hydroxy-5-methyl-6,7-dihydro-5H-cyclopenta[d]pyrimidin-4-yl)piperazin-1-yl)propan-1-one;

2-((R)-3-(4-chlorophenyl)-1-(4-((5R,7R)-7-hydroxy-5-methyl-6,7-dihydro-5H-cyclopenta[d]pyrimidin-4-yl)piperazin-1-yl)-1-oxopropan-2-ylamino)-N-isopropylacetamide;

(R)-3-(4-chlorophenyl)-2-(dimethylamino)-1-(4-((5R,7R)-7-hydroxy-5-methyl-6,7-dihydro-5H-cyclopenta[d]pyrimidin-4-yl)piperazin-1-yl)propan-1-one;

(R)-3-(4-chlorophenyl)-1-(4-((5R,7R)-7-hydroxy-5-methyl-6,7-dihydro-5H-cyclopenta[d]pyrimidin-4-yl)piperazin-1-yl)-2-(2-morpholinoethylamino)propan-1-one;

(R)-3-(4-chlorophenyl)-1-(4-((5R,7R)-7-hydroxy-5-methyl-6,7-dihydro-5H-cyclopenta[d]pyrimidin-4-yl)piperazin-1-yl)-2-(isopropylamino)propan-1-one;

(R)-3-(4-chlorophenyl)-1-(4-((5R,7R)-7-hydroxy-5-methyl-6,7-dihydro-5H-cyclopenta[d]pyrimidin-4-yl)piperazin-1-yl)-2-(tetrahydro-2H-pyran-4-ylamino)propan-1-one;

(R)-3-(4-chlorophenyl)-1-((S)-4-((5R,7R)-7-hydroxy-5-methyl-6,7-dihydro-5H-cyclopenta[d]pyrimidin-4-yl)-3-methylpiperazin-1-yl)-2-(isopropylamino)propan-1-one;

2-((R)-3-(4-chlorophenyl)-1-(4-((5R,7R)-7-hydroxy-5-methyl-6,7-dihydro-5H-cyclopenta[d]pyrimidin-4-yl)piperazin-1-yl)-1-oxopropan-2-ylamino)-N,N-dimethylacetamide;

(S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(1,4-oxazepan-4-yl)propan-1-one;

(R)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(1,4-oxazepan-4-yl)propan-1-one;

(R)-2-(4-chloro-2-fluorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one;

(S)-2-(4-chloro-2-fluorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one;

(S)-2-(2-fluoro-4-(trifluoromethyl)phenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one;

(S)-2-(4-chlorophenyl)-3-(cyclohexylamino)-1-(4-((5R,7R)-7-hydroxy-5-methyl-6,7-dihydro-5H-cyclopenta[d]pyrimidin-4-yl)piperazin-1-yl)propan-1-one;

(S)-2-(4-chlorophenyl)-3-(cyclohexylamino)-1-(4-((5R,7S)-7-hydroxy-5-methyl-6,7-dihydro-5H-cyclopenta[d]pyrimidin-4-yl)piperazin-1-yl)propan-1-one;

(S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(4-methoxycyclohexylamino)propan-1-one;

(S)-2-(3-fluoro-4-(trifluoromethoxy)phenyl)-1-(4-((5R,7R)-7-hydroxy-5-methyl-6,7-dihydro-5H-cyclopenta[d]pyrimidin-4-yl)piperazin-1-yl)-3-(tetrahydro-2H-pyran-4-ylamino)propan-1-one;

(S)-2-(3-fluoro-4-(trifluoromethyl)phenyl)-1-(4-((5R,7R)-7-hydroxy-5-methyl-6,7-dihydro-5H-cyclopenta[d]pyrimidin-4-yl)piperazin-1-yl)-3-(tetrahydro-2H-pyran-4-ylamino)propan-1-one;

(S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-((S)-tetrahydrofuran-3-ylamino)propan-1-one;

(S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(4-methyltetrahydro-2H-pyran-4-ylamino)propan-1-one;

(R)-3-(4-chlorophenyl)-1-(4-((5R,7R)-7-hydroxy-5-methyl-6,7-dihydro-5H-cyclopenta[d]pyrimidin-4-yl)piperazin-1-yl)-2-(2-(tetrahydro-2H-pyran-4-yl)ethylamino)propan-1-one;

(R)-3-(4-chlorophenyl)-1-(4-((5R,7R)-7-hydroxy-5-methyl-6,7-dihydro-5H-cyclopenta[d]pyrimidin-4-yl)piperazin-1-yl)-2-(3,3,3-trifluoropropylamino)propan-1-one;

(R)-3-(4-chlorophenyl)-1-(4-((5R,7R)-7-hydroxy-5-methyl-6,7-dihydro-5H-cyclopenta[d]pyrimidin-4-yl)piperazin-1-yl)-2-((tetrahydro-2H-pyran-4-yl)methylamino)propan-1-one;

(R)-3-(4-chlorophenyl)-1-(4-((5R,7R)-7-hydroxy-5-methyl-6,7-dihydro-5H-cyclopenta[d]pyrimidin-4-yl)piperazin-1-yl)-2-(isopropyl(methyl)amino)propan-1-one;

(S)-3-(tert-butylamino)-2-(4-chlorophenyl)-1-(4-((5R,7R)-7-hydroxy-5-methyl-6,7-dihydro-5H-cyclopenta[d]pyrimidin-4-yl)piperazin-1-yl)propan-1-one;

(R)-3-(tert-butylamino)-2-(4-chlorophenyl)-1-(4-((5R,7R)-7-hydroxy-5-methyl-6,7-dihydro-5H-cyclopenta[d]pyrimidin-4-yl)piperazin-1-yl)propan-1-one;

(S)-2-(4-chloro-3-fluorophenyl)-1-(4-((5R,7R)-7-hydroxy-5-methyl-6,7-dihydro-5H-cyclopenta[d]pyrimidin-4-yl)piperazin-1-yl)-3-(4-methylpiperazin-1-yl)propan-1-one;

(R)-2-(4-chloro-3-fluorophenyl)-1-(4-((5R,7R)-7-hydroxy-5-methyl-6,7-dihydro-5H-cyclopenta[d]pyrimidin-4-yl)piperazin-1-yl)-3-(4-methylpiperazin-1-yl)propan-1-one;

(S)-2-(4-chloro-3-fluorophenyl)-1-(4-((5R,7R)-7-hydroxy-5-methyl-6,7-dihydro-5H-cyclopenta[d]pyrimidin-4-yl)piperazin-1-yl)-3-(4-hydroxypiperidin-1-yl)propan-1-one;

(R)-2-(4-chloro-3-fluorophenyl)-1-(4-((5R,7R)-7-hydroxy-5-methyl-6,7-dihydro-5H-cyclopenta[d]pyrimidin-4-yl)piperazin-1-yl)-3-morpholinopropan-1-one;

(R)-2-(4-chloro-3-fluorophenyl)-1-(4-((5R,7R)-7-hydroxy-5-methyl-6,7-dihydro-5H-cyclopenta[d]pyrimidin-4-yl)piperazin-1-yl)-3-(4-hydroxypiperidin-1-yl)propan-1-one;

(S)-2-(3-fluoro-4-(trifluoromethoxy)phenyl)-1-(4-((5R,7R)-7-hydroxy-5-methyl-6,7-dihydro-5H-cyclopenta[d]pyrimidin-4-yl)piperazin-1-yl)-3-(4-methylpiperazin-1-yl)propan-1-one;

(R)-2-(3-fluoro-4-(trifluoromethoxy)phenyl)-1-(4-((5R,7R)-7-hydroxy-5-methyl-6,7-dihydro-5H-cyclopenta[d]pyrimidin-4-yl)piperazin-1-yl)-3-(4-methylpiperazin-1-yl)propan-1-one;

(S)-3-(cyclopropylmethylamino)-2-(3-fluoro-4-(trifluoromethyl)phenyl)-1-(4-((5R,7R)-7-hydroxy-5-methyl-6,7-dihydro-5H-cyclopenta[d]pyrimidin-4-yl)piperazin-1-yl)propan-1-one;

(S)-3-(cyclopropylmethylamino)-2-(3-fluoro-4-(trifluoromethoxy)phenyl)-1-(4-((5R,7R)-7-hydroxy-5-methyl-6,7-dihydro-5H-cyclopenta[d]pyrimidin-4-yl)piperazin-1-yl)propan-1-one;

(S)-1-(4-((5R,7R)-7-hydroxy-5-methyl-6,7-dihydro-5H-cyclopenta[d]pyrimidin-4-yl)piperazin-1-yl)-3-(isopropylamino)-2-(4-(trifluoromethyl)phenyl)propan-1-one;

(S)-3-amino-2-(4-bromophenyl)-1-(4-((5R,7S)-7-hydroxy-5-methyl-6,7-dihydro-5H-cyclopenta[d]pyrimidin-4-yl)piperazin-1-yl)propan-1-one;

(S)-3-amino-2-(4-chloro-3-fluorophenyl)-1-(4-((5R,7S)-7-hydroxy-5-methyl-6,7-dihydro-5H-cyclopenta[d]pyrimidin-4-yl)piperazin-1-yl)propan-1-one;

(S)-2-(4-bromophenyl)-1-(4-((5R,7R)-7-hydroxy-5-methyl-6,7-dihydro-5H-cyclopenta[d]pyrimidin-4-yl)piperazin-1-yl)-3-(tetrahydro-2H-pyran-4-ylamino)propan-1-one;

3-((S)-2-(4-chlorophenyl)-3-(4-((5R,7R)-7-hydroxy-5-methyl-6,7-dihydro-5H-cyclopenta[d]pyrimidin-4-yl)piperazin-1-yl)-3-oxopropylamino)propanamide;

3-((S)-2-(4-chlorophenyl)-3-(4-((5R,7S)-7-hydroxy-5-methyl-6,7-dihydro-5H-cyclopenta[d]pyrimidin-4-yl)piperazin-1-yl)-3-oxopropylamino)propanamide;

(4-(4-chlorophenyl)piperidin-4-yl)(4-((5R,7R)-7-hydroxy-5-methyl-6,7-dihydro-5H-cyclopenta[d]pyrimidin-4-yl)piperazin-1-yl)methanone;

(S)-2-(4-bromophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one;

(S)-3-amino-2-(4-chloro-3-fluorophenyl)-1-(4-((5R,7R)-7-hydroxy-5-methyl-6,7-dihydro-5H-cyclopenta[d]pyrimidin-4-yl)piperazin-1-yl)propan-1-one;

(S)-3-amino-2-(4-bromophenyl)-1-(4-((5R,7R)-7-hydroxy-5-methyl-6,7-dihydro-5H-cyclopenta[d]pyrimidin-4-yl)piperazin-1-yl)propan-1-one;

(S)-2-(4-bromophenyl)-1-(4-((5R,7S)-7-hydroxy-5-methyl-6,7-dihydro-5H-cyclopenta[d]pyrimidin-4-yl)piperazin-1-yl)-3-(tetrahydro-2H-pyran-4-ylamino)propan-1-one;

(S)-2-(4-chloro-3-fluorophenyl)-1-(4-((5R,7S)-7-hydroxy-5-methyl-6,7-dihydro-5H-cyclopenta[d]pyrimidin-4-yl)piperazin-1-yl)-3-(tetrahydro-2H-pyran-4-ylamino)propan-1-one;

(S)-2-(3,4-dichlorophenyl)-1-(4-((5R,7R)-7-hydroxy-5-methyl-6,7-dihydro-5H-cyclopenta[d]pyrimidin-4-yl)piperazin-1-yl)-3-(tetrahydro-2H-pyran-4-ylamino)propan-1-one;

(S)-3-amino-2-(3,4-dichlorophenyl)-1-(4-((5R,7S)-7-hydroxy-5-methyl-6,7-dihydro-5H-cyclopenta[d]pyrimidin-4-yl)piperazin-1-yl)propan-1-one;

(R)-2-(3,4-dichlorophenyl)-1-(4-((5R,7R)-7-hydroxy-5-methyl-6,7-dihydro-5H-cyclopenta[d]pyrimidin-4-yl)piperazin-1-yl)-3-(4-hydroxypiperidin-1-yl)propan-1-one;

(S)-2-(3,4-dichlorophenyl)-1-(4-((5R,7R)-7-hydroxy-5-methyl-6,7-dihydro-5H-cyclopenta[d]pyrimidin-4-yl)piperazin-1-yl)-3-(4-isopropylpiperazin-1-yl)propan-1-one;

(S)-2-(3-fluoro-4-(trifluoromethoxy)phenyl)-1-(4-((5R,7R)-7-hydroxy-5-methyl-6,7-dihydro-5H-cyclopenta[d]pyrimidin-4-yl)piperazin-1-yl)-3-(4-hydroxypiperidin-1-yl)propan-1-one;

(R)-2-(3-fluoro-4-(trifluoromethoxy)phenyl)-1-(4-((5R,7R)-7-hydroxy-5-methyl-6,7-dihydro-5H-cyclopenta[d]pyrimidin-4-yl)piperazin-1-yl)-3-(4-hydroxypiperidin-1-yl)propan-1-one;

(S)-2-(3-fluoro-4-(trifluoromethoxy)phenyl)-1-(4-((5R,7R)-7-hydroxy-5-methyl-6,7-dihydro-5H-cyclopenta[d]pyrimidin-4-yl)piperazin-1-yl)-3-(4-isopropylpiperazin-1-yl)propan-1-one;

(S)-2-(3,5-difluorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one;

(S)-3-((R)-3-aminopyrrolidin-1-yl)-2-(4-chlorophenyl)-1-(4-((5R,7R)-7-hydroxy-5-methyl-6,7-dihydro-5H-cyclopenta[d]pyrimidin-4-yl)piperazin-1-yl)propan-1-one;

(R)-3-((R)-3-aminopyrrolidin-1-yl)-2-(4-chlorophenyl)-1-(4-((5R,7R)-7-hydroxy-5-methyl-6,7-dihydro-5H-cyclopenta[d]pyrimidin-4-yl)piperazin-1-yl)propan-1-one;

(S)-2-(4-chloro-3-fluorophenyl)-1-(4-((5R,7R)-7-hydroxy-5-methyl-6,7-dihydro-5H-cyclopenta[d]pyrimidin-4-yl)piperazin-1-yl)-3-(4-isopropylpiperazin-1-yl)propan-1-one;

(S)-2-(3-fluoro-4-(trifluoromethoxy)phenyl)-1-(4-((5R,7R)-7-hydroxy-5-methyl-6,7-dihydro-5H-cyclopenta[d]pyrimidin-4-yl)piperazin-1-yl)-3-morpholinopropan-1-one;

(R)-2-(3-fluoro-4-(trifluoromethoxy)phenyl)-1-(4-((5R,7R)-7-hydroxy-5-methyl-6,7-dihydro-5H-cyclopenta[d]pyrimidin-4-yl)piperazin-1-yl)-3-morpholinopropan-1-one;

(S)-3-(4-ethylpiperazin-1-yl)-2-(3-fluoro-4-(trifluoromethoxy)phenyl)-1-(4-((5R,7R)-7-hydroxy-5-methyl-6,7-dihydro-5H-cyclopenta[d]pyrimidin-4-yl)piperazin-1-yl)propan-1-one;

(R)-3-(4-ethylpiperazin-1-yl)-2-(3-fluoro-4-(trifluoromethoxy)phenyl)-1-(4-((5R,7R)-7-hydroxy-5-methyl-6,7-dihydro-5H-cyclopenta[d]pyrimidin-4-yl)piperazin-1-yl)propan-1-one;

(S)-3-(4-acetylpiperazin-1-yl)-2-(3-fluoro-4-(trifluoromethoxy)phenyl)-1-(4-((5R,7R)-7-hydroxy-5-methyl-6,7-dihydro-5H-cyclopenta[d]pyrimidin-4-yl)piperazin-1-yl)propan-1-one;

(R)-3-(4-acetylpiperazin-1-yl)-2-(3-fluoro-4-(trifluoromethoxy)phenyl)-1-(4-((5R,7R)-7-hydroxy-5-methyl-6,7-dihydro-5H-cyclopenta[d]pyrimidin-4-yl)piperazin-1-yl)propan-1-one;

(S)-2-(3,4-dichlorophenyl)-1-(4-((5R,7S)-7-hydroxy-5-methyl-6,7-dihydro-5H-cyclopenta[d]pyrimidin-4-yl)piperazin-1-yl)-3-(tetrahydro-2H-pyran-4-ylamino)propan-1-one;

(S)-2-(4-bromophenyl)-1-(4-((5R,7S)-7-hydroxy-5-methyl-6,7-dihydro-5H-cyclopenta[d]pyrimidin-4-yl)piperazin-1-yl)-3-(isopropylamino)propan-1-one;

(S)-2-(4-chloro-3-fluorophenyl)-1-(4-((5R,7S)-7-hydroxy-5-methyl-6,7-dihydro-5H-cyclopenta[d]pyrimidin-4-yl)piperazin-1-yl)-3-(isopropylamino)propan-1-one;

(S)-2-(4-chloro-3-fluorophenyl)-3-(cyclopropylmethylamino)-1-(4-((5R,7S)-7-hydroxy-5-methyl-6,7-dihydro-5H-cyclopenta[d]pyrimidin-4-yl)piperazin-1-yl)propan-1-one;

(S)-3-(bis(cyclopropylmethyl)amino)-2-(4-chloro-3-fluorophenyl)-1-(4-((5R,7S)-7-hydroxy-5-methyl-6,7-dihydro-5H-cyclopenta[d]pyrimidin-4-yl)piperazin-1-yl)propan-1-one;

(S)-2-(4-bromophenyl)-3-(cyclopropylmethylamino)-1-(4-((5R,7S)-7-hydroxy-5-methyl-6,7-dihydro-5H-cyclopenta[d]pyrimidin-4-yl)piperazin-1-yl)propan-1-one;

(S)-2-(4-chloro-3-fluorophenyl)-1-(4-((5R,7R)-7-hydroxy-5-methyl-6,7-dihydro-5H-cyclopenta[d]pyrimidin-4-yl)piperazin-1-yl)-3-(tetrahydro-2H-pyran-4-ylamino)propan-1-one;

(S)-2-(4-chloro-3-fluorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one;

(S)-2-(4-bromophenyl)-3-((cyclopropylmethyl)(methyl)amino)-1-(4-((5R,7S)-7-hydroxy-5-methyl-6,7-dihydro-5H-cyclopenta[d]pyrimidin-4-yl)piperazin-1-yl)propan-1-one;

(S)-2-(4-chloro-3-fluorophenyl)-3-(cyclopropylmethylamino)-1-(4-((5R,7R)-7-hydroxy-5-methyl-6,7-dihydro-5H-cyclopenta[d]pyrimidin-4-yl)piperazin-1-yl)propan-1-one;

(S)-3-(cyclopropylmethylamino)-2-(3,4-dichlorophenyl)-1-(4-((5R,7R)-7-hydroxy-5-methyl-6,7-dihydro-5H-cyclopenta[d]pyrimidin-4-yl)piperazin-1-yl)propan-1-one;

(S)-1-(4-((5R,7R)-7-hydroxy-5-methyl-6,7-dihydro-5H-cyclopenta[d]pyrimidin-4-yl)piperazin-1-yl)-3-(tetrahydro-2H-pyran-4-ylamino)-2-(4-(trifluoromethoxy)phenyl)propan-1-one;

(R)-2-(4-chlorophenyl)-3-((3S,5R)-3,5-dimethylpiperazin-1-yl)-1-(4-((5R,7R)-7-hydroxy-5-methyl-6,7-dihydro-5H-cyclopenta[d]pyrimidin-4-yl)piperazin-1-yl)propan-1-one;

(R)-2-(4-chlorophenyl)-3-((2S,6R)-2,6-dimethylmorpholino)-1-(4-((5R,7R)-7-hydroxy-5-methyl-6,7-dihydro-5H-cyclopenta[d]pyrimidin-4-yl)piperazin-1-yl)propan-1-one;

(S)-2-(4-chlorophenyl)-3-((2S,6R)-2,6-dimethylmorpholino)-1-(4-((5R,7R)-7-hydroxy-5-methyl-6,7-dihydro-5H-cyclopenta[d]pyrimidin-4-yl)piperazin-1-yl)propan-1-one;

(S)-2-(4-chlorophenyl)-3-((3S,5R)-3,5-dimethylpiperazin-1-yl)-1-(4-((5R,7R)-7-hydroxy-5-methyl-6,7-dihydro-5H-cyclopenta[d]pyrimidin-4-yl)piperazin-1-yl)propan-1-one;

(S)-2-(3-fluoro-4-(trifluoromethyl)phenyl)-1-(4-((5R,7R)-7-hydroxy-5-methyl-6,7-dihydro-5H-cyclopenta[d]pyrimidin-4-yl)piperazin-1-yl)-3-(4-hydroxypiperidin-1-yl)propan-1-one;

(R)-2-(3-fluoro-4-(trifluoromethyl)phenyl)-1-(4-((5R,7R)-7-hydroxy-5-methyl-6,7-dihydro-5H-cyclopenta[d]pyrimidin-4-yl)piperazin-1-yl)-3-(4-hydroxypiperidin-1-yl)propan-1-one;

(S)-2-(3-fluoro-4-(trifluoromethyl)phenyl)-1-(4-((5R,7R)-7-hydroxy-5-methyl-6,7-dihydro-5H-cyclopenta[d]pyrimidin-4-yl)piperazin-1-yl)-3-(4-methylpiperazin-1-yl)propan-1-one;

(R)-2-(3-fluoro-4-(trifluoromethyl)phenyl)-1-(4-((5R,7R)-7-hydroxy-5-methyl-6,7-dihydro-5H-cyclopenta[d]pyrimidin-4-yl)piperazin-1-yl)-3-(4-methylpiperazin-1-yl)propan-1-one;

(S)-2-(3-fluoro-4-(trifluoromethyl)phenyl)-1-(4-((5R,7R)-7-hydroxy-5-methyl-6,7-dihydro-5H-cyclopenta[d]pyrimidin-4-yl)piperazin-1-yl)-3-(4-isopropylpiperazin-1-yl)propan-1-one;

(R)-2-(3-fluoro-4-(trifluoromethyl)phenyl)-1-(4-((5R,7R)-7-hydroxy-5-methyl-6,7-dihydro-5H-cyclopenta[d]pyrimidin-4-yl)piperazin-1-yl)-3-(4-isopropylpiperazin-1-yl)propan-1-one;

(S)-3-(cyclopropylmethylamino)-1-(4-((5R,7R)-7-hydroxy-5-methyl-6,7-dihydro-5H-cyclopenta[d]pyrimidin-4-yl)piperazin-1-yl)-2-(4-(trifluoromethoxy)phenyl)propan-1-one;

(S)-3-amino-2-(4-bromo-3-fluorophenyl)-1-(4-((5R,7R)-7-hydroxy-5-methyl-6,7-dihydro-5H-cyclopenta[d]pyrimidin-4-yl)piperazin-1-yl)propan-1-one;

(S)-3-amino-2-(4-bromo-3-fluorophenyl)-1-(4-((5R,7S)-7-hydroxy-5-methyl-6,7-dihydro-5H-cyclopenta[d]pyrimidin-4-yl)piperazin-1-yl)propan-1-one;

(S)-2-(3,4-dichlorophenyl)-1-(4-((5R,7S)-7-hydroxy-5-methyl-6,7-dihydro-5H-cyclopenta[d]pyrimidin-4-yl)piperazin-1-yl)-3-(isopropylamino)propan-1-one;

(S)-2-(4-bromo-3-fluorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one;

(S)-2-(4-bromo-3-fluorophenyl)-1-(4-((5R,7S)-7-hydroxy-5-methyl-6,7-dihydro-5H-cyclopenta[d]pyrimidin-4-yl)piperazin-1-yl)-3-(isopropylamino)propan-1-one;

(S)-2-(4-bromo-3-fluorophenyl)-1-(4-((5R,7R)-7-hydroxy-5-methyl-6,7-dihydro-5H-cyclopenta[d]pyrimidin-4-yl)piperazin-1-yl)-3-(tetrahydro-2H-pyran-4-ylamino)propan-1-one;

(S)-2-(4-bromo-3-fluorophenyl)-1-(4-((5R,7S)-7-hydroxy-5-methyl-6,7-dihydro-5H-cyclopenta[d]pyrimidin-4-yl)piperazin-1-yl)-3-(tetrahydro-2H-pyran-4-ylamino)propan-1-one;

(S)-2-(4-bromo-3-fluorophenyl)-3-(cyclopropylmethylamino)-1-(4-((5R,7R)-7-hydroxy-5-methyl-6,7-dihydro-5H-cyclopenta[d]pyrimidin-4-yl)piperazin-1-yl)propan-1-one;

(S)-2-(4-bromo-3-fluorophenyl)-3-(cyclopropylmethylamino)-1-(4-((5R,7S)-7-hydroxy-5-methyl-6,7-dihydro-5H-cyclopenta[d]pyrimidin-4-yl)piperazin-1-yl)propan-1-one;

(5)-2-(3-fluoro-4-(trifluoromethyl)phenyl)-1-(4-((5R,7S)-7-hydroxy-5-methyl-6,7-dihydro-5H-cyclopenta[d]pyrimidin-4-yl)piperazin-1-yl)-3-(isopropylamino)propan-1-one;

(S)-2-(4-bromophenyl)-1-(4-((5R,7R)-7-hydroxy-5-methyl-6,7-dihydro-5H-cyclopenta[d]pyrimidin-4-yl)piperazin-1-yl)-3-(4-isopropylpiperazin-1-yl)propan-1-one;

(S)-2-(4-bromophenyl)-1-(4-((5R,7R)-7-hydroxy-5-methyl-6,7-dihydro-5H-cyclopenta[d]pyrimidin-4-yl)piperazin-1-yl)-3-(4-hydroxypiperidin-1-yl)propan-1-one;

(S)-3-(cyclopropylmethylamino)-1-(4-((5R,7R)-7-hydroxy-5-methyl-6,7-dihydro-5H-cyclopenta[d]pyrimidin-4-yl)piperazin-1-yl)-2-(4-(trifluoromethyl)phenyl)propan-1-one;

(S)-1-(4-((5R,7R)-7-hydroxy-5-methyl-6,7-dihydro-5H-cyclopenta[d]pyrimidin-4-yl)piperazin-1-yl)-3-(tetrahydro-2H-pyran-4-ylamino)-2-(4-(trifluoromethyl)phenyl)propan-1-one;

(S)-3-(cyclopropylmethylamino)-2-(2-fluoro-4-(trifluoromethyl)phenyl)-1-(4-((5R,7R)-7-hydroxy-5-methyl-6,7-dihydro-5H-cyclopenta[d]pyrimidin-4-yl)piperazin-1-yl)propan-1-one;

(R)-2-(4-bromo-3-fluorophenyl)-1-(4-((5R,7R)-7-hydroxy-5-methyl-6,7-dihydro-5H-cyclopenta[d]pyrimidin-4-yl)piperazin-1-yl)-3-(4-hydroxypiperidin-1-yl)propan-1-one;

(S)-2-(4-bromophenyl)-1-(4-((5R,7S)-7-hydroxy-5-methyl-6,7-dihydro-5H-cyclopenta[d]pyrimidin-4-yl)piperazin-1-yl)-3-(isopropyl(methyl)amino)propan-1-one;

(S)-3-amino-2-(4-bromo-2-fluorophenyl)-1-(4-((5R,7R)-7-hydroxy-5-methyl-6,7-dihydro-5H-cyclopenta[d]pyrimidin-4-yl)piperazin-1-yl)propan-1-one;

(S)-3-amino-2-(4-bromo-2-fluorophenyl)-1-(4-((5R,7S)-7-hydroxy-5-methyl-6,7-dihydro-5H-cyclopenta[d]pyrimidin-4-yl)piperazin-1-yl)propan-1-one;

(S)-2-(4-bromophenyl)-1-(4-((5R,7R)-7-hydroxy-5-methyl-6,7-dihydro-5H-cyclopenta[d]pyrimidin-4-yl)piperazin-1-yl)-3-(isopropyl(methyl)amino)propan-1-one;

(S)-2-(4-bromo-2-fluorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one;

(S)-2-(4-bromo-2-fluorophenyl)-1-(4-((5R,7S)-7-hydroxy-5-methyl-6,7-dihydro-5H-cyclopenta[d]pyrimidin-4-yl)piperazin-1-yl)-3-(isopropylamino)propan-1-one;

(S)-3-amino-2-(4-chloro-2-fluorophenyl)-1-(4-((5R,7R)-7-hydroxy-5-methyl-6,7-dihydro-5H-cyclopenta[d]pyrimidin-4-yl)piperazin-1-yl)propan-1-one;

2-(4-chlorophenyl)-3-((3S,4R)-4-(dimethylamino)-3-fluoropiperidin-1-yl)-1-(4-((5R,7R)-7-hydroxy-5-methyl-6,7-dihydro-5H-cyclopenta[d]pyrimidin-4-yl)piperazin-1-yl)propan-1-one;

(S)-2-(4-bromo-2-fluorophenyl)-3-(cyclopropylmethylamino)-1-(4-((5R,7S)-7-hydroxy-5-methyl-6,7-dihydro-5H-cyclopenta[d]pyrimidin-4-yl)piperazin-1-yl)propan-1-one;

(S)-3-(tert-butylamino)-1-(4-((5R,7R)-7-hydroxy-5-methyl-6,7-dihydro-5H-cyclopenta[d]pyrimidin-4-yl)piperazin-1-yl)-2-(4-(trifluoromethyl)phenyl)propan-1-one;

(S)-2-(3-fluoro-4-(trifluoromethoxy)phenyl)-1-(4-((5R,7S)-7-hydroxy-5-methyl-6,7-dihydro-5H-cyclopenta[d]pyrimidin-4-yl)piperazin-1-yl)-3-(tetrahydro-2H-pyran-4-ylamino)propan-1-one;

(S)-2-(3-fluoro-4-(trifluoromethyl)phenyl)-1-(4-((5R,7S)-7-hydroxy-5-methyl-6,7-dihydro-5H-cyclopenta[d]pyrimidin-4-yl)piperazin-1-yl)-3-(tetrahydro-2H-pyran-4-ylamino)propan-1-one;

(S)-2-(4-chloro-2-fluorophenyl)-3-(cyclopropylmethylamino)-1-(4-((5R,7R)-7-hydroxy-5-methyl-6,7-dihydro-5H-cyclopenta[d]pyrimidin-4-yl)piperazin-1-yl)propan-1-one;

(S)-2-(4-bromo-2-fluorophenyl)-1-(4-((5R,7R)-7-hydroxy-5-methyl-6,7-dihydro-5H-cyclopenta[d]pyrimidin-4-yl)piperazin-1-yl)-3-(tetrahydro-2H-pyran-4-ylamino)propan-1-one;

(S)-2-(4-chloro-2-fluorophenyl)-1-(4-((5R,7S)-7-hydroxy-5-methyl-6,7-dihydro-5H-cyclopenta[d]pyrimidin-4-yl)piperazin-1-yl)-3-(tetrahydro-2H-pyran-4-ylamino)propan-1-one;

(S)-2-(4-chloro-2-fluorophenyl)-1-(4-((5R,7R)-7-hydroxy-5-methyl-6,7-dihydro-5H-cyclopenta[d]pyrimidin-4-yl)piperazin-1-yl)-3-(tetrahydro-2H-pyran-4-ylamino)propan-1-one;

(S)-1-(4-((5R,7S)-7-hydroxy-5-methyl-6,7-dihydro-5H-cyclopenta[d]pyrimidin-4-yl)piperazin-1-yl)-3-(tetrahydro-2H-pyran-4-ylamino)-2-(4-(trifluoromethyl)phenyl)propan-1-one;

(S)-3-(cyclopropylmethylamino)-1-(4-((5R,7S)-7-hydroxy-5-methyl-6,7-dihydro-5H-cyclopenta[d]pyrimidin-4-yl)piperazin-1-yl)-2-(4-(trifluoromethyl)phenyl)propan-1-one;

(S)-2-(4-bromophenyl)-3-(tert-butylamino)-1-(4-((5R,7R)-7-hydroxy-5-methyl-6,7-dihydro-5H-cyclopenta[d]pyrimidin-4-yl)piperazin-1-yl)propan-1-one;

(S)-2-(4-chloro-3-fluorophenyl)-1-(4-((5R,7R)-7-hydroxy-5-methyl-6,7-dihydro-5H-cyclopenta[d]pyrimidin-4-yl)piperazin-1-yl)-3-(isobutylamino)propan-1-one;

(S)-2-(4-chloro-3-fluorophenyl)-3-(cyclopentylmethylamino)-1-(4-((5R,7R)-7-hydroxy-5-methyl-6,7-dihydro-5H-cyclopenta[d]pyrimidin-4-yl)piperazin-1-yl)propan-1-one;

(S)-2-(4-chloro-3-fluorophenyl)-3-(cyclopentylamino)-1-(4-((5R,7R)-7-hydroxy-5-methyl-6,7-dihydro-5H-cyclopenta[d]pyrimidin-4-yl)piperazin-1-yl)propan-1-one;

(S)-2-(2-fluoro-4-(trifluoromethyl)phenyl)-1-(4-((5R,7R)-7-hydroxy-5-methyl-6,7-dihydro-5H-cyclopenta[d]pyrimidin-4-yl)piperazin-1-yl)-3-(isopropyl(methyl)amino)propan-1-one;

(S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-((2-hydroxyethyl)(isopropyl)amino)propan-1-one;

(S)-2-(2-fluoro-4-(trifluoromethyl)phenyl)-1-(4-((5R,7S)-7-hydroxy-5-methyl-6,7-dihydro-5H-cyclopenta[d]pyrimidin-4-yl)piperazin-1-yl)-3-(isopropylamino)propan-1-one;

(S)-2-(2-fluoro-4-(trifluoromethyl)phenyl)-1-(4-((5R,7S)-7-hydroxy-5-methyl-6,7-dihydro-5H-cyclopenta[d]pyrimidin-4-yl)piperazin-1-yl)-3-(tetrahydro-2H-pyran-4-ylamino)propan-1-one;

(S)-3-amino-2-(2-fluoro-4-(trifluoromethyl)phenyl)-1-(4-((5R,7R)-7-hydroxy-5-methyl-6,7-dihydro-5H-cyclopenta[d]pyrimidin-4-yl)piperazin-1-yl)propan-1-one;

(S)-3-(cyclopropylmethylamino)-2-(3-fluoro-4-(trifluoromethyl)phenyl)-1-(4-((5R,7S)-7-hydroxy-5-methyl-6,7-dihydro-5H-cyclopenta[d]pyrimidin-4-yl)piperazin-1-yl)propan-1-one;

(S)-3-(cyclopropylmethylamino)-2-(3-fluoro-4-(trifluoromethoxy)phenyl)-1-(4-((5R,7S)-7-hydroxy-5-methyl-6,7-dihydro-5H-cyclopenta[d]pyrimidin-4-yl)piperazin-1-yl)propan-1-one;

(S)-2-(4-bromophenyl)-3-(4,4-dimethylcyclohexylamino)-1-(4-((5R,7R)-7-hydroxy-5-methyl-6,7-dihydro-5H-cyclopenta[d]pyrimidin-4-yl)piperazin-1-yl)propan-1-one;

(S)-2-(4-bromophenyl)-3-(3,3-dimethylcyclohexy-
lamino)-1-(4-((5R,7R)-7-hydroxy-5-methyl-6,7-dihy-
dro-5H-cyclopenta[d]pyrimidin-4-yl)piperazin-1-yl)
propan-1-one;

(S)-2-(4-chlorophenyl)-3-(4,4-dimethylcyclohexy-
lamino)-1-(4-((5R,7R)-7-hydroxy-5-methyl-6,7-dihy-
dro-5H-cyclopenta[d]pyrimidin-4-yl)piperazin-1-yl)
propan-1-one;

(S)-2-(4-chlorophenyl)-3-(3,3-dimethylcyclohexy-
lamino)-1-(4-((5R,7R)-7-hydroxy-5-methyl-6,7-dihy-
dro-5H-cyclopenta[d]pyrimidin-4-yl)piperazin-1-yl)
propan-1-one;

(S)-1-(4-((5R,7R)-7-hydroxy-5-methyl-6,7-dihydro-5H-
cyclopenta[d]pyrimidin-4-yl)piperazin-1-yl)-3-(iso-
propylamino)-2-(thiophen-2-yl)propan-1-one;

(S)-2-(5-bromothiophen-2-yl)-1-(4-((5R,7R)-7-hydroxy-
5-methyl-6,7-dihydro-5H-cyclopenta[d]pyrimidin-4-
yl)piperazin-1-yl)-3-(isopropylamino)propan-1-one;

(S)-2-(5-bromothiophen-2-yl)-1-(4-((5R,7S)-7-hydroxy-
5-methyl-6,7-dihydro-5H-cyclopenta[d]pyrimidin-4-
yl)piperazin-1-yl)-3-(isopropylamino)propan-1-one;

(S)-2-(5-bromothiophen-2-yl)-1-(4-((5R,7R)-7-hydroxy-
5-methyl-6,7-dihydro-5H-cyclopenta[d]pyrimidin-4-
yl)piperazin-1-yl)-3-(tetrahydro-2H-pyran-4-ylamino)
propan-1-one;

(R)-2-(5-bromopyridin-2-yl)-1-(4-((5R,7R)-7-hydroxy-5-
methyl-6,7-dihydro-5H-cyclopenta[d]pyrimidin-4-yl)
piperazin-1-yl)-3-(isopropylamino)propan-1-one;

(S)-2-(5-bromopyridin-2-yl)-1-(4-((5R,7R)-7-hydroxy-5-
methyl-6,7-dihydro-5H-cyclopenta[d]pyrimidin-4-yl)
piperazin-1-yl)-3-(isopropylamino)propan-1-one;

(S)-2-(5-bromothiophen-2-yl)-1-(4-((5R,7S)-7-hydroxy-
5-methyl-6,7-dihydro-5H-cyclopenta[d]pyrimidin-4-
yl)piperazin-1-yl)-3-(tetrahydro-2H-pyran-4-ylamino)
propan-1-one;

(S)-2-(5-bromothiophen-2-yl)-3-(cyclopropylmethy-
lamino)-1-(4-((5R,7R)-7-hydroxy-5-methyl-6,7-dihy-
dro-5H-cyclopenta[d]pyrimidin-4-yl)piperazin-1-yl)
propan-1-one;

(S)-2-(5-chlorothiophen-2-yl)-1-(4-((5R,7S)-7-hydroxy-
5-methyl-6,7-dihydro-5-cyclopenta[d]pyrimidin-4-yl)
piperazin-1-yl)-3-(tetrahydro-2H-pyran-4-ylamino)
propan-1-one;

(S)-2-(5-chlorothiophen-2-yl)-1-(4-((5R,7S)-7-hydroxy-
5-methyl-6,7-dihydro-5H-cyclopenta[d]pyrimidin-4-
yl)piperazin-1-yl)-3-(isopropylamino)propan-1-one;

(S)-2-(5-chlorothiophen-2-yl)-1-(4-((5R,7R)-7-hydroxy-
5-methyl-6,7-dihydro-5H-cyclopenta[d]pyrimidin-4-
yl)piperazin-1-yl)-3-(tetrahydro-2H-pyran-4-ylamino)
propan-1-one;

(S)-2-(5-chlorothiophen-2-yl)-3-(cyclopropylmethy-
lamino)-1-(4-((5R,7R)-7-hydroxy-5-methyl-6,7-dihy-
dro-5H-cyclopenta[d]pyrimidin-4-yl)piperazin-1-yl)
propan-1-one; and (S)-2-(5-chlorothiophen-2-yl)-3-(cyclopropylmethy-
lamino)-1-(4-((5R,7S)-7-hydroxy-5-methyl-6,7-dihy-
dro-5H-cyclopenta[d]pyrimidin-4-yl)piperazin-1-yl)
propan-1-one;

and salts thereof.

75. The method of claim 1 wherein the compound is a compound of Formula 1B:

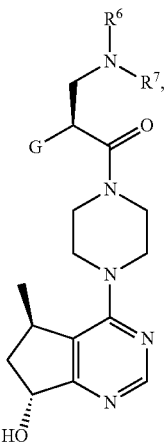

or a resolved enantiomer, resolved diastereomer, or salt thereof, wherein:

G is phenyl optionally substituted by one to four $R^9$ groups or a 5-6 membered heteroaryl optionally substituted by a halogen;

$R^6$ and $R^7$ are independently H, $OCH_3$, $(C_3-C_6$ cycloalkyl)-$(CH_2)$, $(C_3-C_6$ cycloalkyl)-$(CH_2CH_2)$, V—$(CH_2)_{0-1}$ wherein V is a 5-6 membered heteroaryl, W—$(CH_2)_{1-2}$ wherein W is phenyl optionally substituted with F, Cl, Br, I, OMe, $CF_3$ or Me, $C_3-C_6$-cycloalkyl optionally substituted with $C_1-C_3$ alkyl or $O(C_1-C_3$ alkyl), hydroxy-$(C_3-C_6$-cycloalkyl), fluoro-$(C_3-C_6$-cycloalkyl), $CH(CH_3)CH(OH)$phenyl, 4-6 membered heterocycle optionally substituted with F, OH, $C_1-C_3$ alkyl, cyclopropylmethyl or $C(=O)(C_1-C_3$ alkyl), or $C_1-C_6$-alkyl optionally substituted with one or more groups independently selected from OH, oxo, $O(C_1-C_6$-alkyl), CN, F, $NH_2$, $NH(C_1-C_6$-alkyl), $N(C_1-C_6$-alkyl)$_2$, cyclopropyl, phenyl, imidazolyl, piperidinyl, pyrrolidinyl, morpholinyl, tetrahydrofuranyl, oxetanyl or tetrahydropyranyl, or $R^6$ and $R^7$ together with the nitrogen to which they are attached form a 4-7 membered heterocyclic ring optionally substituted with one or more groups independently selected from OH, halogen, oxo, $CF_3$, $CH_2CF_3$, $CH_2CH_2OH$, $O(C_1-C_3$ alkyl), $C(=O)CH_3$, $NH_2$, NHMe, $N(Me)_2$, $S(O)_2CH_3$, cyclopropylmethyl and $C_1-C_3$ alkyl; and each $R^9$ is independently halogen, $C_1-C_6$-alkyl, $C_3-C_6$-cycloalkyl, O—$(C_1-C_6$-alkyl), $CF_3$, $OCF_3$, $S(C_1-C_6$-alkyl), CN, $OCH_2$-phenyl, $CH_2O$-phenyl, $NH_2$, NH—$(C_1-C_6$-alkyl), N—$(C_1-C_6$-alkyl)$_2$, piperidine, pyrrolidine, $CH_2F$, $CHF_2$, $OCH_2F$, $OCHF_2$, OH, $SO_2$ $(C_1-C_6$-alkyl), $C(O)NH_2$, $C(O)NH(C_1-C_6$-alkyl), and $C(O)N(C_1-C_6$-alkyl)$_2$.

76. The method of claim 75, wherein G is phenyl optionally substituted with one or more groups independently selected from F, Cl, Br, I, Me, ethyl, isopropyl, CN, $CF_3$, $OCF_3$, SMe, OMe and $OCH_2Ph$.

77. The method of claim 75, wherein G is phenyl, 2-chlorophenyl, 3-chlorophenyl, 4-chlorophenyl, 4-fluorophenyl, 4-bromophenyl, 4-methylphenyl, 4-ethylphenyl, 4-isopropylphenyl, 4-trifluoromethylphenyl, 4-cyanophenyl, 4-methoxyphenyl, 4-ethoxyphenyl, 4-thiomethylphenyl, 4-trifluoromethoxyphenyl, 4-cyclopropylphenyl, 4-chloro-3-fluorophenyl, 3,4-difluorophenyl, 4-bromo-3-fluorophenyl, 3-fluoro-4-methylphenyl, 3-fluoro-4-methoxyphenyl, 3-fluoro-4-bromophenyl, 3-fluoro-4-trifluoromethylphenyl, 4-cyano-3-fluorophenyl, 3,4-dichlorophenyl, 2,4-dichlorophenyl, 2,4-difluorophenyl, 2-chloro-4-fluorophenyl, 2-fluoro-4-chlorophenyl, 3,5-dichlorophenyl, 3,5-difluorophenyl, 3-chloro-5-fluorophenyl, 3-chloro-4-fluorophenyl, 3-bromo-4-fluorophenyl, 3,5-difluoro-4-chlorophenyl, 2,3-difluoro-4-chlorophenyl, 2,5-difluoro-4-chlorophenyl, 3,5-difluoro-4-bromophenyl, 2,3-difluoro-4-bromophenyl, 2,5-difluoro-4-bromophenyl or 4-(OCH$_2$Ph)-phenyl.

78. The method of claim 4, wherein G is 4-chlorophenyl, 2,4-dichlorophenyl, 3-chloro-4-fluorophenyl, 3,4-difluorophenyl, 4-chloro-3-fluorophenyl, 3-fluoro-4-bromophenyl, 3,4-dichlorophenyl, 4-methoxyphenyl, 4-fluorophenyl, 4-bromophenyl, 4-cyanophenyl, 4-trifluoromethylphenyl, 4-thiomethylphenyl, or 4-methylphenyl.

79. The method of claim 75, wherein G is a thiophene or pyridine optionally substituted by a halogen.

80. The method of claim 79, wherein G is selected from the structures:

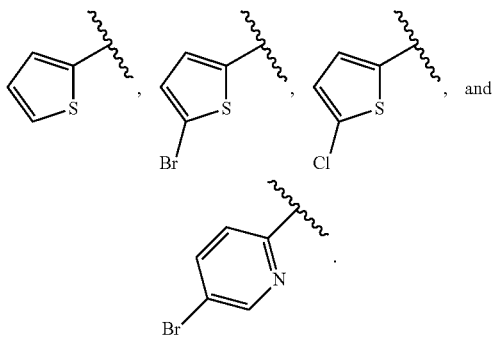

81. The method of claim 75, wherein R$^6$ and R$^7$ are independently selected from H, OCH$_3$, (C$_3$-C$_6$ cycloalkyl)-(CH$_2$), (C$_3$-C$_6$ cycloalkyl)-(CH$_2$CH$_2$), V—(CH$_2$)$_{0-1}$ wherein V is a 5-6 membered heteroaryl having from one to two ring heteroatoms independently selected from N, O and S, W—(CH$_2$)$_{1-2}$ wherein W is phenyl optionally substituted with F, Cl or Me, C$_3$-C$_6$-cycloalkyl optionally substituted with OCH$_3$, hydroxy-(C$_3$-C$_6$-cycloalkyl), fluoro-(C$_3$-C$_6$-cycloalkyl), CH(CH$_3$)CH(OH)phenyl, 5-6 membered heterocycle optionally substituted with CH$_3$ or C(=O)CH$_3$, or C$_1$-C$_6$-alkyl optionally substituted with one or more groups independently selected from OH, oxo, O(C$_1$-C$_6$-alkyl), CN, F, NH$_2$, NH(C$_1$-C$_6$-alkyl), N(C$_1$-C$_6$-alkyl)$_2$, phenyl, imidazolyl, piperidinyl, pyrrolidinyl, morpholinyl, and tetrahydropyranyl.

82. The method of claim 1, wherein R$^6$ and R$^7$ are independently selected from H, methyl, ethyl, isopropyl, isobutyl, tert-butyl, 3-pentyl, OCH$_3$, CH$_2$CH$_2$OH, CH$_2$CH$_2$OMe, CH$_2$CH$_2$CF$_3$, CH$_2$CH(CH$_3$)OH, CH$_2$CH(CF$_3$)OH, CH$_2$CF$_3$, CH$_2$CH$_2$F, CH$_2$C(=O)NH$_2$, CH$_2$C(=O)NH(CH$_3$), CH$_2$C(=O)N(CH$_3$)$_2$, CH$_2$C(=O)NH(iPr), CH$_2$CH$_2$C(=O)NH$_2$, CH$_2$-cyclopropyl, CH$_2$-cyclopentyl, CH$_2$-tBu (neopentyl), cyclopropyl, cyclopentyl, cyclohexyl, 4-methoxycyclohexyl, 4,4-dimethylcyclohexyl, 3,3-dimethylcyclohexyl, CH$_2$-(pyrid-3-yl), 4-hydroxycyclohex-1-yl, CH(CH$_3$)CH(OH)phenyl, CH(phenyl)CH$_2$OH, CH(tetrahydropyranyl)CH$_2$OH, CH$_2$CH$_2$(imidazolyl), CH$_2$CH$_2$(morpholinyl), CH$_2$(tetrahydropyranyl), CH$_2$CH$_2$(tetrahydropyranyl), pyrrolidinyl, piperidinyl, tetrahydropyranyl, tetrahydrofuranyl,

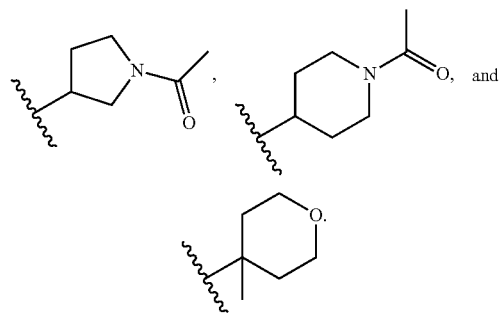

83. The method of claim 75, wherein R$^6$ and R$^7$ together with the nitrogen to which they are attached form a 4-7 membered heterocyclic ring, wherein said heterocyclic ring is optionally substituted with one or more groups independently selected from OH, halogen, oxo, CF$_3$, CH$_2$CF$_3$, CH$_2$CH$_2$OH, OCH$_3$, C(=O)CH$_3$, NH$_2$, NHMe, N(Me)$_2$, S(O)$_2$CH$_3$, and (C$_1$-C$_3$)alkyl.

84. The method of claim 83, wherein NR$^6$R$^7$ is selected from the structures:

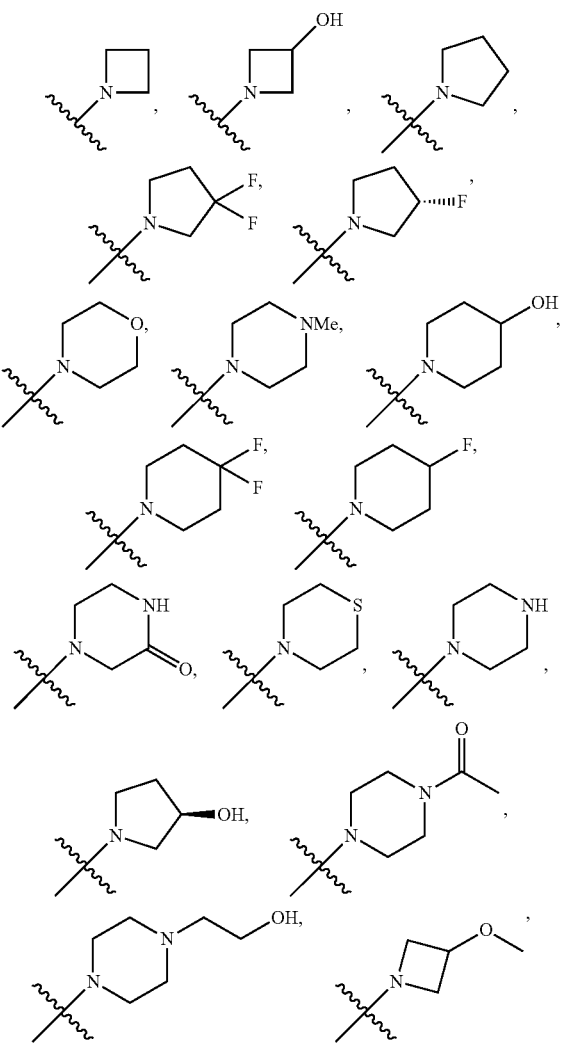

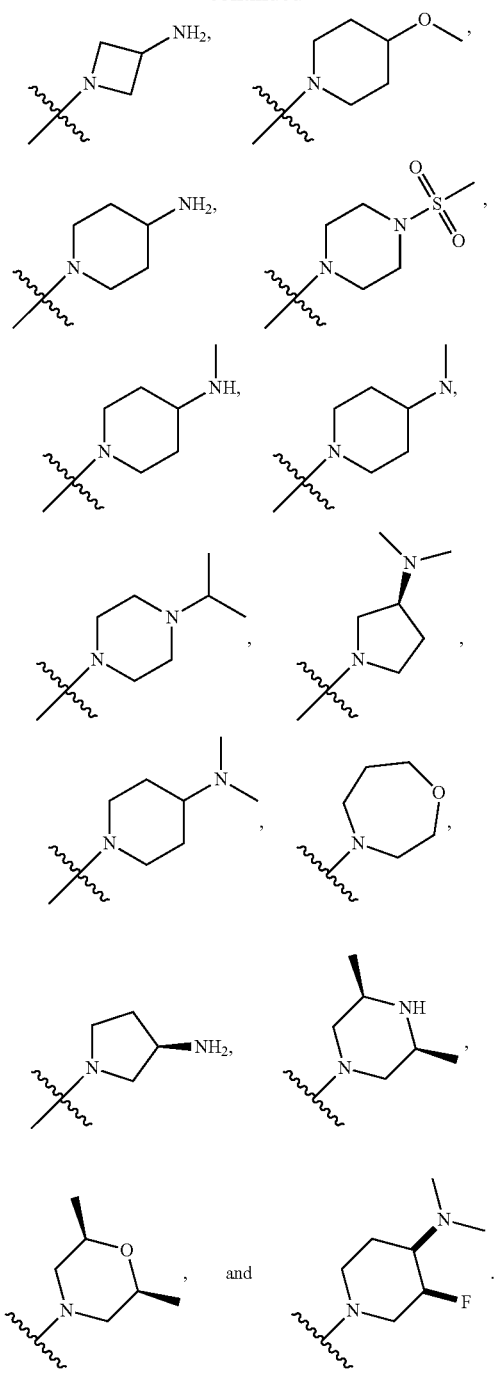

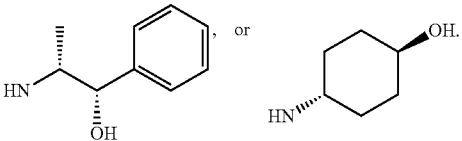

85. The method of claim 75, wherein NR$^6$R$^7$ is NH$_2$, NHMe, NHEt, NHPr, NHiPr, NHtBu, NH(CH$_2$-tBu), NH(CH$_2$-cyclopropyl), NH(CH$_2$-cyclobutyl), NH(cyclopentyl), NH(CH$_2$-pyridyl), NH(cyclohexyl), NH(3-pentyl), NH(CH$_2$CH$_2$OH), NH(CH$_2$CH$_2$CH$_2$OH), NH(CH$_2$CH$_2$OMe), NH(CH$_2$CH$_2$CH$_2$OMe), NH(CH$_2$CN), NMe$_2$, NMeEt, NMePr, NMe(iPr), NMe(CH$_2$-cyclopropyl), NMe(CH$_2$-cyclobutyl), NMe(CH$_2$CH$_2$OH), NMe(CH$_2$CH$_2$CH$_2$OH), NMe(CH$_2$CH$_2$OMe), NMe(CH$_2$CH$_2$CH$_2$OMe), NEt$_2$, NEtPr, NEt(iPr), NEt(CH$_2$-cyclopropyl), NEt(CH$_2$-cyclobutyl), NEt(CH$_2$CH$_2$OH), NEt(CH$_2$CH$_2$CH$_2$OH),

86. The method of claim 1 wherein the compound is selected from:
- (S)-3-amino-2-(4-chlorophenyl)-1-(4-((5R,7R)-7-hydroxy-5-methyl-6,7-dihydro-5H-cyclopenta[d]pyrimidin-4-yl)piperazin-1-yl)propan-1-one;
- (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one;
- (S)-3-amino-2-(3,4-dichlorophenyl)-1-(4-((5R,7R)-7-hydroxy-5-methyl-6,7-dihydro-5H-cyclopenta[d]pyrimidin-4-yl)piperazin-1-yl)propan-1-one;
- (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(methyl(tetrahydro-2H-pyran-4-yl)amino)propan-1-one;
- (S)-2-(5-chlorothiophen-2-yl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one;
- (S)-2-(4-chlorophenyl)-3-(cyclopropylmethylamino)-1-(4-((5R,7R)-7-hydroxy-5-methyl-6,7-dihydro-5H-cyclopenta[d]pyrimidin-4-yl)piperazin-1-yl)propan-1-one;
- (S)-1-(4-((5R,7R)-7-hydroxy-5-methyl-6,7-dihydro-5H-cyclopenta[d]pyrimidin-4-yl)piperazin-1-yl)-3-(isopropylamino)-2-(4-(trifluoromethoxy)phenyl)propan-1-one;
- (S)-2-(4-chlorophenyl)-3-(cyclopropylamino)-1-(4-((5R,7R)-7-hydroxy-5-methyl-6,7-dihydro-5H-cyclopenta[d]pyrimidin-4-yl)piperazin-1-yl)propan-1-one;
- (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(3-hydroxyazetidin-1-yl)propan-1-one;
- (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-((R)-pyrrolidin-3-ylamino)propan-1-one;
- (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-((S)-pyrrolidin-3-ylamino)propan-1-one;
- (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-thiomorpholinopropan-1-one;
- (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(piperazin-1-yl)propan-1-one;
- (S)-2-(4-chlorophenyl)-3-(4-fluoropiperidin-1-yl)-1-(4-((5R,7R)-7-hydroxy-5-methyl-6,7-dihydro-5H-cyclopenta[d]pyrimidin-4-yl)piperazin-1-yl)propan-1-one;
- (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(3-methoxyazetidin-1-yl)propan-1-one;
- (S)-2-(3,4-dichlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one;
- (S)-2-(4-chlorophenyl)-3-(dimethylamino)-1-(4-((5R,7R)-7-hydroxy-5-methyl-6,7-dihydro-5H-cyclopenta[d]pyrimidin-4-yl)piperazin-1-yl)propan-1-one;

(S)-2-(4-fluoro-3-(trifluoromethyl)phenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one;

(S)-2-(3-fluoro-4-(trifluoromethyl)phenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one;

(S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(methoxyamino)propan-1-one;

(S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(4-methoxypiperidin-1-yl)propan-1-one;

(S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(4-hydroxypiperidin-1-yl)propan-1-one;

(S)-3-(4-aminopiperidin-1-yl)-2-(4-chlorophenyl)-1-(4-((5R,7R)-7-hydroxy-5-methyl-6,7-dihydro-5H-cyclopenta[d]pyrimidin-4-yl)piperazin-1-yl)propan-1-one;

(S)-2-(4-chlorophenyl)-1-(4-((5R,7S)-7-hydroxy-5-methyl-6,7-dihydro-5H-cyclopenta[d]pyrimidin-4-yl)piperazin-1-yl)-3-(tetrahydro-2H-pyran-4-ylamino)propan-1-one;

(S)-2-(4-chlorophenyl)-1-(4-((5R,7S)-7-hydroxy-5-methyl-6,7-dihydro-5H-cyclopenta[d]pyrimidin-4-yl)piperazin-1-yl)-3-(methyl(tetrahydro-2H-pyran-4-yl)amino)propan-1-one;

(S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropyl(methyl)amino)propan-1-one;

(S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(4-(methylamino)piperidin-1-yl)propan-1-one;

(S)-2-(4-chloro-3-(trifluoromethoxy)phenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one;

(S)-2-(3-fluoro-4-(trifluoromethoxy)phenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one;

(S)-2-(4-chloro-3-(trifluoromethyl)phenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one;

(S)-2-(4-chlorophenyl)-3-(4-ethylpiperazin-1-yl)-1-(4-((5R,7R)-7-hydroxy-5-methyl-6-dihydro-5H-cyclopenta[d]pyrimidin-4-yl)piperazin-1-yl)propan-1-one;

(S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(4-isopropylpiperazin-1-yl)propan-1-one;

(S)-2-(4-chlorophenyl)-3-((S)-3-(dimethylamino)pyrrolidin-1-yl)-1-(4-((5R,7R)-7-hydroxy-5-methyl-6,7-dihydro-5H-cyclopenta[d]pyrimidin-4-yl)piperazin-1-yl)propan-1-one;

(S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-((R)-tetrahydrofuran-3-ylamino)propan-1-one;

(S)-2-(4-chlorophenyl)-3-(2-fluoroethylamino)-1-(4-((5R,7R)-7-hydroxy-5-methyl-6,7-dihydro-5H-cyclopenta[d]pyrimidin-4-yl)piperazin-1-yl)propan-1-one;

(S)-2-(4-fluoro-3-(trifluoromethoxy)phenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one;

(S)-2-(3-fluoro-4-methoxyphenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one;

(S)-2-(4-chlorophenyl)-3-(4-(dimethylamino)piperidin-1-yl)-1-(4-((5R,7R)-7-hydroxy-5-methyl-6,7-dihydro-5H-cyclopenta[d]pyrimidin-4-yl)piperazin-1-yl)propan-1-one;

(S)-2-(3-chloro-5-fluorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one;

(S)-2-(3-bromo-4-methoxyphenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one;

(S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(1,4-oxazepan-4-yl)propan-1-one;

(S)-2-(4-chloro-2-fluorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one;

(S)-2-(2-fluoro-4-(trifluoromethyl)phenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one;

(S)-2-(4-chlorophenyl)-3-(cyclohexylamino)-1-(4-((5R,7R)-7-hydroxy-5-methyl-6,7-dihydro-5H-cyclopenta[d]pyrimidin-4-yl)piperazin-1-yl)propan-1-one;

(S)-2-(4-bromophenyl)-1-(4-((5R,7R)-7-hydroxy-5-methyl-6,7-dihydro-5H-cyclopenta[d]pyrimidin-4-yl)piperazin-1-yl)-3-(4-isopropylpiperazin-1-yl)propan-1-one;

(S)-2-(4-bromophenyl)-1-(4-((5R,7R)-7-hydroxy-5-methyl-6,7-dihydro-5H-cyclopenta[d]pyrimidin-4-yl)piperazin-1-yl)-3-(4-hydroxypiperidin-1-yl)propan-1-one;

(S)-3-(cyclopropylmethylamino)-1-(4-((5R,7R)-7-hydroxy-5-methyl-6,7-dihydro-5H-cyclopenta[d]pyrimidin-4-yl)piperazin-1-yl)-2-(4-(trifluoromethyl)phenyl)propan-1-one;

(S)-1-(4-((5R,7R)-7-hydroxy-5-methyl-6,7-dihydro-5H-cyclopenta[d]pyrimidin-4-yl)piperazin-1-yl)-3-(tetrahydro-2H-pyran-4-ylamino)-2-(4-(trifluoromethyl)phenyl)propan-1-one;

(S)-3-(cyclopropylmethylamino)-2-(2-fluoro-4-(trifluoromethyl)phenyl)-1-(4-((5R,7R)-7-hydroxy-5-methyl-6,7-dihydro-5H-cyclopenta[d]pyrimidin-4-yl)piperazin-1-yl)propan-1-one;

(S)-3-amino-2-(4-bromo-2-fluorophenyl)-1-(4-((5R,7R)-7-hydroxy-5-methyl-6,7-dihydro-5H-cyclopenta[d]pyrimidin-4-yl)piperazin-1-yl)propan-1-one;

(S)-2-(4-bromophenyl)-1-(4-((5R,7R)-7-hydroxy-5-methyl-6,7-dihydro-5H-cyclopenta[d]pyrimidin-4-yl)piperazin-1-yl)-3-(isopropyl(methyl)amino)propan-1-one;

(S)-2-(4-bromo-2-fluorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one;

(S)-3-amino-2-(4-chloro-2-fluorophenyl)-1-(4-((5R,7R)-7-hydroxy-5-methyl-6,7-dihydro-5H-cyclopenta[d]pyrimidin-4-yl)piperazin-1-yl)propan-1-one;

(S)-3-(tert-butylamino)-1-(4-((5R,7R)-7-hydroxy-5-methyl-6,7-dihydro-5H-cyclopenta[d]pyrimidin-4-yl)piperazin-1-yl)-2-(4-(trifluoromethyl)phenyl)propan-1-one;

(S)-2-(4-chloro-2-fluorophenyl)-3-(cyclopropylmethylamino)-1-(4-((5R,7R)-7-hydroxy-5-methyl-6,7-dihydro-5H-cyclopenta[d]pyrimidin-4-yl)piperazin-1-yl)propan-1-one;

(S)-2-(4-bromo-2-fluorophenyl)-1-(4-((5R,7R)-7-hydroxy-5-methyl-6,7-dihydro-5H-cyclopenta[d]pyrimidin-4-yl)piperazin-1-yl)-3-(tetrahydro-2H-pyran-4-ylamino)propan-1-one;

(S)-2-(4-chloro-2-fluorophenyl)-1-(4-((5R,7R)-7-hydroxy-5-methyl-6,7-dihydro-5H-cyclopenta[d]pyrimidin-4-yl)piperazin-1-yl)-3-(tetrahydro-2H-pyran-4-ylamino)propan-1-one;

(S)-2-(4-bromophenyl)-3-(tert-butylamino)-1-(4-((5R,7R)-7-hydroxy-5-methyl-6,7-dihydro-5H-cyclopenta[d]pyrimidin-4-yl)piperazin-1-yl)propan-1-one;

(S)-2-(4-chloro-3-fluorophenyl)-1-(4-((5R,7R)-7-hydroxy-5-methyl-6,7-dihydro-5H-cyclopenta[d]pyrimidin-4-yl)piperazin-1-yl)-3-(isobutylamino)propan-1-one;

(S)-2-(4-chloro-3-fluorophenyl)-3-(cyclopentylmethylamino)-1-(4-((5R,7R)-7-hydroxy-5-methyl-6,7-dihydro-5H-cyclopenta[d]pyrimidin-4-yl)piperazin-1-yl)propan-1-one;

(S)-2-(4-chloro-3-fluorophenyl)-3-(cyclopentylamino)-1-(4-((5R,7R)-7-hydroxy-5-methyl-6,7-dihydro-5H-cyclopenta[d]pyrimidin-4-yl)piperazin-1-yl)propan-1-one;

(S)-2-(2-fluoro-4-(trifluoromethyl)phenyl)-1-(4-((5R,7R)-7-hydroxy-5-methyl-6,7-dihydro-5H-cyclopenta[d]pyrimidin-4-yl)piperazin-1-yl)-3-(isopropyl(methyl)amino)propan-1-one;

(S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(2-hydroxyethyl)isopropyl)amino)propan-1-one;

(S)-3-amino-2-(2-fluoro-4-(trifluoromethyl)phenyl)-1-(4-((5R,7R)-7-hydroxy-5-methyl-6,7-dihydro-5H-cyclopenta[d]pyrimidin-4-yl)piperazin-1-yl)propan-1-one;

(S)-2-(4-bromophenyl)-3-(4,4-dimethylcyclohexylamino)-1-(4-((5R,7R)-7-hydroxy-5-methyl-6,7-dihydro-5H-cyclopenta[d]pyrimidin-4-yl)piperazin-1-yl)propan-1-one;

(S)-2-(4-bromophenyl)-3-(3,3-dimethyl cyclohexylamino)-1-(4-((5R,7R)-7-hydroxy-5-methyl-6,7-dihydro-5H-cyclopenta[d]pyrimidin-4-yl)piperazin-1-yl)propan-1-one;

(S)-2-(4-chlorophenyl)-3-(4,4-dimethylcyclohexylamino)-1-(4-((5R,7R)-7-hydroxy-5-methyl-6,7-dihydro-5H-cyclopenta[d]pyrimidin-4-yl)piperazin-1-yl)propan-1-one;

(S)-2-(4-chlorophenyl)-3-(3,3-dimethylcyclohexylamino)-1-(4-((5R,7R)-7-hydroxy-5-methyl-6,7-dihydro-5H-cyclopenta[d]pyrimidin-4-yl)piperazin-1-yl)propan-1-one;

(S)-1-(4-((5R,7R)-7-hydroxy-5-methyl-6,7-dihydro-5H-cyclopenta[d]pyrimidin-4-yl)piperazin-1-yl)-3-(isopropylamino)-2-(thiophen-2-yl)propan-1-one;

(S)-2-(5-bromothiophen-2-yl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one;

(S)-2-(5-bromothiophen-2-yl)-1-(4-((5R,7R)-7-hydroxy-5-methyl-6,7-dihydro-5H-cyclopenta[d]pyrimidin-4-yl)piperazin-1-yl)-3-(tetrahydro-2H-pyran-4-ylamino)propan-1-one;

(R)-2-(5-bromopyridin-2-yl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one;

(S)-2-(5-bromothiophen-2-yl)-3-(cyclopropylmethylamino)-1-(4-((5R,7R)-7-hydroxy-5-methyl-6,7-dihydro-5H-cyclopenta[d]pyrimidin-4-yl)piperazin-1-yl)propan-1-one;

(S)-2-(5-chlorothiophen-2-yl)-1-(4-((5R,7R)-7-hydroxy-5-methyl-6,7-dihydro-5H-cyclopenta[d]pyrimidin-4-yl)piperazin-1-yl)-3-(tetrahydro-2H-pyran-4-ylamino)propan-1-one; and (S)-2-(5-chlorothiophen-2-yl)-3-(cyclopropylmethylamino)-1-(4-((5R,7R)-7-hydroxy-5-methyl-6,7-dihydro-5H-cyclopenta[d]pyrimidin-4-yl)piperazin-1-yl)propan-1-one;

and salts thereof.

87. The method of claim 1 wherein the compound is (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one or a salt thereof.

88. The method of claim 1 wherein the compound is (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(methyl(tetrahydro-2H-pyran-4-yl)amino)propan-1-one or a salt thereof.

89. The method of claim 1 wherein the compound is (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(3-hydroxyazetidin-1-yl)propan-1-one or a salt thereof.

90. The method of claim 1 wherein the compound is (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-((R)-pyrrolidin-3-ylamino)propan-1-one or a salt thereof.

91. The method of claim 1 wherein the compound is (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-((S)-pyrrolidin-3-ylamino)propan-1-one or a salt thereof.

92. The method of claim 1 wherein the compound is (S)-3-(1-acetylpiperidin-4-ylamino)-2-(4-chlorophenyl)-1-(4-((5R,7R)-7-hydroxy-5-methyl-6,7-dihydro-5H-cyclopenta[d]pyrimidin-4-yl)piperazin-1-yl)propan-1-one or a salt thereof.

93. The method of claim 1 wherein the compound is (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(tetrahydro-2H-pyran-4-ylamino)propan-1-one or a salt thereof.

94. The method of claim 1 wherein the compound is (S)-2-(3,4-dichlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one or a salt thereof.

95. The method of claim 1 wherein the compound is (S)-2-(4-chlorophenyl)-3-(dimethylamino)-1-(4-((5R,7R)-7-hydroxy-5-methyl-6,7-dihydro-5H-cyclopenta[d]pyrimidin-4-yl)piperazin-1-yl)propan-1-one or a salt thereof.

96. The method of claim 1 wherein the compound is (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropyl(methyl)amino)propan-1-one or a salt thereof.

97. The method of claim 1 wherein the compound is (S)-2-(4-chloro-3-(trifluoromethyl)phenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one or a salt thereof.

98. The method of claim 1 wherein the compound is (S)-2-(4-chlorophenyl)-1-(4-(((5R,7R)-7-hydroxy-5-methyl-6,7-dihydro-5H-cyclopenta[d]pyrimidin-4-yl)piperazin-1-yl)-3-(4-methoxycyclohexylamino)propan-1-one or a salt thereof.

99. The method of claim 1 wherein the compound is (S)-2-(4-bromophenyl)-1-(4-(((5R,7R)-7-hydroxy-5-methyl-6,7-dihydro-5H-cyclopenta[d]pyrimidin-4-yl)piperazin-1-yl)-3-(tetrahydro-2H-pyran-4-ylamino)propan-1-one or a salt thereof.

100. The method of claim 1 wherein the compound is (S)-3-amino-2-(4-chlorophenyl)-1-(4-(((5R,7R)-7-hydroxy-5-methyl-6,7-dihydro-5H-cyclopenta[d]pyrimidin-4-yl)piperazin-1-yl)propan-1-one or a salt thereof.

101. The method of claim 1 wherein the compound is (S)-3-(tert-butylamino)-1-(4-(((5R,7R)-7-hydroxy-5-methyl-6,7-dihydro-5H-cyclopenta[d]pyrimidin-4-yl)piperazin-1-yl)-2-(4-(trifluoromethyl)phenyl)propan-1-one or a salt thereof.

* * * * *